US012577271B2

(12) United States Patent
Graham et al.

(10) Patent No.: US 12,577,271 B2
(45) **Date of Patent: *Mar. 17, 2026**

(54) MODIFIED NUCLEOTIDES AND USES THEREOF

(71) Applicant: Singular Genomics Systems, Inc., La Jolla, CA (US)

(72) Inventors: Ronald Graham, Carlsbad, CA (US); Surya Adhikari, San Diego, CA (US); Rodrigo Rodriguez, San Diego, CA (US); Zachary Terranova, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 1144 days.

This patent is subject to a terminal disclaimer.

(21) Appl. No.: 17/365,361

(22) Filed: Jul. 1, 2021

(65) Prior Publication Data

US 2023/0002436 A1 Jan. 5, 2023

Related U.S. Application Data

(63) Continuation of application No. 17/238,922, filed on Apr. 23, 2021, now Pat. No. 11,174,281.

(60) Provisional application No. 63/107,017, filed on Oct. 29, 2020, provisional application No. 63/014,949, filed on Apr. 24, 2020.

(51) Int. Cl.

| | |
|---|---|
| ***C07H 19/10*** | (2006.01) |
| ***C07H 19/14*** | (2006.01) |
| ***C12N 9/12*** | (2006.01) |
| ***C12Q 1/6869*** | (2018.01) |

(52) U.S. Cl.

CPC ............. *C07H 19/10* (2013.01); *C07H 19/14* (2013.01); *C12N 9/1252* (2013.01); *C12Q 1/6869* (2013.01); *C12Y 207/07007* (2013.01)

(58) Field of Classification Search

CPC ...... C07H 19/10; C07H 19/14; C12N 9/1252; C12Q 1/6969; C12Y 207/07007

See application file for complete search history.

(56) References Cited

U.S. PATENT DOCUMENTS

| | | | | |
|---|---|---|---|---|
| 5,034,506 | A | 7/1991 | Summerton et al. | |
| 5,235,033 | A | 8/1993 | Summerton et al. | |
| 6,664,079 | B2 | 12/2003 | Ju et al. | |
| 10,738,072 | B1 * | 8/2020 | Graham | C07H 19/10 |
| 10,822,653 | B1 * | 11/2020 | Graham | C12N 9/1241 |
| 11,085,076 | B2 | 8/2021 | Ju et al. | |
| 11,174,281 | B1 * | 11/2021 | Graham | C07H 19/10 |
| 11,878,993 | B2 * | 1/2024 | Graham | C12Q 1/6876 |
| 11,946,103 | B2 * | 4/2024 | Graham | C07H 19/20 |
| 11,958,877 | B2 | 4/2024 | Graham et al. | |
| 11,970,735 | B2 * | 4/2024 | Graham | C12Q 1/6806 |
| 12,145,960 | B2 * | 11/2024 | Graham | C07H 19/20 |
| 12,188,089 | B2 * | 1/2025 | Graham | C12Q 1/6876 |
| 12,215,122 | B2 * | 2/2025 | Graham | C12Q 1/6876 |
| 12,215,124 | B2 | 2/2025 | Graham et al. | |
| 2002/0015961 | A1 | 2/2002 | Kwiatkowski | |
| 2002/0064782 | A1 | 5/2002 | Shinoki et al. | |
| 2006/0003383 | A1 | 1/2006 | Graham | |
| 2006/0188901 | A1 | 8/2006 | Barnes et al. | |
| 2007/0009980 | A1 | 1/2007 | Graham | |
| 2009/0047699 | A1 | 2/2009 | Graham | |
| 2011/0014611 | A1 | 1/2011 | Ju et al. | |
| 2012/0156671 | A1 | 6/2012 | Liu et al. | |
| 2013/0264207 | A1 | 10/2013 | Ju et al. | |
| 2016/0002721 | A1 | 1/2016 | Liu et al. | |
| 2016/0108382 | A1 | 4/2016 | Efcavitch et al. | |
| 2016/0355541 | A1 | 12/2016 | Jain et al. | |
| 2017/0137869 | A1 | 5/2017 | Marma et al. | |
| 2017/0166961 | A1 | 6/2017 | Liu et al. | |
| 2017/0283451 | A1 | 10/2017 | Ju et al. | |
| 2018/0274024 | A1 * | 9/2018 | Ju | C07H 19/14 |
| 2018/0274025 | A1 | 9/2018 | Marma et al. | |
| 2019/0077726 | A1 * | 3/2019 | Graham | C07H 21/00 |
| 2020/0131484 | A1 | 4/2020 | Golynskiy et al. | |
| 2020/0181587 | A1 | 6/2020 | Klausing et al. | |
| 2020/0216891 | A1 | 7/2020 | Graham et al. | |
| 2022/0298201 | A1 | 9/2022 | Graham et al. | |
| 2023/0028359 | A1 | 1/2023 | Graham et al. | |
| 2023/0160001 | A1 * | 5/2023 | Tong | C07H 19/20 435/6.11 |
| 2023/0242571 | A1 * | 8/2023 | Graham | C07H 21/04 435/61 |
| 2023/0257414 | A1 | 8/2023 | Graham et al. | |
| 2024/0174709 | A1 | 5/2024 | Graham et al. | |
| 2024/0400602 | A1 | 12/2024 | Francais et al. | |

(Continued)

FOREIGN PATENT DOCUMENTS

| | | | |
|---|---|---|---|
| EP | 2876166 | A1 | 5/2015 |
| EP | 2876166 | B1 | 5/2015 |

(Continued)

OTHER PUBLICATIONS

Aydemir, Murat; Investigation of delayed fluorescence phenomena in conjugated molecules using time-resolved laser spectroscopy, Durham theses, Durham University. (Year: 2016).* International Search Report mailed on Sep. 8, 2021, for PCT Application No. PCT/US2021/028839, filed Apr. 23, 2021, 3 pages.

Written Opinion mailed on Sep. 8, 2021, for PCT Application No. PCT/US2021/028839, filed Apr. 23, 2021, 3 pages.

Bentley, D.R. et al. (Nov. 6, 2008). "Accurate whole human genome sequencing using reversible terminator chemistry," *Nature* 456(7218):53-59.

Bergseid, M. et al. (Nov. 2000). "Small molecule-based chemical affinity system for the purification of proteins," *Bio Techniques* 29(5):1126-1133.

Binauld, S. et al. (Mar. 14, 2013). "Acid-degradable polymers for drug delivery: a decade of innovation," *Chem Commun* 49(21):2082-2102.

(Continued)

*Primary Examiner* — Abigail Vanhorn

(74) *Attorney, Agent, or Firm* — Mintz, Levin, Cohn, Ferris, Glovsky and Popeo, P.C.; Zachary L. Terranova

(57) ABSTRACT

Disclosed herein, inter alia, are compounds, modified nucleotides, compositions, and methods of using the same.

28 Claims, 3 Drawing Sheets

(56) References Cited

U.S. PATENT DOCUMENTS

| | | | | |
|---|---|---|---|---|
| 2025/0084120 | A1 | 3/2025 | Graham et al. | |
| 2025/0101512 | A1* | 3/2025 | Graham | C12Q 1/6876 |

FOREIGN PATENT DOCUMENTS

| | | | |
|---|---|---|---|
| WO | 2004018493 | A1 | 3/2004 |
| WO | WO-2017/058953 | A1 | 4/2017 |
| WO | WO-2017/079498 | A2 | 5/2017 |
| WO | WO-2017/079498 | A3 | 5/2017 |
| WO | WO-2017/176679 | A1 | 10/2017 |
| WO | 2019071474 | A1 | 4/2019 |
| WO | WO-2019/164977 | A1 | 8/2019 |
| WO | WO-2020/086834 | A1 | 4/2020 |
| WO | WO-2020/146397 | A1 | 7/2020 |

OTHER PUBLICATIONS

Blackman, M.L. et al. (Oct. 15, 2008, e-published Sep. 18, 2008). "The Tetrazine ligation: fast bioconjugation based on inverse-electron-demand Diels-Alder reactivity," *J Am Chem Soc* 130(41):13518-13519.

Debets, M.F. et al. (Oct. 14, 2013, e-published Aug. 23, 2013). "Bioorthogonal labelling of biomolecules: new functional handles and ligation methods," *Org Biomol Chem* 11(38):6439-6455.

Grabowski, J. et al. (May 2, 2018). "Preparation of acetals from aldehydes and alcohols under basic conditions," *Org Biomol Chem* 16(17):3114-3120.

Hutter, D. et al. (Nov. 2010). "Labeled nucleoside triphosphates with reversibly terminating aminoalkoxyl groups," *Nucleosides Nucleotides Nucleic Acids* 29(11):879-895.

Jewett, J.C. et al. (Mar. 24, 2010). "Rapid Cu-free click chemistry with readily synthesized biarylazacyclooctynones," *J Am Chem Soc* 132(11):3688-3690.

Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.

Leriche, G. et al. (Jul. 2010). "Optimization of the Azobenzene Scaffold for Reductive Cleavage by Dithionite; Development of an Azobenzene Cleavable Linker for Proteomic Applications," *Eur J Org Chem* 2010(23):4360-4364.

Mag, M. et al. (1992). "Synthesis and Selective Cleavage of an Oligodeoxynucleotide Containing a Bridged Non-Chiral Internucleotide 3'-Phosphoramidate Linkage," *Tetrahedron Letters* 33(48):7319-7322.

Matikonda, S.S. et al. (Jul. 28, 2020). "Core remodeling leads to long wavelength fluoro-coumarins," *Chem. Sci*. 11(28):7302-7307.

PubChem Compound Summary for CID 121486816 (Aug. 16, 2016). Located at <https:pubchem.ncbi.nlm.nih.gov/compound/121486816> last visited Apr. 22, 2019, 7 pages.

PubChem Compound Summary for CID 69188114 (Nov. 30, 2012). Located at <https:pubchem.ncbi.nlm.nih.gov/compound/69188114> last visited Apr. 22, 2019, 7 pages.

Rathod, K.M. et al. (2013). "Synthesis and Antimicrobial Activity of Azo Compounds Containing *m*-Cresol Moiety," *Chem Sci Trans* 2(1):25-28.

Rosenblum, B.B. et al. (Nov. 15, 1997). "New dye-labeled terminators for improved DNA sequencing patterns," *Nucleic Acids Res* 25(22):4500-4504.

Ruparel, H. et al. (Apr. 26, 2005, e-published Apr. 13, 2005). "Design and synthesis of a 3'-*O*-allyl photocleavable fluorescent nucleotide as a reversible terminator for DNA sequencing by synthesis," *PNAS USA* 102(17):5932-5937.

Seio, K. et al. (2002). "A new protecting group for 5'-hydroxyl function of nucleotides in oligonucleotide synthesis without acid treatment utilizing unique properties of tritylthio group," *Nucleic Acids Research* Supplement No. 2, pp. 27-28.

Shenoi, R.A. et al. (Sep. 12, 2012, e-published Aug. 30, 2012). "Branched multifunctional polyether polyketals: variation of ketal group structure enables unprecedented control over polymer degradation in solution and within cells," *J Am Chem Soc* 134(36):14945-14957.

Walker, J.W. et al. (1988). "Photolabile 1-(2-nitrophenyl)ethyl phosphate esters of adenine nucleotide analogs. Synthesis and mechanism of photolysis," *J Am Chem Soc*. 110(21):7170-7177.

Wu, J. et al. (Oct. 16, 2007, e-published Oct. 8, 2007). "3'-*O*-modified nucleotides as reversible terminators for pyrosequencing," *PNAS USA* 104(42):16462-16467.

Zhu, Z. et al. (Aug. 25, 1994). "Directly labeled DNA probes using fluorescent nucleotides with different length linkers," *Nucleic Acids Res* 22(16):3418-3422.

Liu, P. et al. (2008). "Fluorinated nucleosides: Synthesis and biological implication," Journal of fluorine chemistry 129(9): 743-766.

* cited by examiner

Chemical Formula: $C_{18}H_{25}N_2O_{14}P_3S_2$
Exact Mass: 650.00
Molecular Weight: 650.44

MODIFIED NUCLEOTIDES AND USES THEREOF

CROSS-REFERENCES TO RELATED APPLICATIONS

This application is a continuation of U.S. patent application Ser. No. 17/238,922, filed Apr. 23, 2021, which claims the benefit of U.S. Provisional Application No. 63/014,949, filed Apr. 24, 2020, and U.S. Provisional Application No. 63/107,017, filed Oct. 29, 2020, which are incorporated herein by reference in their entirety and for all purposes.

BACKGROUND

DNA sequencing is a fundamental tool in biological and medical research; it is an essential technology for the paradigm of personalized precision medicine. Among various new DNA sequencing methods, sequencing by synthesis (SBS) is the leading method for realizing the goal of the $1,000 genome. Accordingly, there is a need for modified nucleotides and nucleosides that are effectively recognized as substrates by DNA polymerases, that are efficiently and accurately incorporated into growing DNA chains during SBS. Disclosed herein, inter alia, are solutions to these and other problems in the art.

BRIEF SUMMARY

In an aspect is provided a compound having the formula:

(II)

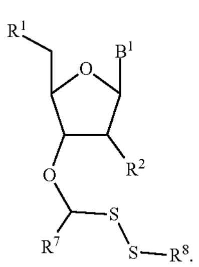

$B^1$ is a nucleobase. $R^7$ is substituted or unsubstituted cycloalkyl, substituted or unsubstituted heterocycloalkyl, substituted or unsubstituted aryl, or substituted or unsubstituted heteroaryl. $R^8$ is substituted or unsubstituted alkyl. $R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. $R^2$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety.

In an aspect is provided a method for sequencing a nucleic acid, including (i) incorporating in series with a nucleic acid polymerase, within a reaction vessel, one of four different compounds into a primer to create an extension strand, wherein the primer is hybridized to the nucleic acid and wherein each of the four different compounds comprises a unique detectable label; (ii) detecting the unique detectable label of each incorporated compound, so as to thereby identify each incorporated compound in the extension strand, thereby sequencing the nucleic acid; wherein each of the four different compounds is independently a compound as described herein, including embodiments.

In an aspect is provided a method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound as described herein, including embodiments.

In an aspect is provided a nucleic acid polymerase complex including a nucleic acid polymerase, wherein the nucleic acid polymerase is bound (e.g., non-covalently bound) to a compound described herein, including embodiments.

BRIEF DESCRIPTION OF THE DRAWINGS

FIG. 1B shows the ylide and related resonance structures for different disulfide-containing reversible terminators. The greater number of resonant structures is a reflection of the greater electron delocalization, which lowers the potential energy of the thioaldehyde, thereby stabilizing the molecule. A more stable thioaldehyde allows for faster cleavage. FIG. 1C shows the chemical structure of a non-limiting example of a synthesized modified nucleotide as described herein.

FIG. 2B reports on the average cleavage halftime for RT #1, #2, and #3, where RT #1 is measured at an elevated temperature (65° C.), and RT #2 and RT #3 are measured at a lower temperature (55° C.) with identical concentrations of a cleaving agent, 1 mM THPP. FIG. 2C reports on the average cleavage halftime for RT #2, #3, #45, and #26 under identical cleavage conditions, 0.1 mM THPP at 55° C.

DETAILED DESCRIPTION

I. Definitions

Figure 1A:
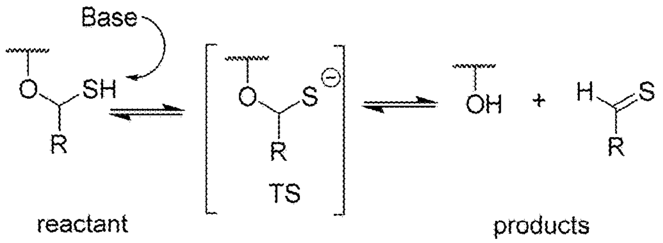
FIGS. 1A-1C. Depicted in FIG. 1A is the proposed fragmentation mechanism, wherein a base removes a hydrogen from the thiol (note, the disulfide bond has already been reduced via a reducing agent). The resulting transition state (TS) is then converted to a hydroxide and a thioaldehyde.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. An alkenyl includes one or more double bonds. An alkynyl includes one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. In embodiments, a bicyclic or multicyclic cycloalkyl ring system refers to multiple rings fused together or multiple spirocyclic rings wherein at least one of the fused or spirocyclic rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together or multiple spirocyclic rings wherein at least one of the fused or spirocyclic rings is a heterocycloalkyl ring and wherein the multiple rings are attached to the parent molecular moiety through any atom contained within a heterocycloalkyl ring of the multiple rings.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a monocyclic cycloalkyl, a monocyclic cycloalkenyl, or a monocyclic heterocyclyl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a 5 or 6 membered monocyclic cycloalkyl, a 5 or 6 membered monocyclic cycloalkenyl, or a 5 or 6 membered monocyclic heterocyclyl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic cycloalkyl, a bicyclic cycloalkenyl, and a bicyclic heterocyclyl; or (ii) two other ring systems independently selected from the group consisting of a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic cycloalkyl, a bicyclic cycloalkenyl, and a bicyclic heterocyclyl; or (ii) two other ring systems independently selected from the group consisting of a monocyclic cycloalkyl, a monocyclic cycloalkenyl, and a monocyclic heterocyclyl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a monocyclic cycloalkyl, a monocyclic cycloalkenyl, or a monocyclic heterocyclyl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic cycloalkyl, a bicyclic cycloalkenyl, and a bicyclic heterocyclyl; or (ii) two ring systems independently selected from the group consisting of a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic cycloalkyl, a bicyclic cycloalkenyl, and a bicyclic heterocyclyl; or (ii) two ring systems independently selected from the group consisting of a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains one heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a monocyclic cycloalkyl, a monocyclic cycloalkenyl, or a monocyclic heterocycle. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a 5 or 6 membered monocyclic cycloalkyl, a 5 or 6 membered monocyclic cycloalkenyl, or a 5 or 6 membered monocyclic heterocyclyl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic cycloalkyl, a bicyclic cycloalkenyl, and a bicyclic heterocyclyl; or (ii) two other ring systems independently selected from the group consisting of a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic cycloalkyl, a bicyclic cycloalkenyl, and a bicyclic heterocyclyl; or (ii) two other ring systems independently selected from the group consisting of a monocyclic cycloalkyl, a monocyclic cycloalkenyl, and a monocyclic heterocyclyl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “  ” denotes the point of attachment of a chemical moiety to the remainder of a molecule or chemical formula. The term “oxo,” as used herein, means an oxygen that is double bonded to a carbon atom.

The term “alkylarylene” as an arylene moiety covalently bonded to an alkylene moiety (also referred to herein as an alkylene linker). In embodiments, the alkylarylene group has the formula:

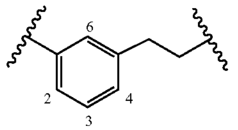

or

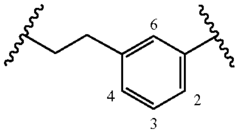

.

An alkylarylene moiety may be substituted (e.g., with a substituent group) on the alkylene moiety or the arylene linker (e.g., at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$, $—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R", —SR', halogen, —SiR'R"R'", —OC(O)R', —C(O)R', $—CO_2R'$, —CONR'R", —OC(O)NR'R", —NR"C(O)R', —NR'—C(O)NR"R'", $—NR"C(O)_2R'$, —NR—C(NR'R"R'")=NR"", —NR—C(NR'R")=NR'", —S(O)R', $—S(O)_2R'$, $—S(O)_2NR'R"$, $—NRSO_2R'$, —NR'NR"R'", —ONR'R", —NR'C(O)NR"NR'"R"", —CN, $—NO_2$, —R', $—N_3$, $—CH(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'— $(C"R"R'")_d$—, where s and d are independently integers from 0 to 3, and X' is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_5$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

A "detectable agent," "detectable compound," "detectable label," or "detectable moiety" is a substance (e.g., element), molecule, or composition detectable by spectroscopic, photochemical, biochemical, immunochemical, chemical, magnetic resonance imaging, or other physical means. For example, detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$ $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), modified oligonucleotides (e.g., moieties described in PCT/US2015/022063, which is incorporated herein by reference), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. In embodiments, a detectable moiety is a moiety (e.g., monovalent form) of a detectable agent.

The terms "fluorophore" or "fluorescent agent" or "fluorescent dye" are used interchangeably and refer to a substance, compound, agent (e.g., a detectable agent), or composition (e.g., compound) that can absorb light at one or more wavelengths and re-emit light at one or more longer wavelengths, relative to the one or more wavelengths of absorbed light. Examples of fluorophores that may be included in the compounds and compositions described herein include fluorescent proteins, xanthene derivatives (e.g., fluorescein, rhodamine, Oregon green, eosin, or Texas red), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5, DRAQ7, or CyTRAK Orange), pyrene derivatives (e.g., cascade blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF Dye™, DRAQ™, CyTRAK™, BODIPY™, Alexa Fluor™, DyLight Fluor™, Atto™, Tracy™ FluoProbes™, Abberior Dyes™, DY™ dyes, MegaStokes Dyes™, Sulfo Cy™, Seta™ dyes, SeTau™ dyes, Square Dyes™, Quasar™ dyes, Cal Fluor™ dyes, SureLight Dyes™, PerCP™ Phycobilisomes™, APC™, APCXL™, RPE™, and/or BPE™. A fluorescent moiety is a radical of a fluorescent agent. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners). In embodiments, the fluorophore is an aromatic (e.g., polyaromatic) moiety having a conjugated π-electron system. In embodiments, the fluorophore is a fluorescent dye moiety, that is, a monovalent fluorophore.

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}Sc$, $^{52}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of detectable agents include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent moiety or fluorescent dye moiety. In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Ppl moiety, evoglow-Bs1 moiety, evoglow-Bs2 moiety, Auramine O moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodaminen Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2', 7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidiumhomodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the dectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(μ-Cl)2Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho 11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kutzing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu203 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-Cl, IRDye® 650 Alkyne, IRDye® 650 Azide, IRDye® 650 Carboxylate, IRDye® 650 DBCO, TRDye® 650 Maleimide, TRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, TRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, TRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, TRDye® QC-1 NHS Ester, Isochrysis galbana-Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoney-Dew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DUPE, Oregon Green 514, Oxazin1, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyltetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor- 770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DUPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride, Tris(4,4-diphenyl-2,2-bipyridine) ruthenium(II) chloride, Tris(4,7-diphenyl-1,10-phenanthroline) ruthenium(II) TMS, TRITC (Weiss), TRITC Dextran (Weiss), Tryptophan, Tyrosine, Vex1, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsienl998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1. In embodiments, $R^4$ is a monovalent moiety of a compound described within this paragraph.

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

Descriptions of compounds (e.g., nucleotide analogues) of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

As used herein, the term "salt" refers to acid or base salts of the compounds described herein. Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, and it is understood an appropriate counter-ion (e.g., chloride ion, fluoride ion, or acetate ion) may also be present, though not explicitly shown. Likewise, for compounds having a negative charge (e.g.,

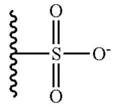), it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g.,

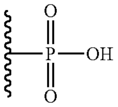 or 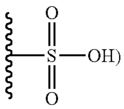)

or an ionic state (e.g.,

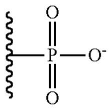 or 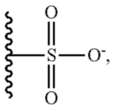, and it is understood these are interchangeable. In embodiments, the counter-ion is represented by the symbol M (e.g., $M^+$ or $M^-$).

The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated, however, that the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "streptavidin" refers to a tetrameric protein (including homologs, isoforms, and functional fragments thereof) capable of binding biotin. The term includes any recombinant or naturally-occurring form of streptavidin variants thereof that maintain streptavidin activity (e.g., within at least 30%, 40%, 50%, 60%, 70%, 80%, 90%, 95%, or 100% activity compared to wildtype streptavidin).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Nucleic acid" refers to nucleotides (e.g., deoxyribonucleotides or ribonucleotides) and polymers thereof in either single-, double- or multiple-stranded form, or complements thereof, or nucleosides (e.g., deoxyribonucleosides or ribonucleosides). In embodiments, "nucleic acid" does not include nucleosides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580*, Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide). The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like. A "nucleic acid moiety" as used herein is a monovalent form of a nucleic acid. In embodiments, the nucleic acid moiety is attached to the 3' or 5' position of a nucleotide or nucleoside.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide (s)" refers to the subset of polynucleotide(s) to be sequenced from within a starting population of polynucleotides.

"Nucleotide," as used herein, refers to a nucleoside-5'-phosphate (e.g., polyphosphate) compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may comprise bases such as adenine (A), cytosine (C), guanine (G), thymine (T), uracil (U), or analogues thereof, and may comprise 1, 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In an embodiment, the nucleotide is a deoxyribonucleotide. In another embodiment, the nucleotide is a ribonucleotide. In embodiments, nucleotides comprise 3 phosphate groups (e.g., a triphosphate group).

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of adenine (A), cytosine (C), guanine (G), thymine (T), or uracil (U) (that is, an analogue or derivative of a nucleotide comprising the base A, G, C, T or U), comprising a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

A "nucleoside" is structurally similar to a nucleotide, but is missing the phosphate moieties. An example of a nucleoside analogue would be one in which the label is linked to the base and there is no phosphate group attached to the sugar molecule. "Nucleoside," as used herein, refers to a glycosyl compound consisting of a nucleobase and a 5-membered ring sugar (e.g., either ribose or deoxyribose). Nucleosides may comprise bases such as adenine (A), cytosine (C), guanine (G), thymine (T), uracil (U), or analogues thereof. Nucleosides may be modified at the base and/or and the sugar. In an embodiment, the nucleoside is a deoxyribonucleoside. In another embodiment, the nucleoside is a ribonucleoside.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52):35095-35101 (1998).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccinimide, -maleimide,

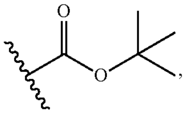

or

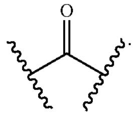

In embodiments, the bioconjugate reactive group may be protected (e.g., with a protecting group). In embodiments, the bioconjugate reactive moiety is

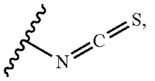

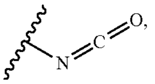

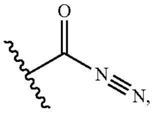

-continued

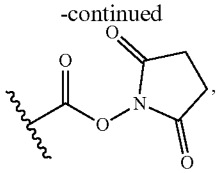

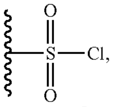

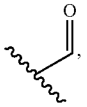

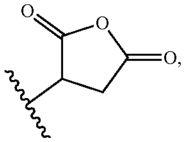

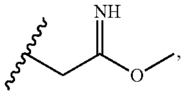

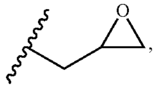

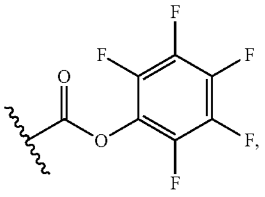

or —$NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —$NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g.,

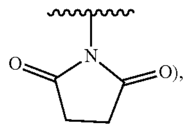

thereby forming a bioconjugate (e.g.,

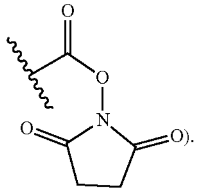

In embodiments, the first bioconjugate reactive group (e.g., —$NH_2$) is covalently attached to the second bioconjugate reactive group (e.g.,

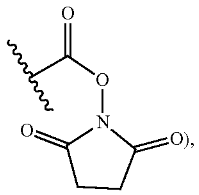

thereby forming a bioconjugate (e.g.,

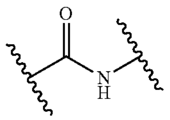

). In embodiments, the first bioconjugate reactive group (e.g., a coupling reagent) is covalently attached to the second bioconjugate reactive group (e.g.,

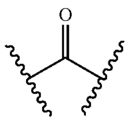

). thereby forming a bioconjugate (e.g.,

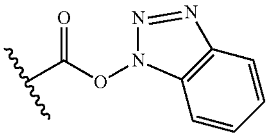

).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The term "monophosphate" is used in accordance with its ordinary meaning in the arts and refers to a moiety having the formula:

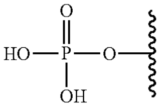

, or ionized forms thereof. The term "polyphosphate" refers to at least two phosphate groups, having the formula:

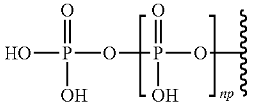

, or ionized forms thereof, wherein np is an integer of 1 or greater. In embodiments, np is an integer from 1 to 5. In embodiments, np is an integer from 1 to 2. In embodiments, np is 2. The term "diphosphate" is used in accordance with its ordinary meaning in the arts and refers to a moiety having the formula:

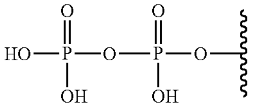

, or ionized forms thereof. The term "triphosphate" is used in accordance with its ordinary meaning in the arts and refers to a moiety having the formula:

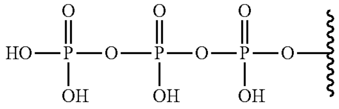

, or ionized forms thereof. In embodiments, a polyphosphate is a diphosphate. In embodiments, a polyphosphate is a triphosphate.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analogue). In embodiments the base is a hybridizing base. In embodiments the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine).

Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, uracil, cytosine, thymine, hypoxanthine, xanthine, theobromine, caffeine, uric acid, or isoguanine, which may be optionally substituted or modified. In embodiments, the base is adenine, guanine, hypoxanthine, xanthine, theobromine, caffeine, uric acid, or isoguanine, which may be optionally substituted or modified.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "anchor moiety" as used herein refers to a chemical moiety capable of interacting (e.g., covalently or non-covalently) with a second, optionally different, chemical moiety (e.g., complementary anchor moiety binder). In embodiments, the anchor moiety is a bioconjugate reactive group capable of interacting (e.g., covalently) with a complementary bioconjugate reactive group (e.g., complementary anchor moiety reactive group, complementary anchor moiety binder). In embodiments, an anchor moiety is a click chemistry reactant moiety. In embodiments, the anchor moiety (an "affinity anchor moiety") is capable of non-covalently interacting with a second chemical moiety (e.g., complementary affinity anchor moiety binder). Non-limiting examples of an anchor moiety include biotin, azide, trans-cyclooctene (TCO) (Blackman, M. L., et al., *J. Am. Chem. Soc.,* 2008, 130, 13518-13519; Debets, M. F., et al. *Org. Biomol. Chem.,* 2013, 11, 6439-6455) and phenyl boric acid (PBA) (Bergseid M., et al., *BioTechniques,* 2000, 29, 1126-1133). In embodiments, an affinity anchor moiety (e.g., biotin moiety) interacts non-covalently with a complementary affinity anchor moiety binder (e.g., streptavidin moiety). In embodiments, an anchor moiety (e.g., azide moiety, trans-cyclooctene (TCO) moiety, phenyl boric acid (PBA) moiety) covalently binds a complementary anchor moiety binder (e.g., dibenzocyclooctyne (DBCO) moiety (Jewett J. C. and Bertozzi C. R. *J. Am. Chem. Soc.,* 2010, 132, 3688-3690), tetrazine (TZ) moiety, salicylhydroxamic acid (SHA) moiety).

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. In embodiments, a cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). In embodiments, a cleavable linker is a self-immolative linker, a trivalent linker, or a linker capable of dendritic amplication of signal, or a self-immolative dendrimer containing linker (e.g., all as described in US 2007/0009980, US 2006/0003383, and US 2009/0047699, which are incorporated by reference in their entirety for any purpose). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase. The term "self-immolative" referring to a linker is used in accordance with its well understood meaning in Chemistry and Biology as used in US 2007/0009980, US 2006/0003383, and US 2009/0047699, which are incorporated by reference in their entirety for any purpose. In embodiments "self-immolative" referring to a linker refers to a linker that is capable of additional cleavage following initial cleavage by an external stimuli. The term dendrimer is used in accordance with its well understood meaning in Chemistry. In embodiments, the term "self-immolative dendrimer" is used as described in US 2007/0009980, US 2006/0003383, and US 2009/0047699, which are incorporated by reference in their entirety for any purpose and in embodiments refers to a dendrimer that is capable of releasing all of its tail units through a self-immolative fragmentation following initial cleavage by an external stimulus.

A "photocleavable linker" (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of a reducing agent (e.g., tris(3-hydroxypropyl)phosphine). In embodiments, the cleavable linker is a dialkylketal linker (Binaulda S., et al., *Chem. Commun.,* 2013, 49, 2082-2102; Shenoi R. A., et al., *J. Am. Chem. Soc.,* 2012, 134, 14945-14957), an azo linker (Rathod, K. M., et al., *Chem. Sci. Tran.,* 2013, 2, 25-28; Leriche G., et al., *Eur. J. Org. Chem.,* 2010, 23, 4360-64), an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent and the agent that cleaves each cleavable linker is different. In embodiments, an orthogonally is a cleavable linker that following cleavage the two separated entities (e.g., fluorescent dye, bioconjugate reactive group) do not further react and form a new orthogonally cleavable linker.

The term "orthogonal detectable label" or "orthogonal detectable moiety" as used herein refer to a detectable label (e.g., fluorescent dye or detectable dye) that is capable of being detected and identified (e.g., by use of a detection means (e.g., emission wavelength, physical characteristic measurement)) in a mixture or a panel (collection of separate samples) of two or more different detectable labels. For example, two different detectable labels that are fluorescent dyes are both orthogonal detectable labels when a panel of the two different fluorescent dyes is subjected to a wavelength of light that is absorbed by one fluorescent dye but not the other and results in emission of light from the fluorescent dye that absorbed the light but not the other fluorescent dye. Orthogonal detectable labels may be separately identified by different absorbance or emission intensities of the orthogonal detectable labels compared to each other and not only be the absolute presence of absence of a signal. An example of a set of four orthogonal detectable labels is the set of Rox-Labeled Tetrazine, Alexa488-Labeled SHA, Cy5-Labeled Streptavidin, and R6G-Labeled Dibenzocyclooctyne.

The term "polymerase-compatible cleavable moiety" or "reversible terminator" as used herein refers to a cleavable moiety which does not interfere with a function of a polymerase (e.g., DNA polymerase, modified DNA polymerase, in incorporating the nucleotide, to which the polymerase-compatible cleavable moiety is attached, to the 3' end of the newly formed nucleotide strand). Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol linking moiety. In embodiments, the polymerase-compatible cleavable moiety is $-NH_2$, $-CN$, $-CH_3$, $C_2$-$C_6$ allyl (e.g., $-CH_2-CH=CH_2$), methoxyalkyl (e.g., $-CH_2-O-CH_3$), or $-CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with a function of a polymerase (e.g., DNA polymerase, modified DNA polymerase).

The term "allyl" as described herein refers to an unsubstituted methylene attached to a vinyl group (i.e., $-CH=CH_2$), having the formula

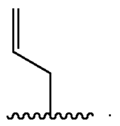 [SMILES: *CC=C]

An "allyl linker" refers to a divalent unsubstituted methylene attached to a vinyl group, having the formula

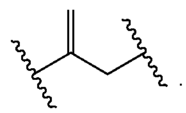 [SMILES: *CC(*)=C]

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer.

The term "polymerase-compatible moiety" as used herein refers a moiety which does not interfere with the function of a polymerase (e.g., DNA polymerase, modified DNA polymerase) in incorporating the nucleotide to which the polymerase-compatible moiety is attached to the 3' end of the newly formed nucleotide strand. The polymerase-compatible moiety does, however, interfere with the polymerase function by preventing the addition of another nucleotide to the 3' oxygen of the nucleotide to which the polymerase-compatible moiety is attached. Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments the polymerase-compatible moiety does not decrease the function of a polymerase relative to the absence of the polymerase-compatible moiety. In embodiments, the polymerase-compatible moiety does not negatively affect DNA polymerase recognition. In embodiments, the polymerase-compatible moiety does not negatively affect (e.g., limit) the read length of the DNA polymerase. Additional examples of a polymerase-compatible moiety may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible moiety includes hydrogen, $-N_3$, $-CN$, or halogen. In embodiments, a polymerase-compatible moiety is a moiety on a nucleotide, nucleobase, nucleoside, or nucleic acid that does not interfere with the function of a polymerase (e.g., DNA polymerase, modified DNA polymerase).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease.

Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or 7-phosphate labeled nucleotides (e.g., Therminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. Chem Bio Chem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9° N polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase.

The phrase "stringent hybridization conditions" refers to conditions under which a primer will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Solid substrate" shall mean any suitable medium present in the solid phase to which a nucleic acid or an agent may be affixed. Non-limiting examples include chips, beads and columns. The solid substrate can be non-porous or porous. Exemplary solid substrates include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides, etc.), nylon, ceramics, resins, Zeonor, silica or silica-based materials including silicon and modified silicon, carbon, metals, inorganic glasses, optical fiber bundles, and polymers. In embodiments, the solid substrate for have at least one surface located within a flow cell. The solid substrate, or regions thereof, can be substantially flat. The solid substrate can have surface features such as wells, pits, channels, ridges, raised regions, pegs, posts or the like. The term solid substrate is encompassing of a substrate (e.g., a flow cell) having a surface comprising a polymer coating covalently attached thereto. In embodiments, the solid substrate is a flow cell. The term "flowcell" or "flow cell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., *Current Protocols in Molecular Biology*, ed. Ausubel, et al., supra.

The term "thio-trigger moiety" refers to a substituent having the formula

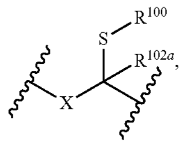

wherein X is —O—, —NH—, or —S—; $R^{100}$ is —$SO_3H$, —$SR^{102}$ or —CN; and $R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the thio-trigger moiety has the formula:

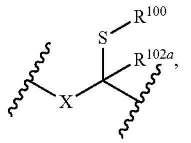

wherein X is —O—, —NH—, or —S—; $R^{100}$ is —$SR^{102}$ or —CN; and $R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the thio-trigger moiety has the formula:

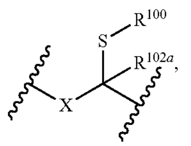

wherein X is —O—, and $R^{100}$ and $R^{102a}$ are as described herein. In embodiments, the thio-trigger moiety has the formula:

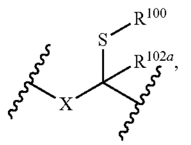

wherein X is —NH—, and $R^{100}$ and $R^{102a}$ are as described herein.

A "thio-trigger containing linker" refers to a covalent linker that includes a thio-trigger moiety. When a reducing agent (e.g., dithiothreitol, THPP, or TCEP) contacts a thio-trigger containing linker, the heteroatom represented by the symbol X (e.g., oxygen) of the thio-trigger moiety is reduced, and breaks the linker apart, according to the example mechanism:

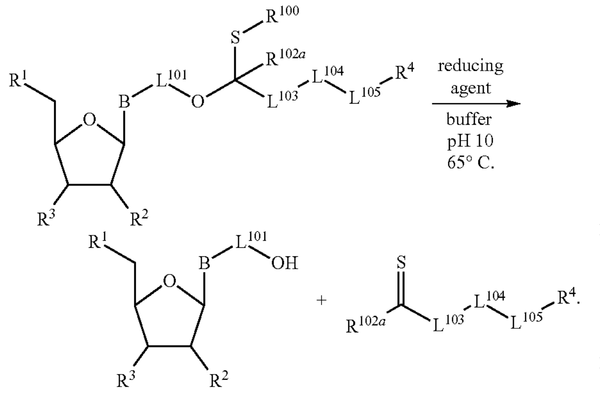

$R^2$, $R^3$, $R^4$, $R^{100}$, $R^{102a}$, $L^{101}$, $L^{103}$, $L^{104}$, and $L^{105}$ are as described herein, including in embodiments.

Where a range of values is provided herein, it is understood that each intervening value, to the tenth of the unit (if appropriate) of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various embodiments of the invention are shown and described herein, it will be understood by those skilled in the art that such embodiments are provided by way of example only. Numerous variations, changes, and substitutes may occur to those skilled in the art without departing from the invention. It should be understood that various alternatives to the embodiments of the invention described herein may be employed.

As used herein, and unless stated otherwise, each of the following terms shall be used in accordance with their plain and ordinary meaning, for example: A indicates the presence of Adenine; C indicates the presence of Cytosine; DNA is Deoxyribonucleic acid; G indicates the presence of Guanine; RNA is Ribonucleic acid; T indicates the presence of Thymine; and U indicates the presence of Uracil. In embodiments, each of the following terms shall have the definition set forth below A—Adenine; C—Cytosine; DNA—Deoxyribonucleic acid; G—Guanine; RNA—Ribonucleic acid; T—Thymine; and U—Uracil.

All embodiments of U.S. Pat. No. 6,664,079 (the contents of which are hereby incorporated by reference) with regard to sequencing a nucleic acid are specifically envisioned here.

"Alkyldithiomethyl" refers to a compound or moiety or portion thereof, comprising a dithio group, where one of the sulfurs is directly connected to a methyl group (i.e., a methylene linking group) and the other sulfur is directly connected to an alkyl group. An example is the structure

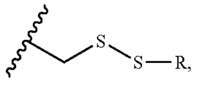

wherein R is an alkyl group (e.g., methyl or ethyl) and the wavy line (e.g., ) represents a point of connection to another portion of the compound. In some cases, the alkyldithiomethyl is methyldithiomethyl, ethyldithiomethyl, propyldithiomethyl, isopropyldithiomethyl, butyldithiomethyl, t-butyldithiomethyl, or phenyldithiomethyl.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts). In embodiments, the protecting group is a nucleoside protecting group. In embodiments, the protecting group is a 5'-O-nucleoside protecting group.

The term "5'-nucleoside protecting group" as used herein refers to a moiety covalently bound to a heteroatom (e.g., O) on the 5' position of sugar to prevent reactivity of the heteroatom during one or more chemical reactions performed prior to removal of the protecting group. Typically a protecting group is bound to a heteroatom (e.g., O) during a part of a multipart synthesis wherein it is not desired to have the heteroatom react (e.g., during a chemical reduction) with the reagent. Following protection the protecting group may be removed by any appropriate means (e.g., by modulating the pH). Non-limiting examples of 5'-O-nucleoside protecting groups include silyl ethers (e.g., tert-butyl-diphenylsilyl (TBDPS), or primary and secondary tert-butyldimethylsilyl (TBDMS)) or trityl (e.g., 4,4'-dimethoxytrityl (DMT)). In embodiments, $R^1$ includes a protecting group found in *Green's Protective Groups in Organic Chemistry*, Wiley, Fourth edition, 2007, Peter G. M. Wuts and Theodora W. Greene, and *Current Protocols in Nucleic Acid Chemistry* (2000) 2.3.1-2.3.34, John Wiley & Sons, Inc. which is incorporated herein by reference in its entirety for all purposes.

The term "deprotect" or "deprotecting" is used in accordance with its ordinary meaning in organic chemistry and refers a process or chemical reaction that remove a protecting group, which is covalently bound to a heteroatom, heterocycloalkyl, or heteroaryl, to recover reactivity of the heteroatom, heterocycloalkyl, or heteroaryl for subsequent chemical reactions or metabolic pathway. The "deprotecting agent" or "deprotecting reagent" is used in accordance with its ordinary meaning in organic chemistry and refers to a molecule used for deprotecting. In embodiments, the deprotecting agent is an acid or a base. In embodiments, the deprotecting agent includes alpha-hydroxy amines (amino alcohol), primary amines and secondary amines. In embodiments, the deprotecting agent is ammonium salt (e.g., ammonium hydroxide, ammonium hydrogen sulfate, ceric ammonium nitrate, or ammonium fluoride). In embodiments, the deprotecting agent is concentrated ammonium hydroxide. The terms "5'-nucleoside protecting group" and "5'-O-nucleoside protecting group" are used interchangeably herein.

The term "reaction vessel" is used in accordance with its ordinary meaning in chemistry or chemical engineering, and refers to a container having an inner volume in which a reaction takes place. In embodiments, the reaction vessel may be designed to provide suitable reaction conditions such as reaction volume, reaction temperature or pressure, and stirring or agitation, which may be adjusted to ensure that the reaction proceeds with a desired, sufficient or highest efficiency for producing a product from the chemical reaction. In embodiments, the reaction vessel is a container for liquid, gas or solid. In embodiments, the reaction vessel may include an inlet, an outlet, a reservoir and the like. In embodiments, the reaction vessel is connected to a pump (e.g., vacuum pump), a controller (e.g., CPU), or a monitoring device (e.g., UV detector or spectrophotometer). In embodiments, the reaction vessel is a flow cell. In embodiments, the reaction vessel is within a sequencing device.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $—CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein, the terms "sequencing", "sequence determination", "determining a nucleotide sequence", and the like include determination of a partial or complete sequence information, including the identification, ordering, or locations of the nucleotides that comprise the polynucleotide being sequenced, and inclusive of the physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode sequence and a template nucleotide sequence. In embodiments, a sequencing read includes reading a template nucleotide sequence. In embodiments, a sequencing read includes reading a barcode and not a template nucleotide sequence.

As used herein, the term "barcode sequence" (which may be referred to as a "tag," a "molecular barcode," a "molecular identifier," an "identifier sequence," or a "unique molecular identifier (UMI)") refers to any material (e.g., a nucleotide sequence, a nucleic acid molecule feature) that is capable of distinguishing an individual molecule in a large heterogeneous population of molecules. Generally, a barcode sequence is unique in a pool of barcode sequences that differ from one another in sequence, or is uniquely associated with a particular sample polynucleotide in a pool of sample polynucleotides. In embodiments, barcode sequences are about or at least about 5, 6, 7, 8, 9, 10, 15, 20, 25, 30, 40, 50, 75 or more nucleotides in length. In embodiments, barcode sequences are shorter than 20, 15, 10, 9, 8, 7, 6, or 5 nucleotides in length. In embodiments, barcode sequences are about 10 to about 50 nucleotides in length, such as about 15 to about 40 or about 20 to about 30 nucleotides in length. In a pool of different barcode sequences, barcode sequences may have the same or different lengths. In general, barcode sequences are of sufficient length and include sequences that are sufficiently different to allow the identification of sequencing reads that originate from the same sample polynucleotide molecule. In embodiments, each barcode sequence in a plurality of barcode sequences differs from every other barcode sequence in the plurality by at least three nucleotide positions, such as at least 3, 4, 5, 6, 7, 8, 9, 10, or more nucleotide positions. In some embodiments, substantially degenerate barcode sequences may be known as random. In some embodiments, a barcode sequence may include a nucleic acid sequence from within a pool of known sequences. In some embodiments, the barcode sequences may be pre-defined.

II. Compounds, Complexes, and Kits

In an aspect is provided a compound having the formula:

(II)

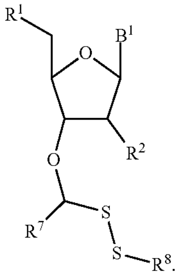

$B^1$ is a nucleobase. $R^7$ is substituted or unsubstituted cycloalkyl, substituted or unsubstituted heterocycloalkyl, substituted or unsubstituted aryl, or substituted or unsubstituted heteroaryl. $R^8$ is substituted or unsubstituted alkyl. $R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. $R^2$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety.

In an aspect is provided a compound having the formula.

(I)

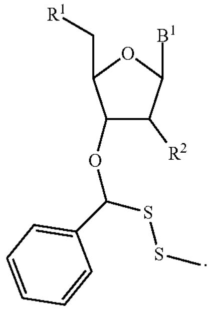

$B^1$ is a nucleobase. $R^1$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. $R^2$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety.

In an aspect is provided a compound having the formula:

(III)

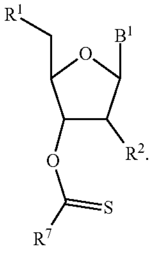

$B^1$ is a nucleobase. $R^7$ is substituted or unsubstituted cycloalkyl, substituted or unsubstituted heterocycloalkyl, substituted or unsubstituted aryl, or substituted or unsubstituted heteroaryl. $R^1$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. $R^2$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety.

In embodiments, the compounds of Formula I, Formula II, and Formula III are referred to as nucleotides. In embodiments, the compounds of Formula I, Formula II, and Formula III include a nucleotide portion and a 3'-O-reversible terminator. For example, the nucleotide portion is

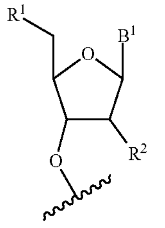

and the 3'-O-reversible terminator portion is

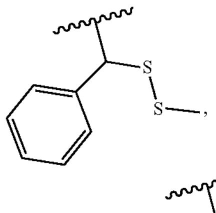

,

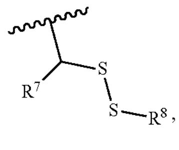

, and

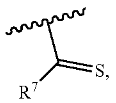

, for Formula I, II, and III respectively.

In embodiments, $R^1$ is $-OH$, a 5'-O-nucleoside protecting group, monophosphate moiety, polyphosphate moiety, or nucleic acid moiety. In embodiments, $R^1$ is a triphosphate moiety. In embodiments, $R^1$ is $-OH$. In embodiments, $R^1$ is a 5'-O-nucleoside protecting group. In embodiments, $R^1$ is a nucleic acid moiety. In embodiments, $R^1$ is independently a monophosphate moiety or a derivative thereof (e.g., including a phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

In embodiments, $R^1$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety. In embodiments, $R^1$ is independently a monophosphate moiety including a phosphodiester derivative. In embodiments, $R^1$ is independently a polyphosphate moiety including a phosphodiester derivative. In embodiments, $R^1$ is independently a nucleic acid moiety including a phosphodiester derivative. In embodiments, $R^1$ is independently a phosphoramidate moiety. In embodiments, $R^1$ is independently a polyphosphate moiety including a phosphoramidate. In embodiments, $R^1$ is independently a nucleic acid moiety including a phosphoramidate. In embodiments, $R^1$ is independently a phosphorothioate moiety. In embodiments, $R^1$ is independently a polyphosphate moiety including a phosphorothioate. In embodiments, $R^1$ is independently a nucleic acid moiety including a phosphorothioate. In embodiments, $R^1$ is independently a phosphorodithioate moiety. In embodiments, $R^1$ is independently a polyphosphate moiety including a phosphorodithioate. In embodiments, $R^1$ is independently a nucleic acid moiety including a phosphorodithioate. In embodiments, $R^1$ is independently an O-methylphosphoroamidite moiety. In embodiments, $R^1$ is independently a polyphosphate moiety including an O-methylphosphoroamidite. In embodiments, $R^1$ is independently a nucleic acid moiety including an O-methylphosphoroamidite. In embodiments, $R^1$ is independently a nucleic acid moiety including a nucleotide analog. In embodiments, $R^1$ is independently a nucleic acid moiety including a plurality of optionally different nucleotide analogs.

In embodiments, $R^1$ is independently a monophosphate moiety. In embodiments, $R^1$ is independently a polyphosphate moiety. In embodiments, $R^1$ is independently a nucleic acid moiety. In embodiments, $R^1$ has the formula:

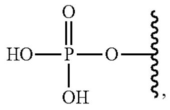

, or ionized forms thereof. In embodiments, $R^1$ has the formula

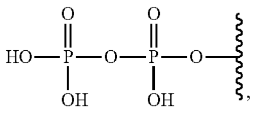 [SMILES: *OP(=O)(O)OP(=O)(O)O]

or ionized forms thereof. In embodiments, $R^1$ has the formula

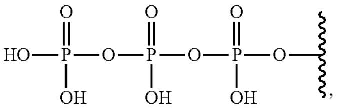 [SMILES: *OP(=O)(O)OP(=O)(O)OP(=O)(O)O]

or ionized forms thereof. In embodiments, $R^1$ has the formula:

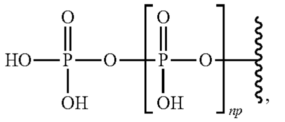

or ionized forms thereof, wherein np is an integer of 1 or greater. In embodiments, np is an integer from 1 to 5. In embodiments, np is 1. In embodiments, np is 2.

In embodiments, $R^1$ is independently a 5'-O-nucleoside protecting group, for example a 5'-O-nucleoside protecting group known in the art include those described in Seliger H. Curr. Protoc Nucleic Acid Chem. 2001; Chapter 2 or K. Seio et al, Nucleic Acids Research Supplement 2, 27-28 (2002); both of which are incorporated by reference for all purposes. Non-limiting examples of 5'-O-nucleoside protecting groups include 2,2,2-Trichloroethyl carbonate (Troc), 2-Methoxyethoxymethyl ether (MEM), 2-Naphthylmethyl ether (Nap), 4-Methoxybenzyl ether (PMB), Acetate (Ac), Benzoate (Bz), Benzyl ether (Bn), Benzyloxymethyl acetal (BOM), Ethoxyethyl acetal (EE), Methoxymethyl acetal (MOM), Methoxypropyl acetal (MOP), Methyl ether, Tetrahydropyranyl acetal (THP), Triethylsilyl ether (TES), Triisopropylsilyl ether (TIPS), Trimethylsilyl ether (TMS), tert-Butyldimethylsilyl ether (TBS, TBDMS), or tert-Butyldiphenylsilyl ether (TBDPS). In embodiments, $R^1$ is

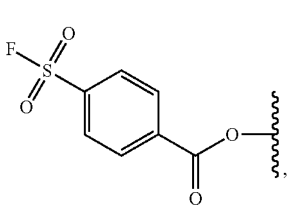

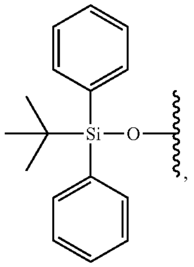

-continued

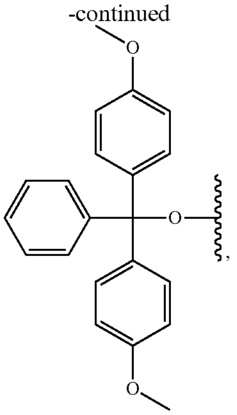

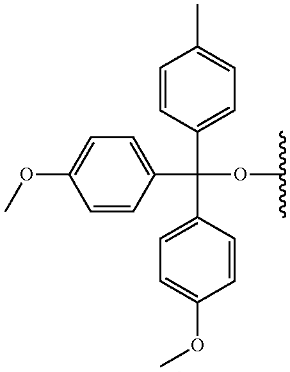

or

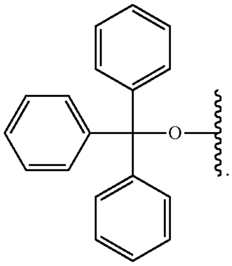

In embodiments, $R^1$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_2NH_2$, $-NHNH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered), or a 5'-O-nucleoside protecting group; or $R^1$ is a monophosphate moiety, polyphosphate moiety, or nucleic acid moiety. In embodiments, $R^1$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_2NH_2$, $—NHNH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10 membered, 5 to 9 membered, or 5 to 6 membered). In embodiments, $R^1$ is a 5'-O-nucleoside protecting group. In embodiments, $R^1$ is a monophosphate moiety, polyphosphate moiety, or nucleic acid moiety. In embodiments, $R^1$ is a monophosphate moiety. In embodiments, $R^1$ is a polyphosphate moiety. In embodiments, $R^1$ is a nucleic acid moiety. In embodiments, $R^1$ is hydrogen. In embodiments, $R^1$ is a triphosphate moiety. In embodiments, $R^1$ is —OH.

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group. In embodiments, when $R^1$ is substituted, it is substituted with 1 to 10 substituent groups. In embodiments, when $R^1$ is substituted, it is substituted with 1 to 10 size-limited substituent groups. In embodiments, when $R^1$ is substituted, it is substituted with 1 to 10 lower substituent groups. In embodiments, when $R^1$ is substituted, it is substituted with 1 to 5 substituent groups. In embodiments, when $R^1$ is substituted, it is substituted with 1 to 5 size-limited substituent groups. In embodiments, when $R^1$ is substituted, it is substituted with 1 to 5 lower substituent groups. In embodiments, when $R^1$ is substituted, it is substituted with a substituent group. In embodiments, when $R^1$ is substituted, it is substituted with a size-limited substituent group. In embodiments, when $R^1$ is substituted, it is substituted with a lower substituent group.

In embodiments, $R^2$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety. In embodiments, $R^2$ is hydrogen. In embodiments, $R^2$ is —OH. In embodiments, $R^2$ is an —O-polymerase-compatible cleavable moiety, wherein the —O— is attached to the 2' position of the ribose sugar of a nucleotide and a polymerase-compatible cleavable moiety is as described herein.

In embodiments, $R^2$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2A}$-substituted or unsubstituted heteroalkyl (e.g., 2 to 20, 8 to 20, 2 to 10, 2 to 8, 2 to 6, or 2 to 4 membered), $R^{2A}$-substituted or unsubstituted cycloalkyl (e.g., $C_3$-$C_8$, $C_3$-$C_6$, or $C_5$-$C_6$), $R^{2A}$-substituted or unsubstituted heterocycloalkyl (e.g., 3 to 8, 3 to 6, or 5 to 6 membered), $R^{2A}$-substituted or unsubstituted aryl (e.g., $C_6$-$C_{10}$, $C_{10}$, or phenyl), or $R^{2A}$-substituted or unsubstituted heteroaryl (e.g., 5 to 10, 5 to 9, or 5 to 6 membered). In embodiments, $R^2$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered); or a polymerase-compatible cleavable moiety.

$R^{2A}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered), or a polymerase-compatible cleavable moiety. In embodiments, $R^{2A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20, 8 to 20, 2 to 10, 2 to 8, 2 to 6, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8, 3 to 6, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10, 5 to 9, or 5 to 6 membered). In embodiments, $R^{2A}$ is independently a polymerase-compatible cleavable moiety.

$R^{2B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, $R^{2C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2C}$-substituted or unsubstituted heteroalkyl (e.g., 2 to 20, 8 to 20, 2 to 10, 2 to 8, 2 to 6, or 2 to 4 membered), $R^{2C}$-substituted or unsubstituted cycloalkyl (e.g., $C_3$-$C_8$, $C_3$-$C_6$, or $C_5$-$C_6$), $R^{2C}$-substituted or unsubstituted heterocycloalkyl (e.g., 3 to 8, 3 to 6, or 5 to 6 membered), $R^{2C}$-substituted or unsubstituted aryl (e.g., $C_6$-$C_{10}$, $C_{10}$, or phenyl), or $R^{2C}$-substituted or unsubstituted heteroaryl (e.g., 5 to 10, 5 to 9, or 5 to 6 membered).

$R^{2C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$NH_3^+$, —$SO_3^-$, —$OPO_3H^-$, —SCN, —$ONO_2$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^2$ is hydrogen. In embodiments, $R^2$ is —OH. In embodiments, $R^2$ is —O-polymerase-compatible cleavable moiety.

In embodiments, $R^2$ is a polymerase-compatible cleavable moiety or an —O-polymerase-compatible cleavable moiety; and the polymerase-compatible cleavable moiety is

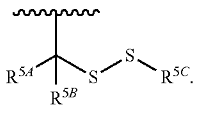

$R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8, 2 to 6, 4 to 6, 2 to 3, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8, 3 to 6, 4 to 6, 4 to 5, or 5 to 6 membered), substituted or unsubstituted aryl (e.g., $C_6$-$C_{10}$ or phenyl), or substituted or unsubstituted heteroaryl (e.g., 5 to 10, 5 to 9, or 5 to 6 membered). $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8, 2 to 6, 4 to 6, 2 to 3, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8, 3 to 6, 4 to 6, 4 to 5, or 5 to 6 membered), substituted or unsubstituted aryl (e.g., $C_6$-$C_{10}$ or phenyl), or substituted or unsubstituted heteroaryl (e.g., 5 to 10, 5 to 9, or 5 to 6 membered). In embodiments, $R^{5A}$ and $R^{5B}$ are combined to form an oxo. $R^{5C}$ is hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8, 2 to 6, 4 to 6, 2 to 3, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8, 3 to 6, 4 to 6, 4 to 5, or 5 to 6 membered), substituted or unsubstituted aryl (e.g., $C_6$-$C_{10}$ or phenyl), or substituted or unsubstituted heteroaryl (e.g., 5 to 10, 5 to 9, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, and $X^{5C}$ are independently —F, —Cl, —Br, or —I.

In embodiments, the polymerase-compatible cleavable moiety is

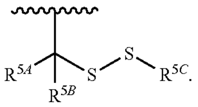

$R^{5A}$, $R^{5B}$ and $R^{5C}$ are as described herein, including in embodiments. In embodiments, $R^2$ is an —O-polymerase-compatible cleavable moiety; and the polymerase-compatible cleavable moiety is

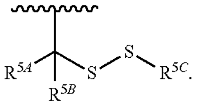

In embodiments, $R^2$ is a polymerase-compatible cleavable moiety or an —O-polymerase-compatible cleavable moiety; and the polymerase-compatible cleavable moiety is

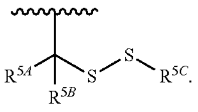

In embodiments, $R^{5A}$ is independently hydrogen, halogen, $—CX^{5A}_3$, $—CHX^{5A}_2$, $—CH_2X^{5A}$, $—OCX^{5A}_3$, $—OCH_2X^{5A}$, $—OCHX^{5A}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5D}$-substituted or unsubstituted alkyl, $R^{5D}$-substituted or unsubstituted heteroalkyl, $R^{5D}$-substituted or unsubstituted cycloalkyl, $R^{5D}$-substituted or unsubstituted heterocycloalkyl, $R^{5D}$-substituted or unsubstituted aryl, or $R^{5D}$-substituted or unsubstituted heteroaryl. $R^{5D}$ is independently halogen, oxo, $—CX^{5D}_3$, $—CHX^{5D}_2$, $—CH_2X^{5D}$, $—OCX^{5D}_3$, $—OCH_2X^{5D}$, $—OCHX^{5D}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5E}$-substituted or unsubstituted alkyl, $R^{5E}$-substituted or unsubstituted heteroalkyl, $R^{5E}$-substituted or unsubstituted cycloalkyl, $R^{5E}$-substituted or unsubstituted heterocycloalkyl, $R^{5E}$-substituted or unsubstituted aryl, or $R^{5E}$-substituted or unsubstituted heteroaryl. $R^{5E}$ is independently halogen, oxo, $—CX^{5E}_3$, $—CHX^{5E}_2$, $—CH_2X^{5E}$, $—OCX^{5E}_3$, $—OCH_2X^{5E}$, $—OCHX^{5E}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5B}$ is independently hydrogen, halogen, $—CX^{5B}_3$, $—CHX^{5B}_2$, $—CH_2X^{5B}$, $—OCX^{5B}_3$, $—OCH_2X^{5B}$, $—OCHX^{5B}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3$—, $—OPO_3H^-$, —SCN, $—ONO_2$, $R^{5F}$-substituted or unsubstituted alkyl, $R^{5F}$-substituted or unsubstituted heteroalkyl, $R^{5F}$-substituted or unsubstituted cycloalkyl, $R^{5F}$-substituted or unsubstituted heterocycloalkyl, $R^{5F}$-substituted or unsubstituted aryl, or $R^{5F}$-substituted or unsubstituted heteroaryl. $R^{5F}$ is independently halogen, oxo, $—CX^{5F}_3$, $—CHX^{5F}_2$, $—CH_2X^{5F}$, $—OCX^{5F}_3$, $—OCH_2X^{5F}$, $—OCHX^{5F}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H$, —SCN, $—ONO_2$, $R^{5G}$-substituted or unsubstituted alkyl, $R^{5G}$-substituted or unsubstituted heteroalkyl, $R^{5G}$-substituted or unsubstituted cycloalkyl, $R^{5G}$-substituted or unsubstituted heterocycloalkyl, $R^{5G}$-substituted or unsubstituted aryl, or $R^{5G}$-substituted or unsubstituted heteroaryl. $R^{5G}$ is independently halogen, oxo, $—CX^{5G}_3$, $—CHX^{5G}_2$, $—CH_2X^{5G}$, $—OCX^{5G}_3$, $—OCH_2X^{5G}$, $—OCHX^{5G}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5A}$ and $R^{5B}$ are combined to form an oxo. In embodiments, $R^{5C}$ is independently hydrogen, halogen, $—CX^{5C}_3$, $—CHX^{5C}_2$, $—CH_2X^{5C}$, $—OCX^{5C}_3$, $—OCH_2X^{5C}$, $—OCHX^{5C}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, $R^{5H}$-substituted or unsubstituted alkyl, $R^{5H}$-substituted or unsubstituted heteroalkyl, $R^{5H}$-substituted or unsubstituted cycloalkyl, $R^{5H}$-substituted or unsubstituted heterocycloalkyl, $R^{5H}$-substituted or unsubstituted aryl, or $R^{5H}$-substituted or unsubstituted heteroaryl. $R^{5H}$ is independently halogen, oxo, $—CX^{5H}_3$, $—CHX^{5H}_2$, $—CH_2X^{5H}$, $—OCX^{5H}_3$, $—OCH_2X^{5H}$, $—OCHX^{5H}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3$—, $—OPO_3H$, —SCN, $—ONO_2$, $R^{5I}$-substituted or unsubstituted alkyl, $R^{5I}$-substituted or unsubstituted heteroalkyl, $R^{5I}$-substituted or unsubstituted cycloalkyl, $R^{5I}$-substituted or unsubstituted heterocycloalkyl, $R^{5I}$-substituted or unsubstituted aryl, or $R^{5I}$-substituted or unsubstituted heteroaryl. $R^{5I}$ is independently halogen, oxo, $—CX^{5I}_3$, $—CHX^{5I}_2$, $—CH_2X^{5I}$, $—OCX^{5I}_3$, $—OCH_2X^{5I}$, $—OCHX^{5I}_2$, —CN, —OH, —SH, $—NH_2$, —COOH, $—CONH_2$, $—NO_2$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $—SF_5$, $—NH_3^+$, $—SO_3^-$, $—OPO_3H^-$, —SCN, $—ONO_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^2$ is a polymerase-compatible cleavable moiety or an —O-polymerase-compatible cleavable moiety; and the polymerase-compatible cleavable moiety is

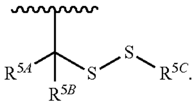

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3$—, —$OPO_3H^-$, —SCN, —$ONO_2$, $R^{5D}$-substituted or unsubstituted alkyl (e.g., $C_1$-$C_8$, $C_1$-$C_6$, $C_1$-$C_4$, or $C_1$—$C_2$), $R^{5D}$-substituted or unsubstituted heteroalkyl (e.g., 2 to 8, 2 to 6, 4 to 6, 2 to 3, or 4 to 5 membered), $R^{5D}$-substituted or unsubstituted cycloalkyl (e.g., $C_3$-$C_8$, $C_3$-$C_6$, $C_4$-$C_6$, or $C_5$-$C_6$), $R^{5D}$-substituted or unsubstituted heterocycloalkyl (e.g., 3 to 8, 3 to 6, 4 to 6, 4 to 5, or 5 to 6 membered), $R^{5D}$-substituted or unsubstituted aryl (e.g., $C_6$-$C_{10}$ or phenyl), or $R^{5D}$-substituted or unsubstituted heteroaryl (e.g., 5 to 10, 5 to 9, or 5 to 6 membered). In embodiments, $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5E}$-substituted or unsubstituted alkyl (e.g., $C_1$-$C_8$, $C_1$-$C_6$, $C_1$-$C_4$, or $C_1$-$C_2$), $R^{5E}$-substituted or unsubstituted heteroalkyl (e.g., 2 to 8, 2 to 6, 4 to 6, 2 to 3, or 4 to 5 membered), $R^{5E}$-substituted or unsubstituted cycloalkyl (e.g., $C_3$-$C_8$, $C_3$-$C_6$, $C_4$-$C_6$, or $C_5$-$C_6$), $R^{5E}$-substituted or unsubstituted heterocycloalkyl (e.g., 3 to 8, 3 to 6, 4 to 6, 4 to 5, or 5 to 6 membered), $R^{5E}$-substituted or unsubstituted aryl (e.g., $C_6$-$C_{10}$ or phenyl), or $R^{5E}$-substituted or unsubstituted heteroaryl (e.g., 5 to 10, 5 to 9, or 5 to 6 membered). In embodiments, $R^{5E}$ is independently halogen, oxo, —$CX^{5E}_3$, —$CHX^{5E}_2$, —$CH_2X^{5E}$, —$OCX^{5E}_3$, —$OCH_2X^{5E}$, —$OCHX^{5E}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered). In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5F}$-substituted or unsubstituted alkyl (e.g., $C_1$-$C_8$, $C_1$-$C_6$, $C_1$-$C_4$, or $C_1$-$C_2$), $R^{5F}$-substituted or unsubstituted heteroalkyl (e.g., 2 to 8, 2 to 6, 4 to 6, 2 to 3, or 4 to 5 membered), $R^{5F}$-substituted or unsubstituted cycloalkyl (e.g., $C_3$-$C_8$, $C_3$-$C_6$, $C_4$-$C_6$, or $C_5$-$C_6$), $R^{5F}$-substituted or unsubstituted heterocycloalkyl (e.g., 3 to 8, 3 to 6, 4 to 6, 4 to 5, or 5 to 6 membered), $R^{5F}$-substituted or unsubstituted aryl (e.g., $C_6$-$C_{10}$ or phenyl), or $R^{5F}$-substituted or unsubstituted heteroaryl (e.g., 5 to 10, 5 to 9, or 5 to 6 membered). In embodiments, R5F is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5G}$-substituted or unsubstituted alkyl (e.g., $C_1$-$C_8$, $C_1$-$C_6$, $C_1$-$C_4$, or $C_1$-$C_2$), $R^{5G}$-substituted or unsubstituted heteroalkyl (e.g., 2 to 8, 2 to 6, 4 to 6, 2 to 3, or 4 to 5 membered), $R^{5G}$-substituted or unsubstituted cycloalkyl (e.g., $C_3$-$C_8$, $C_3$-$C_6$, $C_4$-$C_6$, or $C_5$-$C_6$), $R^{5G}$-substituted or unsubstituted heterocycloalkyl (e.g., 3 to 8, 3 to 6, 4 to 6, 4 to 5, or 5 to 6 membered), $R^{5G}$-substituted or unsubstituted aryl (e.g., $C_6$-$C_{10}$ or phenyl), or $R^{5G}$-substituted or unsubstituted heteroaryl (e.g., 5 to 10, 5 to 9, or 5 to 6 membered). In embodiments, $R^{5G}$ is independently halogen, oxo, —$CX^{5G}_3$, —$CHX^{5G}_2$, —$CH_2X^{5G}$, —$OCX^{5G}_3$, —$OCH_2X^{5G}$, —$OCHX^{5G}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered). In embodiments, $R^{5A}$ and $R^{5B}$ are combined to form an oxo. In embodiments, $R^{5C}$ is independently hydrogen, halogen, —$CX^{5C}_3$, —$CHX^{5C}_2$, —$CH_2X^{5C}$, —$OCX^{5C}_3$, —$OCH_2X^{5C}$, —$OCHX^{5C}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3$—, —$OPO_3H$, —SCN, —$ONO_2$, $R^{5H}$-substituted or unsubstituted alkyl (e.g., $C_1$-$C_8$, $C_1$-$C_6$, $C_1$-$C_4$, or $C_1$-$C_2$), $R^{5H}$-substituted or unsubstituted heteroalkyl (e.g., 2 to 8, 2 to 6, 4 to 6, 2 to 3, or 4 to 5 membered), $R^{5H}$-substituted or unsubstituted cycloalkyl (e.g., $C_3$-$C_8$, $C_3$-$C_6$, $C_4$-$C_6$, or $C_5$-$C_6$), $R^{5H}$-substituted or unsubstituted heterocycloalkyl (e.g., 3 to 8, 3 to 6, 4 to 6, 4 to 5, or 5 to 6 membered), $R^{5H}$-substituted or unsubstituted aryl (e.g., $C_6$-$C_{10}$ or phenyl), or $R^{5H}$-substituted or unsubstituted heteroaryl (e.g., 5 to 10, 5 to 9, or 5 to 6 membered). In embodiments, $R^{5H}$ is independently halogen, oxo, —$CX^{5H}_3$, —$CHX^{5H}_2$, —$CH_2X^{5H}$, —$OCX^{5H}_3$, —$OCH_2X^{5H}$, —$OCHX^{5H}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5I}$-substituted or unsubstituted alkyl (e.g., $C_1$-$C_8$, $C_1$-$C_6$, $C_1$-$C_4$, or $C_1$-$C_2$), $R^{5I}$-substituted or unsubstituted heteroalkyl (e.g., 2 to 8, 2 to 6, 4 to 6, 2 to 3, or 4 to 5 membered), $R^{5I}$-substituted or unsubstituted cycloalkyl (e.g., $C_3$-$C_8$, $C_3$-$C_6$, $C_4$-$C_6$, or $C_5$-$C_6$), $R^{5I}$-substituted or unsubstituted heterocycloalkyl (e.g., 3 to 8, 3 to 6, 4 to 6, 4 to 5, or 5 to 6 membered), $R^{5I}$-substituted or unsubstituted aryl (e.g., $C_6$-$C_{10}$ or phenyl), or $R^{5I}$-substituted or unsubstituted heteroaryl (e.g., 5 to 10, 5 to 9, or 5 to 6 membered). In embodiments, $R^{5I}$ is independently halogen, oxo, —$CX^{5I}_3$, —$CHX^{5I}_2$, —$CH_2X^{5I}$, —$OCX^{5I}_3$, —$OCH_2X^{5I}$, —$OCHX^{5I}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8, 2 to 6, 4 to 6, 2 to 3, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8, 3 to 6, 4 to 6, 4 to 5, or 5 to 6 membered), unsubstituted aryl (e.g., $C_6$-$C_{10}$ or phenyl), or unsubstituted heteroaryl (e.g., 5 to 10, 5 to 9, or 5 to 6 membered). In embodiments, $R^{5C}$ is unsubstituted $C_1$-$C_4$ alkyl. In embodiments, $R^{5C}$ is unsubstituted methyl. In embodiments, $R^{5C}$ is unsubstituted tert-butyl. The symbols $X^{5A}$, $X^{5B}$, $X^{5C}$, $X^{5D}$, $X^{5E}$, $X^{5F}$, $X^{5G}$, $X^{5H}$, and $X^{5I}$ are independently —F, —Cl, —Br, or —I.

In embodiments, $R^{5A}$ is independently hydrogen, halogen, —$CX^{5A}_3$, —$CHX^{5A}_2$, —$CH_2X^{5A}$, —$OCX^{5A}_3$, —$OCH_2X^{5A}$, —$OCHX^{5A}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3$—, —$OPO_3H$, —SCN, —$ONO_2$, $R^{5D}$-substituted $C_1$-$C_4$ alkyl (e.g., $R^{5D}$-substituted $C_1$-$C_3$ alkyl, $R^{5D}$-substituted $C_1$-$C_2$ alkyl, or $R^{5D}$-substituted methyl) or $R^{5D}$-substituted 2 to 8 membered heteroalkyl (e.g., $R^{5D}$-substituted 2 to 6 membered heteroalkyl, $R^{5D}$-substituted 2 to 5 membered heteroalkyl, or $R^{5D}$-substituted 2 to 4 membered heteroalkyl). In embodiments, $R^{5D}$ is independently halogen, oxo, —$CX^{5D}_3$, —$CHX^{5D}_2$, —$CH_2X^{5D}$, —$OCX^{5D}_3$, —$OCH_2X^{5D}$, —$OCHX^{5D}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3$—, —$OPO_3H^-$, —SCN, or —$ONO_2$. In embodiments, $R^{5B}$ is independently hydrogen, halogen, —$CX^{5B}_3$, —$CHX^{5B}_2$, —$CH_2X^{5B}$, —$OCX^{5B}_3$, —$OCH_2X^{5B}$, —$OCHX^{5B}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H^-$, —SCN, —$ONO_2$, $R^{5F}$-substituted $C_1$-$C_4$ alkyl, (e.g., $R^{5F}$-substituted $C_1$-$C_3$ alkyl, $R^{5F}$-substituted $C_1$-$C_2$ alkyl, or $R^{5F}$-substituted methyl) or $R^{5F}$-substituted 2 to 8 membered heteroalkyl (e.g., $R^{5F}$-substituted 2 to 6 membered heteroalkyl, $R^{5F}$-substituted 2 to 5 membered heteroalkyl, or $R^{5F}$-substituted 2 to 4 membered heteroalkyl). In embodiments, $R^{5F}$ is independently halogen, oxo, —$CX^{5F}_3$, —$CHX^{5F}_2$, —$CH_2X^{5F}$, —$OCX^{5F}_3$, —$OCH_2X^{5F}$, —$OCHX^{5F}_2$, —CN, —OH, —SH, —$NH_2$, —COOH, —$CONH_2$, —$NO_2$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$N_3$, —$SF_5$, —$NH_3^+$, —$SO_3^-$, —$OPO_3H$, —SCN, or —$ONO_2$. In embodiments, $R^{5A}$ and $R^{5B}$ are combined to form an oxo. The symbols $X^{5A}$, $X^{5B}$, $X^{5D}$, and $X^{5F}$ are independently —F, —Cl, —Br, or —I.

In embodiments, the -polymerase-compatible cleavable moiety is:

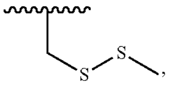 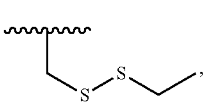

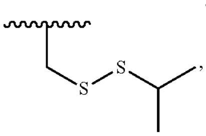 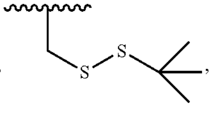

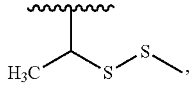 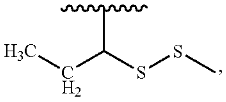

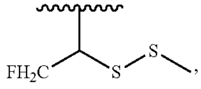 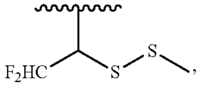

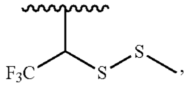 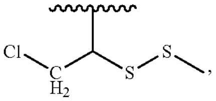

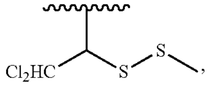 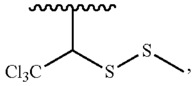

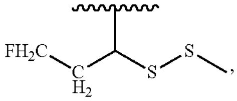 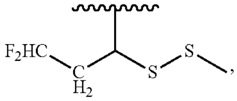

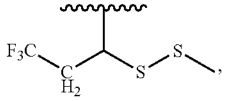 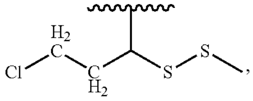

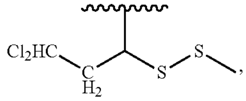 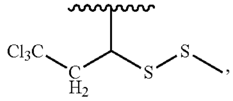

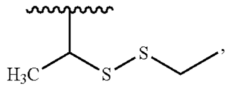 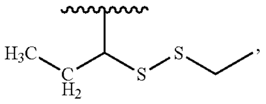

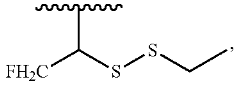 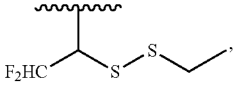

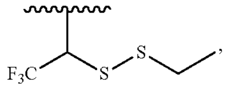 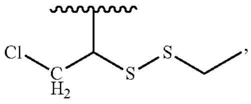

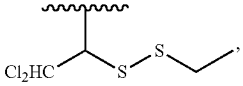 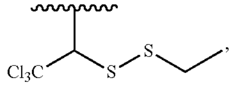

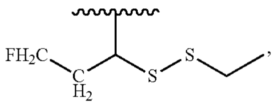 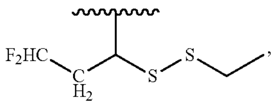

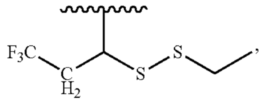 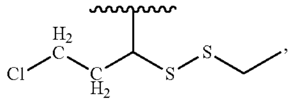

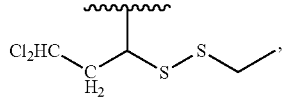 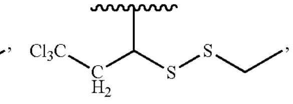

-continued
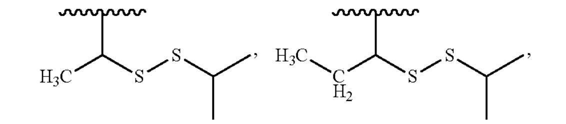
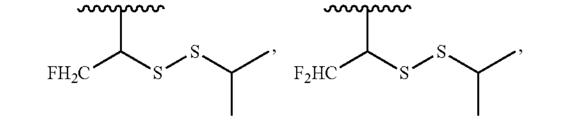
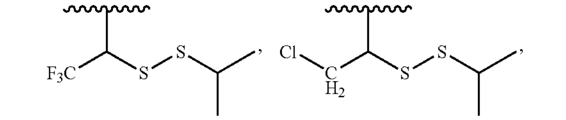
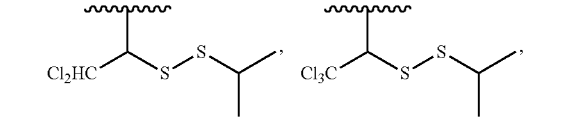
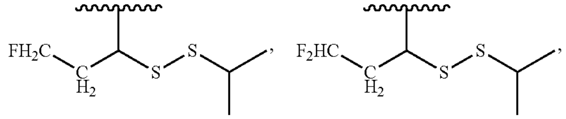
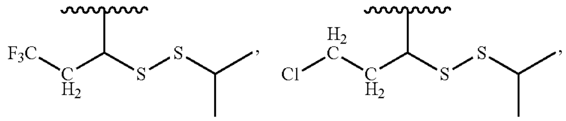
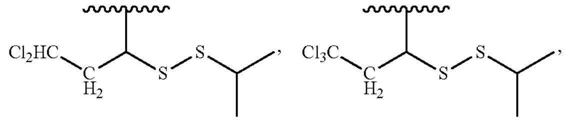
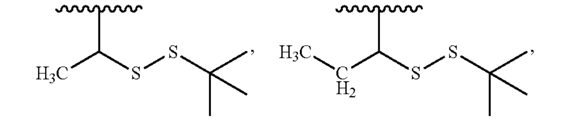
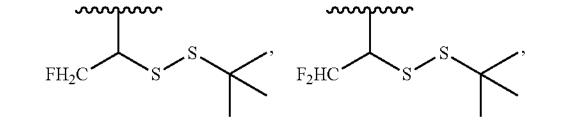
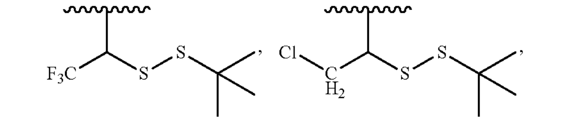
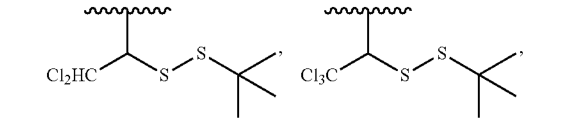
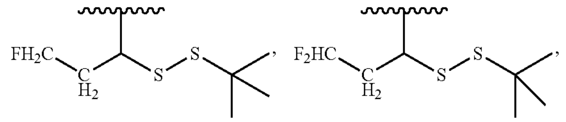
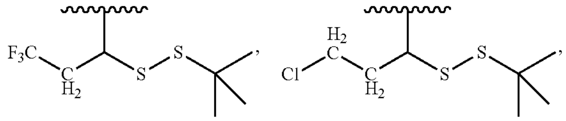
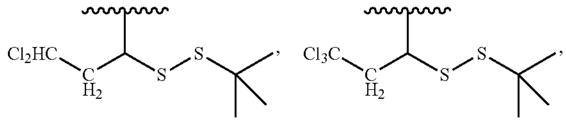
-continued
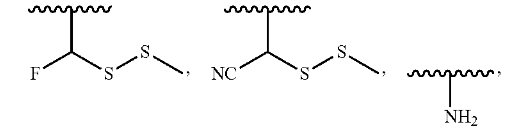
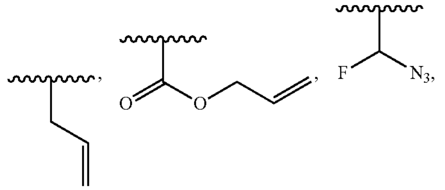
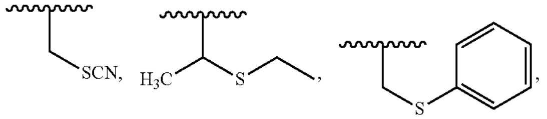
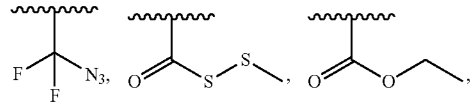
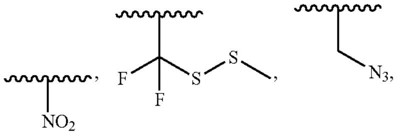
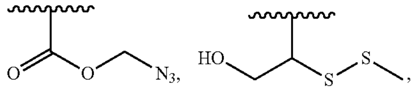
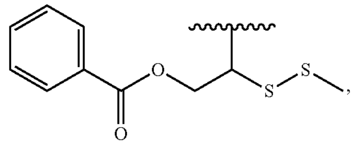
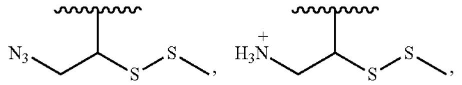
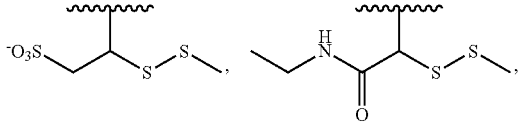
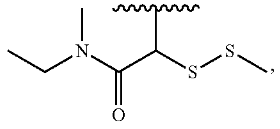
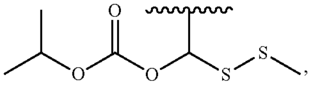
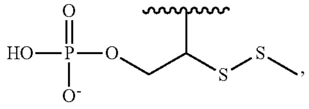
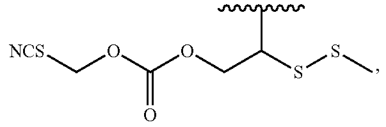
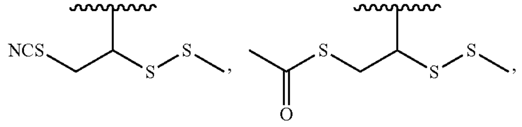

-continued

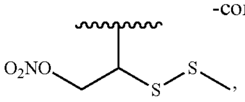,

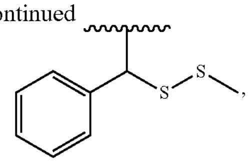, or

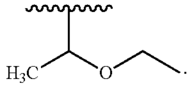.

In embodiments, the -polymerase-compatible cleavable moiety is:

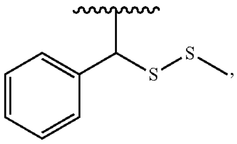,

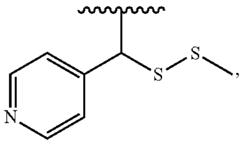,

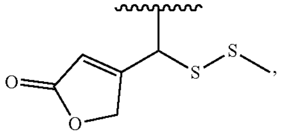, or

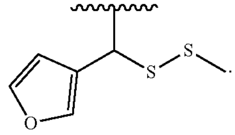.

In embodiments, $R^7$ is substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^7$ is substituted or unsubstituted cycloalkyl (e.g., $C_3$-$C_8$, $C_3$-$C_6$, $C_4$-$C_6$, or $C_5$-$C_6$). In embodiments, $R^7$ is substituted cycloalkyl (e.g., $C_3$-$C_8$, $C_3$-$C_6$, $C_4$-$C_6$, or $C_5$-$C_6$). In embodiments, $R^7$ is an unsubstituted cycloalkyl (e.g., $C_3$-$C_8$, $C_3$-$C_6$, $C_4$-$C_6$, or $C_5$-$C_6$). In embodiments, $R^7$ is substituted or unsubstituted heterocycloalkyl (e.g., 3 to 8 membered, 3 to 6 membered, 4 to 6 membered, 4 to 5 membered, or 5 to 6 membered). In embodiments, $R^7$ is substituted heterocycloalkyl (e.g., 3 to 8 membered, 3 to 6 membered, 4 to 6 membered, 4 to 5 membered, or 5 to 6 membered). In embodiments, $R^7$ is an unsubstituted heterocycloalkyl (e.g., 3 to 8 membered, 3 to 6 membered, 4 to 6 membered, 4 to 5 membered, or 5 to 6 membered).

In embodiments, $R^7$ is substituted or unsubstituted aryl (e.g., $C_6$-$C_{10}$, $C_{10}$, or phenyl). In embodiments, $R^7$ is substituted aryl (e.g., $C_6$-$C_{10}$, $C_{10}$, or phenyl). In embodiments, $R^7$ is unsubstituted aryl (e.g., $C_6$-$C_{10}$, $C_{10}$, or phenyl). In embodiments, $R^7$ is unsubstituted phenyl. In embodiments, $R^7$ is substituted or unsubstituted heteroaryl (e.g., 5 to 10, 5 to 9, or 5 to 6 membered). In embodiments, $R^7$ is substituted heteroaryl (e.g., 5 to 10, 5 to 9, or 5 to 6 membered). In embodiments, $R^7$ is unsubstituted heteroaryl (e.g., 5 to 10, 5 to 9, or 5 to 6 membered). In embodiments, $R^7$ is a substituted or unsubstituted 5 membered heteroaryl. In embodiments, $R^7$ is a substituted or unsubstituted 6 membered heteroaryl. In embodiments, $R^7$ is a substituted or unsubstituted 7 membered heteroaryl. In embodiments, $R^7$ is an unsubstituted 5 membered heteroaryl. In embodiments, $R^7$ is an unsubstituted 6 membered heteroaryl. In embodiments, $R^7$ is an unsubstituted 7 membered heteroaryl.

In embodiments, $R^7$ is $R^{7A}$-substituted or unsubstituted aryl (e.g., $C_6$-$C_{10}$, $C_{10}$, or phenyl), or $R^{7A}$-substituted or unsubstituted heteroaryl (e.g., 5 to 10, 5 to 9, or 5 to 6 membered). $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$OPO_3H$, $R^{7B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7B}$-substituted or unsubstituted heteroalkyl (e.g., 2 to 20, 8 to 20, 2 to 10, 2 to 8, 2 to 6, or 2 to 4 membered), $R^{7B}$-substituted or unsubstituted cycloalkyl (e.g., $C_3$-$C_8$, $C_3$-$C_6$, or $C_5$-$C_6$), $R^{7B}$-substituted or unsubstituted heterocycloalkyl (e.g., 3 to 8, 3 to 6, or 5 to 6 membered), $R^{7B}$-substituted or unsubstituted aryl (e.g., $C_6$-$C_{10}$, $C_{10}$, or phenyl), or $R^{7B}$-substituted or unsubstituted heteroaryl (e.g., 5 to 10, 5 to 9, or 5 to 6 membered). In embodiments, $R^{7A}$ is independently, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, or —$OPO_3H$. $R^{7B}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, $R^{7C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7C}$-substituted or unsubstituted heteroalkyl (e.g., 2 to 20, 8 to 20, 2 to 10, 2 to 8, 2 to 6, or 2 to 4 membered), $R^{7C}$-substituted or unsubstituted cycloalkyl (e.g., $C_3$—$C_8$, $C_3$-$C_6$, or $C_5$-$C_6$), $R^{7C}$-substituted or unsubstituted heterocycloalkyl (e.g., 3 to 8, 3 to 6, or 5 to 6 membered), $R^{7C}$-substituted or unsubstituted aryl (e.g., $C_6$-$C_{10}$, $C_{10}$, or phenyl), or $R^{7C}$-substituted or unsubstituted heteroaryl (e.g., 5 to 10, 5 to 9, or 5 to 6 membered). $R^{7C}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^7$ is $R^{7A}$-substituted cycloalkyl (e.g., $C_3$-$C_8$, $C_3$-$C_6$, $C_4$-$C_6$, or $C_5$-$C_6$). In embodiments, $R^7$ is $R^{7A}$-substituted heterocycloalkyl (e.g., 3 to 8 membered, 3 to 6 membered, 4 to 6 membered, 4 to 5 membered, or 5 to 6 membered). In embodiments, $R^{7A}$ is independently oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, —$OPO_3H$, $R^{7B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{7B}$-substituted or unsubstituted heteroalkyl (e.g., 2 to 20, 8 to 20, 2 to 10, 2 to 8, 2 to 6, or 2 to 4 membered), $R^{7B}$-substituted or unsubstituted cycloalkyl (e.g., $C_3$-$C_8$, $C_3$-$C_6$, or $C_5$-$C_6$), $R^{7B}$-substituted or unsubstituted heterocycloalkyl (e.g., 3 to 8, 3 to 6, or 5 to 6 membered), $R^{7B}$-substituted or unsubstituted aryl (e.g., $C_6$-$C_{10}$, $C_{10}$, or phenyl), or $R^{7B}$-substituted or unsubstituted heteroaryl (e.g., 5 to 10, 5 to 9, or 5 to 6 membered).

Two adjacent $R^{7A}$ substituents may optionally be joined to form a substituted or unsubstituted cycloalkyl, substituted or unsubstituted heterocycloalkyl, substituted or unsubstituted aryl, or substituted or unsubstituted heteroaryl. Two adjacent $R^{7A}$ substituents may optionally be joined to form a $R^{7B}$-substituted or unsubstituted cycloalkyl, $R^{7B}$-substituted or unsubstituted heterocycloalkyl, $R^{7B}$-substituted or unsubstituted aryl, or $R^{7B}$-substituted or unsubstituted heteroaryl. Two adjacent $R^{7A}$ substituents may optionally be joined to form a $R^{7B}$-substituted cycloalkyl, $R^{7B}$-substituted heterocycloalkyl, $R^{7B}$-substituted aryl, or $R^{7B}$-substituted heteroaryl. Two adjacent $R^{7A}$ substituents may optionally be joined to form an unsubstituted cycloalkyl, unsubstituted heterocycloalkyl, unsubstituted aryl, or unsubstituted heteroaryl.

In embodiments, $R^7$ is

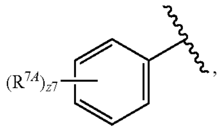

wherein $R^{7A}$ is as described herein and z7 is an integer from 0 to 5. In embodiments, $R^7$ is

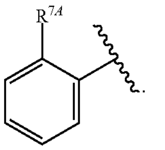

In embodiments, $R^7$ is

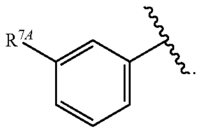

In embodiments, $R^7$ is

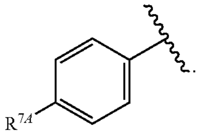

In embodiments, $R^{7A}$ is —CN, —$NO_2$, —$CF_3$, —$N_3$, —$NH_2$, —OMe, —OH, —F, —Cl, or —$CH_3$. In embodiments, $R^{7A}$ is —$N_3$, —$NH_2$, —OMe, —OH, —F, —Cl, or —$CH_3$. In embodiments, $R^7$ is

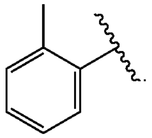 [SMILES: *c1ccccc1C]

In embodiments, $R^7$ is

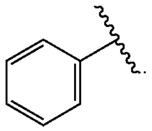

In embodiments, $R^7$ is

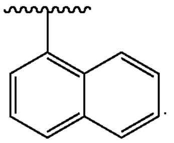 [SMILES: *c1cccc2ccccc12]

In embodiments $R^7$ is

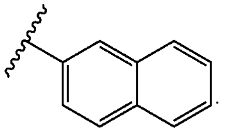 [SMILES: *c1ccc2ccccc2c1]

In embodiments, $R^7$ is

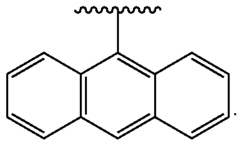 [SMILES: *c1c2ccccc2cc2ccccc12]

In embodiments, $R^7$ is

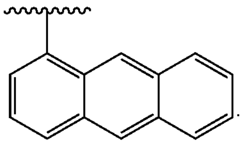 [SMILES: *c1cccc2cc3ccccc3cc12]

In embodiments, $R^7$ is

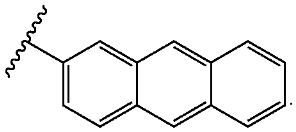 [SMILES: *c1ccc2cc3ccccc3cc2c1]

In embodiments, $R^7$ is

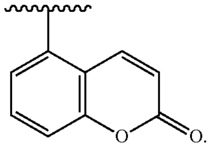 [SMILES: *c1cccc2oc(=O)ccc12]

In embodiments, $R^7$ is

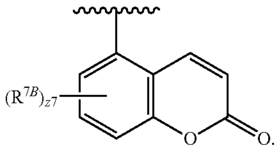

wherein z7 and $R^{7B}$ is as described herein. In embodiments, z7 is 4. In embodiments, z7 is 3. In embodiments, z7 is 2. In embodiments, z7 is 1. In embodiments, $R^7$ is

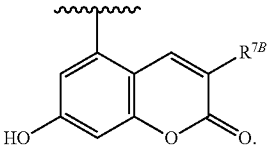

In embodiments, $R^7$ is

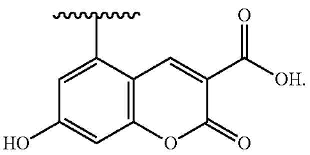 [SMILES: *c1cc(O)cc2oc(=O)c(C(=O)O)cc12]

In embodiments, $R^7$ is

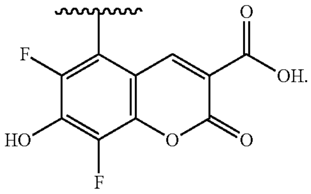 [SMILES: *c1c(F)c(O)c(F)c2oc(=O)c(C(=O)O)cc12]

In embodiments, $R^7$ is

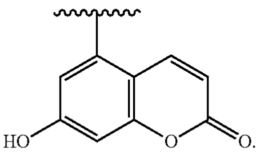 [SMILES: *c1cc(O)cc2oc(=O)ccc12]

In embodiments, $R^7$ is

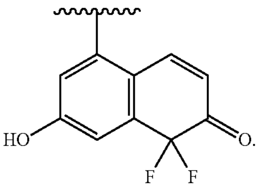 [SMILES: *c1cc(O)cc2c1C=CC(=O)C2(F)F]

In embodiments, $R^7$ is

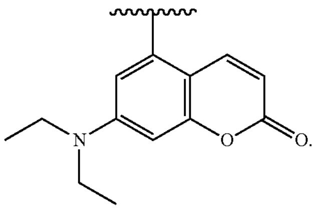 [SMILES: *c1cc(N(CC)CC)cc2oc(=O)ccc12]

In embodiments, $R^7$ is

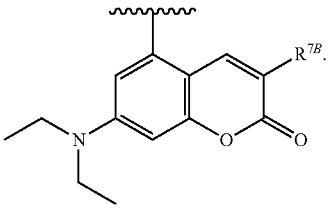

wherein $R^{7B}$ is as described herein.

In embodiments, $R^7$ is

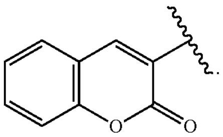 [SMILES: *c1cc2ccccc2oc1=O]

In embodiments, $R^7$ is
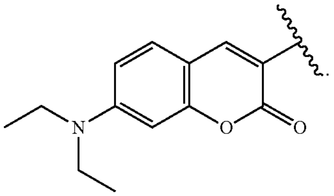 [SMILES: *c1cc2ccc(N(CC)CC)cc2oc1=O]
In embodiments, $R^7$ is
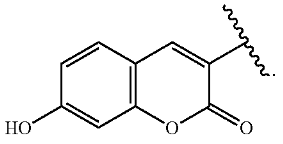 [SMILES: *c1cc2ccc(O)cc2oc1=O]
In embodiments, $R^7$ is
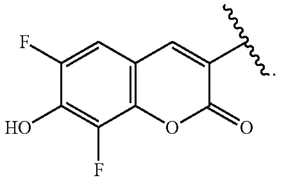 [SMILES: *c1cc2cc(F)c(O)c(F)c2oc1=O]
In embodiments, $R^7$ is
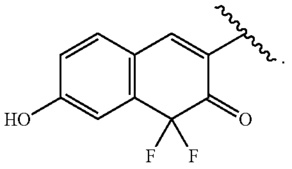 [SMILES: *C1=Cc2ccc(O)cc2C(F)(F)C1=O]
In embodiments, $R^7$ is
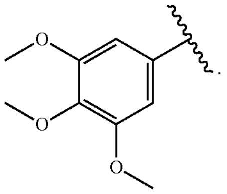 [SMILES: *c1cc(OC)c(OC)c(OC)c1]
In embodiments, $R^7$ is
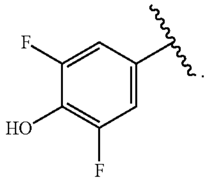
In embodiments, $R^7$ is a moiety depicted in Table 4.
In embodiments, $R^7$ is
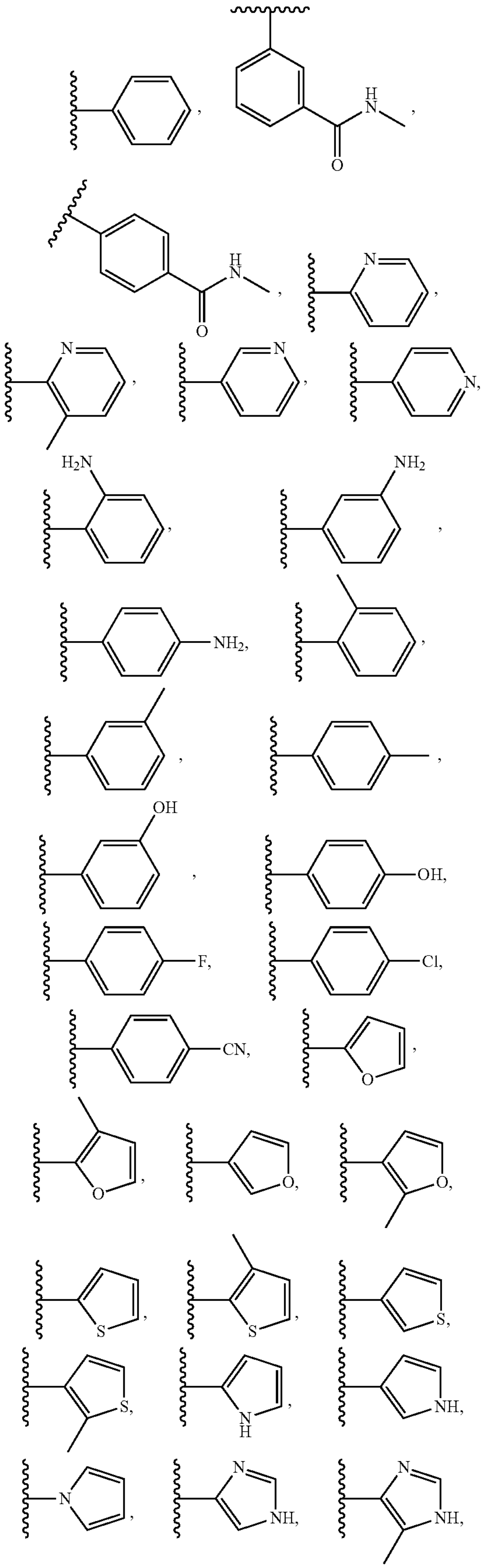

-continued
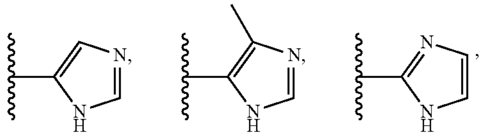
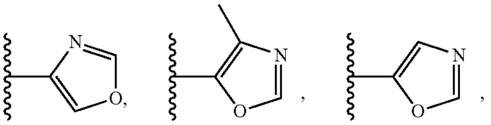
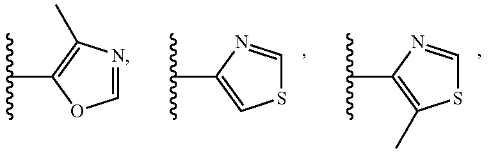
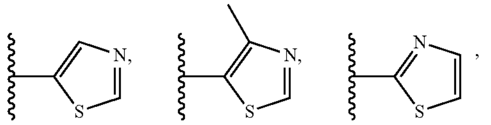
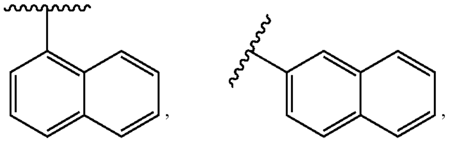
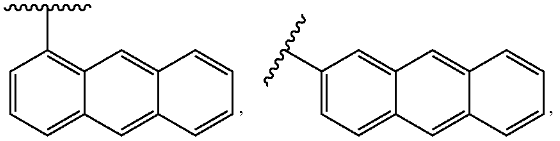
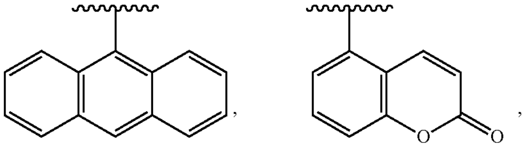
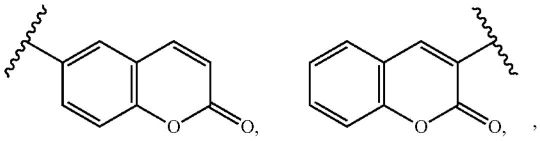
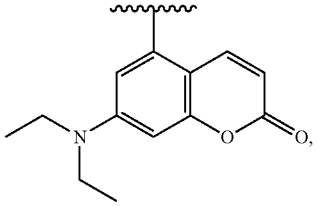
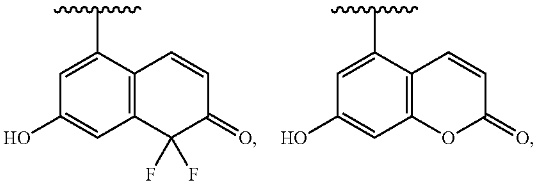
or
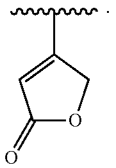
In embodiments $R^7$ is
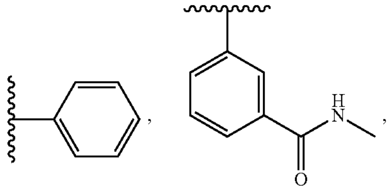
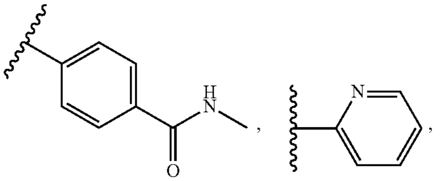
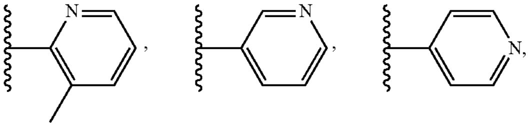
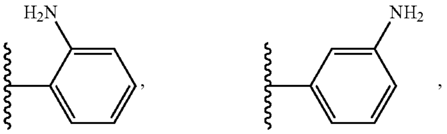
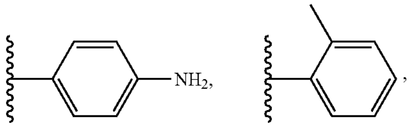
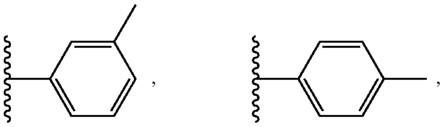
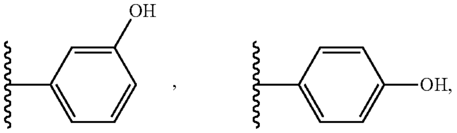
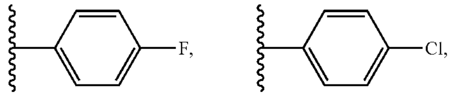
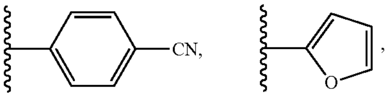
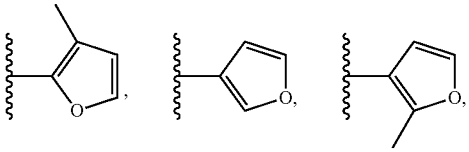
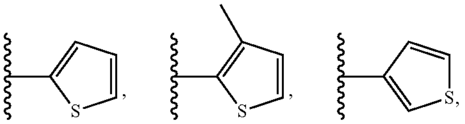
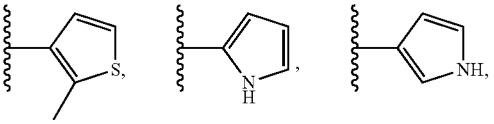
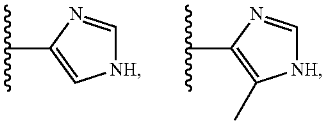

-continued
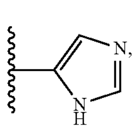 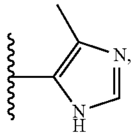 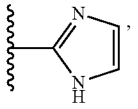
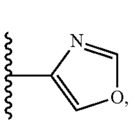 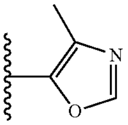, 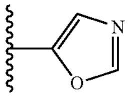,
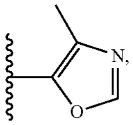 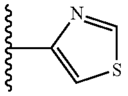, 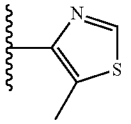,
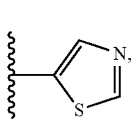 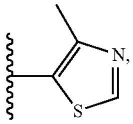 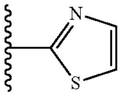,
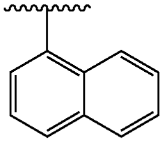, 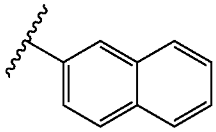,
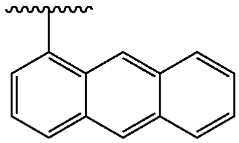, 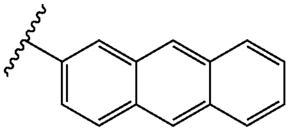,
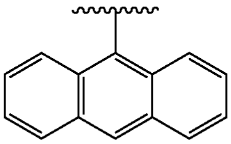, 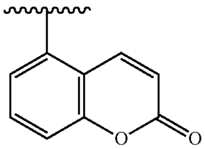,
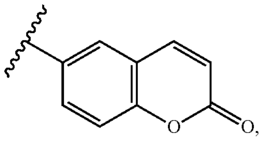 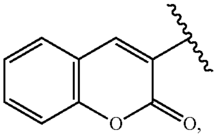,
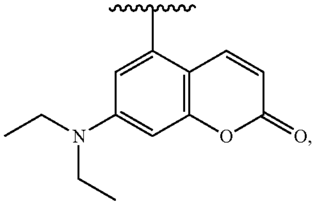
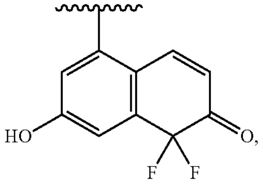 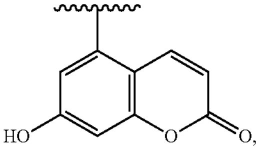 or
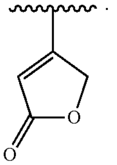
In embodiments, $R^7$ is
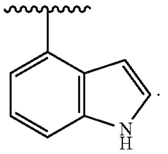 [SMILES: *c1cccc2[nH]ccc12]
In embodiments, $R^7$ is
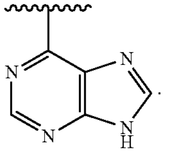
In embodiments, $R^7$ is
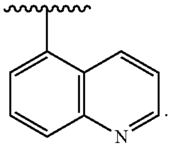 [SMILES: *c1cccc2ncccc12]
In embodiments, $R^7$ is
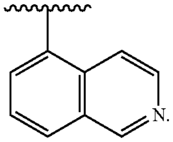 [SMILES: *c1cccc2cnccc12]
In embodiments, $R^7$ is
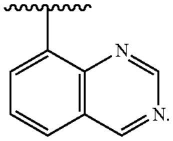 [SMILES: *c1cccc2cncnc12]
In embodiments, $R^7$ is
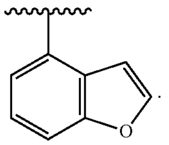 [SMILES: *c1cccc2occc12]

In embodiments, $R^7$ is
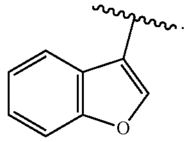 [SMILES: *c1coc2ccccc12]
In embodiments, $R^7$ is
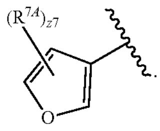
In embodiments, $R^7$ is
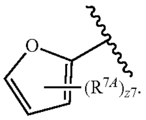
In embodiments, $R^7$ is
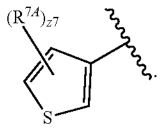
In embodiments, $R^7$ is
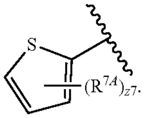
In embodiments, $R^7$ is
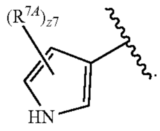
In embodiments, $R^7$ is
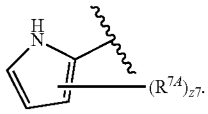
In embodiments, $R^7$ is
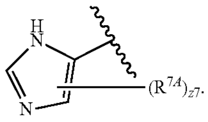
In embodiments, $R^7$ is
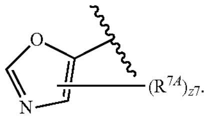
In embodiments, $R^7$ is
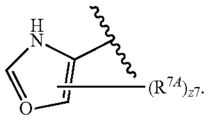
In embodiments, $R^7$ is
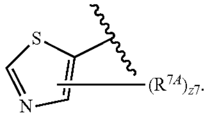
In embodiments, $R^7$ is
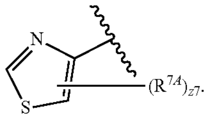
In embodiments, z7 is an integer from 0 to 2. In embodiments, $R^7$ is
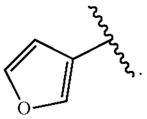
In embodiments, $R^7$ is
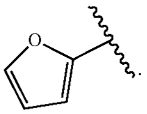 [SMILES: *c1ccco1]

In embodiments, $R^7$ is
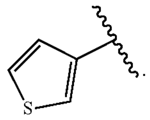 [SMILES: *c1ccsc1]
In embodiments, $R^7$ is
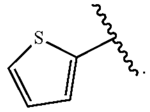 [SMILES: *c1cccs1]
In embodiments, $R^7$ is
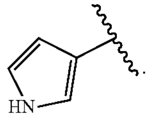 [SMILES: *c1cc[nH]c1]
In embodiments, $R^7$ is
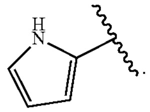 [SMILES: *c1ccc[nH]1]
In embodiments, $R^7$ is
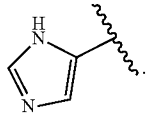 [SMILES: *c1cnc[nH]1]
In embodiments, $R^7$ is
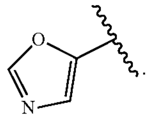 [SMILES: *c1cnco1]
In embodiments, $R^7$ is
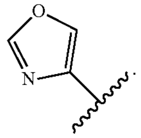 [SMILES: *c1cocn1]
In embodiments, $R^7$ is
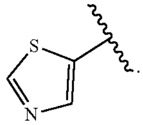 [SMILES: *c1cncs1]
In embodiments, $R^7$ is
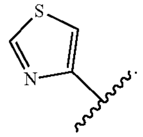 [SMILES: *c1cscn1]
In embodiments, $R^7$ is
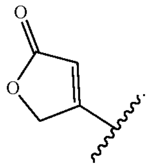 [SMILES: *C1=CC(=O)OC1]
In embodiments, $R^7$ is
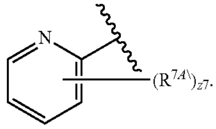
In embodiments, $R^7$ is
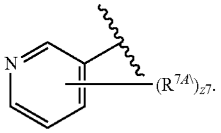
In embodiments, $R^7$ is
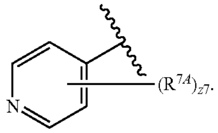
In embodiments, $R^7$ is
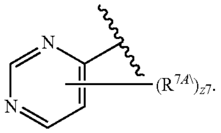

In embodiments, $R^7$ is
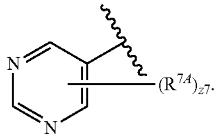
In embodiments, $R^7$ is
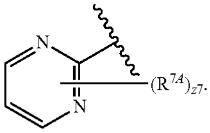
In embodiments, $R^7$ is
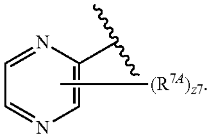
In embodiments, $R^7$ is
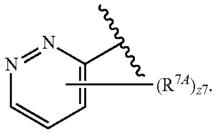
In embodiments, $R^7$ is
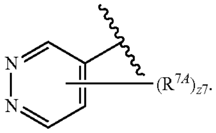
In embodiments, $R^7$ is
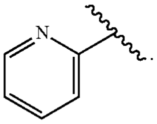 [SMILES: *c1ccccn1]
In embodiments, $R^7$ is
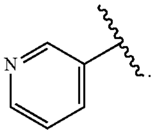 [SMILES: *c1cccnc1]
In embodiments, $R^7$ is
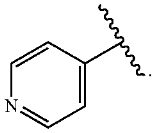 [SMILES: *c1ccncc1]
In embodiments, $R^7$ is
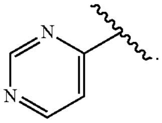 [SMILES: *c1ccncn1]
In embodiments, $R^7$ is
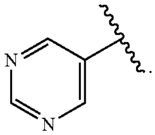 [SMILES: *c1cncnc1]
In embodiments, $R^7$ is
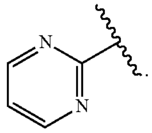 [SMILES: *c1ncccn1]
In embodiments R7 is
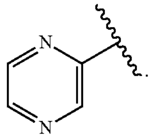 [SMILES: *c1cnccn1]
In embodiments, $R^7$ is
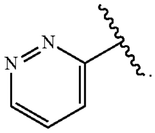 [SMILES: *c1cccnn1]
In embodiments, $R^7$ is
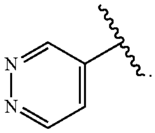 [SMILES: *c1ccnnc1]

In embodiments, $R^7$ is
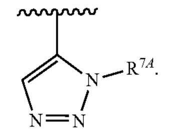
In embodiments, $R^7$ is
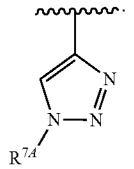
In embodiments, $R^7$ is
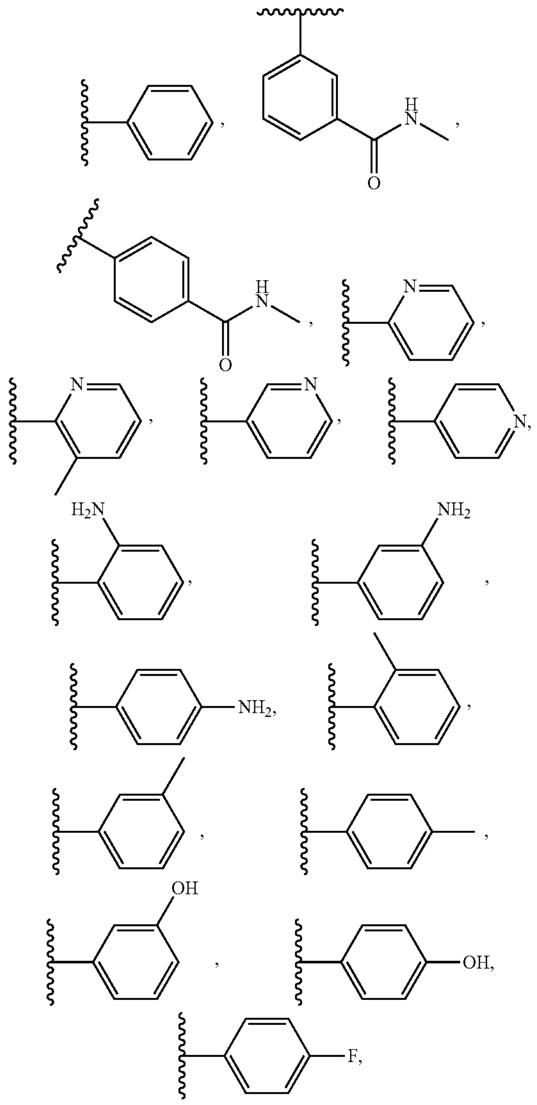
-continued
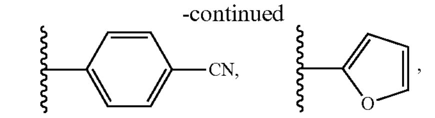
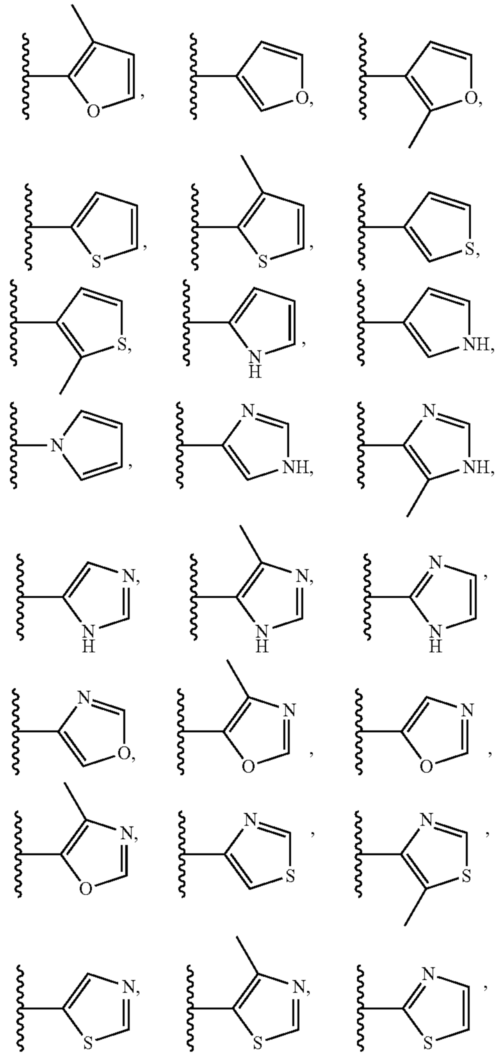
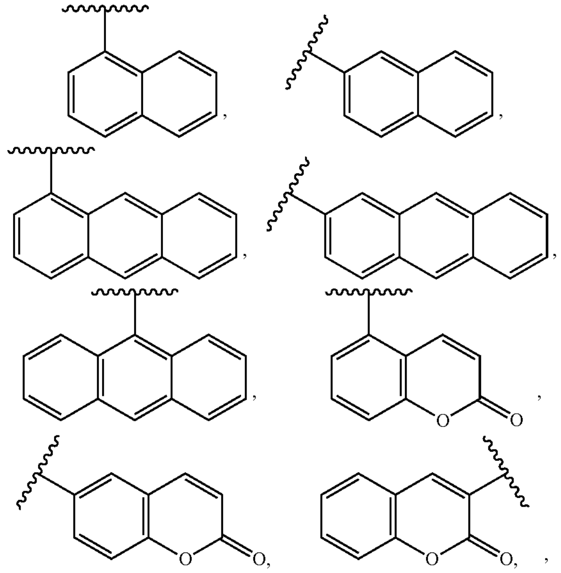

-continued
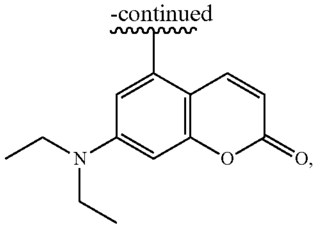
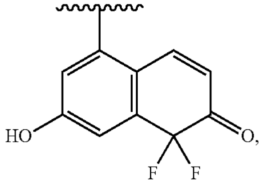 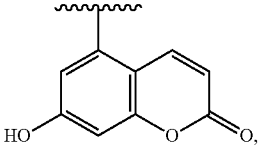
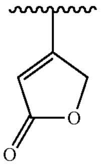, 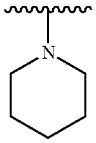, 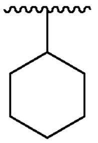, 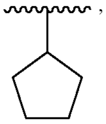,
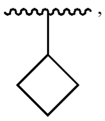, 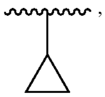, 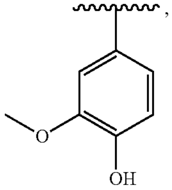,
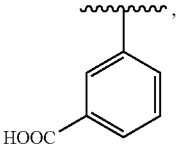, 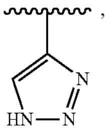, 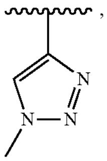,
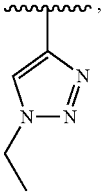, 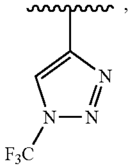, 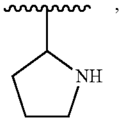, 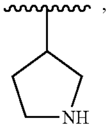,
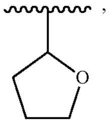, 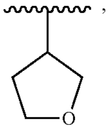, 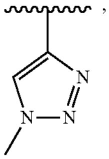, 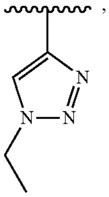,
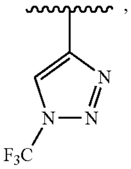, 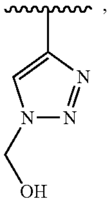, 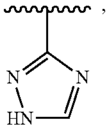, 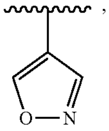,
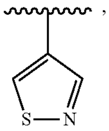, 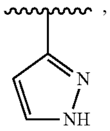, or 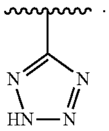.
In embodiments, $R^7$ is
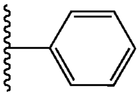
In embodiments, $R^7$ is
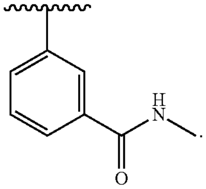 [SMILES: *c1cccc(C(=O)NC)c1]
In embodiments, $R^7$ is
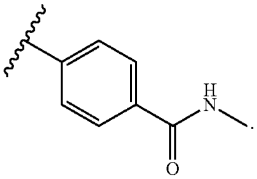 [SMILES: *c1ccc(C(=O)NC)cc1]
In embodiments, $R^7$ is
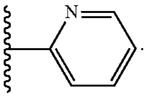 [SMILES: *c1ccccn1]
In embodiments, $R^7$ is
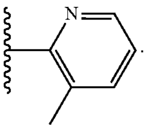 [SMILES: *c1ncccc1C]
In embodiments, $R^7$ is
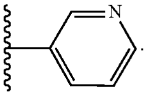 [SMILES: *c1cccnc1]
In embodiments, $R^7$ is
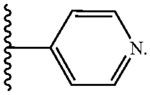

In embodiments, $R^7$ is
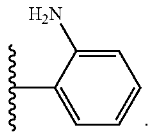 [SMILES: *c1ccccc1N]
In embodiments, $R^7$ is
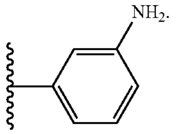 [SMILES: *c1cccc(N)c1]
In embodiments, $R^7$ is
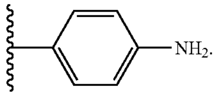 [SMILES: *c1ccc(N)cc1]
In embodiments, $R^7$ is
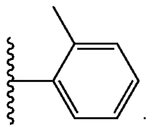 [SMILES: *c1ccccc1C]
In embodiments, $R^7$ is
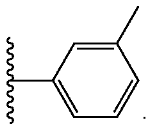 [SMILES: *c1cccc(C)c1]
In embodiments, $R^7$ is
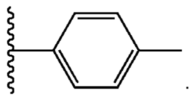 [SMILES: *c1ccc(C)cc1]
In embodiments, $R^7$ is
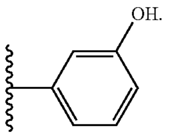 [SMILES: *c1cccc(O)c1]
In embodiments, $R^7$ is
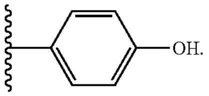
In embodiments, $R^7$ is
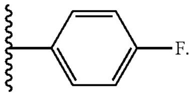 [SMILES: *c1ccc(F)cc1]
In embodiments, $R^7$ is
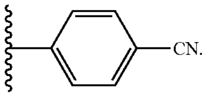 [SMILES: *c1ccc(C#N)cc1]
In embodiments, $R^7$ is
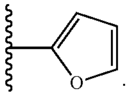 [SMILES: *c1ccco1]
In embodiments, $R^7$ is
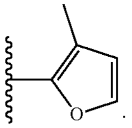 [SMILES: *c1occc1C]
In embodiments, $R^7$ is
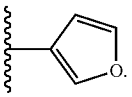 [SMILES: *c1ccoc1]
In embodiments, $R^7$ is
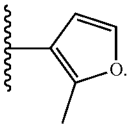 [SMILES: *c1ccoc1C]
In embodiments, $R^7$ is
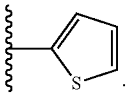

In embodiments, $R^7$ is
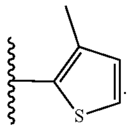
In embodiments, $R^7$ is
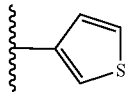
In embodiments, $R^7$ is
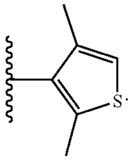 [SMILES: *c1c(C)csc1C]
In embodiments, $R^7$ is
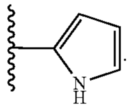 [SMILES: *c1ccc[nH]1]
In embodiments, $R^7$ is
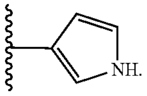 [SMILES: *c1cc[nH]c1]
In embodiments $R^7$ is
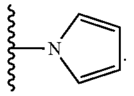
In embodiments, $R^7$ is
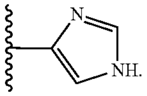 [SMILES: *c1c[nH]cn1]
In embodiments, $R^7$ is
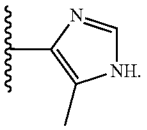 [SMILES: *c1nc[nH]c1C]
In embodiments, $R^7$ is
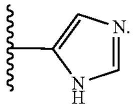
In embodiments, $R^7$ is
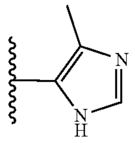 [SMILES: *c1[nH]cnc1C]
In embodiments, $R^7$ is
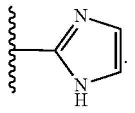
In embodiments, $R^7$ is
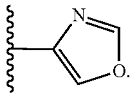
In embodiments, $R^7$ is
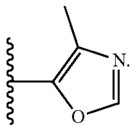 [SMILES: *c1ocnc1C]
In embodiments, $R^7$ is
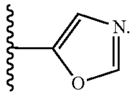

In embodiments, $R^7$ is
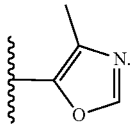
In embodiments, $R^7$ is
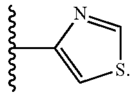
In embodiments, $R^7$ is
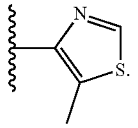
In embodiments, $R^7$ is
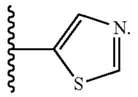
In embodiments, $R^7$ is
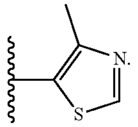
In embodiments, $R^7$ is
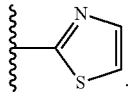
In embodiments, $R^7$ is
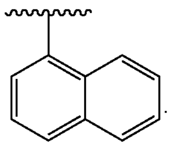 [SMILES: *c1cccc2ccccc12]
In embodiments, $R^7$ is
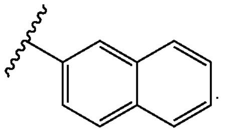 [SMILES: *c1ccc2ccccc2c1]
In embodiments, $R^7$ is
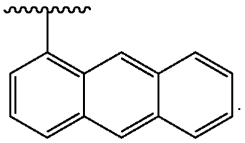
In embodiments, $R^7$ is
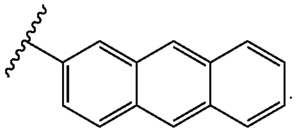 [SMILES: *c1ccc2cc3ccccc3cc2c1]
In embodiments, $R^7$ is
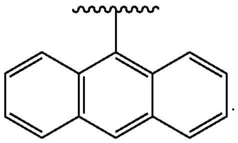 [SMILES: *c1c2ccccc2cc2ccccc12]
In embodiments, $R^7$ is
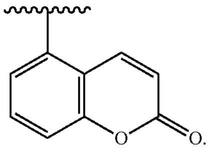 [SMILES: *c1cccc2oc(=O)ccc12]
In embodiments, $R^7$ is
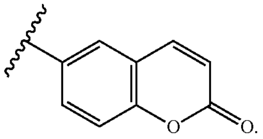 [SMILES: *c1ccc2oc(=O)ccc2c1]
In embodiments, $R^7$ is
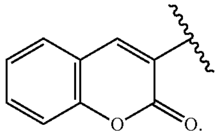 [SMILES: *c1cc2ccccc2oc1=O]

In embodiments, $R^7$ is
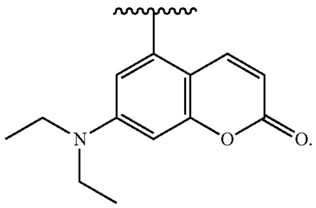 [SMILES: *c1cc(N(CC)CC)cc2oc(=O)ccc12]
In embodiments, $R^7$ is
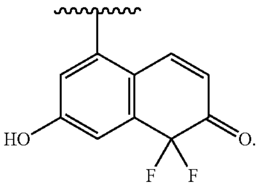 [SMILES: *c1cc(O)cc2c1C=CC(=O)C2(F)F]
In embodiments, $R^7$ is
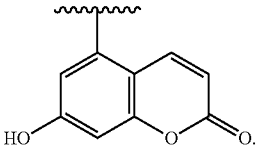 [SMILES: *c1cc(O)cc2oc(=O)ccc12]
In embodiments, $R^7$ is
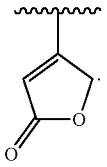 [SMILES: *C1=CC(=O)OC1]
In embodiments, $R^7$ is
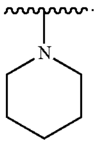 [SMILES: *N1CCCCC1]
In embodiments, $R^7$ is
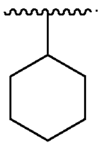
In embodiments, $R^7$ is
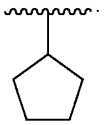
In embodiments, $R^7$ is
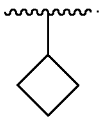 [SMILES: *C1CCC1]
In embodiments, $R^7$ is
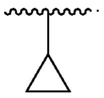 [SMILES: *C1CC1]
In embodiments, $R^7$ is
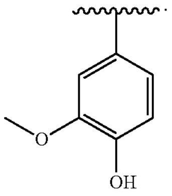 [SMILES: *c1ccc(O)c(OC)c1]
In embodiments, $R^7$ is
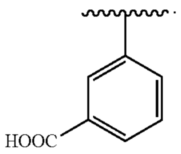
In embodiments, $R^7$ is
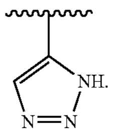 [SMILES: *c1cnn[nH]1]
In embodiments, $R^7$ is
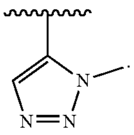

In embodiments, $R^7$ is
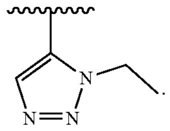 [SMILES: *c1cnnn1CC]
In embodiments, $R^7$ is
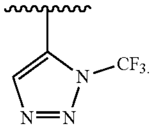 [SMILES: *c1cnnn1C(F)(F)F]
In embodiments, $R^7$ is
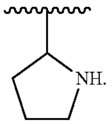 [SMILES: *C1CCCN1]
In embodiments, $R^7$ is
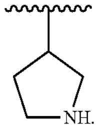
In embodiments, $R^7$ is
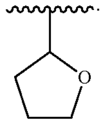 [SMILES: *C1CCCO1]
In embodiments, $R^7$ is
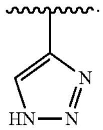
In embodiments, $R^7$ is
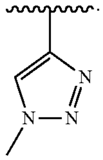 [SMILES: *c1cn(C)nn1]
In embodiments, $R^7$ is
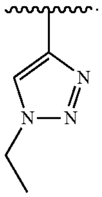 [SMILES: *c1cn(CC)nn1]
In embodiments, $R^7$ is
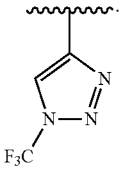
In embodiments, $R^7$ is
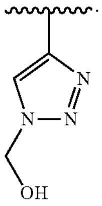 [SMILES: *c1cn(CO)nn1]
In embodiments, $R^7$ is
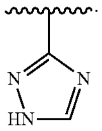
In embodiments, $R^7$ is
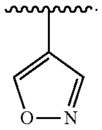
In embodiments, $R^7$ is
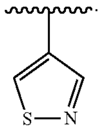

In embodiments, $R^7$ is
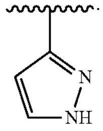
In embodiments, $R^7$ is
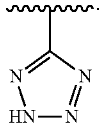
In embodiments, $R^7$ is
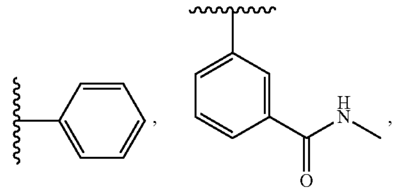
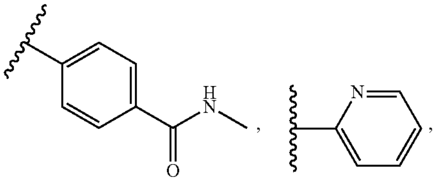
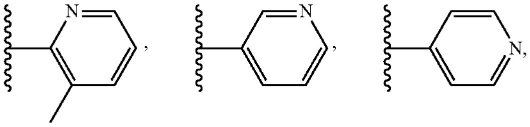
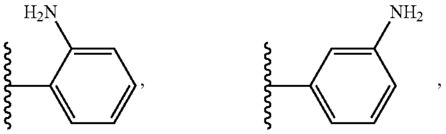
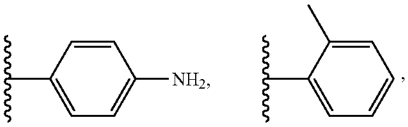
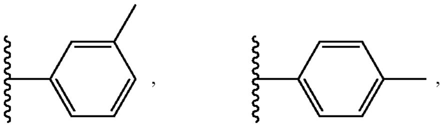
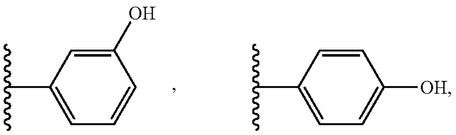
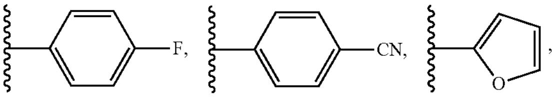
-continued
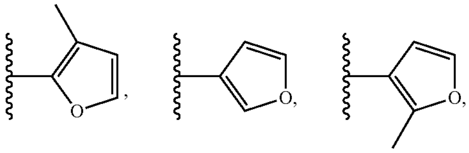
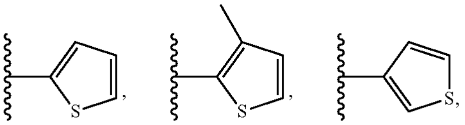
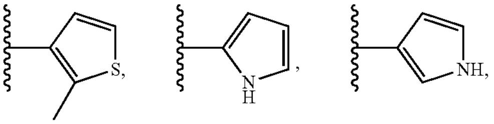
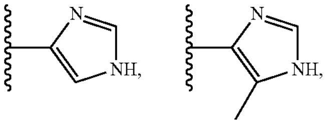
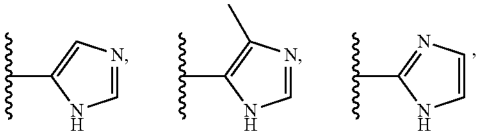
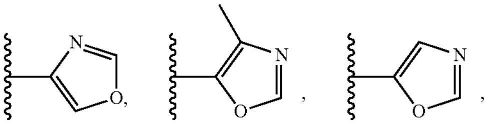
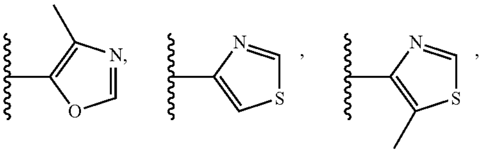
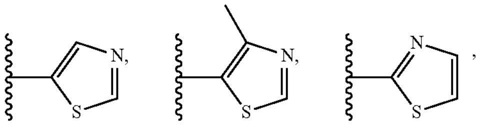
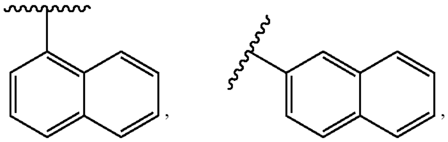
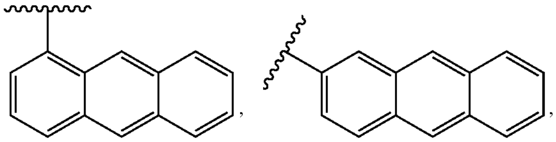
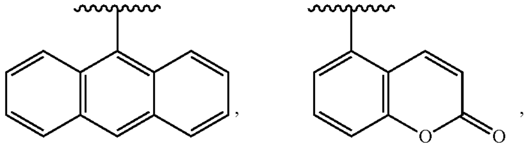
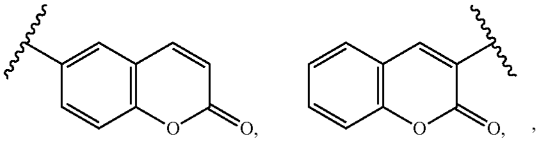

-continued

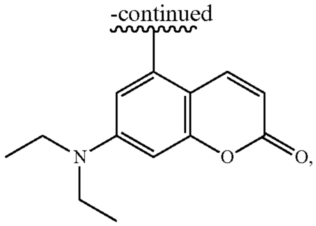,

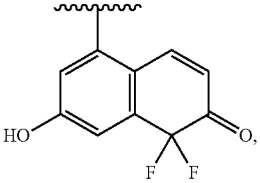, 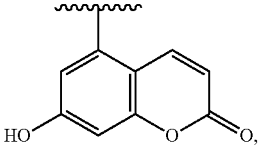,

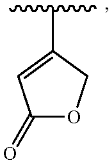, 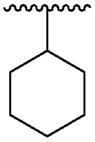, 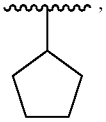,

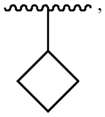, 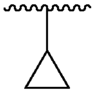, 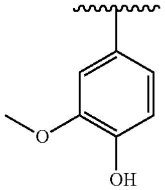,

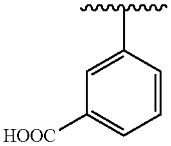, 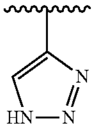, 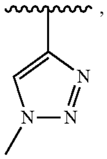,

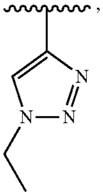, 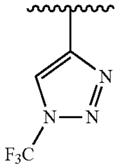, 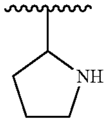, 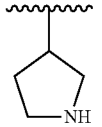,

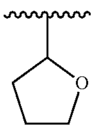, or 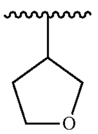.

In embodiments, $R^7$ is

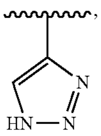, 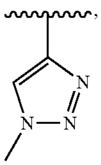, 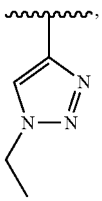, or 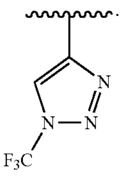.

In embodiments, $R^8$ is substituted alkyl. In embodiments, $R^8$ is substituted $C_1$-$C_6$ or $C_1$-$C_4$ alkyl. In embodiments, $R^8$ is $R^{8A}$-substituted $C_1$-$C_6$ or $C_1$-$C_4$ alkyl. $R^{8A}$ is independently oxo, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^8$ is unsubstituted $C_1$-$C_6$ or $C_1$-$C_4$ alkyl. In embodiments, $R^8$ is unsubstituted $C_1$-$C_4$ alkyl. In embodiments, $R^8$ is unsubstituted $C_1$-$C_6$ alkyl. In embodiments, R' is unsubstituted methyl. In embodiments, $R^8$ is unsubstituted $C_2$ alkyl. In embodiments, $R^8$ is unsubstituted $C_3$ alkyl. In embodiments, $R^8$ is unsubstituted $C_4$ alkyl. In embodiments, $R^8$ is unsubstituted $C_5$ alkyl. In embodiments, $R^8$ is unsubstituted $C_6$ alkyl.

In embodiments, $R^8$ is unsubstituted $C_1$-$C_6$ or $C_1$-$C_4$ saturated alkyl. In embodiments, R' is unsubstituted $C_1$-$C_4$ saturated alkyl. In embodiments, $R^8$ is unsubstituted $C_1$-$C_6$ saturated alkyl. In embodiments, $R^8$ is unsubstituted methyl. In embodiments, $R^8$ is unsubstituted $C_2$ saturated alkyl. In embodiments, $R^8$ is unsubstituted $C_3$ saturated alkyl. In embodiments, $R^8$ is unsubstituted $C_4$ saturated alkyl. In embodiments, $R^8$ is unsubstituted $C_5$ saturated alkyl. In embodiments, $R^8$ is unsubstituted $C_6$ saturated alkyl.

In embodiments, $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

In embodiments, $B^1$ is a monovalent nucleobase, or a derivative thereof. In embodiments, $B^1$ is a monovalent cytosine or a derivative thereof, monovalent guanine or a derivative thereof, monovalent adenine or a derivative thereof, monovalent thymine or a derivative thereof, monovalent uracil or a derivative thereof, monovalent hypoxanthine or a derivative thereof, monovalent xanthine or a derivative thereof, monovalent 7-methylguanine or a derivative thereof, monovalent 5,6-dihydrouracil or a derivative thereof, monovalent 5-methylcytosine or a derivative thereof, or monovalent 5-hydroxymethylcytosine or a derivative thereof. In embodiments, $B^1$ is a monovalent cytosine or a derivative thereof. In embodiments, $B^1$ is a monovalent guanine or a derivative thereof. In embodiments, $B^1$ is a monovalent adenine or a derivative thereof. In embodiments, $B^1$ is a monovalent thymine or a derivative thereof. In embodiments, $B^1$ is a monovalent uracil or a derivative thereof. In embodiments, $B^1$ is a monovalent hypoxanthine or a derivative thereof. In embodiments, $B^1$ is a monovalent xanthine or a derivative thereof. In embodiments, $B^1$ is a monovalent 7-methylguanine or a derivative thereof. In embodiments, $B^1$ is a monovalent 5,6-dihydrouracil or a derivative thereof. In embodiments, $B^1$ is a monovalent 5-methylcytosine or a derivative thereof. In embodiments, $B^1$ is a monovalent 5-hydroxymethylcytosine or a derivative thereof. In embodiments, $B^1$ is a monovalent cytosine. In embodiments, $B^1$ is a monovalent guanine. In embodiments, $B^1$ is a monovalent adenine. In embodiments, $B^1$ is a monovalent thymine. In embodiments, $B^1$ is a monovalent uracil. In embodiments, $B^1$ is a monovalent hypoxanthine. In embodiments, $B^1$ is a monovalent xanthine. In embodiments, $B^1$ is a monovalent 7-methylguanine. In embodiments, $B^1$ is a monovalent 5,6-dihydrouracil. In embodiments, $B^1$ is a monovalent 5-methylcytosine. In embodiments, $B^1$ is a monovalent 5-hydroxymethylcytosine.

In embodiments, $B^1$ is

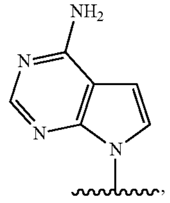
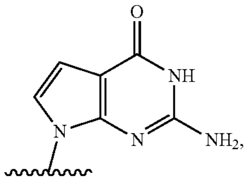
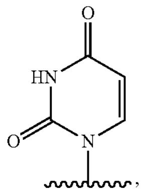
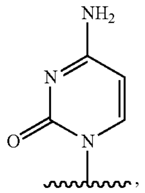
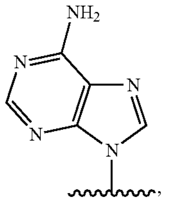
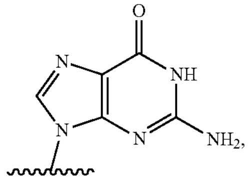
or
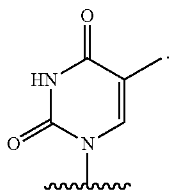

In embodiments, $B^1$ is

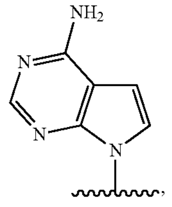
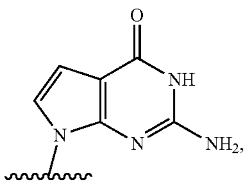
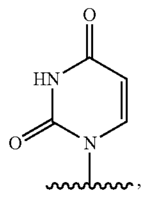
or
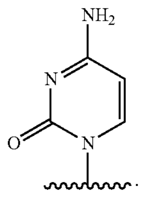

In embodiments, $B^1$ is

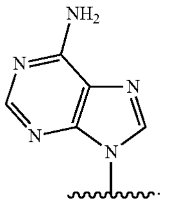 [SMILES: *n1cnc2c(N)ncnc21]

In embodiments, $B^1$ is

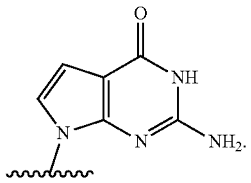 [SMILES: *n1ccc2c(=O)[nH]c(N)nc21]

In embodiments, $B^1$ is

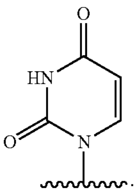

In embodiments, $B^1$ is

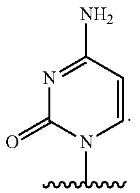

In embodiments, $B^1$ is

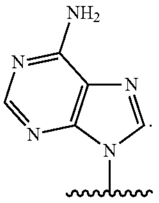 [SMILES: *n1cnc2c(N)ncnc21]

In embodiments, $B^1$ is
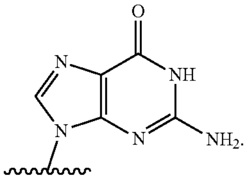 [SMILES: *n1cnc2c(=O)[nH]c(N)nc21]
In embodiments, $B^1$ is
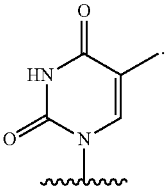 [SMILES: *n1cc(C)c(=O)[nH]c1=O]
In embodiments, $B^1$ is
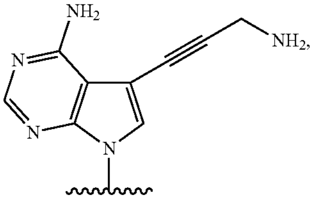
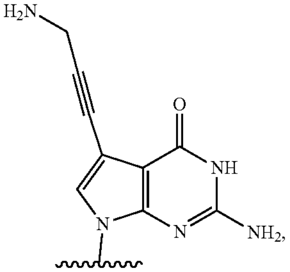
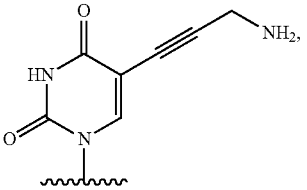
or
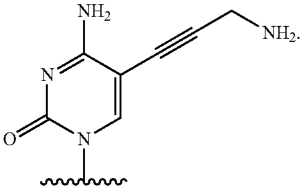
In embodiments, $B^1$ is
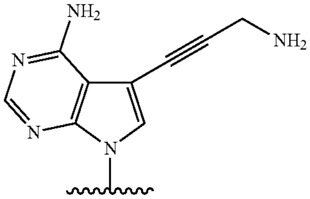 [SMILES: *n1cc(C#CCN)c2c(N)ncnc21]
In embodiments, $B^1$ is
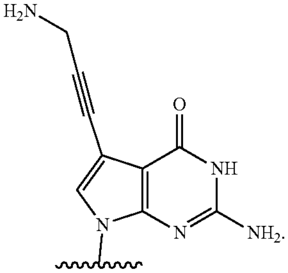 [SMILES: *n1cc(C#CCN)c2c(=O)[nH]c(N)nc21]
In embodiments, $B^1$ is
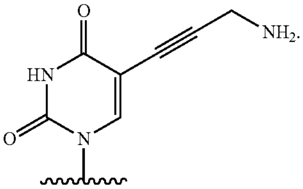 [SMILES: *n1cc(C#CCN)c(=O)[nH]c1=O]
In embodiments, $B^1$ is
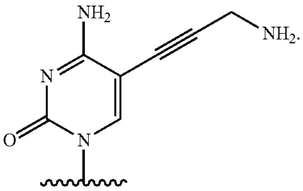 [SMILES: *n1cc(C#CCN)c(N)nc1=O]
In embodiments, $B^1$ is
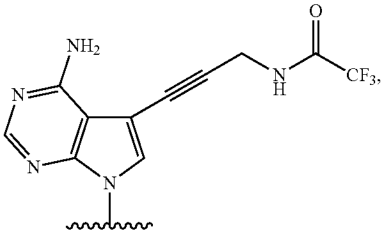

-continued
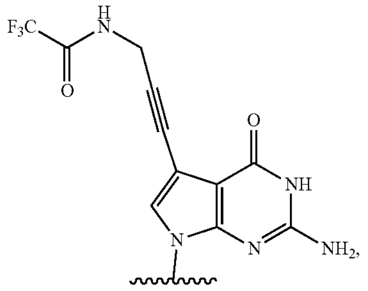
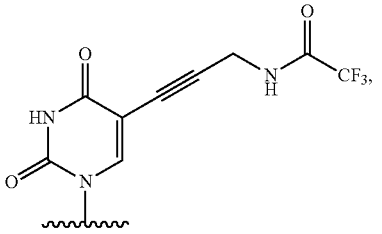 or
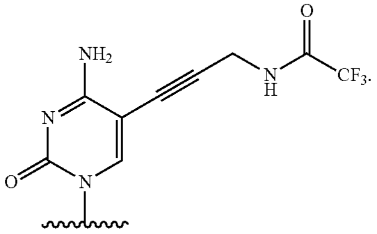
In embodiments, $B^1$ is
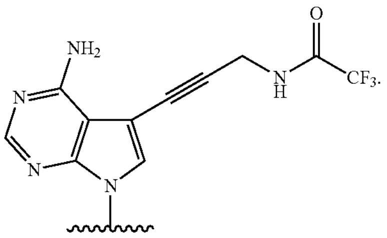 [SMILES: *n1cc(C#CCNC(=O)C(F)(F)F)c2c(N)ncnc21]
In embodiments, $B^1$ is
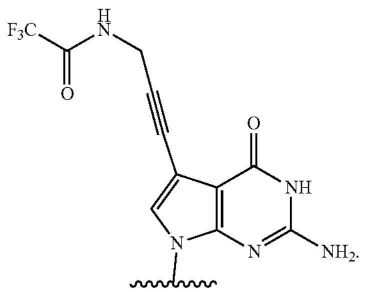 [SMILES: *n1cc(C#CCNC(=O)C(F)(F)F)c2c(=O)[nH]c(N)nc21]
In embodiments, $B^1$ is
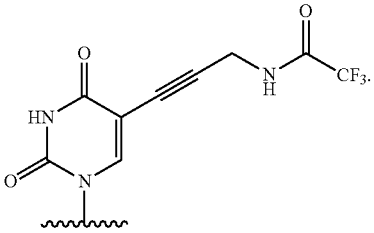
In embodiments, $B^1$ is
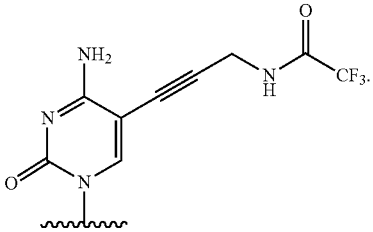
In embodiments, $B^1$ is
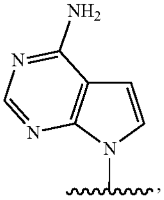,
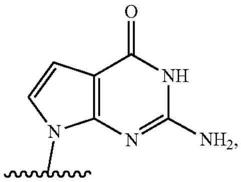,
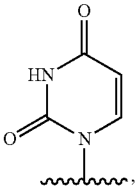,
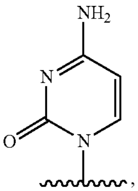,
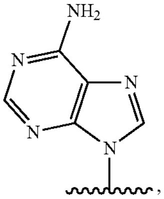,
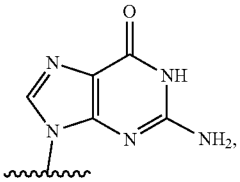 or
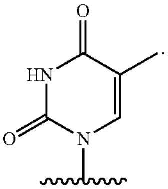
In embodiments, $B^1$ is
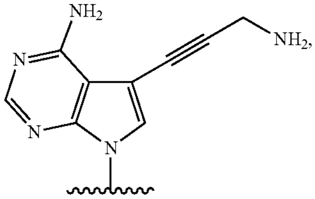

-continued

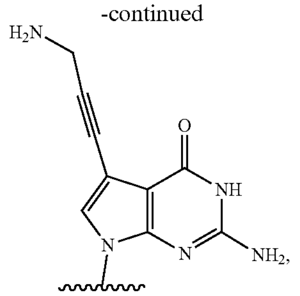

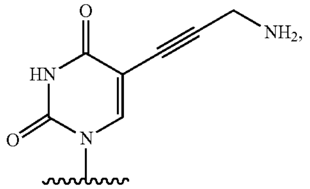

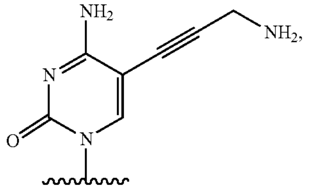

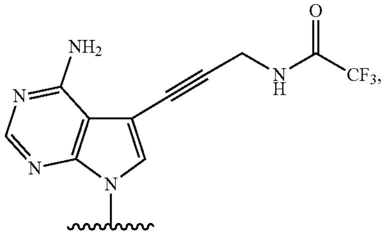

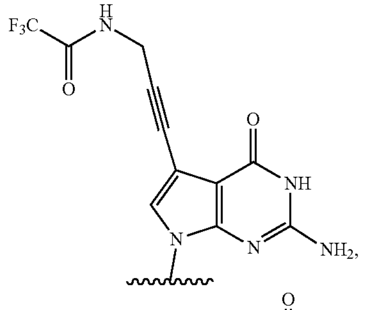

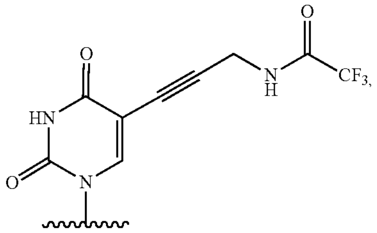 [SMILES: *n1cc(C#CCNC(=O)C(F)(F)F)c(=O)[nH]c1=O]

or

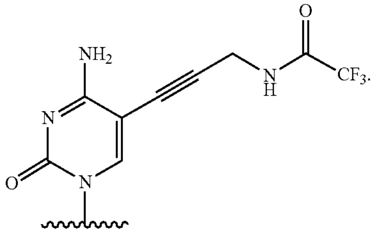 [SMILES: *n1cc(C#CCNC(=O)C(F)(F)F)c(N)nc1=O]

In embodiments, $B^1$ includes a substituted or unsubstituted propargyl amine moiety, which may further include S—S linker, fluorophores or protecting group. In embodiments, the propargyl amine moiety may further include at least one or more fluorophores. In embodiments, the propargyl amine moiety may further be linked via a linker (e.g., an S—S linker) to at least one or more fluorophores. In embodiments, the propargyl amine moiety may further include at least one or more protecting groups. In embodiments, the propargyl amine moiety may further be linked to a S—S— linker, which may be connected to at least one or more protecting groups.

In embodiments, $B^1$ is a divalent nucleobase. In embodiments, $B^1$ is

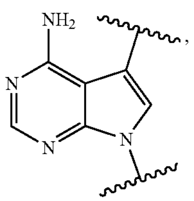

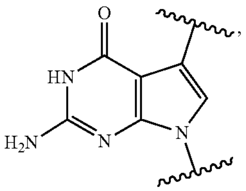

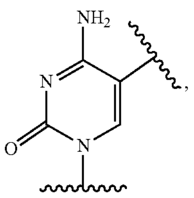

or

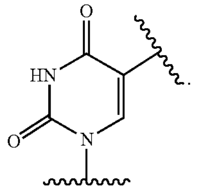

In embodiments, $B^1$ is

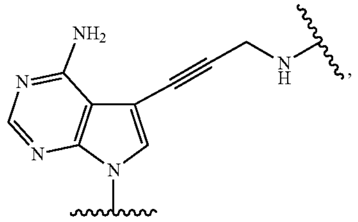

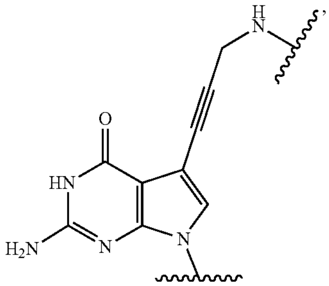

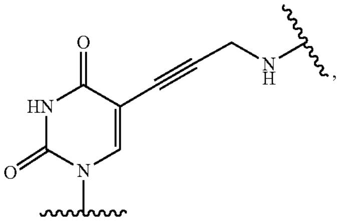

-continued
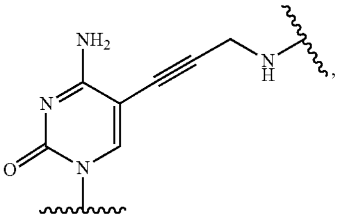
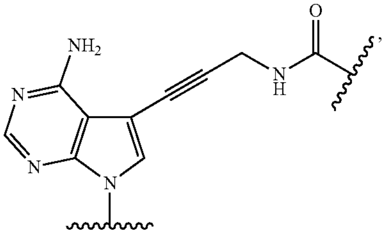
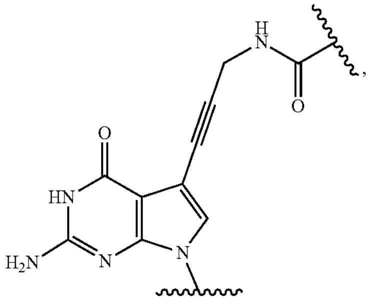
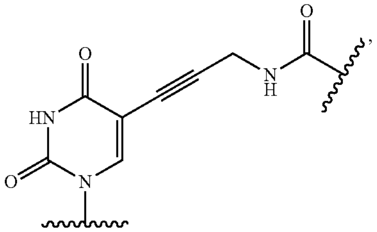
or
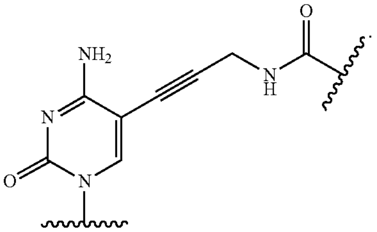
In embodiments, B is a divalent nucleobase. In embodiments, B is
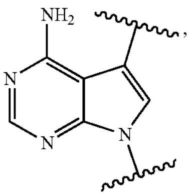
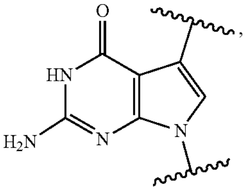
-continued
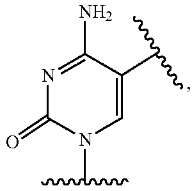
or
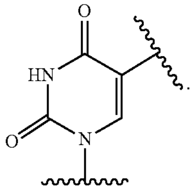
In embodiments, B is
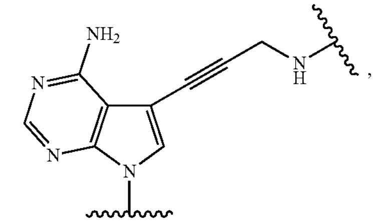
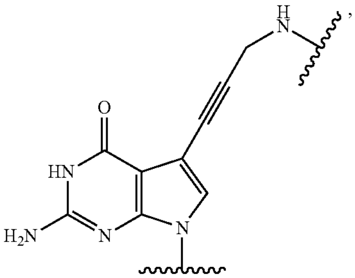
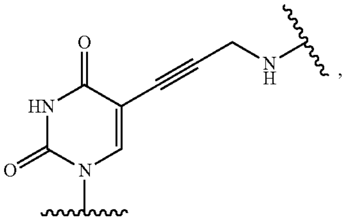
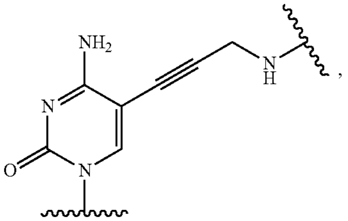
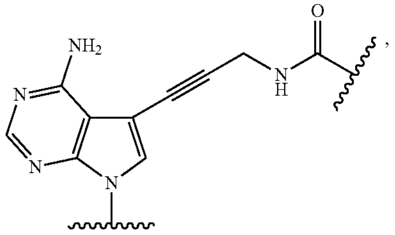

-continued

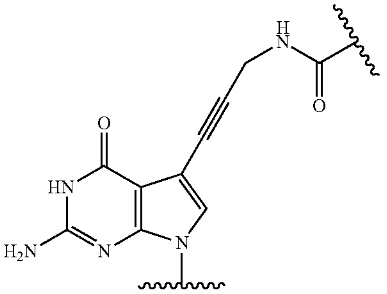

,

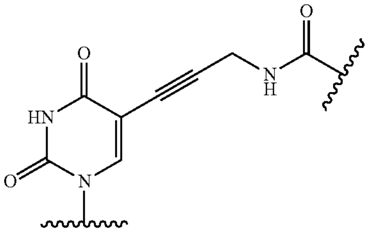

, or

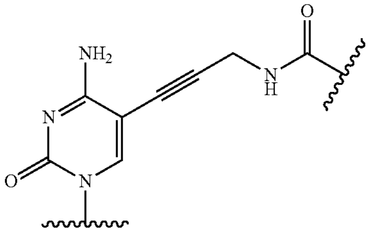

.

In embodiments, $B^1$ is —B-$L^{100}$-$R^4$. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. $L^{100}$ is a divalent linker; and $R^4$ is a detectable moiety. In embodiments, $L^{100}$ includes a thio-trigger moiety.

In embodiments, B is

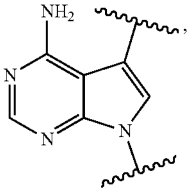

,

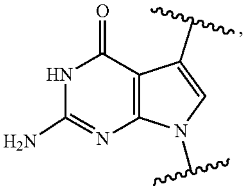

,

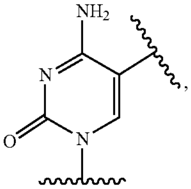

, or

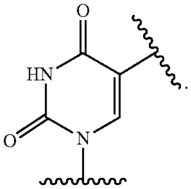

.

In embodiments, B is

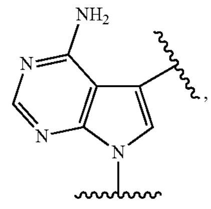

,

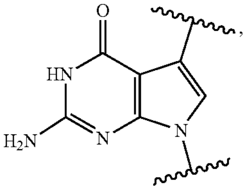

,

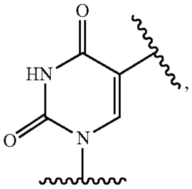

,

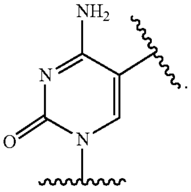

.

In embodiments, B is

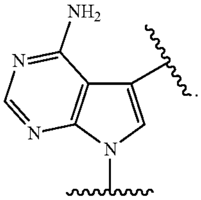

.

In embodiments, B is

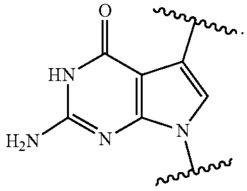 [SMILES: *c1cn(*)c2nc(N)[nH]c(=O)c12]

.

In embodiments, B is

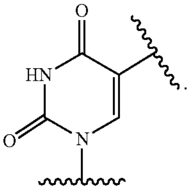

.

In embodiments, B is

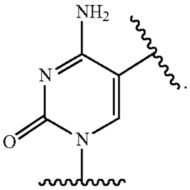 [SMILES: *c1cn(*)c(=O)nc1N]

.

In embodiments, B is

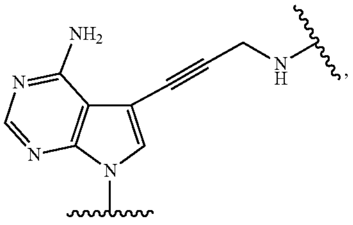

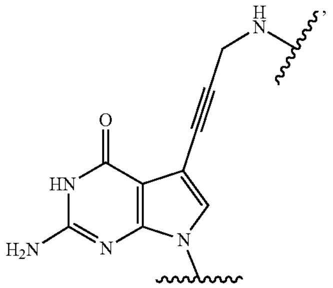

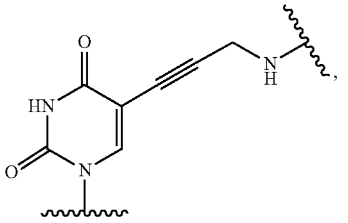

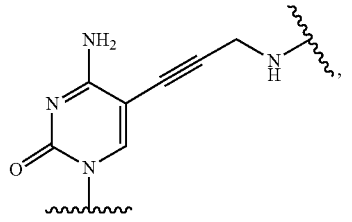

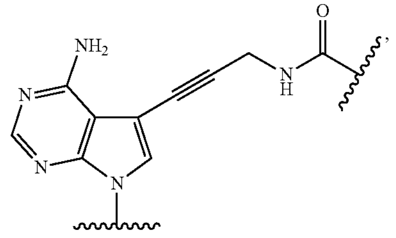

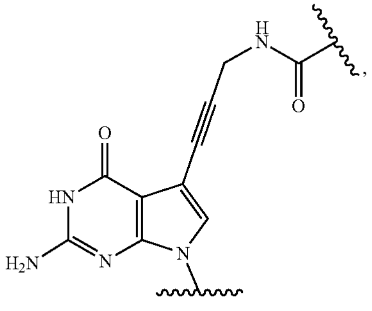

-continued

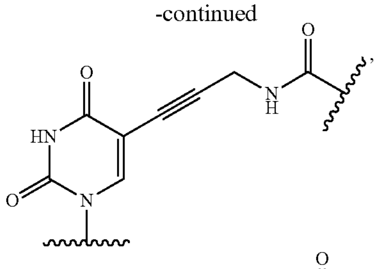

or

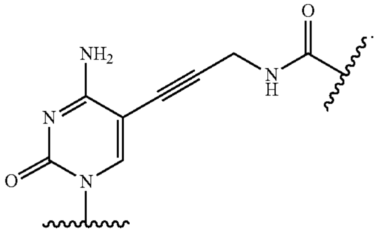

In embodiments, B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. In embodiments, B is a divalent cytosine or a derivative thereof. In embodiments, B is a divalent guanine or a derivative thereof. In embodiments, B is a divalent adenine or a derivative thereof. In embodiments, B is a divalent thymine or a derivative thereof. In embodiments, B is a divalent uracil or a derivative thereof. In embodiments, B is a divalent hypoxanthine or a derivative thereof. In embodiments, B is a divalent xanthine or a derivative thereof. In embodiments, B is a divalent 7-methylguanine or a derivative thereof. In embodiments, B is a divalent 5,6-dihydrouracil or a derivative thereof. In embodiments, B is a divalent 5-methylcytosine or a derivative thereof. In embodiments, B is a divalent 5-hydroxymethylcytosine or a derivative thereof. In embodiments, B is a divalent cytosine. In embodiments, B is a divalent guanine. In embodiments, B is a divalent adenine. In embodiments, B is a divalent thymine. In embodiments, B is a divalent uracil. In embodiments, B is a divalent hypoxanthine. In embodiments, B is a divalent xanthine. In embodiments, B is a divalent 7-methylguanine. In embodiments, B is a divalent 5,6-dihydrouracil. In embodiments, B is a divalent 5-methylcytosine. In embodiments, B is a divalent 5-hydroxymethylcytosine.

In embodiments, $L^{100}$ is $-L^{101}-L^{102}-L^{103}-L^{104}-L^{105}-$. In embodiments, $L^{100}$ is independently a bioconjugate linker; a cleavable linker, a self-immolative linker, a linker capable of dendritic amplification of signal (e.g., capable of increasing fluorescence by releasing fluorophores from the remainder of the linker, optionally wherein the fluorescence is increased following release), a trivalent linker, or a self-immolative dendrimer linker (e.g., capable of increasing fluorescence by releasing fluorophores from the remainder of the linker). In embodiments, $L^{100}$ is independently a bioconjugate linker. In embodiments, $L^{100}$ is independently a cleavable linker. In embodiments, $L^{100}$ is independently a self-immolative linker. In embodiments, $L^{100}$ is independently a linker capable of dendritic amplification of signal (e.g., capable of increasing fluorescence by releasing fluorophores). In embodiments, $L^{100}$ is independently a trivalent linker. In embodiments, $L^{100}$ is independently a self-immolative dendrimer linker (e.g., capable of increasing fluorescence by releasing fluorophores).

In embodiments, $L^{100}$ includes

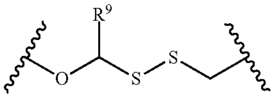

or

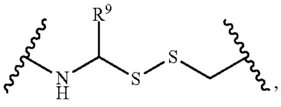

, wherein $R^9$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is a moiety represented by $R^7$. In embodiments, $L^{100}$ includes

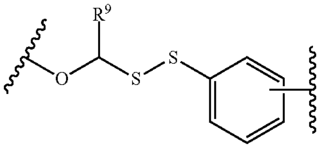

or

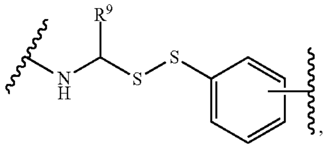

, or w wherein $R^9$ is as described herein. In embodiments, $L^{100}$ includes

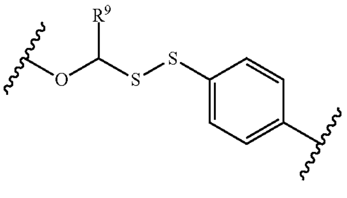

or

-continued

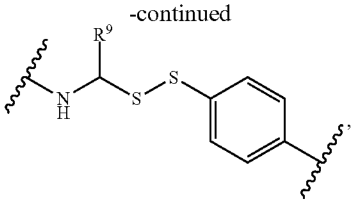

, wherein $R^9$ is as described herein.

In embodiments, $L^{100}$ includes a thio-trigger moiety. In embodiments, $L^{100}$ includes

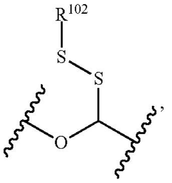

, wherein $R^{102}$ is as described herein. In embodiments, $L^{100}$ includes

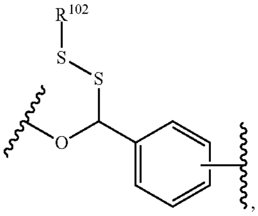

, wherein $R^{102}$ is as described herein. In embodiments, $L^{100}$ includes

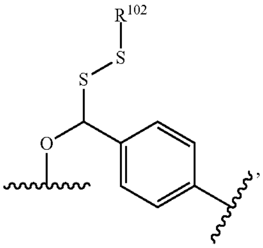

, wherein $R^{102}$ is as described herein. In embodiments, $R^{102}$ is unsubstituted $C_1$-$C_4$ alkyl. In embodiments, $R^{102}$ is unsubstituted $C_1$ alkyl. In embodiments, $R^{102}$ is unsubstituted $C_2$ alkyl. In embodiments, $R^{102}$ is unsubstituted $C_3$ alkyl. In embodiments, $R^{102}$ is unsubstituted $C_4$ alkyl. In embodiments, $L^{100}$ includes

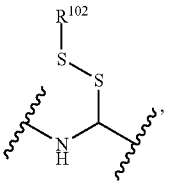

, wherein $R^{102}$ is as described herein. In embodiments, $L^{100}$ includes

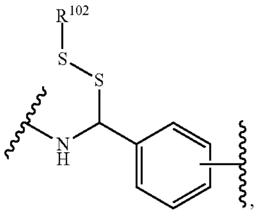

wherein $R^{102}$ is as described herein. In embodiments, $L^{100}$ includes

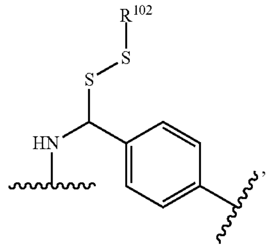

wherein $R^{102}$ is as described herein. In embodiments, $R^{102}$ is unsubstituted $C_1$-$C_4$ alkyl. In embodiments, $R^{102}$ is unsubstituted $C_1$ alkyl. In embodiments, $R^{102}$ is unsubstituted $C_2$ alkyl. In embodiments, $R^{102}$ is unsubstituted $C_3$ alkyl. In embodiments, $R^{102}$ is unsubstituted $C_4$ alkyl.

$L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, thio-trigger moiety, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; a cleavable linker, a self-immolative linker, a linker capable of dendritic amplification of signal (e.g., capable of increasing fluorescence by releasing fluorophores from the remainder of the linker), a trivalent linker, or a self-immolative dendrimer linker (e.g., capable of increasing fluorescence by releasing fluorophores from the remainder of the linker). In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, substituted or unsubstituted alkylene (e.g., —CH(OH)— or —C(CH$_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; or a cleavable linker. In embodiments, $L^{101}$, $L^{102}$, $L^{103}$, $L^{104}$, and $L^{105}$ independently includes PEG. In embodiments, $L^{101}$, $L^{102}$, $L^{103}$, $L^{104}$, and $L^{105}$ independently includes

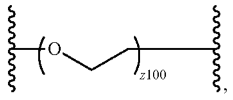

wherein z100 is independently 1 to 8. In embodiments, z100 is 1. In embodiments, z100 is 2. In embodiments, z100 is 3. In embodiments, z100 is 4. In embodiments, z100 is 5. In embodiments, z100 is 6. In embodiments, z100 is 7. In embodiments, z100 is 8. In embodiments, z100 is 2 to 8. In embodiments, z100 is 4 to 6.

In embodiments, at least one of $L^{101}$, $L^{102}$, $L^{103}$, $L^{104}$, and $L^{105}$ independently includes

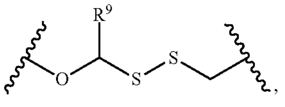

wherein $R^9$ is as described herein. In embodiments, at least one of $L^{101}$, $L^{102}$, $L^{103}$, $L^{104}$, and $L^{105}$ independently includes

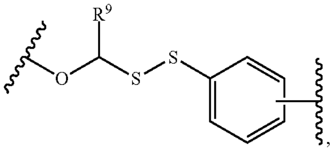

wherein $R^9$ is as described herein. In embodiments, at least one of $L^{101}$, $L^{102}$, $L^{103}$, $L^{104}$, and $L^{105}$ independently includes

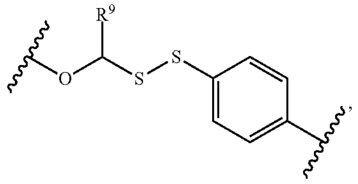

wherein $R^9$ is as described herein. In embodiments, at least one of $L^{101}$, $L^{102}$, $L^{103}$, $L^{104}$, and $L^{105}$ independently includes

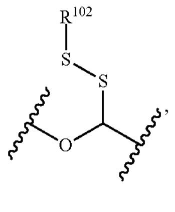

wherein $R^{102}$ is as described herein. In embodiments, at least one of $L^{101}$, $L^{102}$, $L^{103}$, $L^{104}$, and $L^{105}$ independently includes

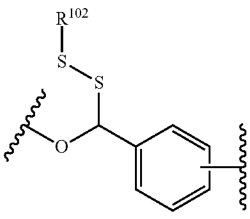

, wherein $R^{102}$ is as described herein. In embodiments, at least one of $L^{101}$, $L^{102}$, $L^{103}$, $L^{104}$, and $L^{105}$ independently includes

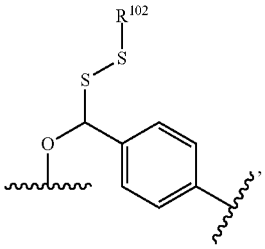

, wherein $R^{102}$ is as described herein. In embodiments, at least one of $L^{101}$, $L^{102}$, $L^{103}$, $L^{104}$, and $L^{105}$ independently includes

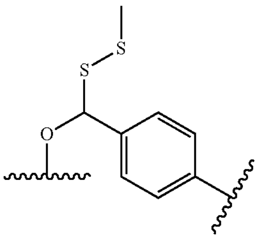

or

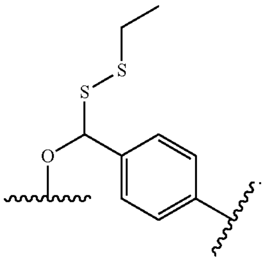

.

In embodiments, at least one of $L^{101}$, $L^{102}$, $L^{103}$, $L^{104}$, and $L^{105}$ independently includes

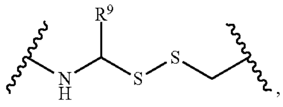

, wherein $R^9$ is as described herein. In embodiments, at least one of $L^{101}$, $L^{102}$, $L^{103}$, $L^{104}$, and $L^{105}$ independently includes

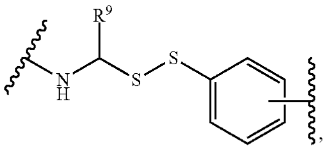

, wherein $R^9$ is as described herein. In embodiments, at least one of $L^{101}$, $L^{102}$, $L^{103}$, $L^{104}$ and $L^{105}$ independently includes

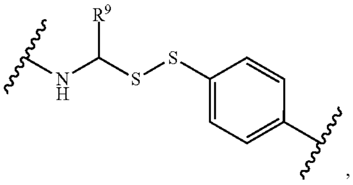

, wherein $R^9$ is as described herein. In embodiments, at least one of $L^{101}$, $L^{102}$, $L^{103}$, $L^{104}$, and $L^{105}$ independently includes

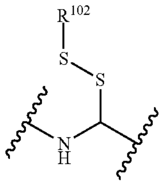

, wherein $R^{102}$ is as described herein. In embodiments, at least one of $L^{101}$, $L^{102}$, $L^{103}$, $L^{104}$, and $L^{105}$ independently includes

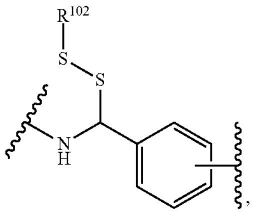

, wherein $R^{102}$ is as described herein. In embodiments, at least one of $L^{101}$, $L^{102}$, $L^{103}$, $L^{104}$, and $L^{105}$ independently includes

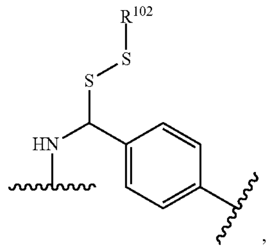

, wherein $R^{102}$ is as described herein. In embodiments, at least one of $L^{101}$, $L^{102}$, $L^{103}$, $L^{104}$, and $L^{105}$ independently includes

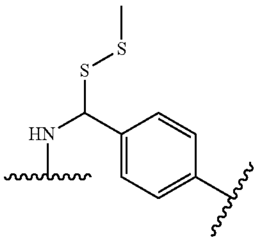

or

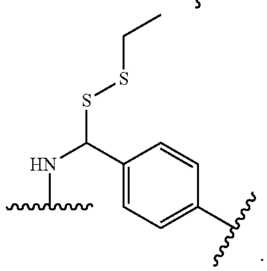

.

In embodiments, $L^{100}$ is $-L^{101}-L^{102}-L^{103}-L^{104}-L^{105}-$. In embodiments, $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{100}$ is $-L^{101}$-O—CH(—$SR^{100}$)-$L^{103}$-$L^{104}$-$L^{105}$-; $-L^{101}$-O—C($CH_3$)(—$SR^{100}$)-$L^{103}$-$L^{104}$-$L^{105}$-; $-L^{101}$-O—CH($N_3$)-$L^{103}$-$L^{104}$-$L^{105}$-; or $-L^{101}$-O—CH($N_3$)—$CH_2$—O-$L^{104}$-$L^{105}$-; wherein $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{100}$ is —$SR^{102}$ or —CN; and $R^{102}$ is $R^{102B}$-substituted or unsubstituted $C_1$-$C_4$ alkyl. In embodiments, $R^{102}$ is unsubstituted $C_1$-$C_4$ alkyl. In embodiments, $R^{100}$ is —$SO_3H$.

In embodiments, $L^{100}$ is $-L^{101}$-O—CH(—$SR^{100}$)-$L^{103}$-$L^{104}$-$L^{105}$- or $-L^{101}$-O—C($CH_3$)(—$SR^{100}$)-$L^{103}$-$L^{104}$-$L^{105}$-; wherein $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene; $R^{100}$ is —$SR^{102}$ or —CN; and $R^{102}$ is $R^{102B}$-substituted or unsubstituted $C_1$-$C_4$ alkyl. In embodiments, $R^{102}$ is unsubstituted $C_1$-$C_4$ alkyl. In embodiments, $R^{100}$ is —$SO_3H$.

In embodiments, $L^{100}$ is $-L^{101}$-O—CH(—$SR^{100}$)-$L^{103}$-$L^{104}$-$L^{105}$- or $-L^{101}$-O—C($CH_3$)(—$SR^{100}$)-$L^{103}$-$L^{104}$-$L^{105}$-; wherein $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; $R^{100}$ is —$SR^{102}$ or —CN; and $R^{102}$ is $R^{102B}$-substituted or unsubstituted $C_1$-$C_4$ alkyl. In embodiments, $R^{102}$ is unsubstituted $C_1$-$C_4$ alkyl. In embodiments, $R^{100}$ is —$SO_3H$.

In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; a bioconjugate linker; or a cleavable linker.

In embodiments, $L^{101}$, $L^{102}$, $L^{103}$, $L^{104}$, and $L^{105}$ are independently a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$, $L^{102}$, $L^{103}$, $L^{104}$, or $L^{105}$ is independently a bioconjugate linker. In embodiments, $L^{101}$, $L^{102}$, $L^{103}$, $L^{104}$, or $L^{105}$ is independently a cleavable linker. In embodiments, $L^{101}$, $L^{102}$, $L^{103}$, $L^{104}$, or $L^{105}$ is independently a self-immolative linker. In embodiments, $L^{101}$, $L^{102}$, $L^{103}$, $L^{104}$, or $L^{105}$ is independently a linker capable of dendritic amplification of signal (e.g., capable of increasing fluorescence by releasing fluorophores). In embodiments, $L^{101}$, $L^{102}$, $L^{103}$, $L^{104}$, or $L^{105}$ is independently a trivalent linker. In embodiments, $L^{101}$, $L^{102}$, $L^{103}$, $L^{104}$, or $L^{105}$ is independently a self-immolative dendrimer linker (e.g., capable of increasing fluorescence by releasing fluorophores).

In embodiments, $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$, $L^{102}$, $L^{103}$, $L^{104}$, and/or $L^{105}$ are independently a bond, —NH—, —S—, —O—, —C(O)—, —C(O)O—, —OC(O)—, —CH(OH)—, —NHC(O)—, —C(O)NH—, —NHC(O)NH—, —NHC(NH)NH—, —C(S)—, or —C($CH_2$)—.

In embodiments, $L^{100}$ is $-L^{101}$-O—CH(—$SR^{100}$)-$L^{103}$-$L^{104}$-$L^{105}$- or $-L^{101}$-O—C($CH_3$)(—$SR^{100}$)-$L^{103}$-$L^{104}$-$L^{105}$. $R^{100}$ is —$SR^{102}$ or —CN. In embodiments, $R^{100}$ is —$SR^{102}$. In embodiments, $R^{100}$ is —CN. $R^{102}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2C_1$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{100}$ is —$SO_3H$.

In embodiments, $L^{100}$ is
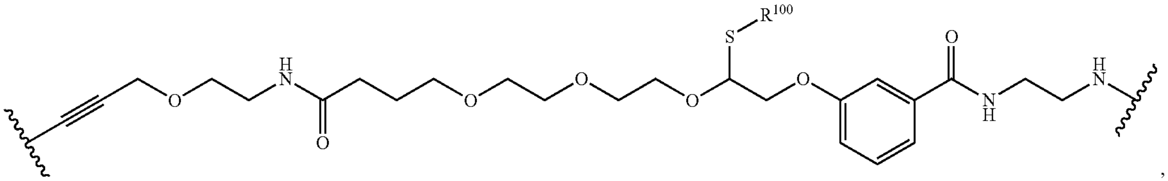
,
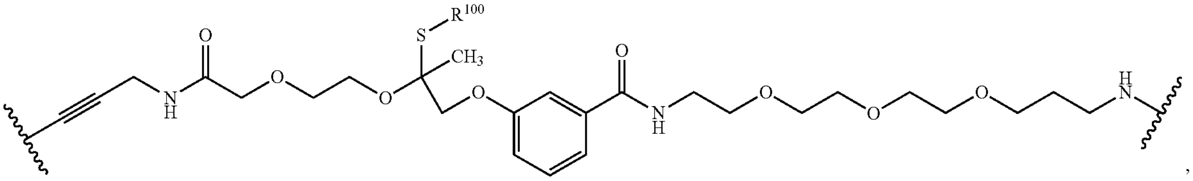
,
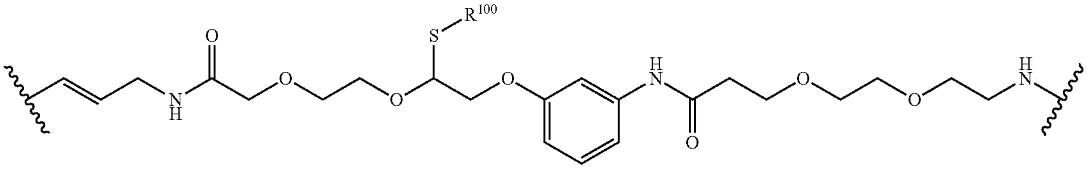
,
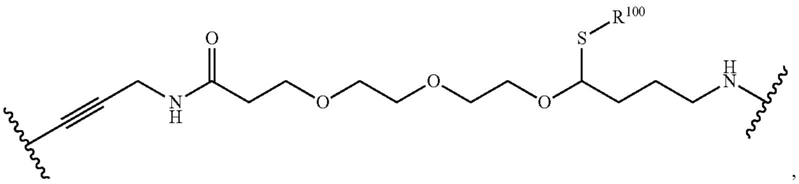
,
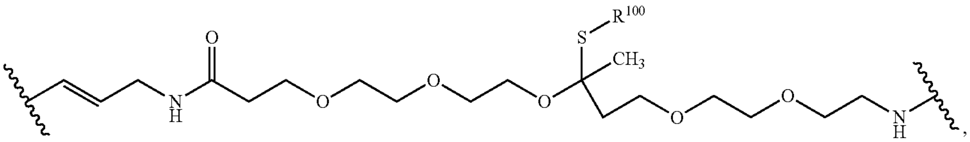
,
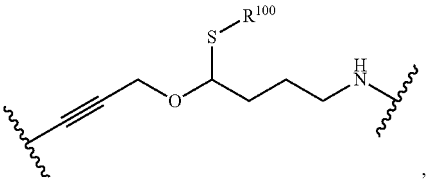
,
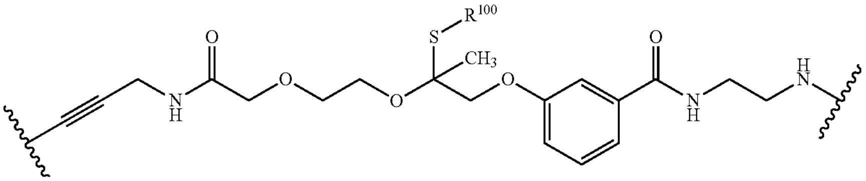
, or
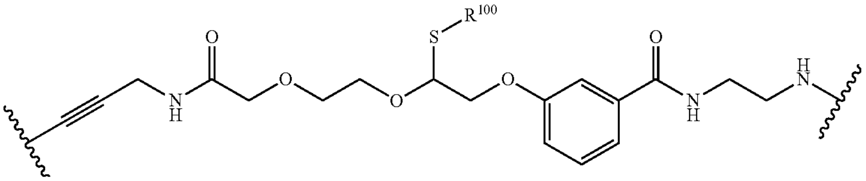
.

In embodiments, $L^{100}$ is
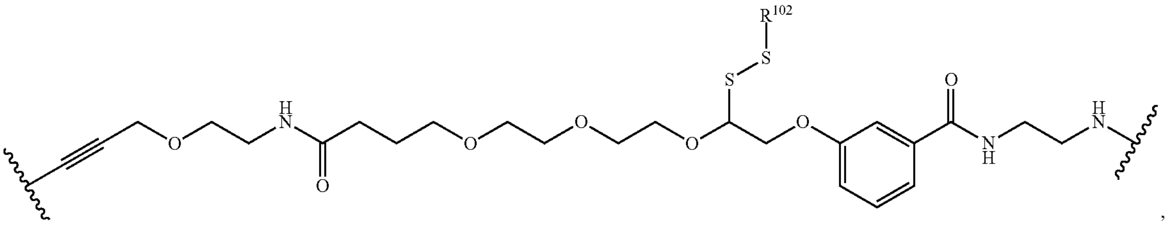
,
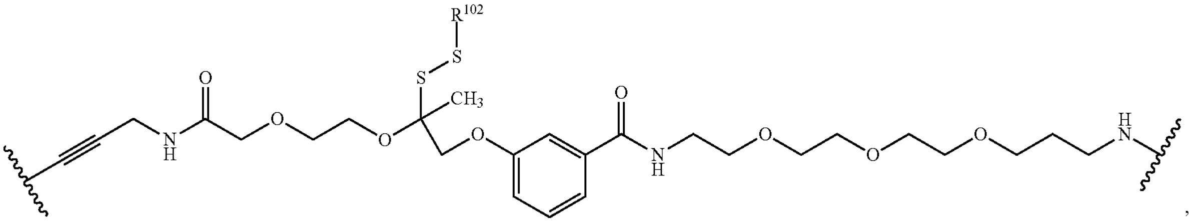
,
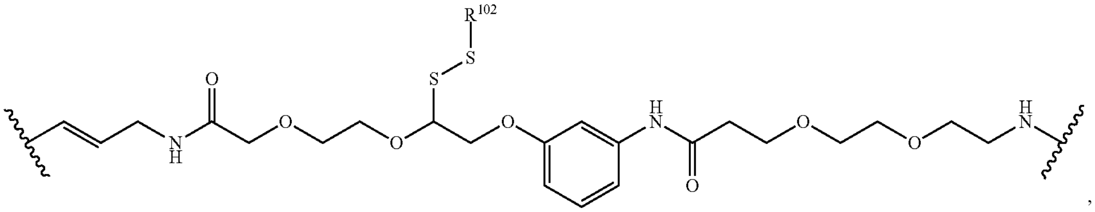
,
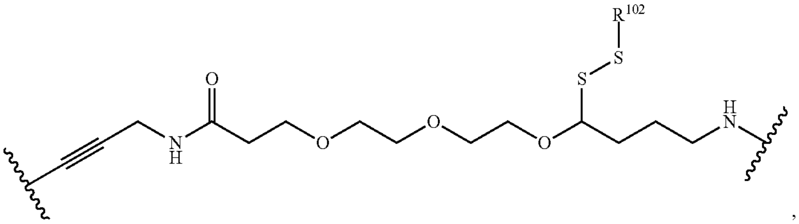
,
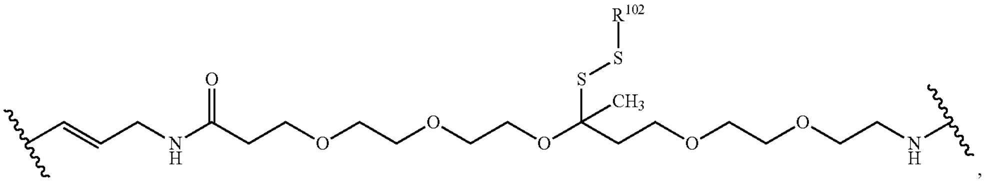
,
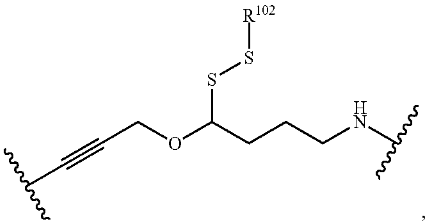
,
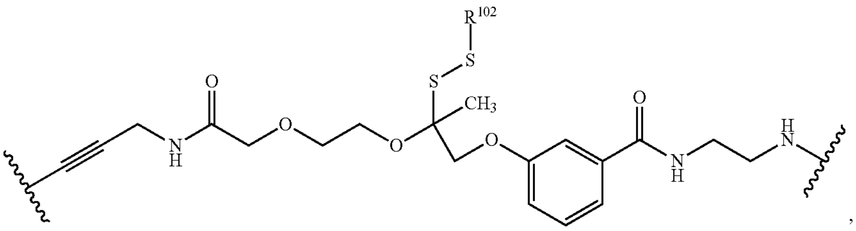
, or -continued

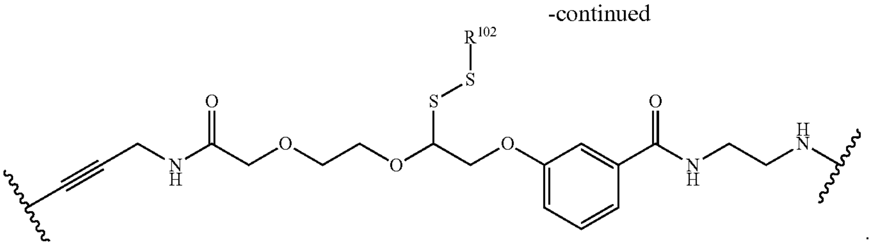

.

In embodiments, $L^{100}$ is

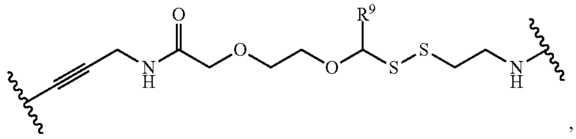

, wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^9$ is substituted or unsubstituted alkyl. In embodiments, $R^9$ is substituted or unsubstituted aryl, or substituted or unsubstituted heteroaryl. In embodiments, $L^{100}$ is

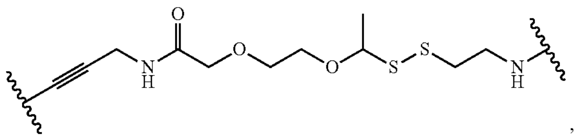

,

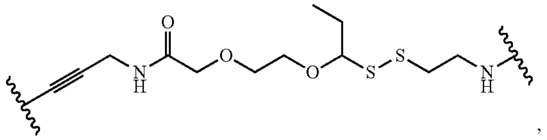

, or

-continued

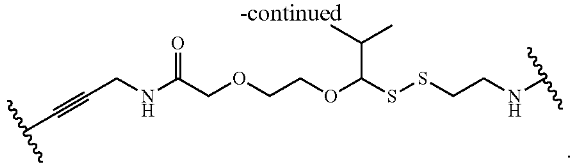

.

In embodiments, $L^{100}$ is

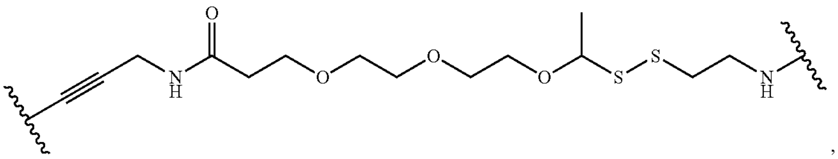

,

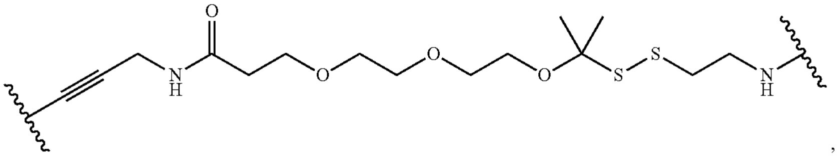

, or

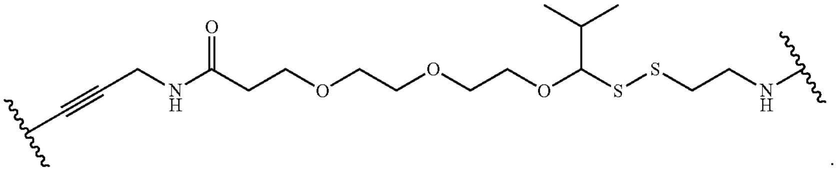

.

In embodiments, $L^{100}$ is

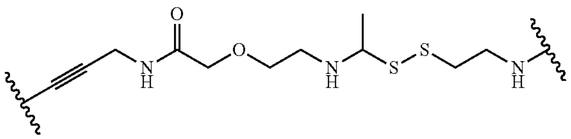

,

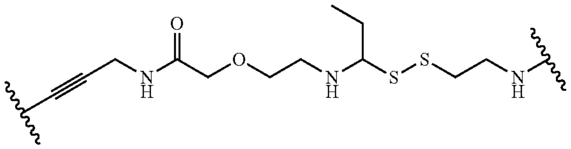

,

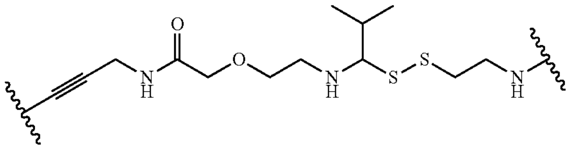

.

In embodiments, $L^{100}$ is
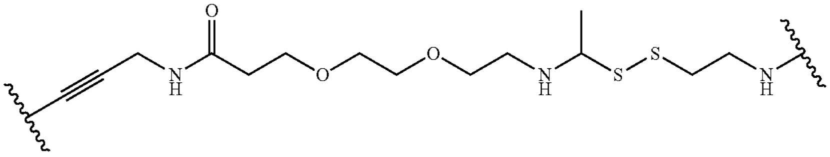
,
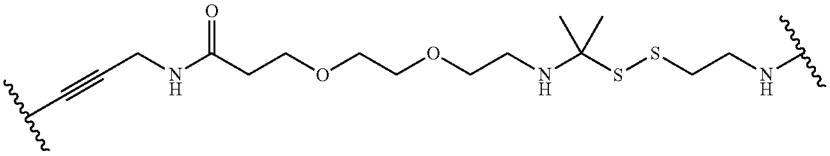
, or
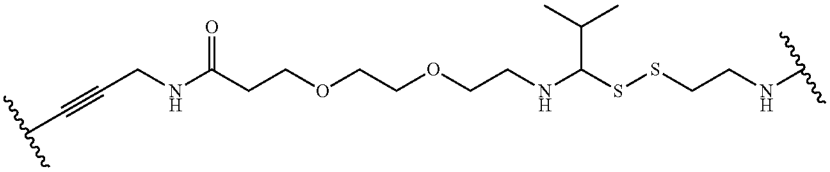
.
In embodiments, $L^{100}$ is
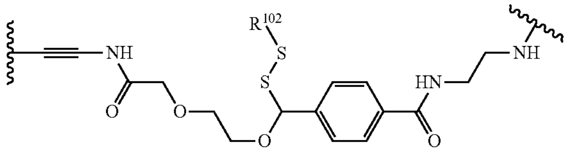
,
wherein $R^{102}$ is as described herein. In embodiments, $L^{100}$ is
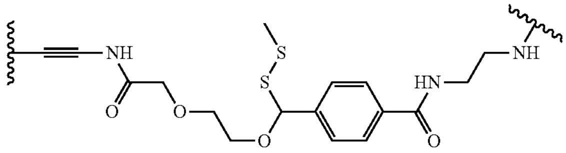
,
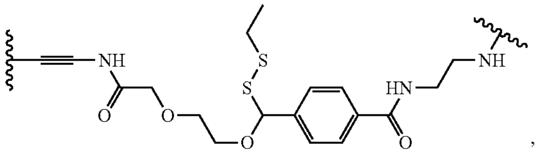
, or
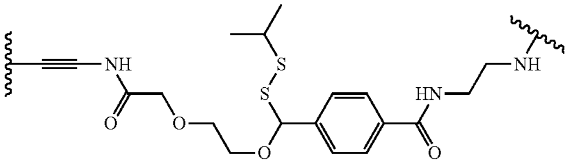
.
In embodiments, $L^{100}$ is
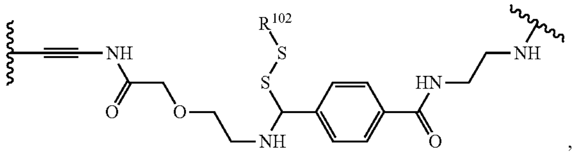
,
wherein $R^{102}$ is as described herein. In embodiments, $L^{100}$ is
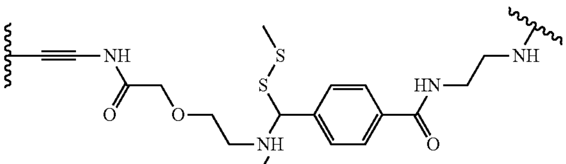
,
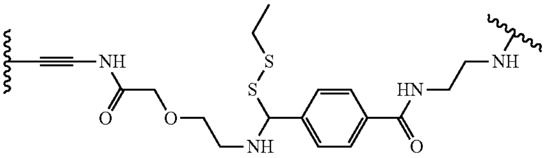
, or
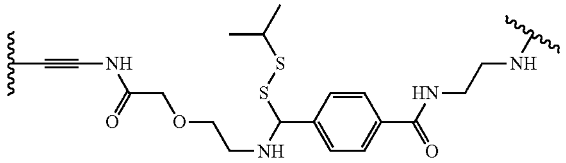
.
In embodiments, $L^{100}$ is
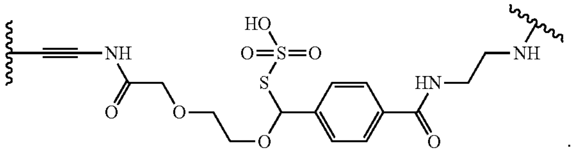 [SMILES: *C#CNC(=O)COCCOC(SS(=O)(=O)O)c1ccc(C(=O)NCCN*)cc1]
.
In embodiments, $L^{100}$ is
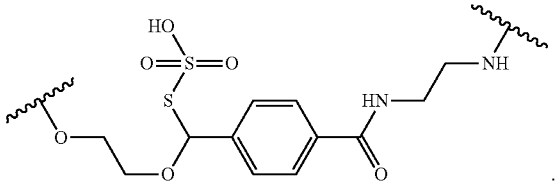 [SMILES: *NCCNC(=O)c1ccc(C(OCCO*)SS(=O)(=O)O)cc1]
.
Methods for cleaving the disulfide bond of —S—$SO_3H$ bonds are known in the art, see for example Meguro et al.

Tetrahedron Letters 61 (2020) 152198, which is incorporated herein by reference in its entirety. In embodiments, the cleaving agent is aqueous sodium sulfide ($Na_2S$). In embodiments, the cleaving agent is TCEP or THPP.

In embodiments, $-L^{101}-L^{102}-L^{103}-L^{104}-L^{105}-$ has the formula:

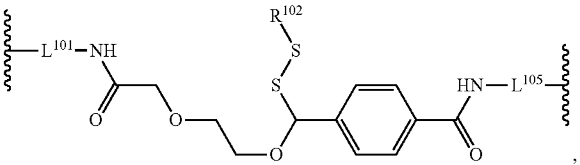

wherein $L^{101}$, $R^{102}$, and $L^{105}$ are as described herein. In embodiments, $R^{102}$ is unsubstituted $C_1$-$C_6$ alkyl. In embodiments, $R^{102}$ is unsubstituted aryl. In embodiments, $R^{102}$ is unsubstituted heteroaryl. In embodiments, $-L^{101}-L^{102}-L^{103}-L^{104}-L^{105}-$ has the formula:

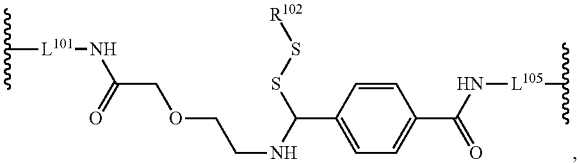

wherein $L^{101}$, $R^{102}$, and $L^{105}$ are as described herein. In embodiments, $R^{102}$ is unsubstituted $C_1$-$C_6$ alkyl. In embodiments, $R^{102}$ is unsubstituted aryl. In embodiments, $R^{102}$ is unsubstituted heteroaryl.

In embodiments, $L^{100}$ is

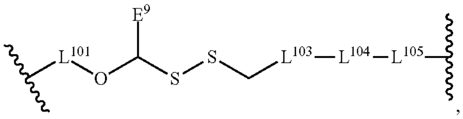

wherein $L^{101}$, $L^{103}$, $L^{104}$, $L^{105}$, and $R^9$ are as described herein. In embodiments, $L^{100}$ is

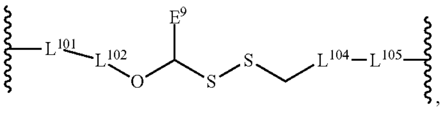

wherein $L^{101}$, $L^{102}$, $L^{104}$, $L^{105}$, and $R^9$ are as described herein. In embodiments, $L^{100}$ is

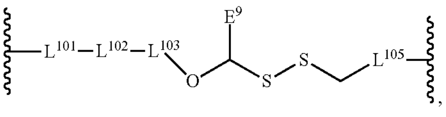

wherein $L^{101}$, $L^{102}$, $L^{103}$, $L^{105}$, and $R^9$ are as described herein. In embodiments, $L^{100}$ is

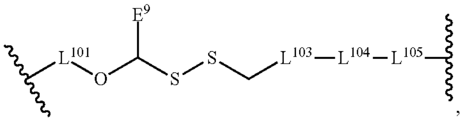

wherein $L^{101}$, $L^{103}$, $L^{104}$, $L^{105}$, and $R^9$ are as described herein. In embodiments, $L^{100}$ is

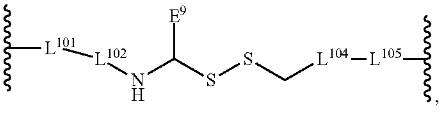

wherein $L^{101}$, $L^{102}$, $L^{104}$, $L^{105}$, and $R^9$ are as described herein. In embodiments, $L^{100}$ is

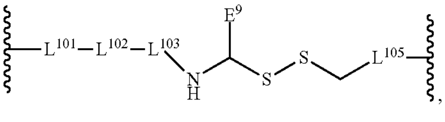

wherein $L^{101}$, $L^{102}$, $L^{103}$, $L^{105}$, and $R^9$ are as described herein.

In embodiments, $L^{102}$ is

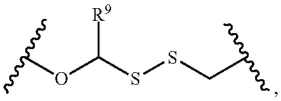

wherein $R^9$ is as described herein. In embodiments, $L^{103}$ is

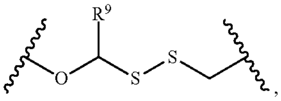

wherein $R^9$ is as described herein. In embodiments, $L^{104}$ is

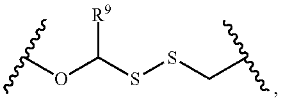

wherein $R^9$ is as described herein. In embodiments, $L^{102}$ is

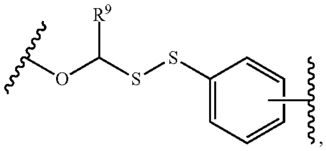

wherein $R^9$ is as described herein. In embodiments, $L^{103}$ is

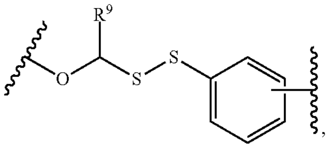

wherein $R^9$ is as described herein. In embodiments, $L^{104}$ is

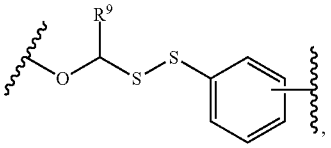

wherein $R^9$ is as described herein. In embodiments, $L^{102}$ is

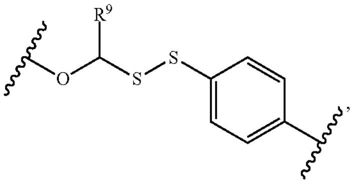

wherein $R^9$ is as described herein. In embodiments, $L^{103}$ is

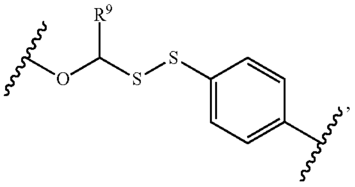

wherein $R^9$ is as described herein. In embodiments, $L^{104}$ is

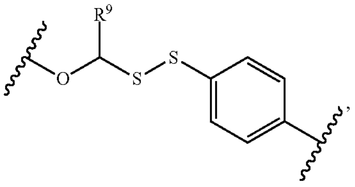

wherein $R^9$ is as described herein.

In embodiments, $L^{102}$ is

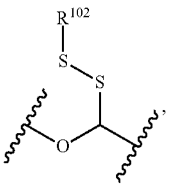

wherein $R^{102}$ is as described herein. In embodiments, $L^{103}$ is

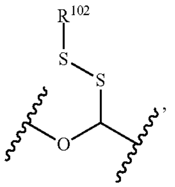

wherein $R^{102}$ is as described herein. In embodiments, $L^{104}$ is

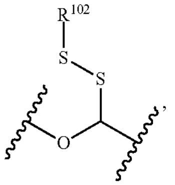

wherein $R^{102}$ is as described herein. In embodiments, $L^{102}$ is

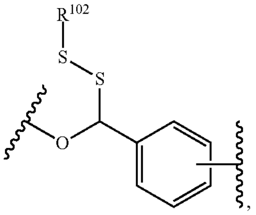

wherein $R^{102}$ is as described herein. In embodiments, $L^{103}$ is

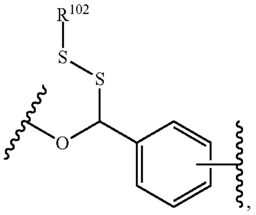

wherein $R^{102}$ is as described herein. In embodiments, $L^{104}$ is

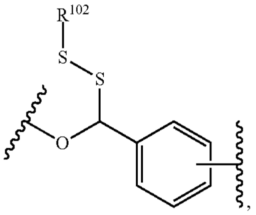

wherein $R^{102}$ is as described herein. In embodiments, $L^{102}$ is

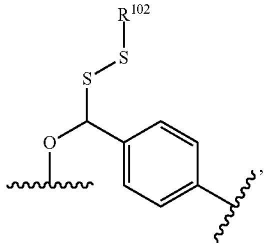

wherein $R^{102}$ is as described herein. In embodiments, $L^{103}$ is

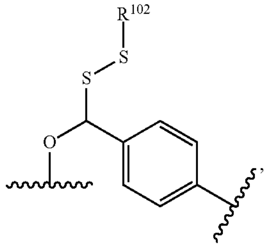

wherein $R^{102}$ is as described herein. In embodiments, $L^{104}$ is

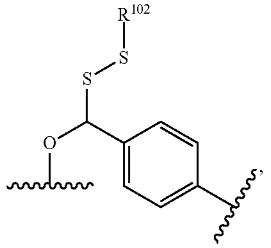

wherein $R^{102}$ is as described herein.

In embodiments, $R^9$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In embodiments, $R^9$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, $R^{10}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10}$-substituted or unsubstituted heteroalkyl (e.g., 2 to 20, 8 to 20, 2 to 10, 2 to 8, 2 to 6, or 2 to 4 membered), $R^{10}$-substituted or unsubstituted cycloalkyl (e.g., $C_3$-$C_8$, $C_3$-$C_6$, or $C_5$-$C_6$), $R^{10}$-substituted or unsubstituted heterocycloalkyl (e.g., 3 to 8, 3 to 6, or 5 to 6 membered), $R^{10}$-substituted or unsubstituted aryl (e.g., $C_6$-$C_{10}$, $C_{10}$, or phenyl), or $R^{10}$-substituted or unsubstituted heteroaryl (e.g., 5 to 10, 5 to 9, or 5 to 6 membered). In embodiments, $R^9$ is $R^{10}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10}$-substituted or unsubstituted heteroalkyl (e.g., 2 to 20, 8 to 20, 2 to 10, 2 to 8, 2 to 6, or 2 to 4 membered), $R^{10}$-substituted or unsubstituted cycloalkyl (e.g., $C_3$-$C_8$, $C_3$-$C_6$, or $C_5$-$C_6$), $R^{10}$-substituted or unsubstituted heterocycloalkyl (e.g., 3 to 8, 3 to 6, or 5 to 6 membered), $R^{10}$-substituted or unsubstituted aryl (e.g., $C_6$-$C_{10}$, $C_{10}$, or phenyl), or $R^{10}$-substituted or unsubstituted heteroaryl (e.g., 5 to 10, 5 to 9, or 5 to 6 membered). In embodiments, $R^9$ is unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^9$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^9$ is independently unsubstituted $C_1$-$C_6$ alkyl. In embodiments, $R^9$ is independently unsubstituted $C_1$-$C_4$ alkyl. In embodiments, $R^9$ is independently unsubstituted methyl. In embodiments, $R^9$ is independently unsubstituted ethyl. In embodiments, $R^9$ is independently unsubstituted propyl. In embodiments, $R^9$ is independently unsubstituted tert-butyl.

In embodiments, $R^9$ is independently unsubstituted $C_3$-$C_8$ cycloalkyl. In embodiments, $R^9$ is independently unsubstituted $C_3$-$C_6$ cycloalkyl. In embodiments, $R^9$ is independently unsubstituted $C_5$-$C_6$ cycloalkyl. In embodiments, $R^9$ is independently unsubstituted 3 to 8 membered heterocycloalkyl. In embodiments, $R^9$ is independently unsubstituted 3 to 6 membered heterocycloalkyl. In embodiments, $R^9$ is independently unsubstituted 5 to 6 membered heterocycloalkyl. In embodiments, $R^9$ is independently unsubstituted phenyl. In embodiments, $R^9$ is independently unsubstituted 5 to 6 membered heteroaryl. In embodiments, $R^9$ is independently unsubstituted 5 membered heteroaryl. In embodiments, $R^9$ is independently unsubstituted 6 membered heteroaryl.

In embodiments, $R^9$ is

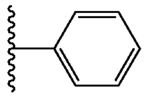,

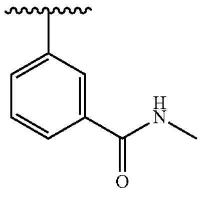,

-continued
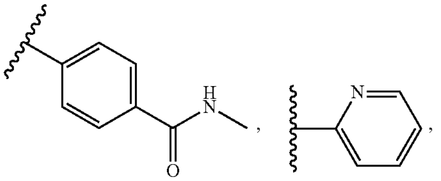
, ,
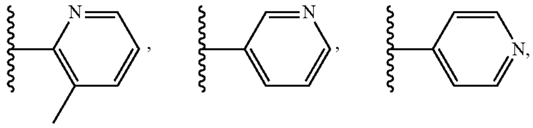
, , ,
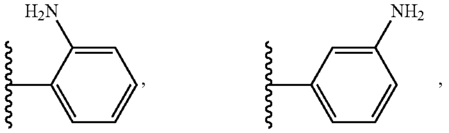
, ,
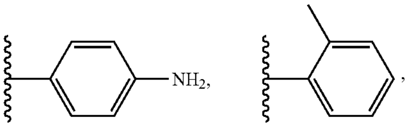
,
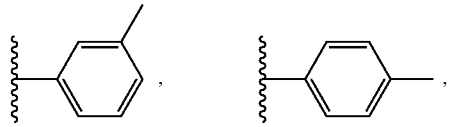
, ,
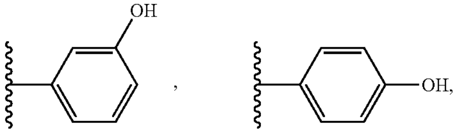
,
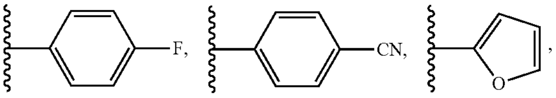
,
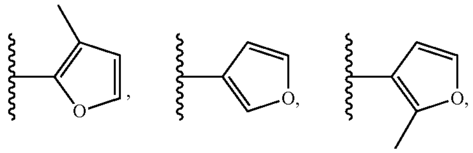
, , ,
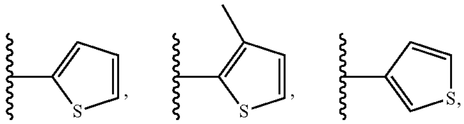
, , ,
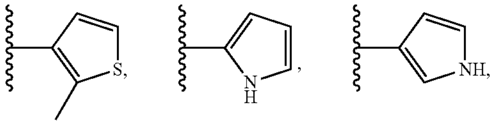
, ,
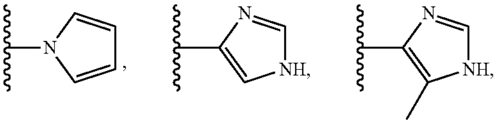
, , ,
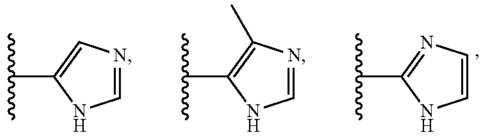
, , ,
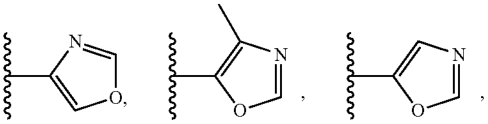
, , ,
-continued
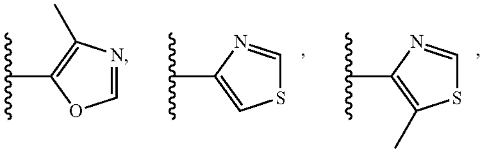
, , ,
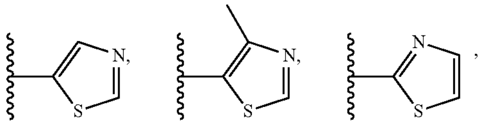
, , ,
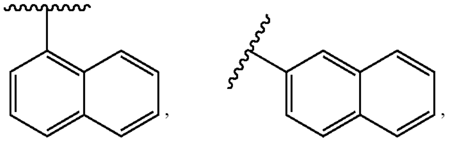
, ,
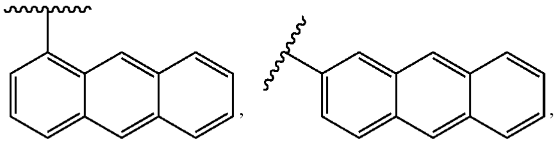
, ,
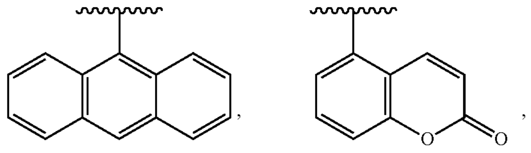
, ,
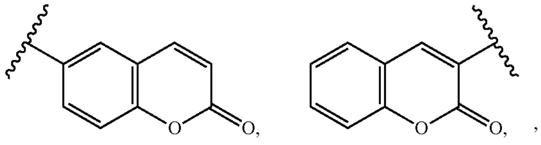
, ,
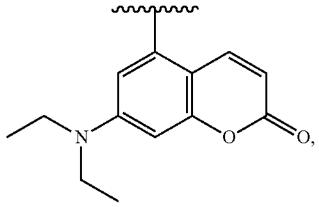
,
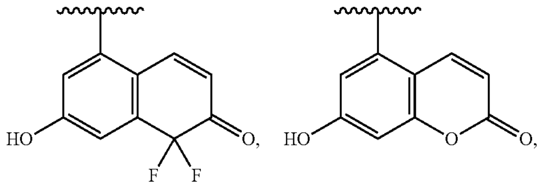
, ,
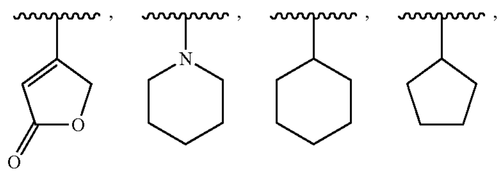
, , , ,
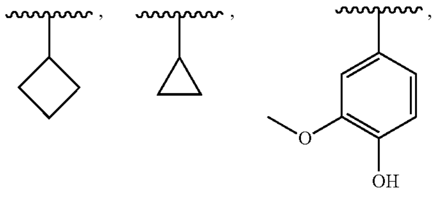
, , , -continued
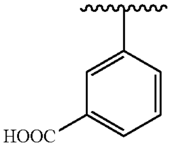, 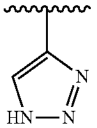, 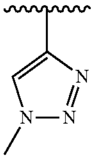,
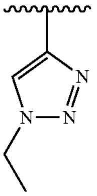, 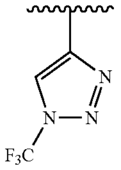, 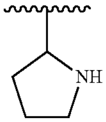, 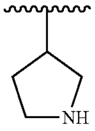,
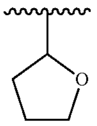, or 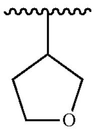.
In embodiments, $R^9$ is
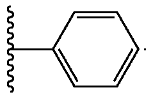
In embodiments, $R^9$ is
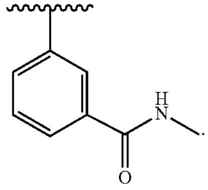 [SMILES: *c1cccc(C(=O)NC)c1]
In embodiments, $R^9$ is
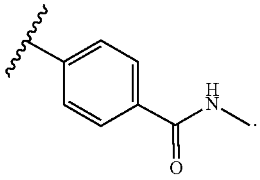 [SMILES: *c1ccc(C(=O)NC)cc1]
In embodiments, $R^9$ is
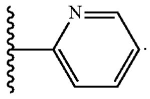 [SMILES: *c1ccccn1]
In embodiments, $R^9$ is
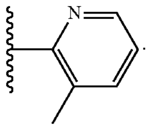 [SMILES: *c1ncccc1C]
In embodiments, $R^9$ is
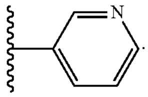
In embodiments, $R^9$ is
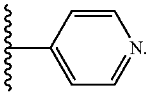 [SMILES: *c1ccncc1]
In embodiments, $R^9$ is
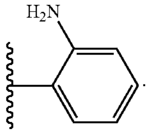 [SMILES: *c1ccccc1N]
In embodiments, $R^9$ is
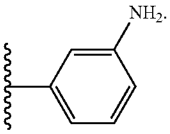 [SMILES: *c1cccc(N)c1]
In embodiments, $R^9$ is
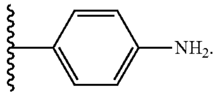
In embodiments, $R^9$ is
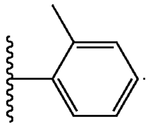 [SMILES: *c1ccccc1C]

In embodiments, $R^9$ is
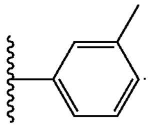
In embodiments, $R^9$ is
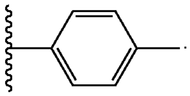
In embodiments, $R^9$ is
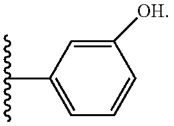 [SMILES: *c1cccc(O)c1]
In embodiments, $R^9$ is
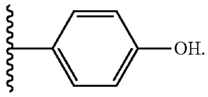 [SMILES: *c1ccc(O)cc1]
In embodiments, $R^9$ is
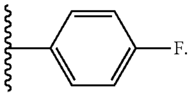 [SMILES: *c1ccc(F)cc1]
In embodiments $R^9$ is
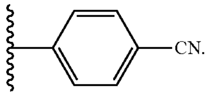
In embodiments, $R^9$ is
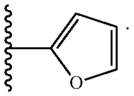
In embodiments, $R^9$ is
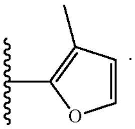 [SMILES: *c1occc1C]
In embodiments, $R^9$ is
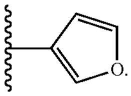
In embodiments, $R^9$ is
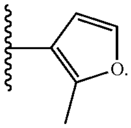
In embodiments, $R^9$ is
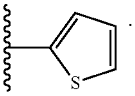
In embodiments, $R^9$ is
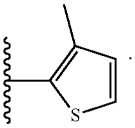
In embodiments, $R^9$ is
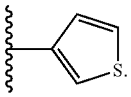 [SMILES: *c1ccoc1]
In embodiments, $R^9$ is
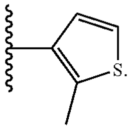 [SMILES: *c1ccoc1C]
In embodiments, $R^9$ is H
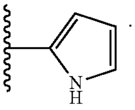

In embodiments, $R^9$ is
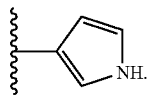 [SMILES: *c1cc[nH]c1]
In embodiments, $R^9$ is
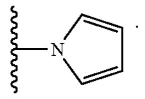
In embodiments, $R^9$ is
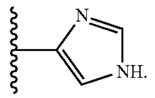 [SMILES: *c1c[nH]cn1]
In embodiments, $R^9$ is
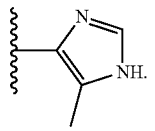 [SMILES: *c1nc[nH]c1C]
In embodiments, $R^9$ is
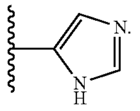
In embodiments, $R^9$ is
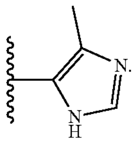 [SMILES: *c1[nH]cnc1C]
In embodiments, $R^9$ is
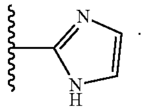 [SMILES: *c1ncc[nH]1]
In embodiments, $R^9$ is
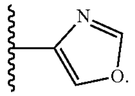
In embodiments, $R^9$ is
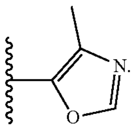 [SMILES: *c1ocnc1C]
In embodiments, $R^9$ is
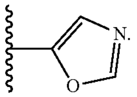
In embodiments, $R^9$ is
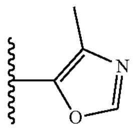 [SMILES: *c1ocnc1C]
In embodiments, $R^9$ is
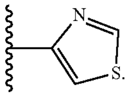 [SMILES: *c1cscn1]
In embodiments, $R^9$ is
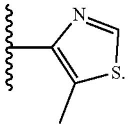 [SMILES: *c1ncsc1C]
In embodiments, $R^9$ is
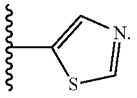 [SMILES: *c1cncs1]
In embodiments, $R^9$ is
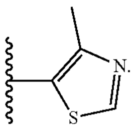 [SMILES: *c1scnc1C]

In embodiments, $R^9$ is
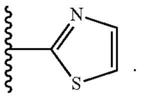
In embodiments $R^9$ is
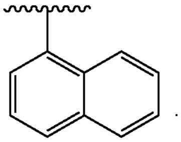 [SMILES: *c1cccc2ccccc12]
In embodiments, $R^9$ is
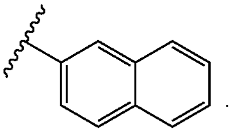 [SMILES: *c1ccc2ccccc2c1]
In embodiments, R9 is
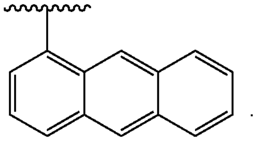 [SMILES: *c1cccc2cc3ccccc3cc12]
In embodiments, $R^9$ is
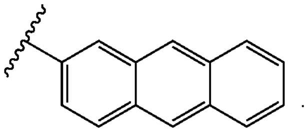 [SMILES: *c1ccc2cc3ccccc3cc2c1]
In embodiments, $R^9$ is
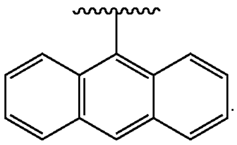 [SMILES: *c1c2ccccc2cc2ccccc12]
In embodiments, $R^9$ is
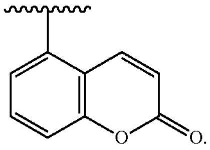 [SMILES: *c1cccc2oc(=O)ccc12]
In embodiments, $R^9$ is
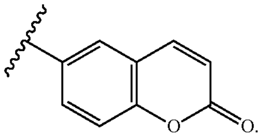 [SMILES: *c1ccc2oc(=O)ccc2c1]
In embodiments, $R^9$ is
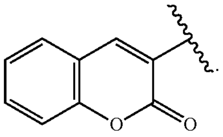 [SMILES: *c1cc2ccccc2oc1=O]
In embodiments, $R^9$ is
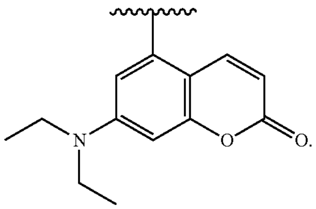 [SMILES: *c1cc(N(CC)CC)cc2oc(=O)ccc12]
In embodiments, $R^9$ is
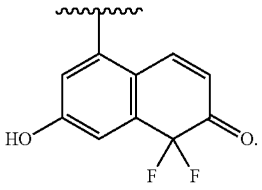 [SMILES: *c1cc(O)cc2c1C=CC(=O)C2(F)F]
In embodiments, $R^9$ is
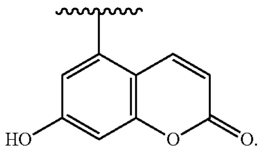 [SMILES: *c1cc(O)cc2oc(=O)ccc12]
In embodiments, $R^9$ is
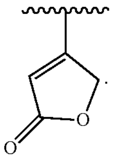 [SMILES: *C1=CC(=O)OC1]

In embodiments, $R^9$ is
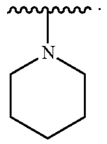
In embodiments, $R^9$ is
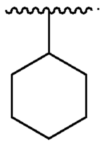
In embodiments $R^9$ is
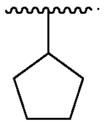
In embodiments, $R^9$ is
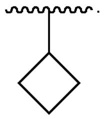
In embodiments, $R^9$ is
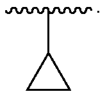 [SMILES: *C1CC1]
In embodiments, $R^9$ is
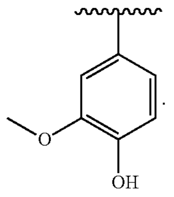 [SMILES: *c1ccc(O)c(OC)c1]
In embodiments, $R^9$ is
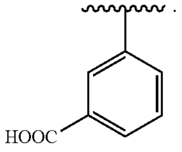
In embodiments $R^9$ is
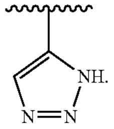 [SMILES: *c1cnn[nH]1]
In embodiments $R^9$ is
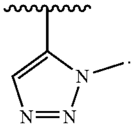 [SMILES: *c1cnnn1C]
In embodiments, $R^9$ is
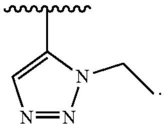 [SMILES: *c1cnnn1CC]
In embodiments, $R^9$ is
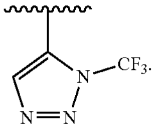 [SMILES: *c1cnnn1C(F)(F)F]
In embodiments, $R^9$ is
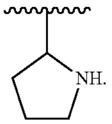 [SMILES: *C1CCCN1]
In embodiments, $R^9$ is
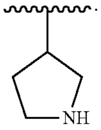 [SMILES: *C1CCNC1]

In embodiments, $R^9$ is

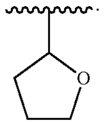 [SMILES: *C1CCCO1]

In embodiments, $R^9$ is

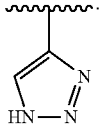 [SMILES: *c1c[nH]nn1]

In embodiments, $R^9$ is

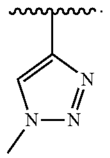

In embodiments, $R^9$ is

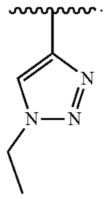 [SMILES: *c1cn(CC)nn1]

In embodiments, $R^9$ is

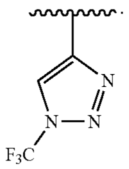

$R^{10}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{100}$ is -$L^{101}$-O—CH($N_3$)-$L^{103}$-$L^{104}$-$L^{105}$-; and $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{100}$ is -$L^{101}$-O—CH($N_3$)-$L^{103}$-$L^{104}$-$L^{105}$-; wherein $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; and $L^{105}$ is independently bond or substituted or unsubstituted 4 to 18 membered heteroalkylene. In embodiments, $L^{100}$ is -$L^{101}$-O—CH($N_3$)—$CH_2$—O-$L^{104}$-$L^{105}$-; wherein $L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{104}$ is unsubstituted phenylene.

In embodiments, $L^{100}$ is -$L^{101}$-O—CH(—$SSR^{102}$)-$L^{103}$-$L^{104}$-$L^{105}$- or -$L^{101}$-O—C($CH_3$)(—$SSR^{102}$)-$L^{103}$-$L^{104}$-$L^{105}$-. In embodiments, $L^{100}$ is -$L^{101}$-O—CH(—$SSR^{102}$)-$L^{103}$-$L^{104}$-$L^{105}$-. In embodiments, $L^{100}$ is -$L^{101}$-O—C($CH_3$)(—$SSR^{102}$)-$L^{103}$-$L^{104}$-$L^{105}$-. In embodiments, $L^{100}$ is -$L^{101}$-O—CH(—SCN)-$L^{103}$-$L^{104}$-$L^{105}$- or -$L^{101}$-O—C($CH_3$)(—SCN)-$L^3$-$L^{104}$-$L^{105}$-. In embodiments, $L^{100}$ is -$L^{101}$-O—CH(—SCN)-$L^{103}$-$L^{104}$-$L^{105}$-. In embodiments, $L^{100}$ is -$L^{101}$-O—C($CH_3$)(—SCN)-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is unsubstituted $C_1$-$C_4$ alkyl.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $R^{102}$ is unsubstituted $C_1$-$C_4$ alkyl. In embodiments, $R^{102}$ is unsubstituted methyl. In embodiments, $R^{102}$ is unsubstituted ethyl. In embodiments, $R^{102}$ is unsubstituted propyl. In embodiments, $R^{102}$ is unsubstituted isopropyl. In embodiments, $R^{102}$ is unsubstituted butyl. In embodiments, $R^{102}$ is unsubstituted tert-butyl.

In embodiments, $L^{100}$ is -$L^{101}$-O—CH(—$SR^{100}$)-$L^{103}$-$L^{104}$-$L^{105}$- or -$L^{101}$-O—C($CH_3$)(—$SR^{100}$)-$L^{103}$-$L^{104}$-$L^{105}$-. In embodiments, $L^{100}$ is -$L^{101}$-O—CH(—$SR^{100}$)-$L^{103}$-$L^{104}$-$L^{105}$-. In embodiments, $L^{100}$ is -$L^{101}$-O—C($CH_3$)(—$SR^{100}$)-$L^{03}$-$L^{14}$-$L^{105}$-.

In embodiments, $L^{100}$ is -$L^{101}$-O—CH(—$SSR^{102}$)-$L^{103}$-$L^{104}$-$L^{105}$- or -$L^{101}$-O—C($CH_3$)(—$SSR^{102}$)-$L^{103}$-$L^{104}$-

$L^{105}$-. In embodiments, $L^{100}$ is $-L^{101}$-O—CH(—$SSR^{102}$)-$L^{103}$-$L^{104}$-$L^{105}$-. In embodiments, $L^{100}$ is $-L^{101}$-O—C($CH_3$)(—$SSR^{102}$)-$L^{103}$-$L^{104}$-$L^{105}$-.

In embodiments, $L^{100}$ is $-L^{101}$-O—CH(—SCN)-$L^{103}$-$L^{104}$-$L^{105}$- or $-L^{101}$-O—C($CH_3$)(—SCN)-$L^{103}$-$L^{104}$-$L^{105}$-. In embodiments, $L^{100}$ is $-L^{101}$-O—CH(—SCN)-$L^{103}$-$L^{104}$-$L^{105}$-. In embodiments, $L^{100}$ is $-L^{101}$-O—C($CH_3$)(—SCN)-$L^{103}$-$L^{104}$-$L^{105}$-.

In embodiments, $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene; and $R^{102}$ is unsubstituted $C_1$-$C_4$ alkyl. In embodiments, $L^{101}$ is independently a substituted or unsubstituted $C_1$-$C_4$ alkylene or substituted or unsubstituted 8 to 20 membered heteroalkylene. In embodiments, $L^{103}$ is independently a bond or substituted or unsubstituted 2 to 10 membered heteroalkylene. In embodiments, $L^{104}$ is independently a bond, substituted or unsubstituted 4 to 18 membered heteroalkylene, or substituted or unsubstituted phenylene. In embodiments, $L^{105}$ is independently bond or substituted or unsubstituted 4 to 18 membered heteroalkylene.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^{104}$ is unsubstituted phenylene; and $R^{102}$ is unsubstituted $C_1$-$C_4$ alkyl. In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{104}$ is unsubstituted phenylene.

In embodiments, $L^{100}$ is $-L^{101}$-O—CH($N_3$)-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; and $L^{105}$ is independently bond or substituted or unsubstituted 4 to 18 membered heteroalkylene. In embodiments, $L^{101}$ is independently a substituted or unsubstituted $C_1$-$C_4$ alkylene or substituted or unsubstituted 8 to 20 membered heteroalkylene. In embodiments, $L^{101}$ is independently an oxo-substituted $C_1$-$C_4$ alkylene or an oxo-substituted 8 to 20 membered heteroalkylene. In embodiments, $L^{103}$ is independently a bond or substituted or unsubstituted 2 to 10 membered heteroalkylene. In embodiments, $L^{103}$ is independently a bond or an unsubstituted 2 to 10 membered heteroalkylene. In embodiments, $L^{104}$ is independently a bond, substituted or unsubstituted 4 to 18 membered heteroalkylene, or substituted or unsubstituted phenylene. In embodiments, $L^{105}$ is independently a bond or substituted or unsubstituted 4 to 18 membered heteroalkylene. In embodiments, $L^{105}$ is independently a bond or an oxo-substituted 4 to 18 membered heteroalkylene. In embodiments, $L^{105}$ is independently a bond or an unsubstituted 4 to 18 membered heteroalkylene.

In embodiments, $L^{100}$ is $-L^{101}$-O—CH($N_3$)—$CH_2$—O-$L^{104}$-$L^{105}$-.

In embodiments, $L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{104}$ is unsubstituted phenylene. In embodiments, $L^{101}$ and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{101}$ is oxo-substituted heteroalkylene. In embodiments, $L^{104}$ is unsubstituted phenylene. In embodiments, $L^{105}$ is oxo-substituted heteroalkylene.

In embodiments, $L^{100}$ is $-L^{101}$-SS-$L^{103}$-$L^{104}$-$L^{105}$-;

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{103}$ is a bond or unsubstituted phenylene.

In embodiments, $L^{101}$ is independently a substituted or unsubstituted 8 to 20 membered heteroalkylene; $L^{103}$ is independently a bond or substituted or unsubstituted phenylene; $L^{104}$ is independently a bond or substituted or unsubstituted 4 to 18 membered heteroalkylene; and $L^{105}$ is independently a bond or substituted or unsubstituted 4 to 18 membered heteroalkylene. In embodiments, $L^{101}$ is independently a substituted or unsubstituted 8 to 20 membered heteroalkylene. In embodiments, $L^{101}$ is independently an oxo-substituted 8 to 20 membered heteroalkylene. In embodiments, $L^{103}$ is independently a bond. In embodiments, $L^{103}$ is independently a substituted phenylene. In embodiments, $L^{103}$ is independently an unsubstituted phenylene. In embodiments, $L^{103}$ is independently

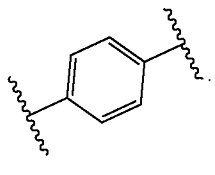 [SMILES: *c1ccc(*)cc1]

In embodiments, $L^{104}$ is independently a bond, or substituted or unsubstituted 4 to 18 membered heteroalkylene. In embodiments, $L^{104}$ is independently a bond or an oxo-substituted 4 to 18 membered heteroalkylene. In embodiments, $L^{105}$ is independently a bond or substituted or unsubstituted 4 to 18 membered heteroalkylene. In embodiments, $L^{105}$ is independently a bond or an unsubstituted 4 to 18 membered heteroalkylene.

In embodiments, $L^{100}$ is $-L^{101}$-SS—$C(CH_3)_2$-$L^{104}$-$L^{105}$-.

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —$C(CH_2)$—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted 8 to 20 membered heteroalkylene; $L^{104}$ is independently a bond or substituted or unsubstituted 4 to 18 membered heteroalkylene; and $L^{105}$ is independently bond or substituted or unsubstituted 4 to 18 membered heteroalkylene. In embodiments, $L^{101}$ is independently a substituted or unsubstituted 8 to 20 membered heteroalkylene. In embodiments, $L^{101}$ is independently an oxo-substituted 8 to 20 membered heteroalkylene. In embodiments, $L^{104}$ is independently a bond, or substituted or unsubstituted 4 to 18 membered heteroalkylene. In embodiments, $L^{104}$ is independently a bond or an oxo-substituted 4 to 18 membered heteroalkylene. In embodiments, $L^{105}$ is independently a bond or substituted or unsubstituted 4 to 18 membered heteroalkylene. In embodiments, $L^{105}$ is independently a bond or an unsubstituted 4 to 18 membered heteroalkylene.

In embodiments, $L^{100}$ is -($L^{101}$)-SS-($L^{103}$)-($L^{104}$)-($L^{105}$)-. $L^{101}$, $L^{103}$, $L^{104}$, and $L^{105}$ are as described herein. In embodiments, $L^{100}$ is -($L^{101}$)-OCH($R^{102}$)—SS-($L^{103}$)-($L^{104}$)-($L^{105}$)-. $L^{101}$, $L^{104}$, and $L^{105}$ are as described herein.

In embodiments, $L^{100}$ is $-L^{101}$-CH(OH)—CH(OH)-$L^{104}$-$L^{105}$-.

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —$C(CH_2)$—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted 3 to 10 membered heteroalkylene; $L^{104}$ is independently a bond or substituted or unsubstituted 2 to 10 membered heteroalkylene; and $L^{105}$ is independently bond or substituted or unsubstituted 2 to 10 membered heteroalkylene. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{104}$ is independently a bond or substituted or unsubstituted 2 to 10 membered heteroalkylene. In embodiments, $L^{104}$ is independently a bond or oxo-substituted 2 to 10 membered heteroalkylene. In embodiments, $L^{105}$ is independently a bond or substituted or unsubstituted 2 to 10 membered heteroalkylene. In embodiments, $L^{105}$ is independently a bond or unsubstituted 2 to 10 membered heteroalkylene.

In embodiments, $L^{100}$ is $-L^{101}$-$C(CH_2)$-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —$C(CH_2)$—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted 3 to 10 membered heteroalkylene; $L^{103}$ is independently a bond or substituted or unsubstituted 2 to 10 membered heteroalkylene; $L^{104}$ is independently a bond or substituted or unsubstituted 2 to 10 membered heteroalkylene; and $L^{105}$ is independently bond or substituted or unsubstituted 2 to 10 membered heteroalkylene. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{103}$ is independently a bond or substituted or unsubstituted 2 to 10 membered heteroalkylene. In embodiments, $L^{103}$ is independently a bond or unsubstituted 2 to 10 membered heteroalkylene. In embodiments, $L^{104}$ is independently a bond or substituted or unsubstituted 2 to 10 membered heteroalkylene. In embodiments, $L^{104}$ is independently a bond or unsubstituted 2 to 10 membered heteroalkylene. In embodiments, $L^{105}$ is independently a bond or substituted or unsubstituted 2 to 10 membered heteroalkylene. In embodiments, $L^{105}$ is independently a bond or unsubstituted 2 to 10 membered heteroalkylene.

In embodiments, $L^{100}$ is $-L^{101}$-$L^{102}$-$L^{103}$-$L^{104}$-$L^{105}$-.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, —N═N—, substituted or unsubstituted alkylene (e.g., —CH(OH)— or —$C(CH_2)$—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $L^{102}$ and $L^{104}$ are substituted or unsubstituted phenylene. In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, —N═N—, substituted or unsubstituted alkylene (e.g., —CH(OH)— or —$C(CH_2)$—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{103}$ is independently —N═N—. In embodiments, $L^{102}$ is independently a substituted phenylene. In embodiments, $L^{102}$ is independently an unsubstituted phenylene. In embodiments, $L^{102}$ is independently

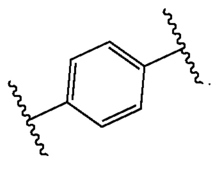 [SMILES: *c1ccc(*)cc1]

In embodiments, $L^{104}$ is independently a substituted phenylene. In embodiments, $L^{104}$ is independently an unsubstituted phenylene. In embodiments, $L^{104}$ is independently

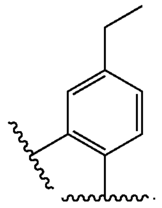 [SMILES: *c1ccc(CC)cc1*]

In embodiments, $L^{104}$ is independently

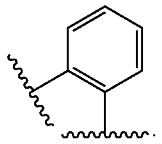 [SMILES: *c1ccccc1*]

In embodiments, $L^{101}$ is independently a substituted or unsubstituted 3 to 10 membered heteroalkylene; $L^{103}$ is independently a bond or substituted or unsubstituted 2 to 10 membered heteroalkylene; $L^{105}$ is independently bond or substituted or unsubstituted 5 to 16 membered heteroalkylene; and $L^{102}$ and $L^{104}$ are substituted or unsubstituted phenylene. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{103}$ is independently a bond or substituted or unsubstituted 2 to 10 membered heteroalkylene. In embodiments, $L^{103}$ is independently a bond or unsubstituted 2 to 10 membered heteroalkylene. In embodiments, $L^{103}$ is independently —N═N—. In embodiments, $L^{105}$ is independently bond or substituted or unsubstituted 5 to 16 membered heteroalkylene. In embodiments, $L^{105}$ is independently bond or unsubstituted 5 to 16 membered heteroalkylene. In embodiments, $L^{102}$ is independently a substituted phenylene. In embodiments, $L^{102}$ is independently an unsubstituted phenylene. In embodiments, $L^{104}$ is independently a substituted phenylene. In embodiments, $L^{104}$ is independently an unsubstituted phenylene.

In embodiments, $L^{100}$ is $-L^{101}$-O—CH($R^{102}$)-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is $R^{102B}$-substituted $C_1$-$C_4$ alkyl. In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{102}$ is $R^{102B}$-substituted $C_1$-$C_4$ alkyl. $R^{102B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{102B}$ is independently —CN.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is $R^{102B}$-substituted $C_1$-$C_4$ alkyl. In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{102}$ is $R^{102B}$-substituted $C_1$-$C_4$ alkyl. In embodiments, $R^{102B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{102B}$ is independently —CN.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is $R^{102B}$-substituted $C_1$-$C_4$ alkyl. In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{102}$ is $R^{102B}$-substituted $C_1$-$C_4$ alkyl. In embodiments, $R^{102B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$, $C_1$-$C_6$, or $C_1$-$C_4$), unsubstituted heteroalkyl (e.g., 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{102B}$ is independently —CN.

In embodiments, $L^{100}$ is -$L^{101}$-O—CH($CH_2R^{102}$)-$L^{103}$-$L^{104}$-$L^{105}$-.

In embodiments, $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is independently oxo, hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$, $C_1$-$C_6$, or $C_1$-$C_4$), unsubstituted heteroalkyl (e.g., 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{102}$ is independently oxo, hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$, $C_1$-$C_6$, or $C_1$-$C_4$), unsubstituted heteroalkyl (e.g., 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{102}$ is independently —CN.

In embodiments, $L^{101}$ is independently a substituted or unsubstituted 3 to 10 membered heteroalkylene; $L^{103}$ is independently a bond or substituted or unsubstituted 5 to 16 membered heteroalkylene; $L^{104}$ is independently a bond or substituted or unsubstituted 5 to 16 membered heteroalkylene; $L^{105}$ is independently bond or substituted or unsubstituted 5 to 16 membered heteroalkylene; and $R^{102}$ is independently —CN. In embodiments, $L^{101}$ is independently a substituted or unsubstituted 3 to 10 membered heteroalkylene. In embodiments, $L^{101}$ is independently oxo-substituted 3 to 10 membered heteroalkylene. In embodiments, $L^{103}$ is independently a bond or substituted or unsubstituted 5 to 16 membered heteroalkylene. In embodiments, $L^{103}$ is independently a bond or unsubstituted 5 to 16 membered heteroalkylene. In embodiments, $L^{104}$ is independently a bond or substituted or unsubstituted 5 to 16 membered heteroalkylene. In embodiments, $L^{104}$ is independently a bond or unsubstituted 5 to 16 membered heteroalkylene. In embodiments, $L^{105}$ is independently a bond or substituted or unsubstituted 5 to 16 membered heteroalkylene. In embodiments, $L^{105}$ is independently a bond or unsubstituted 5 to 16 membered heteroalkylene. In embodiments, $R^{102}$ is independently —CN.

In embodiments, $L^{100}$ is -$L^{101}$-O—CH($CH_2R^{102}$)—$CH_2$—O-$L^{104}$-$L^{105}$-.

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^{102}$ is independently oxo, hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$, $C_1$-$C_6$, or $C_1$-$C_4$), unsubstituted heteroalkyl (e.g., 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $R^{102}$ is independently oxo, hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_8$, $C_1$-$C_6$, or $C_1$-$C_4$), unsubstituted heteroalkyl (e.g., 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{102}$ is independently —CN.

In embodiments, $L^{100}$ is -$L^{101}$-O—CH($CH_2$CN)—$CH_2$—O-$L^{104}$-$L^{105}$-.

In embodiments, $L^{101}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene (e.g., —CH(OH)— or —C($CH_2$)—), substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{101}$ is a bond, —NH—, —$NR^{101}$—, —S—, —O—, —C(O)—, —C(O)O—, —OC(O)—, —NHC(O)—, —C(O)NH—, —NHC(O)NH—, —NHC(NH)NH—, —C(S)—, $R^{101}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{101}$-substituted or unsubstituted heteroalkylene (e.g., 2 to 20 membered, 8 to 20 membered, 2 to 10 membered, 3 to 10 membered, 2 to 8 membered, 2 to 6 membered, or 2 to 4 membered), $R^{101}$-substituted or unsubstituted cycloalkylene (e.g., $C_3$-$C_8$, $C_3$-$C_6$, or $C_5$-$C_6$), $R^{101}$-substituted or unsubstituted heterocycloalkylene (e.g., 3 to 8, 3 to 6, or 5 to 6 membered), $R^{101}$-substituted or unsubstituted arylene (e.g., $C_6$-$C_{10}$, $C_{10}$, or phenylene), or $R^{101}$-substituted or unsubstituted heteroarylene (e.g., 5 to 10, 5 to 9, or 5 to 6 membered). In embodiments, $L^{101}$ is a bond. In embodiments, $L^{101}$ is —NH—. In embodiments, $L^{101}$ is —$NR^{101}$—. In embodiments, $L^{101}$ is -5-. In embodiments, $L^{101}$ is —O—. In embodiments, $L^{101}$ is —C(O)—. In embodiments, $L^{101}$ is —C(O)O—. In embodiments, $L^{101}$ is —OC(O)—. In embodiments, $L^{101}$ is —NHC(O)—. In embodiments, $L^{101}$ is —C(O)NH—. In embodiments, $L^{101}$ is —NHC(O)NH—. In embodiments, $L^{101}$ is —NHC(NH)NH—. In embodiments, $L^{101}$ is —C(S)—. In embodiments, $L^{101}$ is $R^{101}$-substituted or unsubstituted $C_1$-$C_{20}$ alkylene. In embodiments, $L^{101}$ is $R^{101}$-substituted or unsubstituted 2 to 20 membered heteroalkylene. In embodiments, $L^{101}$ is $R^{101}$-substituted or unsubstituted 3 to 10 membered heteroalkylene. In embodiments, $L^{101}$ is $R^{101}$-substituted or unsubstituted $C_3$-$C_8$ cycloalkylene. In embodiments, $L^{101}$ is $R^{101}$-substituted or unsubstituted 3 to 8 membered heterocycloalkylene. In embodiments, $L^{101}$ is $R^{101}$-substituted or unsubstituted $C_6$-$C_{10}$ arylene. In embodiments, $L^{101}$ is $R^{101}$-substituted or unsubstituted 5 to 10 membered heteroarylene.

In embodiments, $L^{101}$ is a bond, —NH—, —$NR^{101}$—, —S—, —O—, —C(O)—, —C(O)O—, —OC(O)—, —NHC(O)—, —C(O)NH—, —NHC(O)NH—, —NHC(NH)NH—, —C(S)—, —CH(OH)—, or —$C(CH_2)$—. In embodiments, $L^{101}$ is a bond. In embodiments, $L^{101}$ is —NH—. In embodiments, $L^{101}$ is —$NR^{101}$—. In embodiments, $L^{101}$ is —S—. In embodiments, $L^{101}$ is —O—. In embodiments, $L^{101}$ is —C(O)—. In embodiments, $L^{101}$ is —C(O)O—. In embodiments, $L^{101}$ is —OC(O)—. In embodiments, $L^{101}$ is —NHC(O)—. In embodiments, $L^{101}$ is —C(O)NH—. In embodiments, $L^{101}$ is —NHC(O)NH—. In embodiments, $L^{101}$ is —NHC(NH)NH—. In embodiments, $L^{101}$ is —C(S)—. In embodiments, $L^{101}$ is —CH(OH)—. In embodiments, $L^{101}$ is —$C(CH_2)$—.

In embodiments, $L^{101}$ is —$(CH_2CH_2O)_b$—. In embodiments, $L^{101}$ is —$CCCH_2(OCH_2CH_2)_a$—NHC(O)—$(CH_2)$, $(OCH_2CH_2)_b$—. In embodiments, $L^{101}$ is —$CHCHCH_2$—NHC(O)—$(CH_2)$, $(OCH_2CH_2)_b$—. In embodiments, $L^{101}$ is —$CCCH_2$—NHC(O)—$(CH_2)$, $(OCH_2CH_2)_b$—. In embodiments, $L^{101}$ is —$CCCH_2$—. The symbol a is an integer from 0 to 8. In embodiments, a is 1. In embodiments, a is 0. The symbol b is an integer from 0 to 8. In embodiments, b is 0. In embodiments, b is 1 or 2. In embodiments, b is an integer from 2 to 8. In embodiments, b is 1. The symbol c is an integer from 0 to 8. In embodiments, c is 0. In embodiments, c is 1. In embodiments, c is 2. In embodiments, c is 3.

$R^{101}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{101A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101A}$-substituted or unsubstituted heteroalkyl (e.g., 2 to 20, 8 to 20, 2 to 10, 2 to 8, 2 to 6, or 2 to 4 membered), $R^{101A}$-substituted or unsubstituted cycloalkyl (e.g., $C_3$-$C_8$, $C_3$-$C_6$, or $C_5$-$C_6$), $R^{101A}$-substituted or unsubstituted heterocycloalkyl (e.g., 3 to 8, 3 to 6, or 5 to 6 membered), $R^{101A}$-substituted or unsubstituted aryl (e.g., $C_6$-$C_{10}$, $C_{10}$, or phenyl), or $R^{101A}$-substituted or unsubstituted heteroaryl (e.g., 5 to 10, 5 to 9, or 5 to 6 membered).

In embodiments, $R^{101}$ is independently —$NH_2$. In embodiments, $R^{101}$ is independently —OH. In embodiments, $R^{101}$ is independently halogen. In embodiments, $R^{101}$ is independently —CN. In embodiments, $R^{101}$ is independently oxo. In embodiments, $R^{101}$ is independently —$CF_3$. In embodiments, $R^{101}$ is independently —COOH. In embodiments, $R^{101}$ is independently —$CONH_2$. In embodiments, $R^{101}$ is independently —F. In embodiments, $R^{101}$ is independently —Cl. In embodiments, $R^{101}$ is independently —Br. In embodiments, $R^{101}$ is independently —I.

$R^{101A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{101B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{101B}$-substituted or unsubstituted heteroalkyl (e.g., 2 to 20, 8 to 20, 2 to 10, 2 to 8, 2 to 6, or 2 to 4 membered), $R^{101B}$-substituted or unsubstituted cycloalkyl (e.g., $C_3$-$C_8$, $C_3$-$C_6$, or $C_5$-$C_6$), $R^{101B}$-substituted or unsubstituted heterocycloalkyl (e.g., 3 to 8, 3 to 6, or 5 to 6 membered), $R^{101B}$-substituted or unsubstituted aryl (e.g., $C_6$-$C_{10}$, $C_{10}$, or phenyl), or $R^{101B}$-substituted or unsubstituted heteroaryl (e.g., 5 to 10, 5 to 9, or 5 to 6 membered).

$R^{101B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$—$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{102}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered). In embodiments, $L^{102}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{102}$ is a bond, —NH—, —OC(—$SR^{100}$)($R^{102a}$)—, —OC(—$SSR^{102}$)($R^{102a}$)—, —OC(—SCN)($R^{102a}$)—, —OC($N_3$)($R^{102a}$)—, —OCH($R^{102}$)—, —OCH($CH_2R^{102}$)—, —OCH($CH_2$CN)—, —S—, —O—, —C(O)—, —C(O)O—, —OC(O)—, —NHC(O)—, —C(O)NH—, —NHC(O)NH—, —NHC(NH)NH—, —C(S)—, —SS—, $R^{102}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{102}$-substituted or unsubstituted heteroalkylene (e.g., 2 to 20, 8 to 20, 2 to 10, 2 to 8, 2 to 6, or 2 to 4 membered), $R^{102}$-substituted or unsubstituted cycloalkylene (e.g., $C_3$-$C_8$, $C_3$-$C_6$, or $C_5$-$C_6$), $R^{102}$-substituted or unsubstituted heterocycloalkylene (e.g., 3 to 8, 3 to 6, or 5 to 6 membered), $R^{102}$-substituted or unsubstituted arylene (e.g., $C_6$-$C_{10}$, $C_{10}$, or phenylene), or $R^{102}$-substituted or unsubstituted heteroarylene (e.g., 5 to 10, 5 to 9, or 5 to 6 membered). In embodiments, $L^{102}$ is a bond. In embodiments, $L^{102}$ is —NH—. In embodiments, $L^{102}$ is —OC(—$SR^{100}$)($R^{102a}$)—. In embodiments, $L^{102}$ is —OC(—$SSR^{102}$)($R^{102a}$)—. In embodiments, $L^{102}$ is —OC(—SCN)($R^{102a}$)—. In embodiments, $L^{102}$ is —OC($N_3$)($R^{102a}$)—. In embodiments, $L^{102}$ is —OC(—$SR^{100}$)($CH_3$)—. In embodiments, $L^{102}$ is —OC(—$SSR^{102}$)($CH_3$)—. In embodiments, $L^{102}$ is —OC(—SCN)($CH_3$)—. In embodiments, $L^{102}$ is —OC($N_3$)($CH_3$)—. In embodiments, $L^{102}$ is —OCH(—$SR^{100}$)—. In embodiments, $L^{102}$ is —OCH(—$SSR^{102}$)—. In embodiments, $L^{102}$ is —OCH(—SCN)—. In embodiments, $L^{102}$ is —OCH($N_3$)—. In embodiments, $L^{102}$ is —OCH($R^{102}$)—. In embodiments, $L^{102}$ is —OCH($CH_2R^{102}$)—. In embodiments, $L^{102}$ is —OCH($CH_2$CN)—. In embodiments, $L^{102}$ is —S—. In embodiments, $L^{102}$ is —O—. In embodiments, $L^{102}$ is —C(O)—. In embodiments, $L^{102}$ is —C(O)O—. In embodiments, $L^{102}$ is —OC(O)—. In embodiments, $L^{102}$ is —NHC(O)—. In embodiments, $L^{102}$ is —C(O)NH—. In embodiments, $L^{102}$ is —NHC(O)NH—. In embodiments, $L^{102}$ is —NHC(NH)NH—. In embodiments, $L^{102}$ is —C(S)—. In embodiments, $L^{102}$ is —SS—. In embodiments, $L^{102}$ is $R^{102}$-substituted or unsubstituted $C_1$-$C_{20}$ alkylene. In embodiments, $L^{102}$ is $R^{102}$-substituted or unsubstituted 2 to 20 membered heteroalkylene. In embodiments, $L^{102}$ is $R^{102}$-substituted or unsubstituted $C_3$-$C_8$ cycloalkylene. In embodiments, $L^{102}$ is $R^{102}$-substituted or unsubstituted 3 to 8 membered heterocycloalkylene. In embodiments, $L^{102}$ is $R^{102}$-substituted or unsubstituted $C_6$-$C_{10}$ arylene. In embodiments, $L^{102}$ is $R^{102}$-substituted or unsubstituted phenylene. In embodiments, $L^{102}$ is $R^{102}$-substituted or unsubstituted 5 to 10 membered heteroarylene.

In embodiments, $L^{102}$ is a bond, —NH—, —OC(—$SR^{100}$)($R^{102a}$)—, —OC(—$SSR^{102}$)($R^{102a}$)—, —OC(—SCN)($R^{102a}$)—, —OC($N_3$)($R^{102a}$)—, —OCH($R^{102}$)—, —OCH($CH_2R^{102}$)—, —OCH($CH_2$CN)—, —S—, —O—, —C(O)—, —C(O)O—, —OC(O)—, —NHC(O)—, —C(O)NH—, —NHC(O)NH—, —NHC(NH)NH—, —C(S)—, —SS—, —CH(OH)—, or —C($CH_2$)—. In embodiments, $L^{102}$ is a bond. In embodiments, $L^{102}$ is —NH—. In embodiments, $L^{102}$ is —OC(—$SR^{100}$)($R^{102a}$)—. In embodiments, $L^{102}$ is —OC(—$SSR^{102}$)($R^{102a}$)—. In embodiments, $L^{102}$ is —OC(—SCN)($R^{102a}$)—. In embodiments, $L^{102}$ is —OC($N_3$)($R^{102a}$)—. In embodiments, $L^{102}$ is —OC(—$SR^{100}$)($CH_3$)—. In embodiments, $L^{102}$ is —OC(—$SSR^{102}$)($CH_3$)—. In embodiments, $L^{102}$ is —OC(—SCN)($CH_3$)—. In embodiments, $L^{102}$ is —OC($N_3$)($CH_3$)—. In embodiments, $L^{102}$ is —OCH(—$SR^{100}$)—. In embodiments, $L^{102}$ is —OCH(—$SSR^{102}$)—. In embodiments, $L^{102}$ is —OCH(—SCN)—. In embodiments, $L^{102}$ is —OCH($N_3$)—. In embodiments, $L^{102}$ is —OCH($R^{102}$)—. In embodiments, $L^{102}$ is —OCH($CH_2R^{102}$)—. In embodiments, $L^{102}$ is —OCH($CH_2$CN)—. In embodiments, $L^{102}$ is —S—. In embodiments, $L^{102}$ is —O—. In embodiments, $L^{102}$ is —C(O)—. In embodiments, $L^{102}$ is —C(O)O—. In embodiments, $L^{102}$ is —OC(O)—. In embodiments, $L^{102}$ is —NHC(O)—. In embodiments, $L^{102}$ is —C(O)NH—. In embodiments, $L^{102}$ is —NHC(O)NH—. In embodiments, $L^{102}$ is —NHC(NH)NH—. In embodiments, $L^{102}$ is —C(S)—. In embodiments, $L^{102}$ is —SS—. In embodiments, $L^{102}$ is —CH(OH)—. In embodiments, $L^{102}$ is —C($CH_2$)—.

$R^{100}$ is —$SO_3$H, —$SR^{102}$, or —CN. In embodiments, $R^{100}$ is —$SR^{102}$. In embodiments, $R^{100}$ is —CN. In embodiments, $R^{100}$ is

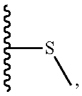,
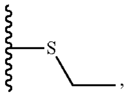,
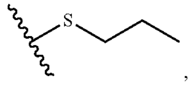,
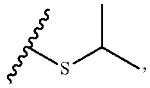,
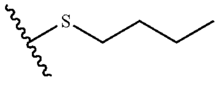,
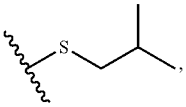, or
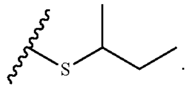.

or In embodiments, $R^{100}$ is

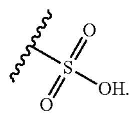 [SMILES: *S(=O)(=O)O]

In embodiments, $R^{100}$ is —$SR^{102}$ or —CN. In embodiments, $R^{100}$ is —$SR^{102}$. In embodiments, $R^{100}$ is —CN. In embodiments, $R^{100}$ is

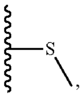,
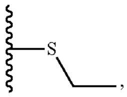,
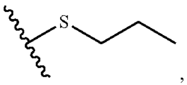,
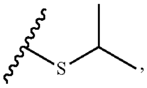,
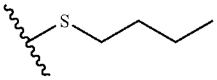,
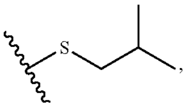, or
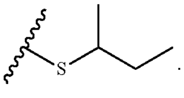.

$R^{102}$ and $R^{102a}$ are independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered).

In embodiments, $R^{102}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{102B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102B}$-substituted or unsubstituted heteroalkyl (e.g., 2 to 20, 8 to 20, 2 to 10, 2 to 8, 2 to 6, or 2 to 4 membered), $R^{102B}$-substituted or unsubstituted cycloalkyl (e.g., $C_3$-$C_8$, $C_3$-$C_6$, or $C_5$-$C_6$), $R^{102B}$-substituted or unsubstituted heterocycloalkyl (e.g., 3 to 8, 3 to 6, or 5 to 6 membered), $R^{102B}$-substituted or unsubstituted aryl (e.g., $C_6$-$C_{10}$, $C_{10}$, or phenyl), or $R^{102B}$-substituted or unsubstituted heteroaryl (e.g., 5 to 10, 5 to 9, or 5 to 6 membered).

In embodiments, $R^{102}$ is independently -MB. In embodiments, $R^{102}$ is independently —OH. In embodiments, $R^{102}$ is independently halogen. In embodiments, $R^{102}$ is independently —CN. In embodiments, $R^{102}$ is independently oxo. In embodiments, $R^{102}$ is independently —$CF_3$. In embodiments, $R^{102}$ is independently —COOH. In embodiments, $R^{102}$ is independently -COMB. In embodiments, $R^{102}$ is independently —F. In embodiments, $R^{102}$ is independently —Cl. In embodiments, $R^{102}$ is independently —Br. In embodiments, $R^{102}$ is independently —I.

In embodiments, $R^{102}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102}$ is independently unsubstituted $C_1$-$C_6$ alkyl. In embodiments, $R^{102}$ is independently unsubstituted $C_1$-$C_4$ alkyl. In embodiments, $R^{102}$ is independently unsubstituted methyl. In embodiments, $R^{102}$ is independently unsubstituted tert-butyl. In embodiments, $R^{102}$ is independently hydrogen.

In embodiments, $R^{102B}$ is independently oxo, halogen, —$CCl_3$, —$CBr_3$, —$CF_3$, —$CI_3$, —CN, —OH, -MB, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, substituted or unsubstituted alkyl (e.g., $C_1$-$C_{20}$, $C_{10}$-$C_{20}$, $C_1$-$C_8$, $C_1$-$C_6$, or $C_1$-$C_4$), substituted or unsubstituted heteroalkyl (e.g., 2 to 20, 8 to 20, 2 to 10, 2 to 8, 2 to 6, or 2 to 4 membered), substituted or unsubstituted cycloalkyl (e.g., $C_3$-$C_8$, $C_3$-$C_6$, or $C_5$-$C_6$), substituted or unsubstituted heterocycloalkyl (e.g., 3 to 8, 3 to 6, or 5 to 6 membered), substituted or unsubstituted aryl (e.g., $C_6$-$C_{10}$, $C_{10}$, or phenyl), or substituted or unsubstituted heteroaryl (e.g., 5 to 10, 5 to 9, or 5 to 6 membered). In embodiments, $R^{102B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{102C}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{102C}$-substituted or unsubstituted heteroalkyl (e.g., 2 to 20, 8 to 20, 2 to 10, 2 to 8, 2 to 6, or 2 to 4 membered), $R^{102C}$-substituted or unsubstituted cycloalkyl (e.g., $C_3$-$C_8$, $C_3$-$C_6$, or $C_5$-$C_6$), $R^{102C}$-substituted or unsubstituted heterocycloalkyl (e.g., 3 to 8, 3 to 6, or 5 to 6 membered), $R^{102C}$-substituted or unsubstituted aryl (e.g., $C_6$-$C_{10}$, $C_{10}$, or phenyl), or $R^{102C}$-substituted or unsubstituted heteroaryl (e.g., 5 to 10, 5 to 9, or 5 to 6 membered).

$R^{102C}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $R^{102a}$ is independently hydrogen, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SF_5$, substituted (e.g., substituted with a substituent group, size-limited substituent group, or lower substituent group) or unsubstituted alkyl (e.g., $C_1$-$C_8$, $C_1$-$C_6$, $C_1$-$C_4$, or $C_1$-$C_2$), substituted (e.g., substituted with a substituent group, size-limited substituent group, or lower substituent group) or unsubstituted heteroalkyl (e.g., 2 to 8, 2 to 6, 4 to 6, 2 to 3, or 4 to 5 membered), substituted (e.g., substituted with a substituent group, size-limited substituent group, or lower substituent group) or unsubstituted cycloalkyl (e.g., $C_3$-$C_8$, $C_3$-$C_6$, $C_4$-$C_6$, or $C_5$-$C_6$), substituted (e.g., substituted with a substituent group, size-limited substituent group, or lower substituent group) or unsubstituted heterocycloalkyl (e.g., 3 to 8, 3 to 6, 4 to 6, 4 to 5, or 5 to 6 membered), substituted (e.g., substituted with a substituent group, size-limited substituent group, or lower substituent group) or unsubstituted aryl (e.g., $C_6$-$C_{10}$ or phenyl), or substituted (e.g., substituted with a substituent group, size-limited substituent group, or lower substituent group) or unsubstituted heteroaryl (e.g., 5 to 10, 5 to 9, or 5 to 6 membered).

In embodiments, a substituted $R^{102a}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{102a}$ is substituted with a plurality of groups selected from substituent groups, size-limited substituent groups, and lower substituent groups; each substituent group, size-limited substituent group, and/or lower substituent group may optionally be different. In embodiments, when $R^{102a}$ is substituted, it is substituted with at least one substituent group. In embodiments, when $R^{102a}$ is substituted, it is substituted with at least one size-limited substituent group. In embodiments, when $R^{102a}$ is substituted, it is substituted with at least one lower substituent group. In embodiments, when $R^{102a}$ is substituted, it is substituted with 1 to 10 substituent groups. In embodiments, when $R^{102a}$ is substituted, it is substituted with 1 to 10 size-limited substituent groups. In embodiments, when $R^{102a}$ is substituted, it is substituted with 1 to 10 lower substituent groups. In embodiments, when $R^{102a}$ is substituted, it is substituted with 1 to 5 substituent groups. In embodiments, when $R^{102a}$ is substituted, it is substituted with 1 to 5 size-limited substituent groups. In embodiments, when $R^{102a}$ is substituted, it is substituted with 1 to 5 lower substituent groups. In embodiments, when $R^{102a}$ is substituted, it is substituted with a substituent group. In embodiments, when $R^{102a}$ is substituted, it is substituted with a size-limited substituent group. In embodiments, when $R^{102a}$ is substituted, it is substituted with a lower substituent group.

In embodiments, $R^{102a}$ is independently hydrogen, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered). In embodiments, $R^{102a}$ is independently hydrogen or unsubstituted alkyl (e.g., $C_1$-$C_{20}$, $C_{10}$-$C_{20}$, $C_1$-$C_8$, $C_1$-$C_6$, or $C_1$-$C_4$).

In embodiments, $R^{102a}$ is independently unsubstituted alkyl (e.g., $C_1$-$C_{20}$, $C_{10}$-$C_{20}$, $C_1$-$C_8$, $C_1$-$C_6$, or $C_1$-$C_4$). In embodiments, $R^{102a}$ is independently unsubstituted $C_1$-$C_6$ alkyl. In embodiments, $R^{102a}$ is independently unsubstituted $C_1$-$C_4$ alkyl. In embodiments, $R^{102a}$ is independently unsubstituted methyl. In embodiments, $R^{102a}$ is independently unsubstituted tert-butyl. In embodiments, $R^{102a}$ is independently hydrogen.

In embodiments, $R^{102}$ and $R^{102a}$ are independently hydrogen or unsubstituted alkyl. In embodiments, $R^{102}$ is unsubstituted $C_1$-$C_4$ alkyl. In embodiments, $R^{102a}$ is hydrogen or unsubstituted methyl.

In embodiments, $L^{103}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkyl ene, substituted or unsubstituted arylene, or substituted or unsubstituted heteroaryl ene.

In embodiments, $L^{103}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20, 8 to 20, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkyl ene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{103}$ is a bond, —NH—, —$NR^{103}$—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, $R^{103}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{103}$-substituted or unsubstituted heteroalkylene (e.g., 2 to 20 membered, 8 to 20 membered, 5 to 16 membered, 2 to 10, 2 to 8, 2 to 6, or 2 to 4 membered), $R^{103}$-substituted or unsubstituted cycloalkylene (e.g., $C_3$-$C_8$, $C_3$-$C_6$, or $C_5$-$C_6$), $R^{103}$-substituted or unsubstituted heterocycloalkylene (e.g., 3 to 8, 3 to 6, or 5 to 6 membered), $R^{103}$-substituted or unsubstituted arylene (e.g., $C_6$-$C_{10}$, $C_{10}$, or phenylene), or $R^{103}$-substituted or unsubstituted heteroarylene (e.g., 5 to 10, 5 to 9, or 5 to 6 membered). In embodiments, $L^{103}$ is a bond. In embodiments, $L^{103}$ is —NH—. In embodiments, $L^{103}$ is —$NR^{103}$—. In embodiments, $L^{103}$ is —S—. In embodiments, $L^{103}$ is —O—. In embodiments, $L^{103}$ is —C(O)—. In embodiments, $L^{103}$ is —C(O)O—. In embodiments, $L^{103}$ is —OC(O)—. In embodiments, $L^{103}$ is —NHC(O)—. In embodiments, $L^{103}$ is —C(O)NH—. In embodiments, $L^{103}$ is —NHC(O)NH—. In embodiments, $L^{103}$ is —NHC(NH)NH—. In embodiments, $L^{103}$ is —C(S)—. In embodiments, $L^{103}$ is —N═N—. In embodiments, $L^{103}$ is —SS—. In embodiments, $L^{103}$ is $R^{103}$-substituted or unsubstituted $C_1$-$C_{20}$ alkylene. In embodiments, $L^{103}$ is $R^{103}$-substituted or unsubstituted 2 to 20 membered heteroalkylene. In embodiments, $L^{103}$ is $R^{103}$-substituted or unsubstituted 5 to 16 membered heteroalkylene. In embodiments, $L^{103}$ is $R^{103}$-substituted or unsubstituted 2 to 10 membered heteroalkylene. In embodiments, $L^{103}$ is $R^{103}$-substituted or unsubstituted $C_3$-$C_8$ cycloalkylene. In embodiments, $L^{103}$ is $R^{103}$-substituted or unsubstituted 3 to 8 membered heterocycloalkylene. In embodiments, $L^{103}$ is $R^{103}$-substituted or unsubstituted $C_6$-$C_{10}$ arylene. In embodiments, $L^{103}$ is $R^{103}$-substituted or unsubstituted 5 to 10 membered heteroarylene.

In embodiments, $L^{103}$ is a bond, —NH—, —$NR^{103}$—, —S—, —O—, —C(O)—, —C(O)O—, —OC(O)—, —NHC(O)—, —C(O)NH—, —NHC(O)NH—, —NHC(NH)NH—, —C(S)—, —N═N—, —SS—, —CH(OH)—, or —$C(CH_2)$—. In embodiments, $L^{103}$ is a bond. In embodiments, $L^{103}$ is —NH—. In embodiments, $L^{103}$ is —$NR^{103}$—. In embodiments, $L^{103}$ is —S—. In embodiments, $L^{103}$ is —O—. In embodiments, $L^{103}$ is —C(O)—. In embodiments, $L^{103}$ is —C(O)O—. In embodiments, $L^{103}$ is —OC(O)—. In embodiments, $L^{103}$ is —NHC(O)—. In embodiments, $L^{103}$ is —C(O)NH—. In embodiments, $L^{103}$ is —NHC(O)NH—. In embodiments, $L^{103}$ is —NHC(NH)NH—. In embodiments, $L^{103}$ is —C(S)—. In embodiments, $L^{103}$ is —N=N—. In embodiments, $L^{103}$ is —SS—. In embodiments, $L^{103}$ is —CH(OH)—. In embodiments, $L^{103}$ is —$C(CH_2)$—.

In embodiments, $L^{103}$ is —$(CH_2CH_2O)_d$—. In embodiments, $L^{103}$ is —$(CH_2O)_d$—. In embodiments, $L^{103}$ is —$(CH_2)_d$—. In embodiments, $L^{103}$ is —$(CH_2)_d$—NH—. In embodiments, $L^{103}$ is -(unsubstituted phenylene)-. In embodiments, $L^{103}$ is

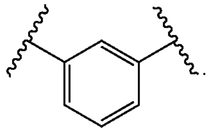 [SMILES: *c1cccc(*)c1]

In embodiments, $L^{103}$ is -(unsubstituted phenylene)-C(O)NH—. In embodiments, $L^{103}$ is

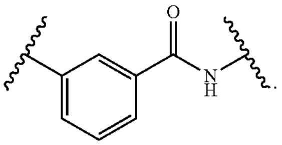 [SMILES: *NC(=O)c1cccc(*)c1]

In embodiments, $L^{103}$ is -(unsubstituted phenylene)-NHC(O)—. In embodiments, $L^{103}$ is

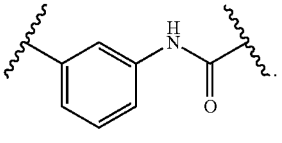 [SMILES: *C(=O)Nc1cccc(*)c1]

The symbol d is an integer from 0 to 8. In embodiments, d is 3. In embodiments, d is 1. In embodiments, d is 2. In embodiments, d is 0.

$R^{103}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{103A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103A}$-substituted or unsubstituted heteroalkyl (e.g., 2 to 20, 8 to 20, 2 to 10, 2 to 8, 2 to 6, or 2 to 4 membered), $R^{103A}$-substituted or unsubstituted cycloalkyl (e.g., $C_3$-$C_8$, $C_3$-$C_6$, or $C_5$-$C_6$), $R^{103A}$-substituted or unsubstituted heterocycloalkyl (e.g., 3 to 8, 3 to 6, or 5 to 6 membered), $R^{103A}$-substituted or unsubstituted aryl (e.g., $C_6$-$C_{10}$, $C_{10}$, or phenyl), or $R^{103A}$-substituted or unsubstituted heteroaryl (e.g., 5 to 10, 5 to 9, or 5 to 6 membered).

In embodiments, $R^{103}$ is independently —$NH_2$. In embodiments, $R^{103}$ is independently —OH. In embodiments, $R^{103}$ is independently halogen. In embodiments, $R^{103}$ is independently —CN. In embodiments, $R^{103}$ is independently oxo. In embodiments, $R^{103}$ is independently —$CF_3$. In embodiments, $R^{103}$ is independently —COOH. In embodiments, $R^{103}$ is independently —$CONH_2$. In embodiments, $R^{103}$ is independently —F. In embodiments, $R^{103}$ is independently —Cl. In embodiments, $R^{103}$ is independently —Br. In embodiments, $R^{103}$ is independently —I.

$R^{103A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{103B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{103B}$-substituted or unsubstituted heteroalkyl (e.g., 2 to 20, 8 to 20, 2 to 10, 2 to 8, 2 to 6, or 2 to 4 membered), $R^{103B}$-substituted or unsubstituted cycloalkyl (e.g., $C_3$-$C_8$, $C_3$-$C_6$, or $C_5$-$C_6$), $R^{103B}$-substituted or unsubstituted heterocycloalkyl (e.g., 3 to 8, 3 to 6, or 5 to 6 membered), $R^{103B}$-substituted or unsubstituted aryl (e.g., $C_6$-$C_{10}$, $C_{10}$, or phenyl), or $R^{103B}$-substituted or unsubstituted heteroaryl (e.g., 5 to 10, 5 to 9, or 5 to 6 membered).

$R^{103B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{104}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkyl ene, substituted or unsubstituted arylene, or substituted or unsubstituted heteroaryl ene.

In embodiments, $L^{104}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 5 to 16 membered, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{104}$ is a bond, —NH—, —$NR^{104}$—, —S—, —O—, —C(O)—, —C(O)O—, —OC(O)—, —NHC(O)—, —C(O)NH—, —NHC(O)NH—, —NHC(NH)NH—, —C(S)—, $R^{104}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{104}$-substituted or unsubstituted heteroalkylene (e.g., 2 to 20 membered, 8 to 20 membered, 5 to 16 membered, 2 to 10, 2 to 8, 2 to 6, or 2 to 4 membered), $R^{104}$-substituted or unsubstituted cycloalkylene (e.g., $C_3$-$C_8$, $C_3$-$C_6$, or $C_5$-$C_6$), $R^{104}$-substituted or unsubstituted heterocycloalkylene (e.g., 3 to 8, 3 to 6, or 5 to 6 membered), $R^{104}$-substituted or unsubstituted arylene (e.g., $C_6$-$C_{10}$, $C_{10}$, or phenylene), or $R^{104}$-substituted or unsubstituted heteroarylene (e.g., 5 to 10, 5 to 9, or 5 to 6 membered). In embodiments, $L^{104}$ is a bond. In embodiments, $L^{104}$ is —NH—. In embodiments, $L^{104}$ is —$NR^{104}$—. In embodiments, $L^{104}$ is —S—. In embodiments, $L^{104}$ is —O—. In embodiments, $L^{104}$ is —C(O)—. In embodiments, $L^{104}$ is —C(O)O—. In embodiments, $L^{104}$ is —OC(O)—. In embodiments, $L^{104}$ is —NHC(O)—. In embodiments, $L^{104}$ is —C(O)NH—. In embodiments, $L^{104}$ is —NHC(O)NH—. In embodiments, $L^{104}$ is —NHC(NH)NH—. In embodiments, $L^{104}$ is —C(S)—. In embodiments, $L^{104}$ is $R^{104}$-substituted or unsubstituted $C_1$-$C_{20}$ alkylene. In embodiments, $L^{104}$ is $R^{104}$-substituted or unsubstituted 2 to 20 membered heteroalkylene. In embodiments, $L^{104}$ is $R^{104}$-substituted or unsubstituted 5 to 16 membered heteroalkylene. In embodiments, $L^{104}$ is $R^{104}$-substituted or unsubstituted 2 to 10 membered heteroalkylene. In embodiments, $L^{104}$ is $R^{104}$-substituted or unsubstituted $C_3$-$C_8$ cycloalkylene. In embodiments, $L^{104}$ is $R^{104}$-substituted or unsubstituted 3 to 8 membered heterocycloalkylene. In embodiments, $L^{104}$ is $R^{104}$-substituted or unsubstituted $C_6$-$C_{10}$ arylene. In embodiments, $L^{104}$ is $R^{104}$-substituted or unsubstituted 5 to 10 membered heteroarylene. In embodiments, $L^{104}$ is $R^{104}$-substituted or unsubstituted phenylene.

In embodiments, $L^{104}$ is a bond, —NH—, —$NR^{104}$—, —S—, —O—, —C(O)—, —C(O)O—, —OC(O)—, —NHC(O)—, —C(O)NH—, —NHC(O)NH—, —NHC(NH)NH—, —C(S)—, —CH(OH)—, or —$C(CH_2)$—. In embodiments, $L^{104}$ is a bond. In embodiments, $L^{104}$ is —NH—. In embodiments, $L^{104}$ is —$NR^{104}$—. In embodiments, $L^{104}$ is —S—. In embodiments, $L^{104}$ is —O—. In embodiments, $L^{104}$ is —C(O)—. In embodiments, $L^{104}$ is —C(O)O—. In embodiments, $L^{104}$ is —OC(O)—. In embodiments, $L^{104}$ is —NHC(O)—. In embodiments, $L^{104}$ is —C(O)NH—. In embodiments, $L^{104}$ is —NHC(O)NH—. In embodiments, $L^{104}$ is —NHC(NH)NH—. In embodiments, $L^{104}$ is —C(S)—. In embodiments, $L^{104}$ is —CH(OH)—. In embodiments, $L^{104}$ is —$C(CH_2)$—.

In embodiments, $L^{104}$ is —$(CH_2CH_2O)_e$—. In embodiments, $L^{104}$ is —$(CH_2O)_e$—. In embodiments, $L^{104}$ is —$(CH_2)_e$—. In embodiments, $L^{104}$ is —$(CH_2)_e$—NH—. In embodiments, $L^{104}$ is -(unsubstituted phenylene)-. In embodiments, $L^{104}$ is

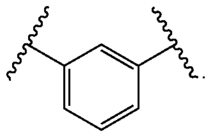 [SMILES: *c1cccc(*)c1]

In embodiments, $L^{104}$ is -(unsubstituted phenylene)-C(O)NH—. In embodiments, $L^{104}$ is

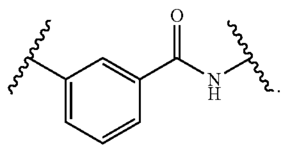 [SMILES: *NC(=O)c1cccc(*)c1]

In embodiments, $L^{104}$ is -(unsubstituted phenylene)-NHC(O)—. In embodiments, $L^{104}$ is

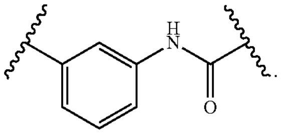 [SMILES: *C(=O)Nc1cccc(*)c1]

The symbol e is an integer from 0 to 8. In embodiments, e is 3. In embodiments, e is 1. In embodiments, e is 2.

$R^{104}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{104A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{104A}$-substituted or unsubstituted heteroalkyl (e.g., 2 to 20, 8 to 20, 2 to 10, 2 to 8, 2 to 6, or 2 to 4 membered), $R^{104A}$-substituted or unsubstituted cycloalkyl (e.g., $C_3$-$C_8$, $C_3$-$C_6$, or $C_5$-$C_6$), $R^{104A}$-substituted or unsubstituted heterocycloalkyl (e.g., 3 to 8, 3 to 6, or 5 to 6 membered), $R^{104A}$-substituted or unsubstituted aryl (e.g., $C_6$-$C_{10}$, $C_{10}$, or phenyl), or $R^{104A}$-substituted or unsubstituted heteroaryl (e.g., 5 to 10, 5 to 9, or 5 to 6 membered).

In embodiments, $R^{104}$ is independently —$NH_2$. In embodiments, $R^{104}$ is independently —OH. In embodiments, $R^{104}$ is independently halogen. In embodiments, $R^{104}$ is independently —CN. In embodiments, $R^{104}$ is independently oxo. In embodiments, $R^{104}$ is independently —$CF_3$. In embodiments, $R^{104}$ is independently —COOH. In embodiments, $R^{104}$ is independently —$CONH_2$. In embodiments, $R^{104}$ is independently —F. In embodiments, $R^{104}$ is independently —Cl. In embodiments, $R^{104}$ is independently —Br. In embodiments, $R^{104}$ is independently —I.

$R^{104A}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{104B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{104B}$-substituted or unsubstituted heteroalkyl (e.g., 2 to 20, 8 to 20, 2 to 10, 2 to 8, 2 to 6, or 2 to 4 membered), $R^{104B}$-substituted or unsubstituted cycloalkyl (e.g., $C_3$-$C_8$, $C_3$-$C_6$, or $C_5$-$C_6$), $R^{104B}$-substituted or unsubstituted heterocycloalkyl (e.g., 3 to 8, 3 to 6, or 5 to 6 membered), $R^{104B}$-substituted or unsubstituted aryl (e.g., $C_6$-$C_{10}$, $C_{10}$, or phenyl), or $R^{104B}$-substituted or unsubstituted heteroaryl (e.g., 5 to 10, 5 to 9, or 5 to 6 membered).

$R^{104B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{105}$ is independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkyl ene, substituted or unsubstituted arylene, or substituted or unsubstituted heteroaryl ene.

In embodiments, $L^{105}$ is a bond, —NH—, —S—, —O—, —C(O)—, —C(O)O—, —OC(O)—, —NHC(O)—, —C(O)NH—, —NHC(O)NH—, —NHC(NH)NH—, —C(S)—, substituted or unsubstituted alkylene (e.g., $C_1$-$C_{20}$, $C_{10}$-$C_{20}$, $C_1$-$C_8$, $C_1$-$C_6$, or $C_1$-$C_4$), substituted or unsubstituted heteroalkylene (e.g., 2 to 20 membered, 8 to 20 membered, 5 to 16 membered, 2 to 10, 2 to 8, 2 to 6, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8, 3 to 6, or 5 to 6 membered), substituted or unsubstituted arylene (e.g., $C_6$-$C_{10}$, $C_{10}$, or phenylene), or substituted or unsubstituted heteroarylene (e.g., 5 to 10, 5 to 9, or 5 to 6 membered).

In embodiments, $L^{105}$ is a bond, —NH—, —$NR^{105}$—, —S—, —O—, —C(O)—, —C(O)O—, —OC(O)—, —NHC(O)—, —C(O)NH—, —NHC(O)NH—, —NHC(NH)NH—, —C(S)—, $R^{105}$-substituted or unsubstituted alkylene (e.g., $C_1$-$C_{20}$, $C_{10}$-$C_{20}$, $C_1$-$C_8$, $C_1$-$C_6$, or $C_1$-$C_4$), $R^{105}$-substituted or unsubstituted heteroalkylene (e.g., 2 to 20 membered, 8 to 20 membered, 5 to 16 membered, 2 to 10, 2 to 8, 2 to 6, or 2 to 4 membered), $R^{105}$-substituted or unsubstituted cycloalkylene (e.g., $C_3$-$C_8$, $C_3$-$C_6$, or $C_5$-$C_6$), $R^{105}$-substituted or unsubstituted heterocycloalkylene (e.g., 3 to 8, 3 to 6, or 5 to 6 membered), $R^{105}$-substituted or unsubstituted arylene (e.g., $C_6$-$C_{10}$, $C_{10}$, or phenylene), or $R^{105}$-substituted or unsubstituted heteroarylene (e.g., 5 to 10, 5 to 9, or 5 to 6 membered). In embodiments, $L^{105}$ is a bond. In embodiments, $L^{105}$ is —NH—. In embodiments, $L^{105}$ is —$NR^{105}$—. In embodiments, $L^{105}$ is —S—. In embodiments, $L^{105}$ is —O—. In embodiments, $L^{105}$ is —C(O)—. In embodiments, $L^{105}$ is —C(O)O—. In embodiments, $L^{105}$ is —OC(O)—. In embodiments, $L^{105}$ is —NHC(O)—. In embodiments, $L^{105}$ is —C(O)NH—. In embodiments, $L^{105}$ is —NHC(O)NH—. In embodiments, $L^{105}$ is —NHC(NH)NH—. In embodiments, $L^{105}$ is —C(S)—. In embodiments, $L^{105}$ is $R^{105}$-substituted or unsubstituted $C_1$-$C_{20}$ alkylene. In embodiments, $L^{105}$ is $R^{105}$-substituted or unsubstituted 2 to 20 membered heteroalkylene. In embodiments, $L^{105}$ is $R^{105}$-substituted or unsubstituted 5 to 16 membered heteroalkylene. In embodiments, $L^{105}$ is $R^{105}$-substituted or unsubstituted 2 to 10 membered heteroalkylene. In embodiments, $L^{105}$ is $R^{105}$-substituted or unsubstituted $C_3$-$C_8$ cycloalkylene. In embodiments, $L^{105}$ is $R^{105}$-substituted or unsubstituted 3 to 8 membered heterocycloalkylene. In embodiments, $L^{105}$ is $R^{105}$-substituted or unsubstituted $C_6$-$C_{10}$ arylene. In embodiments, $L^{105}$ is $R^{105}$-substituted or unsubstituted 5 to 10 membered heteroarylene.

In embodiments, $L^{105}$ is a bond, —NH—, —$NR^{105}$—, —S—, —O—, —C(O)—, —C(O)O—, —OC(O)—, —NHC(O)—, —C(O)NH—, —NHC(O)NH—, —NHC(NH)NH—, —C(S)—, —CH(OH)—, or —C($CH_2$)—. In embodiments, $L^{105}$ is a bond. In embodiments, $L^{105}$ is —NH—. In embodiments, $L^{105}$ is —$NR^{105}$—. In embodiments, $L^{105}$ is —S—. In embodiments, $L^{105}$ is —O—. In embodiments, $L^{105}$ is —C(O)—. In embodiments, $L^{105}$ is —C(O)O—. In embodiments, $L^{105}$ is —OC(O)—. In embodiments, $L^{105}$ is —NHC(O)—. In embodiments, $L^{105}$ is —C(O)NH—. In embodiments, $L^{105}$ is —NHC(O)NH—. In embodiments, $L^{105}$ is —NHC(NH)NH—. In embodiments, $L^{105}$ is —C(S)—. In embodiments, $L^{105}$ is —CH(OH)—. In embodiments, $L^{105}$ is —C($CH_2$)—.

In embodiments, $L^{105}$ is —$(CH_2CH_2O)_f$—. In embodiments, $L^{105}$ is —$(CH_2O)_f$—. In embodiments, $L^{105}$ is —$(CH_2)_f$—. In embodiments, $L^{105}$ is —$(CH_2)_f$—NH—. In embodiments, $L^{105}$ is —C(O)NH$(CH_2)_f$—NH—. In embodiments, $L^{105}$ is —$(CH_2CH_2O)_f$—$(CH_2)_g$—NH—. In embodiments, $L^{105}$ is —$(CH_2)_g$—. In embodiments, $L^{105}$ is —$(CH_2)_g$—NH—. In embodiments, $L^{105}$ is —NHC(O)—$(CH_2)_f$—NH—. In embodiments, $L^{105}$ is —NHC(O)—$(CH_2)_f$—NH—. In embodiments, $L^{105}$ is —NHC(O)—$(CH_2CH_2O)_f$—$(CH_2)_g$—NH—. In embodiments, $L^{105}$ is —NHC(O)—$(CH_2)_g$—. In embodiments, $L^{105}$ is —NHC(O)—$(CH_2)_g$—NH—. In embodiments, $L^{105}$ is —C(O)NH$(CH_2)_f$—NH—. In embodiments, $L^{105}$ is —C(O)NH—$(CH_2CH_2O)_f$—$(CH_2)_g$—NH—. In embodiments, $L^{105}$ is —C(O)NH—$(CH_2)_g$—. In embodiments, $L^{105}$ is —C(O)NH—$(CH_2)_g$—NH—. The symbol f is an integer from 0 to 8. In embodiments, f is 3. In embodiments, f is 1. In embodiments, f is 2. In embodiments, f is 0. The symbol g is an integer from 0 to 8. In embodiments, g is 3. In embodiments, g is 1. In embodiments, g is 2. In embodiments, g is 0.

$R^{105}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, $R^{105A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{105A}$-substituted or unsubstituted heteroalkyl (e.g., 2 to 20, 8 to 20, 2 to 10, 2 to 8, 2 to 6, or 2 to 4 membered), $R^{105A}$-substituted or unsubstituted cycloalkyl (e.g., $C_3$-$C_8$, $C_3$-$C_6$, or $C_5$-$C_6$), $R^{105A}$-substituted or unsubstituted heterocycloalkyl (e.g., 3 to 8, 3 to 6, or 5 to 6 membered), $R^{105A}$-substituted or unsubstituted aryl (e.g., $C_6$-$C_{10}$, $C_{10}$, or phenyl), or $R^{105A}$-substituted or unsubstituted heteroaryl (e.g., 5 to 10, 5 to 9, or 5 to 6 membered).

In embodiments, $R^{105}$ is independently -MB. In embodiments, $R^{105}$ is independently —OH. In embodiments, $R^{105}$ is independently halogen. In embodiments, $R^{105}$ is independently —CN. In embodiments, $R^{105}$ is independently oxo. In embodiments, $R^{105}$ is independently —$CF_3$. In embodiments, $R^{105}$ is independently —COOH. In embodiments, $R^{105}$ is independently —$CONH_2$. In embodiments, $R^{105}$ is independently —F. In embodiments, $R^{105}$ is independently —Cl. In embodiments, $R^{105}$ is independently —Br. In embodiments, $R^{105}$ is independently —I.

$R^{105A}$ is independently oxo, halogen, —$CCl_3$, —$CBr_3$, —$CF_3$, —$CI_3$, —CN, —OH, -MB, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —OCB, —$OCHCl_2$, —$OCHBr_2$, —$OCHI_2$, —$OCHF_2$, —$N_3$, $R^{105B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{105B}$-substituted or unsubstituted heteroalkyl (e.g., 2 to 20, 8 to 20, 2 to 10, 2 to 8, 2 to 6, or 2 to 4 membered), $R^{105B}$-substituted or unsubstituted cycloalkyl (e.g., $C_3$-$C_8$, $C_3$-$C_6$, or $C_5$-$C_6$), $R^{105B}$-substituted or unsubstituted heterocycloalkyl (e.g., 3 to 8, 3 to 6, or 5 to 6 membered), $R^{105B}$-substituted or unsubstituted aryl (e.g., $C_6$-$C_{10}$, $C_{10}$, or phenyl), or $R^{105B}$-substituted or unsubstituted heteroaryl (e.g., 5 to 10, 5 to 9, or 5 to 6 membered).

$R^{105B}$ is independently oxo, halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$N_3$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20, 8 to 20, 2 to 10, 2 to 8, 2 to 6, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8, 3 to 6, or 5 to 6 membered), unsubstituted aryl (e.g., $C_6$-$C_{10}$, $C_{10}$, or phenyl), or unsubstituted heteroaryl (e.g., 5 to 10, 5 to 9, or 5 to 6 membered).

In embodiments, $L^{101}$, $L^{103}$, $L^{104}$, and $L^{105}$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently a bond, substituted or unsubstituted 4 to 18 membered heteroalkylene, or substituted or unsubstituted phenylene; $L^{105}$ is independently bond or substituted or unsubstituted 4 to 18 membered heteroalkylene.

In embodiments, $L^{101}$, $L^{103}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{104}$ is unsubstituted phenylene.

In embodiments, $L^{101}$ is independently a substituted or unsubstituted $C_1$-$C_4$ alkylene or substituted or unsubstituted 8 to 20 membered heteroalkylene. In embodiments, $L^{103}$ is independently a bond or substituted or unsubstituted 2 to 10 membered heteroalkylene. In embodiments, $L^{104}$ is independently an unsubstituted phenylene. In embodiments, $L^{105}$ is independently bond or substituted or unsubstituted 4 to 18 membered heteroalkylene.

In embodiments, $L^{101}$ is independently a substituted or unsubstituted $C_1$-$C_4$ alkylene or substituted or unsubstituted 8 to 20 membered heteroalkylene; $L^{103}$ is independently a bond or substituted or unsubstituted 2 to 10 membered heteroalkylene; $L^{104}$ is independently an unsubstituted phenylene; $L^{105}$ is independently bond or substituted or unsubstituted 4 to 18 membered heteroalkylene; and $R^{102}$ is unsubstituted $C_1$-$C_4$ alkyl; and $R^{102a}$ is hydrogen or unsubstituted methyl.

In embodiments, -($L^{101}$)-OC($SSR^{102}$)($R^{102a}$)-($L^{103}$)-($L^{104}$)-($L^{105}$)- is

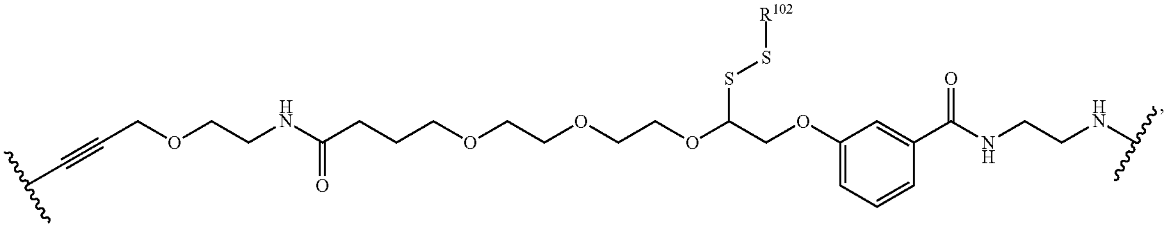

,

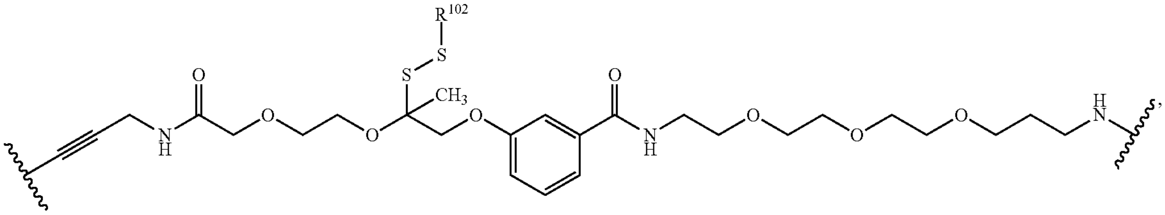

,

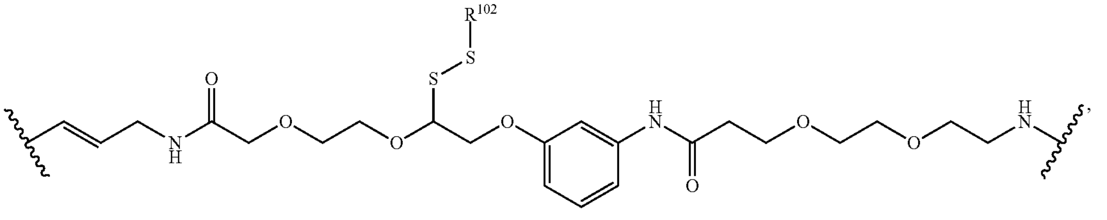

,

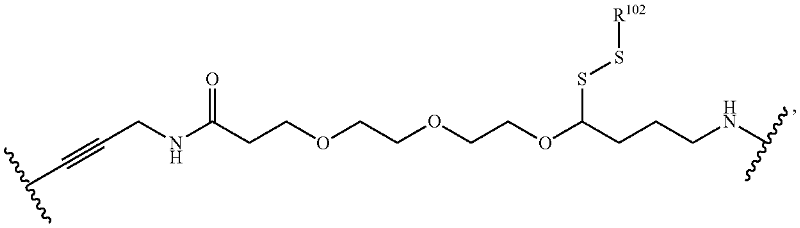

,

-continued
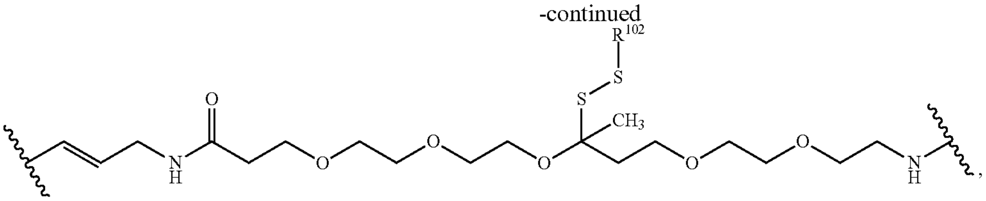
,
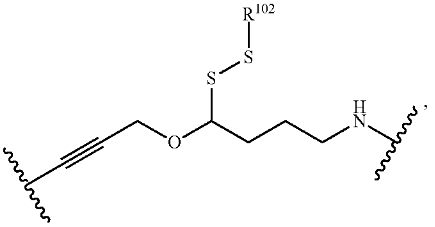
,
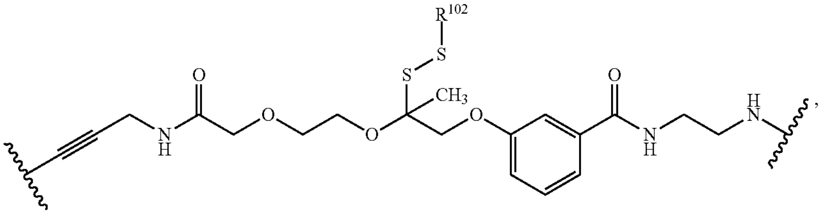
, or
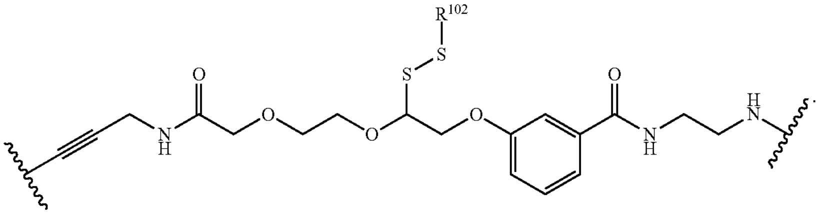
.
$R^{102}$ is as described herein, including in embodiments.
In embodiments, $-(L^{101})-OC(SSR^{102})(R^{102a})-(L^{103})-(L^{104})-(L^{105})-$ is
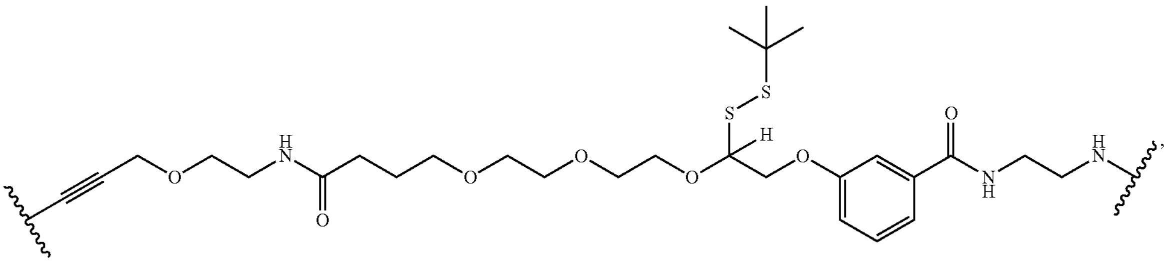
,
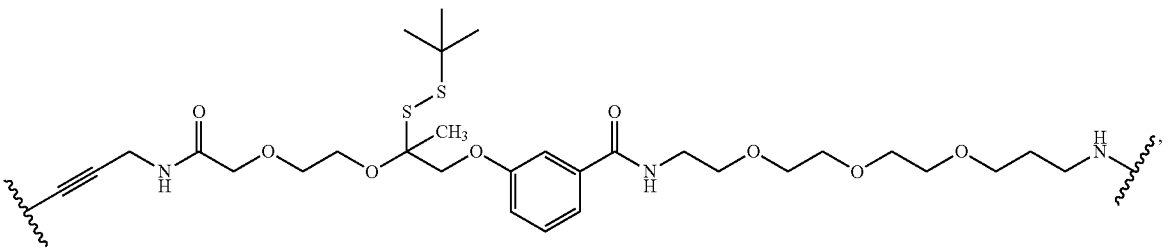
, -continued
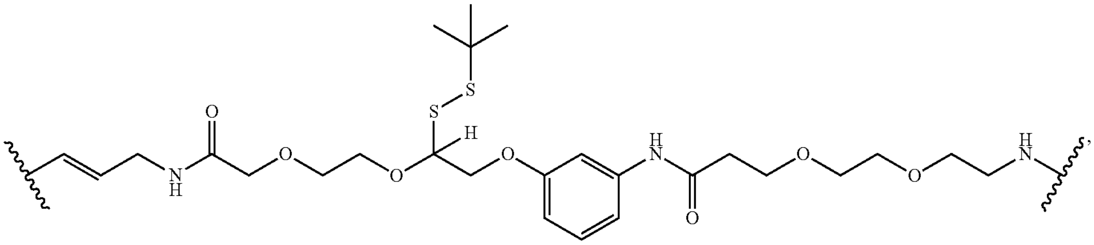
,
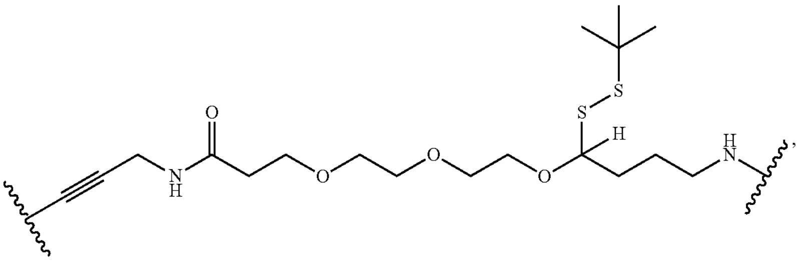
,
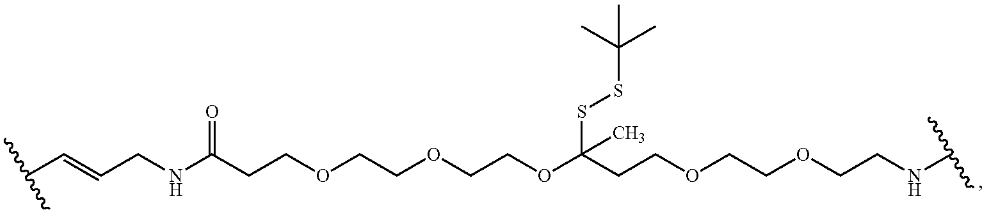
,
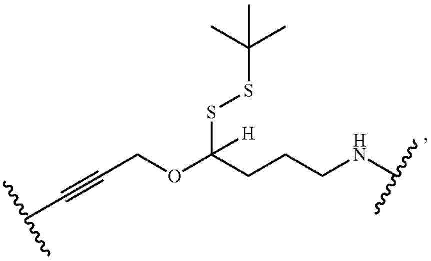
,
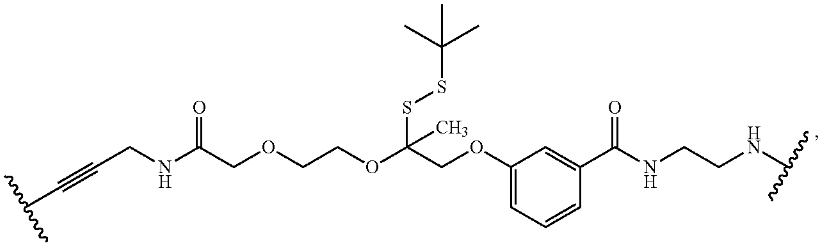
, or
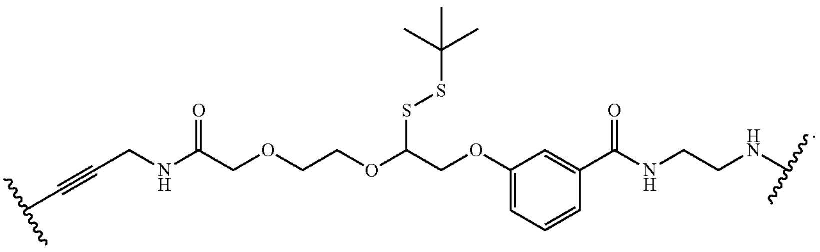 [SMILES: *C#CCNC(=O)COCCOC(COc1cccc(C(=O)NCCN*)c1)SSC(C)(C)C]
.

In embodiments, -($L^{101}$)-OC($SSR^{102}$)($R^{102a}$)-($L^{103}$)-($L^{104}$)-($L^{105}$)- is
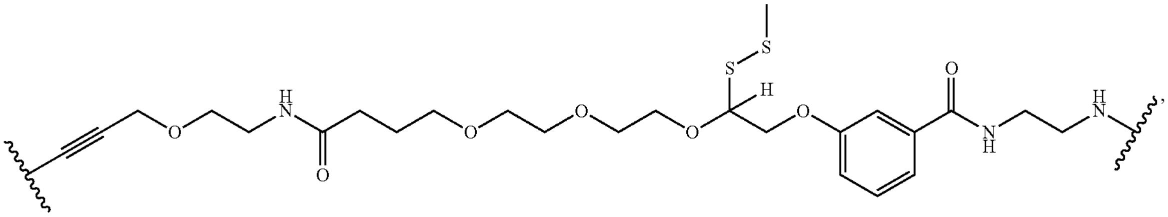
,
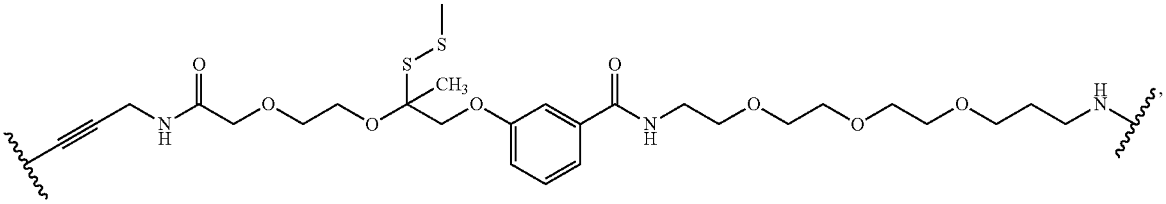
,
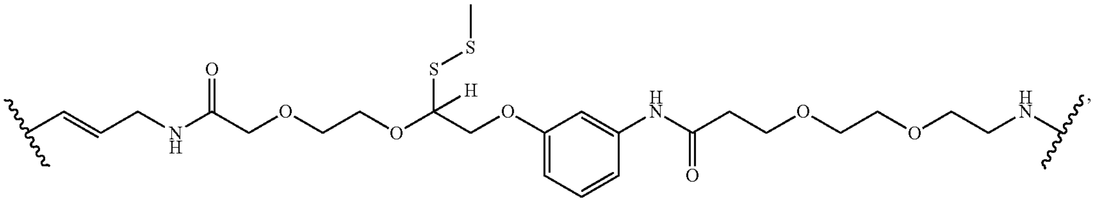
,
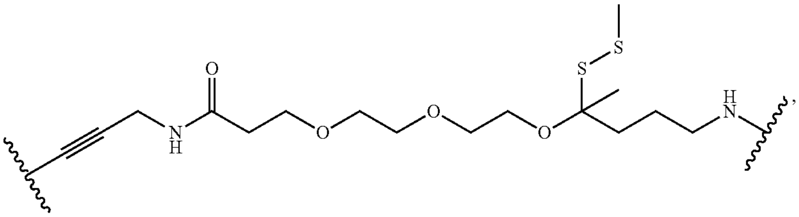
,
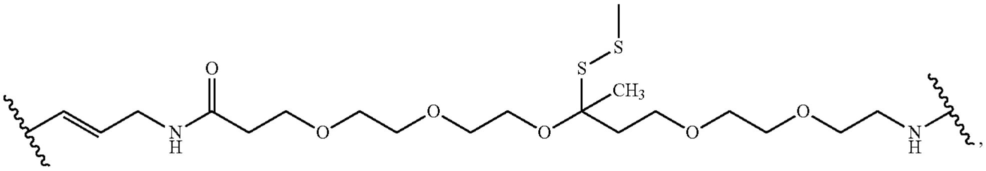
,
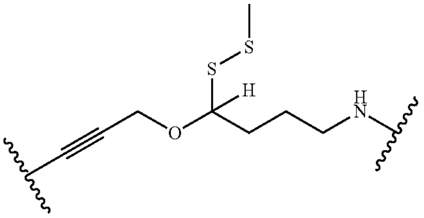
,
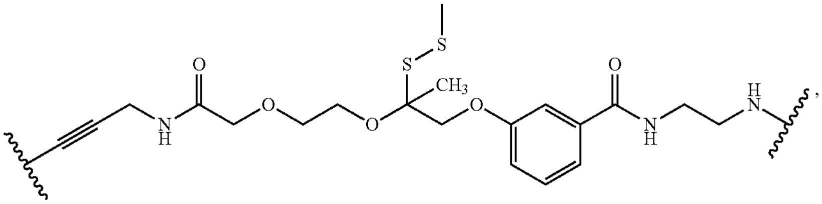
, or
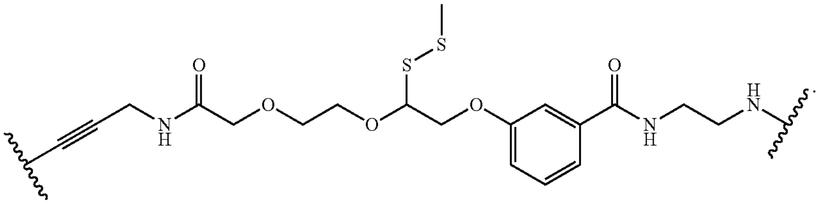 [SMILES: *C#CCNC(=O)COCCOC(COc1cccc(C(=O)NCCN*)c1)SSC]
.

In embodiments, $-(L^{101})-OC(SSR^{102})(R^{102a})-(L^{103})-(L^{104})-(L^{105})-$ is
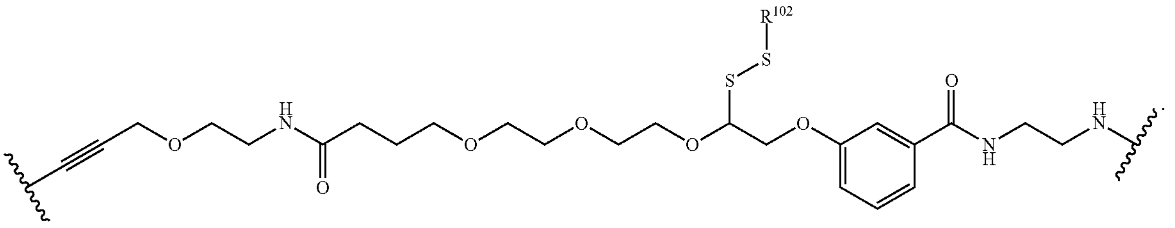
In embodiments, $-(L^{101})-OC(SSR^{102})(R^{102a})-(L^{103})-(L^{104})-(L^{105})-$ is
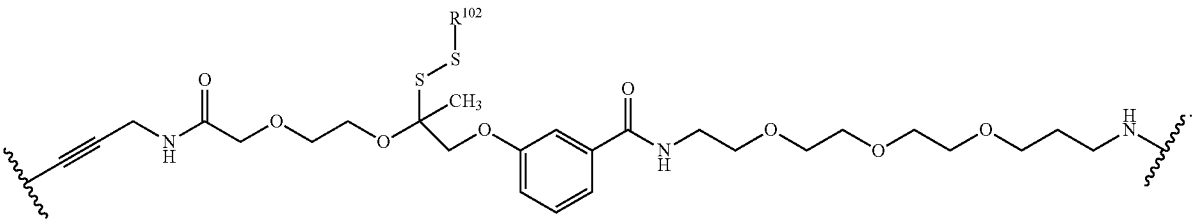
In embodiments, $-(L^{101})-OC(SSR^{102})(R^{102a})-(L^{103})-(L^{104})-(L^{105})-$ is
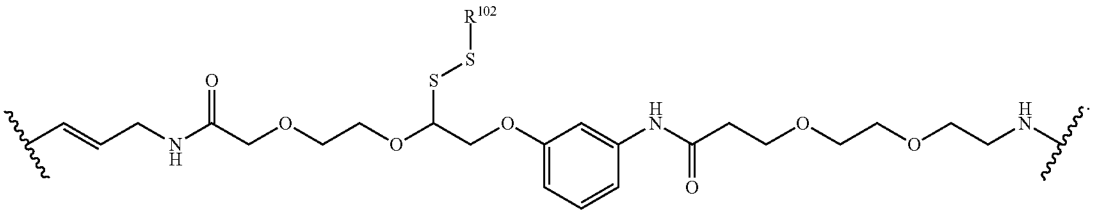
In embodiments, $-(L^{101})-OC(SSR^{102})(R^{102a})-(L^{103})-(L^{104})-(L^{105})-$ is
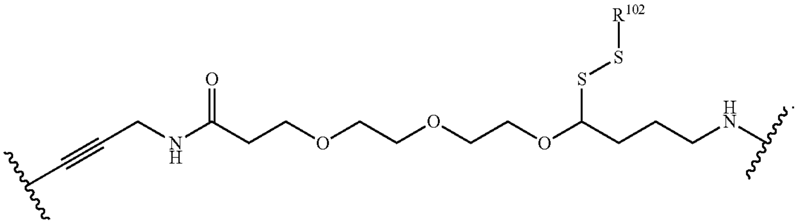
In embodiments, $-(L^{101})-OC(SSR^{102})(R^{102a})-(L^{103})-(L^{104})-(L^{105})-$ is

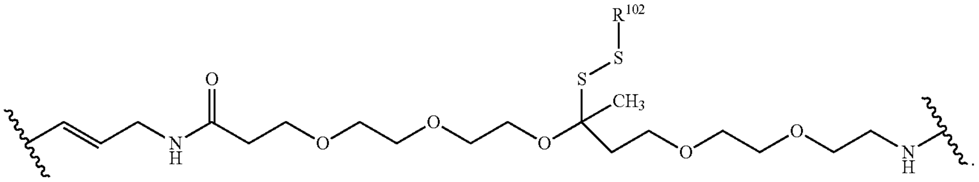
In embodiments, -($L^{101}$)-OC($SSR^{102}$)($R^{102a}$)-($L^{103}$)-($L^{104}$)-($L^{105}$)- is
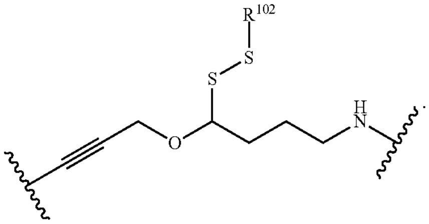
In embodiments, -($L^{101}$)-OC($SSR^{102}$)($R^{102a}$)-($L^{103}$)-($L^{104}$)-($L^{105}$)- is
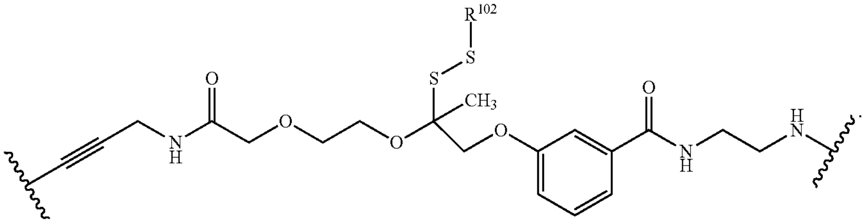
In embodiments, -($L^{101}$)-OC($SSR^{102}$)($R^{102a}$)-($L^{103}$)-($L^{104}$)-($L^{105}$)- is
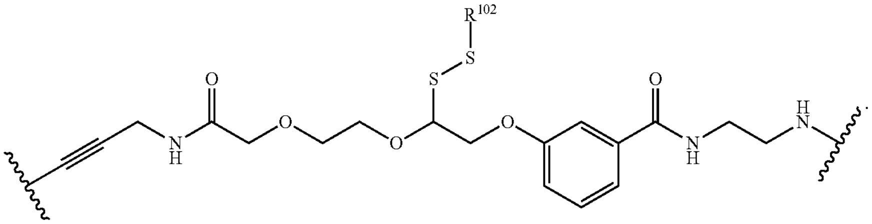
In embodiments, -($L^{101}$)-OC($SSR^{102}$)($R^{102a}$)-($L^{103}$)-($L^{104}$)-($L^{105}$)- is

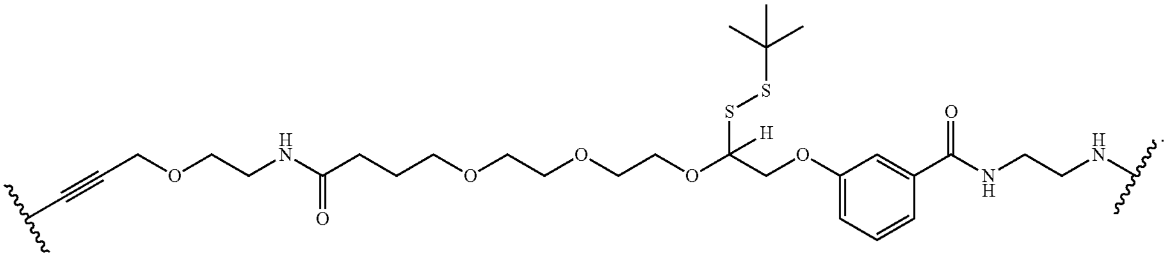 [SMILES: *C#CCOCCNC(=O)CCCOCCOCCOC(COc1cccc(C(=O)NCCN*)c1)SSC(C)(C)C]
In embodiments, -($L^{101}$)-OC($SSR^{102}$)($R^{102a}$)-($L^{103}$)-($L^{104}$)-($L^{105}$)- is
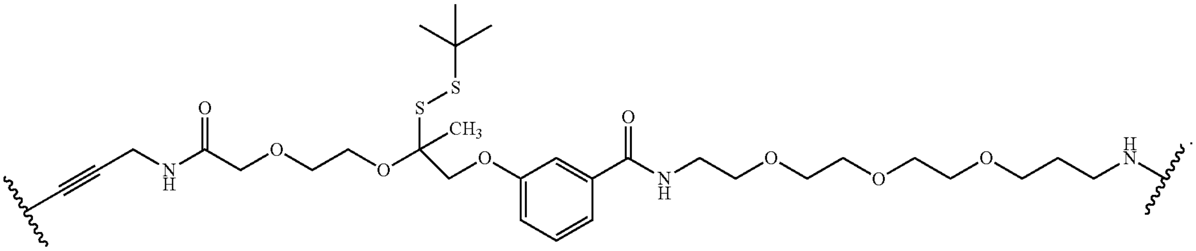 [SMILES: *C#CCNC(=O)COCCOC(C)(COc1cccc(C(=O)NCCOCCOCCOCCCN*)c1)SSC(C)(C)C]
In embodiments, -($L^{101}$)-OC($SSR^{102}$)($R^{102a}$)-($L^{103}$)-($L^{104}$)-($L^{105}$)- is
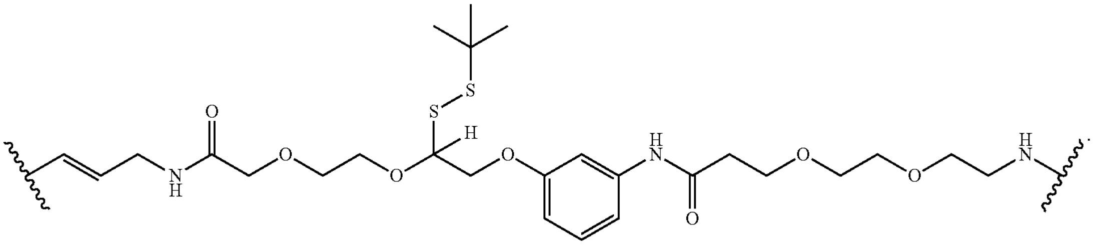 [SMILES: */C=C/CNC(=O)COCCOC(COc1cccc(NC(=O)CCOCCOCCN*)c1)SSC(C)(C)C]
In embodiments, -($L^{101}$)-OC($SSR^{102}$)($R^{102a}$)-($L^{103}$)-($L^{104}$)-($L^{105}$)- is
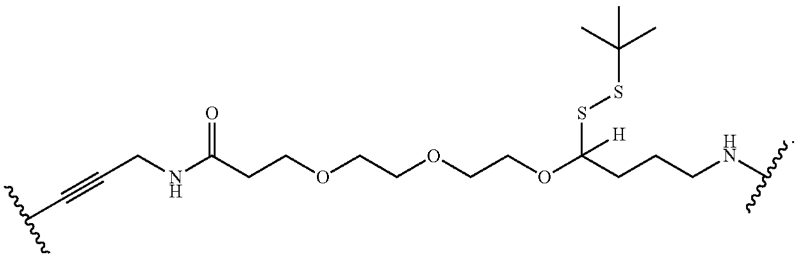 [SMILES: *C#CCNC(=O)CCOCCOCCOC(CCCN*)SSC(C)(C)C]
In embodiments, -($L^{101}$)-OC($SSR^{102}$)($R^{102a}$)-($L^{103}$)-($L^{104}$)-($L^{105}$)- is

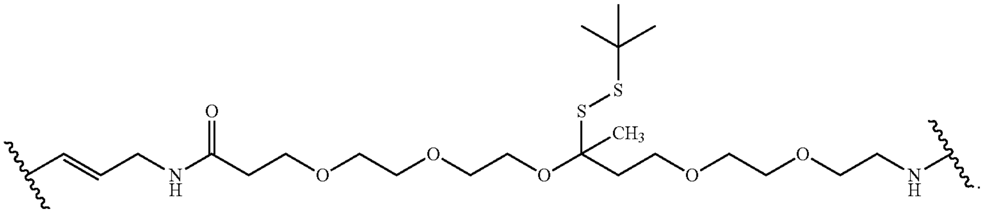 [SMILES: */C=C/CNC(=O)CCOCCOCCOC(C)(CCOCCOCCN*)SSC(C)(C)C]
In embodiments, $-(L^{101})-OC(SSR^{102})(R^{102a})-(L^{103})-(L^{104})-(L^{105})-$ is
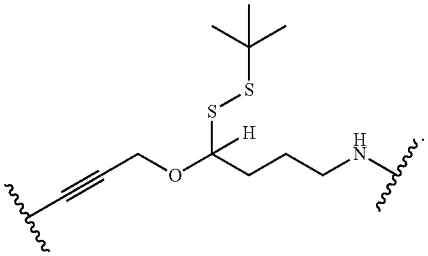 [SMILES: *C#CCOC(CCCN*)SSC(C)(C)C]
In embodiments, $-(L^{101})-OC(SSR^{102})(R^{102a})-(L^{103})-(L^{104})-(L^{105})-$ is
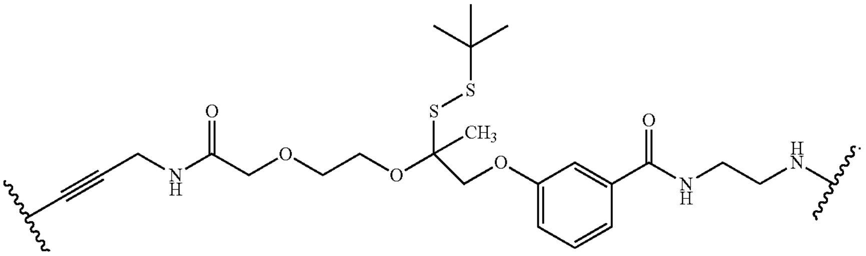 [SMILES: *C#CCNC(=O)COCCOC(C)(COc1cccc(C(=O)NCCN*)c1)SSC(C)(C)C]
In embodiments, $-(L^{101})-OC(SSR^{102})(R^{102a})-(L^{103})-(L^{104})-(L^{105})-$ is
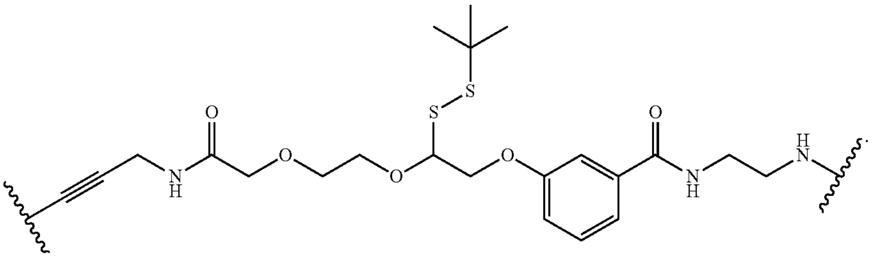 [SMILES: *C#CCNC(=O)COCCOC(COc1cccc(C(=O)NCCN*)c1)SSC(C)(C)C]
In embodiments, $-(L^{101})-OC(SSR^{102})(R^{102a})-(L^{103})-(L^{104})-(L^{105})-$ is

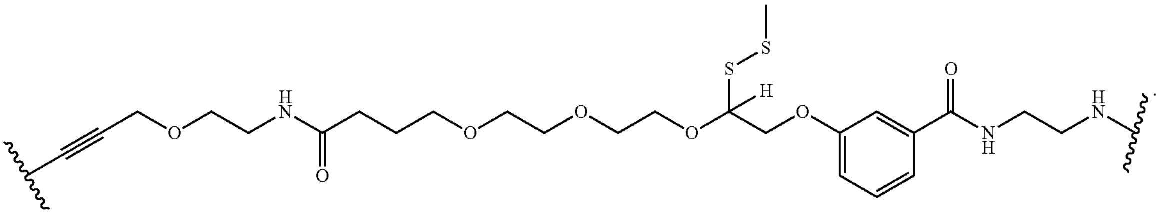 [SMILES: *C#CCOCCNC(=O)CCCOCCOCCOC(COc1cccc(C(=O)NCCN*)c1)SSC]
In embodiments, $-(L^{101})-OC(SSR^{102})(R^{102a})-(L^{103})-(L^{104})-(L^{105})-$ is
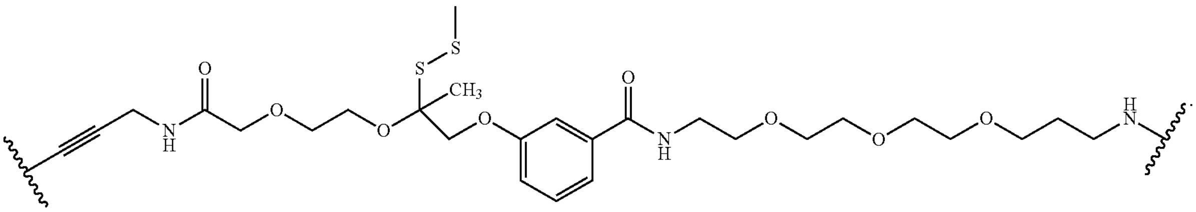 [SMILES: *C#CCNC(=O)COCCOC(C)(COc1cccc(C(=O)NCCOCCOCCOCCCN*)c1)SSC]
In embodiments, $-(L^{101})-OC(SSR^{102})(R^{102a})-(L^{103})-(L^{104})-(L^{105})-$ is
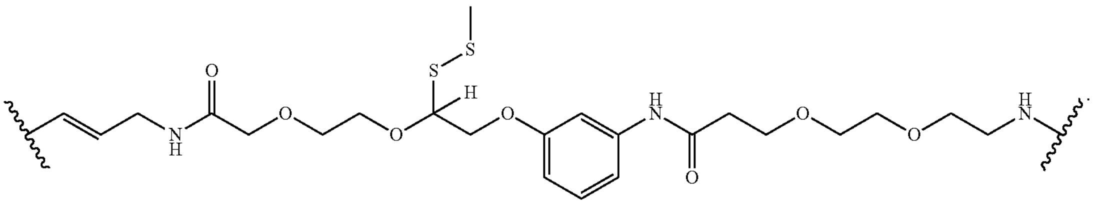 [SMILES: */C=C/CNC(=O)COCCOC(COc1cccc(NC(=O)CCOCCOCCN*)c1)SSC]
In embodiments, $-(L^{101})-OC(SSR^{102})(R^{102a})-(L^{103})-(L^{104})-(L^{105})-$ is
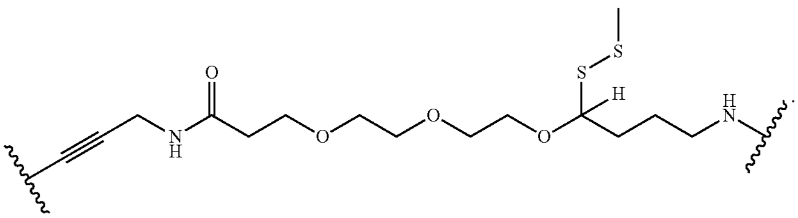 [SMILES: *C#CCNC(=O)CCOCCOCCOC(CCCN*)SSC]
In embodiments, $-(L^{101})-OC(SSR^{102})(R^{102a})-(L^{103})-(L^{104})-(L^{105})-$ is
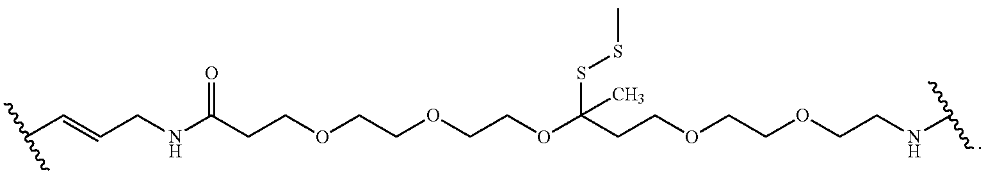 [SMILES: */C=C/CNC(=O)CCOCCOCCOC(C)(CCOCCOCCN*)SSC]
In embodiments, $-(L^{101})-OC(SSR^{102})(R^{102a})-(L^{103})-(L^{104})-(L^{105})-$ is

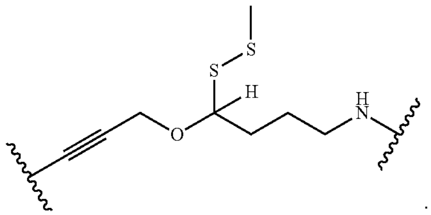 [SMILES: *C#CCOC(CCCN*)SSC]
.
In embodiments, -($L^{101}$)-OC($SSR^{102}$)($R^{102a}$)-($L^{103}$)-($L^{104}$)-($L^{105}$)- is
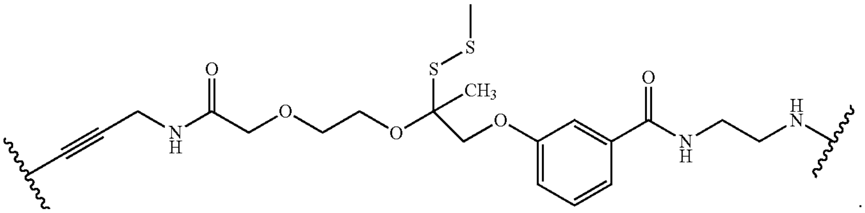 [SMILES: *C#CCNC(=O)COCCOC(C)(COc1cccc(C(=O)NCCN*)c1)SSC]
.
In embodiments, -($L^{101}$)-OC($SSR^{102}$)($R^{102a}$)-($L^{103}$)-($L^{104}$)-($L^{105}$)- is
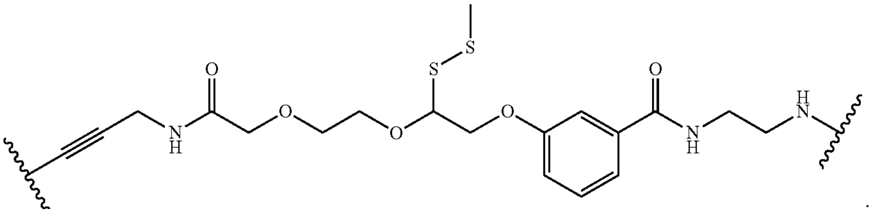 [SMILES: *C#CCNC(=O)COCCOC(COc1cccc(C(=O)NCCN*)c1)SSC]
.
In embodiments, -($L^{101}$)-OC(SCN)($R^{102a}$)-($L^{103}$)-($L^{104}$)-($L^{105}$)- is
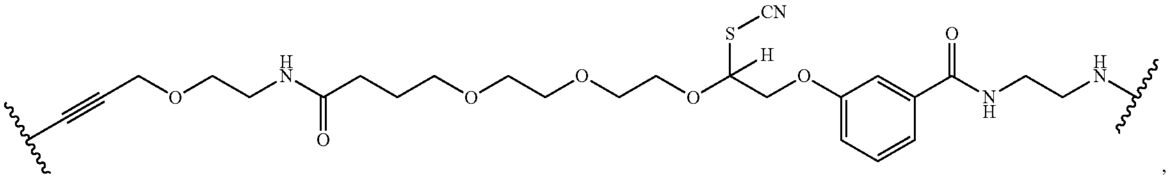
,
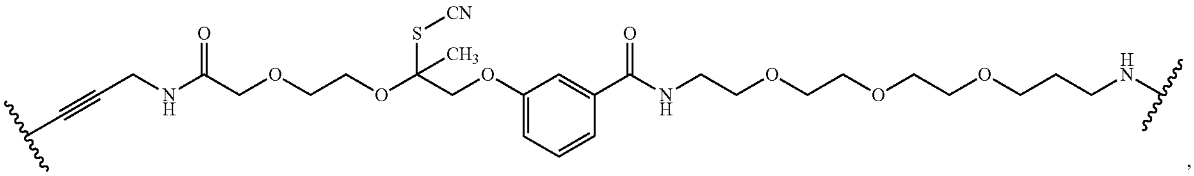
,
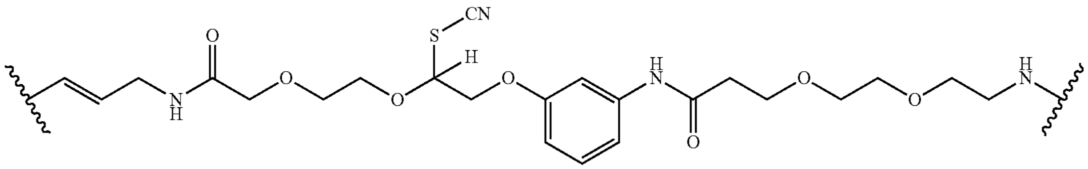
, -continued
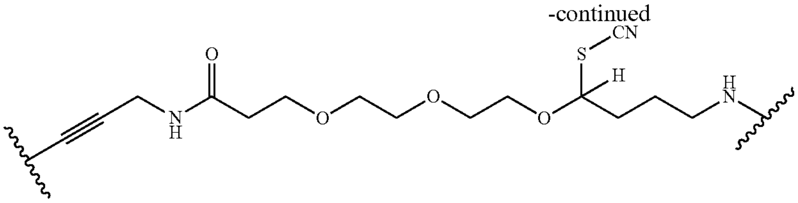
,
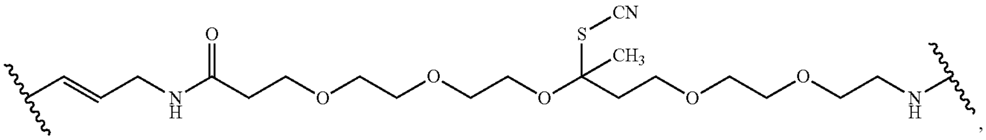
,
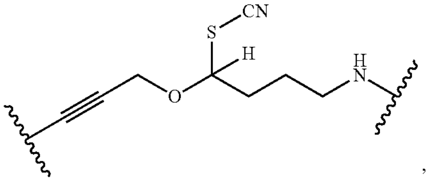
,
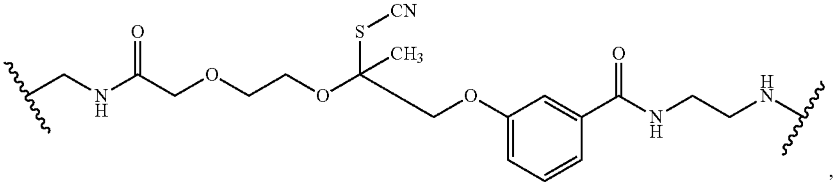
, or
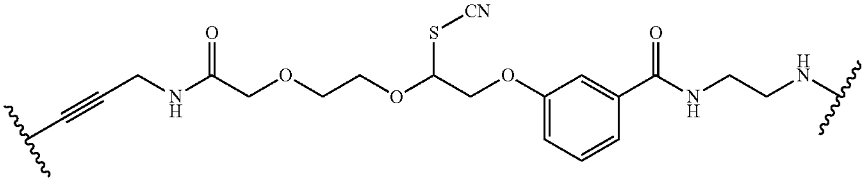
.
In embodiments, $-(L^{101})-OC(SCN)(R^{102a})-(L^{103})-(L^{104})-(L^{105})-$ is
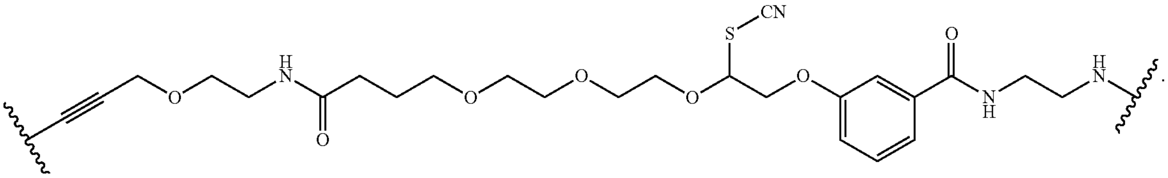 [SMILES: *C#CCOCCNC(=O)CCCOCCOCCOC(COc1cccc(C(=O)NCCN*)c1)SC#N]
In embodiments, $-(L^{101})-OC(SCN)(R^{102a})-(L^{103})-(L^{104})-(L^{105})-$ is
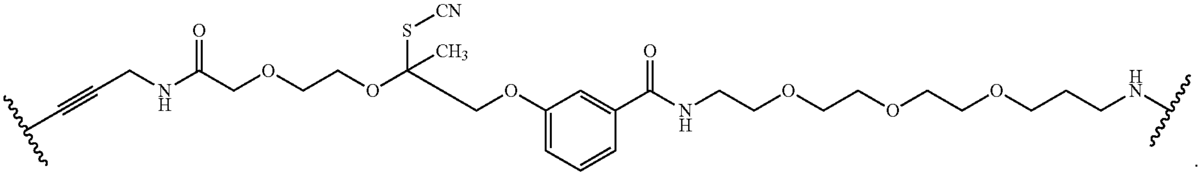 [SMILES: *C#CCNC(=O)COCCOC(C)(COc1cccc(C(=O)NCCOCCOCCOCCCN*)c1)SC#N]
.
In embodiments, $-(L^{101})-OC(SCN)(R^{102a})-(L^{103})-(L^{104})-(L^{105})-$ is

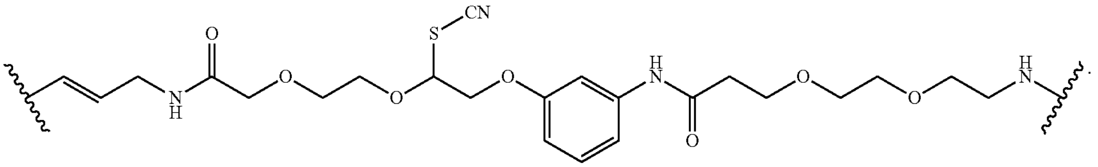 [SMILES: */C=C/CNC(=O)COCCOC(COc1cccc(NC(=O)CCOCCOCCN*)c1)SC#N]
In embodiments, $-(L^{101})-OC(SCN)(R^{102a})-(L^{103})-(L^{104})-(L^{105})-$ is
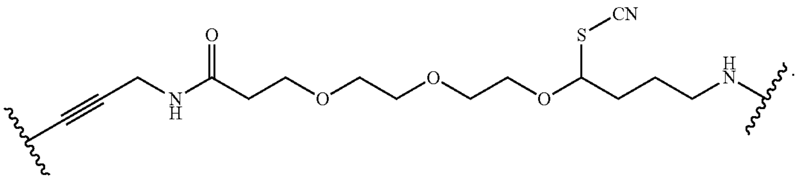 [SMILES: *C#CCNC(=O)CCOCCOCCOC(CCCN*)SC#N]
In embodiments, $-(L^{101})-OC(SCN)(R^{102a})-(L^{103})-(L^{104})-(L^{105})-$ is
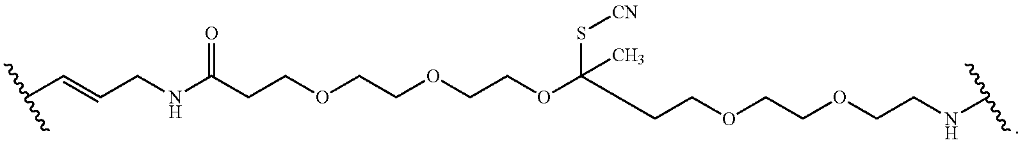 [SMILES: */C=C/CNC(=O)CCOCCOCCOC(C)(CCOCCOCCN*)SC#N]
In embodiments, $-(L^{101})-OC(SCN)(R^{102a})-(L^{103})-(L^{104})-(L^{105})-$ is
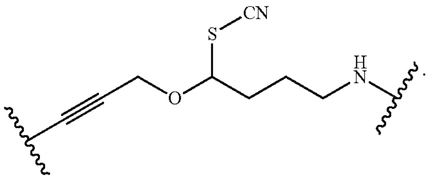 [SMILES: *C#CCOC(CCCN*)SC#N]
In embodiments, $-(L^{101})-OC(SCN)(R^{102a})-(L^{103})-(L^{104})-(L^{105})-$ is
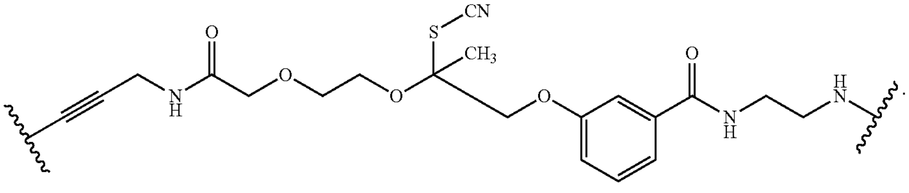 [SMILES: *C#CCNC(=O)COCCOC(C)(COc1cccc(C(=O)NCCN*)c1)SC#N]
In embodiments, $-(L^{101})-OC(SCN)(R^{102a})-(L^{103})-(L^{104})-(L^{105})-$ is

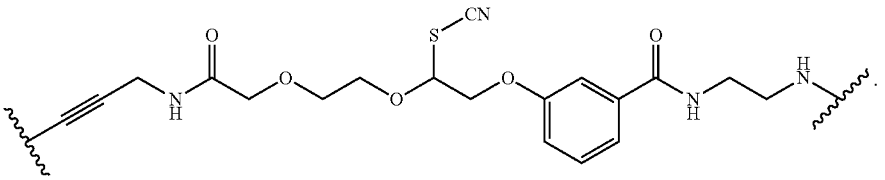 [SMILES: *C#CCNC(=O)COCCOC(COc1cccc(C(=O)NCCN*)c1)SC#N]

In embodiments, $L^{101}$ is $—CCCH_2—NHC(O)—O—(CH_2)_c—$. In embodiments, $L^{101}$ is $—CCCH_2—NHC(O)—NH—(CH_2)_c—$. In embodiments, $L^{101}$ is $—CCCH_2—NHC(O)—(CH_2)_c—$. The symbol c is an integer from 0 to 8. In embodiments, c is 0. In embodiments, c is 1. In embodiments, c is 2. In embodiments, c is 3. In embodiments, c is 4. In embodiments, $L^{101}$ is $—CCCH_2—NHC(O)—O—(CH_2)_4—$. In embodiments, $L^{101}$ is $—CCCH_2—NHC(O)—NH—(CH_2)_4—$. In embodiments, $L^{101}$ is $—CCCH_2—NHC(O)—(CH_2)_2$-. In embodiments, $L^{101}$ is $—CCCH_2—NHC(O)—O—(CH_2)_c—OCH(R^{102})—$. In embodiments, $L^{101}$ is $—CCCH_2—NHC(O)—NH—(CH_2)_c—OCH(R^{102})—$.

In embodiments, $L^{102}$ is a bond. In embodiments, $L^{102}$ is $—OCH(R^{102})—$. In embodiments, $L^{102}$ is $—OCH(CH_3)—$. In embodiments, $L^{102}$ is

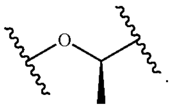 [SMILES: *O[C@@H](*)C]

In embodiments, $L^{102}$ is

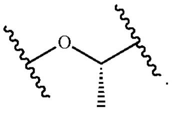 [SMILES: *O[C@H](*)C]

In embodiments, $L^{103}$ is —SS—. In embodiments, $R^{102}$ is $—CH_3$.

In embodiments, $L^{104}$ is a bond. In embodiments, $L^{104}$ is $—(CH_2CH_2O)_e—$. In embodiments, $L^{104}$ is $—(C(CH_3)_2)—(CH_2CH_2O)_e—$. In embodiments, $L^{104}$ is $—(CH_2)_e—$. In embodiments, $L^{104}$ is $—(CH_2)_e—NH—$. In embodiments, $L^{104}$ is $—(C(CH_3)_2)—(CH_2CH_2O)—$. In embodiments, $L^{104}$ is $—(CH_2)—NH—$. In embodiments, $L^{104}$ is $—(CH_2)_2—NH—$. In embodiments, $L^{104}$ is -(unsubstituted phenylene)-. In embodiments, $L^{104}$ is

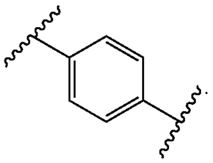 [SMILES: *c1ccc(*)cc1]

The symbol e is an integer from 0 to 8. In embodiments, e is 3. In embodiments, e is 1. In embodiments, e is 2. In embodiments, e is 0. In embodiments, $L^{104}$ is -(unsubstituted phenylene)-$CH_2C(O)NH—$. In embodiments, $L^{104}$ is $—(C(CH_3)_2)—(CH_2CH_2O)—C(O)NH—$.

In embodiments, $L^{105}$ is a bond. In embodiments, $L^{105}$ is $—(CH_2)_f—NH—$. In embodiments, $L^{105}$ is $—(CH_2)_2—NH—$. In embodiments, $L^{105}$ is $—C(O)NH(CH_2)_f—NH—$. In embodiments, $L^{105}$ is $—(CH_2CH_2O)_f—(CH_2)_g—NH—$. In embodiments, $L^{105}$ is $—CH_2—C(O)NH—(CH_2CH_2O)_f—(CH_2)_g—NH—$. In embodiments, $L^{105}$ is $—CH_2—C(O)NH—(CH_2CH_2O)_3—(CH_2)_2—NH—$. In embodiments, $L^{105}$ is $—C(O)NH—(CH_2CH_2O)_f—(CH_2)_g—NH—$. In embodiments, $L^{105}$ is $—C(O)NH—(CH_2CH_2O)_2—(CH_2)_2—NH—$. The symbol f is an integer from 0 to 8. In embodiments, f is 3. In embodiments, f is 1. In embodiments, f is 2. In embodiments, f is 0. The symbol g is an integer from 0 to 8. In embodiments, g is 3. In embodiments, g is 1. In embodiments, g is 2. In embodiments, g is 0.

In embodiments, $L^{100}$ is -($L^{101}$)-($L^{102}$)-SS-($L^{104}$)-($L^{105}$)-. $L^{101}$, $L^{102}$, $L^{104}$, and $L^{105}$ are as described herein. In embodiments, $L^{100}$ is -($L^{101}$)-$OCH(R^{102})$—SS-($L^{104}$)-($L^{105}$)-. $L^{101}$, $L^{104}$, and $L^{105}$ are as described herein.

In embodiments, -($L^{101}$)-($L^{102}$)-SS-($L^{104}$)-($L^{105}$)- is

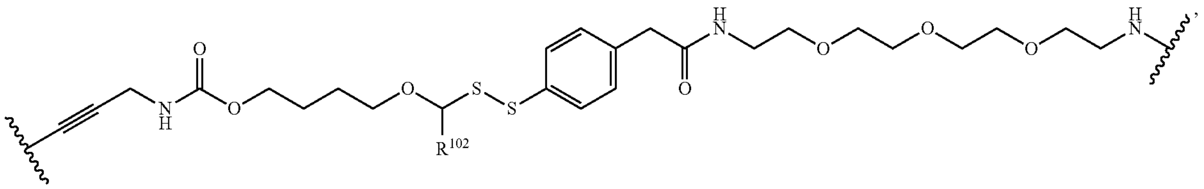

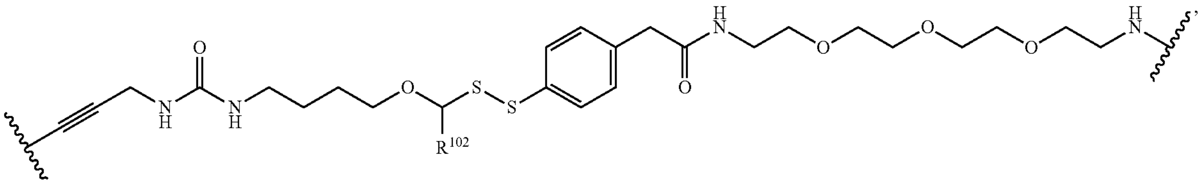

-continued
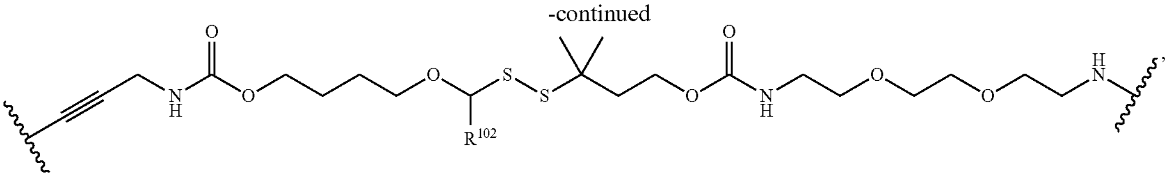
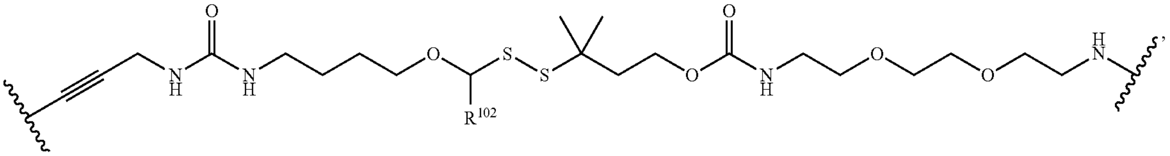
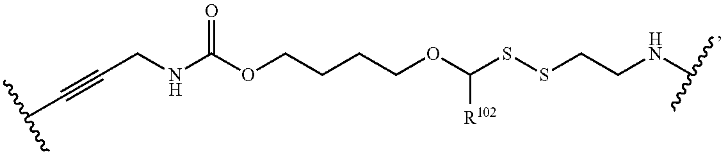
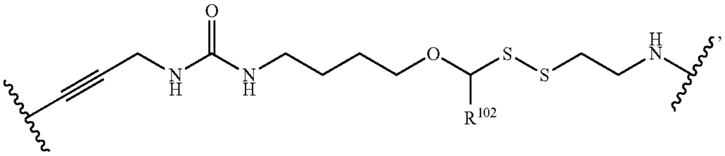
or
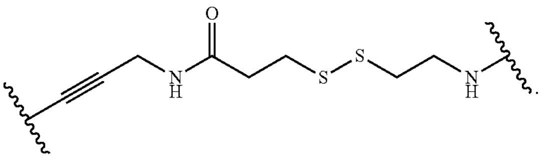
In embodiments, $-(L^{101})-(L^{102})-SS-(L^{104})-(L^{105})-$ is
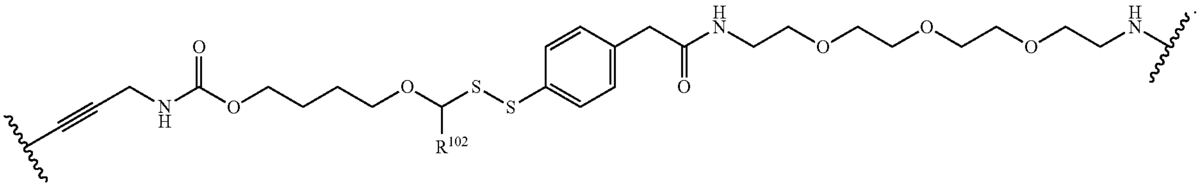
In embodiments, $-(L^{101})-(L^{102})-SS-(L^{104})-(L^{105})-$ is
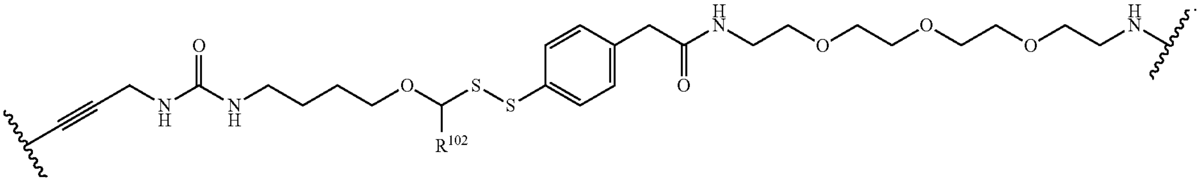
In embodiments, $-(L^{101})-(L^{102})-SS-(L^{104})-(L^{105})-$ is
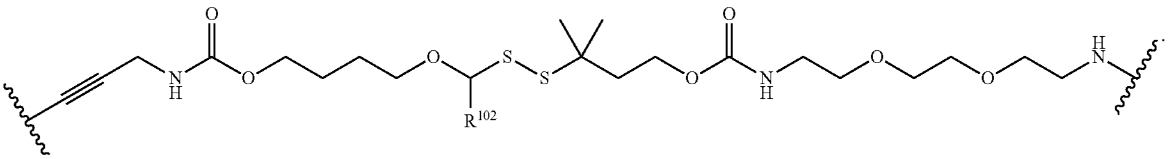

In embodiments, $-(L^{101})-(L^{102})-SS-(L^{104})-(L^{105})-$ is
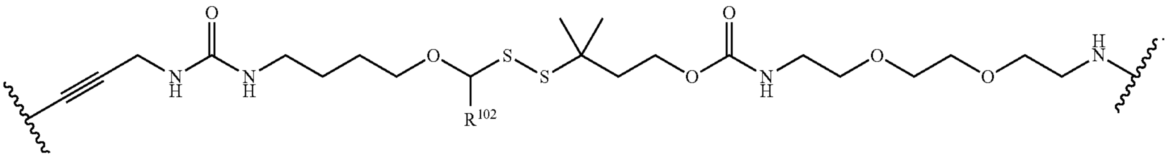
In embodiments, $-(L^{101})-(L^{102})-SS-(L^{104})-(L^{105})-$ is
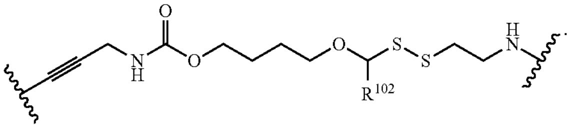
In embodiments, $-(L^{101})-(L^{102})-SS-(L^{104})-(L^{105})-$ is
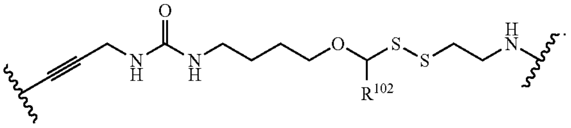
In embodiments, $-(L^{101})-(L^{102})-SS-(L^{104})-(L^{105})-$ is
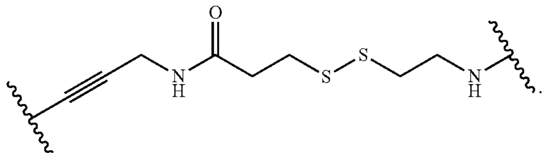 [SMILES: *C#CCNC(=O)CCSSCCN*]
$R^{102}$ is as described herein, including in embodiments.
In embodiments, $-(L^{101})-(L^{102})-SS-(L^{104})-(L^{105})-$ is
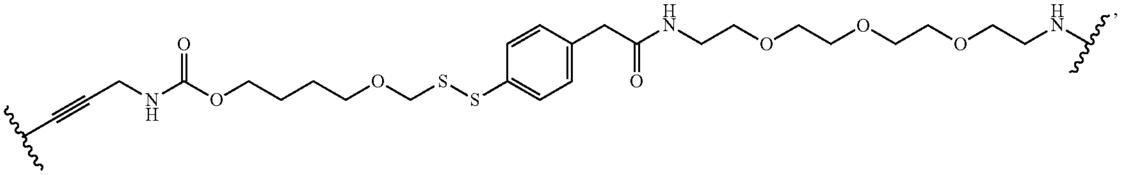
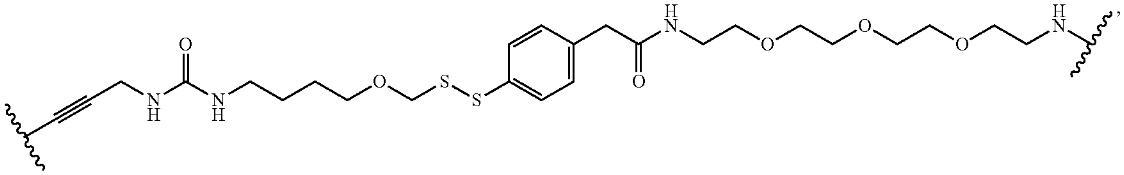
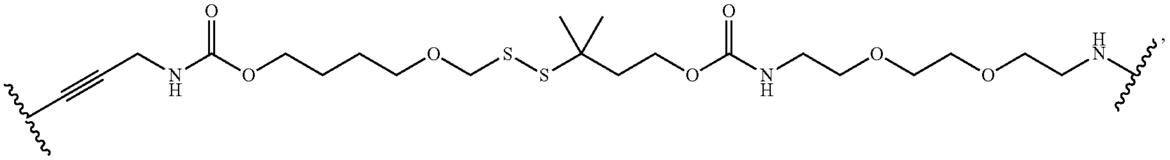
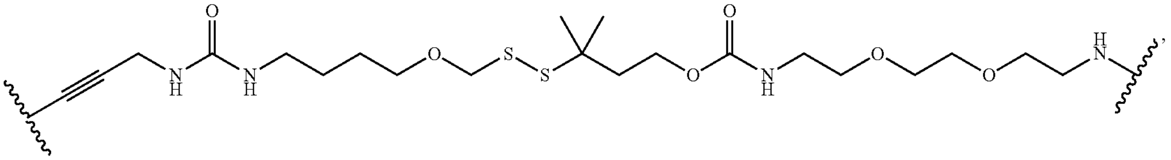
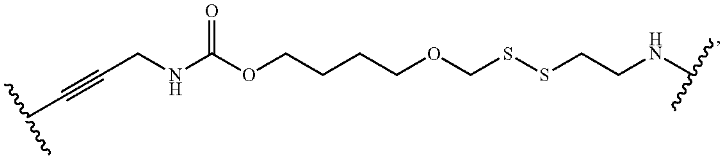

-continued
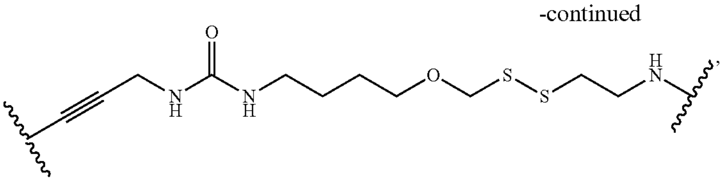
or
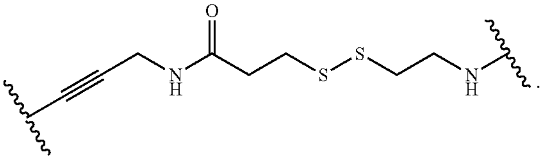
In embodiments, -($L^{101}$)-($L^{102}$)-SS-($L^{104}$)-($L^{105}$)- is
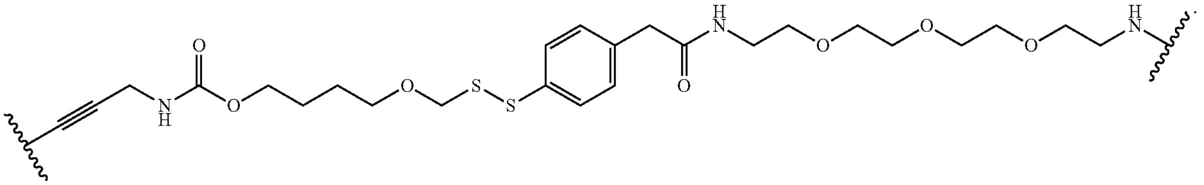 [SMILES: *C#CCNC(=O)OCCCCOCSSc1ccc(CC(=O)NCCOCCOCCOCCN*)cc1]
In embodiments, -($L^{101}$)-($L^{102}$)-SS-($L^{104}$)-($L^{105}$)- is
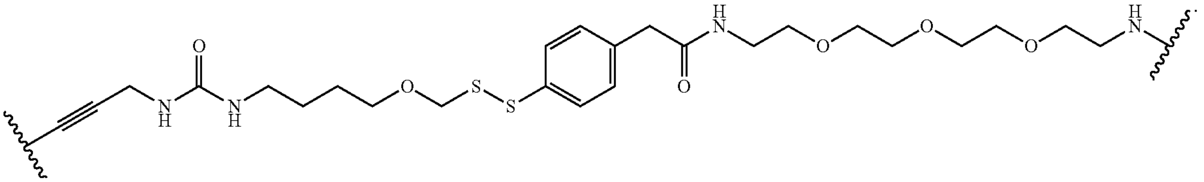 [SMILES: *C#CCNC(=O)NCCCCOCSSc1ccc(CC(=O)NCCOCCOCCOCCN*)cc1]
In embodiments, -($L^{101}$)-($L^{102}$)-SS-($L^{104}$)-($L^{105}$)- is
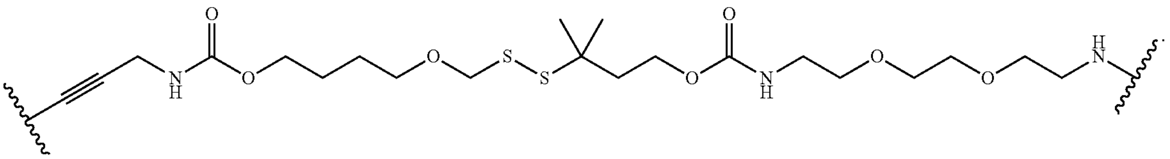 [SMILES: *C#CCNC(=O)OCCCCOCSSC(C)(C)CCOC(=O)NCCOCCOCCN*]
In embodiments, -($L^{101}$)-($L^{102}$)-SS-($L^{104}$)-($L^{105}$)- is
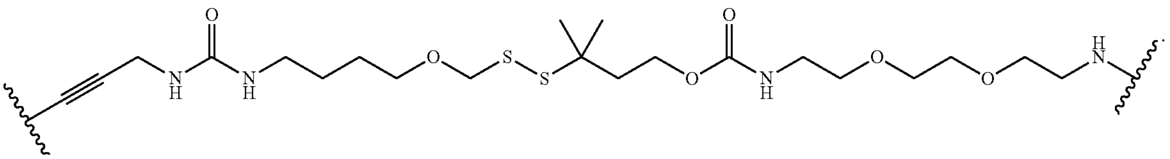 [SMILES: *C#CCNC(=O)NCCCCOCSSC(C)(C)CCOC(=O)NCCOCCOCCN*]
In embodiments, -($L^{101}$)-($L^{102}$)-SS-($L^{104}$)-($L^{105}$)- is
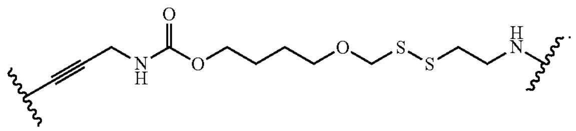 [SMILES: *C#CCNC(=O)OCCCCOCSSCCN*]

In embodiments, -($L^{101}$)-($L^{102}$)-SS-($L^{104}$)-($L^{105}$)- is
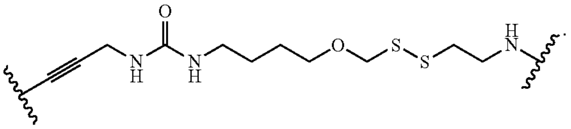 [SMILES: *C#CCNC(=O)NCCCCOCSSCCN*]
In embodiments, -($L^{101}$)-($L^{102}$)-SS-($L^{104}$)-($L^{105}$)- is
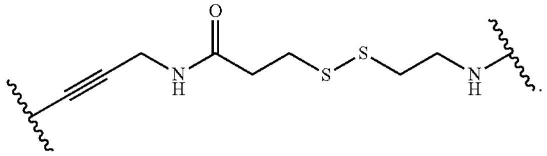 [SMILES: *C#CCNC(=O)CCSSCCN*]
In embodiments, -($L^{101}$)-($L^{102}$)-SS-($L^{104}$)-($L^{105}$)- is
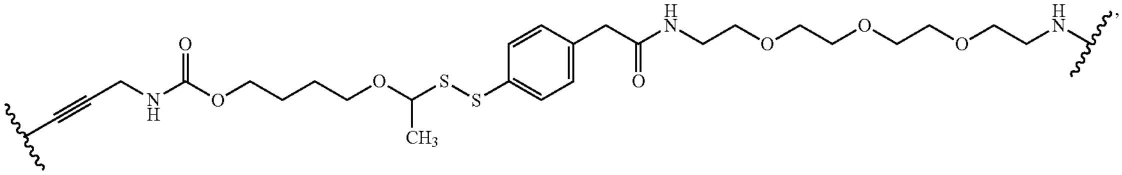
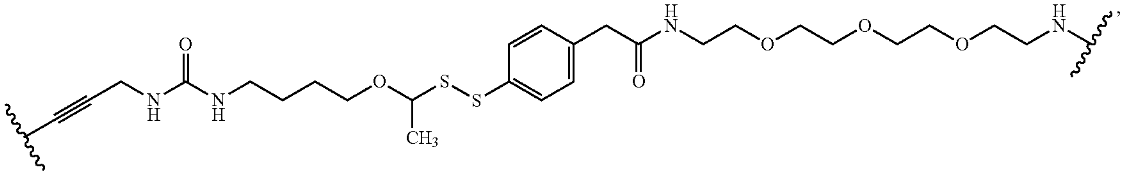
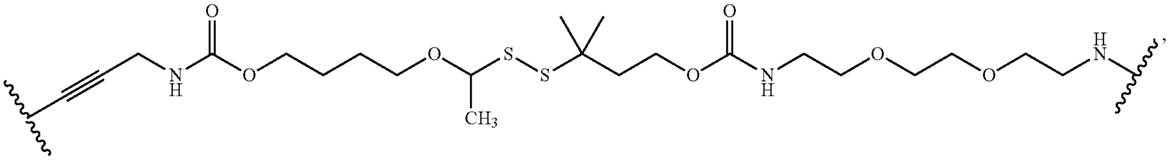
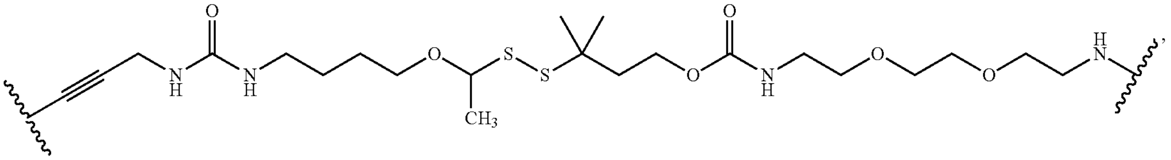
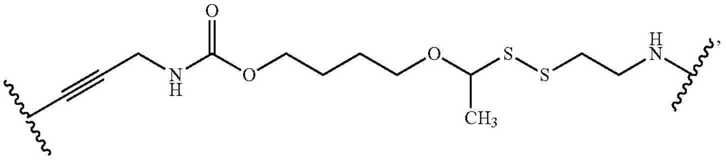
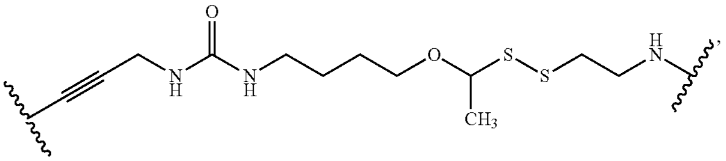
or
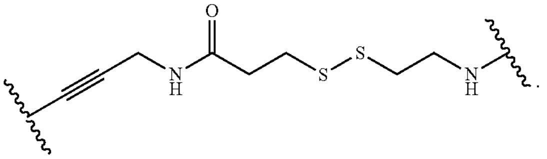

In embodiments, -($L^{101}$)-($L^{102}$)-SS-($L^{104}$)-($L^{105}$)- is
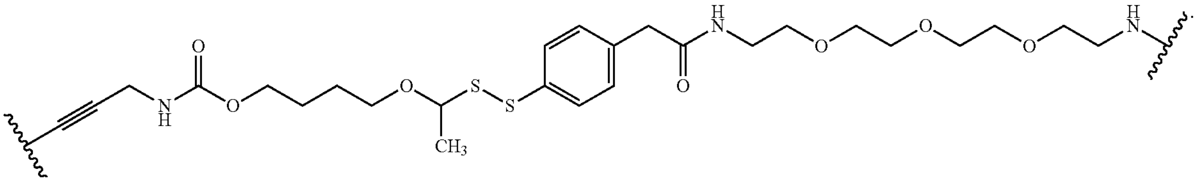 [SMILES: *C#CCNC(=O)OCCCCOC(C)SSc1ccc(CC(=O)NCCOCCOCCOCCN*)cc1]
In embodiments, -($L^{101}$)-($L^{102}$)-SS-($L^{104}$)-($L^{105}$)- is
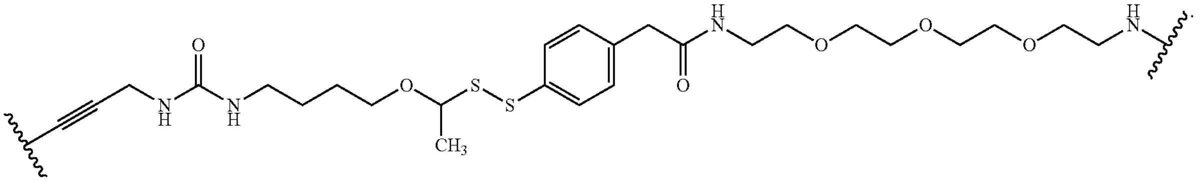 [SMILES: *C#CCNC(=O)NCCCCOC(C)SSc1ccc(CC(=O)NCCOCCOCCOCCN*)cc1]
In embodiments, -($L^{101}$)-($L^{102}$)-SS-($L^{104}$)-($L^{105}$)- is
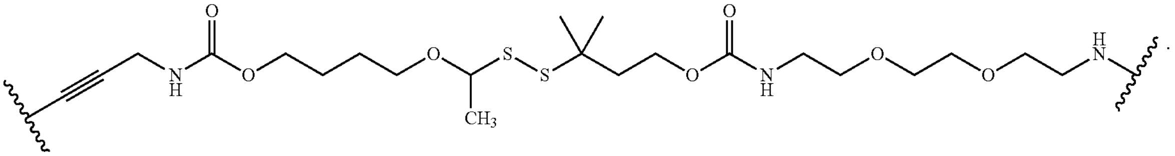 [SMILES: *C#CCNC(=O)OCCCCOC(C)SSC(C)(C)CCOC(=O)NCCOCCOCCN*]
In embodiments, -($L^{101}$)-($L^{102}$)-SS-($L^{104}$)-($L^{105}$)- is
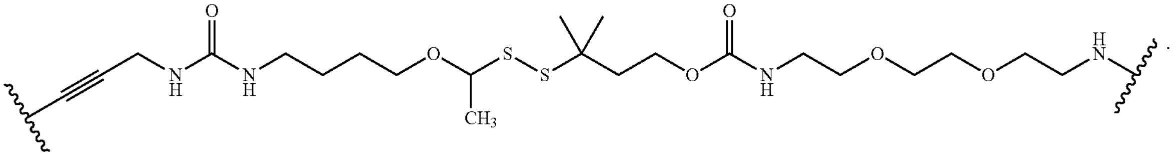 [SMILES: *C#CCNC(=O)NCCCCOC(C)SSC(C)(C)CCOC(=O)NCCOCCOCCN*]
In embodiments, -($L^{101}$)-($L^{102}$)-SS-($L^{104}$)-($L^{105}$)- is
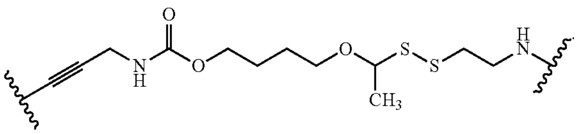 [SMILES: *C#CCNC(=O)OCCCCOC(C)SSCCN*]
In embodiments, -($L^{101}$)-($L^{102}$)-SS-($L^{104}$)-($L^{105}$)- is
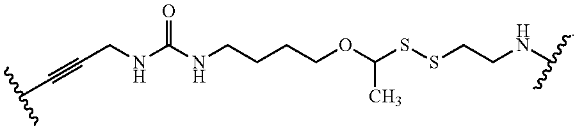 [SMILES: *C#CCNC(=O)NCCCCOC(C)SSCCN*]
In embodiments, -($L^{101}$)-($L^{102}$)-SS-($L^{104}$)-($L^{105}$)- is
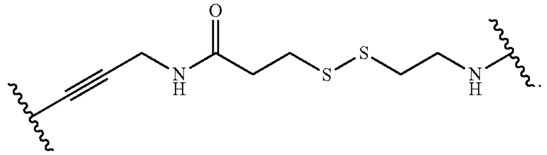 [SMILES: *C#CCNC(=O)CCSSCCN*]
In embodiments, $L^{101}$ is
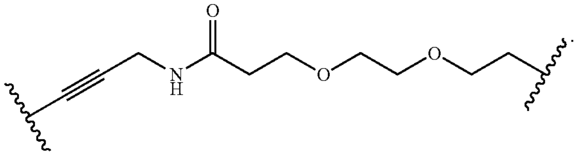 [SMILES: *C#CCNC(=O)CCOCCOCC*]

In embodiments, $L^{101}$ is
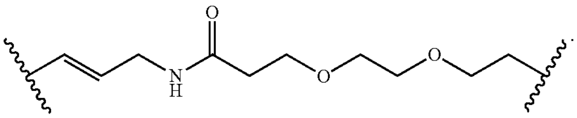 [SMILES: */C=C/CNC(=O)CCOCCOCC*]
In embodiments, $L^{101}$ is —CCCH$_2$—. In embodiments, $L^{101}$ is
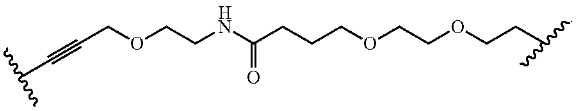 [SMILES: *C#CCOCCNC(=O)CCCOCCOCC*]
In embodiments, $L^{101}$ is
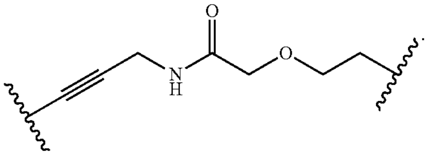 [SMILES: *C#CCNC(=O)COCC*]
In embodiments, $L^{101}$ is
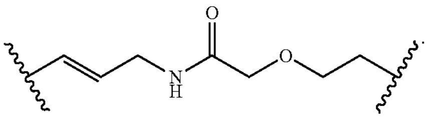 [SMILES: */C=C/CNC(=O)COCC*]
In embodiments, $L^{103}$ is
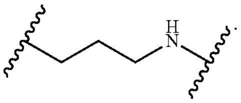 [SMILES: *CCCN*]
In embodiments, $L^{103}$ is
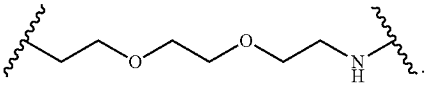 [SMILES: *CCOCCOCCN*]
In embodiments, $L^{103}$ is
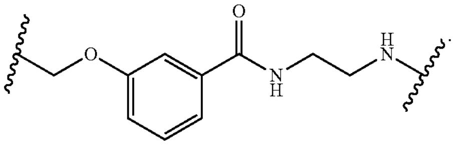 [SMILES: *COc1cccc(C(=O)NCCN*)c1]
In embodiments, $L^{103}$ is
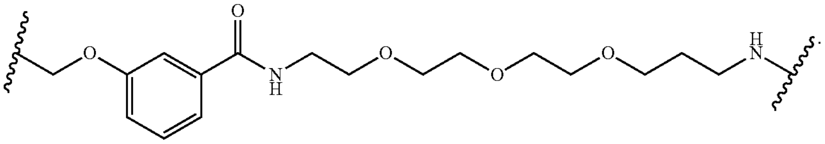 [SMILES: *COc1cccc(C(=O)NCCOCCOCCOCCCN*)c1]
In embodiments, $L^{103}$ is
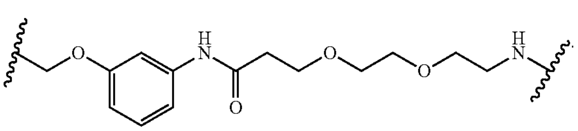 [SMILES: *COc1cccc(NC(=O)CCOCCOCCN*)c1]
In embodiments, $L^{103}$ is a bond.
In embodiments, $L^{104}$ is
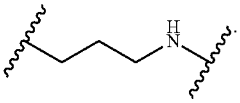 [SMILES: *CCCN*]
In embodiments, $L^{104}$ is
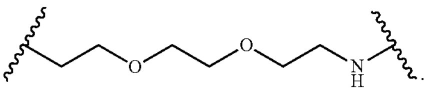 [SMILES: *CCOCCOCCN*]
In embodiments, $L^{104}$ is
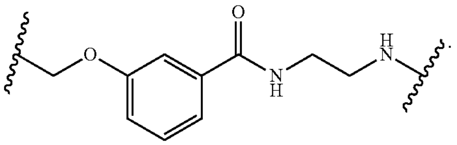 [SMILES: *COc1cccc(C(=O)NCCN*)c1]

In embodiments, $L^{104}$ is
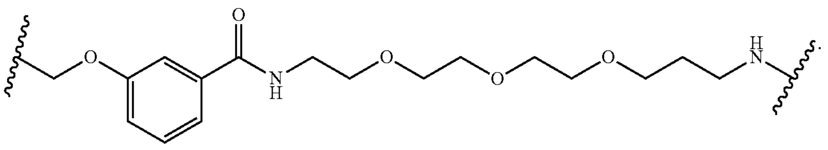 [SMILES: *COc1cccc(C(=O)NCCOCCOCCOCCCN*)c1]
In embodiments, $L^{104}$ is
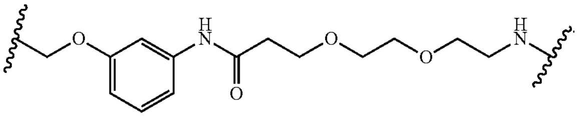 [SMILES: *COc1cccc(NC(=O)CCOCCOCCN*)c1]
In embodiments, $L^{104}$ is a bond.
In embodiments, $L^{105}$ is
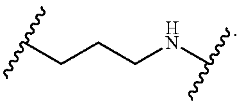 [SMILES: *CCCN*]
In embodiments, $L^{105}$ is
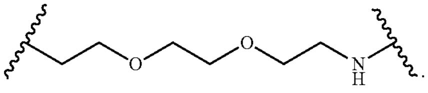 [SMILES: *CCOCCOCCN*]
In embodiments, $L^{105}$ is
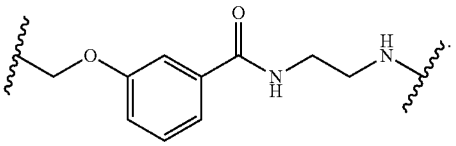 [SMILES: *COc1cccc(C(=O)NCCN*)c1]
In embodiments, $L^{105}$ is
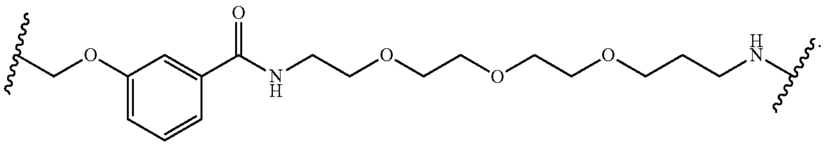 [SMILES: *COc1cccc(C(=O)NCCOCCOCCOCCCN*)c1]
In embodiments, $L^{105}$ is
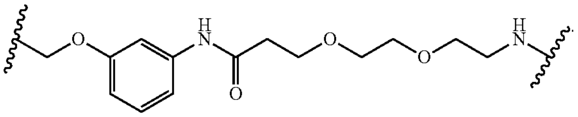 [SMILES: *COc1cccc(NC(=O)CCOCCOCCN*)c1]
In embodiments, $L^{105}$ is a bond.
In embodiments, $L^{103}$-$L^{104}$-$L^{105}$- is
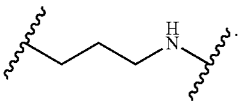
In embodiments, $L^{103}$-$L^{104}$-$L^{105}$- is
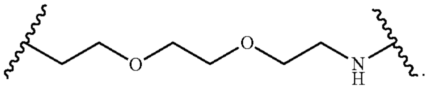 [SMILES: *CCOCCOCCN*]
In embodiments, $L^{103}$-$L^{104}$-$L^{105}$- is
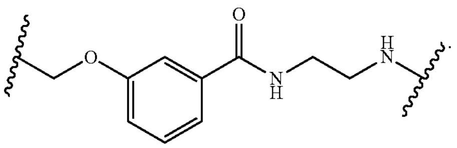 [SMILES: *COc1cccc(C(=O)NCCN*)c1]

In embodiments, $L^{103}$-$L^{104}$-$L^{105}$- is
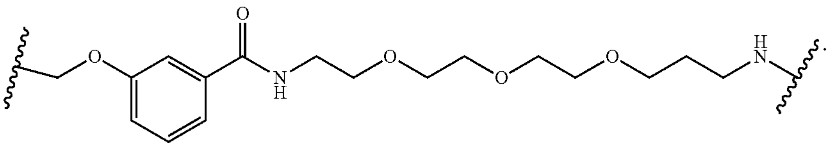 [SMILES: *COc1cccc(C(=O)NCCOCCOCCOCCCN*)c1]
In embodiments, $L^{103}$-$L^{104}$-$L^{105}$- is
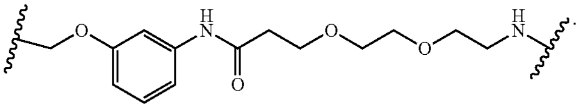 [SMILES: *COc1cccc(NC(=O)CCOCCOCCN*)c1]
In embodiments, $L^{100}$ is
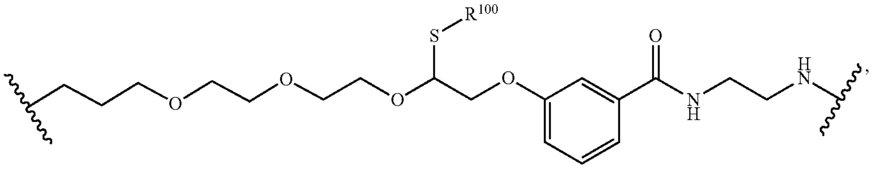
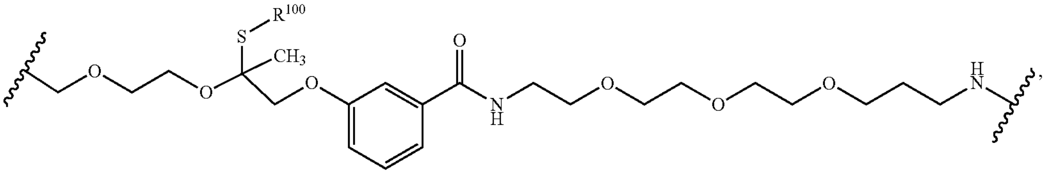
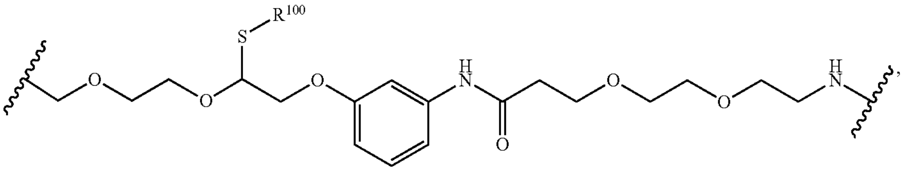
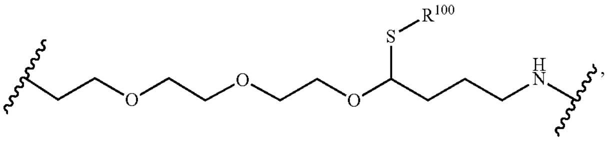
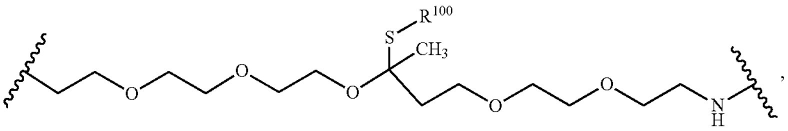
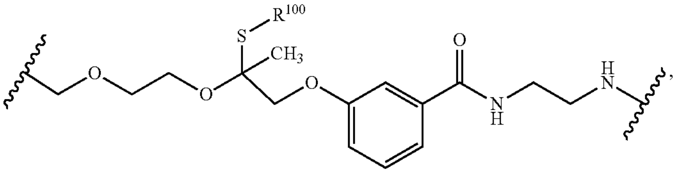
or
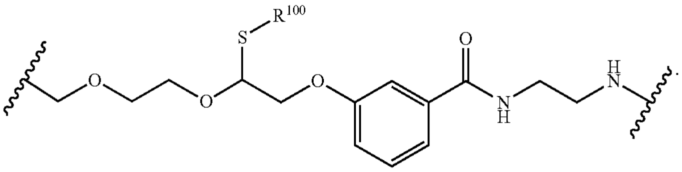
$R^{100}$ is as described herein, including in embodiments.

In embodiments, B is
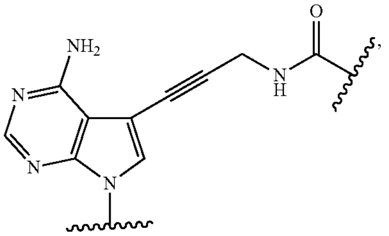
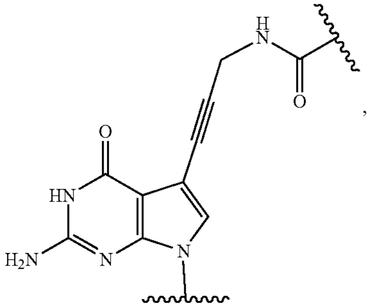
,
-continued
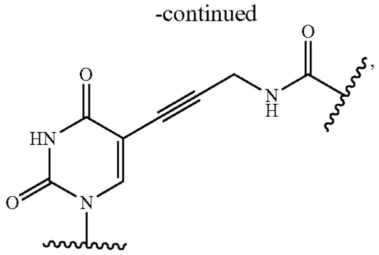
, or
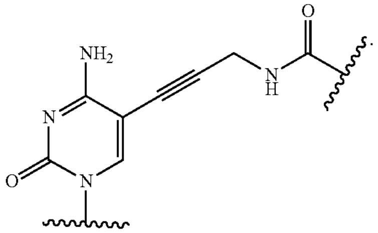
In embodiments, $L^{100}$ is
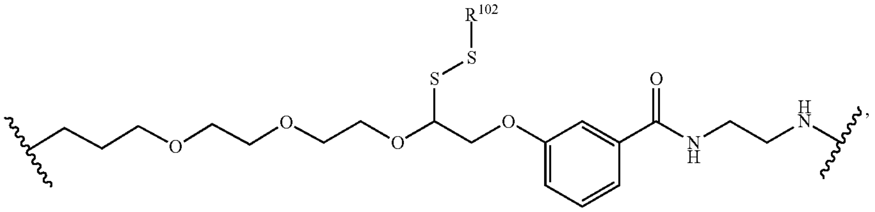
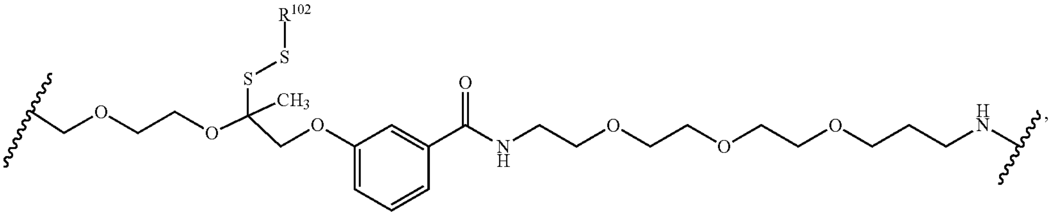
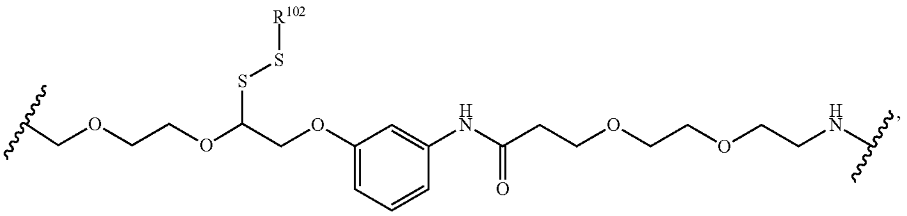
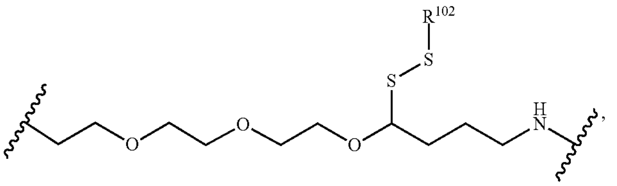
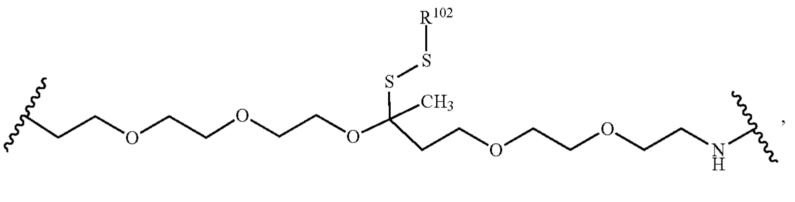

-continued
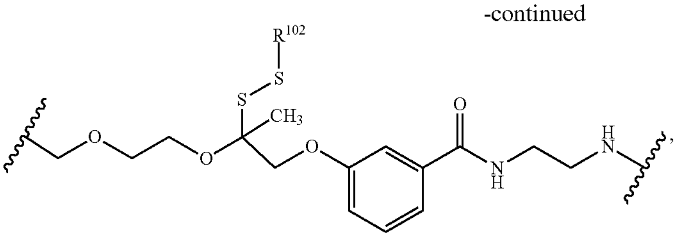
, or
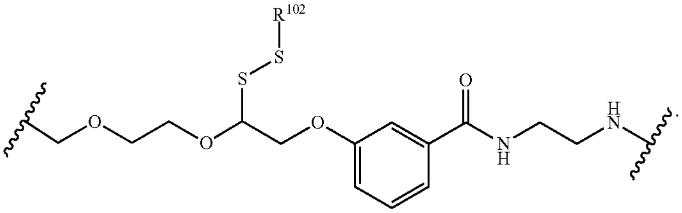
.
$R^{102}$ is as described herein, including in embodiments. In embodiments, B is
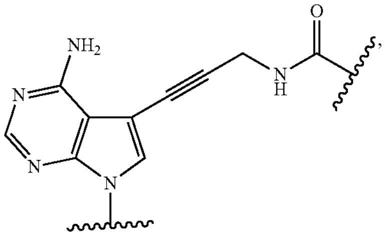
,
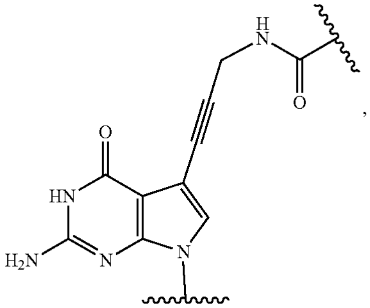
,
-continued
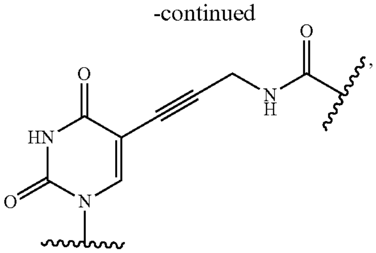
, or
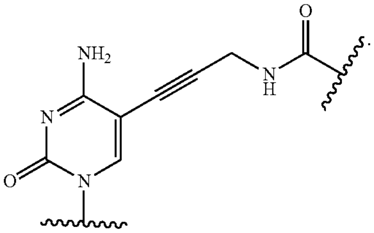
.
In embodiments, $L^{100}$ is
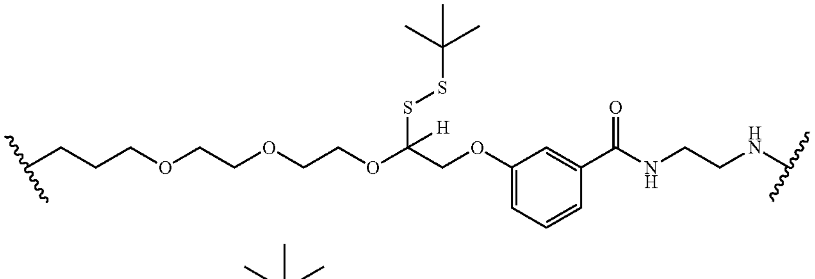
,
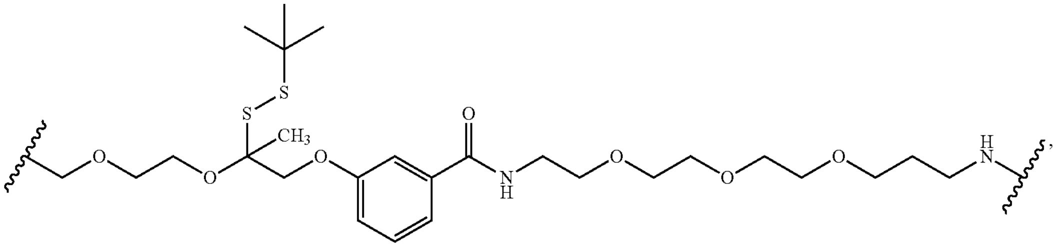
, -continued
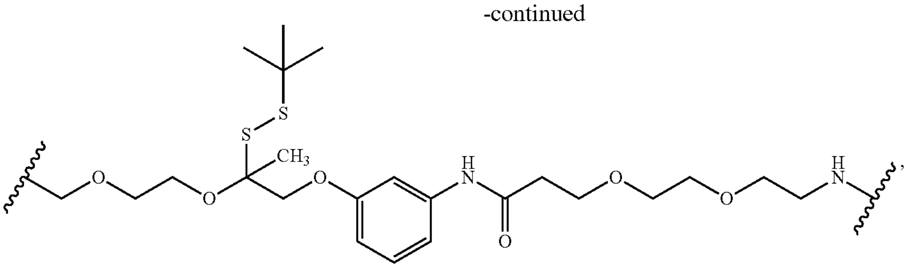
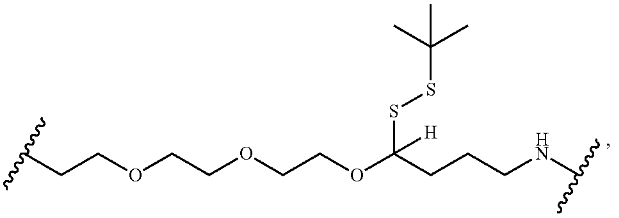
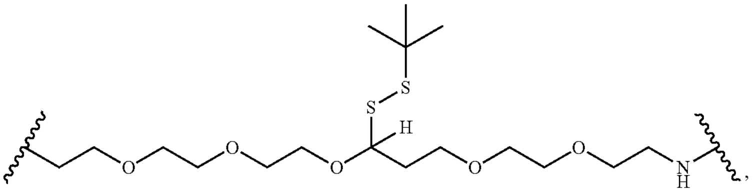
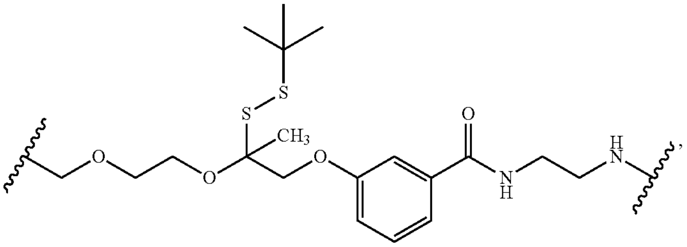
or
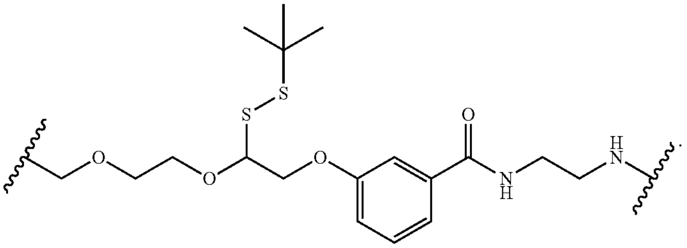
In embodiments, B is
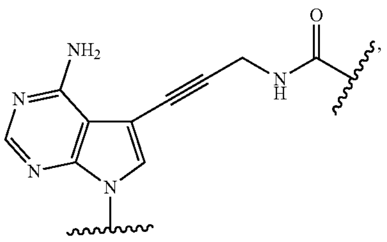
-continued
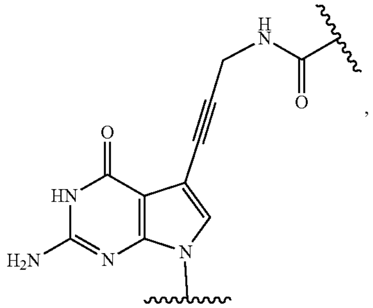

-continued
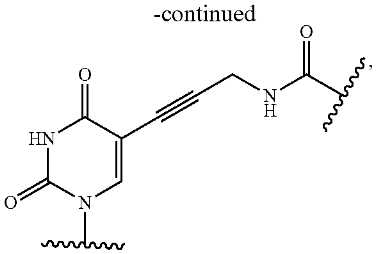
, or
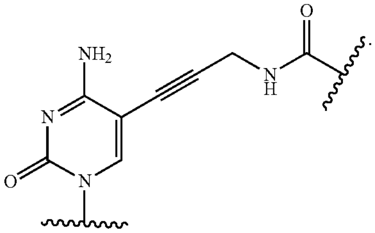
.
In embodiments, B is
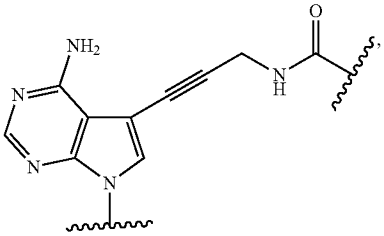
,
In embodiments, $L^{100}$ is
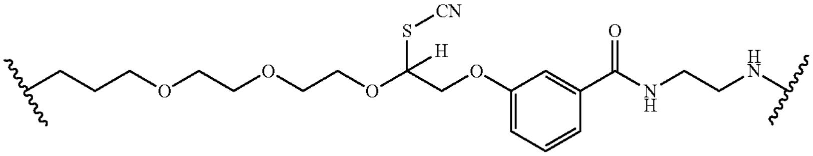
,
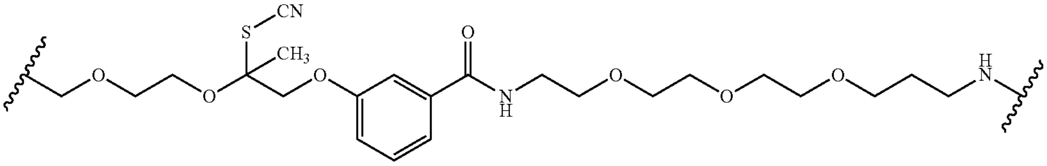
,
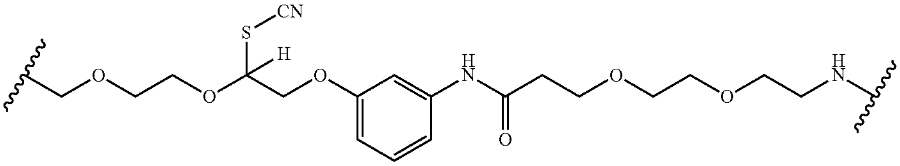
,
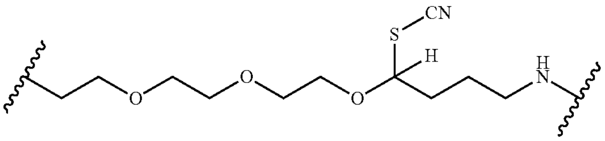
,
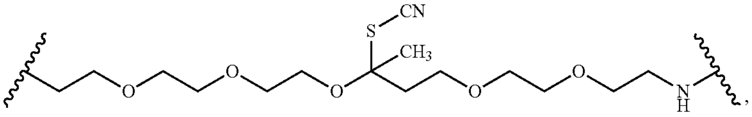
,
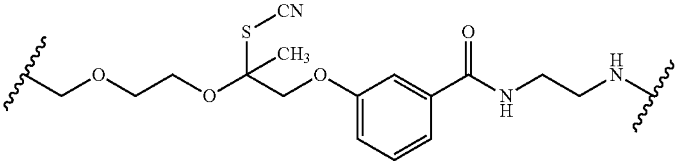
, or
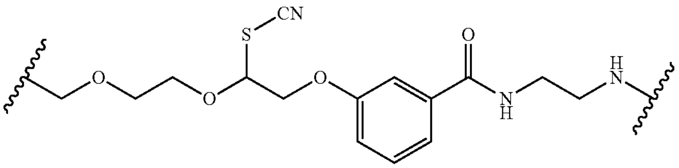
.

-continued
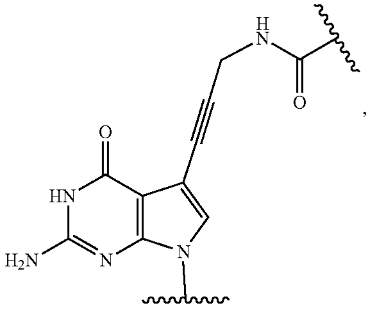
,
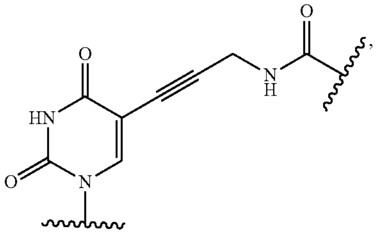
, or
-continued
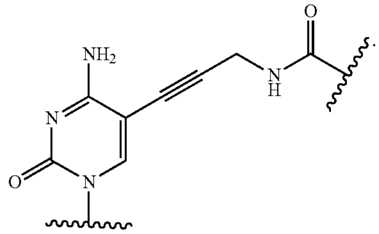
.
In embodiments, $L^{100}$ is
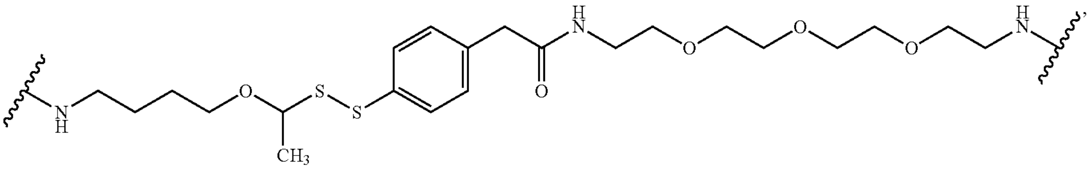
,
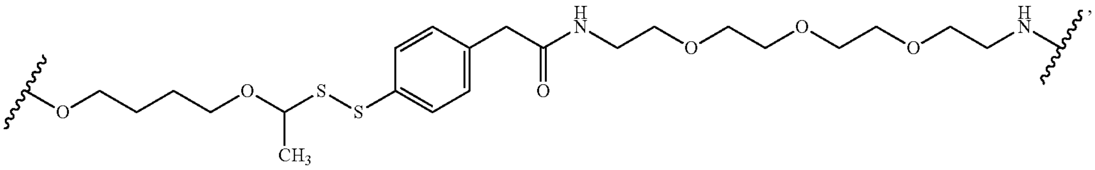
,
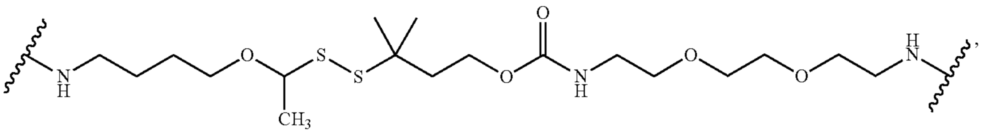
,
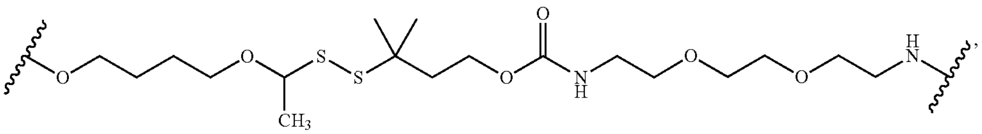
,
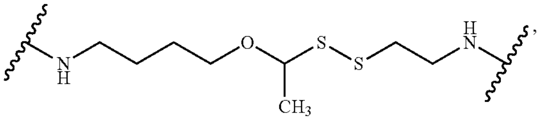
,
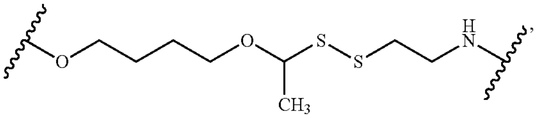
,
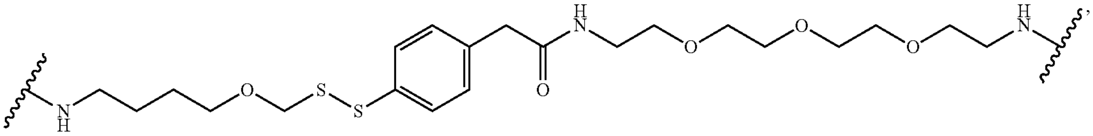
,
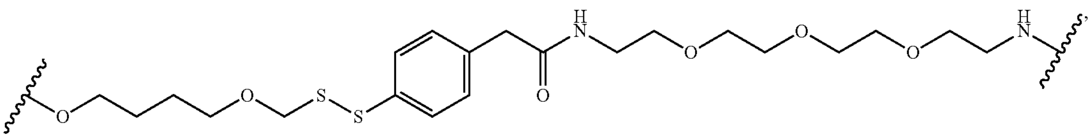
, -continued
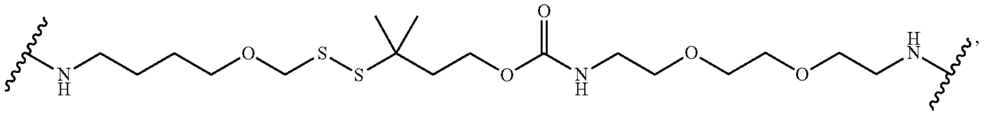
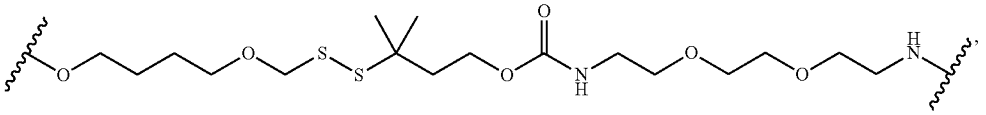
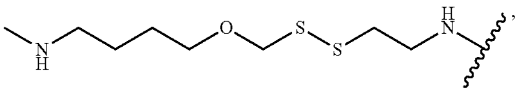
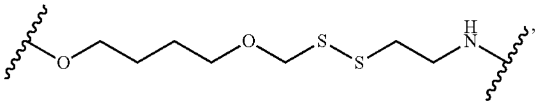
or
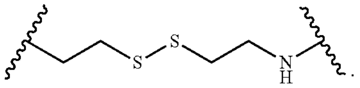
In embodiments, B is
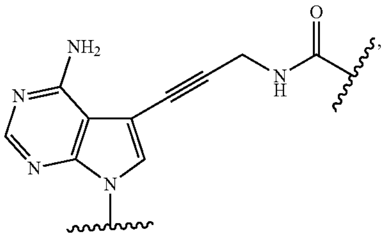
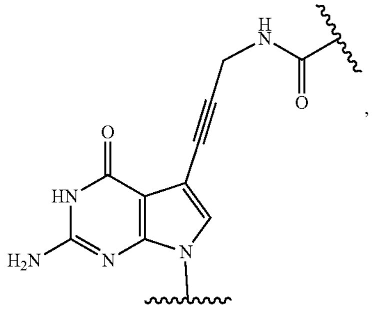
-continued
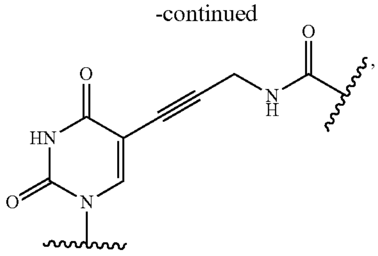
or
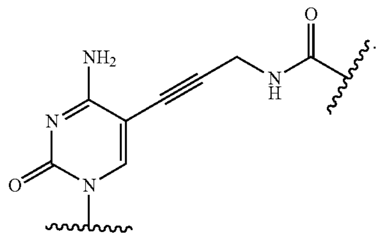
In embodiments, $L^{100}$ is
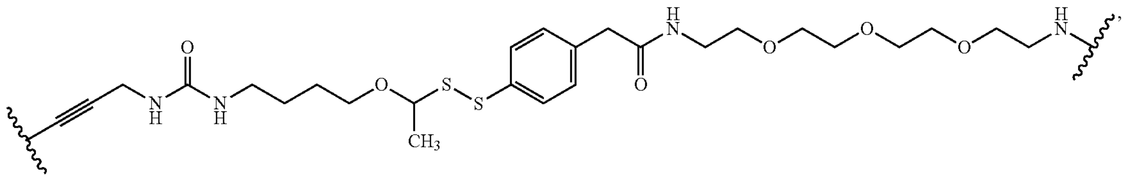
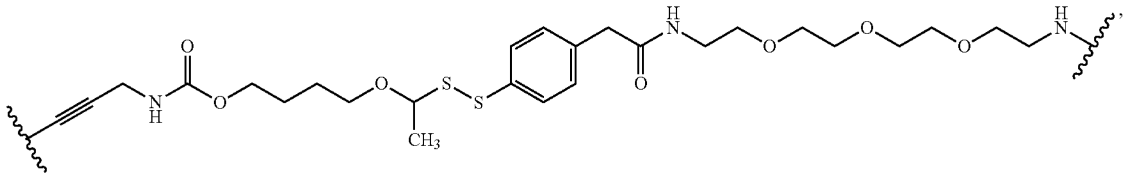
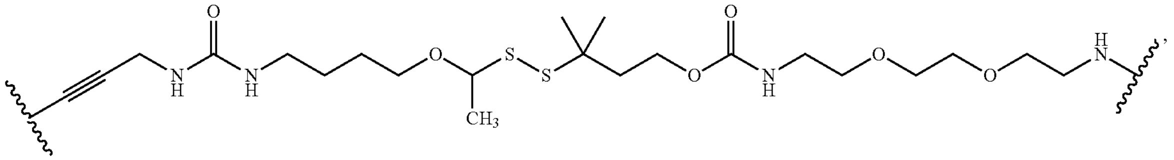

-continued
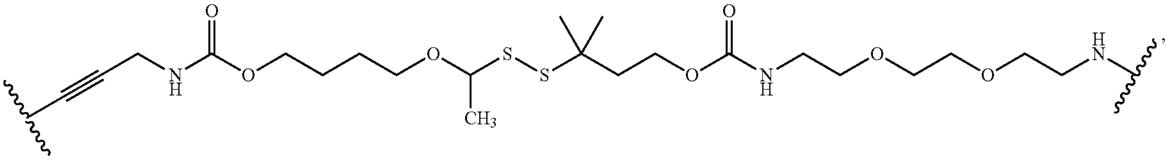
,
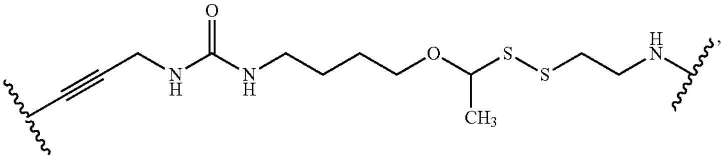
,
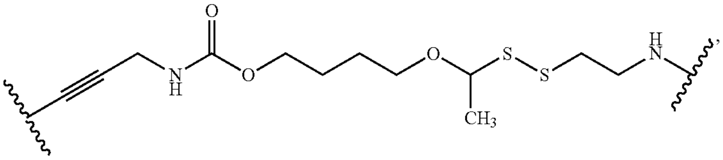
,
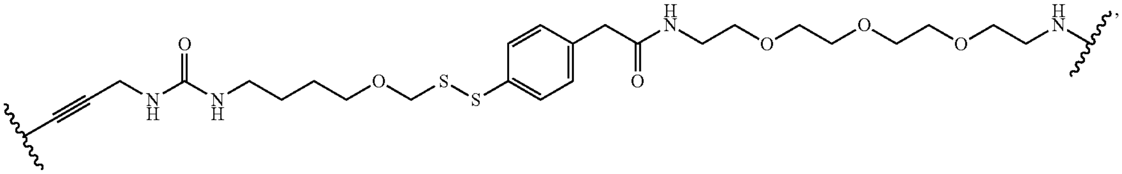
,
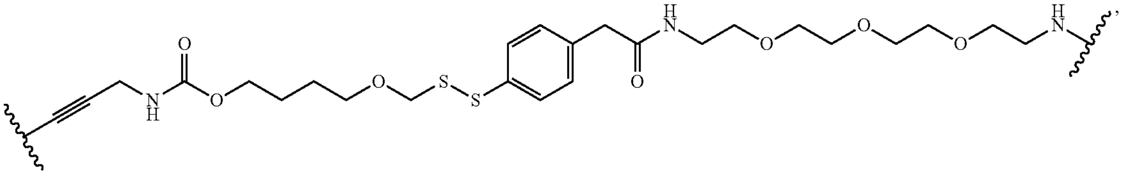
,
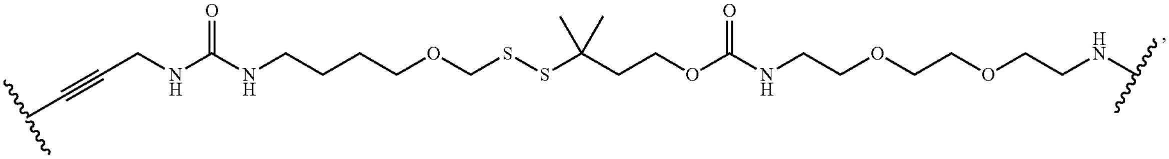
,
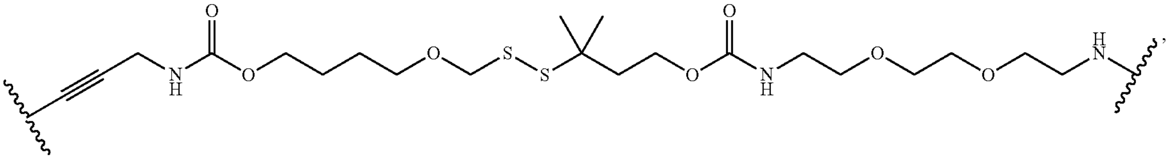
,
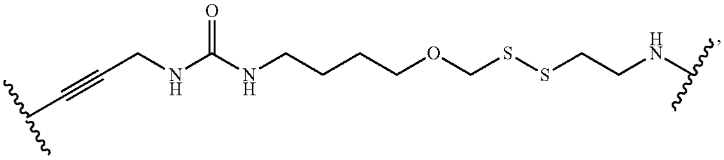
,
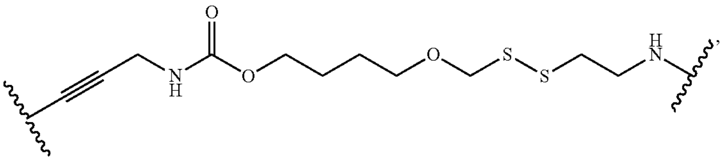
, or
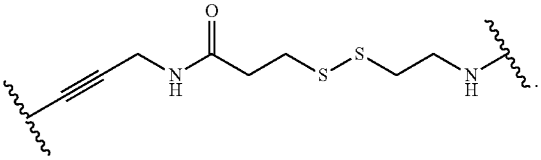
.

In embodiments, $L^{100}$ is
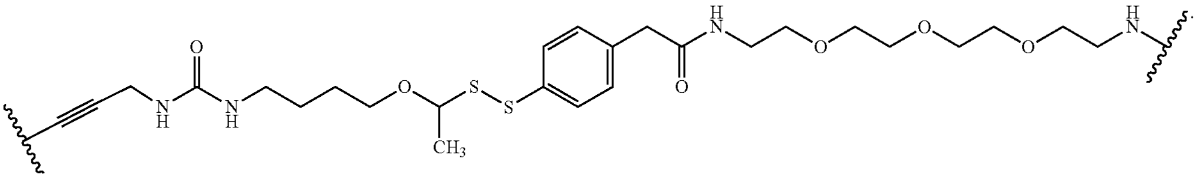 [SMILES: *C#CCNC(=O)NCCCCOC(C)SSc1ccc(CC(=O)NCCOCCOCCOCCN*)cc1]
In embodiments, $L^{100}$ is
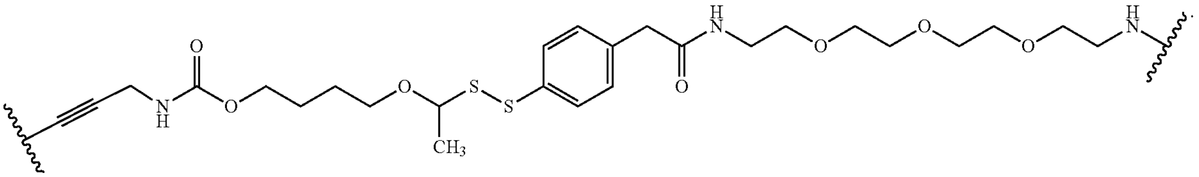 [SMILES: *C#CCNC(=O)OCCCCOC(C)SSc1ccc(CC(=O)NCCOCCOCCOCCN*)cc1]
In embodiments, $L^{100}$ is
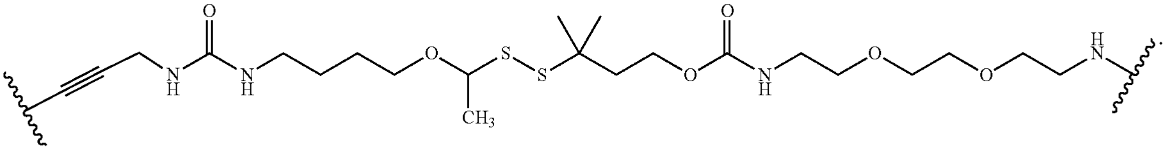 [SMILES: *C#CCNC(=O)NCCCCOC(C)SSC(C)(C)CCOC(=O)NCCOCCOCCN*]
In embodiments, $L^{100}$ is
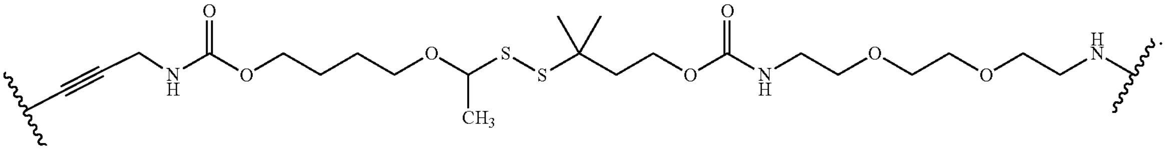 [SMILES: *C#CCNC(=O)OCCCCOC(C)SSC(C)(C)CCOC(=O)NCCOCCOCCN*]
In embodiments, $L^{100}$ is
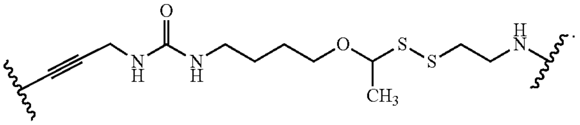
In embodiments, $L^{100}$ is
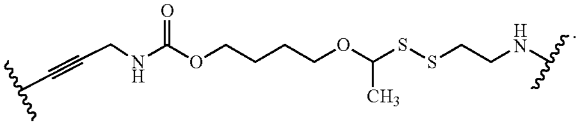 [SMILES: *C#CCNC(=O)OCCCCOC(C)SSCCN*]
In embodiments, $L^{100}$ is
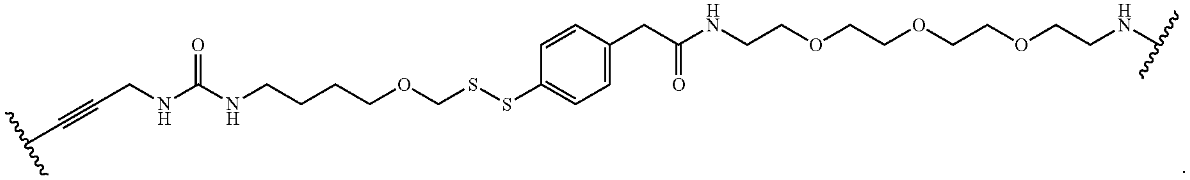 [SMILES: *C#CCNC(=O)NCCCCOCSSc1ccc(CC(=O)NCCOCCOCCOCCN*)cc1]

In embodiments, $L^{100}$ is
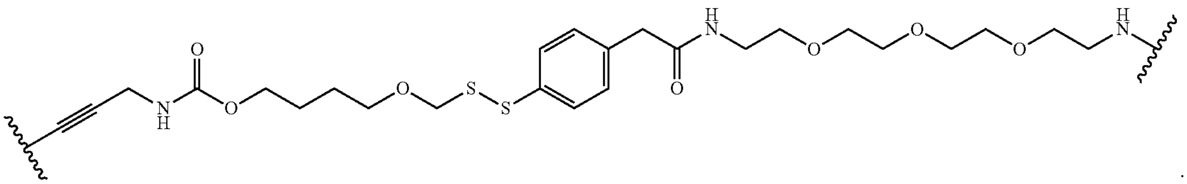 [SMILES: *C#CCNC(=O)OCCCCOCSSc1ccc(CC(=O)NCCOCCOCCOCCN*)cc1]
.
In embodiments, $L^{100}$ is
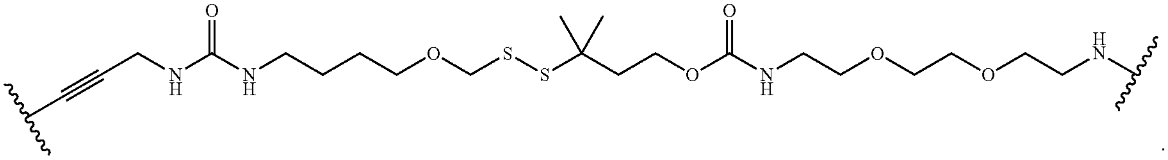 [SMILES: *C#CCNC(=O)NCCCCOCSSC(C)(C)CCOC(=O)NCCOCCOCCN*]
.
In embodiments, $L^{100}$ is
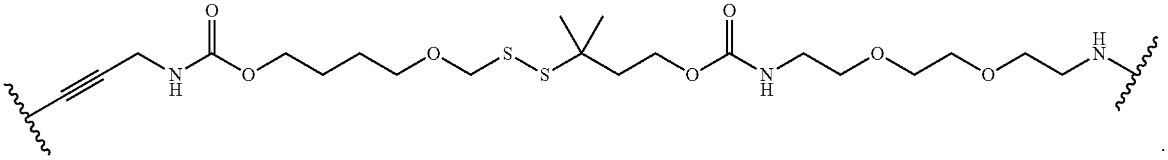 [SMILES: *C#CCNC(=O)OCCCCOCSSC(C)(C)CCOC(=O)NCCOCCOCCN*]
.
In embodiments, $L^{100}$ is
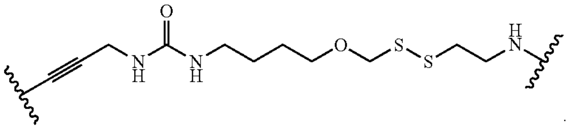 [SMILES: *C#CCNC(=O)NCCCCOCSSCCN*]
.
In embodiments, $L^{100}$ is
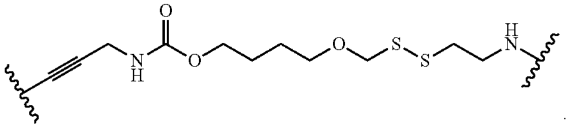 [SMILES: *C#CCNC(=O)OCCCCOCSSCCN*]
.
In embodiments, $L^{100}$ is
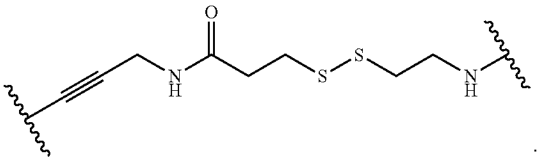 [SMILES: *C#CCNC(=O)CCSSCCN*]
.
In embodiments, $L^{100}$ is
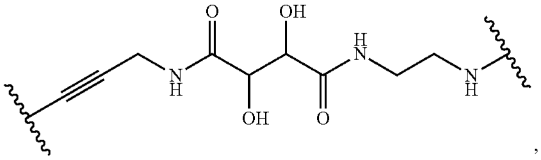
,
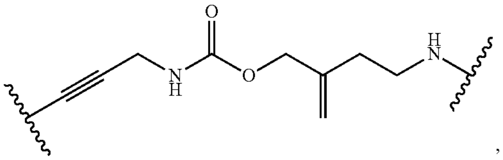
, -continued
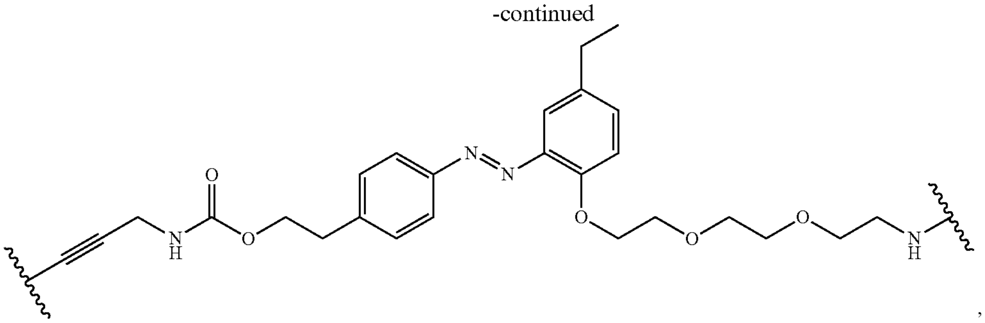
, or
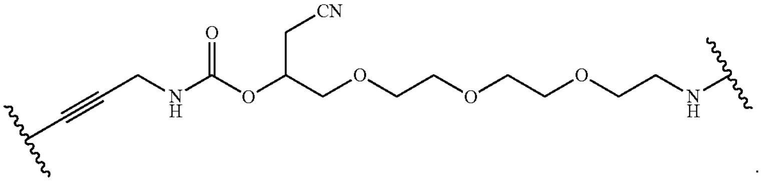
.
In embodiments, $L^{100}$ is
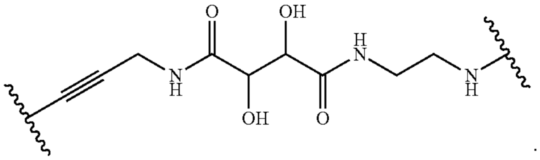 [SMILES: *C#CCNC(=O)C(O)C(O)C(=O)NCCN*]
.
In embodiments, $L^{100}$ is
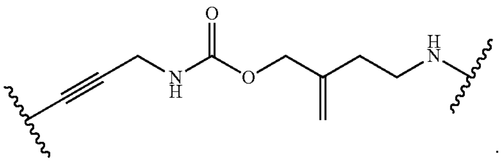 [SMILES: *C#CCNC(=O)OCC(=C)CCN*]
.
In embodiments, $L^{100}$ is
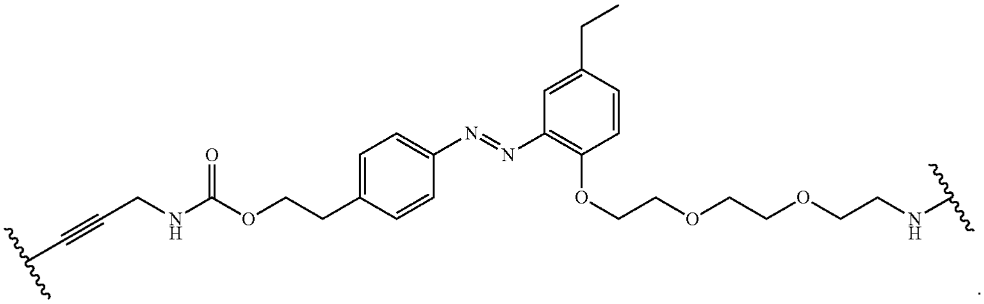 [SMILES: *C#CCNC(=O)OCCc1ccc(/N=N/c2cc(CC)ccc2OCCOCCOCCN*)cc1]
.
In embodiments, $L^{100}$ is
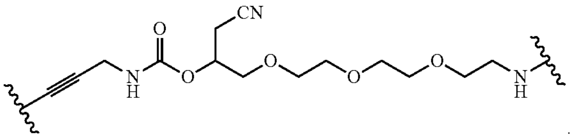 [SMILES: *C#CCNC(=O)OC(CC#N)COCCOCCOCCN*]
.

In embodiments, $L^{100}$ is
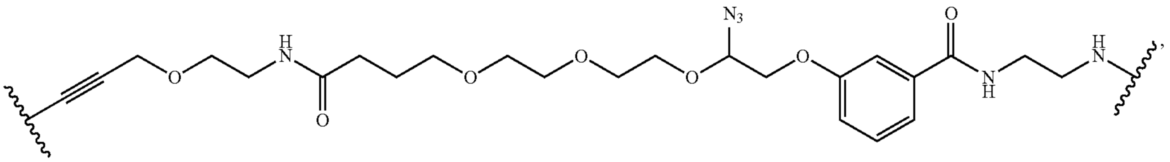
,
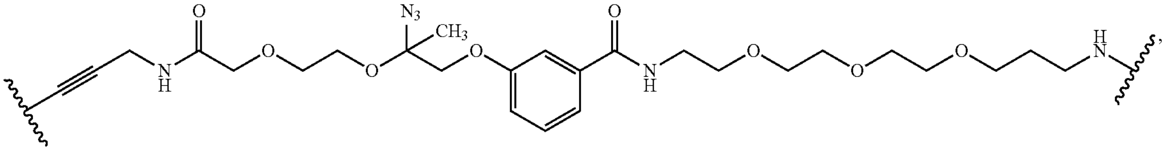
,
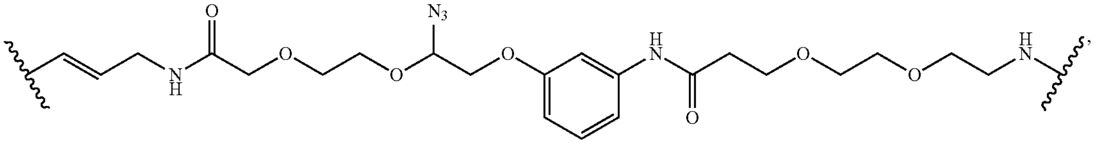
,
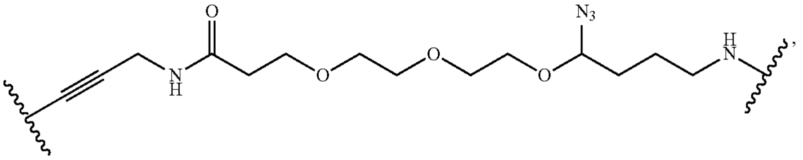
,
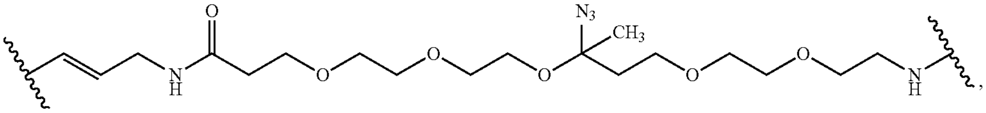
,
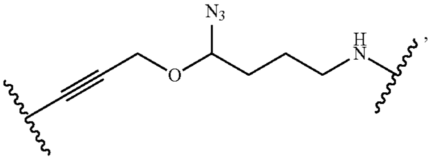
,
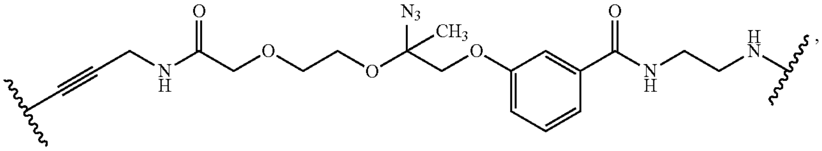
, or
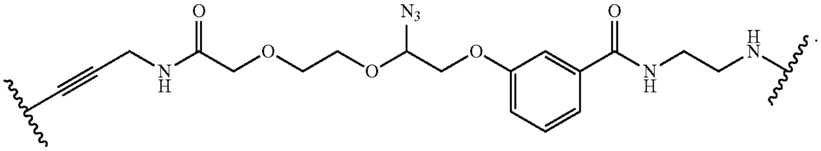
.
In embodiments, $L^{100}$ is
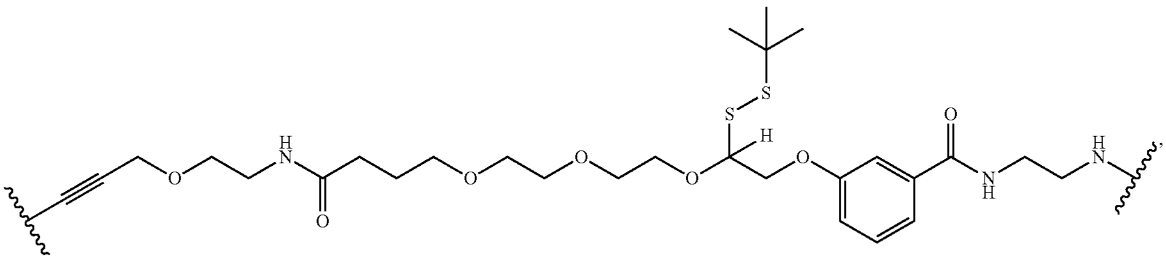
, -continued
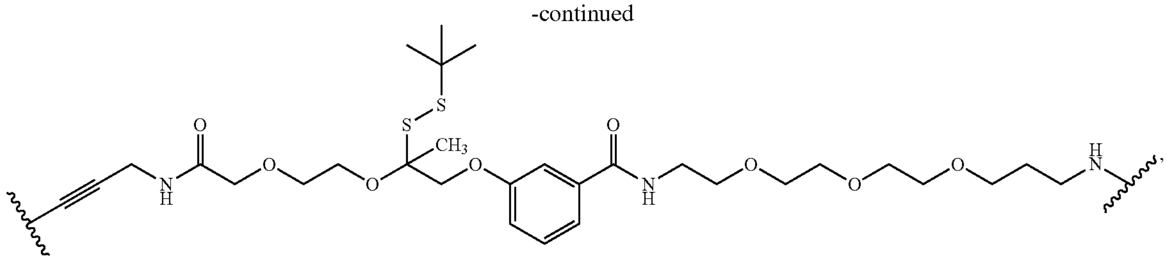
,
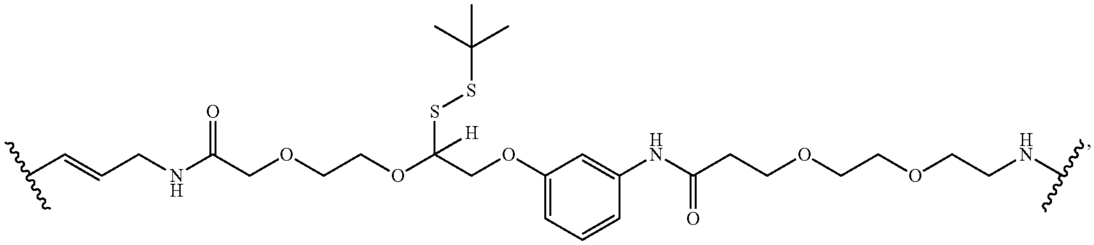
,
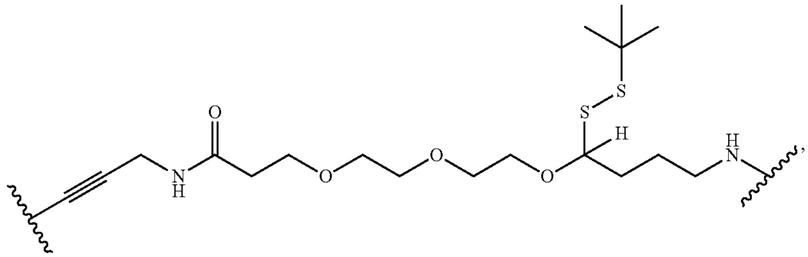
,
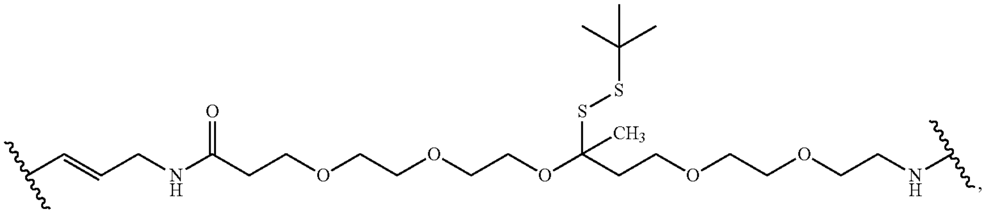
,
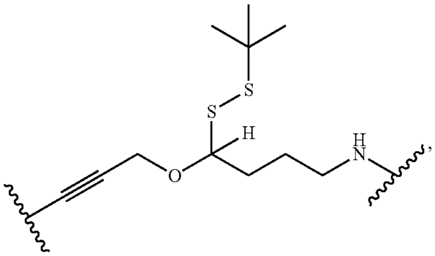
,
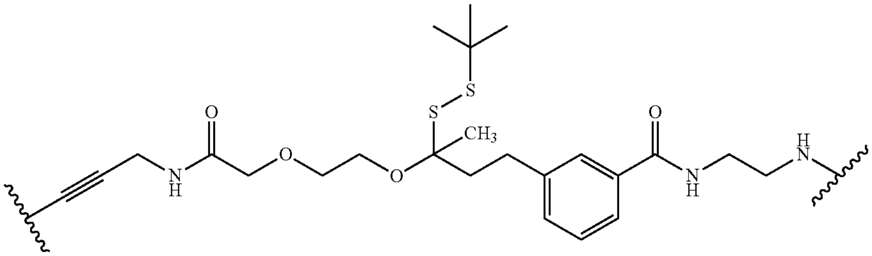
,
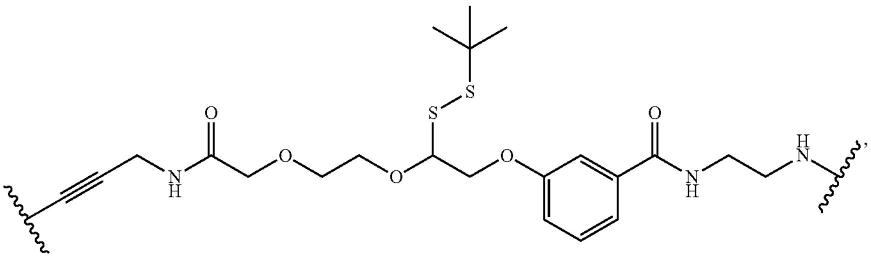
, -continued
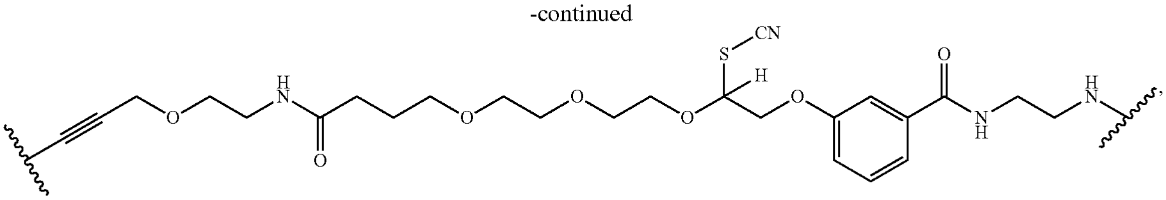,
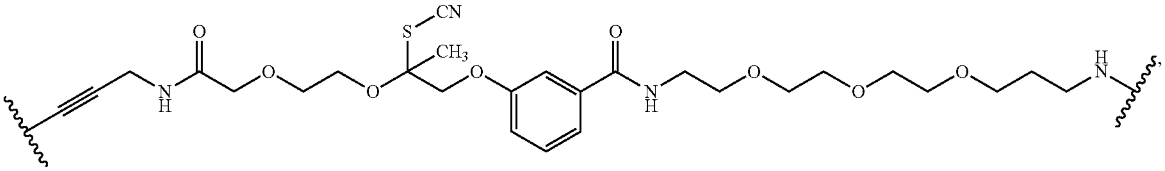,
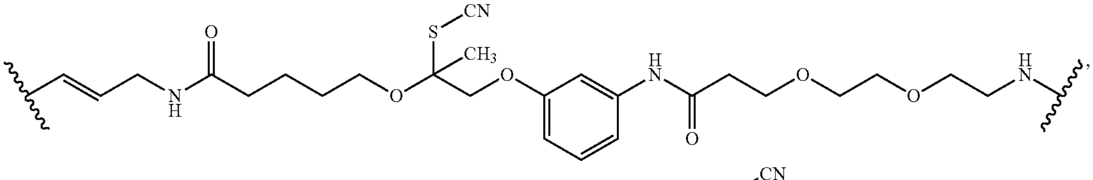,
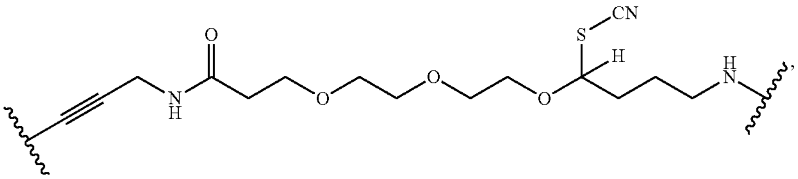,
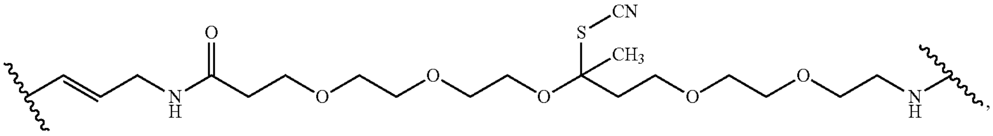,
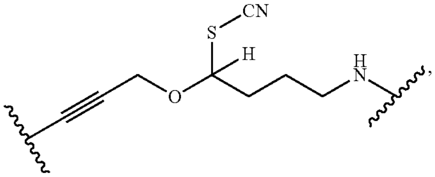,
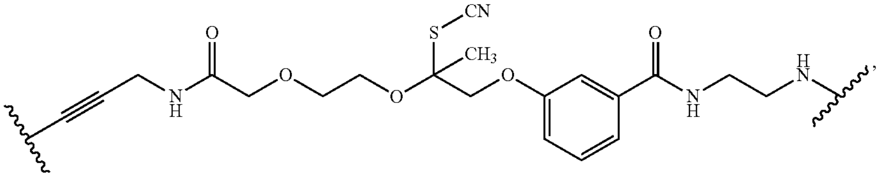, or
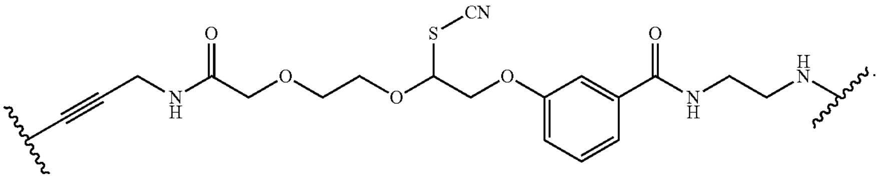.
In embodiments, $L^{100}$ is
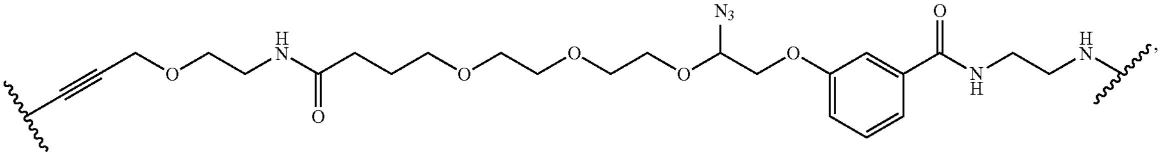, -continued
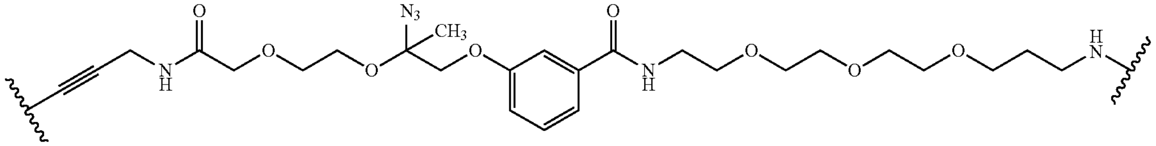
,
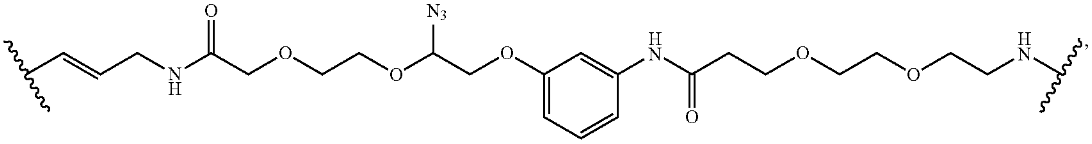
,
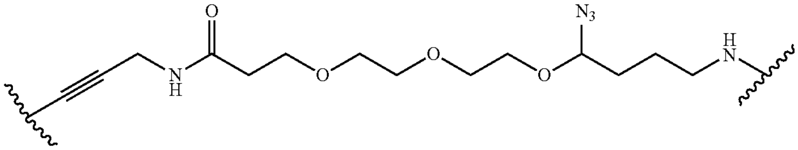
,
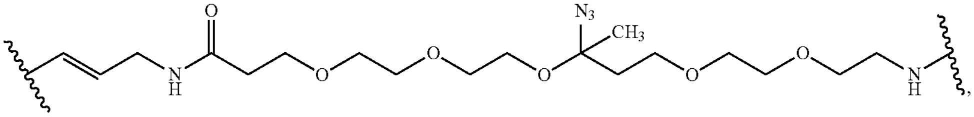
,
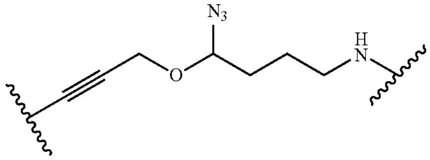
,
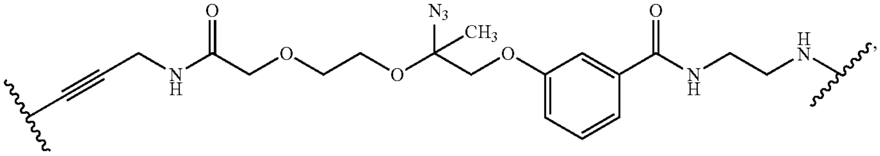
,
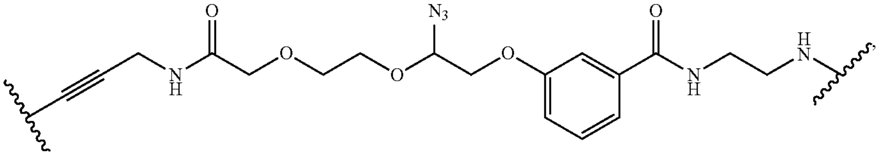
,
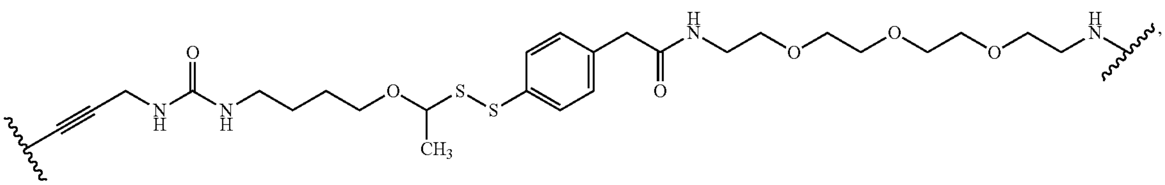
,
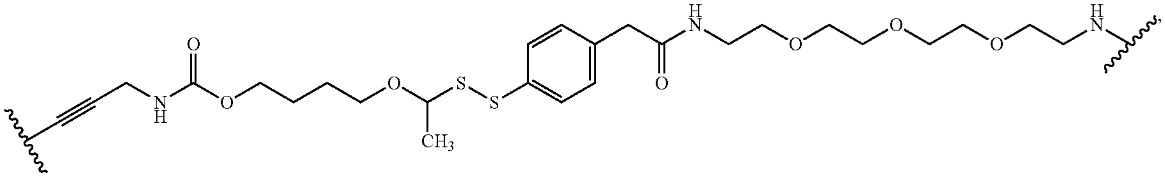
,
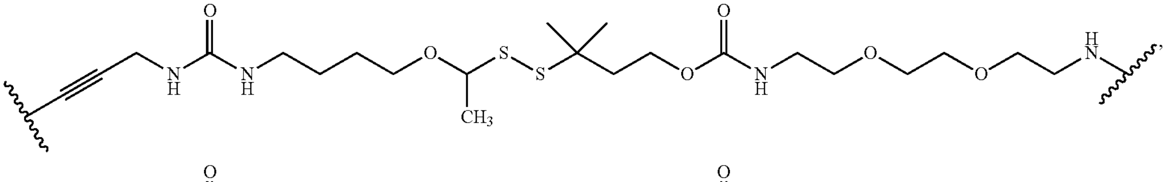
,
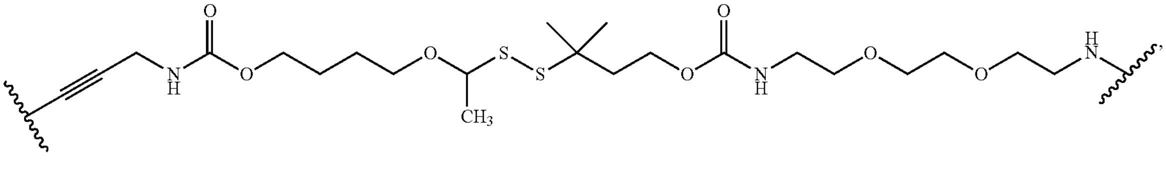
, -continued
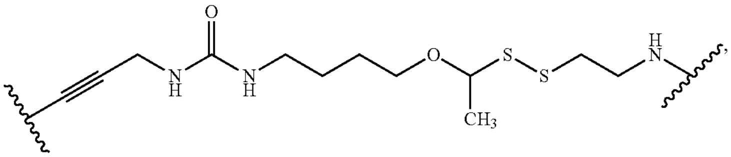
,
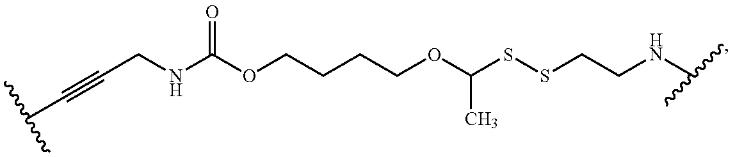
,
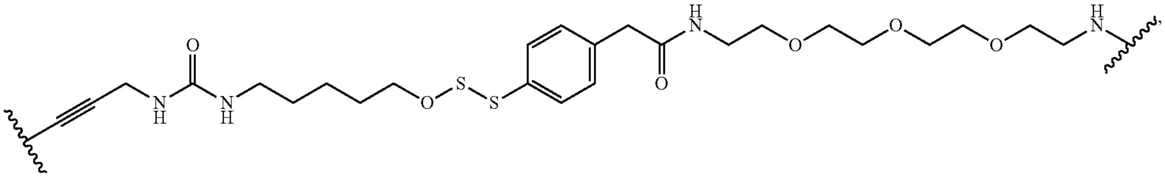
,
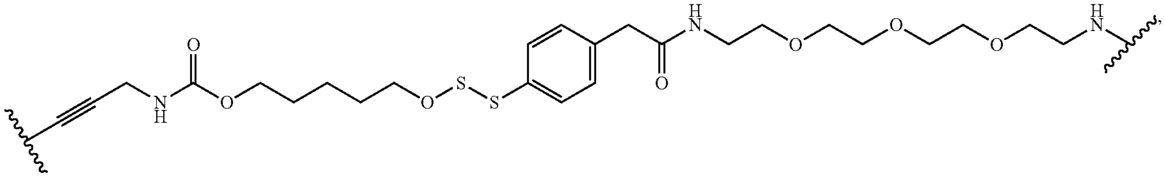
,
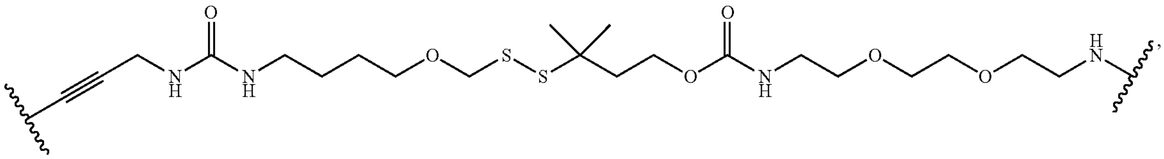
,
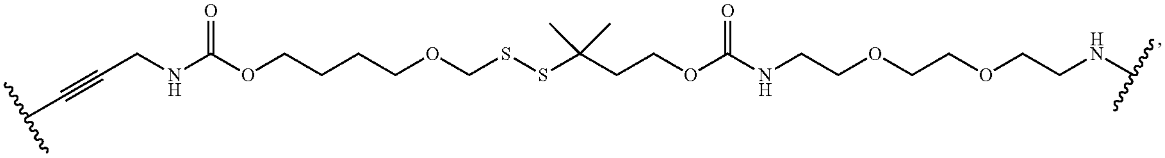
,
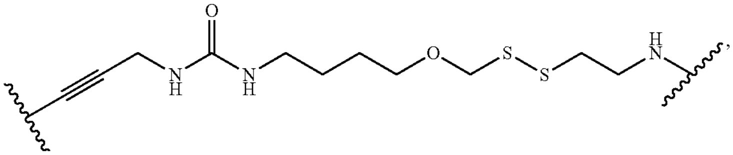
,
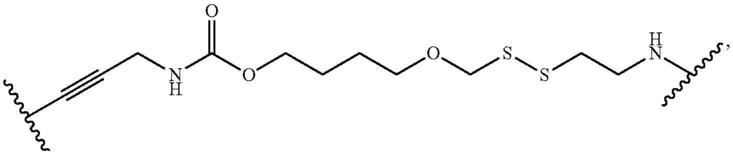
,
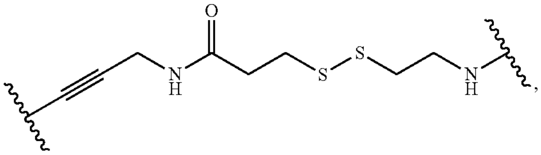
,
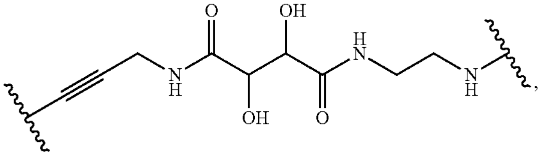
, -continued
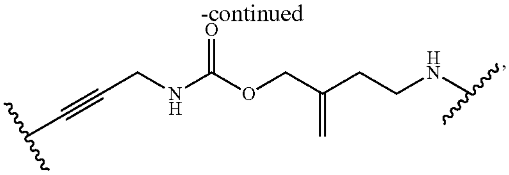
,
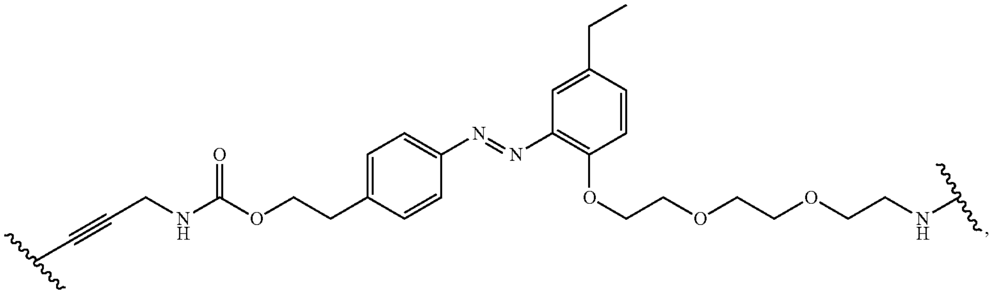
, or
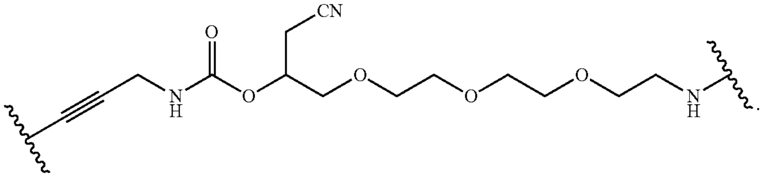
.
In embodiments, $L^{100}$ is
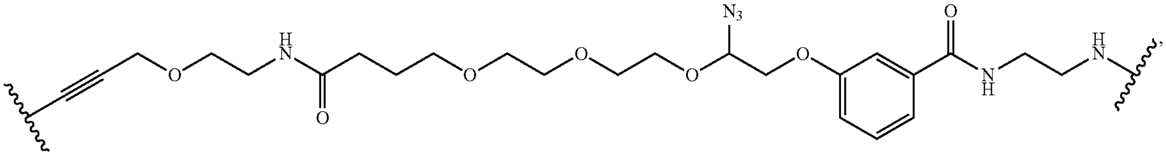 [SMILES: *C#CCOCCNC(=O)CCCOCCOCCOC(COc1cccc(C(=O)NCCN*)c1)N=[N+]=[N-]]
,
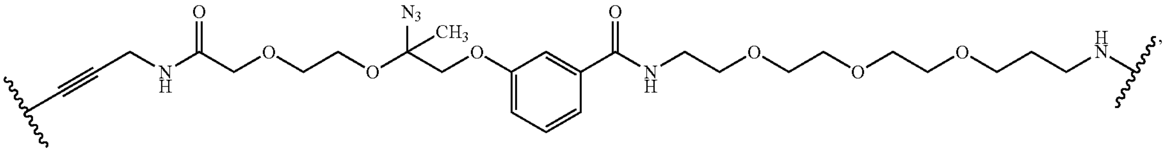
,
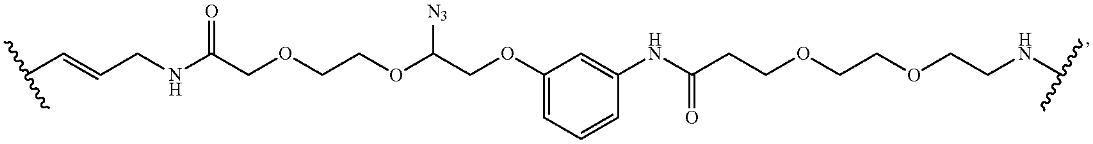
,
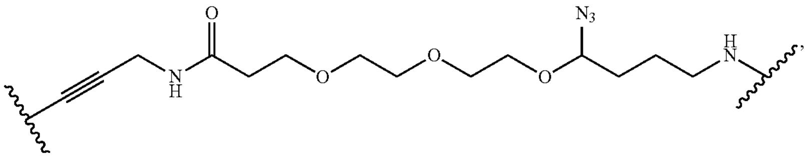
,
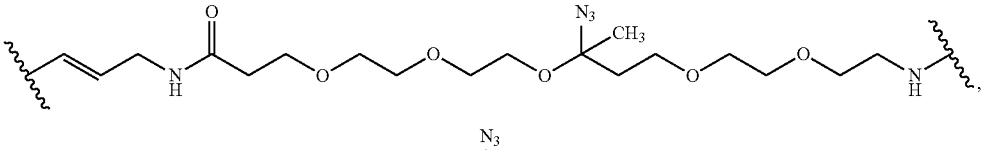
,
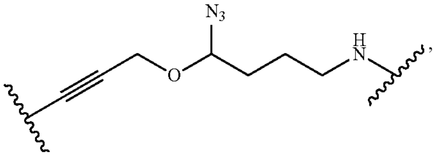
, -continued
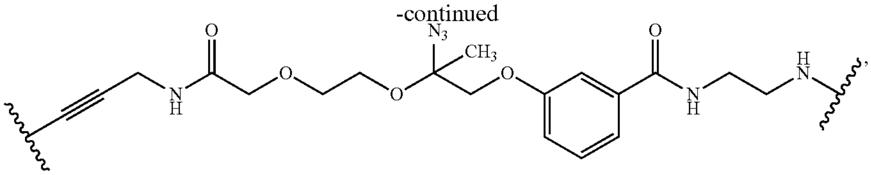
, or
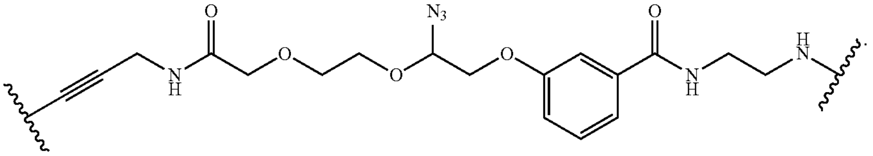
In embodiments, $L^{100}$ is
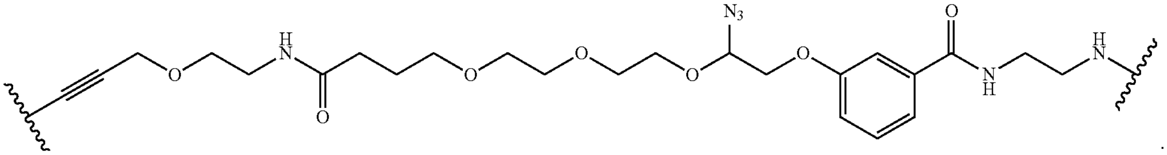
In embodiments, $L^{100}$ is
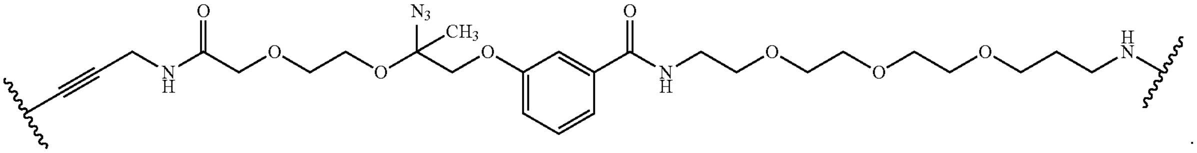 [SMILES: *C#CCNC(=O)COCCOC(C)(COc1cccc(C(=O)NCCOCCOCCOCCCN*)c1)N=[N+]=[N-]]
In embodiments, $L^{100}$ is
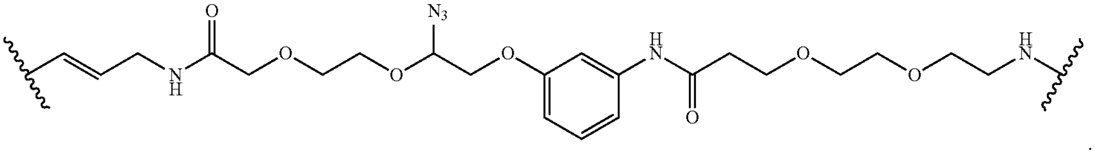 [SMILES: */C=C/CNC(=O)COCCOC(COc1cccc(NC(=O)CCOCCOCCN*)c1)N=[N+]=[N-]]
In embodiments, $L^{100}$ is
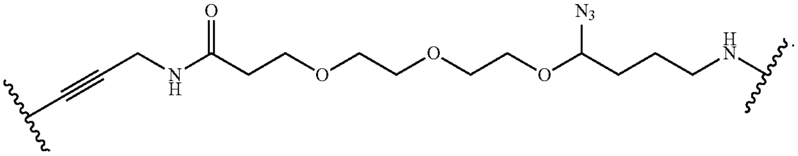 [SMILES: *C#CCNC(=O)CCOCCOCCOC(CCCN*)N=[N+]=[N-]]
In embodiments, $L^{100}$ is
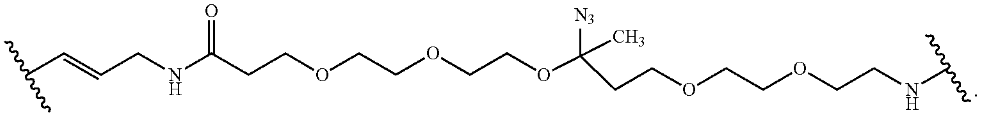 [SMILES: */C=C/CNC(=O)CCOCCOCCOC(C)(CCOCCOCCN*)N=[N+]=[N-]]

In embodiments, $L^{100}$ is
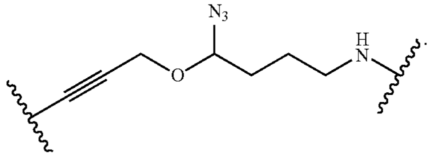 [SMILES: *C#CCOC(CCCN*)N=[N+]=[N-]]
In embodiments, $L^{100}$ is
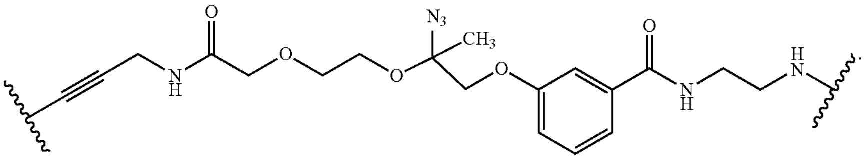 [SMILES: *C#CCNC(=O)COCCOC(C)(COc1cccc(C(=O)NCCN*)c1)N=[N+]=[N-]]
In embodiments, $L^{100}$ is
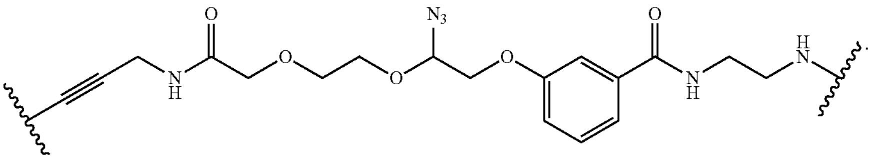 [SMILES: *C#CCNC(=O)COCCOC(COc1cccc(C(=O)NCCN*)c1)N=[N+]=[N-]]
In embodiments, $L^{100}$ is
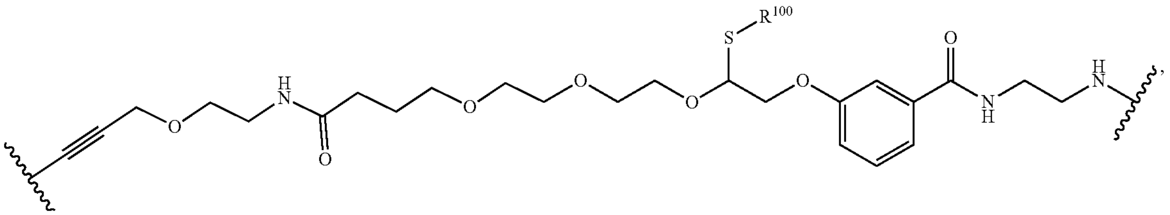
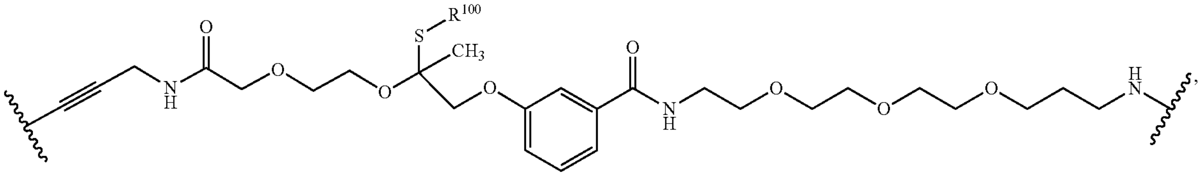
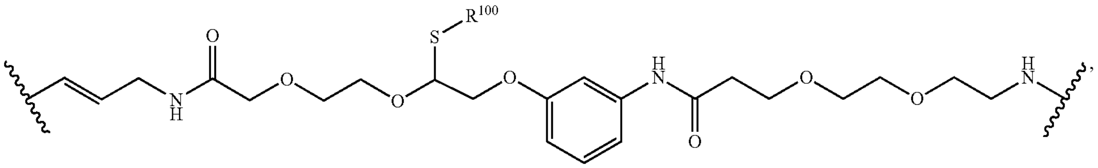
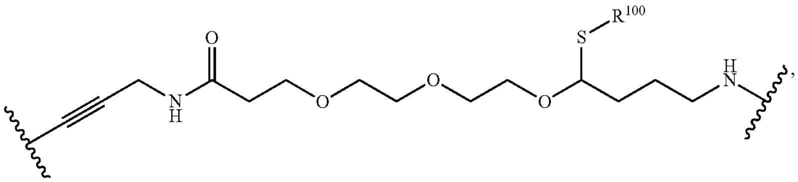

-continued
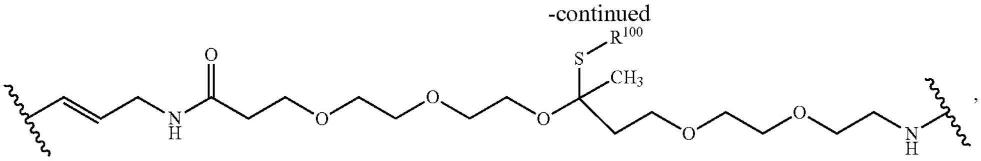
,
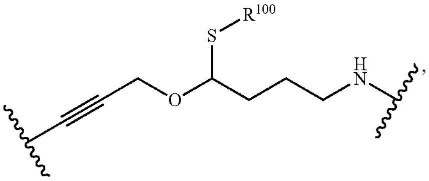
,
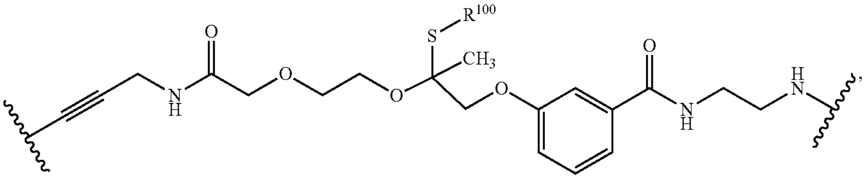
, or
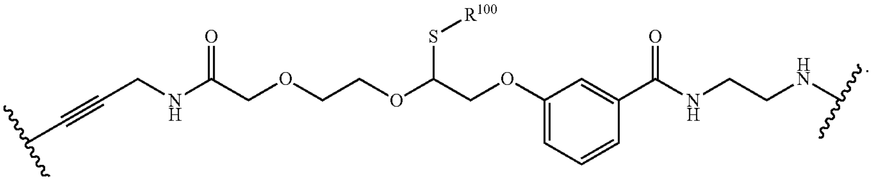
.
In embodiments, $L^{100}$ is
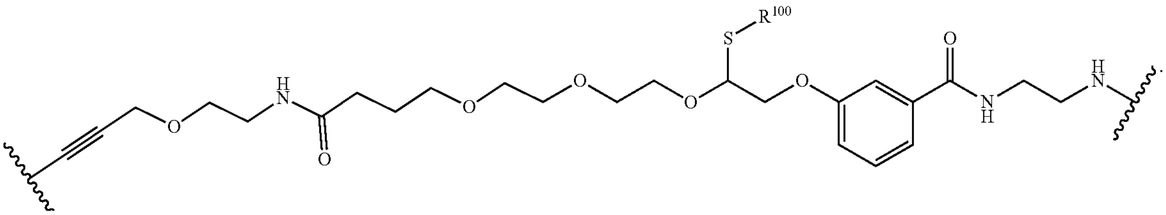
.
In embodiments, $L^{100}$ is
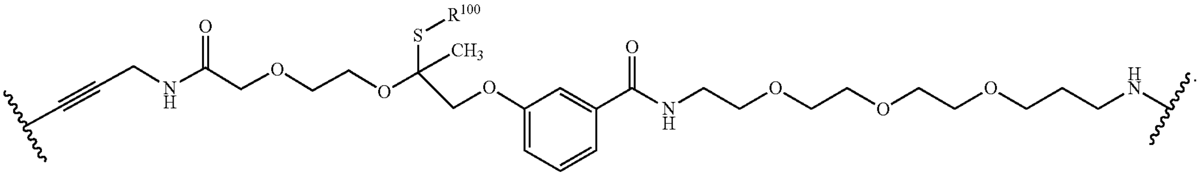
.
In embodiments, $L^{100}$ is
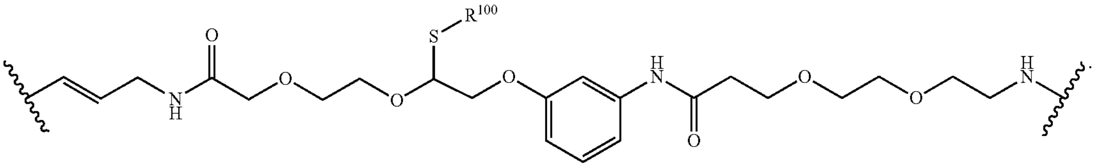
.

In embodiments, $L^{100}$ is
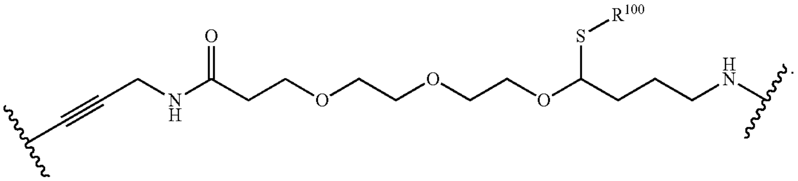
In embodiments, $L^{100}$ is
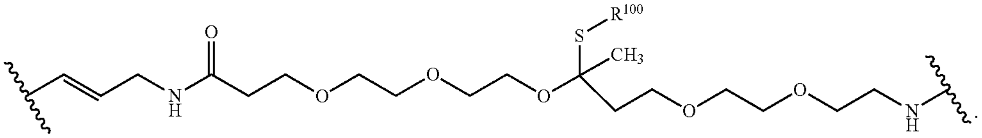
In embodiments, $L^{100}$ is
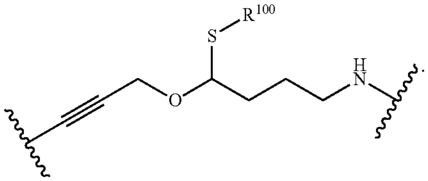
In embodiments, $L^{100}$ is
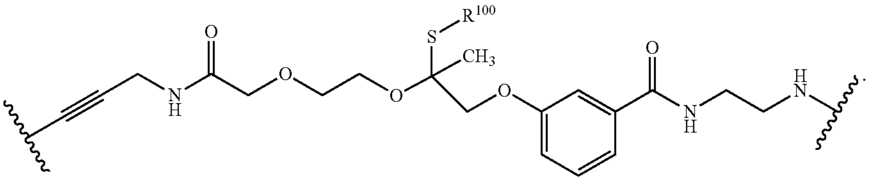
In embodiments, $L^{100}$ is
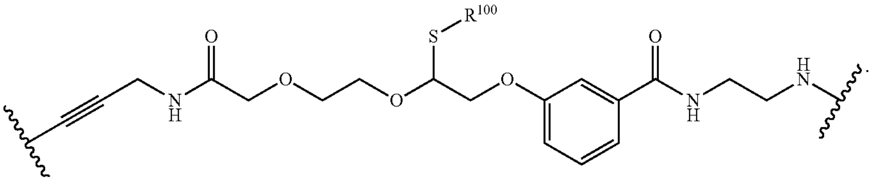
$R^{100}$ is as described herein, including in embodiments.
In embodiments, $L^{100}$ is
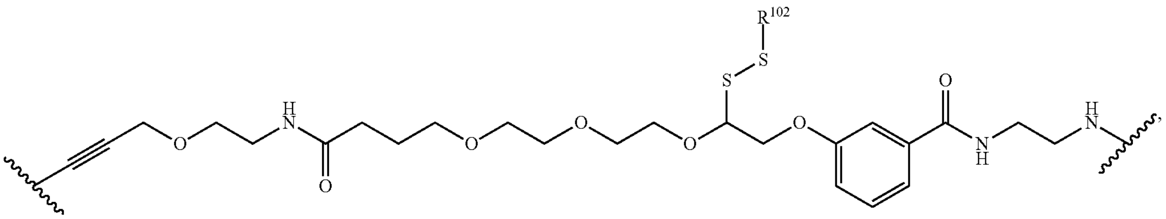

-continued
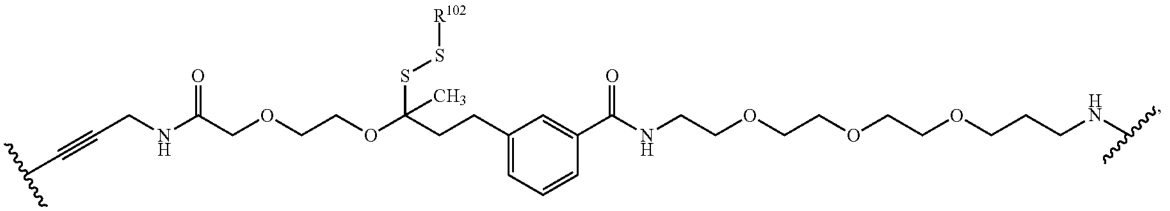
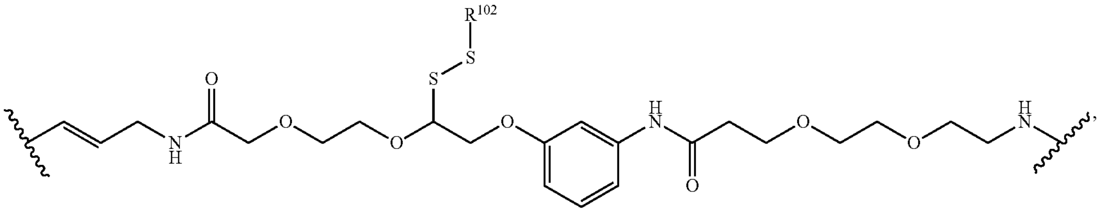
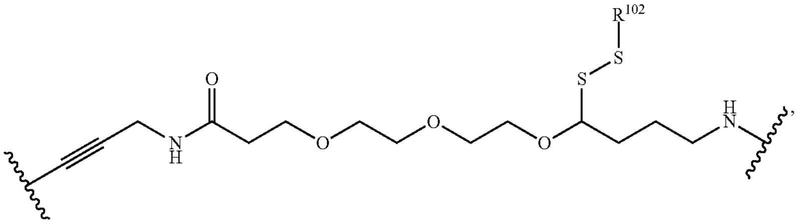
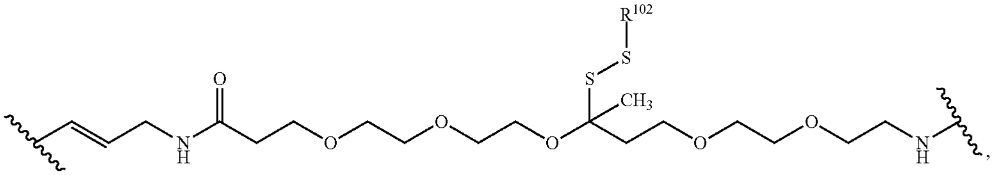
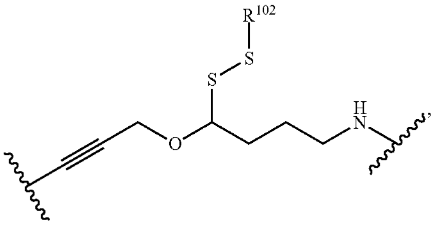
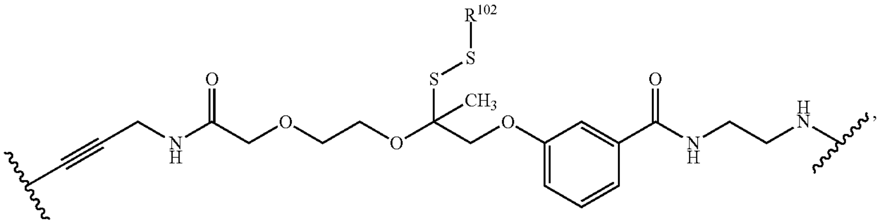
or
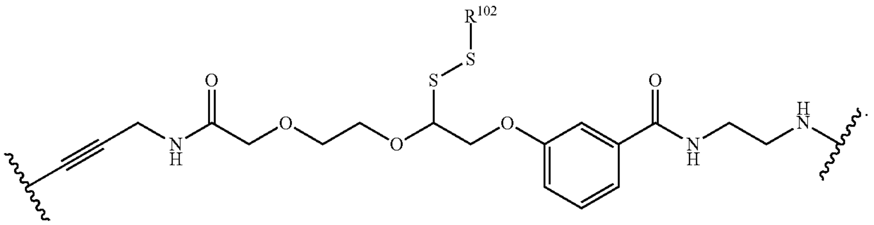

In embodiments, $L^{100}$ is
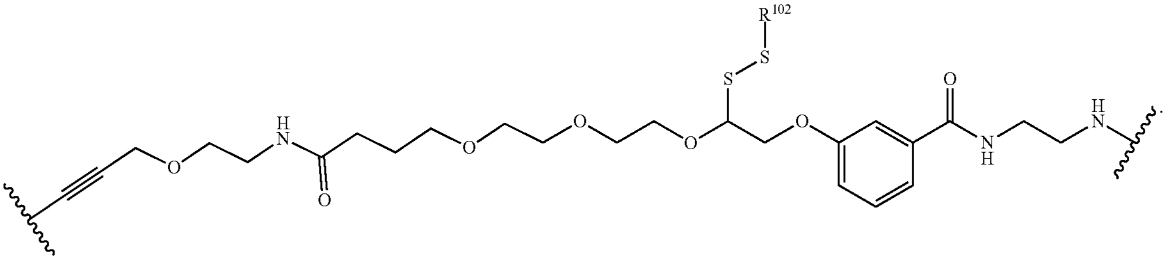
In embodiments, $L^{100}$ is
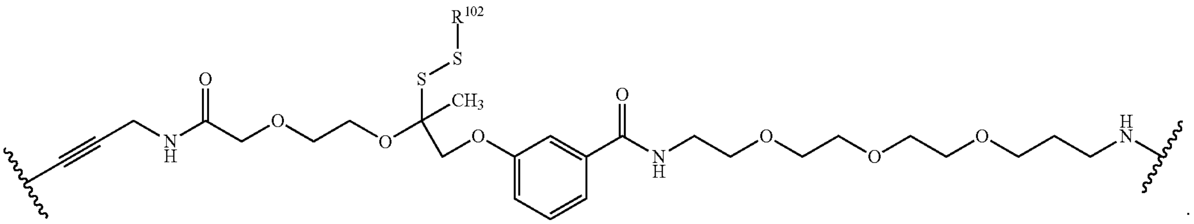
In embodiments, $L^{100}$ is
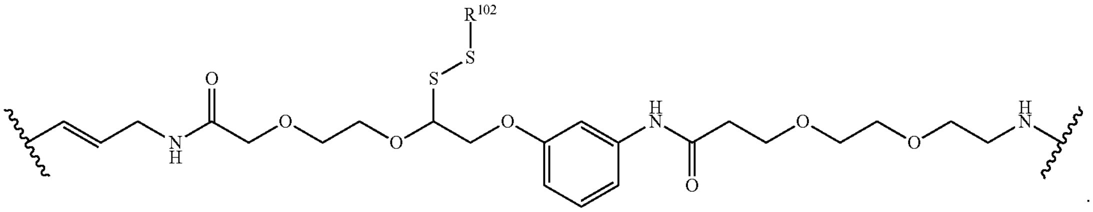
In embodiments, $L^{100}$ is
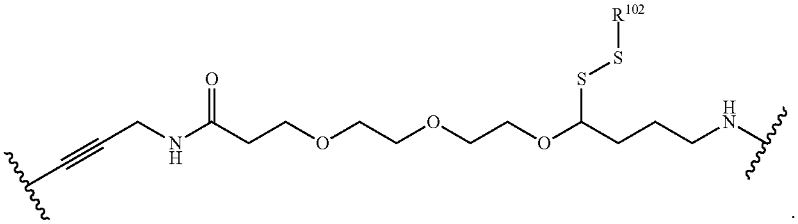
In embodiments, $L^{100}$ is
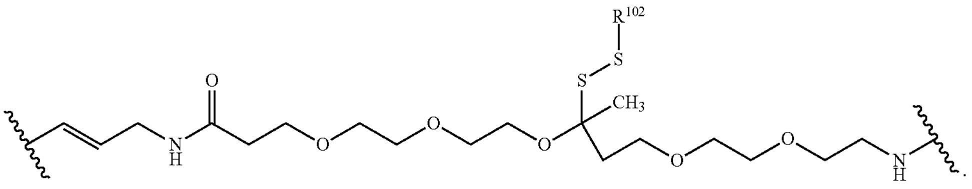

In embodiments, $L^{100}$ is
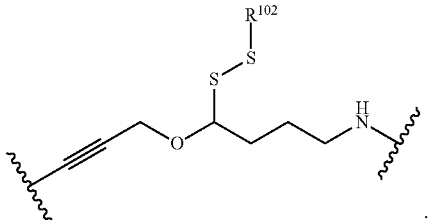
.
In embodiments, $L^{100}$ is
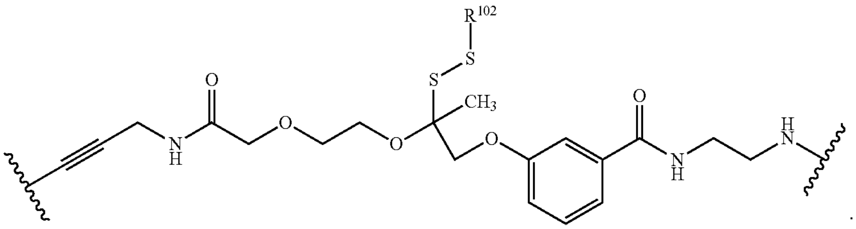
.
In embodiments, $L^{100}$ is
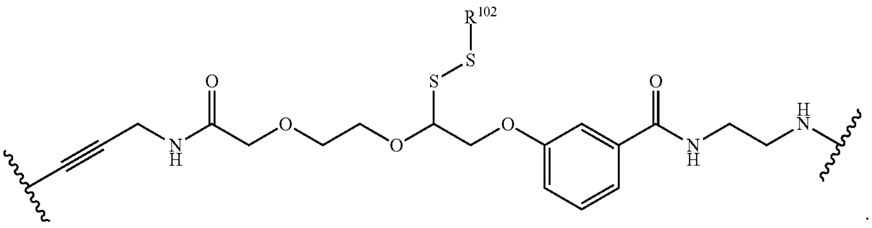
.
$R^{102}$ is as described herein, including in embodiments.
In embodiments, $L^{100}$ is
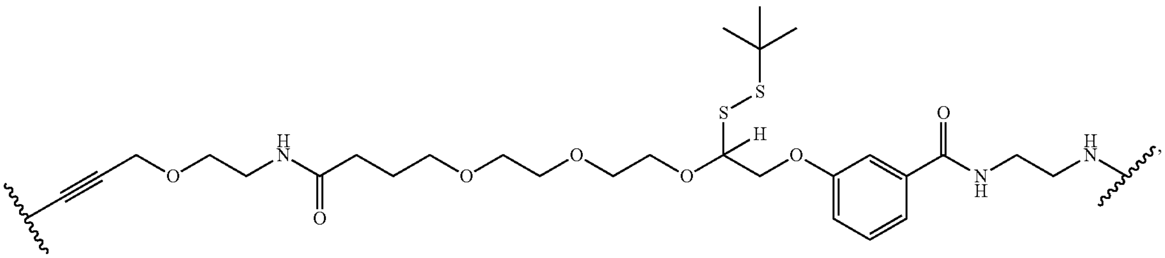
,
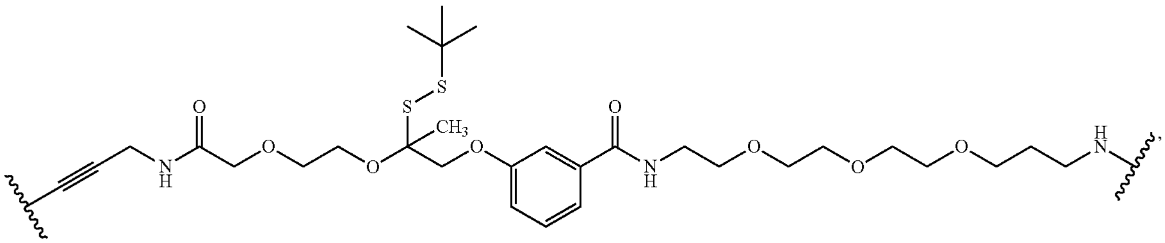
, -continued
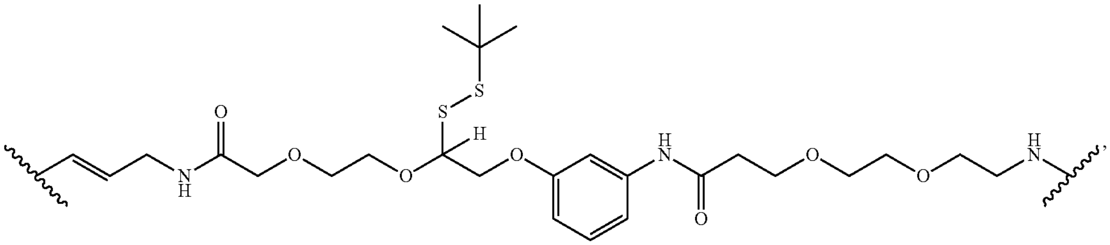
,
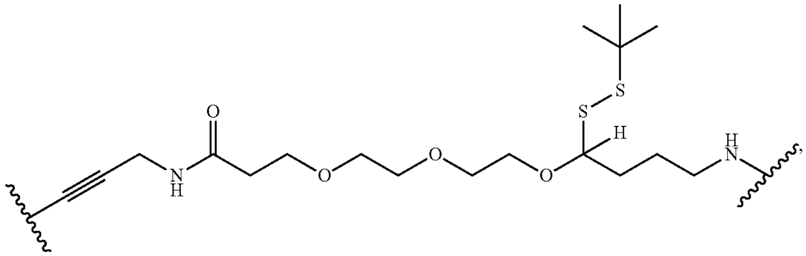
,
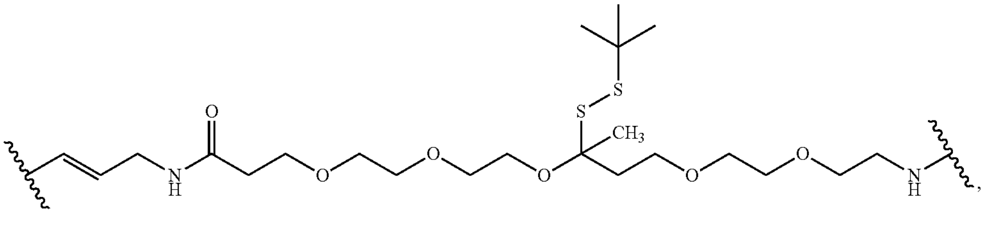
,
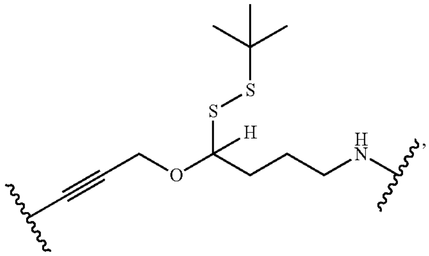
,
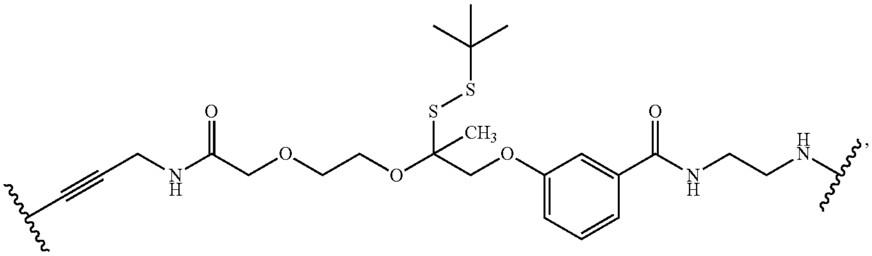
, or
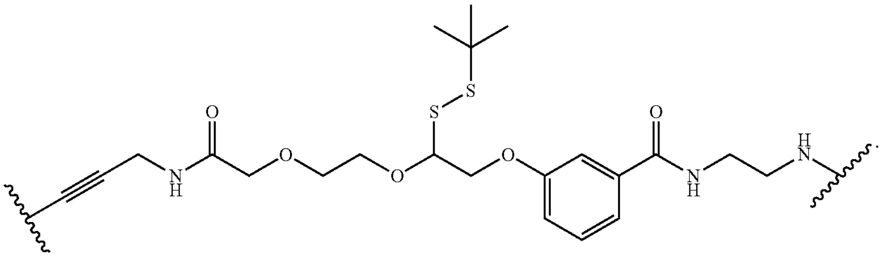
.

In embodiments, $L^{100}$ is
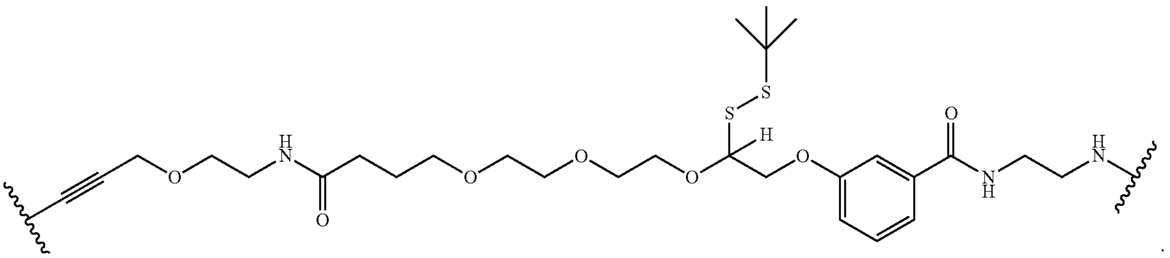 [SMILES: *C#CCOCCNC(=O)CCCOCCOCCOC(COc1cccc(C(=O)NCCN*)c1)SSC(C)(C)C]
In embodiments, $L^{100}$ is
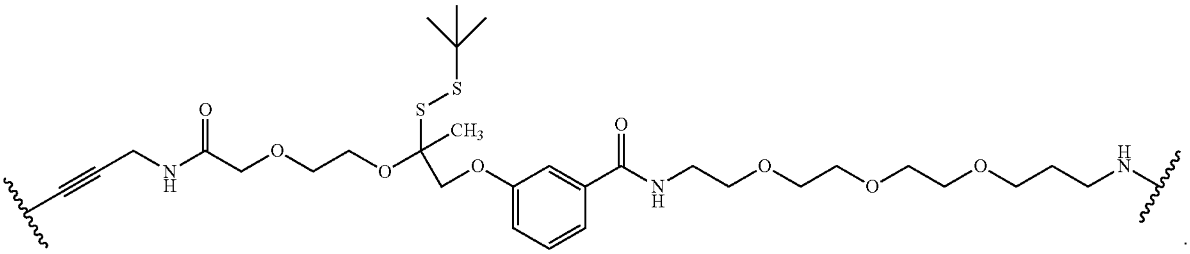 [SMILES: *C#CCNC(=O)COCCOC(C)(COc1cccc(C(=O)NCCOCCOCCOCCCN*)c1)SSC(C)(C)C]
In embodiments, $L^{100}$ is
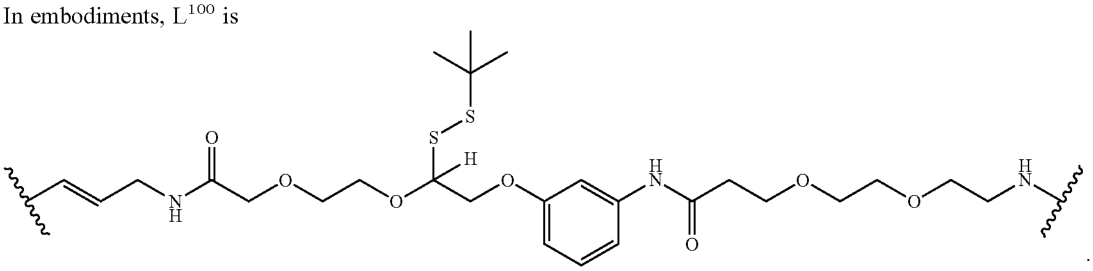
In embodiments, $L^{100}$ is
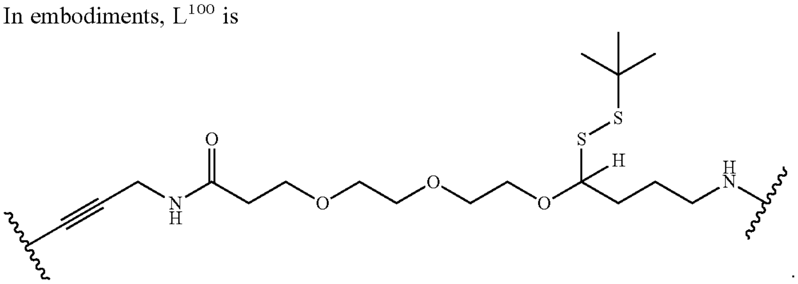
In embodiments, $L^{100}$ is
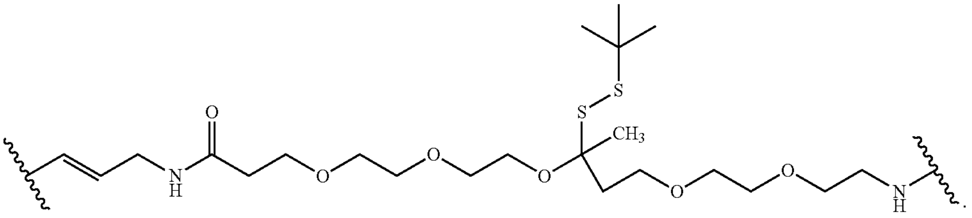 [SMILES: */C=C/CNC(=O)CCOCCOCCOC(C)(CCOCCOCCN*)SSC(C)(C)C]

In embodiments, $L^{100}$ is
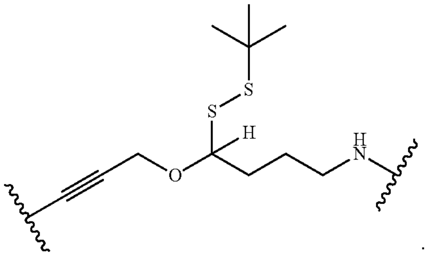 [SMILES: *C#CCOC(CCCN*)SSC(C)(C)C]
In embodiments, $L^{100}$ is
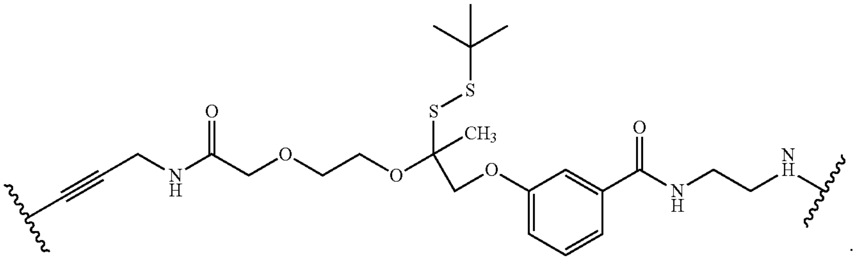 [SMILES: *C#CCNC(=O)COCCOC(C)(COc1cccc(C(=O)NCCN*)c1)SSC(C)(C)C]
In embodiments, $L^{100}$ is
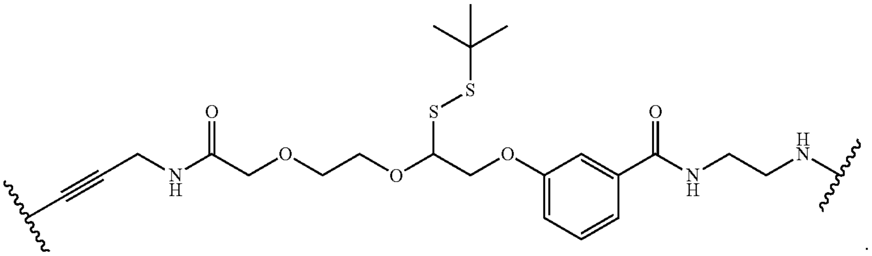 [SMILES: *C#CCNC(=O)COCCOC(COc1cccc(C(=O)NCCN*)c1)SSC(C)(C)C]
In embodiments, $L^{100}$ is
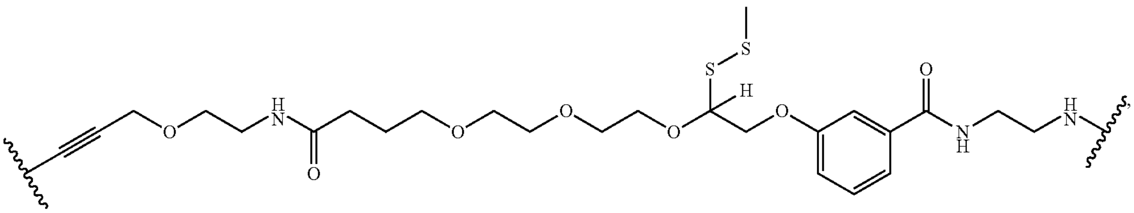
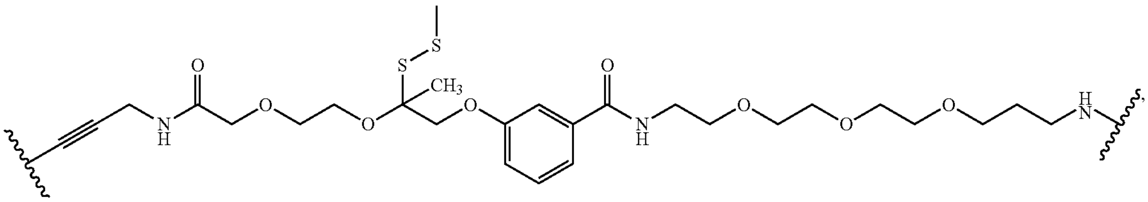

-continued
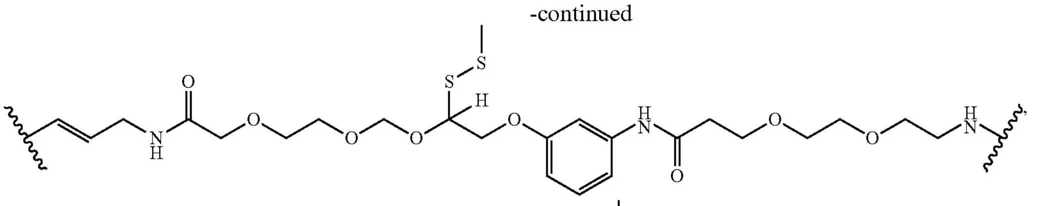
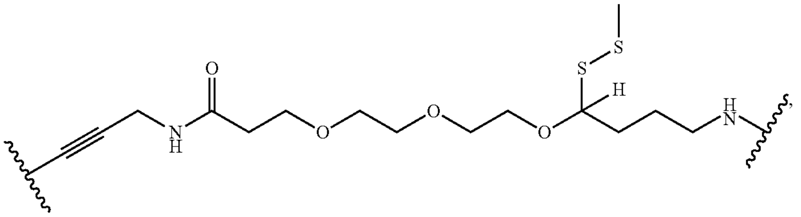
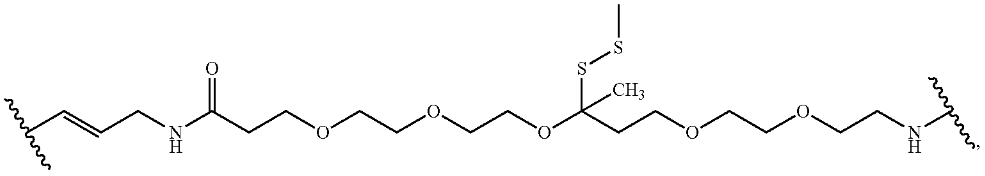
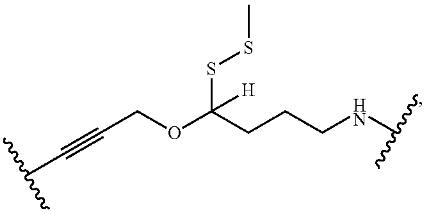
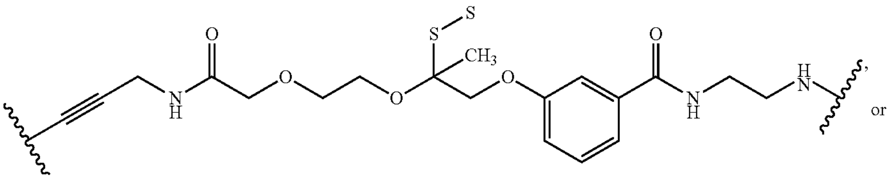
or
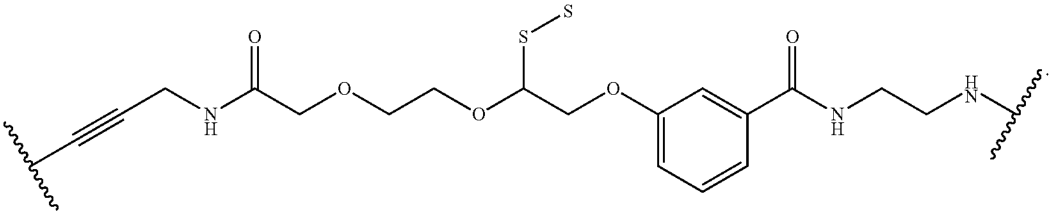
In embodiments, $L^{100}$ is
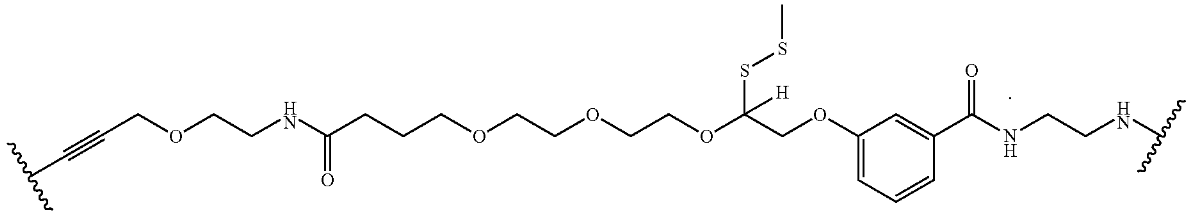 [SMILES: *C#CCOCCNC(=O)CCCOCCOCCOC(COc1cccc(C(=O)NCCN*)c1)SSC]

In embodiments, $L^{100}$ is
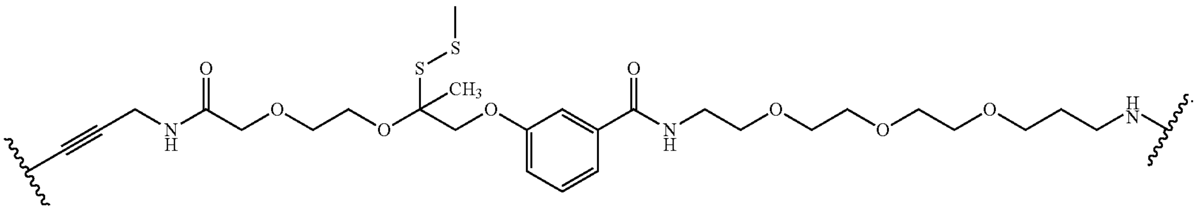 [SMILES: *C#CCNC(=O)COCCOC(C)(COc1cccc(C(=O)NCCOCCOCCOCCCN*)c1)SSC]
In embodiments, $L^{100}$ is
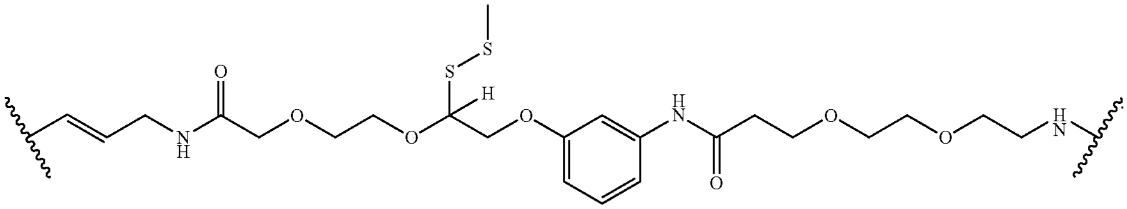 [SMILES: */C=C/CNC(=O)COCCOC(COc1cccc(NC(=O)CCOCCOCCN*)c1)SSC]
In embodiments, $L^{100}$ is
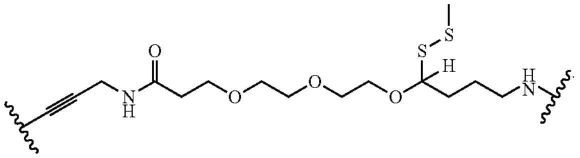 [SMILES: *C#CCNC(=O)CCOCCOCCOC(CCCN*)SSC]
In embodiments, $L^{100}$ is
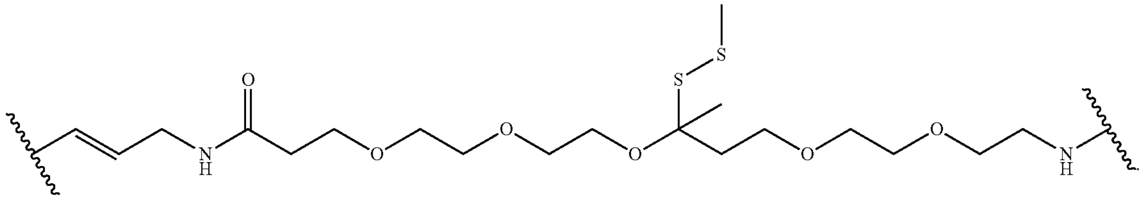 [SMILES: */C=C/CNC(=O)CCOCCOCCOC(C)(CCOCCOCCN*)SSC]
In embodiments, $L^{100}$ is
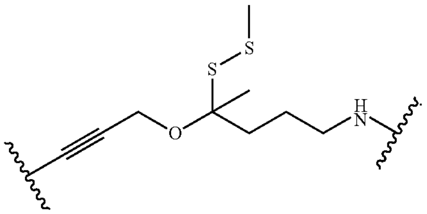 [SMILES: *C#CCOC(C)(CCCN*)SSC]
In embodiments, $L^{100}$ is
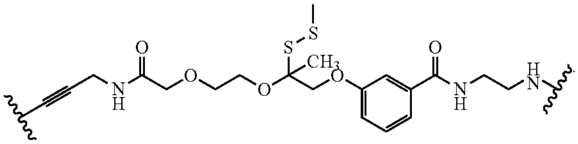 [SMILES: *C#CCNC(=O)COCCOC(C)(COc1cccc(C(=O)NCCN*)c1)SSC]
In embodiments, $L^{100}$ is
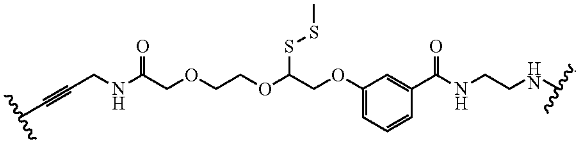 [SMILES: *C#CCNC(=O)COCCOC(COc1cccc(C(=O)NCCN*)c1)SSC]

In embodiments, $L^{100}$ is
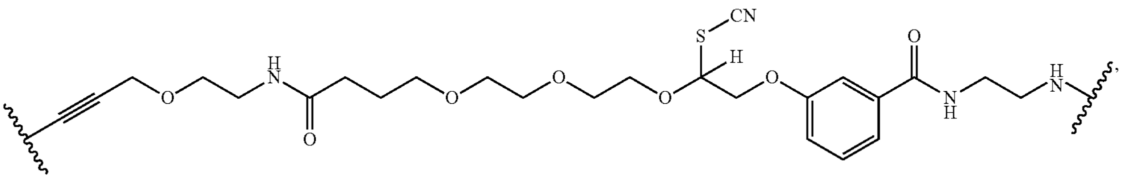
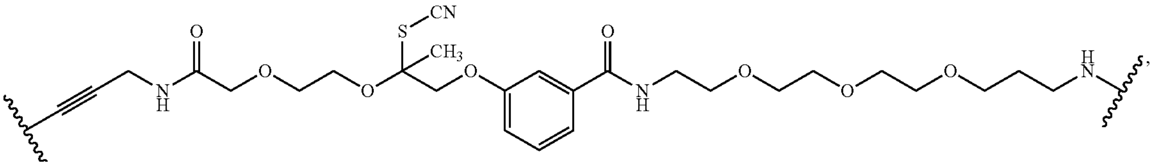
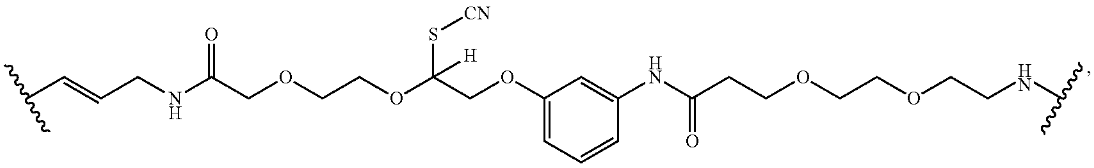
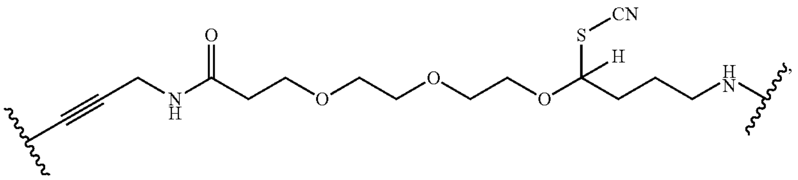
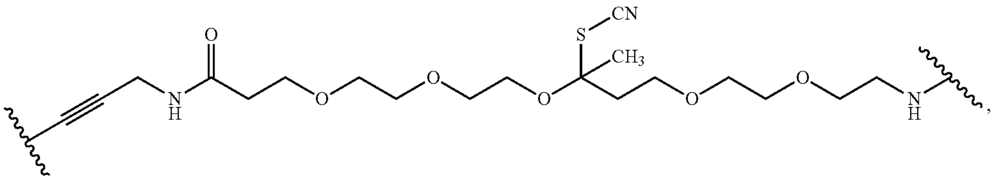
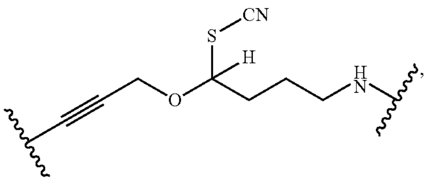
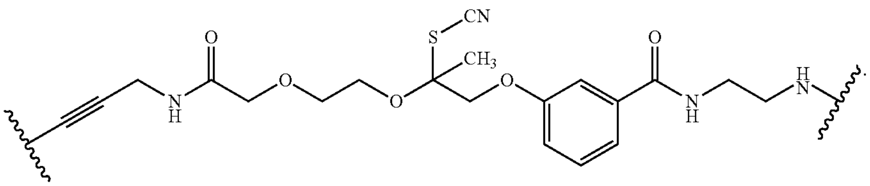
or
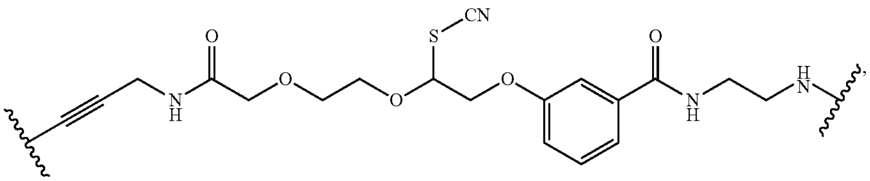

In embodiments, $L^{100}$ is
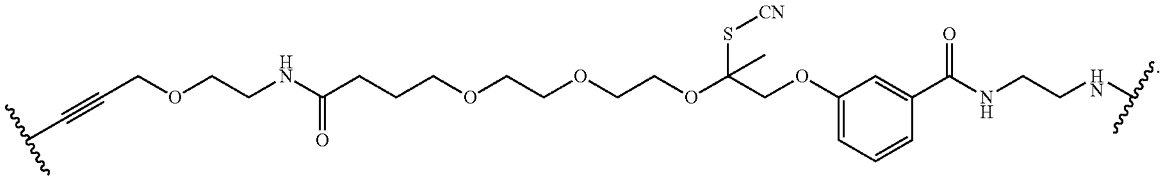 [SMILES: *C#CCOCCNC(=O)CCCOCCOCCOC(C)(COc1cccc(C(=O)NCCN*)c1)SC#N]
In embodiments, $L^{100}$ is
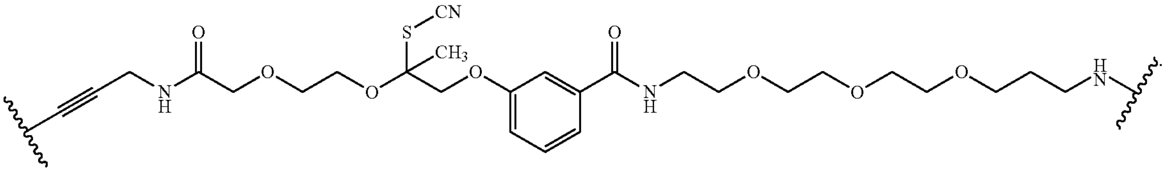 [SMILES: *C#CCNC(=O)COCCOC(C)(COc1cccc(C(=O)NCCOCCOCCOCCCN*)c1)SC#N]
In embodiments, $L^{100}$ is
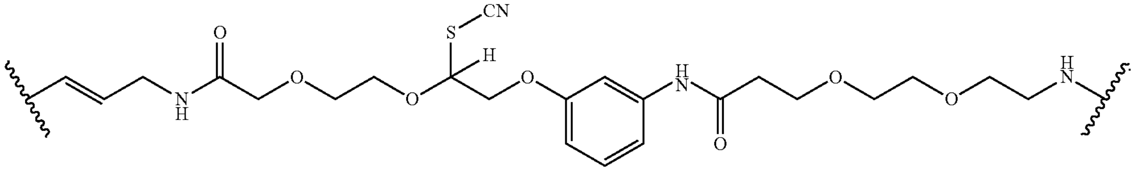 [SMILES: */C=C/CNC(=O)COCCOC(COc1cccc(NC(=O)CCOCCOCCN*)c1)SC#N]
In embodiments, $L^{100}$ is
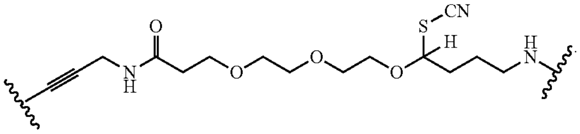
In embodiments, $L^{100}$ is
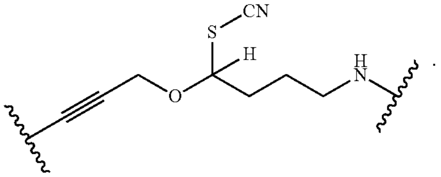
In embodiments, $L^{100}$ is
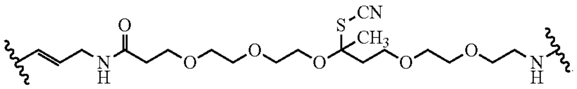 [SMILES: */C=C/CNC(=O)CCOCCOCCOC(C)(CCOCCOCCN*)SC#N]
In embodiments, $L^{100}$ is
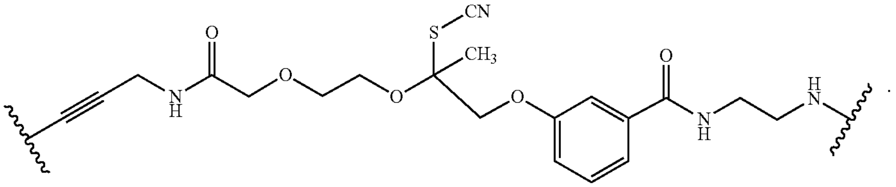 [SMILES: *C#CCNC(=O)COCCOC(C)(COc1cccc(C(=O)NCCN*)c1)SC#N]

In embodiments, $L^{100}$ is
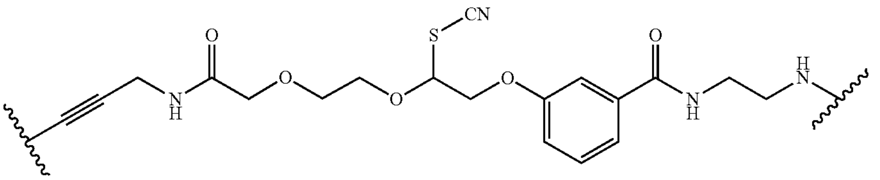
.
In embodiments, $L^{100}$ is
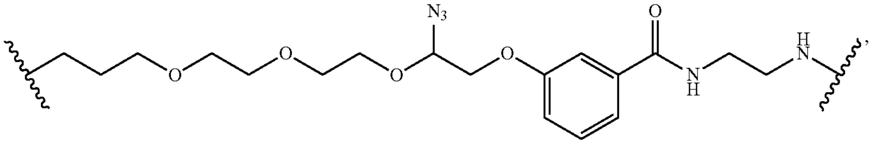
,
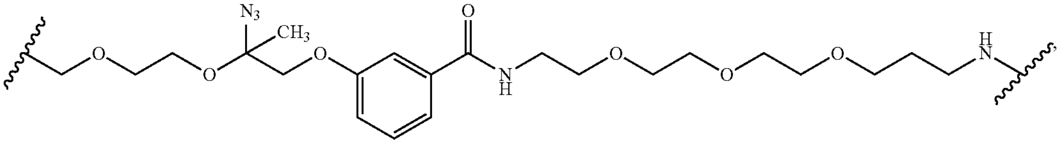
,
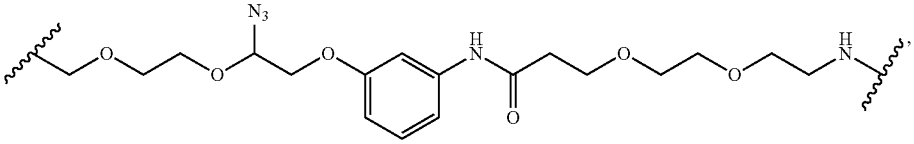
,
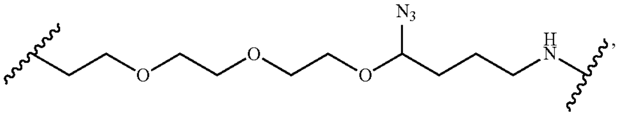
,
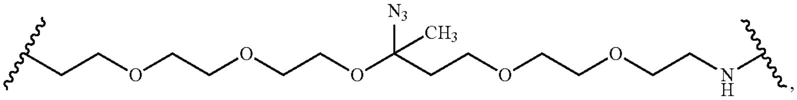
,
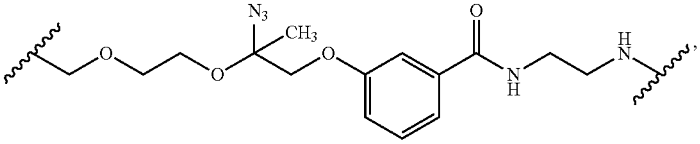
, or
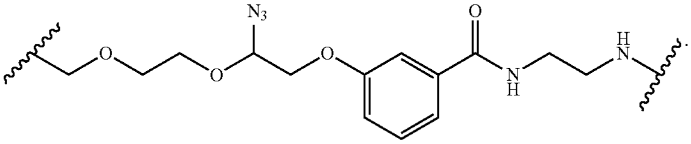
.
In embodiments, $L^{100}$ is
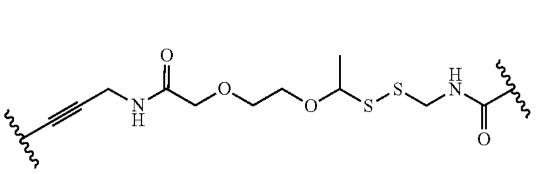
,
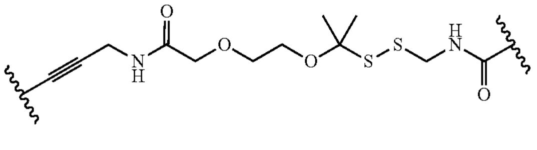
,
-continued
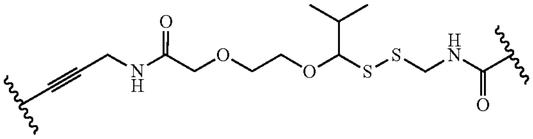
,
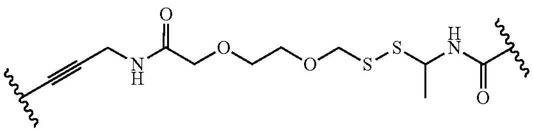
, -continued
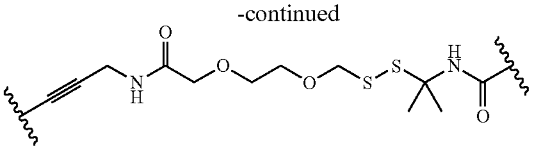
, or
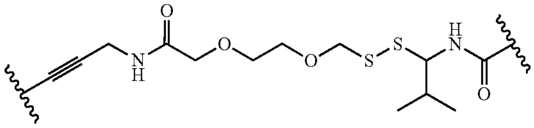
,
In embodiments, $L^{100}$ is
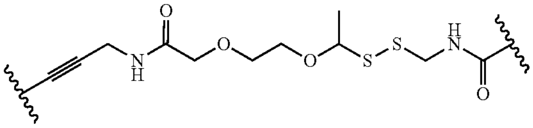
,
-continued
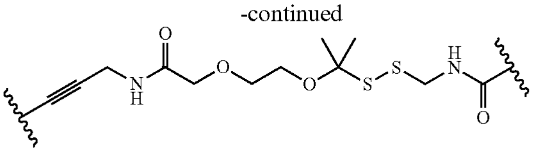
, or
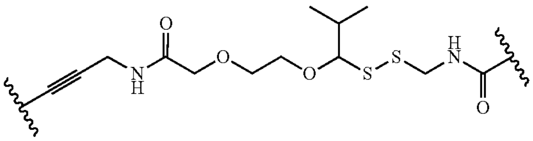
,
In embodiments, $L^{100}$ is
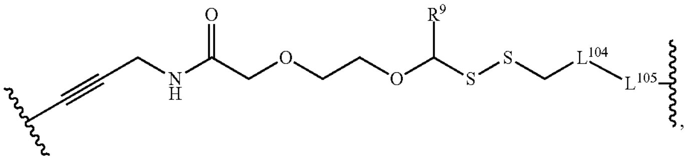
,
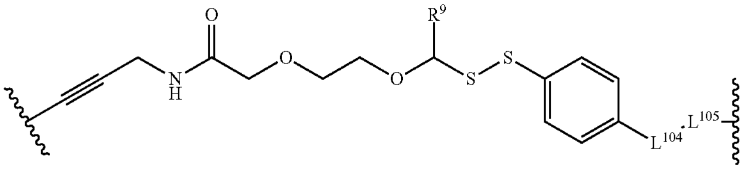
,
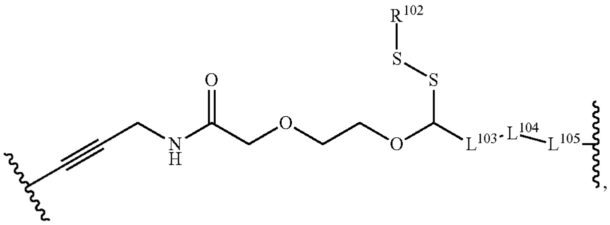
,
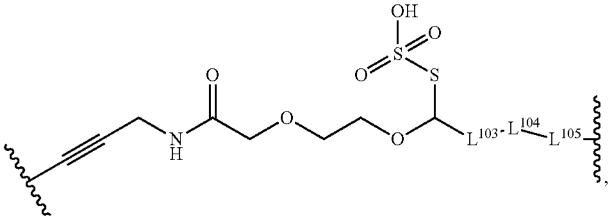
,
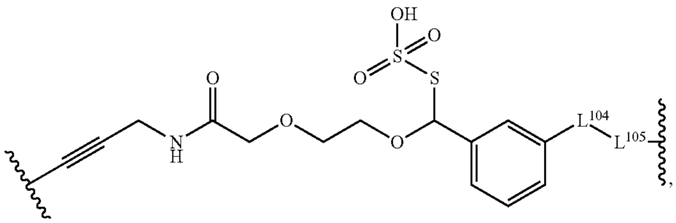
, -continued
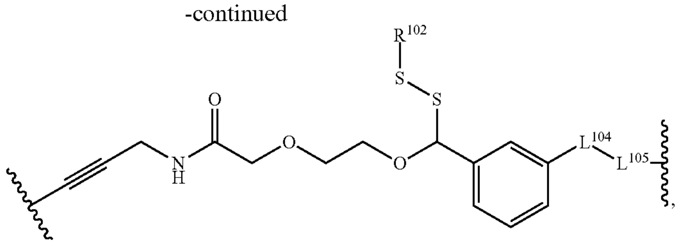
wherein $R^9$, $L^{104}$, $L^{105}$, and $R^{102}$ are as described herein. In embodiments, $L^{100}$ is
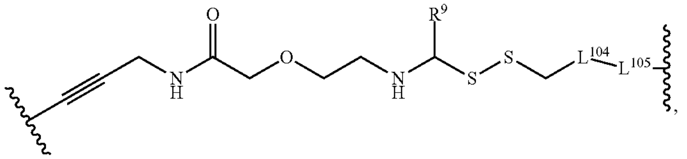
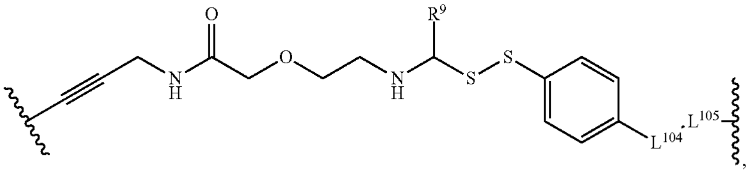
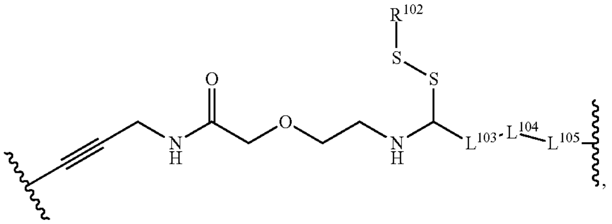
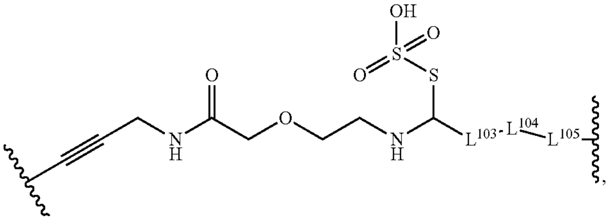
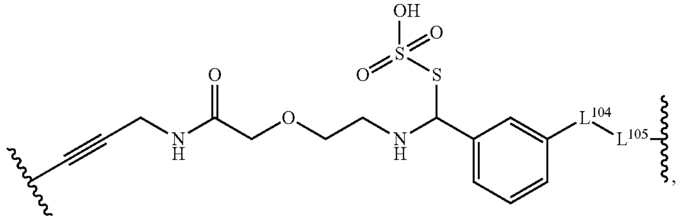
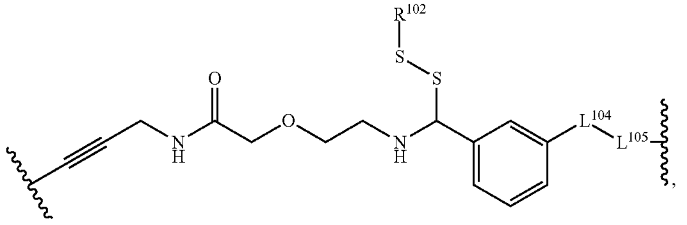
wherein $R^9$, $L^{104}$, $L^{105}$, and $R^{102}$ are as described herein.

In embodiments, $L^{100}$ is
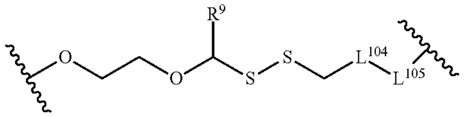
,
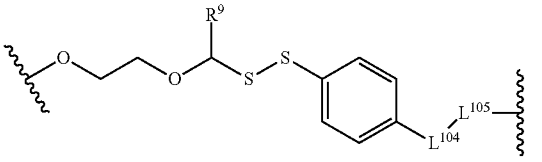
,
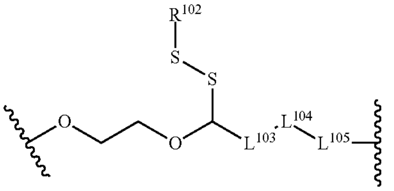
,
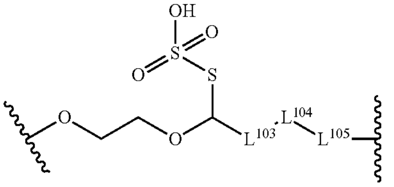
,
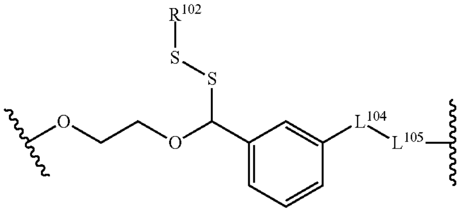
,
wherein $R^9$, $L^{104}$, $L^{105}$, and $R^{102}$ are as described herein. In embodiments, $L^{100}$ is
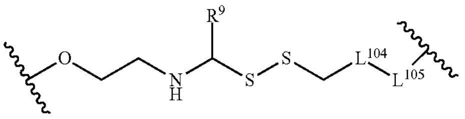
,
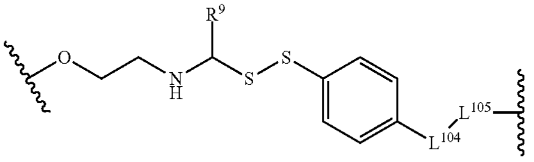
,
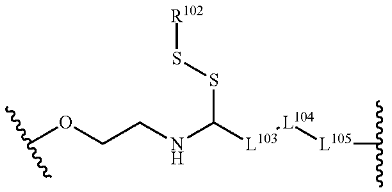
,
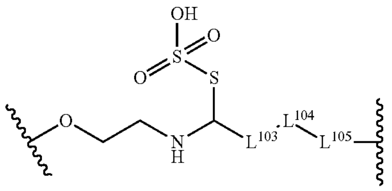
,
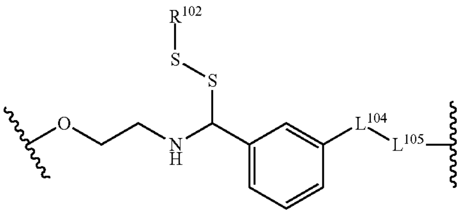
,
wherein $R^9$, $L^{104}$, $L^{105}$, and $R^{102}$ are as described herein. In embodiments, $L^{100}$ is
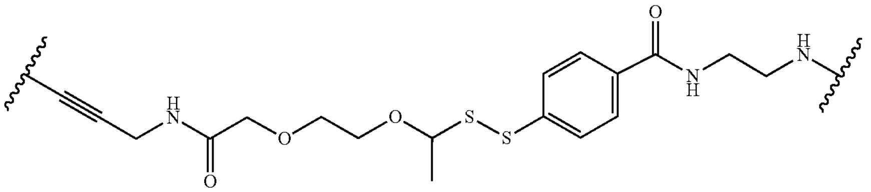
,
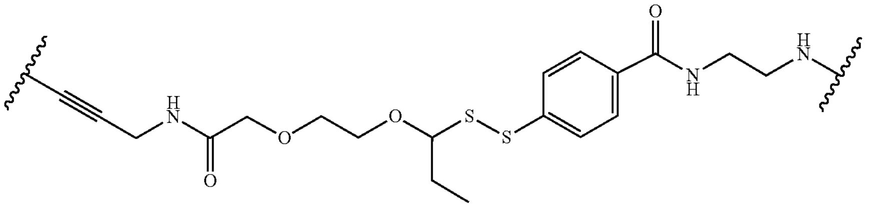
, or
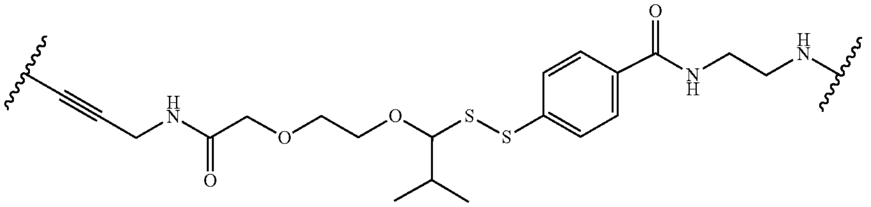
.

In embodiments, $L^{100}$ is
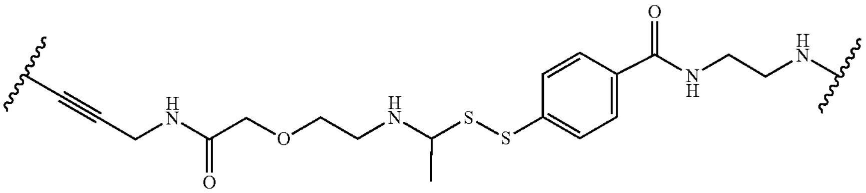
,
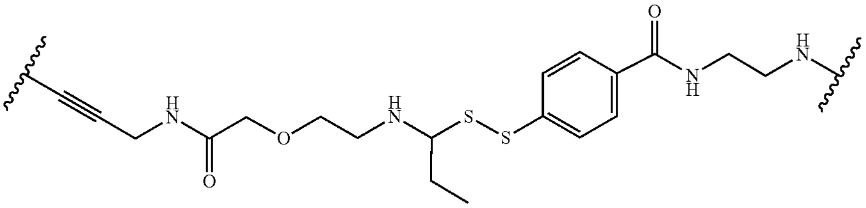
, or
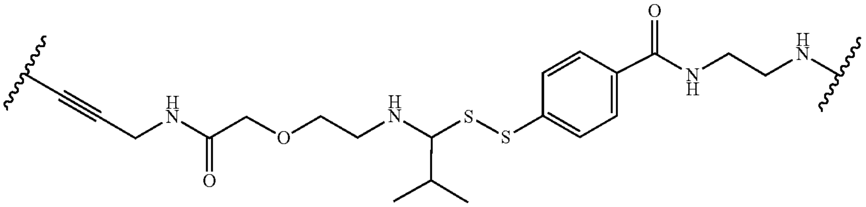
.
In embodiments, $L^{100}$ is
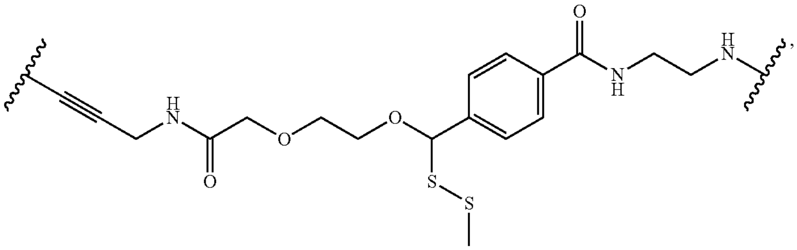
,
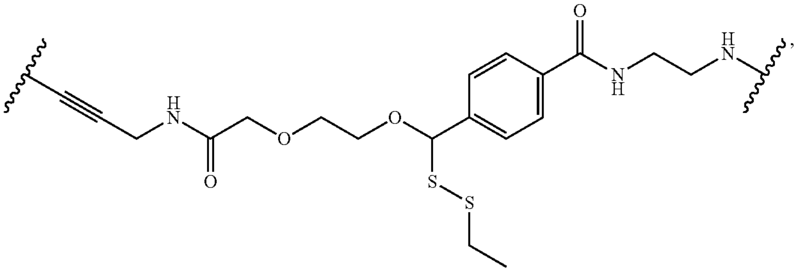
, or
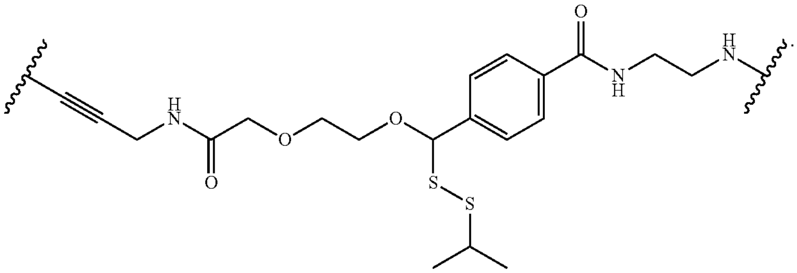
.

In embodiments, $L^{100}$ is

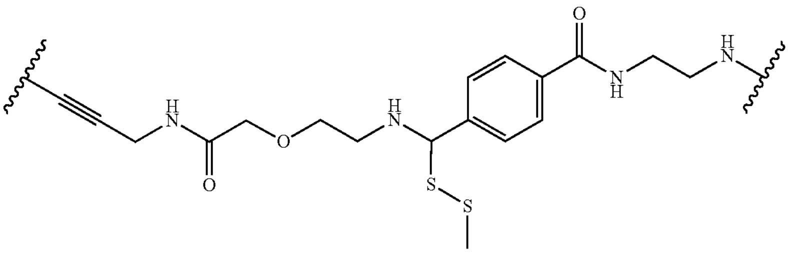

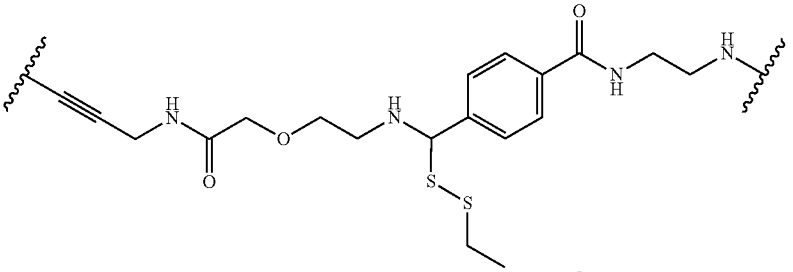

, or

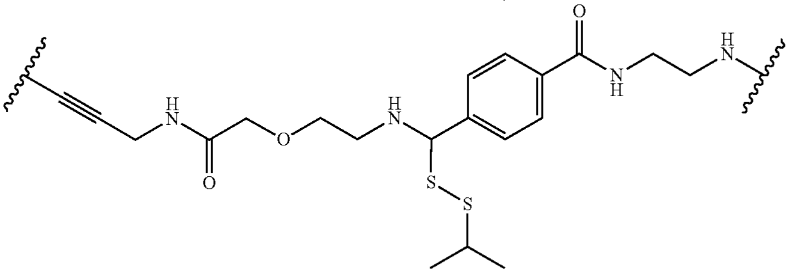

.

In embodiments, $L^{100}$ is

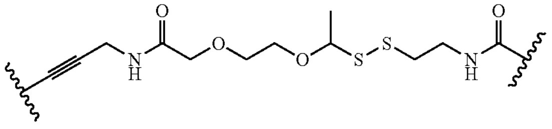

,

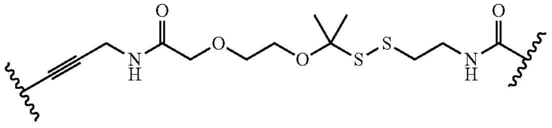

,

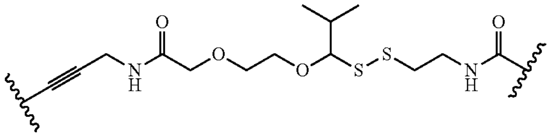

.

In embodiments, $L^{100}$ is

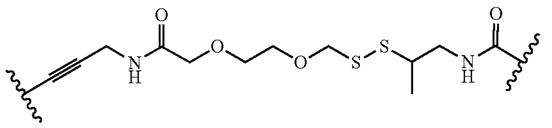

,

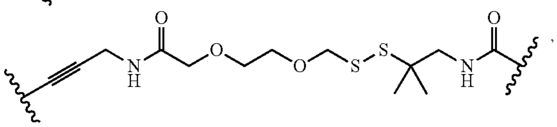

, or

-continued

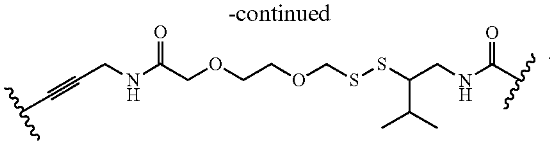

.

In embodiments, $R^4$ is a detectable moiety. In embodiments, $R^4$ is a fluorescent dye moiety. In embodiments, $R^4$ is a detectable moiety described herein (e.g., Table 1). In embodiments, $R^4$ is a detectable moiety described in Table 1.

TABLE 1

Detectable moieties to be used in selected embodiments.

| Nucleoside/nucleotide abbreviation | Dye name | λmax (nm) |
|---|---|---|
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

In embodiments, $R^4$ is

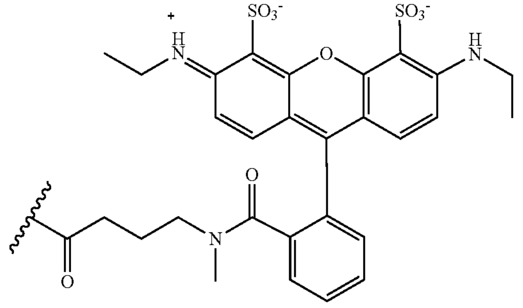

,

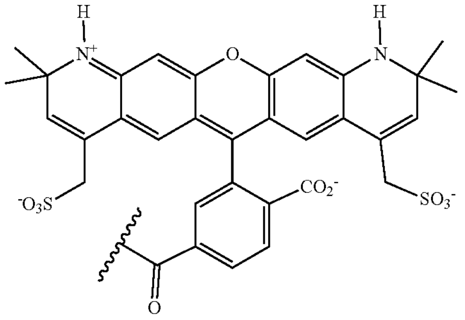

,

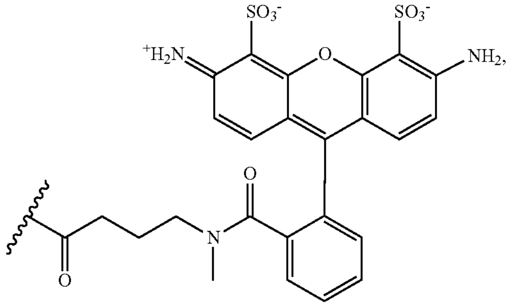

or

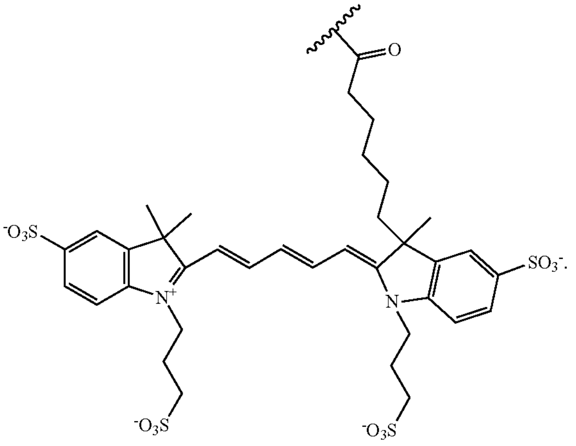

In embodiments, the compound has the formula:

(IIA)

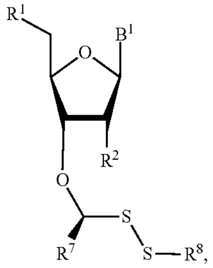

wherein $R^1$, $R^7$, $R^8$, $B^1$, and $R^2$ are as described herein. In embodiments, the compound has the formula:

(IIB)

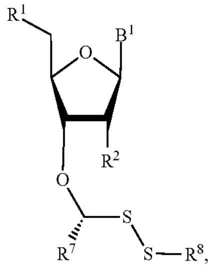

wherein $R^1$, $R^7$, $R^8$, $B^1$, and $R^2$ are as described herein.

In embodiments, the compound has the formula:

(IA)

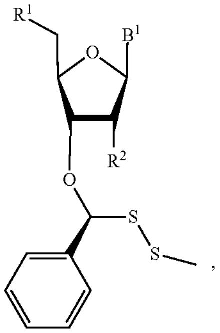

wherein $R^1$, $B^1$, and $R^2$ are as described herein. In embodiments, the compound has the formula:

(IB)

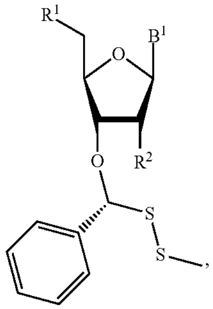

wherein $R^1$, $B^1$, and $R^2$ are as described herein. In embodiments, the compound has the formula:

(IC)

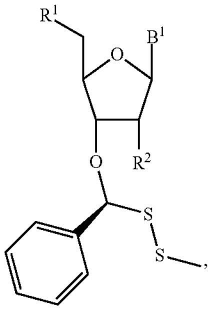

wherein $R^1$, $B^1$, and $R^2$ are as described herein. In embodiments, the compound has the formula:

(ID)

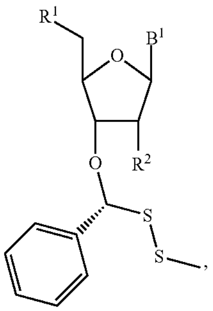

wherein $R^1$, $B^1$, and $R^2$ are as described herein.

In embodiments, the compound has the formula:

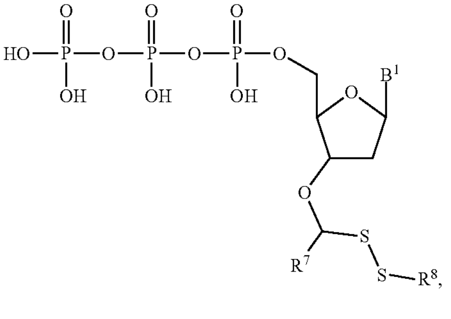

wherein $B^1$, $R^7$, and $R^8$ are as described herein, including embodiments. In embodiments, the compound has the formula:

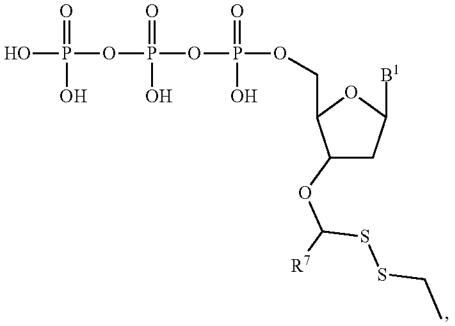

wherein $B^1$ and $R^7$ are as described herein, including embodiments.

In embodiments, the compound has the formula:

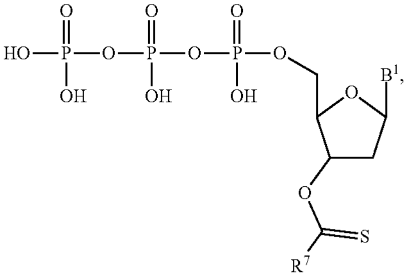

wherein $B^1$, and $R^7$ are as described herein, including embodiments. In embodiments, $R^7$ is a substituted or unsubstituted aryl or substituted or unsubstituted heteroaryl. In embodiments, $R^7$ is a substituted or unsubstituted heteroaryl wherein the atom bonded to the thiocarbonyl carbon is not a heteroatom (e.g., nitrogen).

In embodiments, the compound has the formula:

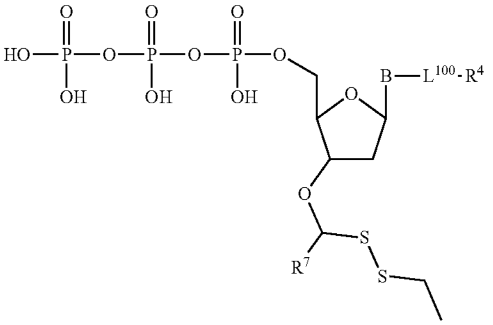

or

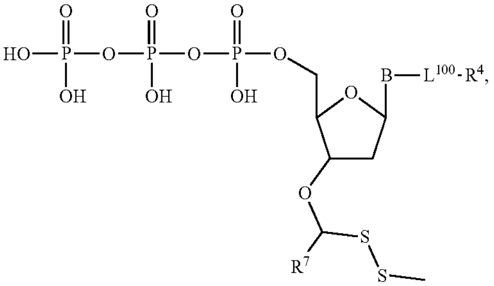

wherein B, $R^7$, $L^{100}$, and $R^4$ are as described herein, including in embodiments.

In embodiments, the compound has the formula:

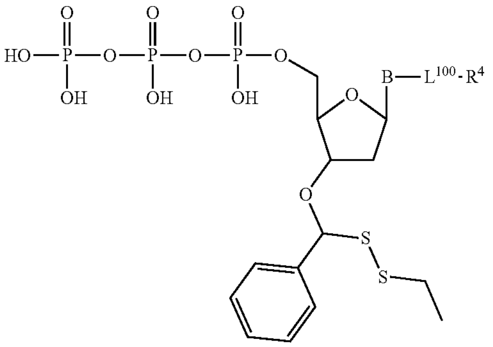

or

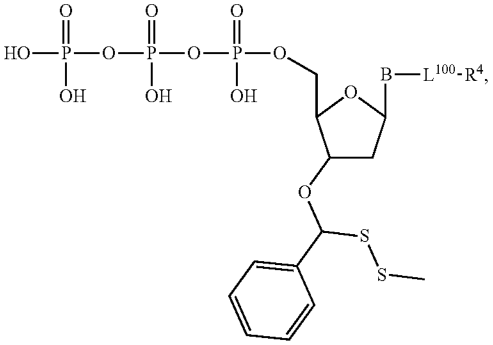

wherein B, $L^{100}$, and $R^4$ are as described herein, including in embodiments. In embodiments, the compound has the formula:

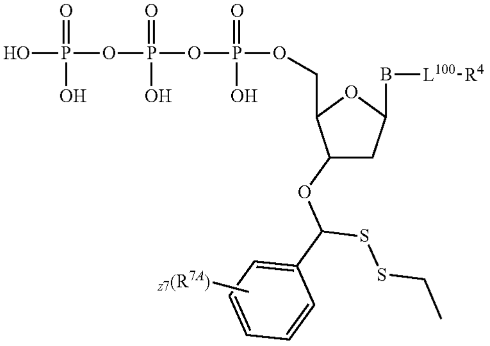

or

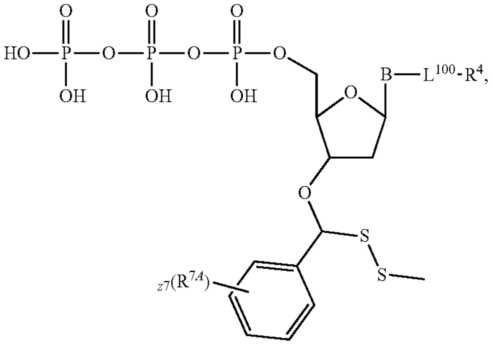

wherein z7, B, $L^{100}$, $R^{7A}$, and $R^4$ are as described herein, including in embodiments. In embodiments, the compound has the formula:

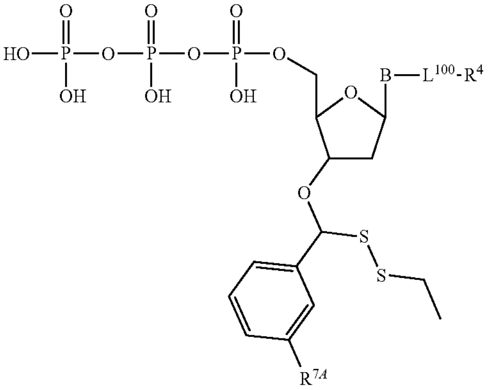

or

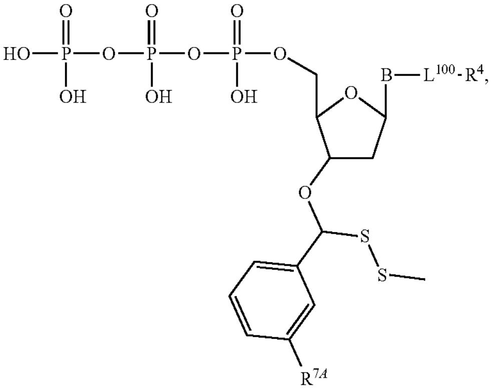

wherein B, $L^{100}$, $R^{7A}$, and $R^4$ are as described herein, including in embodiments. In embodiments, the compound has the formula:

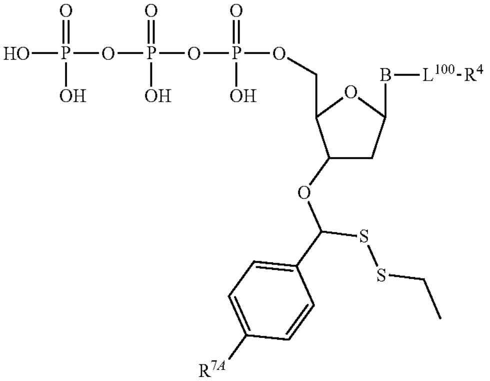

or

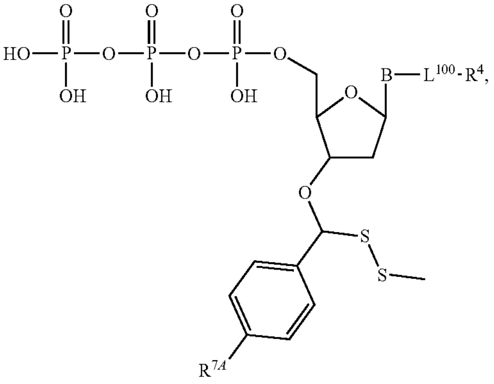

wherein B, $L^{100}$, $R^{7A}$, and $R^4$ are as described herein, including in embodiments. In embodiments, the compound has the formula:

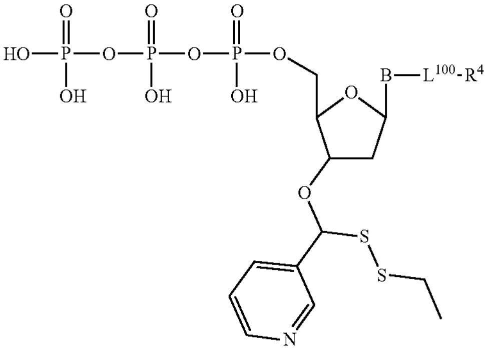

or

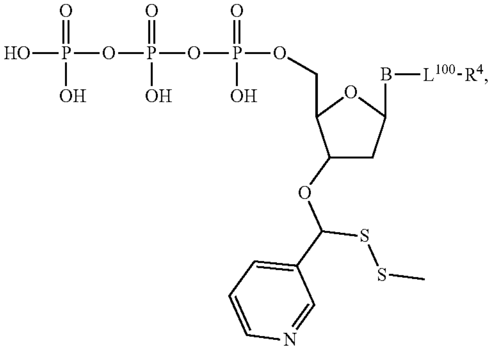

wherein B, $L^{100}$, and $R^4$ are as described herein, including in embodiments. In embodiments, the compound has the formula:

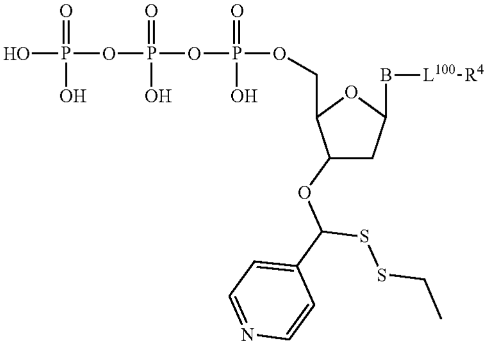

or

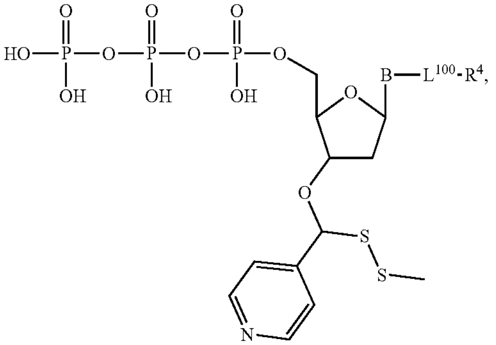

wherein B, $L^{100}$, and $R^4$ are as described herein, including in embodiments. In embodiments, the compound has the formula:

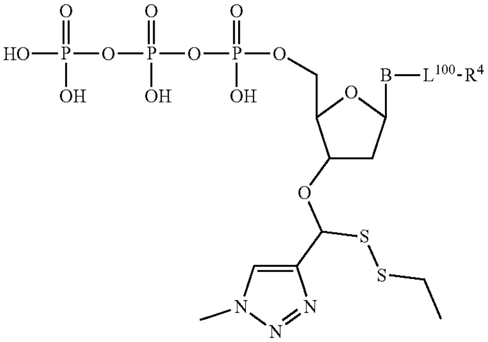

or

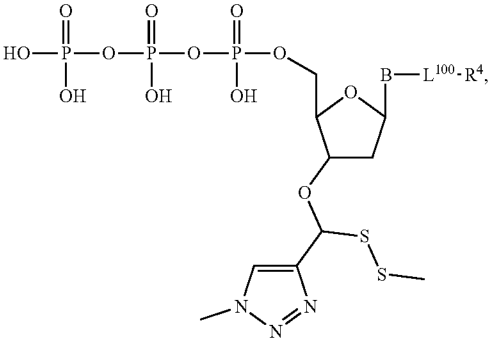

wherein B, $L^{100}$, and $R^4$ are as described herein, including in embodiments.

In embodiments, the compound has the formula:

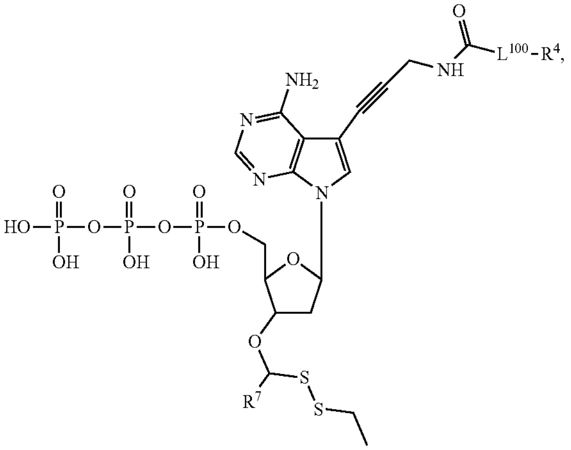

-continued

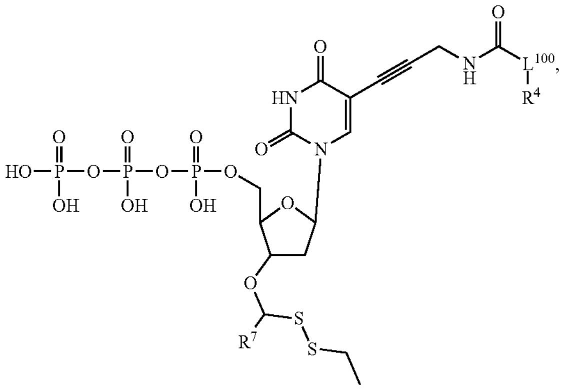

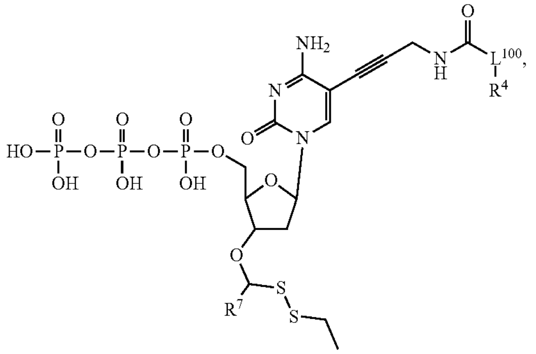

or

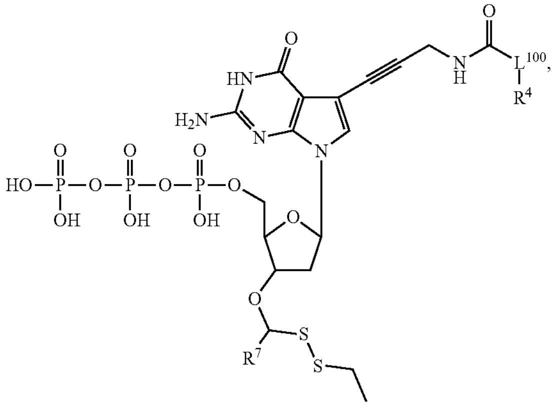

$R^7$, $L^{100}$, and $R^4$ are as described herein, including in embodiments. In embodiments, $L^{100}$ is a cleavable linker. In embodiments, $R^4$ is a fluorescent dye moiety. In embodiments, $R^7$ is a substituted or unsubstituted aryl or substituted or unsubstituted heteroaryl. In embodiments, $R^7$ is a substituted or unsubstituted cycloalkyl or substituted or unsubstituted heterocycloalkyl. In embodiments, $R^7$ is

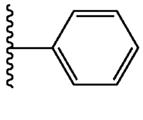

,

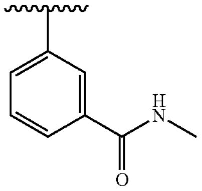

,

-continued

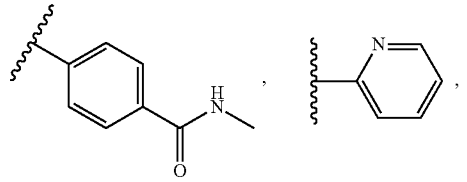

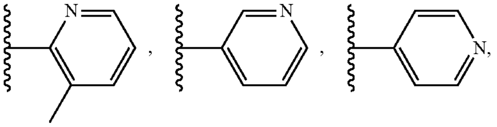

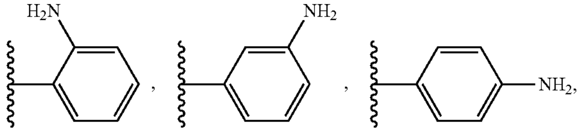

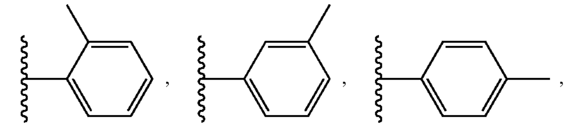

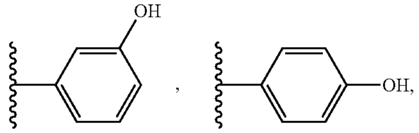

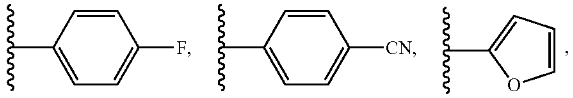

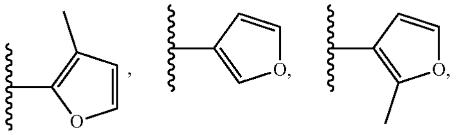

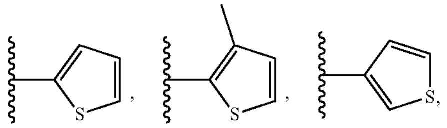

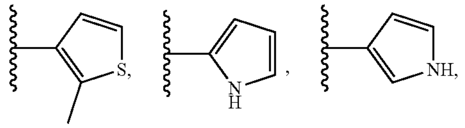

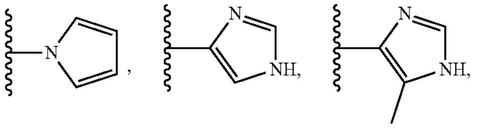

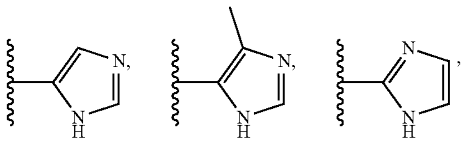

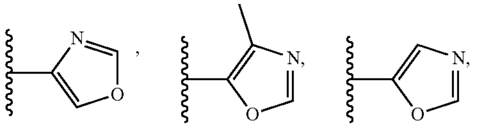

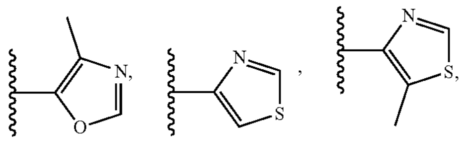

-continued
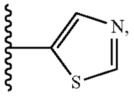
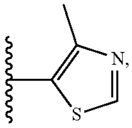
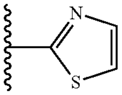
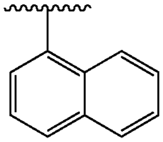
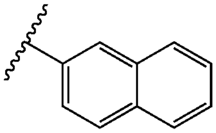
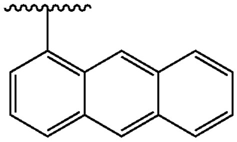
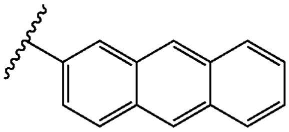
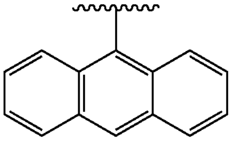
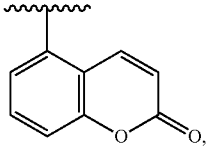
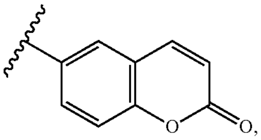
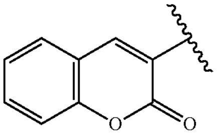
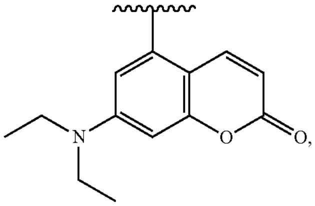
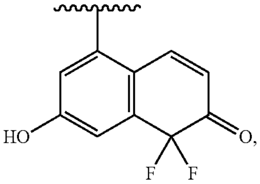
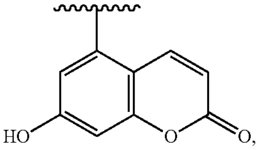
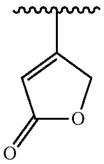
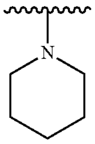
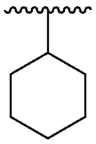
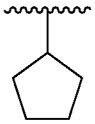
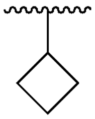
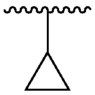
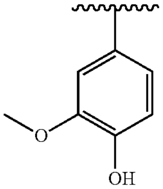
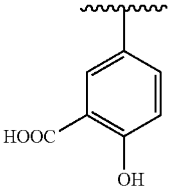
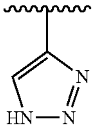
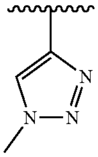
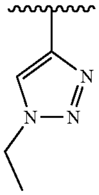
-continued
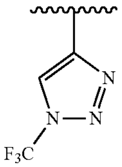
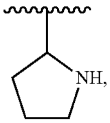
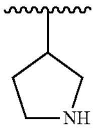
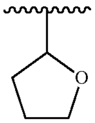
or
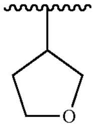
In embodiments, $R^7$ is
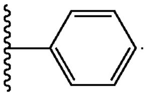
In embodiments, the compound has the formula:
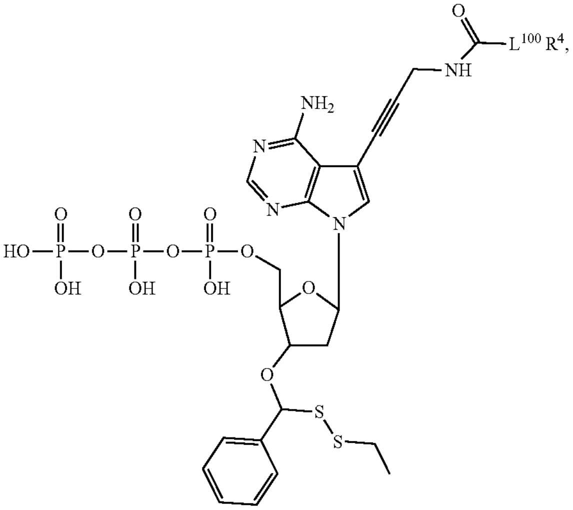
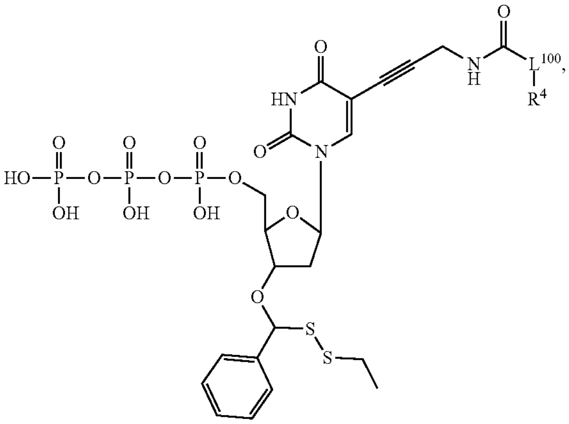

-continued

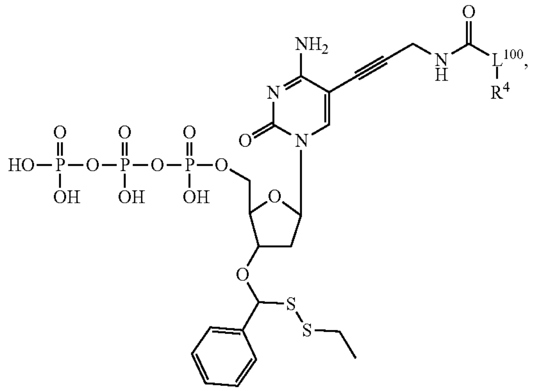

or

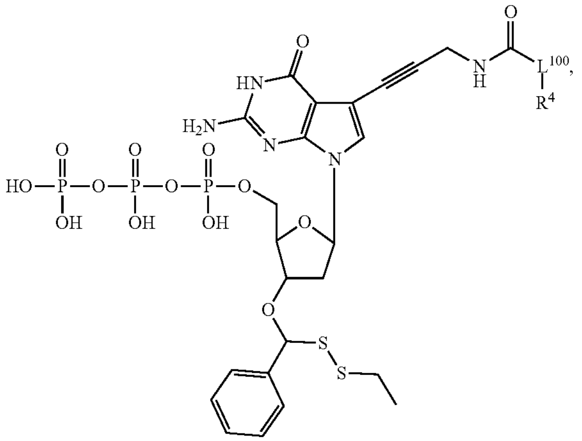

$L^{100}$ and $R^4$ are as described herein, including in embodiments. In embodiments, $L^{100}$ is a cleavable linker. In embodiments, $R^4$ is a fluorescent dye moiety.

In embodiments, the compound has the formula:

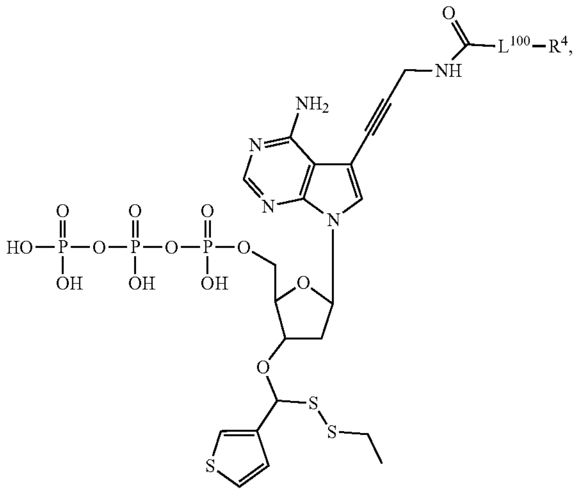

-continued

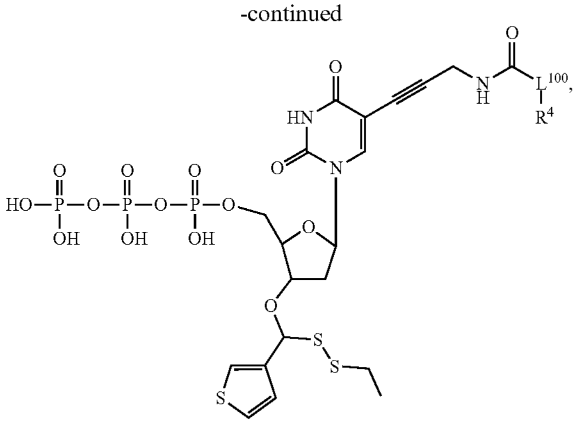

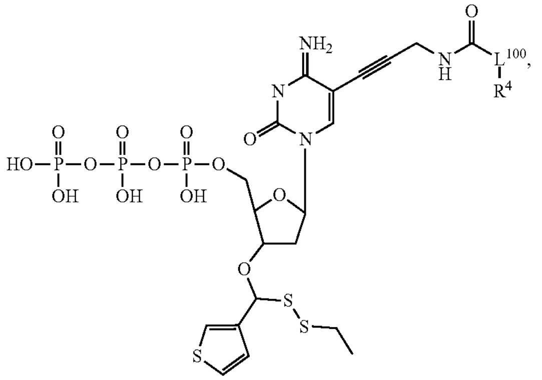

or

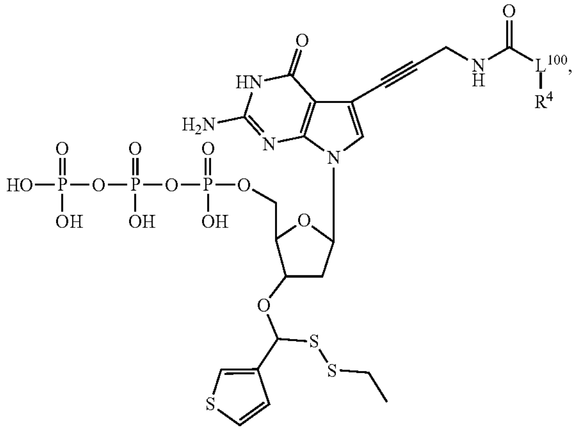

$L^{100}$ and $R^4$ are as described herein, including in embodiments. In embodiments, $L^{100}$ is a cleavable linker. In embodiments, $R^4$ is a fluorescent dye moiety.

In embodiments, the compound has the formula:

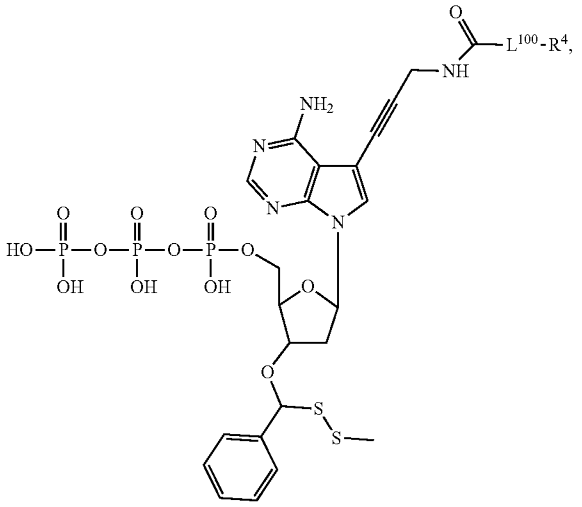

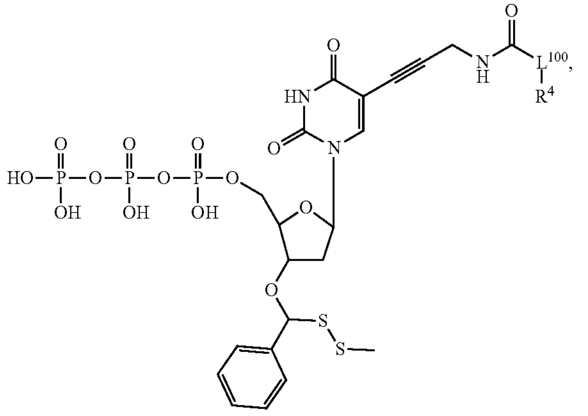

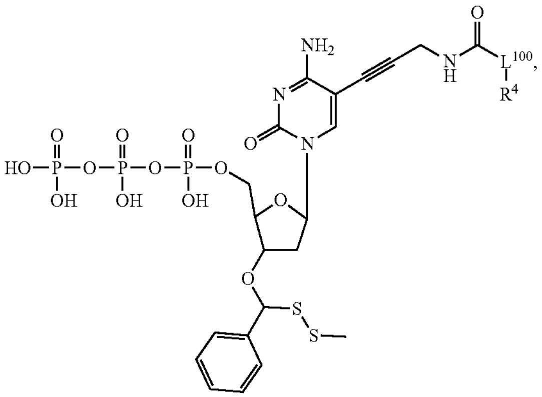

or

-continued

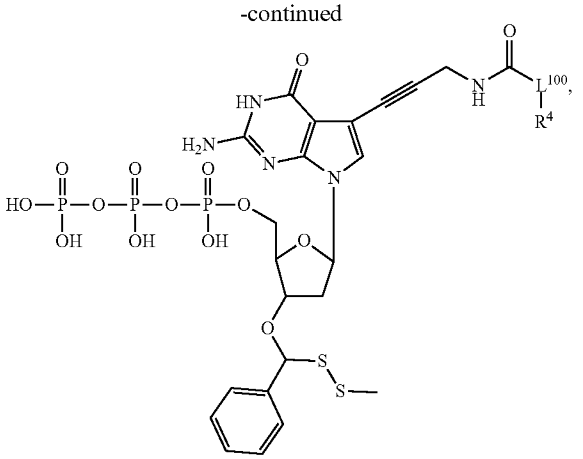

$L^{100}$ and $R^4$ are as described herein, including in embodiments. In embodiments, $L^{100}$ is a cleavable linker. In embodiments, $R^4$ is a fluorescent dye moiety.

In embodiments, the compound has the formula:

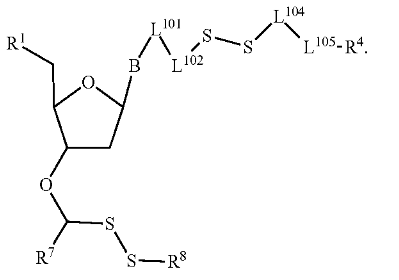

$R^1$, B, $R^7$, $R^8$, $L^{101}$, $L^{102}$, $L^{104}$, $L^{105}$, and $R^4$ are as described herein, including in embodiments. In embodiments, the compound has the formula:

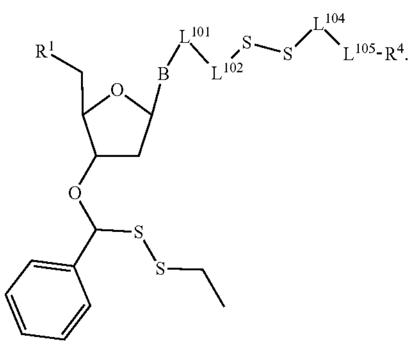

$R^1$, B, $L^{101}$, $L^{102}$, $L^{104}$, $L^{105}$, and $R^4$ are as described herein, including in embodiments. In embodiments, the compound has the formula:

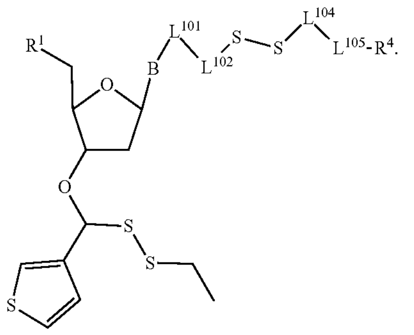

$R^1$, B, $L^{101}$, $L^{102}$, $L^{104}$, $L^{105}$, and $R^4$ are as described herein, including in embodiments. In embodiments, the compound has the formula:

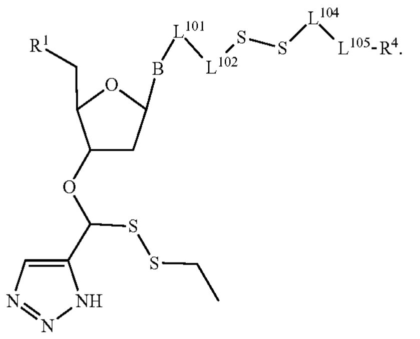

$R^1$, B, $L^{101}$, $L^{102}$, $L^{104}$, $L^{105}$, and $R^4$ are as described herein, including in embodiments. In embodiments, the compound has the formula:

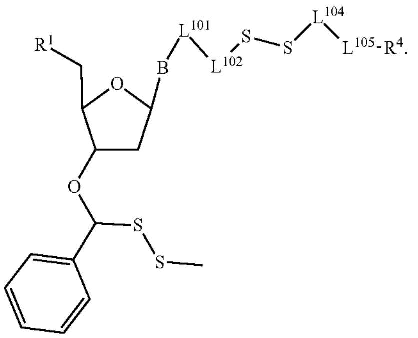

$R^1$, B, $L^{101}$, $L^{102}$, $L^{104}$, $L^{105}$, and $R^4$ are as described herein, including in embodiments.

In embodiments, the compound has the formula:

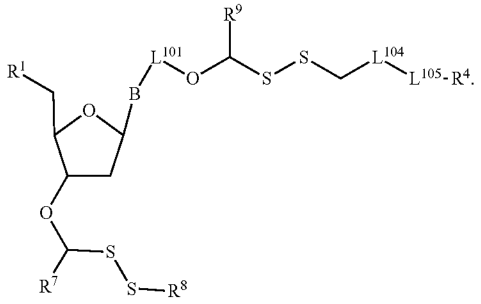

$R^1$, B, $R^7$, $R^8$, $L^{101}$, $L^{104}$, $L^{105}$, and $R^4$ are as described herein, including in embodiments. In embodiments, the compound has the formula:

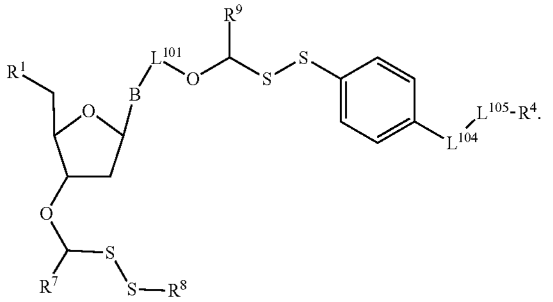

$R^1$, B, $R^7$, $R^8$, $L^{101}$, $L^{104}$, $L^{105}$, and $R^4$ are as described herein, including in embodiments. In embodiments, the compound has the formula:

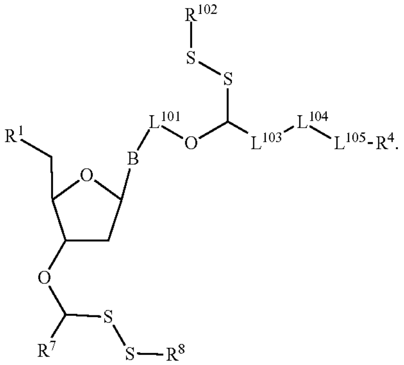

$R^1$, B, $R^7$, $R^8$, $R^{102}$, $L^{101}$, $L^{103}$, $L^{104}$, $L^{105}$, and $R^4$ are as described herein, including in embodiments. In embodiments, the compound has the formula:

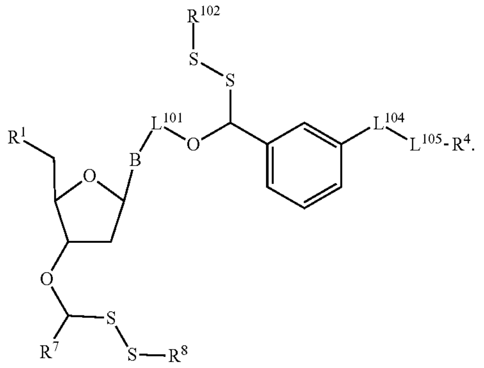

$R^1$, B, $R^7$, $R^8$, $R^{102}$, $L^{101}$, $L^{104}$, $L^{105}$, and $R^4$ are as described herein, including in embodiments. In embodiments, the compound has the formula:

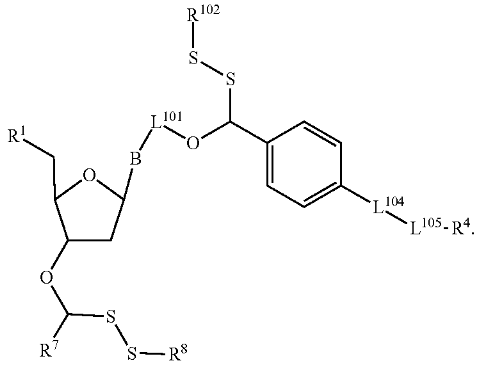

$R^1$, B, $R^7$, $R^8$, $L^{101}$, $L^{104}$, $L^{105}$, and $R^4$ are as described herein, including in embodiments. In embodiments, the compound has the formula:

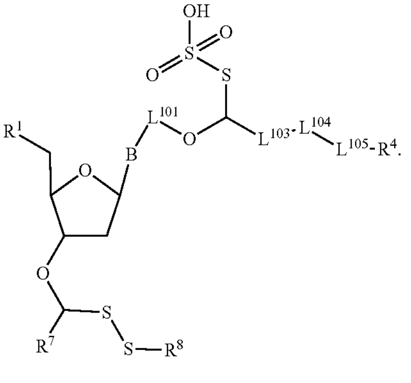

$R^1$, B, $R^7$, $R^8$, $R^{102}$, $L^{101}$, $L^{103}$, $L^{104}$, $L^{105}$, and $R^4$ are as described herein, including in embodiments. In embodiments, the compound has the formula:

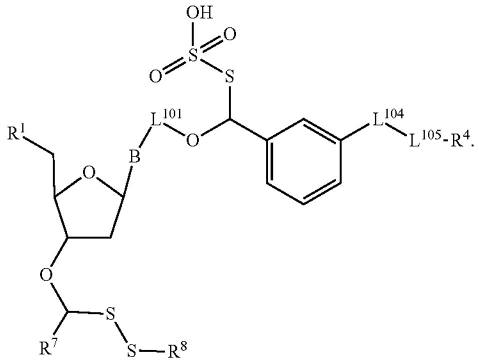

$R^1$, B, $R^7$, $R^8$, $R^{102}$, $L^{101}$, $L^{104}$, $L^{105}$, and $R^4$ are as described herein, including in embodiments. In embodiments, $L^{101}$ is

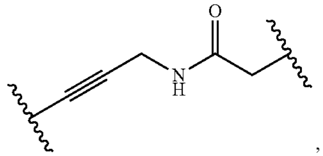

,

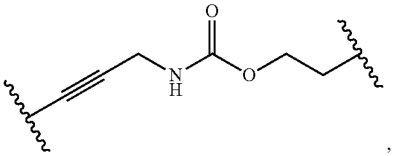

,

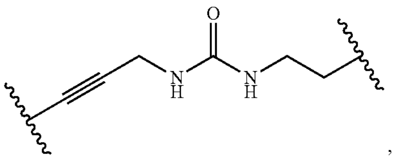

, or

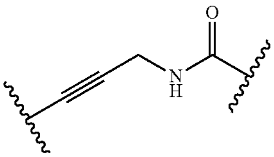

.

In embodiments, $R^8$ is an unsubstituted $C_1$-$C_2$ alkyl.

In embodiments, the compound has the formula:
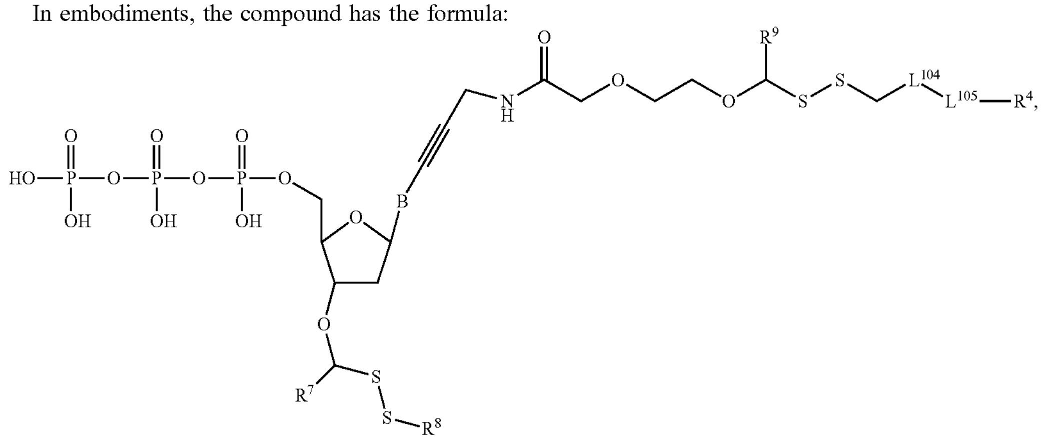
wherein B, $R^7$, $R^8$, $R^9$, $L^{104}$, $L^{105}$, and $R^4$ are as described herein, including in embodiments. In embodiments, the compound has the formula:
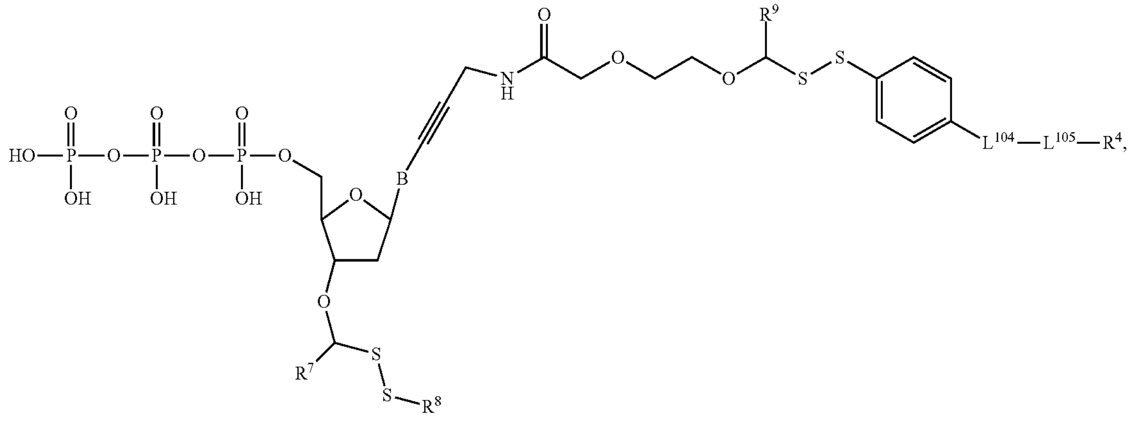
wherein B, $R^7$, $R^8$, $R^9$, $L^{104}$, $L^{105}$, and $R^4$ are as described herein, including in embodiments. In embodiments, the compound has the formula:
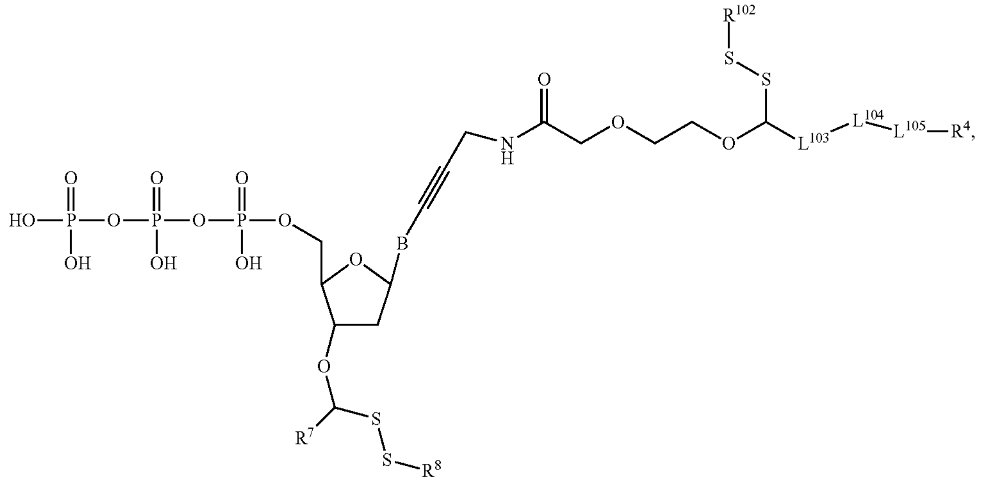

wherein B, $R^7$, $R^8$, $R^{102}$, $L^{103}$, $L^{104}$, $L^{105}$, and $R^4$ are as described herein, including in embodiments. In embodiments, the compound has the formula:
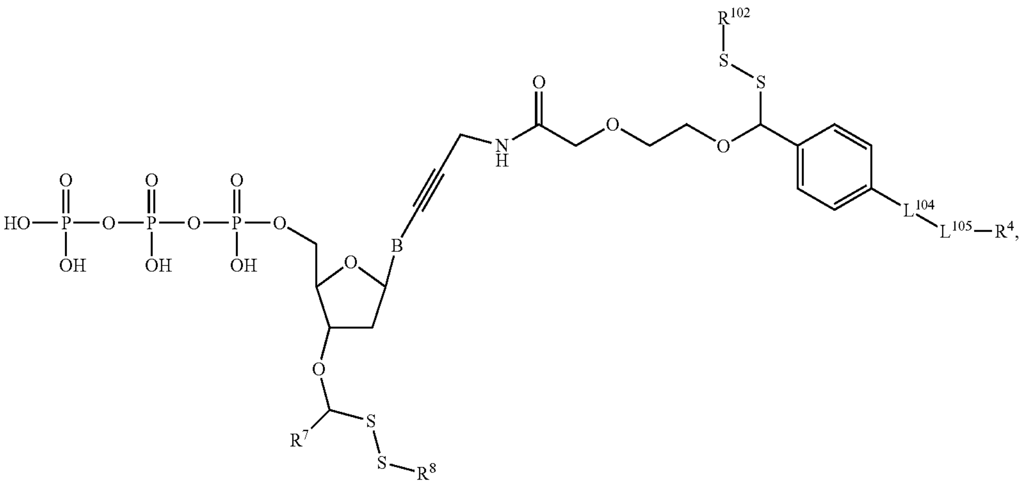
$R^8$, $R^{102}$, $L^{104}$, $L^{105}$, and $R^4$ are as described herein, including in embodiments. In embodiments, $R^8$ is an unsubstituted $C_1$-$C_2$ alkyl.
In embodiments, the compound has the formula:
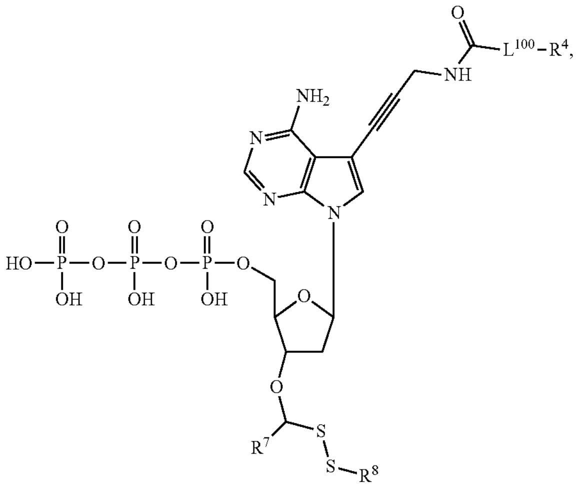
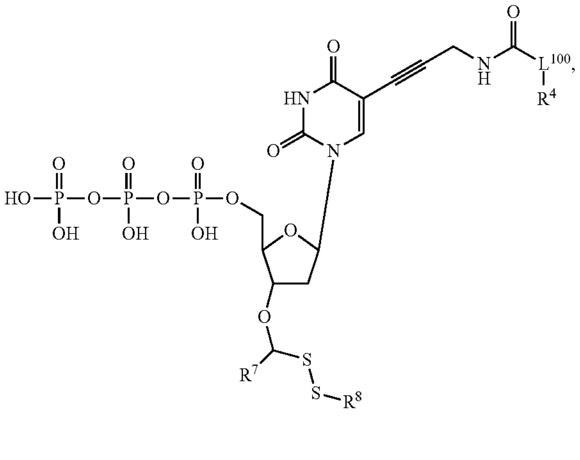
-continued
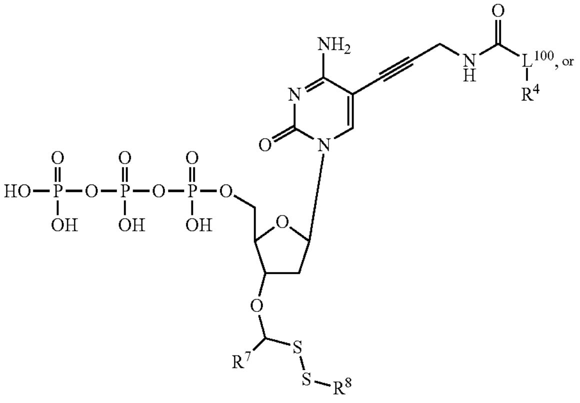
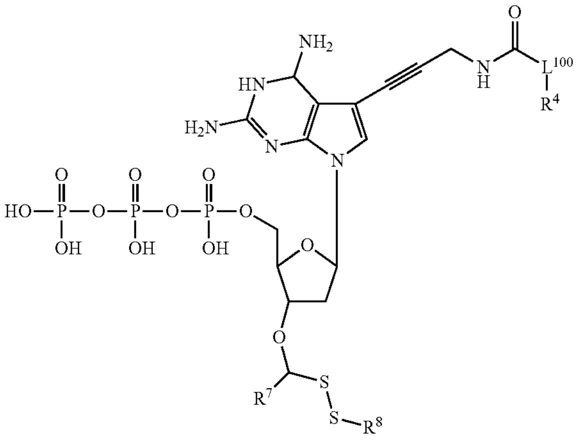

wherein $L^{100}$ is a cleavable linker. In embodiments, $L^{100}$ is

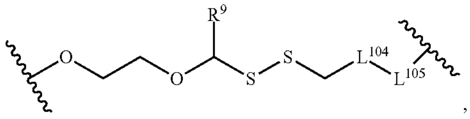
,
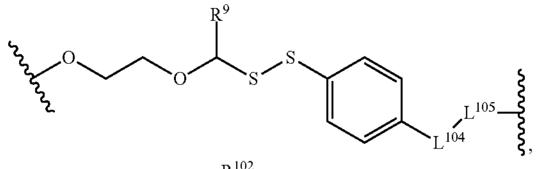
,
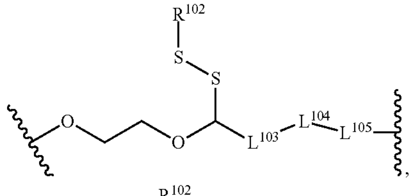
, or
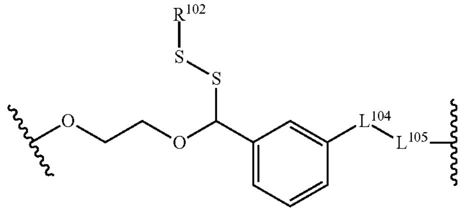
, wherein $R^9$, $L^{104}$, $L^{105}$, and $R^{102}$ are as described herein.

In embodiments, the compound is not a compound described in WO 2017/079498.

In an aspect is provided a nucleic acid polymerase complex, wherein the nucleic acid polymerase is bound (e.g., non-covalently bound) to a compound described herein, including embodiments. In embodiments, the nucleic acid polymerase is bound to a primer.

In embodiments, the nucleic acid polymerase is a Taq polymerase, Therminator γ, 9° N polymerase (exo-), Therminator II, Therminator III, or Therminator IX. In embodiments, the nucleic acid polymerase is Therminator γ. In embodiments, the nucleic acid polymerase is 9° N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9° N and mutants thereof. In embodiments, the nucleic acid polymerase is Phi29 and mutants thereof. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

In embodiments, the 3' moiety of a compound described herein is chemically cleaved faster than a control nucleotide. In embodiments, the 3' moiety of a compound described herein is chemically cleaved faster than a nucleotide with a 3'-$OCH_2SSCH_3$ moiety under identical cleavage conditions (e.g., same reaction time, same reaction temperature, and/or the same reducing agent). In embodiments, the 3' moiety of a compound described herein is chemically cleaved faster than a nucleotide with a 3'-$OCH_2N_3$ moiety under identical cleavage conditions (e.g., same reaction time, same reaction temperature, and/or the same reducing agent). In embodiments, a compound of formula I, II, or III (e.g., in an aspect or embodiment) is chemically cleaved faster than an identical compound wherein the 3'-O-reversible terminator portion is

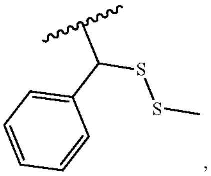
,
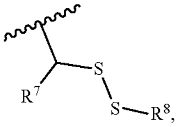
, and
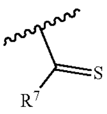

for Formula I, II, and III respectively is replaced with a 3'-$OCH_2SSCH_3$ (e.g., under identical cleavage conditions). In embodiments, a compound of formula I (e.g., in an aspect or embodiment) is chemically cleaved faster than an identical compound wherein the 3'-OCH(phenyl)$SSCH_3$ is replaced with a 3'-$OCH_2SSCH_3$ (e.g., under identical cleavage conditions).

In embodiments, chemical cleavage of a compound described herein (e.g., in an aspect or embodiment) is at least 1.1-fold (e.g., 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or 100000-fold) faster than chemical cleavage of an identical compound wherein the 3'-$OCH(R^7)SSCH_3$ is replaced with a 3'-$OCH_2SSCH_3$ or 3'-$OCH_2N_3$ (e.g., under identical cleavage conditions). In embodiments, chemical cleavage of a compound described herein (e.g., in an aspect or embodiment) is about 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or about 100000-fold faster than chemical cleavage of an identical compound wherein the 3'-$OCH(R^7)SSCH_3$ is replaced with a 3'-$OCH_2SSCH_3$ or 3'-$OCH_2N_3$ (e.g., under identical cleavage conditions). In embodiments, chemical cleavage of a compound described herein (e.g., in an aspect or embodiment) is 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000, 10000, or 100,000-fold faster than chemical cleavage of an identical compound wherein the 3'-OCH(phenyl)$SSCH_3$ is replaced with a 3'-$OCH_2SSCH_3$ or 3'-$OCH_2N_3$ (e.g., under identical cleavage conditions). In embodiments, chemical cleavage is cleavage of the SS bond (e.g., in a 3' moiety). In embodiments, chemical cleavage is release of a 3' moiety from a nucleotide, nucleoside, or residue (e.g., from being bound to the 3' carbon of the sugar) to leave a 3'-OH on the nucleotide, nucleoside, or residue (e.g., attached to 3' carbon of the sugar). In embodiments, chemical cleavage is cleavage of the SS bond in a 3' moiety and release of a 3' moiety from a nucleotide, nucleoside, or residue (e.g., from being bound to the 3' carbon of the sugar) to leave a 3'-OH on the nucleotide, nucleoside, or residue (e.g., attached to 3' carbon of the sugar).

In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with a reducing agent (e.g., tris(hydroxypropyl)phosphine (THPP), tris-(2-carboxyethyl)phosphine (TCEP), tris(hydroxymethyl)phosphine (THMP), or tris(hydroxyethyl)phosphine (THEP), DTT, dithiobutylamine (DTBA)). In embodiments, chemical cleavage of a compound (e.g., cleavage of the 3' moiety of a compound described herein or cleavage of an SS bond in a 3' moiety of a compound described herein) described herein (e.g., in an aspect or embodiment) includes contacting the compound with THPP (e.g., about 10 mM THPP, or at least 1 mM THPP). In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at less than about 65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at less than 65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about 45-65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at 45-65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about 55° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at a temperature of at least 55° C. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at about pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed at pH 9.5. In embodiments, chemical cleavage of a compound (e.g., cleavage of the 3' moiety of a compound described herein or cleavage of an SS bond in a 3' moiety of a compound described herein) described herein (e.g., in an aspect or embodiment) is performed using 0.1, 0.2, 0.3, 0.4, 0.5, 0.6, 0.7, 0.8, 0.9, or 1.0 mM of THPP. In embodiments, the chemical cleavage is performed using less than 1.0 mM THPP. In embodiments, the chemical cleavage is performed using about 1.0 mM THPP. In embodiments, the chemical cleavage is performed using about 0.05 to about 1.0 mM THPP. In embodiments, the chemical cleavage is performed using about 1.0 to about 5.0 mM THPP. In embodiments, the chemical cleavage is performed using about 10 mM THPP. In embodiments, the chemical cleavage is performed using 1.0 mM THPP. In embodiments, the chemical cleavage is performed using about 0.05 to 1.0 mM THPP. In embodiments, the chemical cleavage is performed using 1.0 to about 5.0 mM THPP. In embodiments, the chemical cleavage is performed using 10 mM THPP.

In embodiments, the compounds described herein provide superior stability in solution during storage, or reagent handling during sequencing applications, compared to the same compounds that have 3'-OH reversible terminating groups disclosed in the prior art, such as for example the 3'-O-azidomethyl reversible terminator.

In an aspect is provided a kit. Some embodiments disclosed herein relate to kits including a labeled nucleoside or nucleotide (e.g., a compound as described herein) including a linker between the fluorophore and the nucleoside or nucleotide, wherein the linker is a linker as described herein. In embodiments, the kit includes a compound described herein. In embodiments, the kit includes a plurality of compounds described herein. In embodiments, the kit includes labeled nucleotides including differently labeled nucleotides (e.g., compounds described herein). In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label.

In embodiments, the sequencing solution includes a buffer solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. Additionally, other buffer agents that can be used in enzyme reactions, hybridization reactions, and detection reactions are well known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$.

In embodiments, the buffered solution can contain one or more divalent cations at a concentration sufficient to permit hybridization of a nucleic acid. In some embodiments, a concentration can be more than about 1 μM, more than about 2 μM, more than about 5 μM, more than about 10 μM, more than about 25 μM, more than about 50 μM, more than about 75 μM, more than about 100 μM, more than about 200 μM, more than about 300 μM, more than about 400 μM, more than about 500 μM, more than about 750 μM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1 M.

III. Methods of Use

In an aspect is provided a method for sequencing a nucleic acid, including (i) incorporating in series with a nucleic acid polymerase, within a reaction vessel, one of four different compounds into a primer to create an extension strand, wherein the primer is hybridized to the nucleic acid and wherein each of the four different compounds includes a unique detectable label; (ii) detecting the unique detectable label of each incorporated compound, so as to thereby identify each incorporated compound in the extension strand, thereby sequencing the nucleic acid; wherein each of the four different compounds is independently a compound as described herein, including embodiments. In embodiments, the compound includes at least one of the following: cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methyl guanine or a derivative thereof, 5,6-dihydrouracil or a derivative thereof, 5-methylcytosine or a derivative thereof, and 5-hydroxymethylcytosine or a derivative thereof. In embodiments, the compound includes at least one of the following: cytosine or a derivative thereof, guanine or a derivative thereof, adenine or a derivative thereof, thymine or a derivative thereof, and uracil or a derivative thereof. In embodiments, the compound includes at least one of the following: cytosine or a derivative thereof, guanine or a derivative thereof, adenine or a derivative thereof, and thymine or a derivative thereof. In embodiments, the compound includes at least one of the following: cytosine or a derivative thereof, guanine or a derivative thereof, adenine or a derivative thereof, and uracil or a derivative thereof. In embodiments, the method further includes, after incorporating, contacting the compound with a cleaving agent. In embodiments, the method includes incorporating a first nucleotide including a 3'-O-reversible terminator (e.g.,

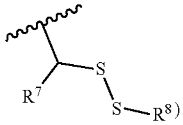

)

and a first detectable label; detecting the first detectable label; and removing the 3'-O-reversible terminator from the first nucleotide to generate a nucleotide including a 3'-OH. In embodiments, the method includes generating one or more sequencing reads.

In embodiments, the nucleic acid to be sequenced is DNA or RNA, or a hybrid molecule comprised of deoxynucleotides and ribonucleotides. In embodiments, the nucleic acid to be sequenced is attached to a solid substrate via any suitable linkage method known in the art, e.g., using covalent linkage. In embodiments, the nucleic acid is attached directly to a solid substrate. In embodiments, the surface of the solid support includes a polymer that provides the attachment points for the nucleic acid.

In embodiments, the nucleic acid is within a cluster. The terms "cluster" and "colony" are used interchangeably throughout this application and refer to a discrete site on a solid support comprised of a plurality of immobilized nucleic acid strands. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

In an aspect is provided a method of incorporating a compound into a primer, the method including combining a polymerase, a primer hybridized to nucleic acid template and the compound within a reaction vessel and allowing the polymerase to incorporate the compound into the primer thereby forming an extended primer, wherein the compound is a compound as described herein, including embodiments. In embodiments, incorporating a compound into a primer refers to the 5' phosphate joining in phosphodiester linkage to the 3'—OH group of a second (modified or unmodified) nucleotide, which may itself form part of a longer polynucleotide chain.

In embodiments, the method further including, after each of the incorporating steps, adding to the reaction vessel four different unlabeled compounds (e.g., nucleotide analogues). In embodiments, the unlabeled compounds have the formula:

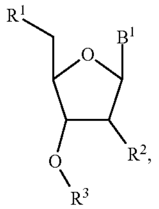

wherein $R^1$, $R^2$, and $B^1$ are as described herein, and $R^3$ is a polymerase-compatible cleavable moiety or reversible terminator (e.g.,

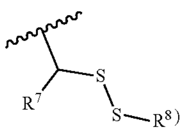

as described herein. In embodiments, $B^1$ is a monovalent nucleobase (e.g., is

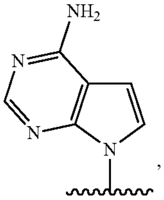 , 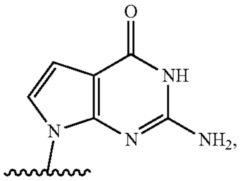 , 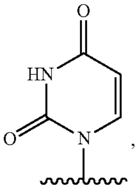 ,

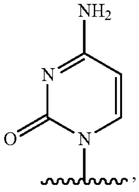 , 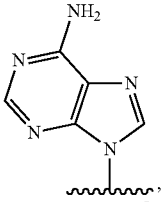 ,

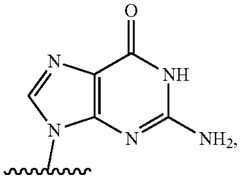 or 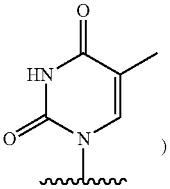 ).

In embodiments, each of the four different unlabeled compounds (e.g., nucleotide analogues) are of the structure as described herein, including embodiments, wherein in the first of the four different unlabeled compounds, $B^1$ is a thymidine or uridine hybridizing base; in the second of the four different unlabeled compounds, $B^1$ is an adenosine hybridizing base; in the third of the four different unlabeled compounds, $B^1$ is a guanosine hybridizing base; and in the fourth of the four different unlabeled compounds, $B^1$ is a cytosine hybridizing base.

In embodiments, the nucleic acid polymerase is a Taq polymerase, Therminator γ, 9° N polymerase (exo-), Therminator II, Therminator III, or Therminator IX. In embodiments, the nucleic acid polymerase is Therminator γ. In embodiments, the nucleic acid polymerase is 9° N polymerase (exo-). In embodiments, the nucleic acid polymerase is Therminator II. In embodiments, the nucleic acid polymerase is Therminator III. In embodiments, the nucleic acid polymerase is Therminator IX. In embodiments, the nucleic acid polymerase is a Taq polymerase. In embodiments, the nucleic acid polymerase is a nucleic acid polymerase. In embodiments, the nucleic acid polymerase is 9° N and mutants thereof. In embodiments, the nucleic acid polymerase is Phi29 and mutants thereof. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, both of which are incorporated by reference herein). In embodiments, the polymerase is DNA polymerase, a terminal deoxynucleotidyl transferase, or a reverse transcriptase. In embodiments, the enzyme is a DNA polymerase, such as DNA polymerase 812 (Pol 812) or DNA polymerase 1901 (Pol 1901), e.g., a polymerase described in US 2020/0131484, and US 2020/0181587, both of which are incorporated by reference herein.

In embodiments, the method includes simultaneously sequencing a plurality of different nucleic acids, including: a) extending a plurality of primer DNA strands hybridized to template DNAs, each of which includes one of the primer DNA strands, by incorporating a labeled nucleotide (i.e., a compound as described herein) in the presence of an enzyme; and b) identifying each labeled nucleotide, so as to simultaneously sequence the plurality of different nucleic acids. In embodiments, the labeled nucleotide is a compound described herein.

In an aspect is provided a method of determining the sequence of a target single-stranded polynucleotide. In embodiments, the method includes incorporating a compound as described herein, (e.g., a compound of Formula I, Formula II, or Formula III) into an oligonucleotide strand complementary to at least a portion of the target polynucleotide strand; and detecting the identity of the compound incorporated into the oligonucleotide strand. In embodiments, the compound includes a 3'-O-polymerase-compatible cleavable moiety as described herein and a detectable label. In embodiments, the method further includes chemically removing the detectable label and the 3'-O-polymerase-compatible cleavable moiety from the compound incorporated into the oligonucleotide strand. In embodiments, the 3'-O-polymerase-compatible cleavable moiety and the detectable label of the incorporated compound are removed prior to introducing the next complementary compound. In embodiments, the 3'-O-polymerase-compatible cleavable moiety and the detectable label are removed in a single step of chemical reaction. In embodiments, the sequential incorporation described herein is performed at least 50 times, at least 100 times, at least 150 times, at least 200 times, at least 250 times, at least 300 times, at least 350 times, at least 400 times, at least 450 times, or at least 500 times. In embodiments, the sequential incorporation is performed 80 to 200 times. In embodiments, the sequential incorporation is performed 100 to 200 times. In embodiments, the sequential incorporation is performed 120 to 250 times.

In embodiments, the method further including, after the incorporating, cleaving the linker (e.g., $L^{100}$ or $-(L^{101})-OC(SR^{100})(R^{102a})-(L^{103})-(L^{104})-(L^{105})-)$ with a cleaving reagent (e.g., tris(hydroxypropyl)phosphine (THPP), dithiobutylamine (DTBA), or DTT). In embodiments, the cleaving reagent is in a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

In embodiments, the method further including, after the incorporating, cleaving the linker (e.g., $L^{100}$ or $-(L^{101})-OC(SR^{100})(R^{102a})-(L^{103})-(L^{104})-(L^{105})-$) with a cleaving reagent (e.g., a water-soluble phosphine, such as tris(hydroxypropyl)phosphine (THPP)). In embodiments, the cleaving reagent is a reducing agent. In embodiments, the cleaving agent is a phosphine containing agent. In embodiments, the cleaving agent is a thiol containing agent. In embodiments, the cleaving agent is di-mercaptopropane sulfonate (DMPS). In embodiments, the cleaving agent is aqueous sodium sulfide ($Na_2S$). In embodiments, the cleaving reagent is Tris-(2-carboxyethyl)phosphines trisodium salt (TCEP), tris(hydroxypropyl)phosphine (THPP), guanidine, urea, cysteine, 2-mercaptoethylamine, or dithiothreitol (DTT). In embodiments, the cleaving reagent is an acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$). In embodiments, the method includes contacting the compound (e.g., a compound described herein) with a reducing agent. In embodiments, the method further including, after the incorporating, cleaving the linker at about 55° C. In embodiments, the method further including, after the incorporating, cleaving the linker at about 45° C. to about 60° C. In embodiments, the method further including, after the incorporating, cleaving the linker at about 55° C. to about 80° C. In embodiments, the method further including, after the incorporating, cleaving the linker at about 60° C. to about 70° C. In embodiments, the method further including, after the incorporating, cleaving the linker at about 50° C. to about 60° C. In embodiments, the method further including, after the incorporating, cleaving the linker at about 65° C. to about 75° C. In embodiments, the method further including, after the incorporating, cleaving the linker at about 65° C. In embodiments, the method further including, after the incorporating, cleaving the linker at about 55° C. In embodiments, the method further including, after the incorporating, cleaving the linker at about 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or about 80° C. In embodiments, the method further including, after the incorporating, cleaving the linker at a pH at about 8.0 to 11.0. In embodiments, the pH is 9.0 to 11.0. In embodiments, the pH is 9.5. In embodiments, the pH is 10.0. In embodiments, the pH is 8.0, 8.5, 9.0, 9.5, 10.0, 10.5, or 11.0. In embodiments, the pH is from 9.0 to 11.0, and the temperature is about 60° C. to about 70° C. In embodiments, the pH is from 9.0 to 11.0, and the temperature is about 50° C. to about 60° C.

In embodiments, the cleaving reagent cleaves both the linker (e.g., $L^{100}$) and the polymerase-compatible cleavable moiety (e.g., the 3'-O-reversible terminator

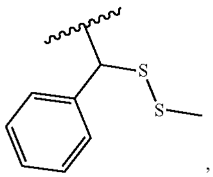
,
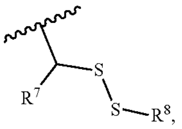
and
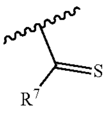

for Formula I, II, and III respectively) simultaneously.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1. Novel Modified Nucleotides

In the context of nucleic acid sequencing, the use of nucleotides bearing a 3' reversible terminator (RT) (also referred to herein as a polymerase-compatible cleavable moiety) allows successive nucleotides to be incorporated into a polynucleotide chain in a controlled manner. The DNA template for a sequencing reaction will typically comprise a double-stranded region having a free 3' hydroxyl group which serves as a primer or initiation point for the addition of further nucleotides in the sequencing reaction. The region of the DNA template to be sequenced will overhang this free 3' hydroxyl group on the complementary strand. The primer bearing the free 3' hydroxyl group may be added as a separate component (e.g., a short oligonucleotide) which hybridizes to a region of the template to be sequenced. Following the addition of a single nucleotide to the DNA template, the presence of the 3' reversible terminator prevents incorporation of a further nucleotide into the polynucleotide chain. While the addition of subsequent nucleotides is prevented, the identity of the incorporated nucleotide is detected (e.g., exciting a unique detectable label that is linked to the incorporated nucleotide). The reversible terminator is then removed (and optionally the cleavable linker is removed simultaneously), leaving a free 3' hydroxyl group for addition of the next nucleotide. The sequencing cycle can then continue with the incorporation of the next blocked, labeled nucleotide.

Sequencing by synthesis of nucleic acids ideally requires the controlled (i.e., one at a time), yet rapid, incorporation of the correct complementary nucleotide opposite the oligonucleotide being sequenced. This allows for accurate sequencing by adding nucleotides in multiple cycles as each nucleotide residue is sequenced one at a time, thus preventing an uncontrolled series of incorporations occurring. Nucleotides bearing a 3' RT have been described in the literature, see for example U.S. Pat. No. 6,664,079 or Ju J. et al. (2006) Proc Natl Acad. Sci USA 103(52): 19635-19640, however despite the recent advances only a few solutions have been presented, most of which cause other problems, including inefficient or incomplete incorporation by the polymerase, inefficient or incomplete cleavage of the removable group, or harsh conditions needed for the cleaving step causing spurious problems with the remainder of the assay and/or fidelity of the target sequence.

There are many limitations on types of reversible terminators that can be added onto a nucleotide and still be suitable. The reversible terminator should prevent additional nucleotide molecules from being added to the polynucleotide while simultaneously being easily removable from the sugar moiety without causing damage to the polynucleotide or sequencing enzyme (e.g., DNA polymerase or reverse transcriptase). Ideal reversible terminators therefore possess long term stability, can be efficiently incorporated by the sequencing enzyme, can prevent secondary or further nucleotide incorporation, and have the ability to be removed under mild conditions that do not cause damage to any sequencing component (e.g., nucleotides, primers, enzymes, polymers, etc.) preferably under aqueous conditions. Developing a truly reversible set of nucleotide RTs and cleavable linkers that are stable and cleave rapidly has been a goal for many years.

An important property of a reversible terminator on a nucleotide is that it can be rapidly cleaved under conditions that do not adversely affect the DNA. Removal of a disulfide containing reversible terminator to form the 3'-OH requires the formation of a thiol, followed by conversion to a hydroxide (see scheme 1), via a tandem nucleophilic fragmentation reaction. FIG. 1A describes a simplified schematic identifying a potential transition state.

Scheme 1. A generalized overview of the cleavage process of an incorporated modified nucleotide to produce a 3′-OH and a thioaldehyde from a disulfide containing RT. In the scheme, B is a nucleobase (e.g., A, T, G, C), $R^8$ is an alkyl moiety, and $R^7$ is as described herein.

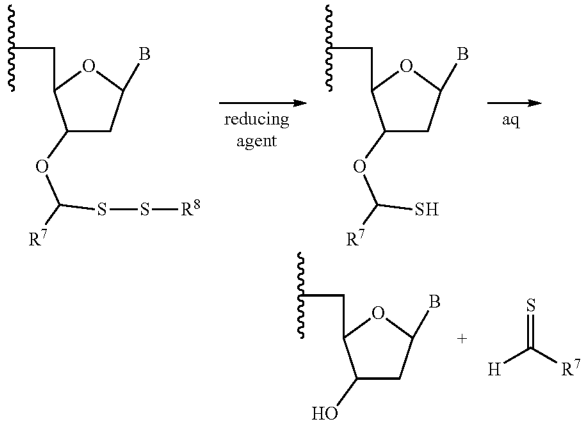

The stability of the resultant thioaldehyde influences the cleavage rate of the thioacetal. For example, an RT having the structure

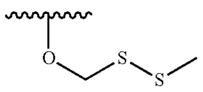 [SMILES: *OCSSC]

Figure 1B:
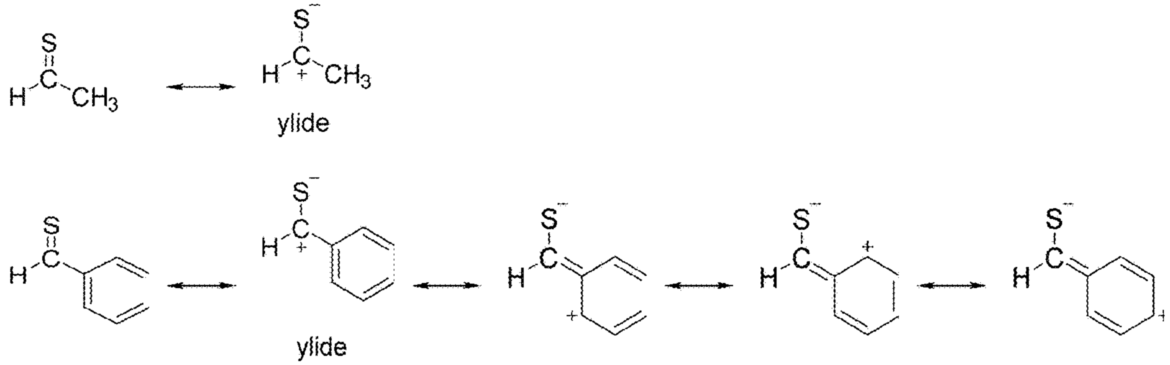
Figure 1C:
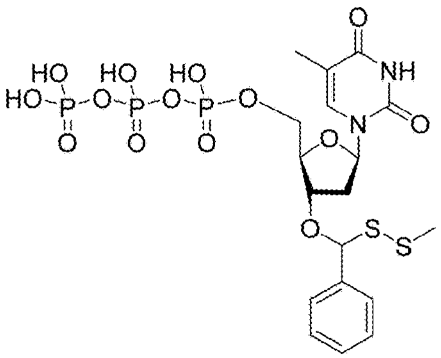

(referred to as a methylene disulfide, or RT #1), wherein the oxygen is attached to the 3' position of the deoxyribose, results in the formation of thioformaldehyde, a notoriously unstable molecule which rapidly oligomerizes to 1,3,5-trithiane. Thioformaldehydes are highly reactive and inherently unstable species due to the lack of steric and resonance stabilization afforded to the sp2 carbon by the hydrogens. In accordance with the Hammond Postulate, the transition state is geometrically more similar to the thioaldehyde for this particular reaction (see for example March's Advanced Organic Chemistry, 6th Ed., Wiley, 2007, Michael B. Smith and Jerry March, Chapter 6 Methods of determining mechanisms, page 308). Conceptualizing the thioaldehyde with all available resonance geometries (see FIG. 1B) suggests a stable ylide structure that is geometrically similar to the resultant thioaldehyde will be more thermodynamically favored. Therefore, increasing the resonance stabilization to the sp2 carbon by including a resonance-stabilizing moiety (e.g., a cyclic moiety, such as an aromatic or heteroaromatic moiety) involves only a small reorganization of the molecular structures and thus permits faster cleavage. This concept is further illustrated in FIG. 1B and supported vide infra. For example, an RT that includes a methyl substituent on the methylene carbon having the structure

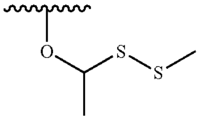 [SMILES: *OC(C)SSC]

(RT #2) increases the cleavage rate approximately 10-fold relative to RT #1. In contrast, substituents incapable of forming a stabilized ylide (e.g., substituents described in US 2016/0002721, such as —$CH_2F$ or —$CHF_2$) are likely not stabilizing. Additionally, merely extending the alkyl chain

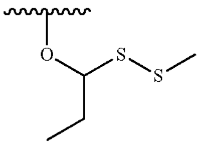 [SMILES: *OC(CC)SSC]

(RT #2a) did not improve the cleavage rate relative to RT #2. Without wishing to be bound by theory, aliphatic thioaldehydes (e.g., such as the thioaldehyde produced when cleaving RT #2 or RT #2a) may polymerize and their isolation may be problematic, suggesting substituents which further stabilize the resultant thioaldehyde (i.e., have a greater number of resonant structures) results in an increased cleavage rate. Aromatic thioaldehydes are more stable (see Moldoveanu, S. Chapter 10—Pyrolysis of Aldehydes and Ketones, Pyrolysis of Organic Molecules (Second Edition), Elsevier, 2019, Pages 391-418), therefore the cleavage rate of disulfide-containing reversible terminators (i.e., nucleotides having formula I, II, or III as described herein comprising the reversible terminator at the 3'O-position,

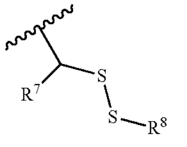

or

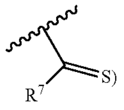

that produce aromatic thioaldehydes increases relative to a methylene disulfide. Thus, the modified nucleotides as described herein are stable and rapidly cleaved under mild conditions.

Example 2. Chemical Synthesis of Modified Nucleotides

Included in Scheme 2 is a generalized overview for synthesizing a modified nucleotide as described herein. Introducing the resonance-stabilizing moiety (e.g., cyclic moiety such as an aromatic or heteroaromatic moiety) in the reversible terminator is achieved by introducing a functionalized acetal. The acetal may be formed via an aldehyde conversion reaction using mild conditions, as depicted in Scheme 5, and reported in Grabowski et al Org. Biomol. Chem., 2018, 16, 3114.

Scheme 2. A generalized synthetic protocol for producing a nucleotide as described herein, wherein $R^7$ is as described herein. For simplicity, $R^8$ is depicted as unsubstituted methyl in scheme 2, however it is understood that the synthetic scheme is identical for all possible $R^8$ substitutents as described herein. Optionally, an oxidizing agent (e.g., tert-butyl hydroperoxide) is added during the final purification step to prevent premature deblocking

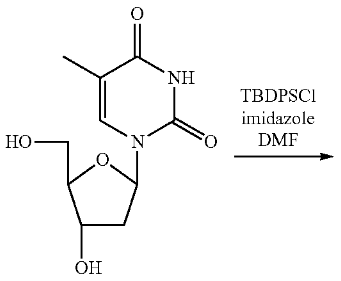

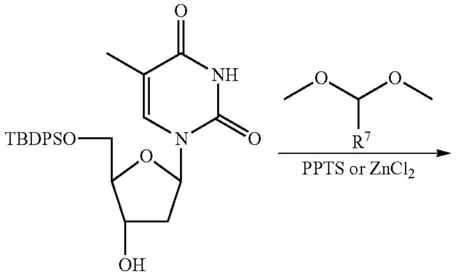

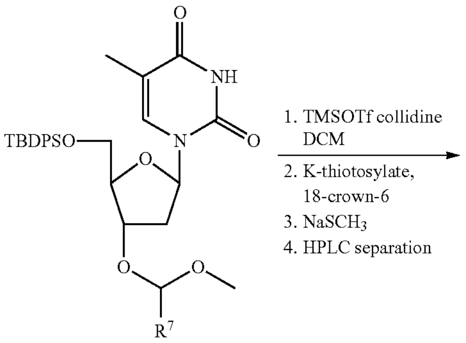

-continued

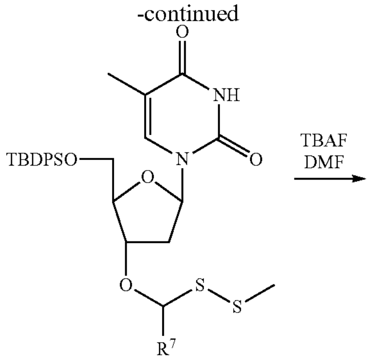

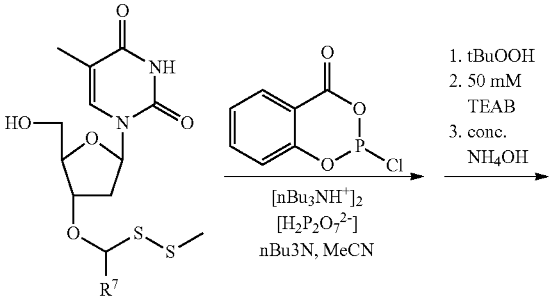

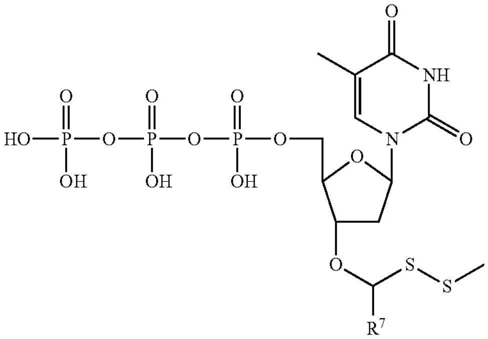

Scheme 3. Synthetic protocol for the synthesis of acetals under basic conditions from aldehydes, wherein $R^7$ is a described herein. This reaction is modified to generate alternative acetals (e.g., generating an ethyl acetal to provide a compound of Formula I wherein $R^8$ is unsubstituted ethyl) by modifying the reactants (e.g. sodium ethoxide is substituted for sodium methoxide).

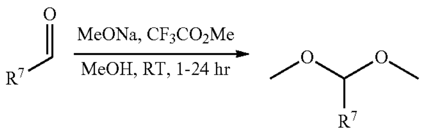

Alternatively, the starting nucleoside may include a protected propargyl amine off the base, as shown in Scheme 4. Nucleosides containing a protected propargyl amine off the base may be used as the input nucleoside in Scheme 4, following a similar protocol to produce a reversible terminator containing nucleotide with a protected propargyl amine off the base. The protecting group is then removed by exposing the nucleoside containing a protected propargyl amine off the base to concentrated ammonium hydroxide.

Scheme 4. Synthetic protocol for generating an input nucleoside containing a propargyl amine on the base.

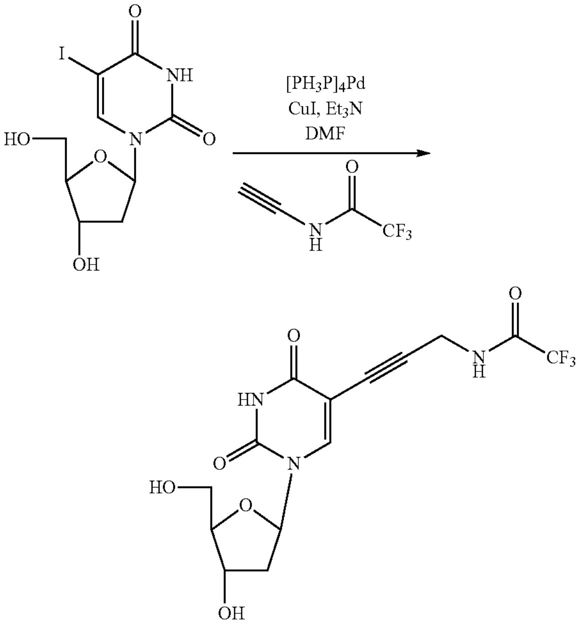

Included in Scheme 7 is a generalized overview for synthesizing a modified nucleotide of Formula III, wherein $R^7$ is as described herein.

Scheme 7. A generalized synthetic protocol for producing a nucleotide as described herein, wherein $R^7$ is as described herein.

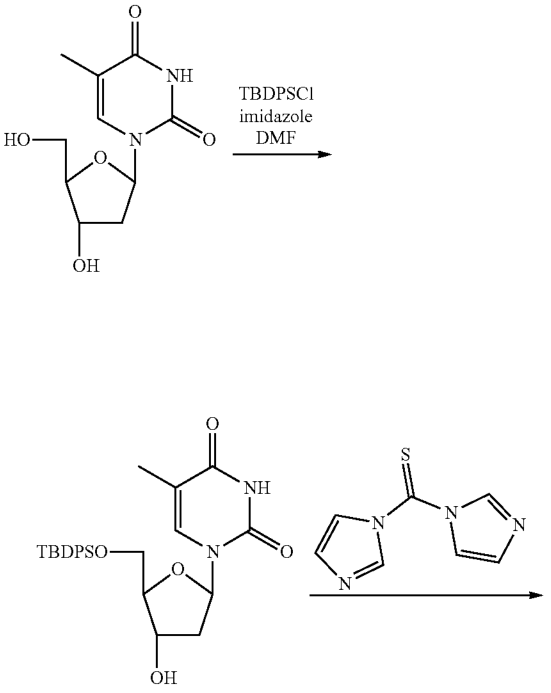

-continued

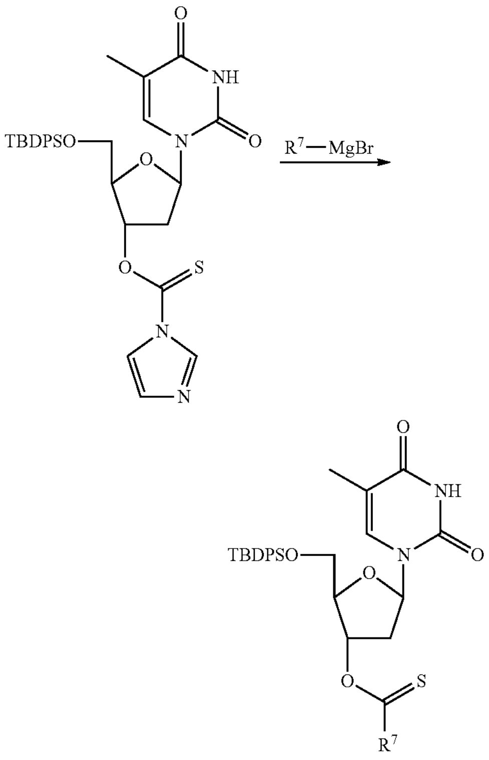

Scheme 8. Cleavage mechanism for compounds of Formula III.

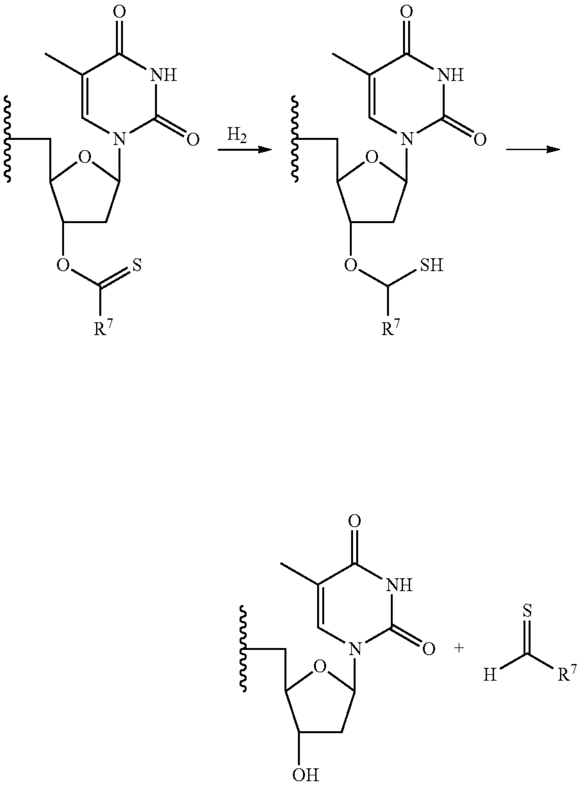

Scheme 9. Alternative synthetic protocols to generate triazole RTs (e.g., RT #64-RT #67 or RT #72-RT #75). For example, shown above is the synthetic protocol used to synthesized RT #74; by changing the azido group, i.e., $CF_3N_3$ shown in Scheme 9, it is possible to generate alternative triazole containing nucleotides. The azido/alkynyl reaction occurs in the

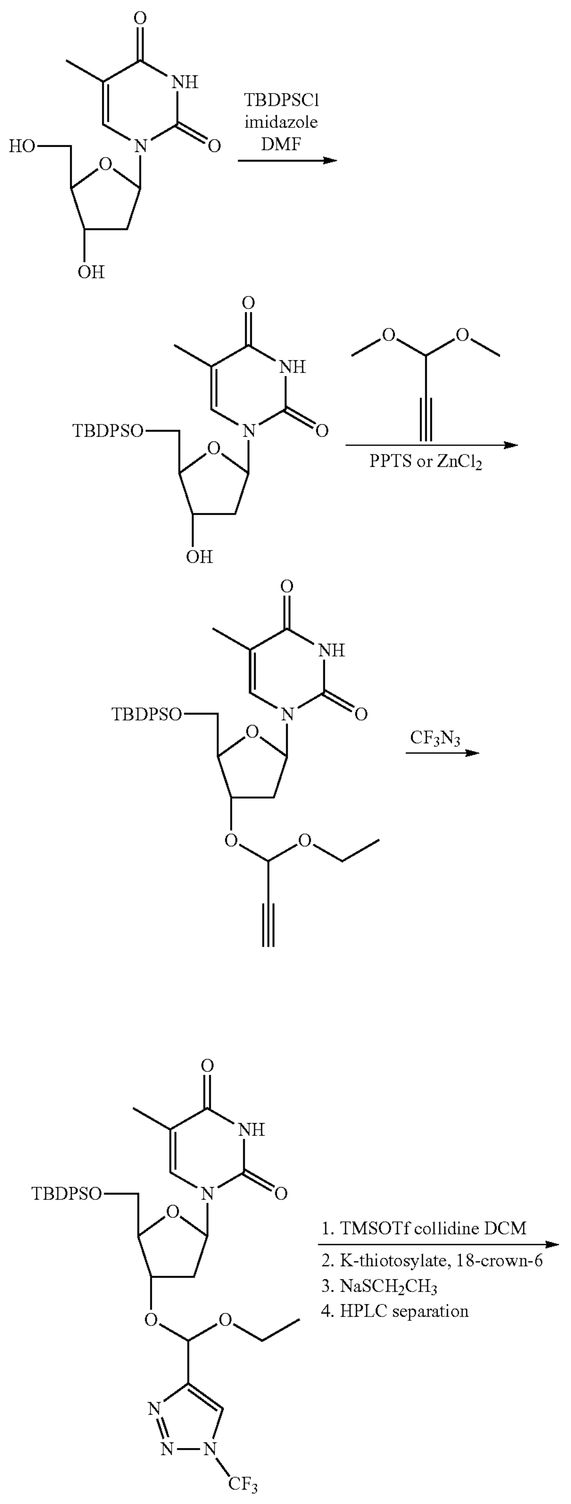

-continued

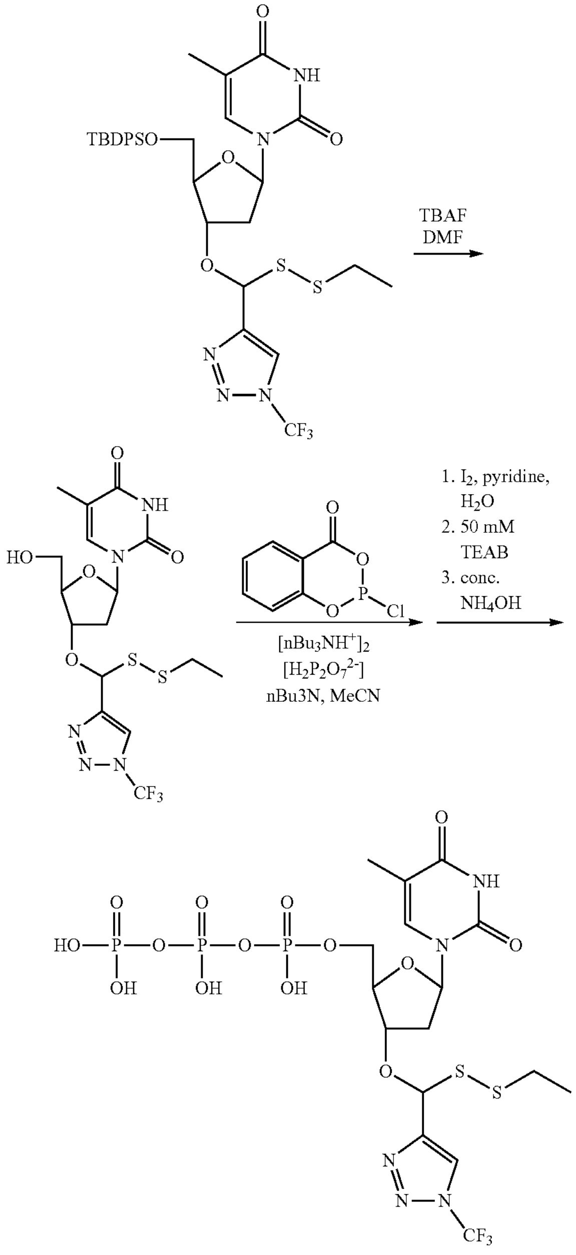

presence of copper, e.g., copper sulfate or

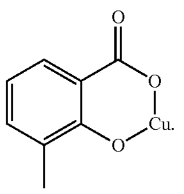

Example 3. Incorporation of Modified Nucleotides

A modified nucleotide (e.g., the nucleotide compounds described herein) should be capable of being rapidly incorporated by a DNA polymerase. Naturally occurring DNA polymerases are typically not capable of incorporating nucleotides modified with reversible terminator at the 3' position on the ribose of the nucleotide. As known in the art, a number of thermophilic polymerases have been engineered to enable the incorporation of nucleotides modified with 3' terminators. For example, the thermophilic polymerase is a mutant *P. abyssi* polymerase (e.g., such as a mutant *P. abyssi* polymerase described in WO 2018/148723 or WO 2020/056044, both incorporated herein by reference for any use).

The data presented within Table 2 shows the half-time for incorporation of RT #2, RT #3, RT #45, RT #22, and RT #26, by a modified thermophilic polymerase. The reaction was carried out in a buffered solution at pH 8.5, with nucleotides at 200 nM concentration, 4 mM Mg, at a temperature of 55° C. The polymerase was pre-bound to the primed DNA template. All terminated nucleotides were efficiently incorporated by the modified DNA polymerase. Surprisingly, the incorporation of RT #2, RT #3, RT #26, RT #22 are comparable, despite the latter compounds (i.e., RT #3, RT #22, and RT #26) bearing relatively bulkier substituents. For the larger naphthalenyl substituent, RT #45, the polymerase takes nearly twice as long to incorporate the nucleotide. The average incorporation half time is reported in Table 2.

TABLE 2

Incorporation halftime for a variety of compounds described herein, keeping the nucleobase, enzyme, buffer, and temperature the same for all experiments. The symbol $R^8$ is indicative of the $R^8$ substituent as provided in Formula II. †RT#3 is averaged over all four nucleotides (dA, dT, dC, and dG).

| | Incorporation Half time (s) |
|---|---|
| RT #2m<br>$R^8$ = unsubstituted methyl | 8.8 ± 3 |
| RT #3m<br>$R^8$ = unsubstituted methyl | 6.3 ± 3† |
| RT #3e<br>$R^8$ = unsubstituted ethyl | 5.3 ± 3 |
| RT #3np<br>$R^8$ = unsubstituted n-propyl | 10.5 ± 3 |
| RT #3ip<br>$R^8$ = unsubstituted isopropyl | 15.1 ± 3 |
| RT #45e;<br>$R^8$ = unsubstituted ethyl | 25.3 ± 3 |
| RT #26e<br>$R^8$ = unsubstituted ethyl | 6.3 ± 3 |
| RT #13e<br>$R^8$ = unsubstituted ethyl | 23.3 ± 3 |

Example 4. Cleavage Kinetics

Figure 2A:
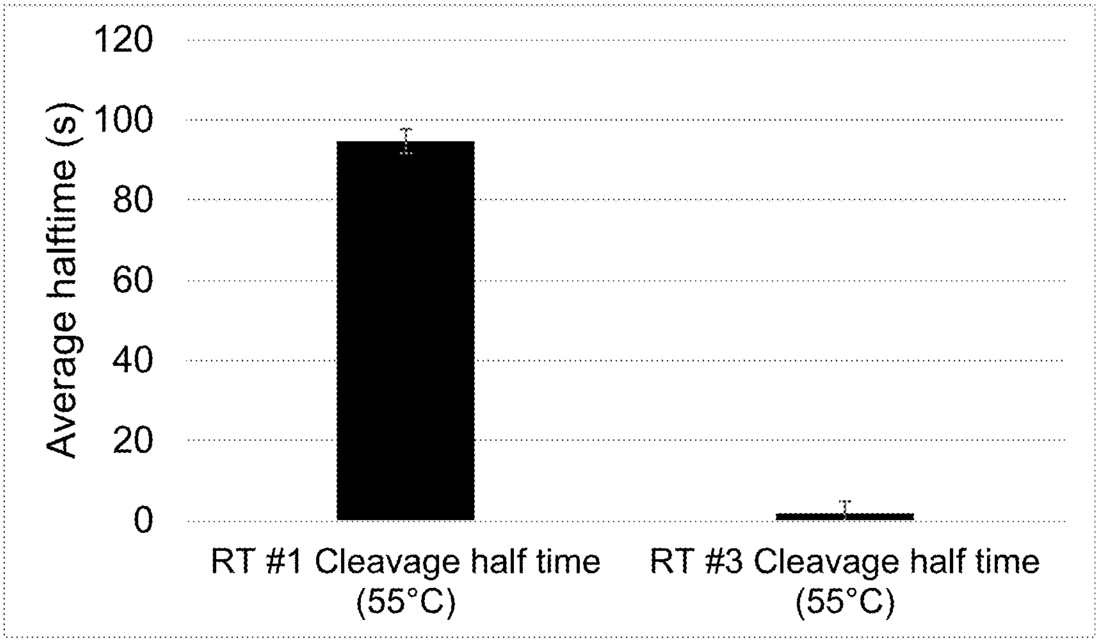
FIGS. 2A-2C. Cleavage kinetics of three nucleotides bearing reversible terminators. The cleavage kinetics are improved relative to RT #1 and RT #2.
Figure 2B:
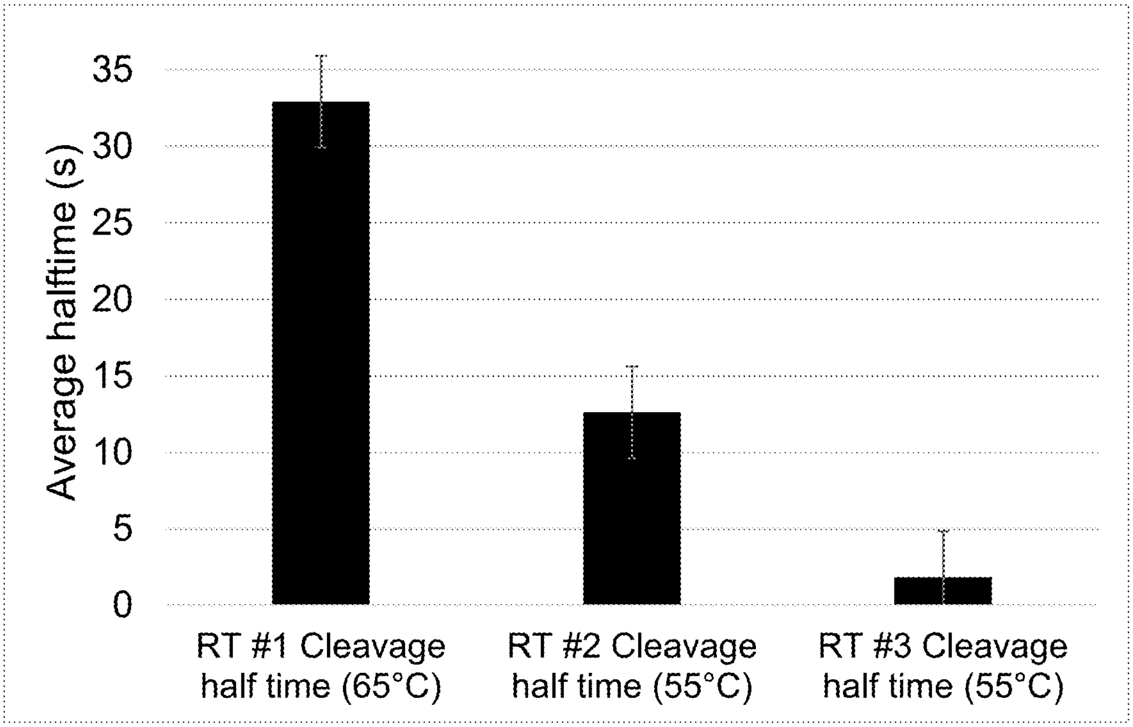

An important property of a reversible terminator on a nucleotide is that it can be rapidly cleaved under conditions that do not adversely affect the DNA. FIGS. 2A-2B reports the cleavage halftime rates for three different reversible terminated nucleotides. RT #1 is

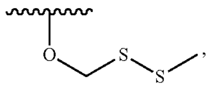 [SMILES: *OCSSC]

wherein the oxygen is attached to the 3' position of the deoxyribose; RT #2 is the methyl-substituted methylene, e.g., having the formula

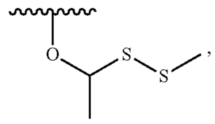 [SMILES: *OC(C)SSC]

wherein the oxygen is attached to the 3' position of the deoxyribose; and RT #3 is

Figure 2C:
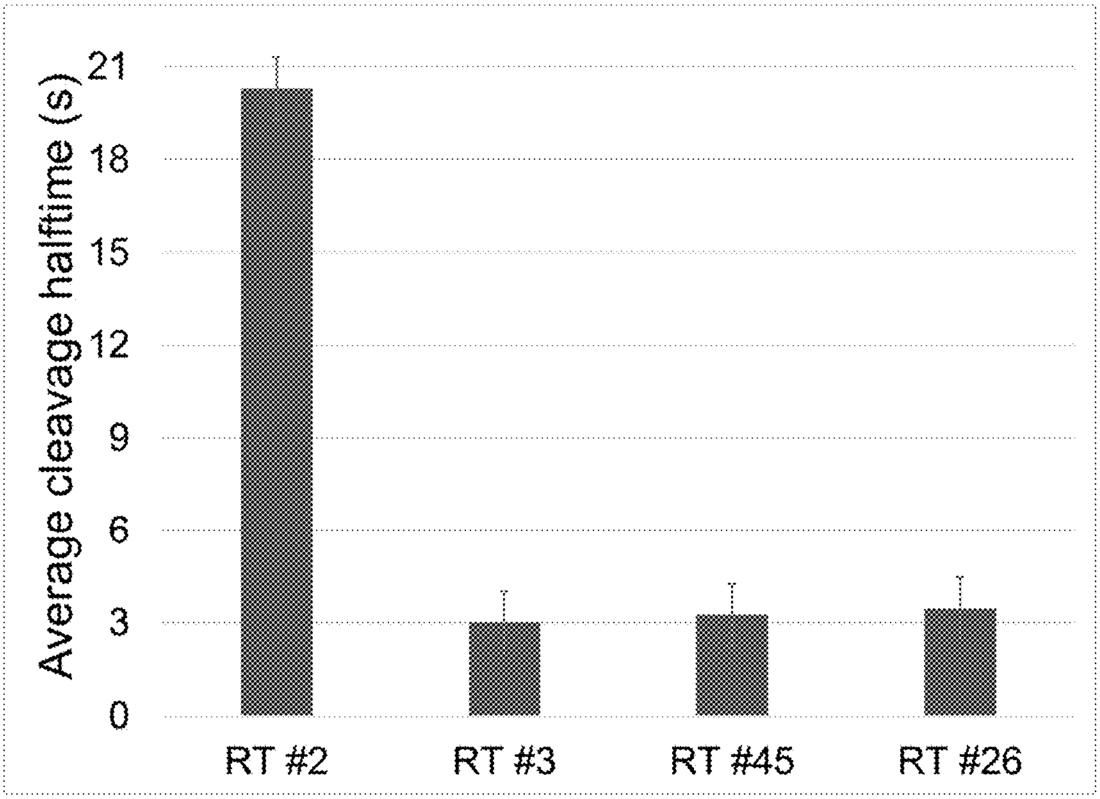

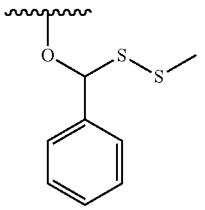 [SMILES: *OC(SSC)c1ccccc1]

wherein the oxygen is attached to the 3' position of the deoxyribose. To calculate the cleavage half time, a dTTP nucleotide with each 3' moiety was incorporated into a growing DNA strand immobilized on a solid support. Excess nucleotides were washed away. Next, a cleavage solution containing 1 mM THPP as a reducing agent was introduced for controlled periods of time. The cleavage reaction was carried out at 55° C., in a buffered solution at 9.5 pH. The cleavage reaction for RT #1 was slow at 55° C., as shown in FIG. 2A, so to make a meaningful comparison to the other RT moieties, the temperature for only RT #1 was increased to 65° C., as shown in FIG. 2B. As observed in FIGS. 2A-2C, there is a drastic improvement in the cleavage kinetics (i.e., a reduction in halftime) of RT #3 compared to RT #1 and RT #2. While the cleavage of the disulfide bond (reversible terminator) is rapid in both cases, the subsequent hydrolysis reaction that removes the residual portion of the 3' moiety is much faster with the new 3' moieties of Formula I, II, and III. Modifying the reaction conditions (e.g., elevating the temperature to 65° C., increasing the pH, increasing the amount or concentration of the reducing agent) results in faster cleavage.

The kinetics of the disulfide cleavage are not significantly affected by the terminal alkyl group. As indicated in Table 2, the incorporation kinetics are more sensitive to the terminal alkyl group (i.e., $R^8$ in Formula II). Data presented within Table 3 show that when $R^7$ is methyl and $R^8$ is methyl or ethyl, the kinetics are relatively invariant. Similarly, when $R^7$ is unsubstituted phenyl and $R^8$ is unsubstituted methyl, unsubstituted ethyl, or unsubstituted propyl, the cleavage kinetics are comparable. Advantageously, the cleavage kinetics for the compounds described herein are surprisingly 10× faster than control compounds (e.g., when $R^7$ and $R^8$ are methyl). Each sequencing cycle is directly correlated to the cleavage kinetics; faster cleavage results in a faster sequencing cycle. Sequencing a 150 bp template polynucleotide which typically takes about 18 hours of sequencing time, assuming a 7 minute sequencing cycle, can now be accomplished in about 5-8 hours using the nucleotides described herein.

TABLE 3

Cleavage kinetics measurements varying $R^7$ and $R^8$ for dTTP nucleotides. Cleavage conditions include measurements of disulfide cleavage using 0.1 mM THPP at 55° C.

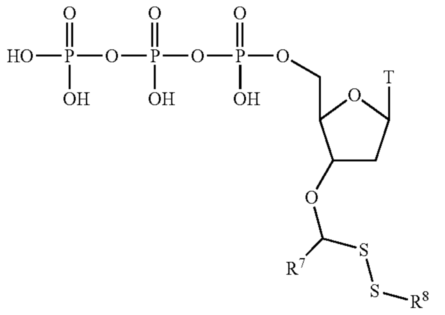

| $R^7$ | $R^8$ | Cleavage halftime (s) |
|---|---|---|
| 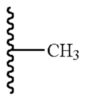 | 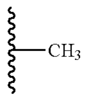 | 21.2 ± 3 |
| 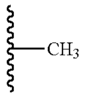 | 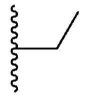 | 20.3 ± 3 |
| 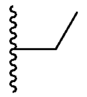 | 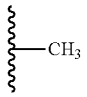 | 21.1 ± 3 |
| 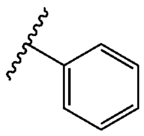 [SMILES: *c1ccccc1] | 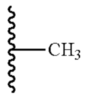 | 1.6 ± 3 |
| 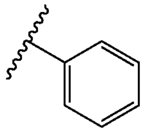 | 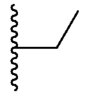 | 2.8 ± 3 |
| 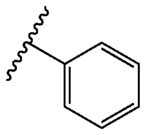 [SMILES: *c1ccccc1] | 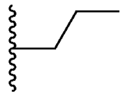 [SMILES: *CCC] | 2.9 ± 3 |
| 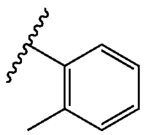 [SMILES: *c1ccccc1C] | 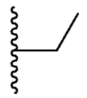 | 0.9 ± 3 |
| 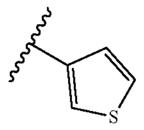 [SMILES: *c1ccsc1] | 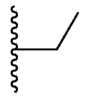 | 2.7 ± 3 |
| 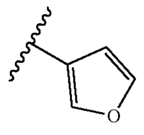 [SMILES: *c1ccoc1] | 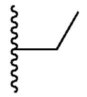 | 2.0 ± 3 |

TABLE 3-continued

Cleavage kinetics measurements varying $R^7$ and $R^8$ for dTTP nucleotides. Cleavage conditions include measurements of disulfide cleavage using 0.1 mM THPP at 55° C.

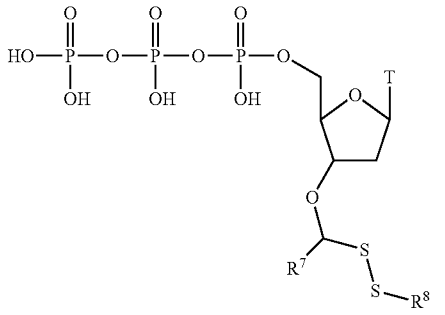

| $R^7$ | $R^8$ | Cleavage halftime (s) |
|---|---|---|
| 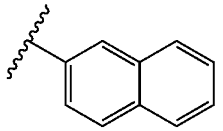 [SMILES: *c1ccc2ccccc2c1] | 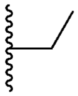 | 3.5 ± 3 |

Example 5. Chemical Stability

A modified nucleotide is of no use in sequencing if it is not chemical stable during storage and use. Any degradation that results in loss of the reversible terminator and/or premature cleavage of the linker is particularly problematic, as the unterminated nucleotides will be incorporated during the sequencing reaction, causing some of the growing DNA strands to be extended by two bases rather than one, in what is known as a dephasing or leading effect.

The modified nucleotides as described herein, e.g., a nucleotide of formulas I, II, or III, were found to be stable (i.e., did not degrade) at 4° C. for at least 7 days. The compounds described herein may confer at least 5%, 10%, 20%, 30%, 40%, 50%, 60%, 70%, 80%, 90%, 100%, 200%, 300%, 400%, 500%, 600%, 700%, 800%, 900%, 1000%, 1500%, 2000%, 2500%, or 3000% improved stability compared to a nucleotide having a 3'-O-azidomethyl protecting group at the same condition for the same period of time. In some embodiments, the stability is measured at ambient temperature or a temperature below ambient temperature (e.g., 4-10° C.). In embodiments, the stability is measured at an elevated temperature, e.g., 40° C., 45° C., 50° C., 55° C., 60° C., or 65° C. In embodiments, the stability is measured in solution in a basic pH environment, e.g., at pH 9.0, 9.2, 9.4, 9.6, 9.8. or 10.0. In some such embodiments, the stability is measured with or without the presence of an enzyme, such as a polymerase (e.g., a DNA polymerase), a terminal deoxynucleotidyl transferase, or a reverse transcriptase. In embodiments, the stability is reflected in the out-of-phase metric (e.g., % lead), which directly correlates with the amount of 3' deblocking. In embodiments, the % lead is less than 0.3%. In embodiments, the % lead is less than 0.2%. In embodiments, the % lead is less than 0.1%.

Example 6. Phasing

As used herein, the term "out-of-phase" refers to phenomena in sequencing by synthesis that is caused by incomplete removal of the 3' reversible terminators and fluorophores, and/or failure to complete nucleotide incorporation of a portion of DNA strands within clusters for a given sequencing cycle. Sequencing by synthesis of nucleic acids ideally requires the controlled (i.e., one at a time), yet rapid, incorporation of the correct complementary nucleotide opposite the oligonucleotide being sequenced. Following detection, the removal of the reversible terminator leaves a free 3' hydroxyl group for addition of the next nucleotide. If, however, the reversible terminator is removed prematurely, or the solution of reversibly terminated nucleotides contains impurities (e.g., nucleotides bearing a 3' hydroxyl group), these unterminated nucleotides may be incorporated into the polynucleotide. This leads to the clusters of monoclonal amplicons being out-of-phase, reducing sequencing accuracy and limiting sequencing read lengths.

The unprotected 3'-OH nucleotides could be generated during the manufacturing processes or possibly during the storage and reagent handling processes. Accordingly, the discovery of nucleotide analogues which decrease the incidence of phasing errors provides a great advantage in SBS applications over existing nucleotide analogues. For example, the nucleotide compounds described herein results in faster SBS cycle time, lower out-of-phase values, and permit longer sequencing read length.

Example 7. Synthesis of Linkers

The process for using polymerase-compatible cleavable moiety containing molecules generally involves incorporation of a labeled nucleotide analog into the growing polynucleotide chain, followed by detection of the label, then cleavage of the nucleotide analog to remove the covalent modification blocking continued synthesis (e.g., polymerase-compatible cleavable moiety). The cleaving step may be accomplished using an enzyme or by chemical cleavage. Modifications of nucleotides may be made on the 5' terminal phosphate or the 3' hydroxyl group. Developing a truly reversible set of nucleotide terminators has been a goal for many years. Despite the recent advances only a few solutions have been presented, most of which cause other problems, including inefficient or incomplete incorporation by the polymerase, inefficient or incomplete cleavage of the removable group, or harsh conditions needed to for the cleaving step causing spurious problems with the remainder of the assay and/or fidelity of the target sequence. Disclosed herein is a new class of fluorescently labeled nucleotides that include a new RT bonded to the 3' oxygen.

Experimental Procedures for a Linker:

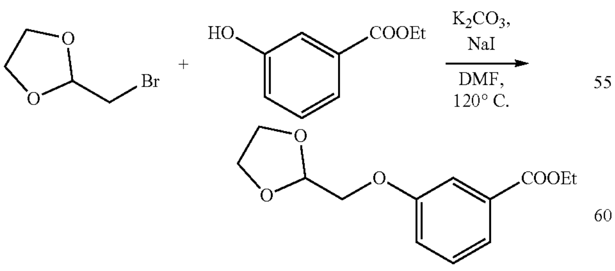

Sodium iodide (1.5 g, 10.0 mmol) and potassium carbonate (6.9 g, 50 mmol) were added to a stirred solution of ethyl 3-hydroxybenzoate (4.15 g, 25 mmol), 2-bromomethyl-1,3-dioxolane (10.4 mL, 100 mmol) in DMF (15 mL) and was heated to 120° C. The progress of the reaction was monitored by HPLC (100 mM TEAA/MeCN, 60% to 100% over 15 min, hold for 5 min at 100%). The reaction mixture was cooled to room temperature when the amount of ethyl-3-hydroxybenzoate was less than 5%. The suspension was filtered and washed with ether (2×50 mL). The combined filtrates were washed with water (3×50 mL) and brine (50 mL), dried over sodium sulfate and concentrated in vacuo. The crude product was purified by silica gel chromatography (hexanes/ethyl acetate, 80:20) to obtain the desired compound, ethyl 3-((1,3-dioxolan-2-yl)methoxy)benzoate as colorless clear liquid (5.57 g, 88%). $^1$H NMR (500 MHz, DMSO) δ 7.59-7.52 (m, 1H), 7.48-7.39 (m, 2H), 7.25 (ddd, J=8.3, 2.7, 1.0 Hz, 1H), 5.22 (t, 3.9 Hz, 1H), 4.35-4.25 (m, 2H), 4.07 (d, J=3D Hz, 2H), 4.01-3.91 (m, 2H), 3.86 (ddd, J=15.2, 9.1, 5.6 Hz, 2H), 1.31 (q, J=12 Hz, 3H); MS: calc'd for $[C_{13}H_{16}O_5+Na]$: 275.1, found 275.3.

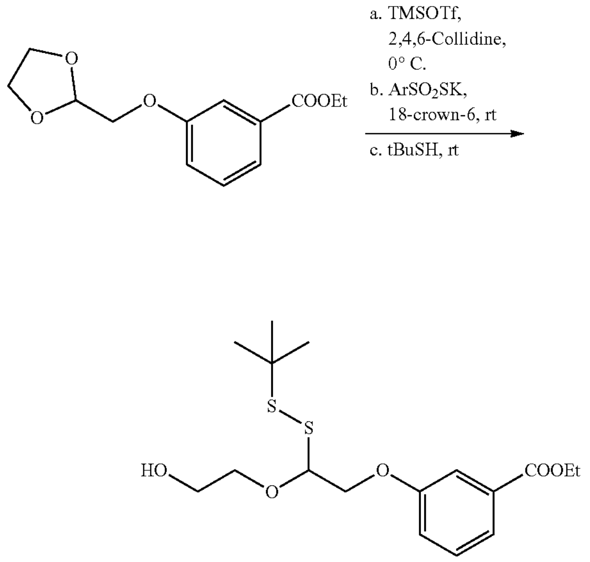 [SMILES: CCOC(=O)c1cccc(OCC2OCCO2)c1 ; CCOC(=O)c1cccc(OCC(OCCO)SSC(C)(C)C)c1]

2,4,6-Collidine (2.38 mmol, 3.0 equiv.) was added to a stirred solution of ethyl 3-((1,3-dioxolan-2-yl)methoxy)benzoate (0.2 g, 0.79 mmol) in DCM (0.1 M) at 0° C. under Ar atmosphere followed by the addition of trimethylsilyl triflate (1.59 mmol, 2.0 equiv.). The mixture was stirred at the same temperature until the disappearance of an acetal on TLC and formation of highly polar compound was observed, after which potassium thiotosylate (1.59 mmol, 2.0 equiv.) and 18-crown-6 (1.59 mmol, 2.0 equiv.) were added to the reaction mixture. Disappearance of the polar component was confirmed by TLC, after which tert- butyl thiol (1.59 mmol, 2.0 equiv.) was added. The reaction mixture was loaded on to silica gel column upon completion of the reaction and the desired product, ethyl 3-(2-(tert-butyldisulfaneyl)-2-(2-hydroxyethoxy)ethoxy)benzoate was eluted with 20% ethyl acetate and hexanes mixture as a colorless oil (235.6 mg, 63% yield). NMR (500 MHz, DMSO) δ 7.57 (dd, J=6.6, 1.2 Hz, 1H), 7.51-7.42 (m, 2H), 7.27 (ddd, J=8.2, 2.7, 0.8 Hz, 1H), 4.92 (t, J=5.4 Hz, 1H), 4.69 (t, J=5.4 Hz, 1H), 4.35-4.25 (m, 4H), 3.89-3.80 (m, 1H), 3.61-3.49 (m, 3H), 1.37-1.28 (m, 12H). MS: calc'd for $[C_{17}H_{26}O_5S_2+Na]$: 397.1, found 397.3.

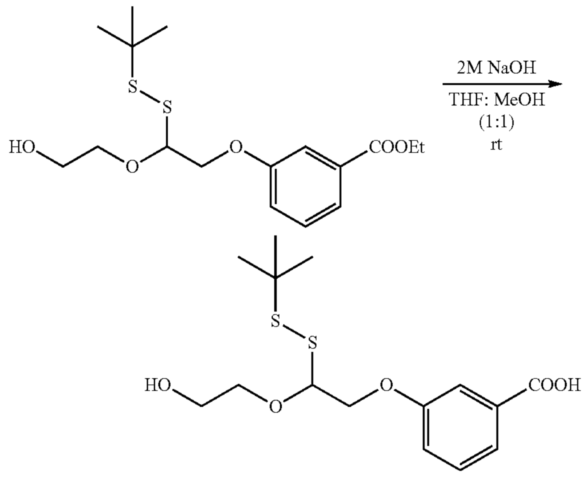

Sodium hydroxide (0.7 mL, 2 M) was added to a stirred solution of ethyl 3-(2-(tert-butyldisulfaneyl)-2-(2-hydroxyethoxy)ethoxy)benzoate (131 mg, 0.35 mmol) in 1:1 methanol (0.33 mL) and THF (0.33 mL) mixture. The solution was initially heterogeneous but became homogenous after 1 hour of stirring. The reaction progress was monitored by HPLC (100 mM TEAA/MeCN, 60% to 100% over 15 min, hold for 5 min at 100%). Upon completion, the reaction mixture was concentrated and HCl (1 M, 1.382 mL) was added dropwise with stirring until the milky swirl persisted. The aqueous suspension was extracted with DCM (3×15 mL) and the extracts were dried over sodium sulfate. The crude product was purified using silica gel chromatography (50% ethyl acetate:hexanes) and 3-(2-(tert-butyldisulfaneyl)-2-(2-hydroxyethoxy)ethoxy)benzoic acid was obtained as a colorless oil (87 mg, 72% yield). $^1$H NMR (500 MHz, DMSO) δ 13.00 (s, 1H), 7.58-7.52 (m, 1H), 7.47 (dt, J=11.9, 6.1 Hz, 1H), 7.42 (t, J=7.9 Hz, 1H), 7.21-7.19 (m, 1H), 4.92 (t, J=5.4 Hz, 1H), 4.69 (s, 1H), 4.34-4.24 (m, 2H), 3.88-3.82 (m, 1H), 3.61-3.50 (m, 3H), 1.35-1.26 (m, 9H). MS: calc'd for $[C_{15}H_{22}O_5S_2+Na]$: 369.1, found 369.2.

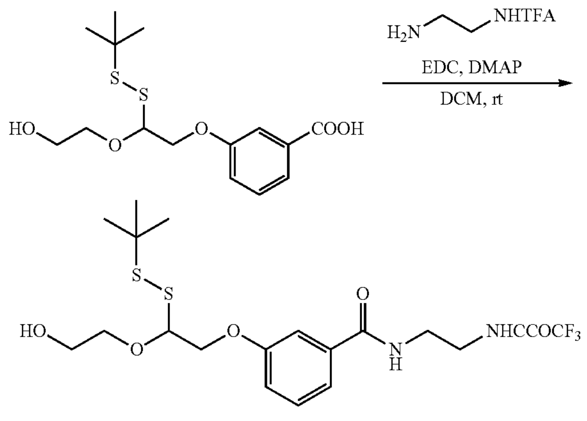

To a mixture of 3-(2-(tert-butyldisulfaneyl)-2-(2-hydroxyethoxy)ethoxy)benzoic acid (43 mg, 0.124 mmol), N-(2-aminoethyl)-2,2,2-trifluoroacetamide (28.6 mg, 0.148 mmol, 1.2 equiv.), 4-N,N-dimethylaminopyridine (4.5 mg, 0.037 mmol, 0.3 equiv.) in DCM (0.2 mL, 0.6 M) at 0° C., was added A-(3-dimethylaminopropyl)—N'-ethylcarbodiimide hydrochloride (33 mg, 0.174 mmol, 1.4 equiv.) in DCM dropwise. The reaction was stirred at room temperature until the disappearance of the starting material as monitored by HPLC (100 mM TEAA/MeCN, 60% to 100% over 15 min, hold for 5 min at 100%). The reaction mixture was diluted with water and extracted with ethyl acetate (3×15 mL) and dried over sodium sulfate. The crude was purified by silica gel chromatography (60% ethyl acetate: hexanes) and 3-(2-(A/7-butyldisulfaneyl)-2-(2-hydroxyethoxy)ethoxy)-N-(2-(2,2,2-trifluoroacetamido)ethyl)benzamide was obtained as colorless liquid (38 mg, 63.3% yield). NMR (500 MHz, DMSO) δ 9.49 (d, J=5.5 Hz, 1H), 8.59 (t, J=5.5 Hz, 1H), 7.40 (dq, J=22.8, 7.7 Hz, 3H), 7.12 (dd, J=8.0, 1.6 Hz, 1H), 4.92 (t, J=5.4 Hz, 1H), 4.70 (t, J=5.3 Hz, 1H), 4.35-4.19 (m, 2H), 3.87 (dt, J=9.6, 4.3 Hz, 1H), 3.62-3.50 (m, 3H), 3.43-3.33 (m, 4H), 1.31 (s, 9H). MS: calc'd for $[C_{19}H_{27}F_3N_2O_5S_2+Na]$: 507.1, found 507.2.

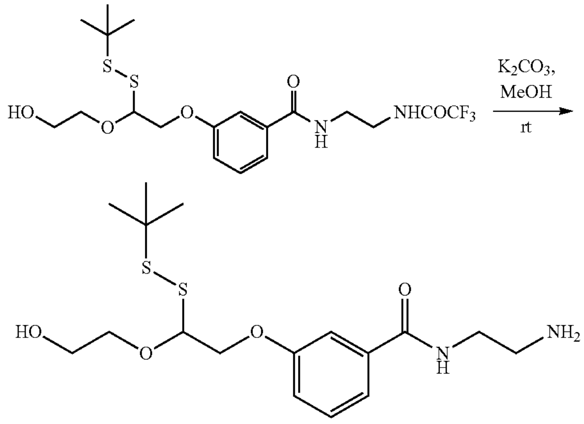

To a stirred solution of 3-(2-(tert-butyldisulfaneyl)-2-(2-hydroxyethoxy)ethoxy)-N-(2-(2,2,2-trifluoroacetamido)ethyl)benzamide (55 mg, 0.115 mmol) in methanol (0.5 mL), potassium carbonate (45.5 mg, 0.329 mmol, 2.9 equiv.) was added. The reaction progress was monitored by HPLC (100 mM TEAA/MeCN, 60% to 100% over 15 min, hold for 5 min at 100%) and upon completion, the reaction mixture was diluted with water and extracted with ethyl acetate (3×5 mL). The organic fractions were collected, dried over sodium sulfate and purified by HPLC to obtain A-(2-aminoethyl)-3-(2-(tert-butyldisulfaneyl)-2-(2-hydroxyethoxy)ethoxy)benzamide as colorless liquid. $^1$H NMR (500 MHz, DMSO) δ 8.43 (d, J=5.0 Hz, 1H), 7.45 (t, J=5.8 Hz, 2H), 7.37 (t, J=7.8 Hz, 1H), 7.11 (dd, 7=7.8, 2.1 Hz, 1H), 4.92 (t, 7=5.3 Hz, 1H), 4.71 (s, 1H), 4.28 (d, J=5.9 Hz, 2H), 3.87 (dt, J=9.4, 4.2 Hz, 1H), 3.63-3.50 (m, 3H), 3.32-3.22 (m, 4H), 2.71 (t, J=6.5 Hz, 2H), 1.31 (s, 9H). MS: calc'd for $[C_{17}H_{28}N_2O_4S_2+H]$: 389.2, found 389.4.

Scheme 5. SCN linker scheme

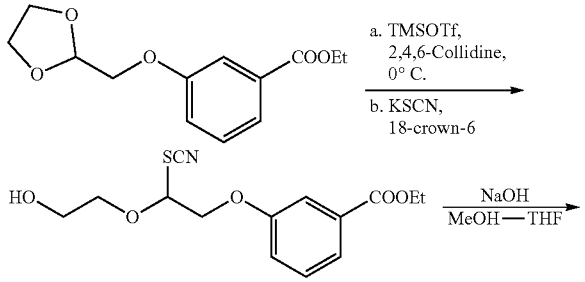

-continued

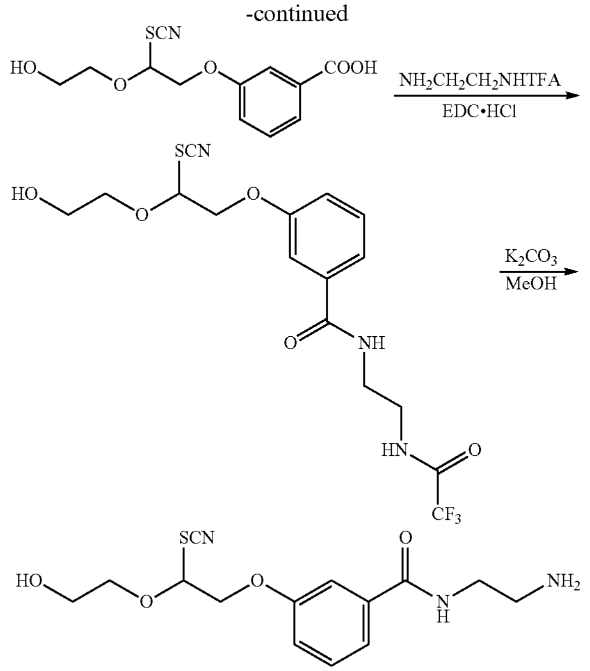

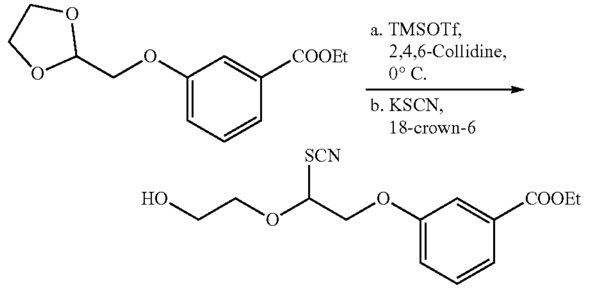

2,4,6-Collidine (0.59 mmol, 3.0 equiv.) was added to a stirred solution of ethyl 3-((1,3-dioxolan-2-yl)methoxy)benzoate (0.05 g, 0.79 mmol) in DCM (0.1 M) at 0° C. under Ar atmosphere followed by the addition of trimethylsilyl triflate (0.4 mmol, 2.0 equiv.). The mixture was stirred at the same temperature until the disappearance of an acetal on TLC and formation of highly polar compound was observed, after which a solution of potassium thiocyanate (0.99 mmol, 5.0 equiv.) and 18-crown-6 (0.99 mmol, 5.0 equiv.) in acetone (0.2 mL) was added to it. Disappearance of the polar component was confirmed by TLC. The product formation was confirmed by mass analysis, MS: calc'd for $[C_{14}H_{17}NO_5S—H]^-$: 311.0, found 310.0.

Example 8. Scarless Sequencing

Typical modified nucleotides were designed based on the rationale that each of the nucleotides is modified by attaching a unique cleavable fluorophore to the specific location of the base and capping the 3'-OH group with a small reversible-terminating moiety so they are still recognized by DNA polymerase as substrates. A potential disadvantage of this approach is the production of a small molecular "scar" (e.g., a propargylamine or a modified propargylamino moiety) at the nucleotide base after cleavage of the fluorescent dye from the incorporated nucleotide in the polymerase reaction. The growing DNA chain accumulates these scars through each successive round of SBS. In embodiments described herein, some compounds include a cyclic moiety (e.g., substituted or unsubstituted cycloalkyl, heterocycloalkyl, aryl, or heteroaryl) off the 3'-oxygen position (i.e., $R^7$ of Formula I, II, or III) permitting the compounds to be "scarless" nucleotide reversible terminators (NRT) for DNA sequencing by synthesis (SBS). In embodiments, the base of the scarless nucleotides is a monovalent base. The 3' attached reporter indicated by the symbol $R^7$, may be fluorescent (e.g., a coumarin or coumarin derivative; non-limiting examples of coumarin derivatives are provided in Matikonda et al. Chem. Sci., 2020,11, 7302-7307, which is incorporated herein by reference). Such novel NRTs may be employed in a set for use in SBS, wherein each NRT is 3'-O reversibly blocked and is labeled with a fluorescent dye that has a unique fluorescence emission corresponding to the type of base of each nucleotide (e.g., a separate emission for A, T, G, and C respectively), thereby installing dual functions (serving as both a reversible blocker and a cleavable fluorescence reporter) to the 3'-O-modified nucleotide analogues. During SBS, after a nucleotide is incorporated, and the fluorescent reporter imaged, the 3'-O-dye will be cleaved with a cleaving agent (cleaving agents may include THPP or TCEP) to generate a 3'-OH group that is ready for subsequent extension reactions. Many fluorescent dye species (several of which are identified herein) are suitable for polymerase incorporation when attached to the 3'-0 of these nucleotide analogues.

In embodiments, $R^7$ is a coumarin dye or a derivative thereof. In embodiments, $R^7$ is

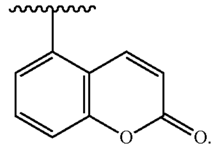 [SMILES: *c1cccc2oc(=O)ccc12]

In embodiments, $R^7$ is

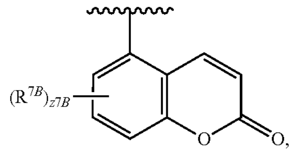

wherein z7B is an integer from 0 to 5. In embodiments, $R^7$ is

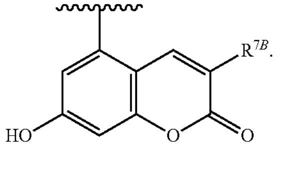

In embodiments, $R^7$ is

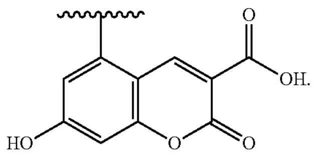 [SMILES: *c1cc(O)cc2oc(=O)c(C(=O)O)cc12]

In embodiments, $R^7$ is

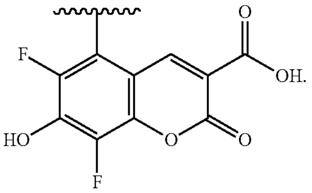 [SMILES: *c1c(F)c(O)c(F)c2oc(=O)c(C(=O)O)cc12]

In embodiments, $R^7$ is

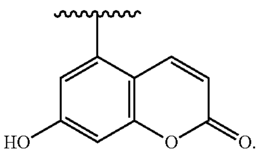 [SMILES: *c1cc(O)cc2oc(=O)ccc12]

In embodiments, $R^7$ is

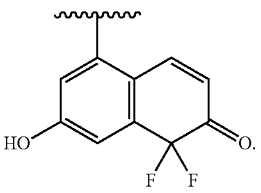 [SMILES: *c1cc(O)cc2c1C=CC(=O)C2(F)F]

In embodiments, $R^7$ is

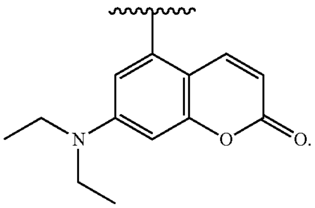 [SMILES: *c1cc(N(CC)CC)cc2oc(=O)ccc12]

In embodiments, $R^7$ is

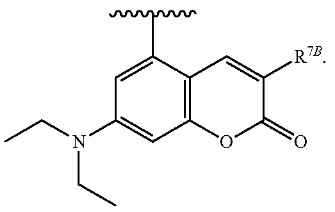

wherein $R^{7B}$ is as described herein. In embodiments, $R^7$ is

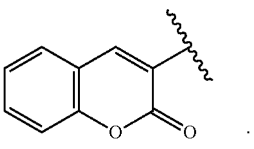 [SMILES: *c1cc2ccccc2oc1=O]

In embodiments, $R^7$ is

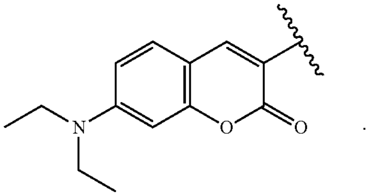 [SMILES: *c1cc2ccc(N(CC)CC)cc2oc1=O]

In embodiments, $R^7$ is

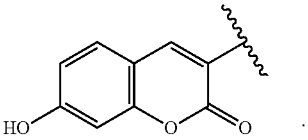 [SMILES: *c1cc2ccc(O)cc2oc1=O]

In embodiments, $R^7$ is

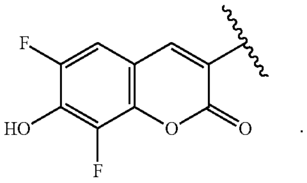 [SMILES: *c1cc2cc(F)c(O)c(F)c2oc1=O]

In embodiments, $R^7$ is

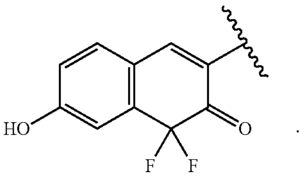 [SMILES: *C1=Cc2ccc(O)cc2C(F)(F)C1=O]

In an aspect is provided a compound having the formula:

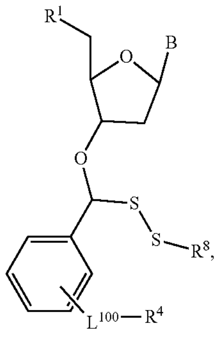

wherein $R^1$, B, $R^8$, $L^{100}$, and $R^4$ are as described herein, including embodiments.

Example 9. Thioaldehyde Stability

The kinetics of a reaction depend on the activation energy, i.e., the difference between the energy of the reactants and the transition state. However, transition states have only a transitory existence and are difficult, if not impossible, to observe, isolate, and quantify. A generalization to predicting reaction rates is provided in the Hammond Postulate, which suggests the activation energy of the rate determining step is inversely proportional to the stability of the transition state. In an endothermic reaction the transition state structure is closer to the structure of the products, and so it follows that a more stable product reflects a more stable transition state and has a lower activation energy.

Invoking the Hammond Postulate for the reaction of interest, i.e., the thiol bearing nucleotide converting to the free 3'OH and a thioaldehyde, depicted in scheme 6, posits the thermodynamic stability of the resultant thioaldehyde influences the cleavage rate. Simple thermodynamics provides the enthalpy changes of the reaction, ΔH, as a measure of the thermodynamic stability. The enthalpy change is calculated as the difference in the enthalpy of the products and reactants, $\Delta H=\Delta H_{products}-\Delta H_{reactants}$.

Scheme 6. A nucleotide containing an alkylthiol converting to the free 3′OH nucleotide and a thioaldehyde.

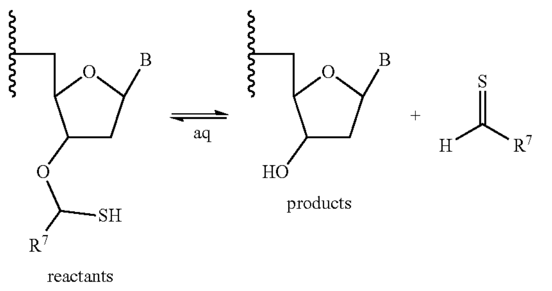

Figure 3:
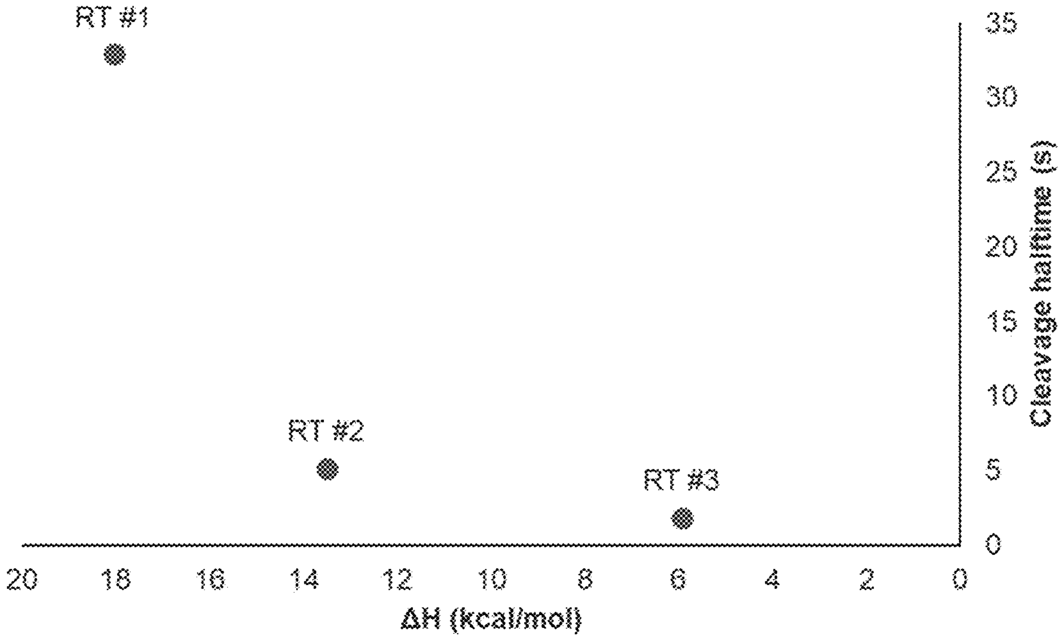
FIG. 3. Experimentally measured average cleavage halftimes under identical conditions for RT #1, RT #2, and RT #3 as a function of the ΔH. We found that in general, reducing the energetic burden on the system, i.e., reducing the enthalpy, correlates with faster cleavage.

Using ΔH as a corollary for the reaction rate, it is possible to predict which reversible terminators will cleave rapidly under suitable conditions. Gas phase calculations were performed using hybrid Density Functional Theory (B3LYP) with a large basis set (Valence triple-zeta with two sets of polarization functions); to determine the optimized structure and energy of the reactants and the products were performed to derive a ΔH for a variety of compounds, see Table 4. Experimental evidence supports using ΔH as a proxy for the reaction rate, as reported in Example 1 and depicted in FIG. 3, showing the experimentally derived cleavage halftime for RT #1, RT #2, and RT #3 as a function of the calculated ΔH. Reducing the energetic burden on the system, i.e., reducing the enthalpy, corresponds to faster cleavage rates. This is readily observed in FIG. 3 showing that as the enthalpy decreases for RT #1, RT #2, and RT #3, the cleavage halftime similarly reduces. In embodiments, the compound has an enthalpy of about 5 to about 12 kcal/mol.

TABLE 4

Calculated enthalpies for Scheme 6 reactions.

| $R^7$ (of Scheme 6) | Internal Ref No. | ΔH (kcal/mol) |
|---|---|---|
| 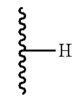 | RT #1 | 18.0 |
| 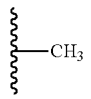 | RT #2 | 13.5 |
| 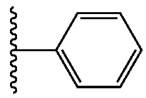 [SMILES: *c1ccccc1] | RT #3 | 5.6 |
| 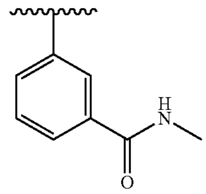 [SMILES: *c1cccc(C(=O)NC)c1] | RT #4 | 4.1 |
| 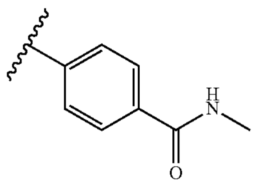 [SMILES: *c1ccc(C(=O)NC)cc1] | RT #5 | 3.6 |
| 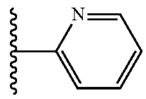 | RT #6 | 5.4 |
| 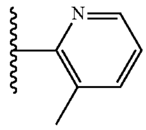 [SMILES: *c1ncccc1C] | RT #7 | 6.6 |
| 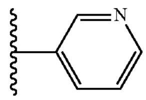 | RT #8 | 5.8 |
| 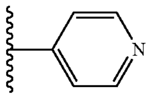 | RT #9 | 7.9 |
| 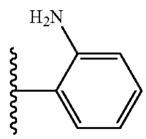 [SMILES: *c1ccccc1N] | RT #10 | 6.8 |
| 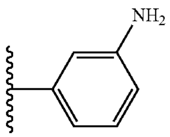 [SMILES: *c1cccc(N)c1] | RT #11 | 5.7 |
| 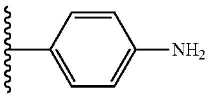 [SMILES: *c1ccc(N)cc1] | RT #12 | 2.5 |

TABLE 4-continued
Calculated enthalpies for Scheme 6 reactions.
| $R^7$ (of Scheme 6) | Internal Ref No. | ΔH (kcal/mol) |
|---|---|---|
| 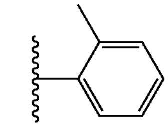 [SMILES: *c1ccccc1C] | RT #13 | 6.3 |
| 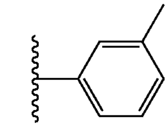 [SMILES: *c1cccc(C)c1] | RT #14 | 5.5 |
| 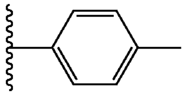 [SMILES: *c1ccc(C)cc1] | RT #15 | 4.9 |
| 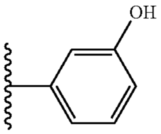 [SMILES: *c1cccc(O)c1] | RT #16 | 6.3 |
| 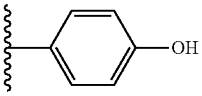 [SMILES: *c1ccc(O)cc1] | RT #17 | 3.8 |
| 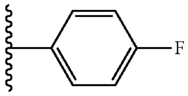 [SMILES: *c1ccc(F)cc1] | RT #18 | 5.3 |
| 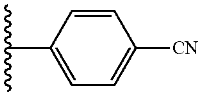 [SMILES: *c1ccc(C#N)cc1] | RT #19 | 7.2 |
| 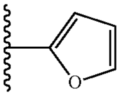 [SMILES: *c1ccco1] | RT #20 | 3.7 |
| 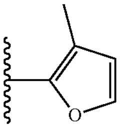 [SMILES: *c1occc1C] | RT #21 | 2.2 |
| 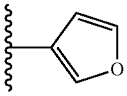 [SMILES: *c1ccoc1] | RT #22 | 7.2 |
| 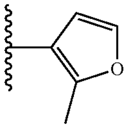 [SMILES: *c1ccoc1C] | RT #23 | 3.0 |
| 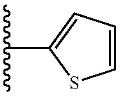 [SMILES: *c1cccs1] | RT #24 | 2.7 |
TABLE 4-continued
Calculated enthalpies for Scheme 6 reactions.
| $R^7$ (of Scheme 6) | Internal Ref No. | ΔH (kcal/mol) |
|---|---|---|
| 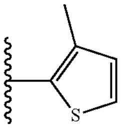 [SMILES: *c1sccc1C] | RT #25 | 0.7 |
| 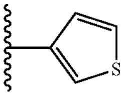 | RT #26 | 6.7 |
| 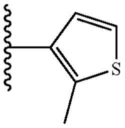 [SMILES: *c1ccsc1C] | RT #27 | 6.3 |
| 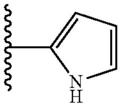 [SMILES: *c1ccc[nH]1] | RT #28 | −1.2 |
| 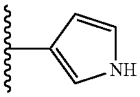 | RT #29 | 4.2 |
| 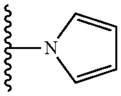 | RT #30 | 0.1 |
| 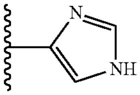 [SMILES: *c1c[nH]cn1] | RT #31 | 4.9 |
| 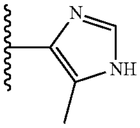 [SMILES: *c1nc[nH]c1C] | RT #32 | 2.4 |
| 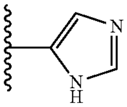 [SMILES: *c1cnc[nH]1] | RT #33 | 0.8 |
| 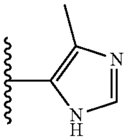 [SMILES: *c1[nH]cnc1C] | RT #34 | −1.0 |
| 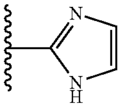 [SMILES: *c1ncc[nH]1] | RT #35 | 2.6 |
| 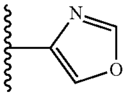 | RT #36 | 7.4 |

TABLE 4-continued
Calculated enthalpies for Scheme 6 reactions.
| $R^7$ (of Scheme 6) | Internal Ref No. | ΔH (kcal/mol) |
|---|---|---|
| 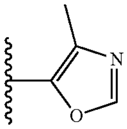 [SMILES: *c1ocnc1C] | RT #37 | 4.8 |
| 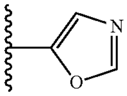 | RT #38 | 5.2 |
| 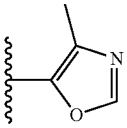 [SMILES: *c1ocnc1C] | RT #39 | 3.2 |
| 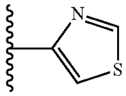 | RT #40 | 7.3 |
| 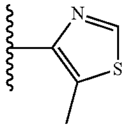 | RT #41 | 5.5 |
| 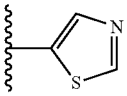 | RT #42 | 4.1 |
| 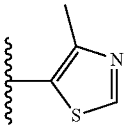 [SMILES: *c1scnc1C] | RT #43 | 3.3 |
| 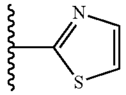 [SMILES: *c1nccs1] | RT #44 | 6.1 |
| 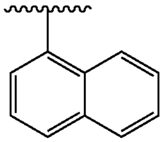 [SMILES: *c1cccc2ccccc12] | RT #45 | 8.0 |
| 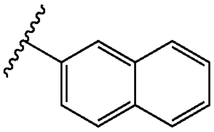 [SMILES: *c1ccc2ccccc2c1] | RT #46 | 5.9 |
| 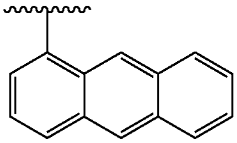 [SMILES: *c1cccc2cc3ccccc3cc12] | RT #47 | 2.8 |
| 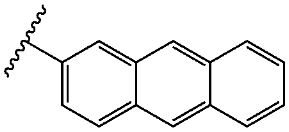 [SMILES: *c1ccc2cc3ccccc3cc2c1] | RT #48 | 0.5 |
| 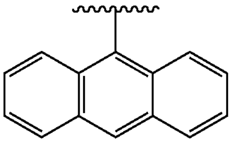 [SMILES: *c1c2ccccc2cc2ccccc12] | RT #49 | 6.2 |
| 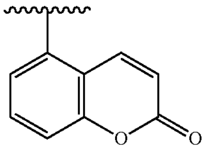 [SMILES: *c1cccc2oc(=O)ccc12] | RT #50 | 9.2 |
| 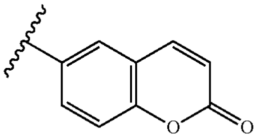 [SMILES: *c1ccc2oc(=O)ccc2c1] | RT #51 | 6.4 |
| 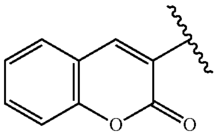 [SMILES: *c1cc2ccccc2oc1=O] | RT #52 | 6.0 |
| 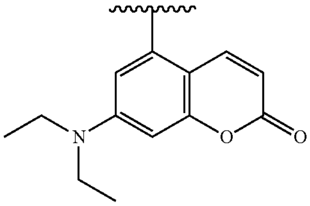 [SMILES: *c1cc(N(CC)CC)cc2oc(=O)ccc12] | RT #53 | 10.0 |
| 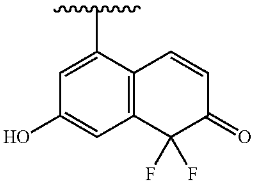 [SMILES: *c1cc(O)cc2c1C=CC(=O)C2(F)F] | RT #54 | 10.8 |
| 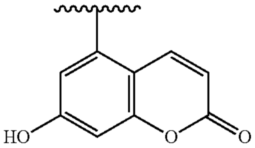 [SMILES: *c1cc(O)cc2oc(=O)ccc12] | RT #55 | 9.8 |
| 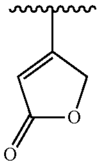 | RT #56 | 11.2 |

TABLE 4-continued
Calculated enthalpies for Scheme 6 reactions.
| $R^7$ (of Scheme 6) | Internal Ref No. | ΔH (kcal/mol) |
|---|---|---|
| 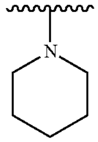 [SMILES: *N1CCCCC1] | RT #57 | −5.6 |
| 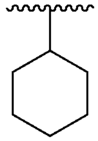 [SMILES: *C1CCCCC1] | RT #58 | 10.6 |
| 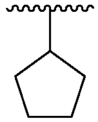 [SMILES: *C1CCCC1] | RT #59 | 10.2 |
| 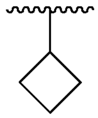 [SMILES: *C1CCC1] | RT #60 | 10.5 |
| 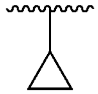 | RT #61 | 6.6 |
| 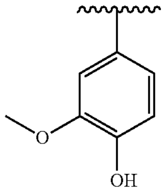 [SMILES: *c1ccc(O)c(OC)c1] | RT #62 | 5.6 |
| 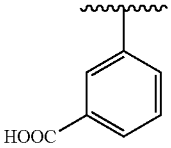 | RT #63 | 7.9 |
| 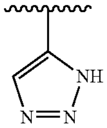 | RT #64 | 5.8 |
| 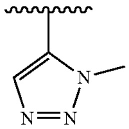 [SMILES: *c1cnnn1C] | RT #65 | 5.1 |
| 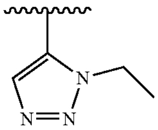 | RT #66 | 4.9 |
| 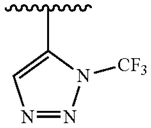 [SMILES: *c1cnnn1C(F)(F)F] | RT #67 | 10.3 |
| 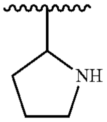 [SMILES: *C1CCCN1] | RT #68 | 9.3 |
| 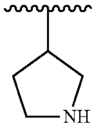 | RT #69 | 10.0 |
| 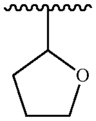 [SMILES: *C1CCCO1] | RT #70 | 14.7 |
| 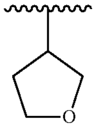 [SMILES: *C1CCOC1] | RT #71 | 10.4 |
| 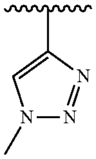 [SMILES: *c1cn(C)nn1] | RT #72 | 8.1 |
| 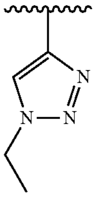 [SMILES: *c1cn(CC)nn1] | RT #73 | 9.2 |
| 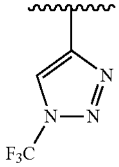 | RT #74 | 9.3 |
| 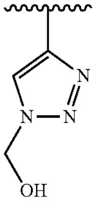 [SMILES: *c1cn(CO)nn1] | RT #75 | 7.1 |

TABLE 4-continued

| Calculated enthalpies for Scheme 6 reactions. | | |
|---|---|---|
| $R^7$ (of Scheme 6) | Internal Ref No. | ΔH (kcal/mol) |
| 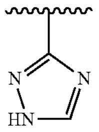 | RT #76 | 9.1 |
| 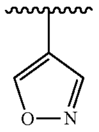 | RT #77 | 5.3 |
| 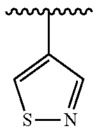 [SMILES: *c1cnsc1] | RT #78 | 5.4 |
| 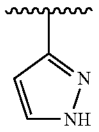 | RT #79 | 4.6 |
| 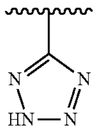 | RT #80 | 10.6 |

NUMBERED EMBODIMENTS

The present disclosure provides the following illustrative embodiments.

Embodiment P1. A compound having the formula:

(I)

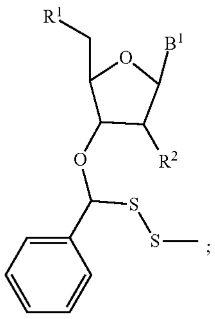

wherein $B^1$ is a nucleobase;

$R^1$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-nucleoside protecting group, monophosphate moiety, polyphosphate moiety, or nucleic acid moiety; and $R^2$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety.

Embodiment P2. The compound of embodiment P1, having the formula:

(IA)

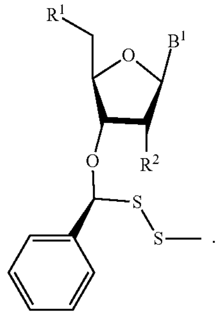

Embodiment P3. The compound of embodiment P1, having the formula.

(IB)

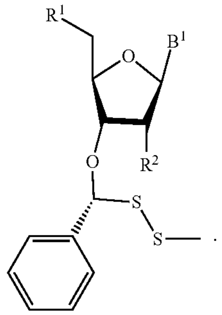

Embodiment P4. The compound of any one of embodiments P1 to P3, wherein $R^2$ is hydrogen.

Embodiment P5. The compound of any one of embodiments P1 to P4, wherein R' is —OH, a 5'-nucleoside protecting group, monophosphate moiety, polyphosphate moiety, or nucleic acid moiety.

Embodiment P6. The compound of any one of embodiments P1 to P4, wherein $R^1$ is a triphosphate moiety.

Embodiment P7. The compound of any one of embodiments P1 to P6, wherein $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment P8. The compound of any one of embodiments P1 to P6, wherein $B^1$ is

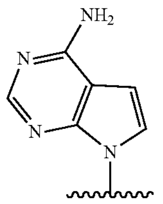

,

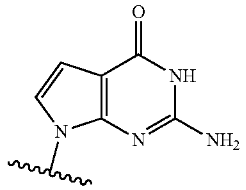

,

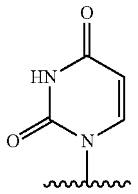

,

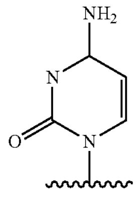

,

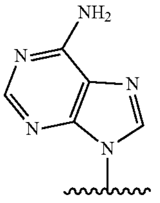

,

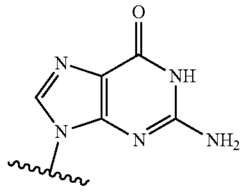

, or

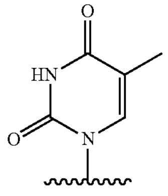

.

Embodiment P9. The compound of any one of embodiments P1 to P6, wherein $B^1$ is

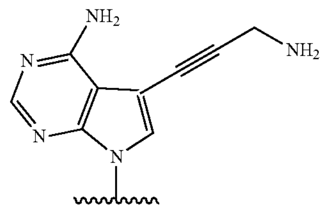

,

-continued

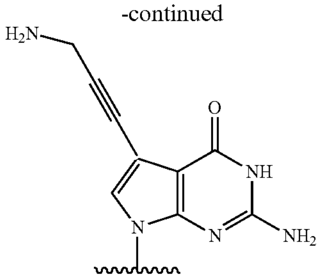

,

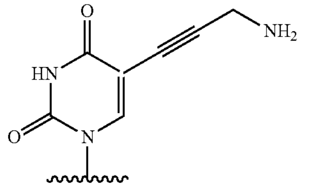

,

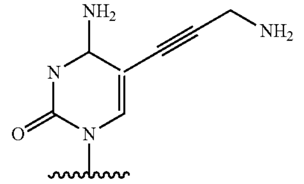

,

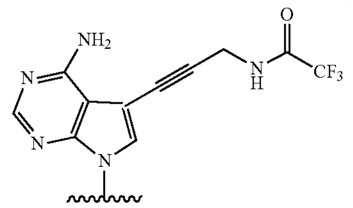

,

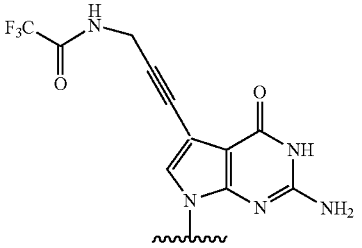

,

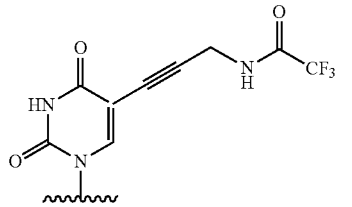

, or

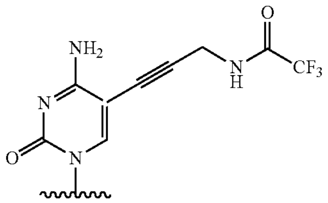

.

Embodiment P10. The compound of any one of embodiments P1 to P6, wherein $B^1$ is —B-$L^{100}$-$R^4$; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, $L^{100}$ is a divalent linker; and $R^4$ is a detectable moiety.

Embodiment P11. The compound of embodiment P10, wherein B is

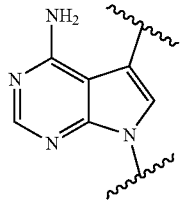

,

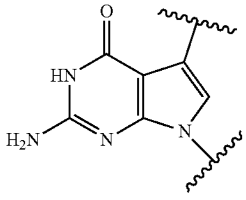

,

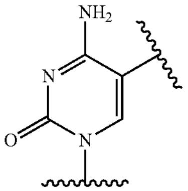

, or

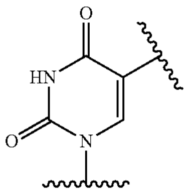

.

Embodiment P12. The compound of embodiment P10 or P11, wherein $L^{100}$ is $-L^{101}-L^{102}-L^{103}-L^{104}-L^{105}-$; $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P13. The compound of embodiment P10 or P11, wherein $L^{100}$ is $-L^{101}-O-CH(-SR^{100})-L^{103}-L^{104}-L^{105}-$, $-L^{101}-O-C(CH_3)(-SR^{100})-L^{103}-L^{104}-L^{105}-$, $-L^{101}-O-CH(N_3)-L^{103}-L^{104}-L^{105}-$, or $-L^{101}-O-CH(N_3)-CH_2-O-L^{104}-L^{105}-$; $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{100}$ is $-SR^{102}$ or —CN; and $R^{102}$ is unsubstituted $C_1$-$C_4$ alkyl.

Embodiment P14. The compound of embodiment P10 or P11, wherein $L^{100}$ is

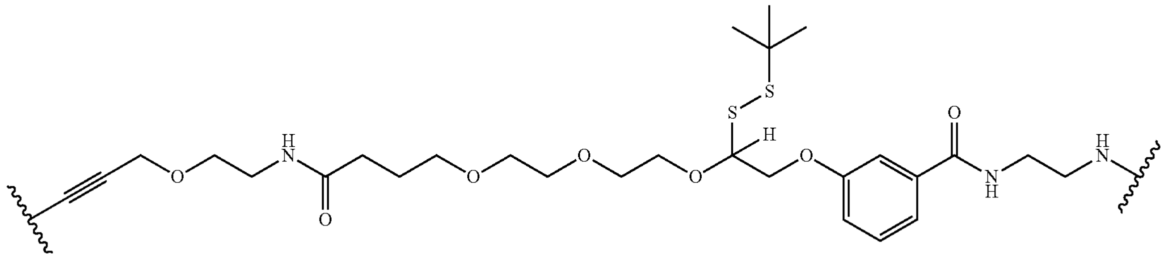

,

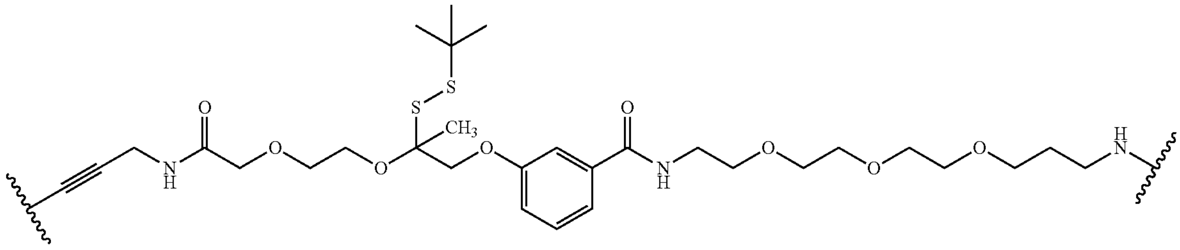

,

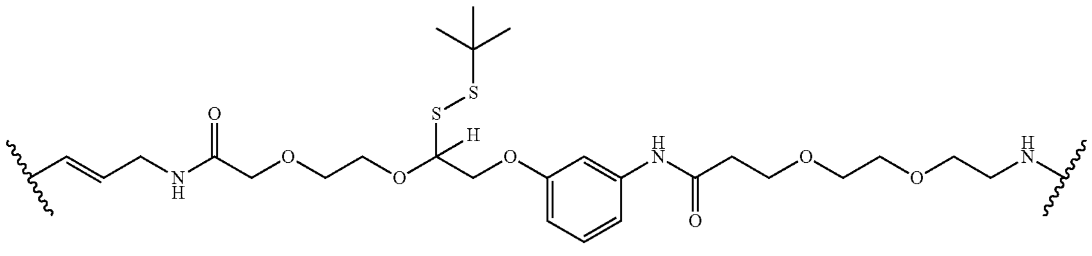

,

-continued
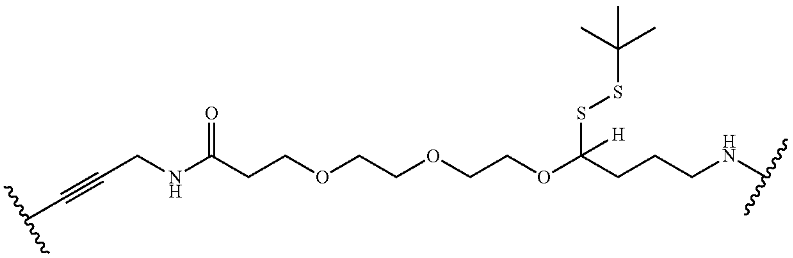
,
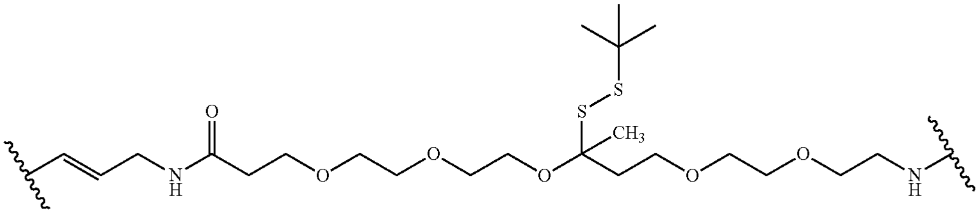
,
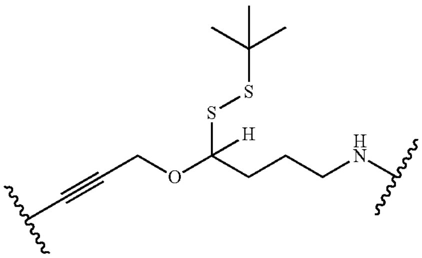
,
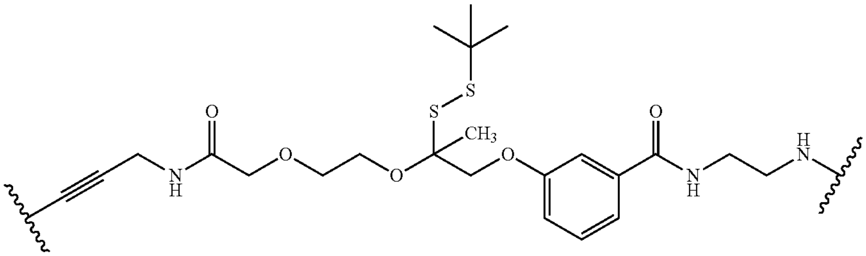
,
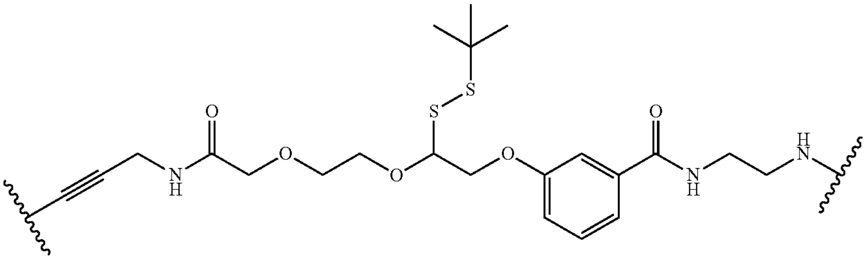
,
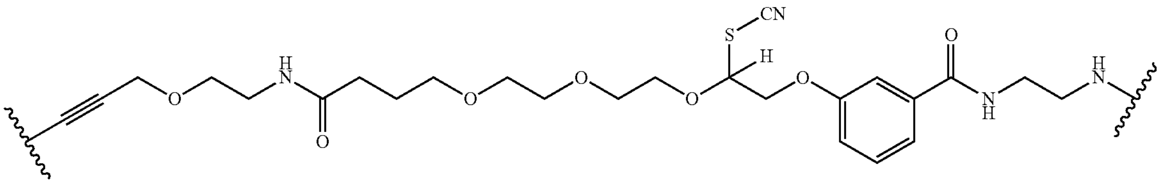
,
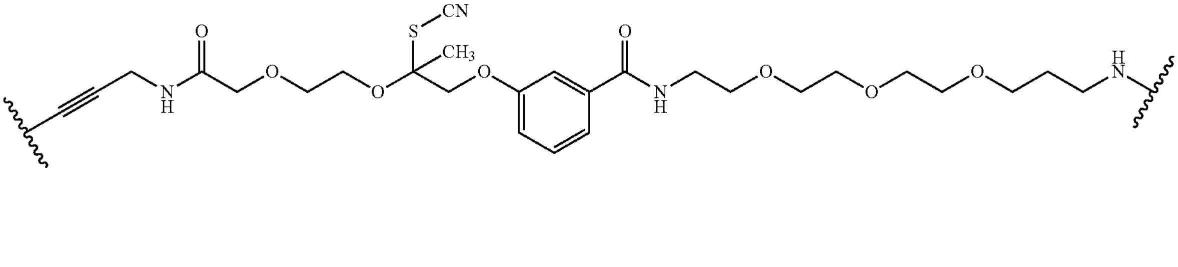
, -continued
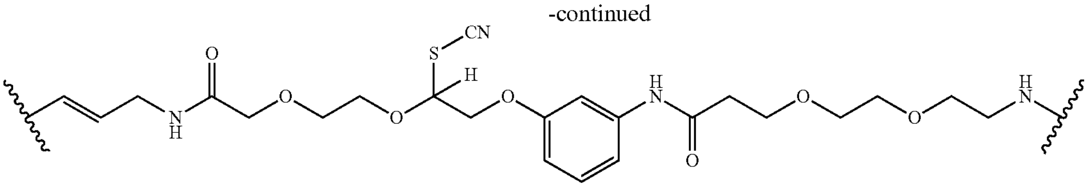
,
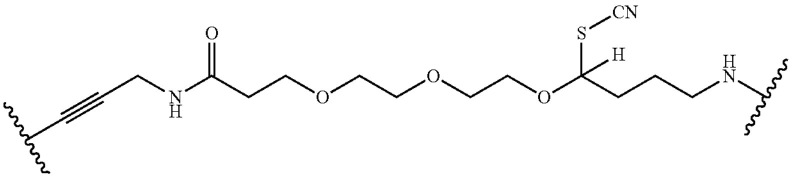
,
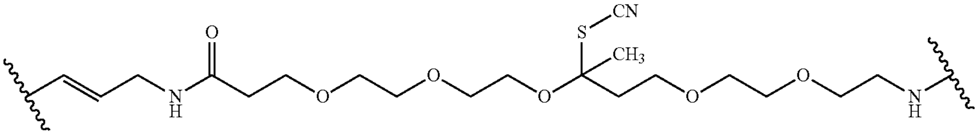
,
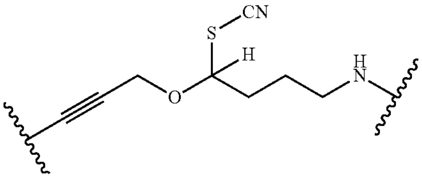
,
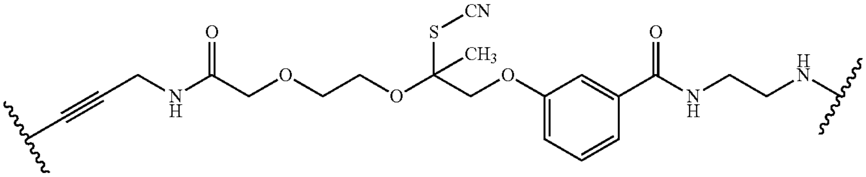
, or
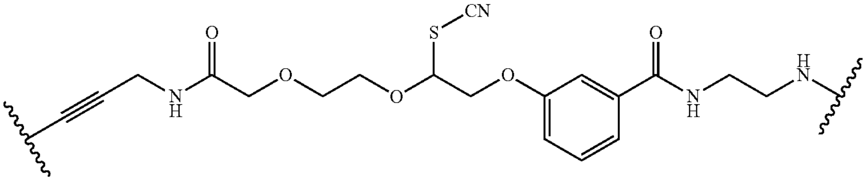
.
Embodiment P15. The compound of embodiment P10 or P11, wherein $L^{100}$ is
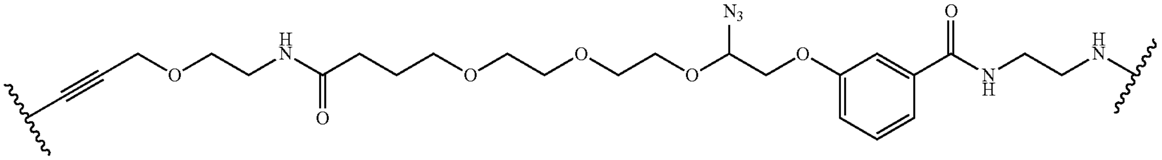
,
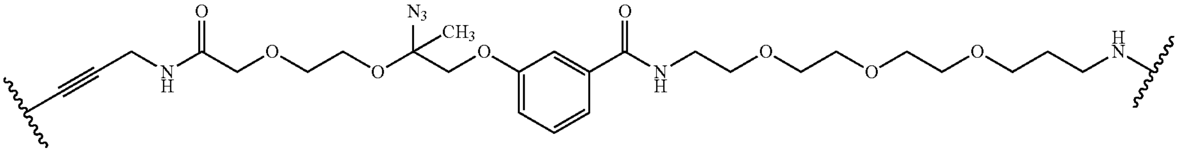
,
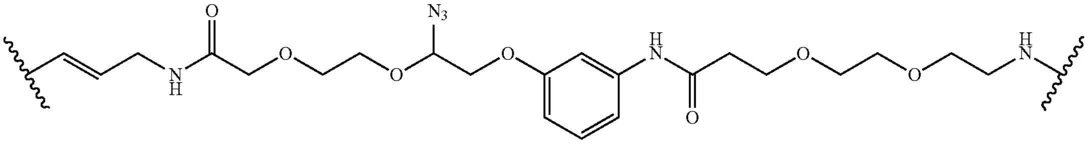
, -continued
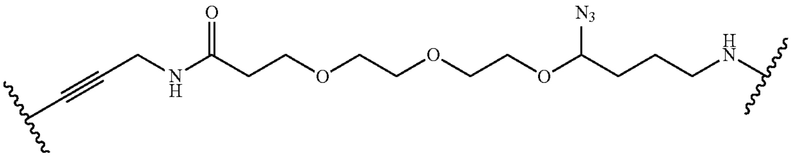
,
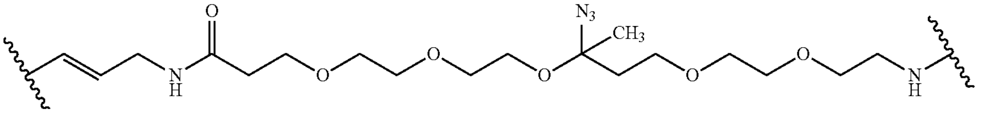
,
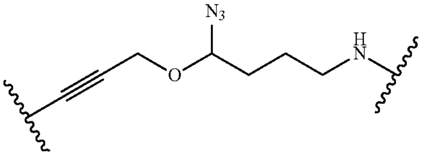
,
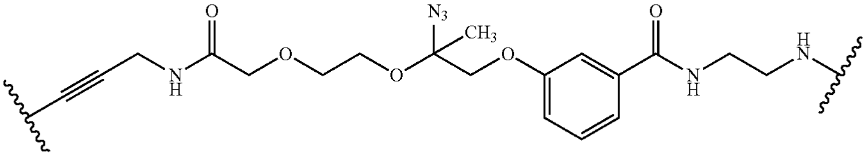
,
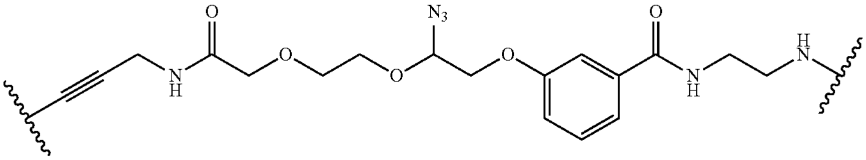
.
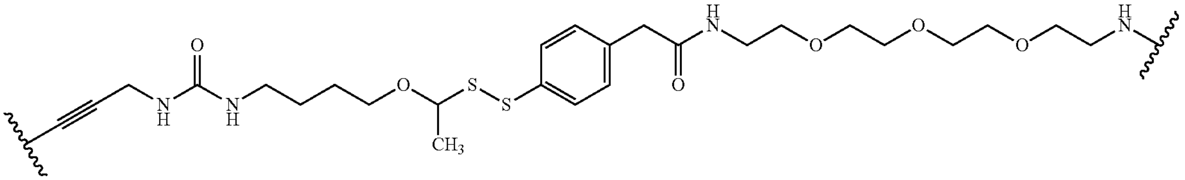
,
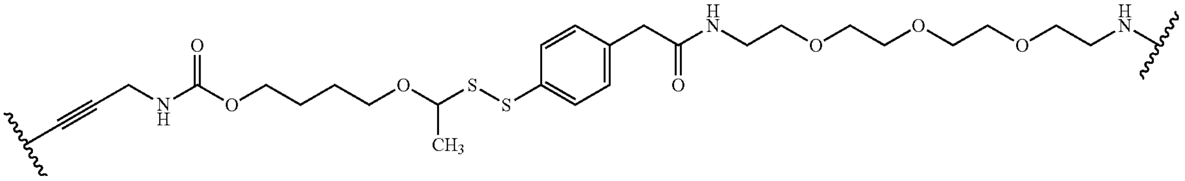
,
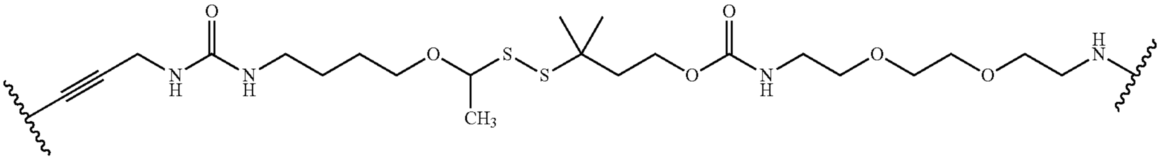
,
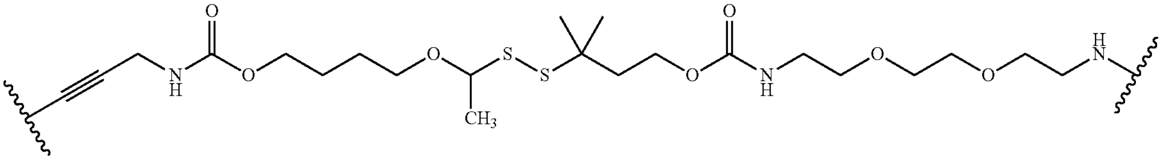
,
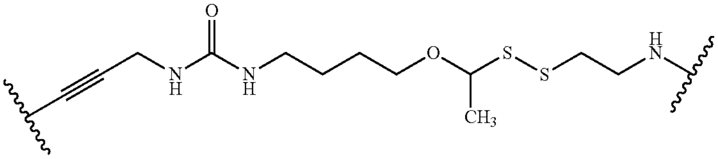
, -continued
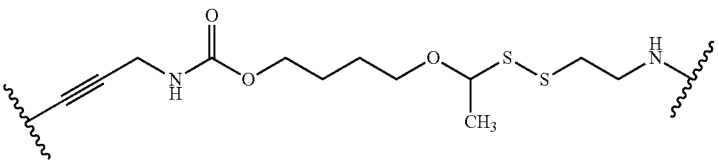,
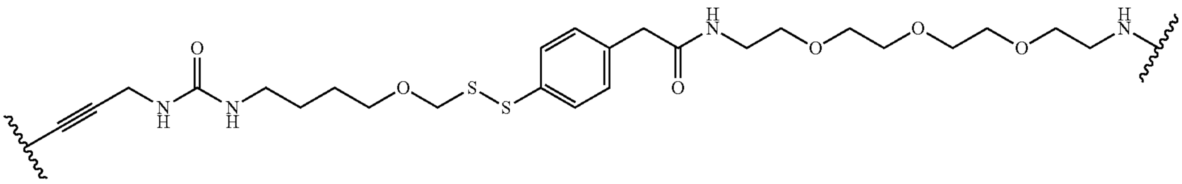,
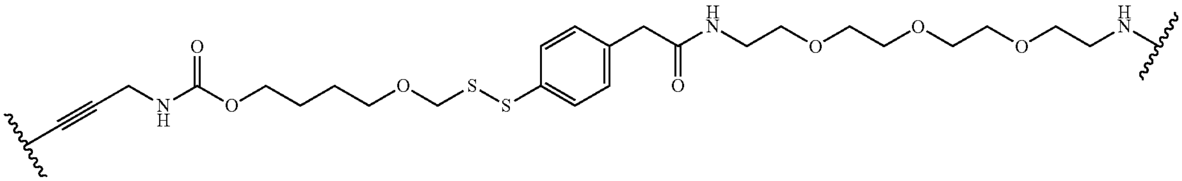,
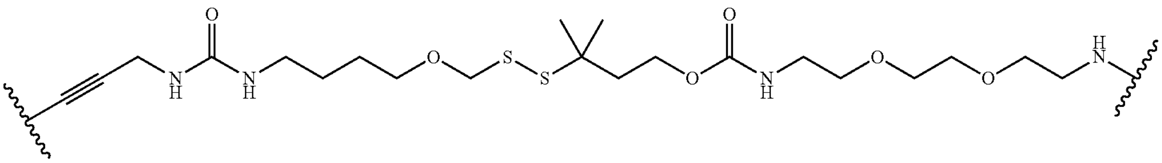,
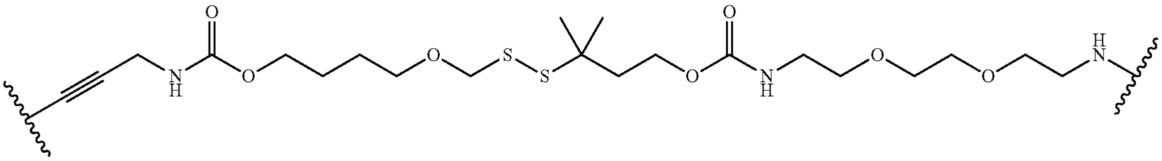,
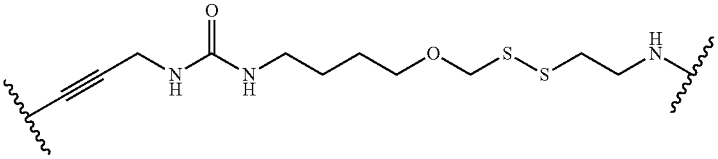,
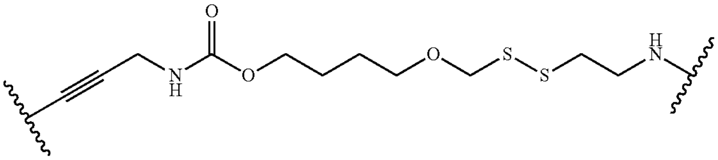,
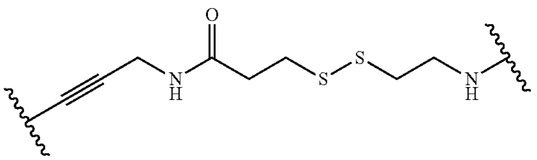, 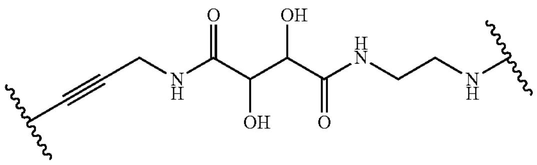,
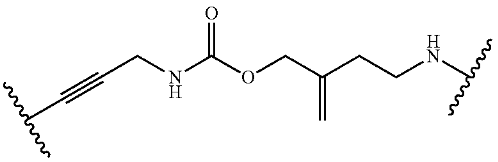, -continued
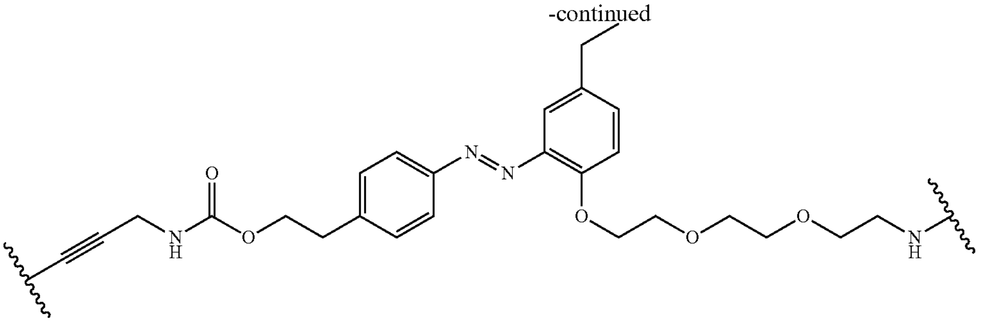
, or
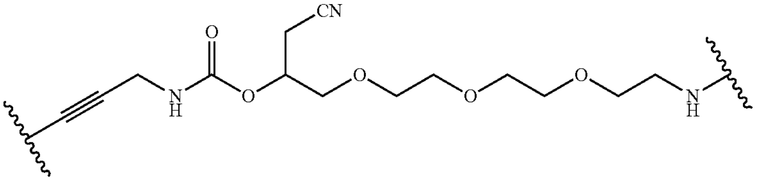
.
Embodiment P16. The compound of any one of embodiments P1 to P15, wherein $R^4$ is
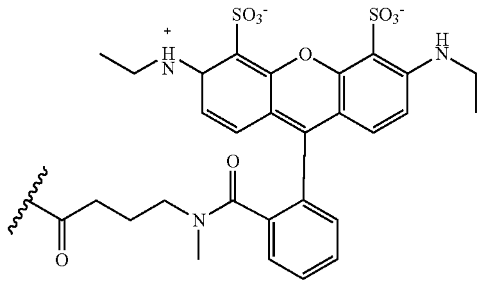
,
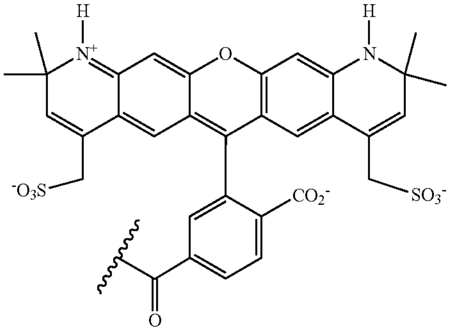
,
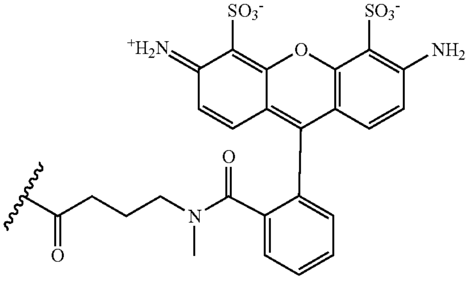
, or
-continued
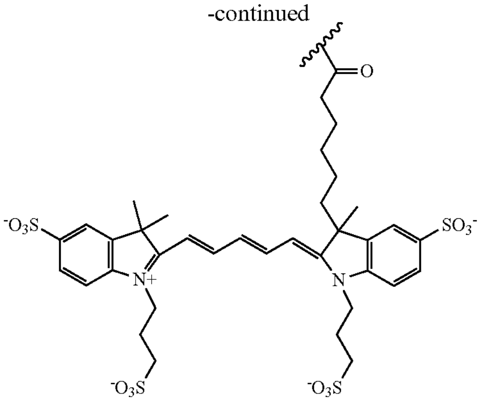
.
Embodiment P17. The compound of embodiment P10, having the formula:
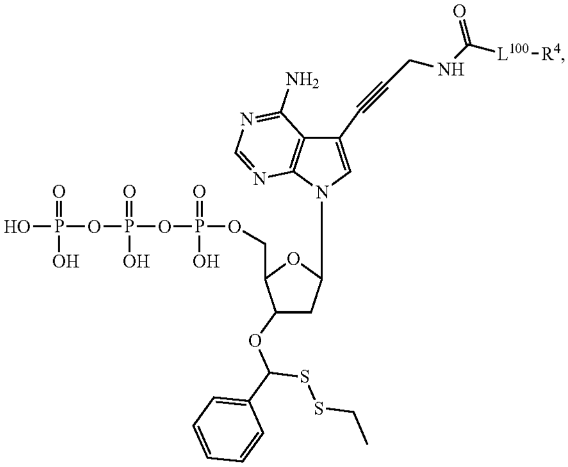
$L^{100}$-$R^4$, -continued

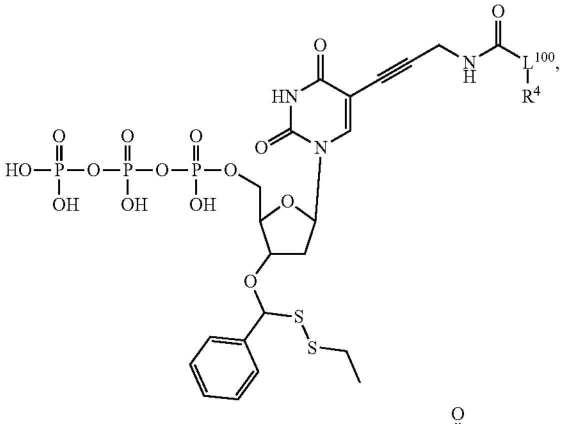

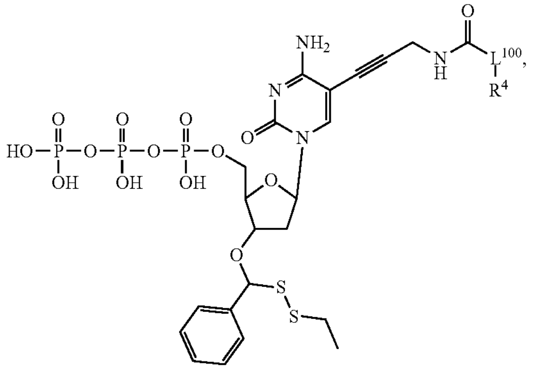

or

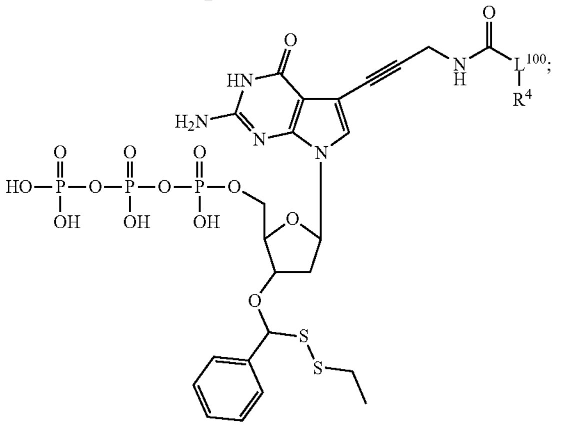

wherein $L^{100}$ is a cleavable linker.

Embodiment P18. A method for sequencing a nucleic acid, comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label; (ii) detecting said unique detectable label of each incorporated compound, so as to thereby identify each incorporated compound in said extension strand, thereby sequencing the nucleic acid; wherein each of said four different compounds is independently a compound of any one of embodiments P1 to P17.

Embodiment P19. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of of any one of embodiments P1 to P17.

Embodiment P20. A nucleic acid polymerase complex comprising a nucleic acid polymerase, wherein said nucleic acid polymerase is bound to a compound of any one of embodiments P1 to P17.

Embodiment P21. A compound having the formula:

(II)

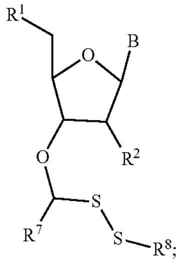

wherein $B^1$ is a nucleobase;

$R^1$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, a 5'-O-nucleoside protecting group, monophosphate moiety, polyphosphate moiety, or nucleic acid moiety;

$R^2$ is independently hydrogen, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety or an —O-polymerase-compatible cleavable moiety; $R^7$ is substituted or unsubstituted aryl, or substituted or unsubstituted heteroaryl; and $R^8$ is unsubstituted $C_1$-$C_6$ alkyl.

Embodiment P22. The compound of embodiment P21, having the formula:

(IIA)

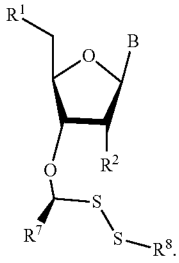

Embodiment P23. The compound of embodiment P21, having the formula:

(IIB)

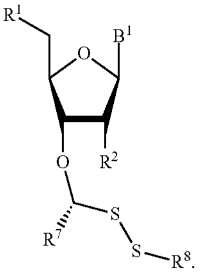

Embodiment P24. The compound of any one of embodiments P21 to P23, wherein $R^2$ is hydrogen.

Embodiment P25. The compound of any one of embodiments P21 to P24, wherein $R^1$ is —OH, a 5'-O-nucleoside protecting group, monophosphate moiety, polyphosphate moiety, or nucleic acid moiety.

Embodiment P26. The compound of any one of embodiments P21 to P24, wherein $R^1$ is a triphosphate moiety.

Embodiment P27. The compound of any one of embodiments P21 to P26, wherein $R^8$ is unsubstituted $C_1$-$C_4$ alkyl.

Embodiment P28. The compound of any one of embodiments P21 to P26, wherein $R^8$ is unsubstituted methyl or unsubstituted ethyl.

Embodiment P29. The compound of any one of embodiments P21 to P28, wherein $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment P30. The compound of any one of embodiments P21 to P28, wherein $B^1$ is

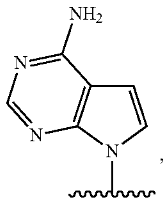

,

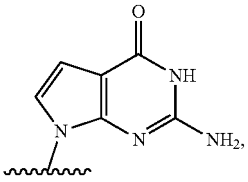

-continued

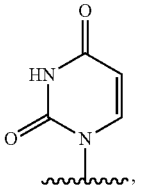

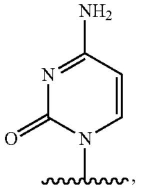

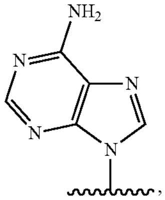

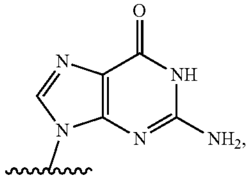

or

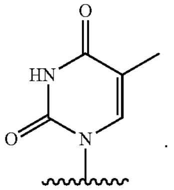

Embodiment P31. The compound of any one of embodiments P21 to P28, wherein $B^1$ is

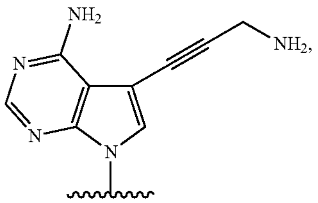

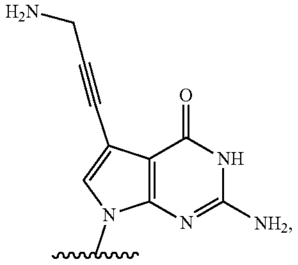

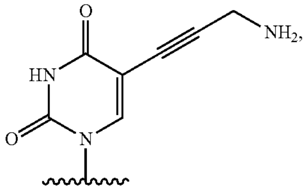

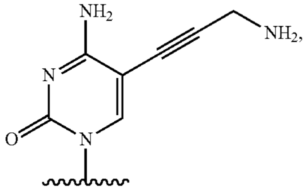

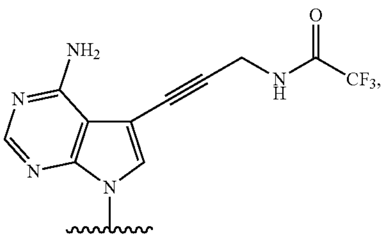

-continued

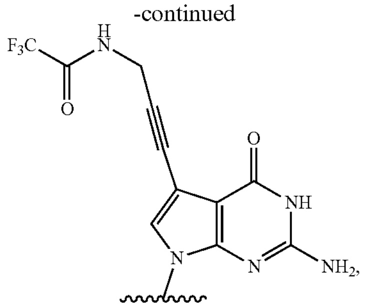

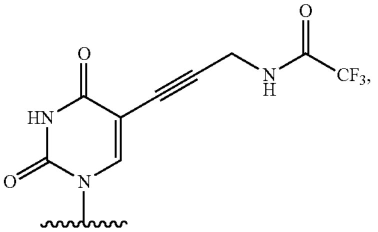

or

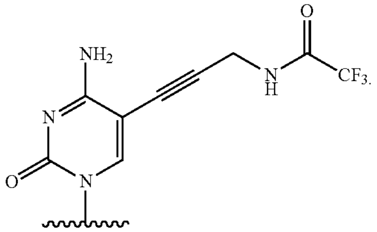

Embodiment P32. The compound of any one of embodiments P21 to P28, wherein $B^1$ is —B-$L^{100}$-$R^4$; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, $L^{100}$ is a divalent linker; and $R^4$ is a detectable moiety.

Embodiment P33. The compound of embodiment P32, wherein B is

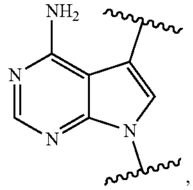

,

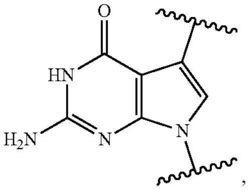

,

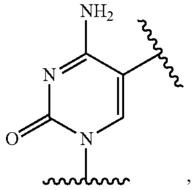

, or

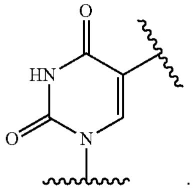

.

Embodiment P34. The compound of embodiment P32 or P33, wherein $L^{100}$ is -$L^{101}$-$L^{102}$-$L^{103}$-$L^{104}$-$L^{105}$-; $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment P35. The compound of embodiment P32 or P33, wherein $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH(N)$L^{103}$-$L^{104}$-$L^{105}$-, or -$L^{101}$-O—CH($N_3$)—$CH_2$—O-$L^{104}$-$L^{105}$-; $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{100}$ is —$SR^{102}$ or —CN; and $R^{102}$ is unsubstituted $C_1$-$C_4$ alkyl.

Embodiment P36. The compound of embodiment P32 or P33, wherein $L^{100}$ is

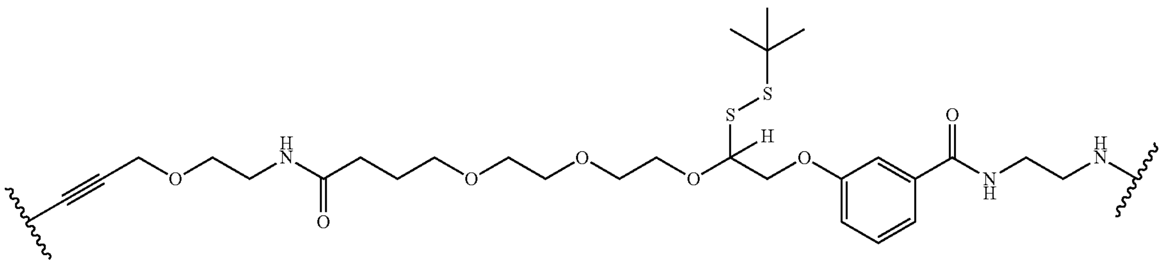

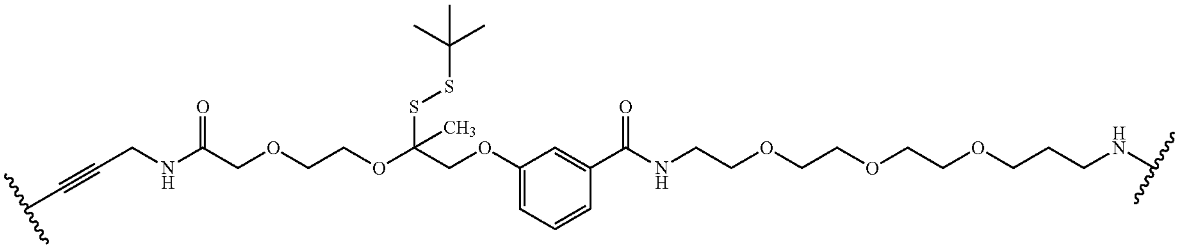

-continued
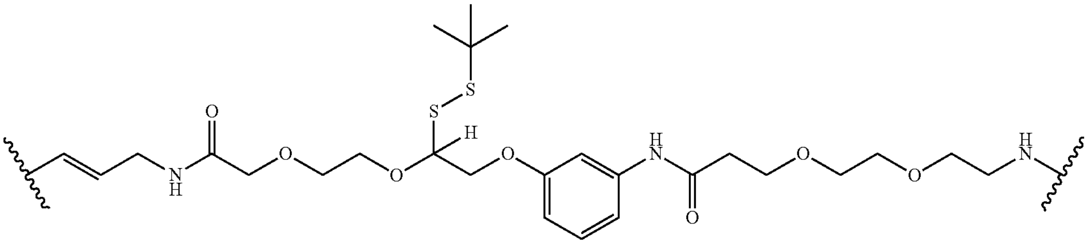
,
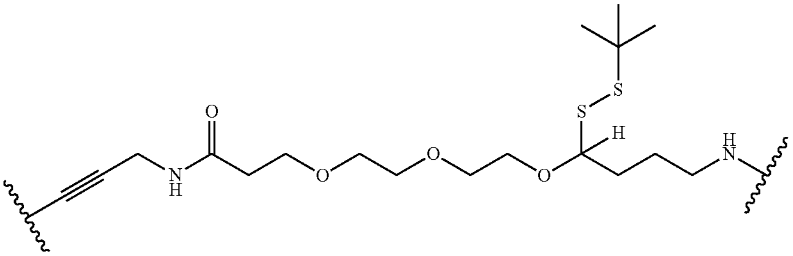
,
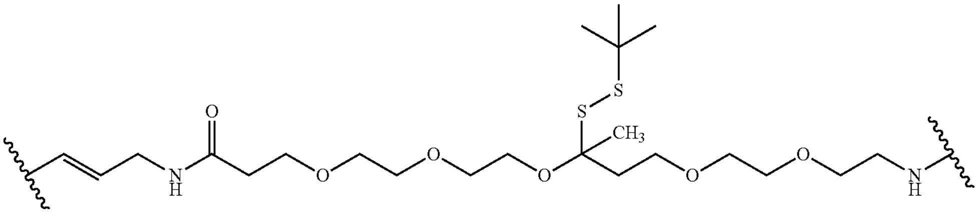
,
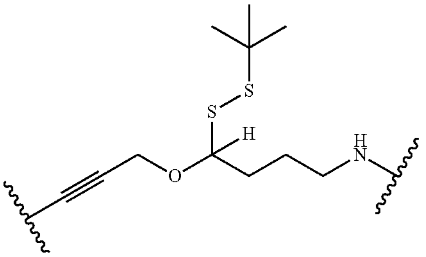
,
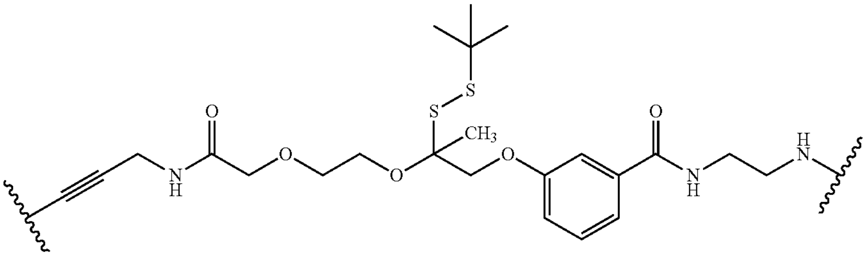
,
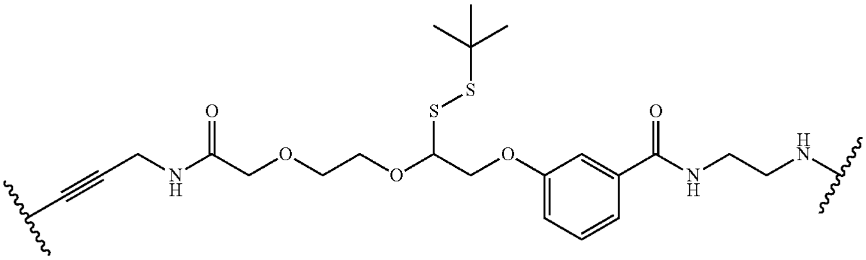
,
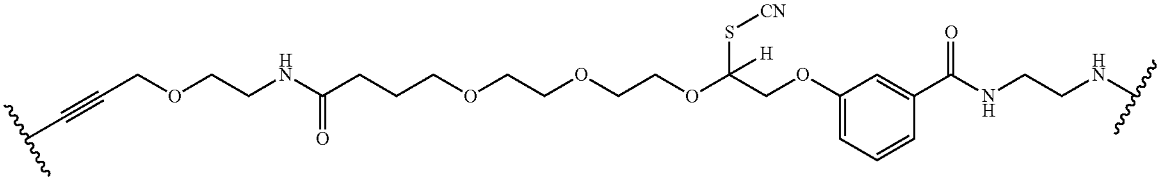
, -continued
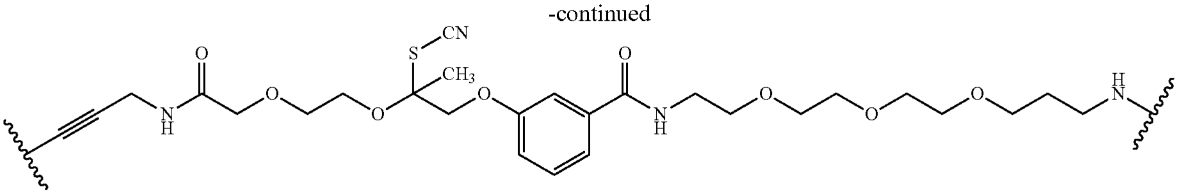,
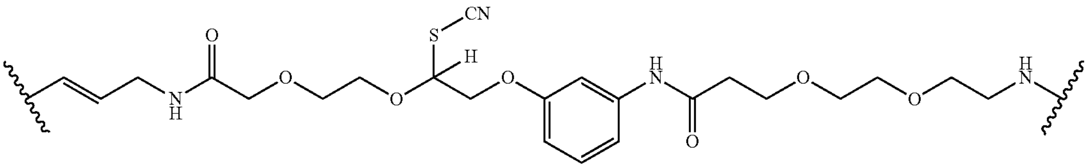,
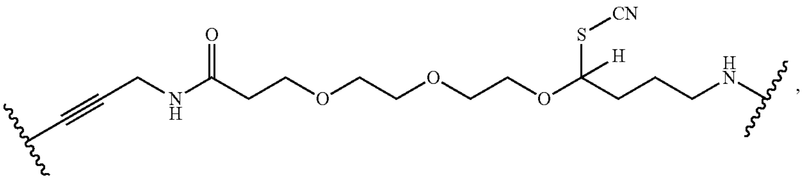,
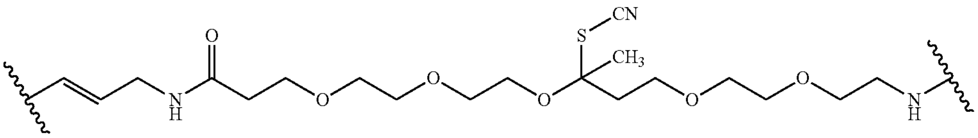,
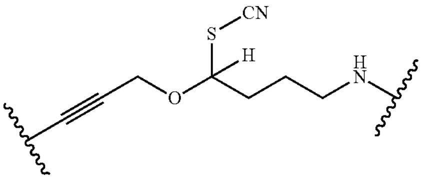,
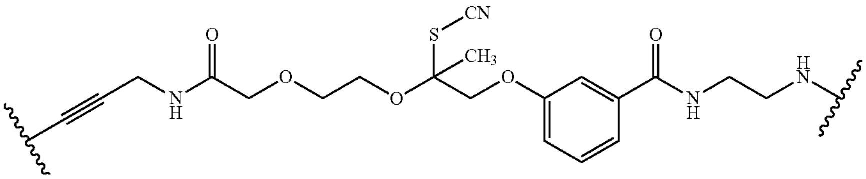, or
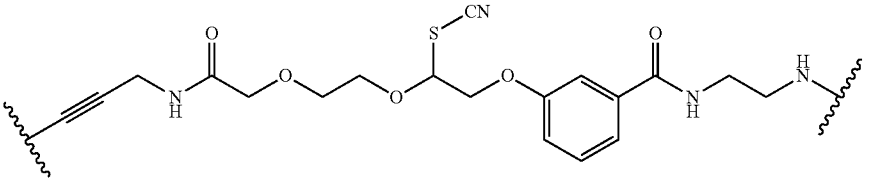.
Embodiment P37. The compound of embodiment P32 or P33, wherein $L^{100}$ is
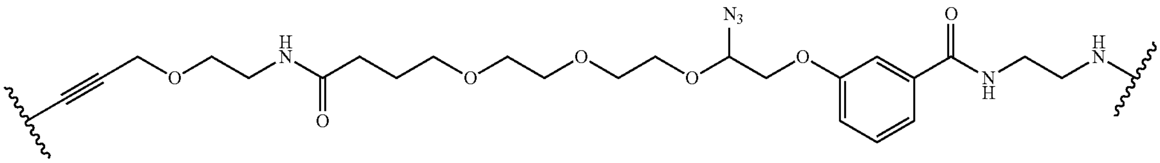,
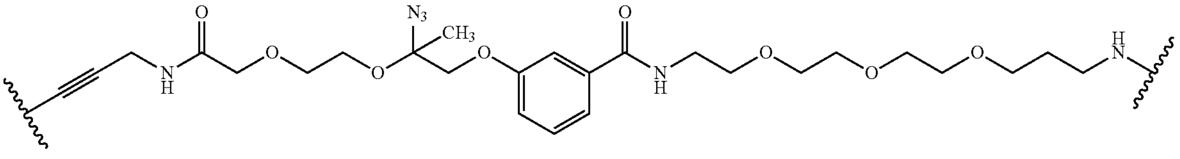, -continued
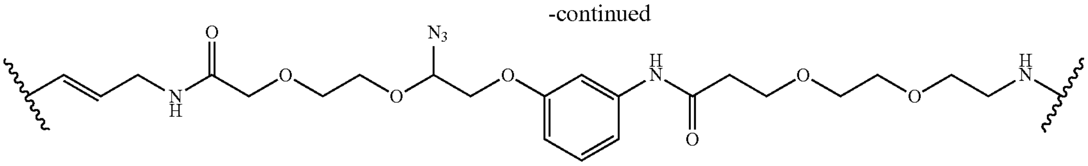
,
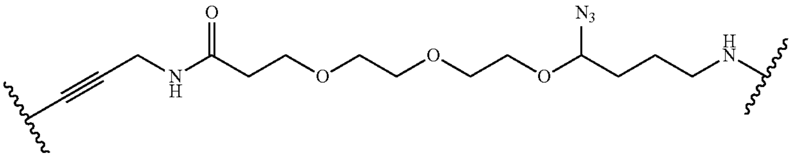
,
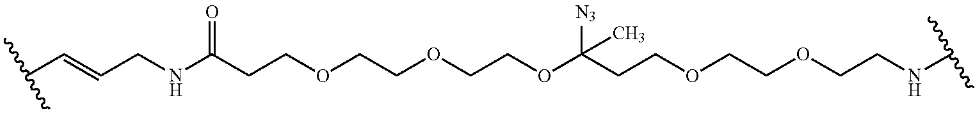
,
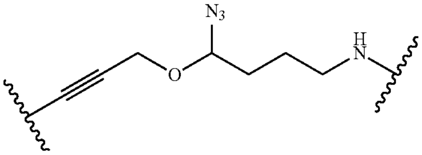
,
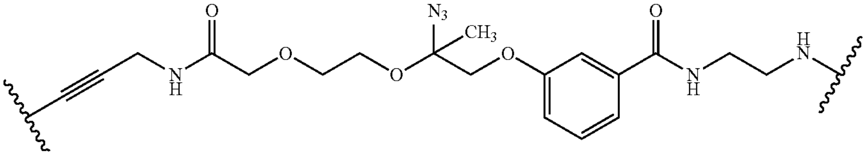
,
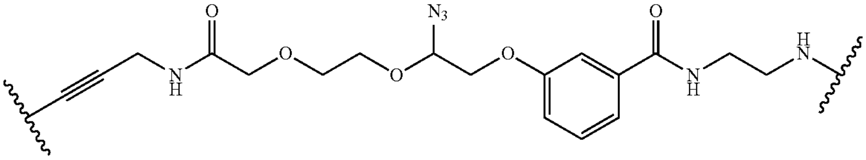
.
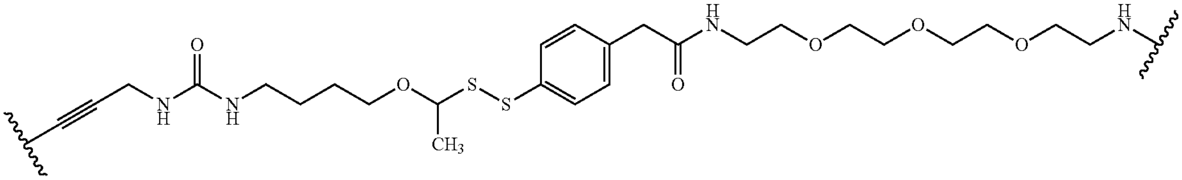
,
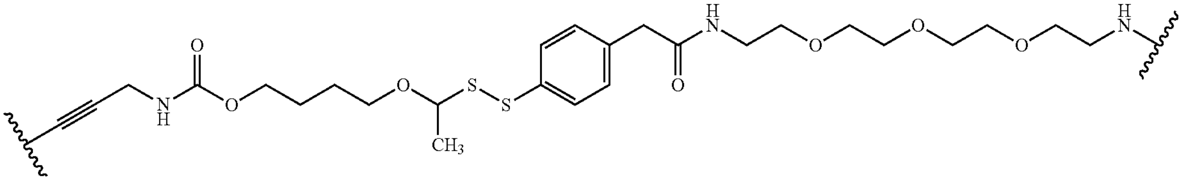
,
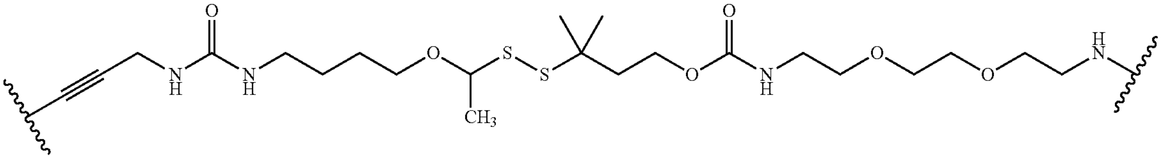
,
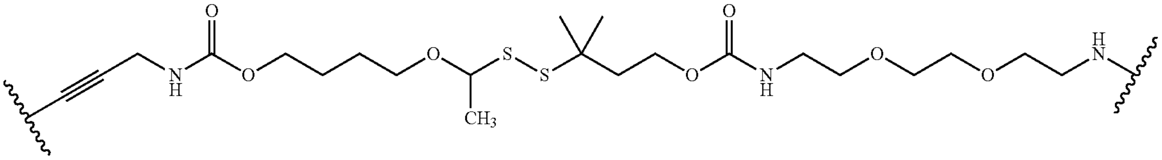
,
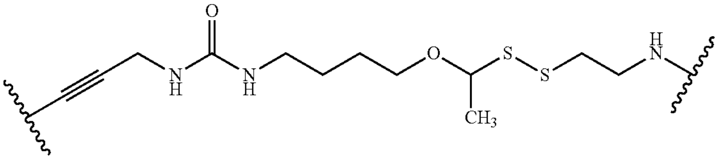
, -continued
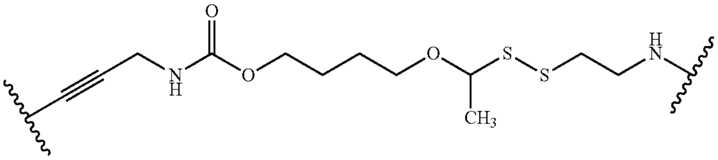,
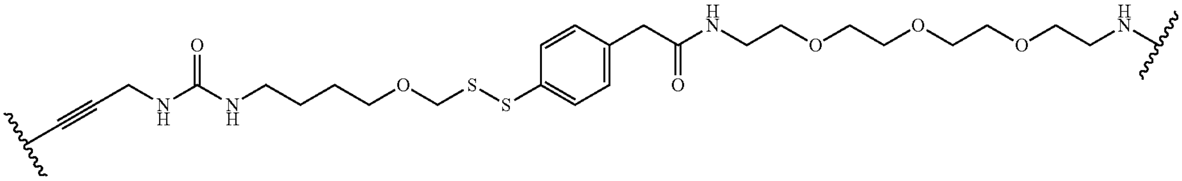,
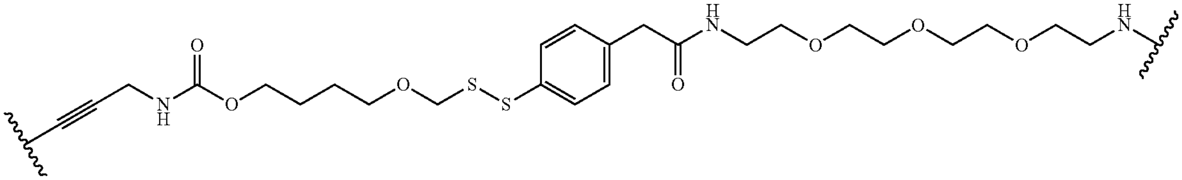,
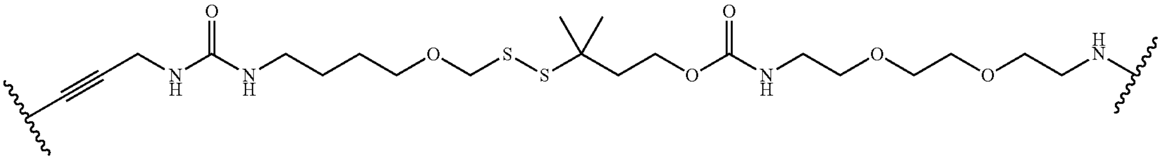,
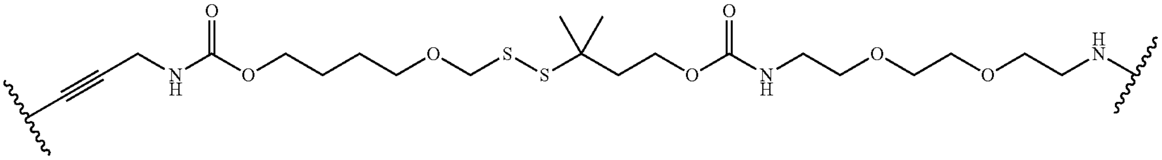,
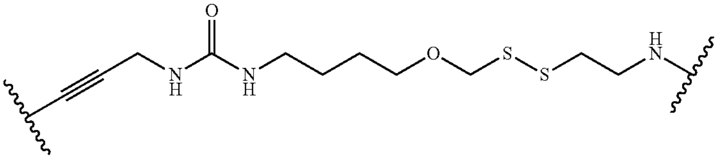,
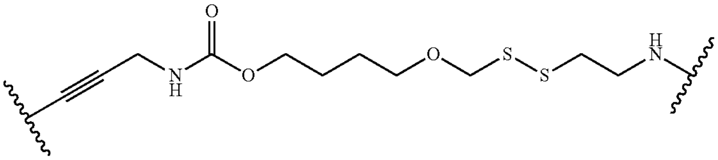,
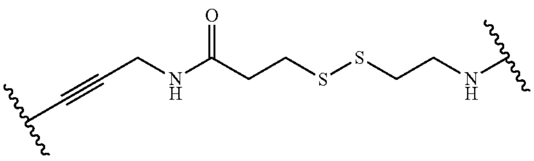, 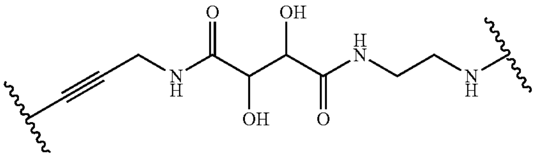,
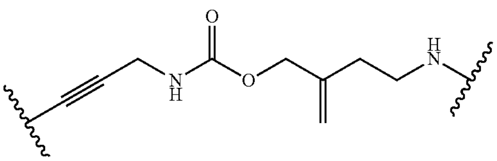, -continued

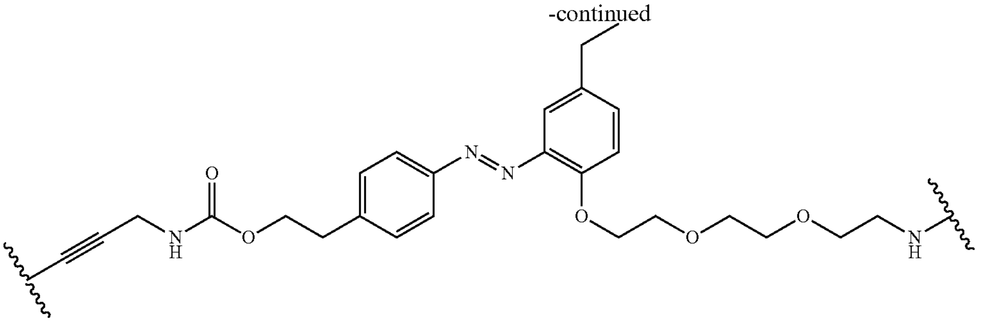

, or

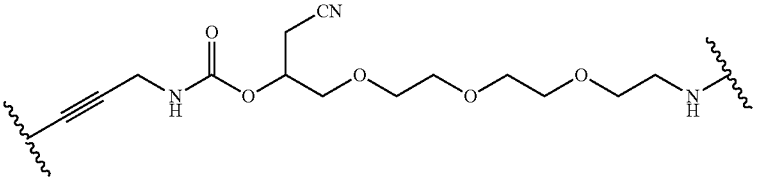

.

Embodiment P38. The compound of any one of embodiments P21 to P37, wherein $R^7$ is substituted or unsubstituted aryl.

Embodiment P39. The compound of any one of embodiments P21 to P37, wherein $R^7$ is unsubstituted aryl.

Embodiment P40. The compound of any one of embodiments P21 to P37, wherein $R^7$ is unsubstituted phenyl.

Embodiment P41. The compound of any one of embodiments P21 to P37, wherein $R^7$ is substituted or unsubstituted heteroaryl.

Embodiment P42. The compound of any one of embodiments P21 to P37, wherein $R^7$ is substituted or unsubstituted 5 to 6 membered heteroaryl.

Embodiment P43. The compound of embodiment P32, having the formula:

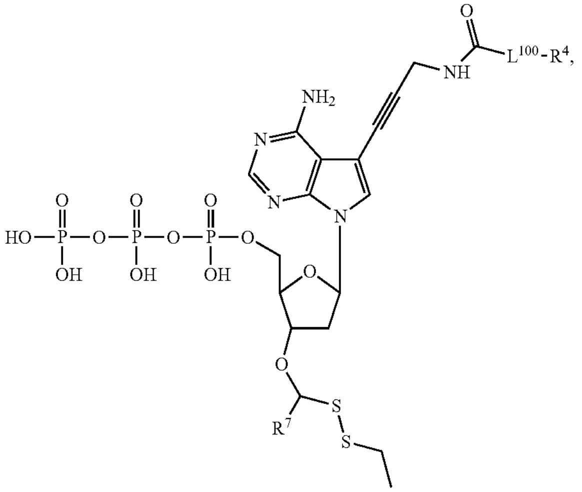

-continued

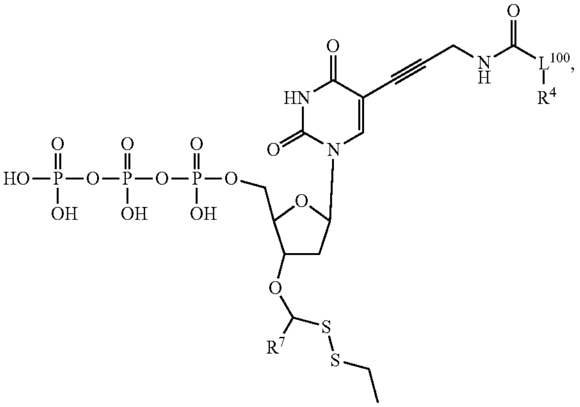

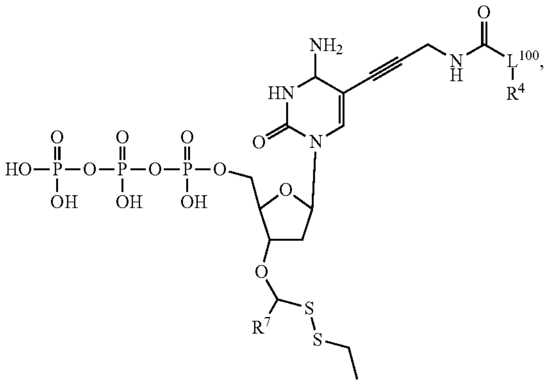

or

-continued

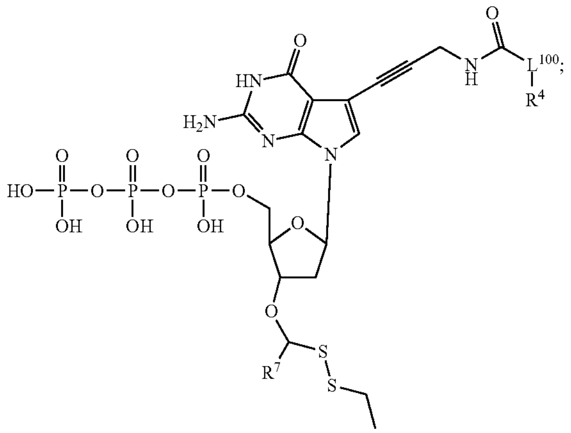

wherein $L^{100}$ is a cleavable linker.

Embodiment P44. The compound of embodiment P43, wherein $R^7$ is substituted or unsubstituted aryl.

Embodiment P45. The compound of embodiment P43, wherein $R^7$ is substituted or unsubstituted heteroaryl.

Embodiment P46. The compound of embodiment P32, having the formula:

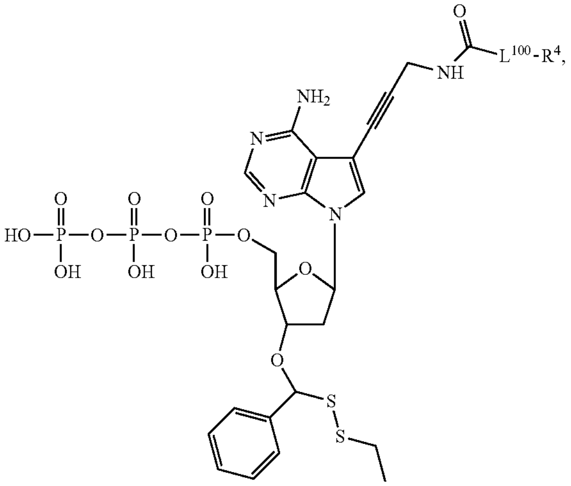

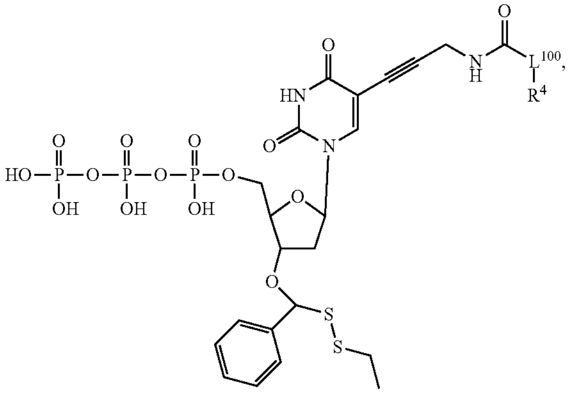

-continued

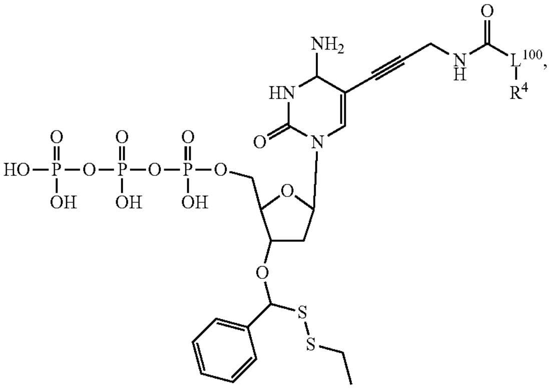

or

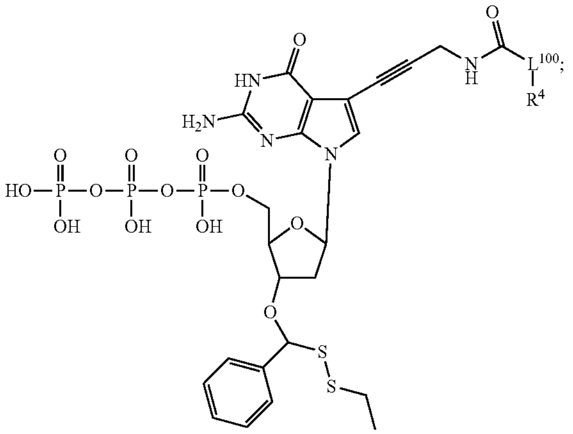

wherein $L^{100}$ is a cleavable linker.

Embodiment P47. The compound of embodiment P32, having the formula:

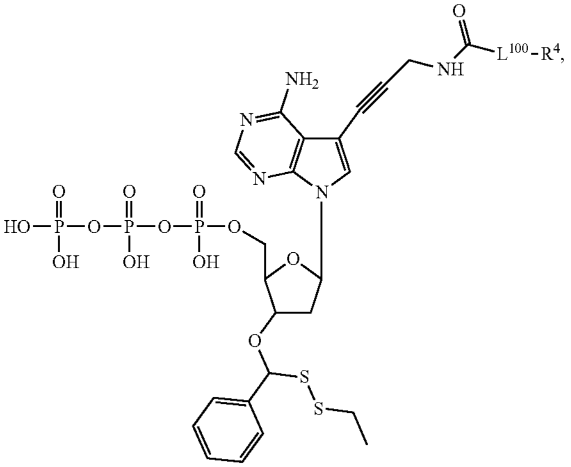

-continued

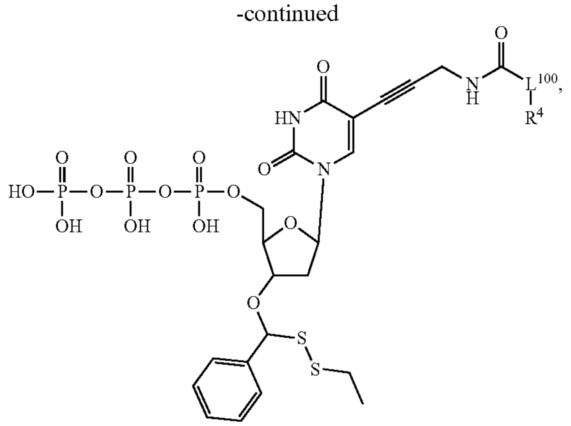

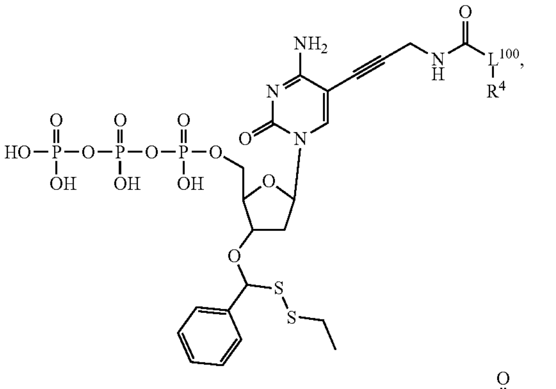

or

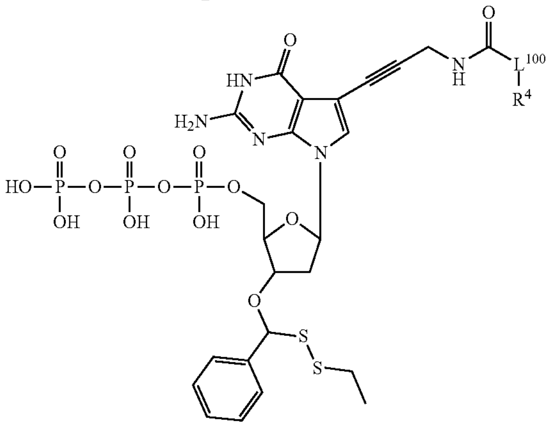

wherein $L^{100}$ is a cleavable linker.

Embodiment P48. A method for sequencing a nucleic acid, comprising: (i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label; (ii) detecting said unique detectable label of each incorporated compound, so as to thereby identify each incorporated compound in said extension strand, thereby sequencing the nucleic acid; wherein each of said four different compounds is independently a compound of any one of embodiments P21 to P47.

Embodiment P49. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of any one of embodiments P21 to P47.

Embodiment P50. A nucleic acid polymerase complex comprising a nucleic acid polymerase, wherein said nucleic acid polymerase is bound to a compound of any one of embodiments P21 to P47.

ADDITIONAL EMBODIMENTS

Embodiment 1. A compound having the formula:

(II)

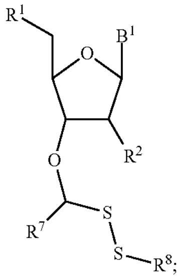

wherein $B^1$ is a nucleobase; $R^1$ is independently a polyphosphate moiety, 5'-O-nucleoside protecting group, monophosphate moiety, nucleic acid moiety, hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is independently hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or a polymerase-compatible cleavable moiety; $R^7$ is unsubstituted or substituted aryl, or substituted or unsubstituted heteroaryl; and $R^8$ is unsubstituted $C_1$-$C_6$ alkyl.

Embodiment 2. The compound of Embodiment 1, having the formula:

(IIA)

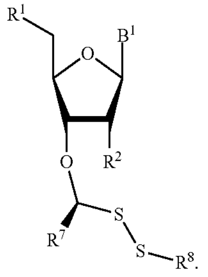

Embodiment 3. The compound of Embodiment 1, having the formula:

(IIB)

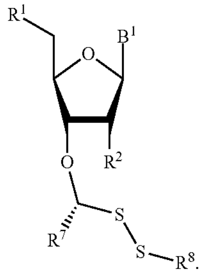

Embodiment 4. The compound of any one of Embodiments 1 to 3, wherein $R^2$ is hydrogen.

Embodiment 5. The compound of any one of Embodiments 1 to 4, wherein $R^1$ is —OH, a 5'-O-nucleoside protecting group, monophosphate moiety, polyphosphate moiety, or nucleic acid moiety.

Embodiment 6. The compound of any one of Embodiments 1 to 4, wherein $R^1$ is a triphosphate moiety.

Embodiment 7. The compound of any one of Embodiments 1 to 6, wherein $R^8$ is unsubstituted $C_1$-$C_4$ alkyl.

Embodiment 8. The compound of any one of Embodiments 1 to 6, wherein $R^8$ is unsubstituted methyl or unsubstituted ethyl.

Embodiment 9. The compound of any one of Embodiments 1 to 8, wherein $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

Embodiment 10. The compound of any one of Embodiments 1 to 8, wherein $B^1$ is

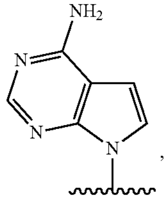
,
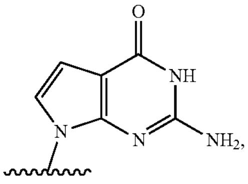

-continued

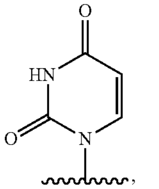
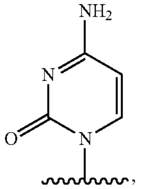
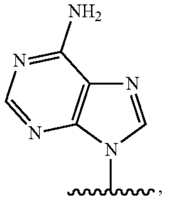
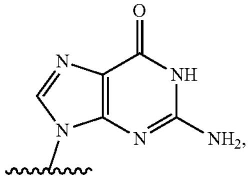
or
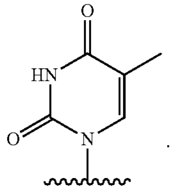

Embodiment 11. The compound of any one of Embodiments 1 to 8, wherein $B^1$ is

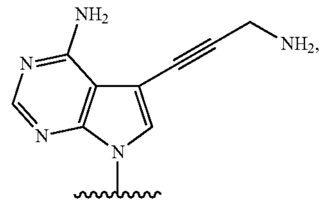
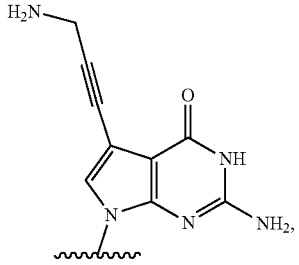
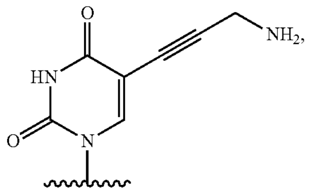
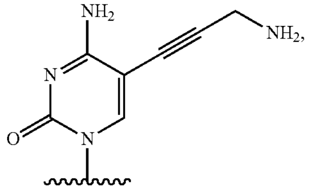
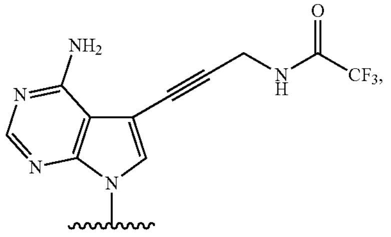

-continued

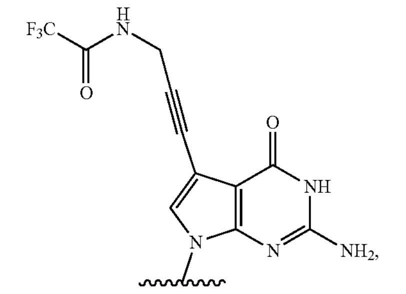

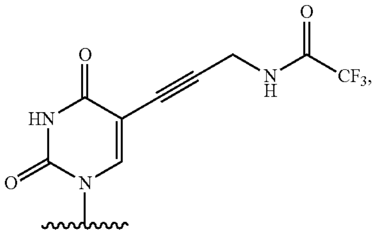 or

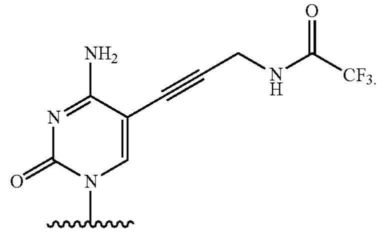

Embodiment 12. The compound of any one of Embodiments 1 to 8, wherein $B^1$ is —B-$L^{100}$-$R^4$; B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof, $L^{100}$ is a divalent linker; and $R^4$ is a detectable moiety.

Embodiment 13. The compound of Embodiment 12, wherein B is

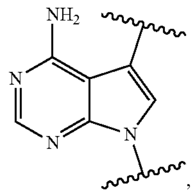,

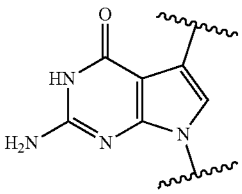,

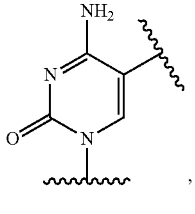, or

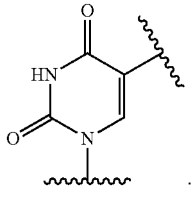.

Embodiment 14. The compound of Embodiment 12 or 13, wherein $L^{100}$ is a divalent linker comprising

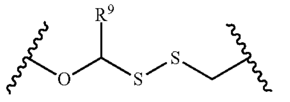 or

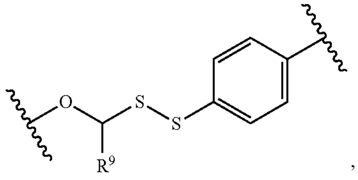, wherein, $R^9$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 15. The compound of Embodiment 12 or 13, wherein $L^{100}$ is a divalent linker comprising

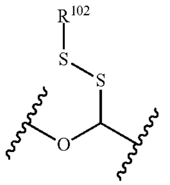 or

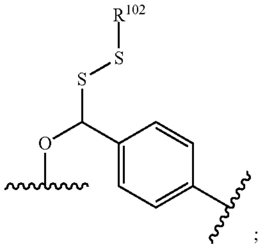;

wherein, $R^{102}$ is unsubstituted $C_1$-$C_4$ alkyl.

Embodiment 16. The compound of Embodiments 12 or 13, wherein $L^{100}$ is -$L^{101}$-$L^{102}$-$L^{103}$-$L^{104}$-$L^{105}$-; $L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

Embodiment 17. The compound of Embodiments 12 or 13, wherein $L^{100}$ is -$L^{101}$-O—CH(—$SR^{100}$)-$L^{103}$-$L^{104}$-$L^{105}$-, -$L^{101}$-O—C($CH_3$)(—$SR^{100}$)-$L^{103}$-$L^{104}$-$L^{105}$-, -$L^{101}$-O—CH($N_3$)-$L^{03}$-$L^{104}$-$L^{105}$-, or -$L^{101}$-O—CH($N_3$)—$CH_2$—O-$L^{104}$-$L^{105}$-; $L^{101}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^{100}$ is —$SR^{102}$ or —CN; and $R^{102}$ is unsubstituted $C_1$-$C_4$ alkyl.

Embodiment 18. The compound of Embodiment 16, wherein $L^{100}$ is

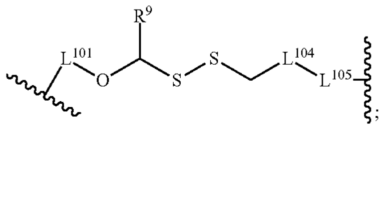;

-continued
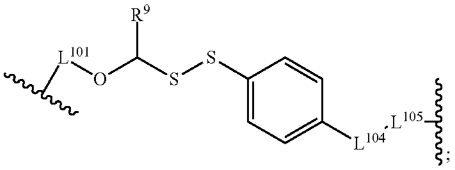
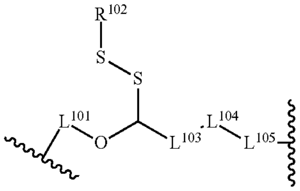
; or
-continued
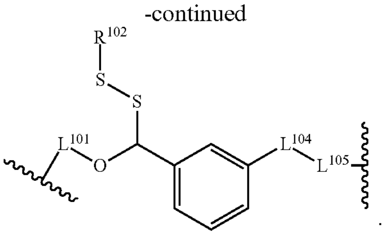
Embodiment 19. The compound of Embodiment 16, wherein $L^{100}$ is
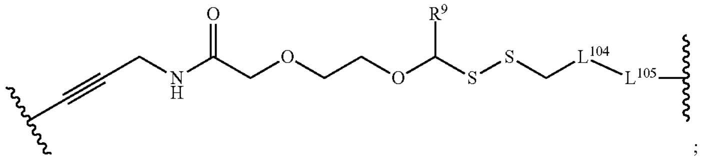
;
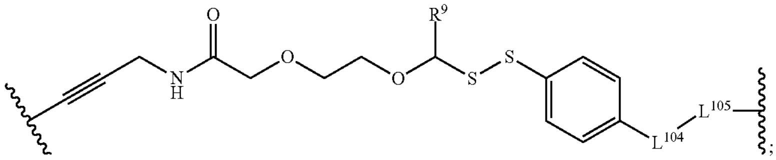
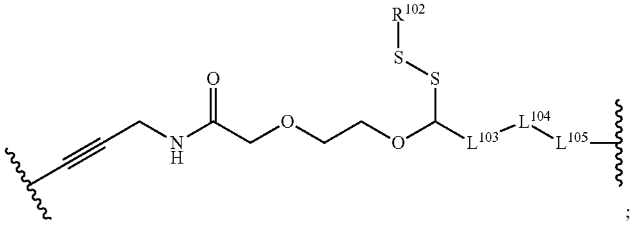
; or
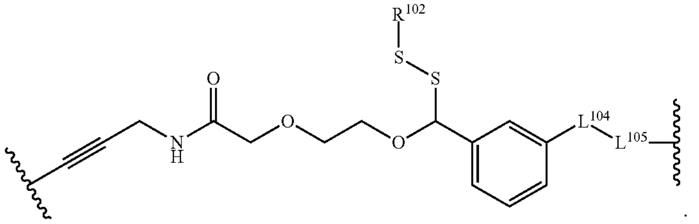
Embodiment 20. The compound of Embodiment 12 or 13, wherein $L^{100}$ is
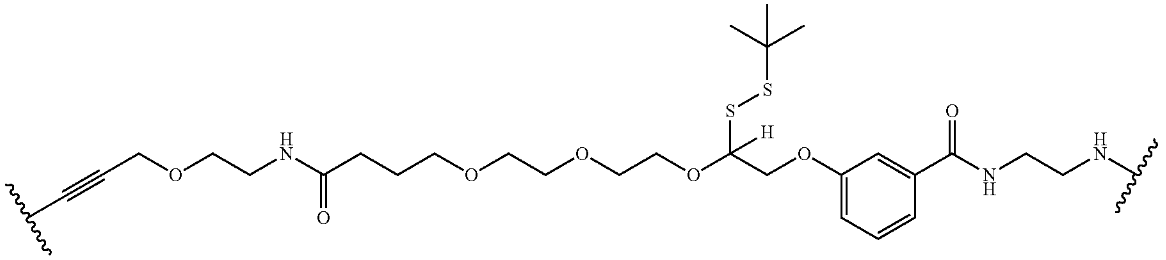
, -continued
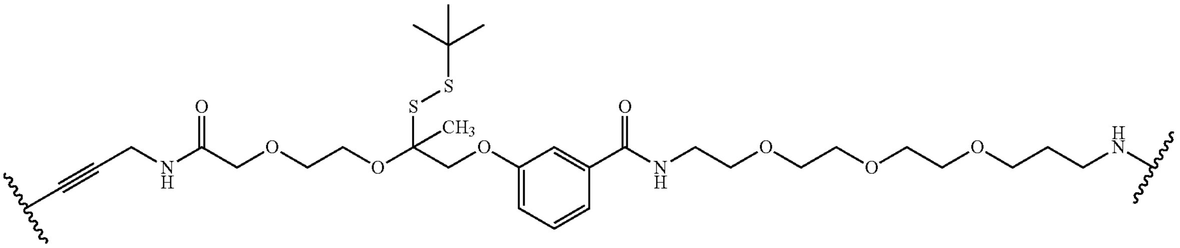
,
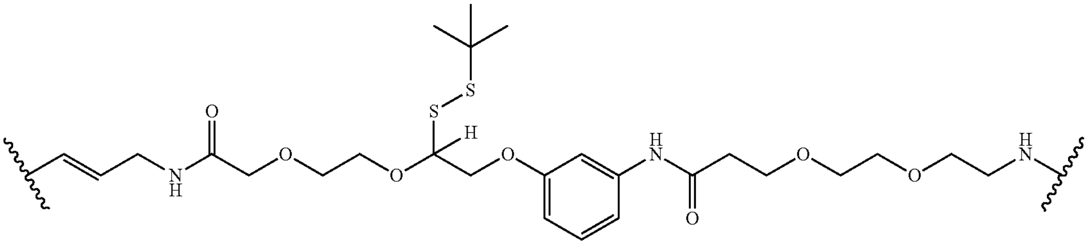
,
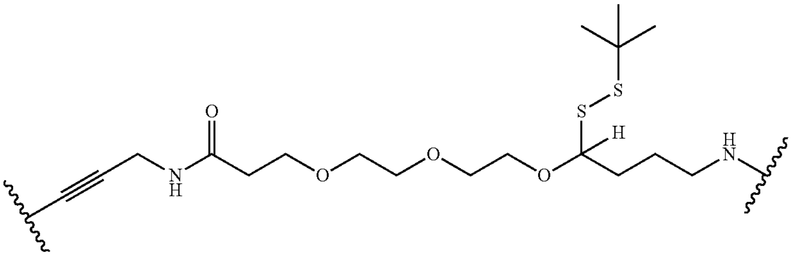
,
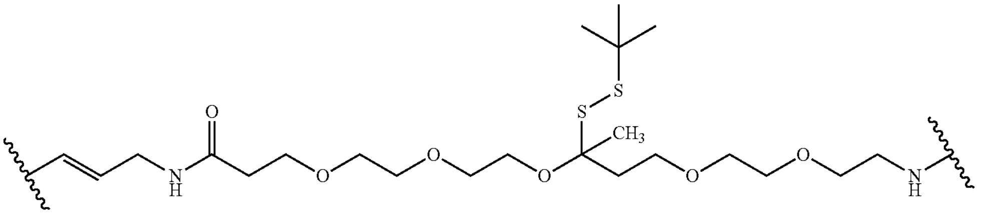
,
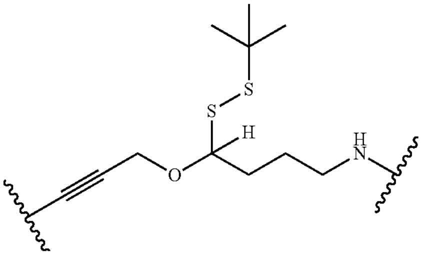
,
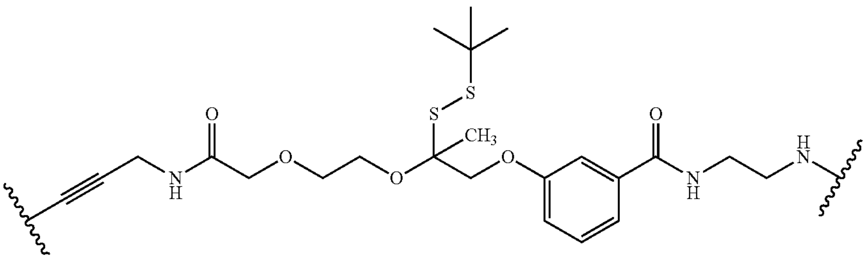
, -continued
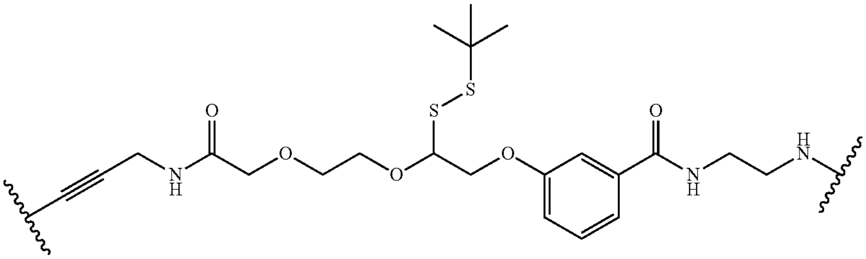
,
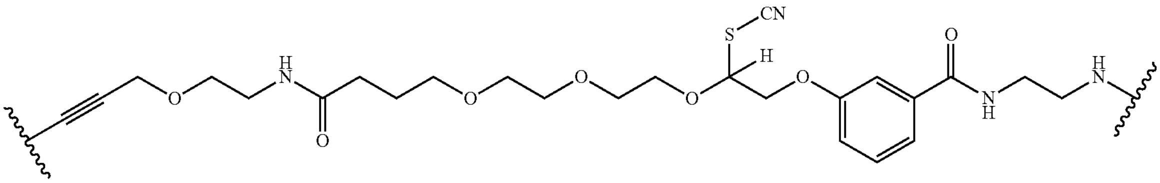
,
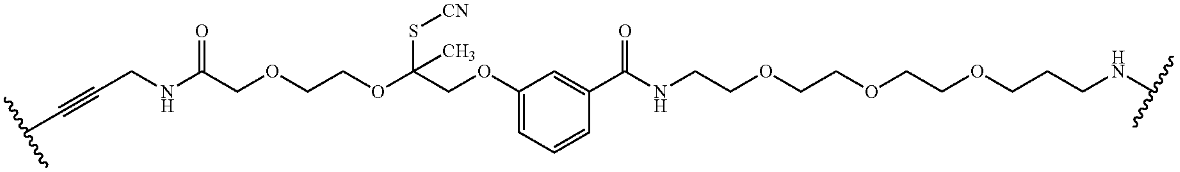
,
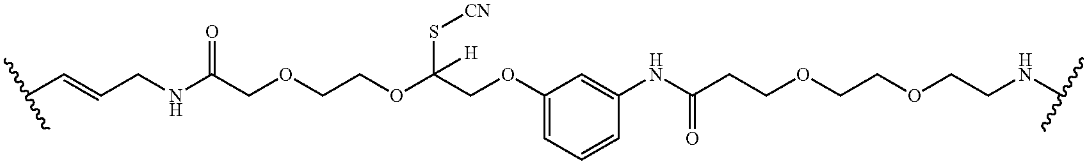
,
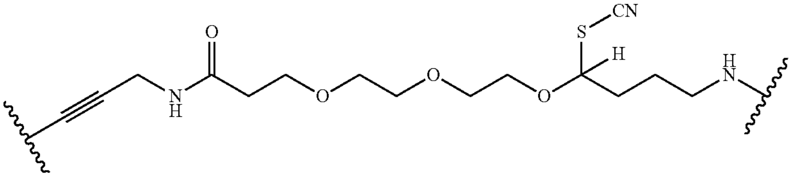
,
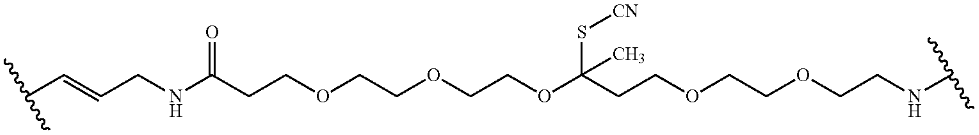
,
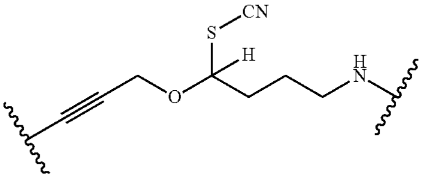
,
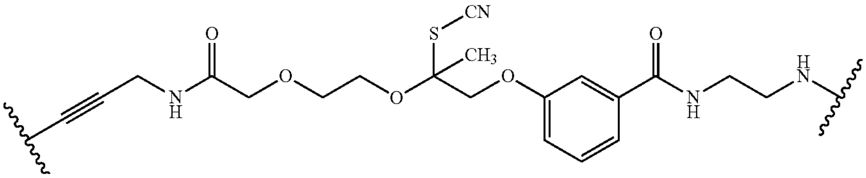
,
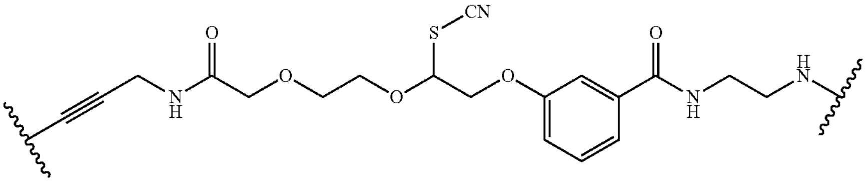
, -continued
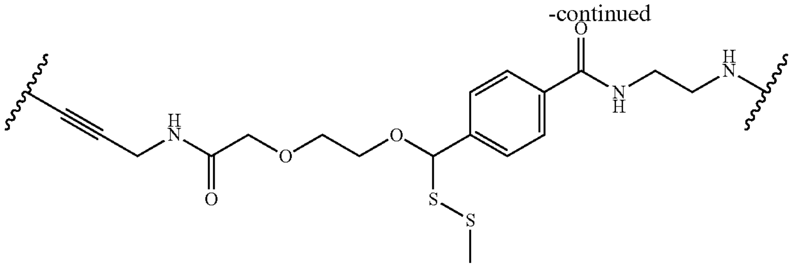
,
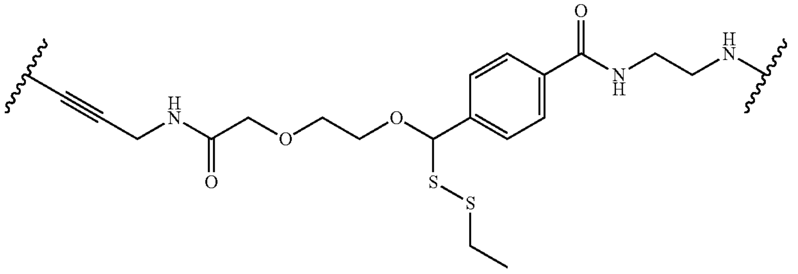
, or
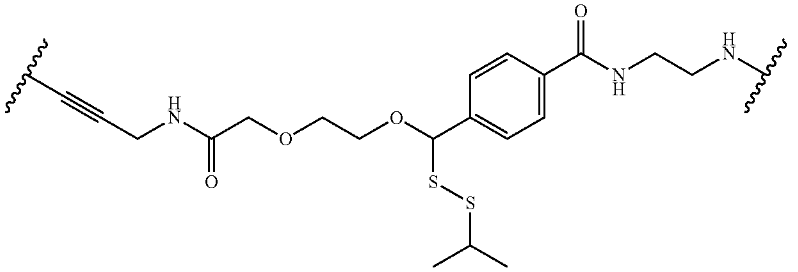
.
Embodiment 21. The compound of Embodiment 12 or 13, wherein $L^{100}$ is
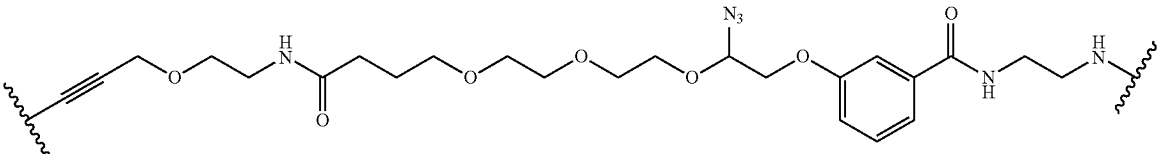
,
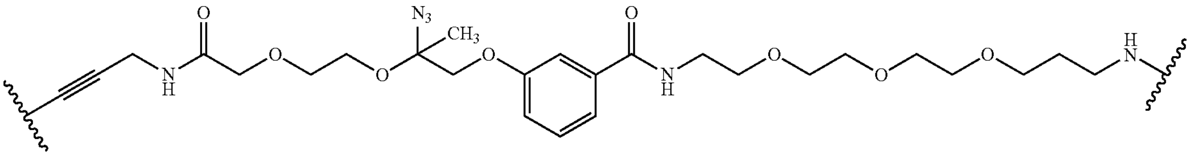
,
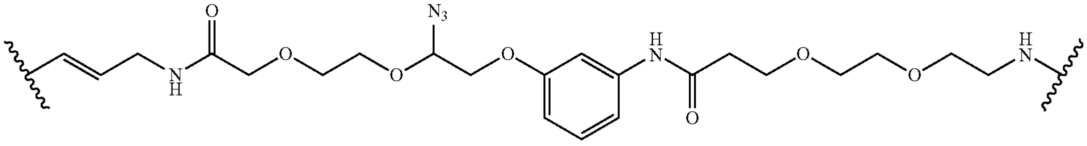
,
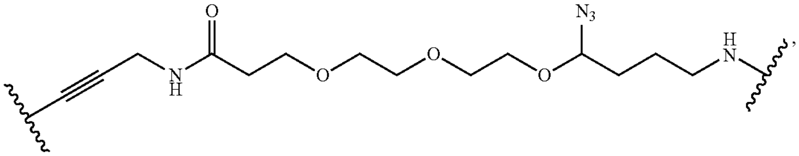
,
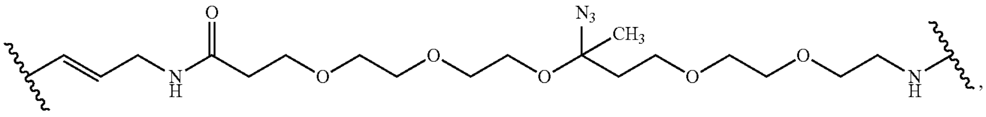
, -continued
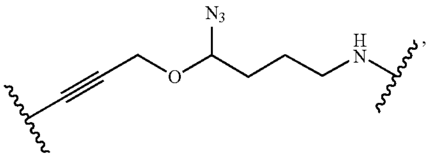
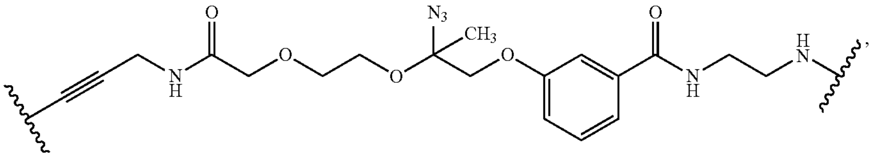
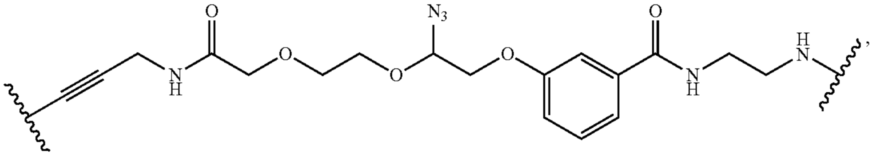
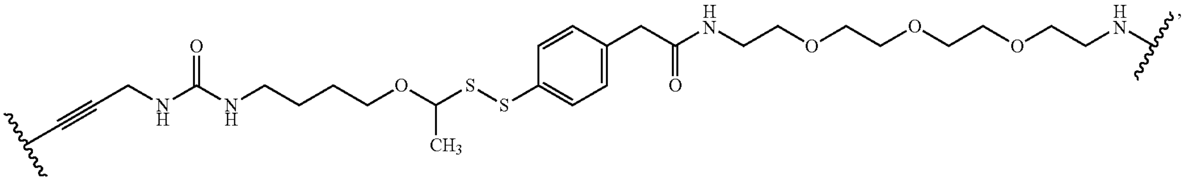
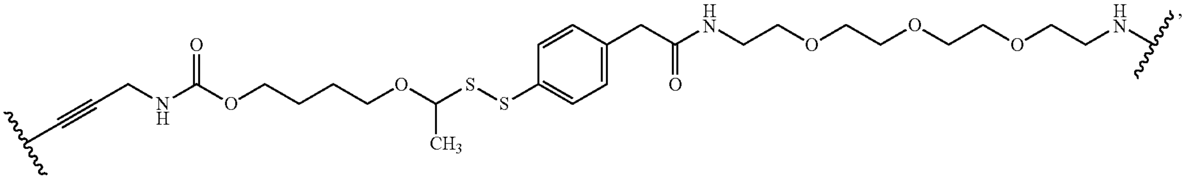
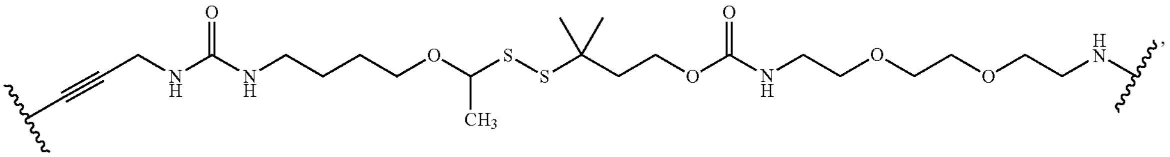
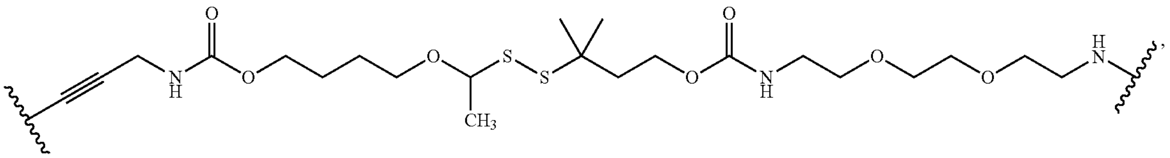
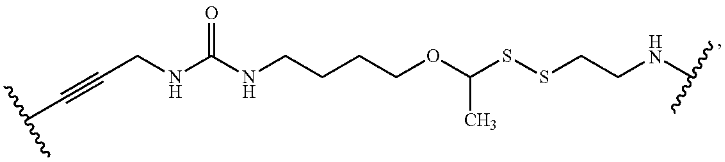
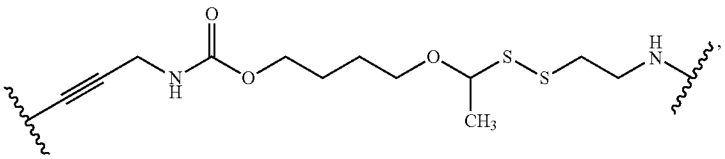
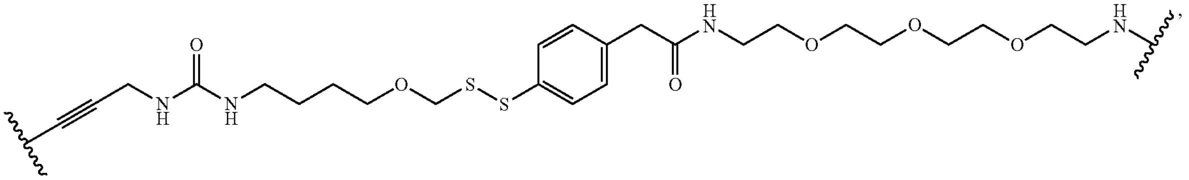

-continued
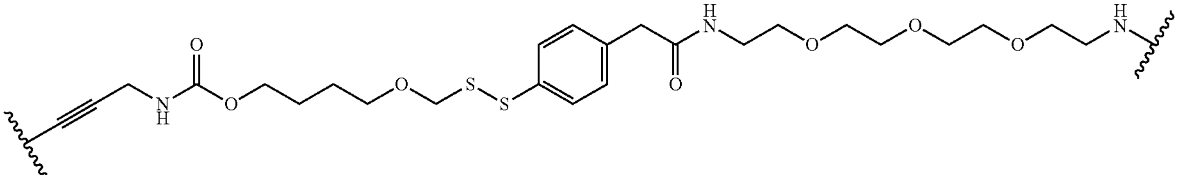,
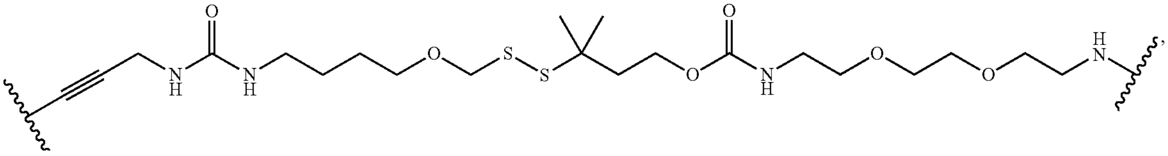,
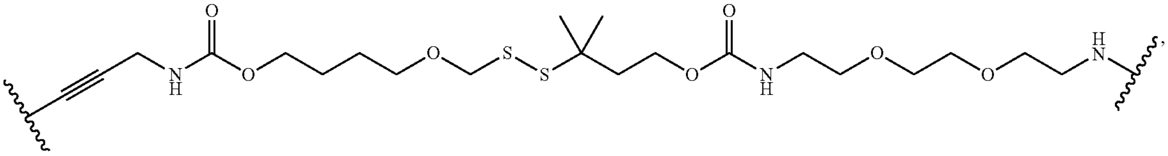,
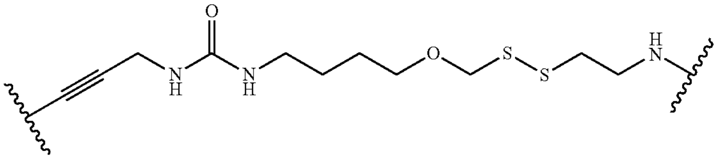,
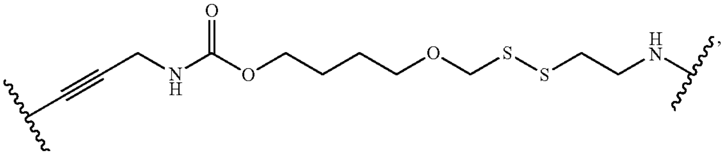,
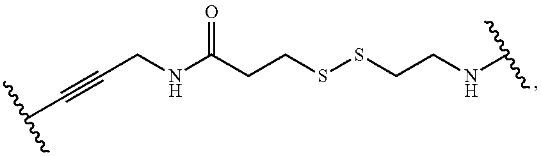, 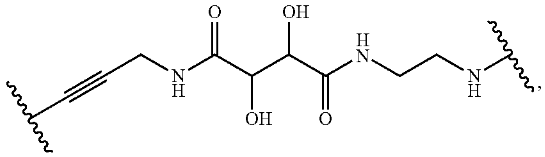,
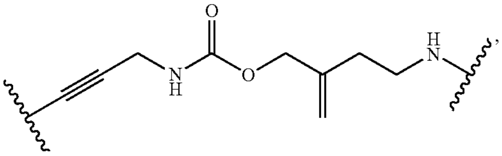,
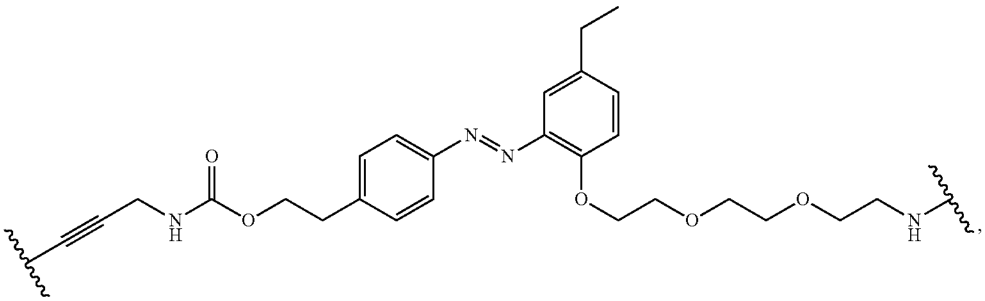,
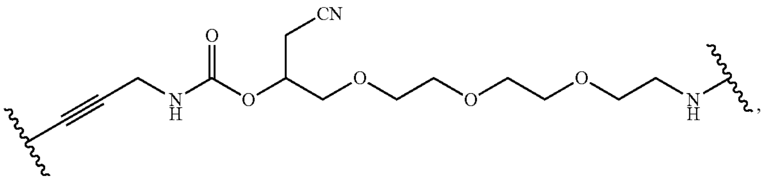, -continued
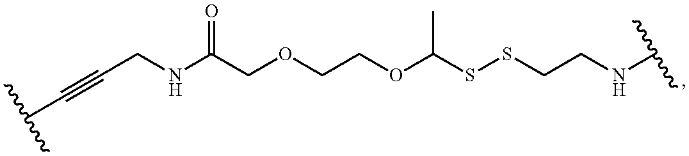
,
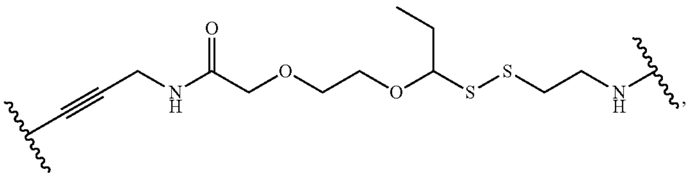
,
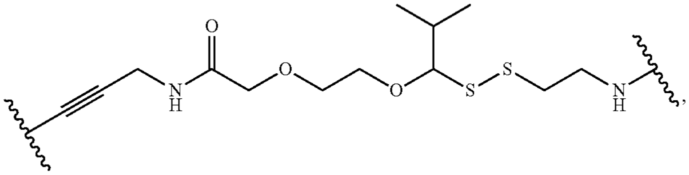
,
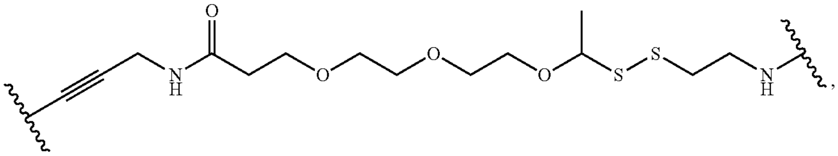
,
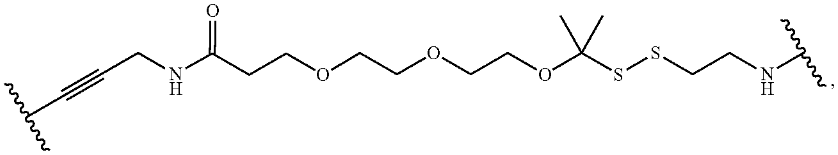
,
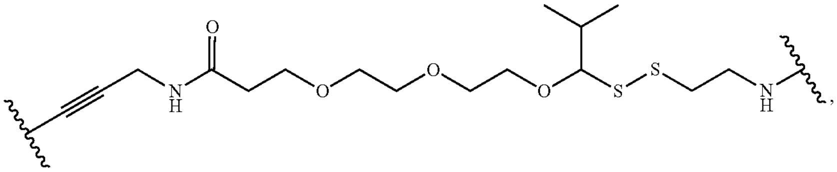
,
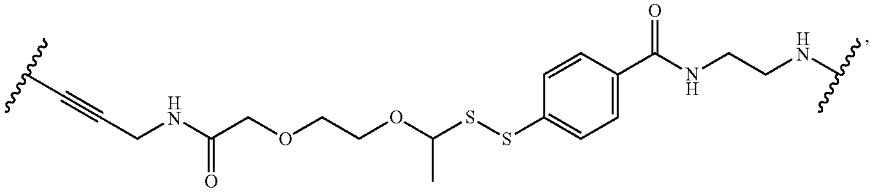
,
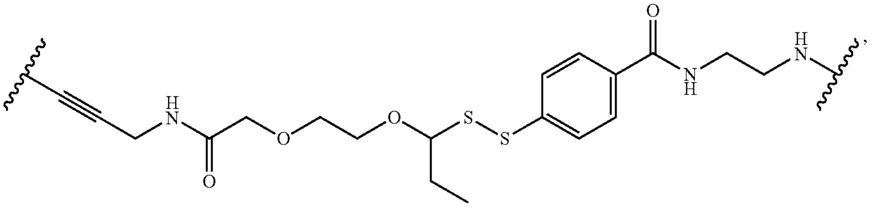
, or
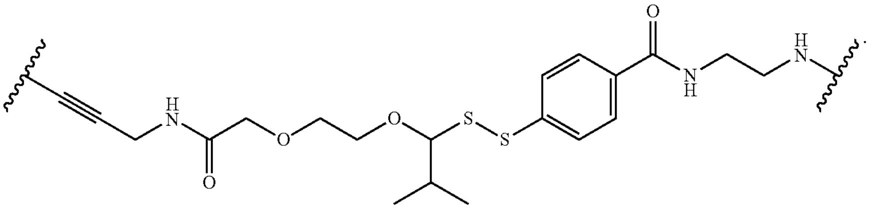
.

Embodiment 22. The compound of any one of Embodiments 1 to 21, wherein $R^7$ is substituted or unsubstituted aryl.

Embodiment 23. The compound of any one of Embodiments 1 to 21, wherein $R^7$ is unsubstituted aryl.

Embodiment 24. The compound of any one of Embodiments 1 to 21, wherein $R^7$ is unsubstituted phenyl.

Embodiment 25. The compound of any one of Embodiments 1 to 21, wherein $R^7$ is substituted or unsubstituted heteroaryl.

Embodiment 26. The compound of any one of Embodiments 1 to 21, wherein $R^7$ is substituted or unsubstituted 5 to 6 membered heteroaryl.

Embodiment 27. The compound of any one of Embodiments 1 to 21, wherein $R^7$ is substituted or unsubstituted 5 to 6 membered heteroaryl.

Embodiment 28. The compound of any one of Embodiments 1 to 21, wherein $R^7$ is

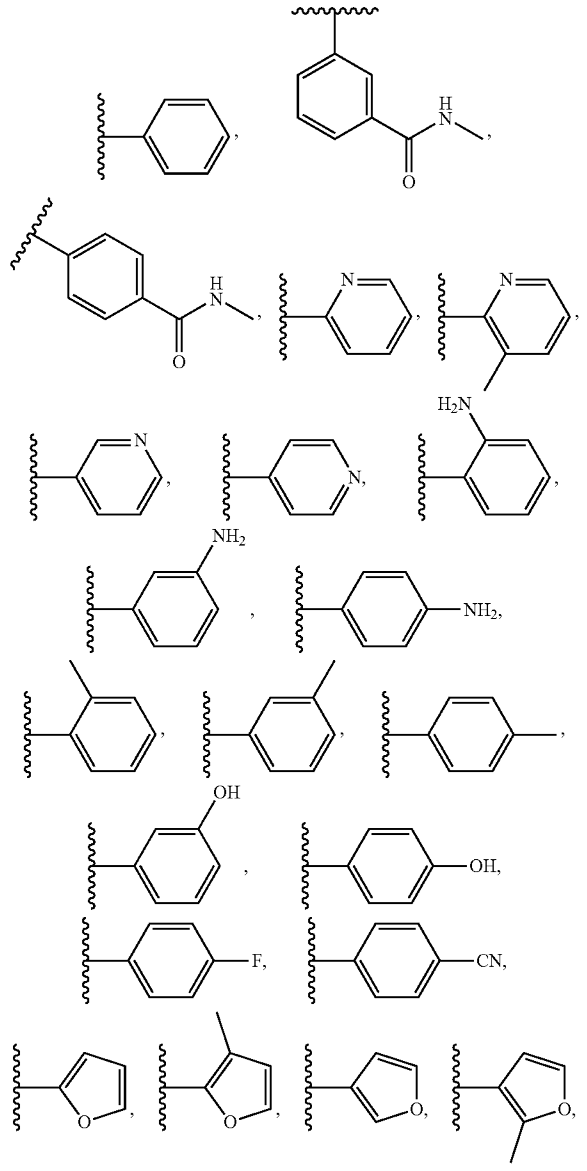

-continued

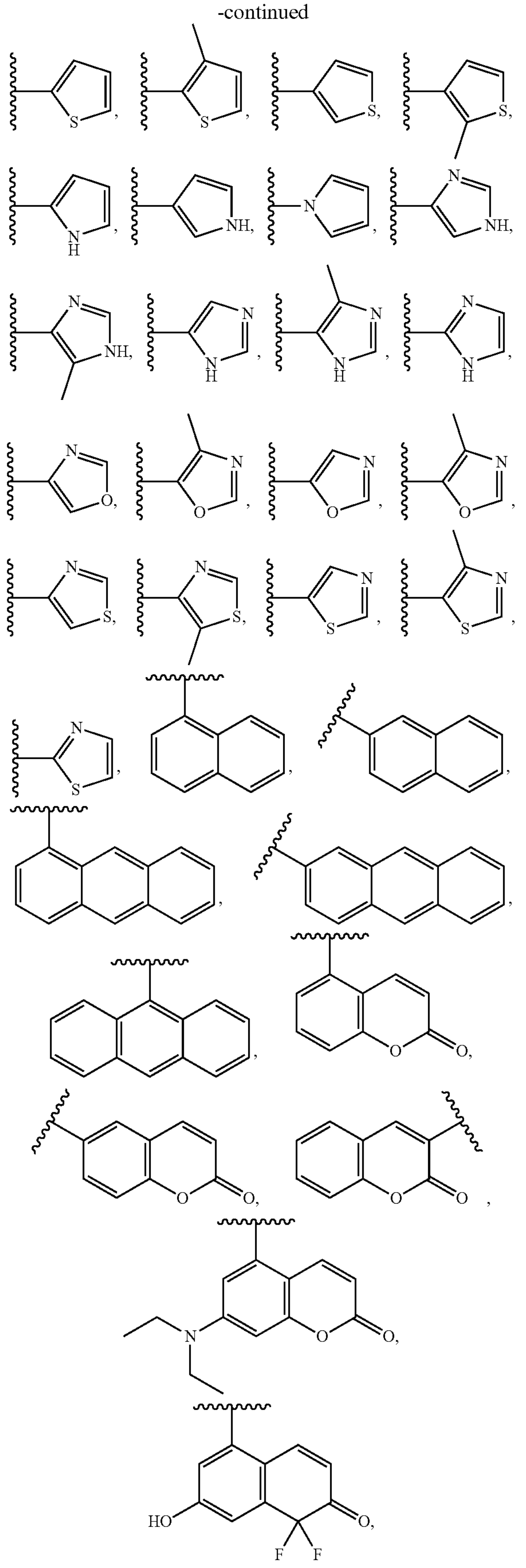

-continued

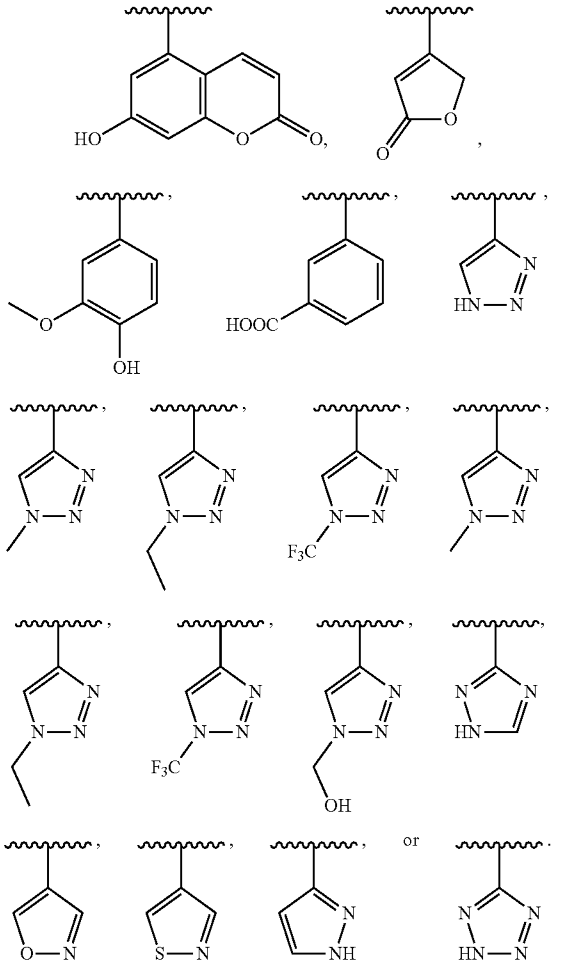

Embodiment 29. The compound of Embodiment 12, having the formula:

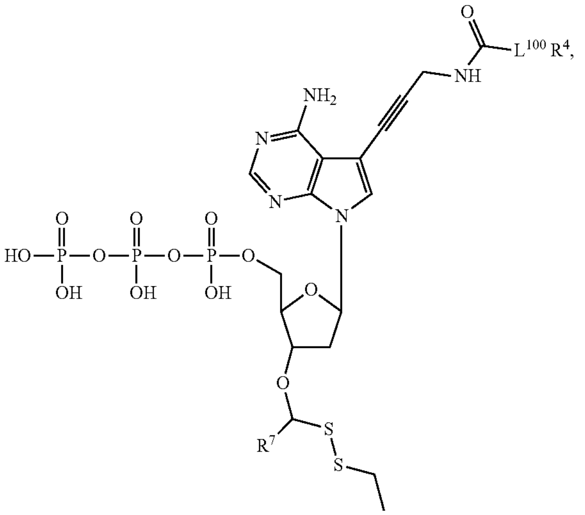

-continued

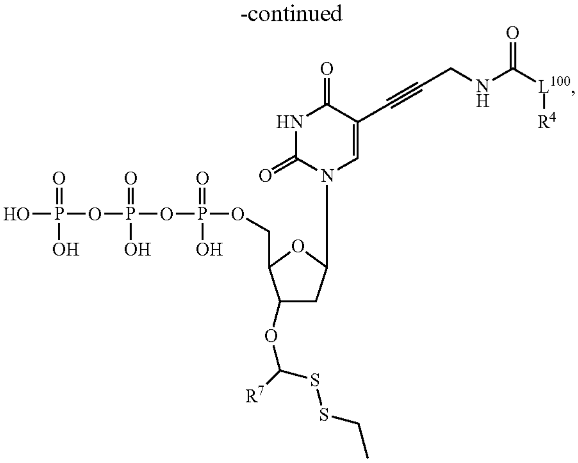

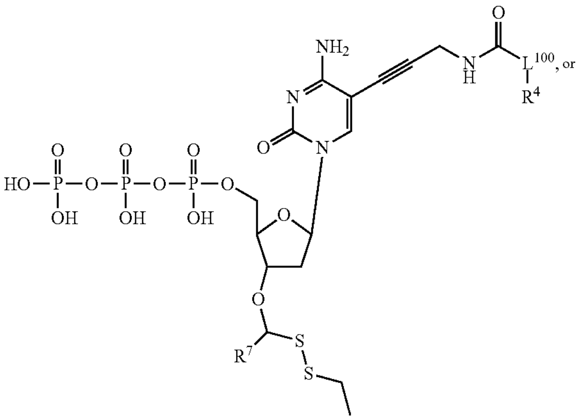

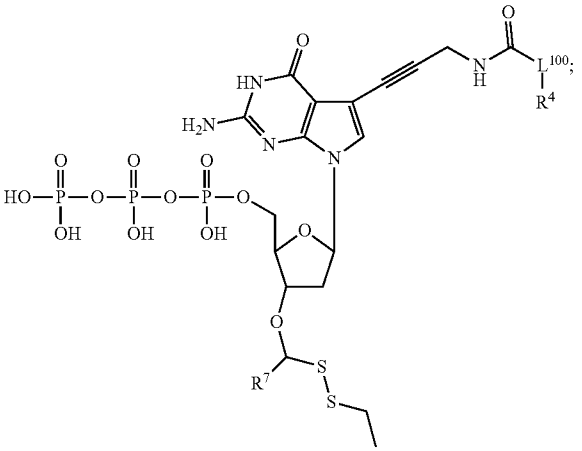

wherein $L^{100}$ is a cleavable linker.

Embodiment 30. The compound of Embodiment 29, wherein $R^7$ is substituted or unsubstituted aryl.

Embodiment 31. The compound of Embodiment 29, wherein $R^7$ is substituted or unsubstituted heteroaryl.

Embodiment 32. The compound of Embodiment 29, wherein $R^7$ is

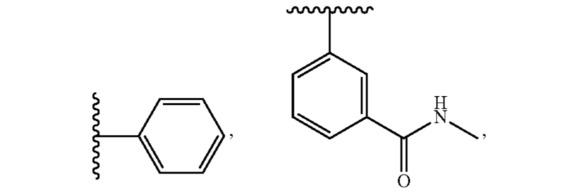
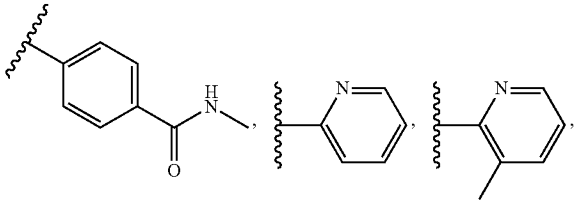
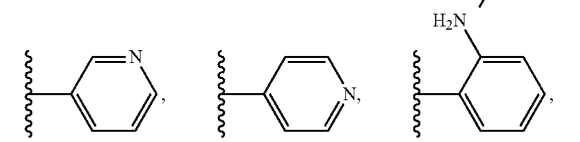
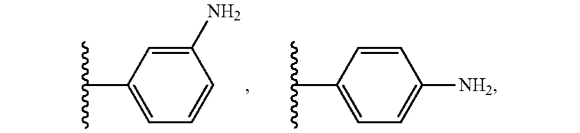
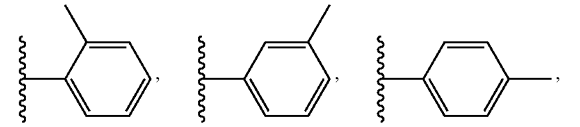
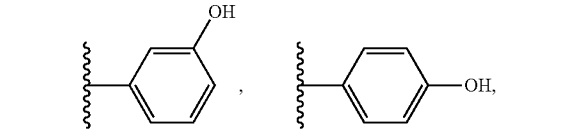
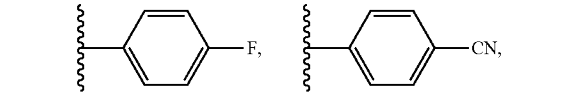
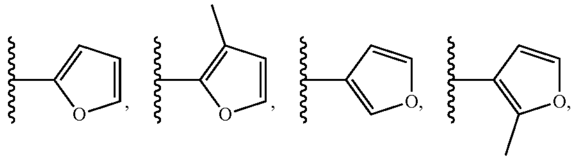
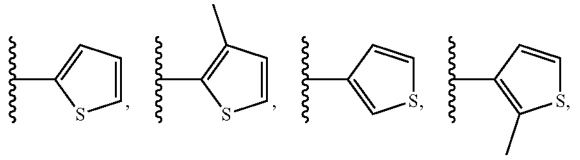
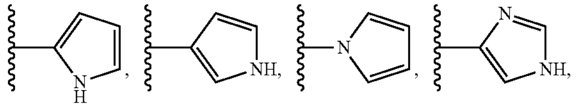
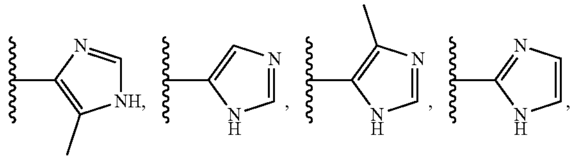
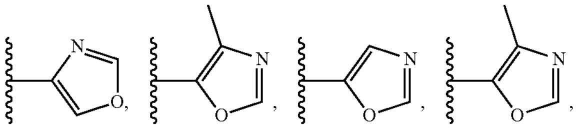
-continued
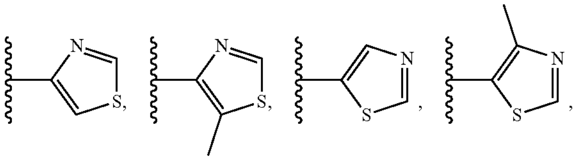
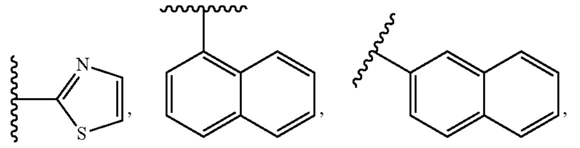
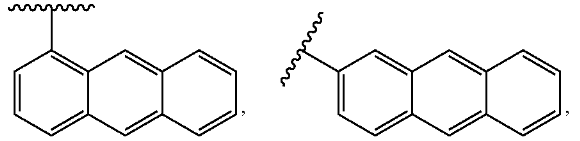
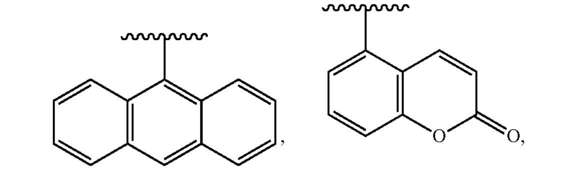
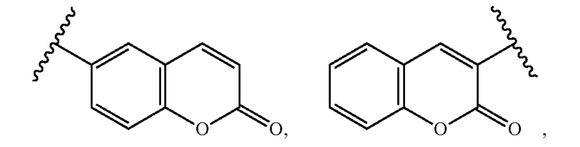
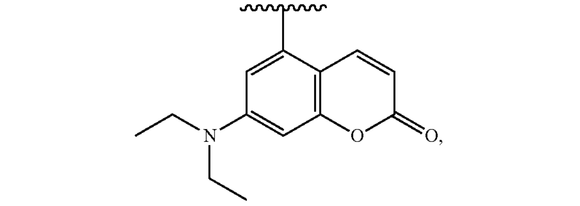
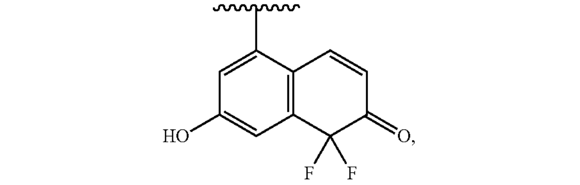
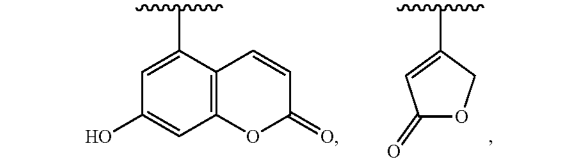
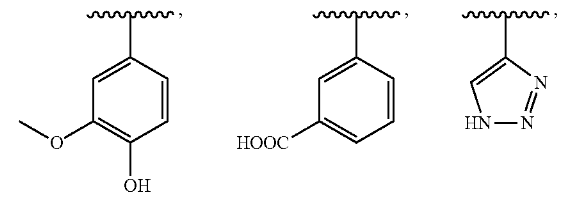
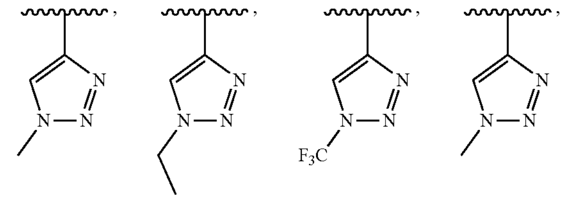

-continued
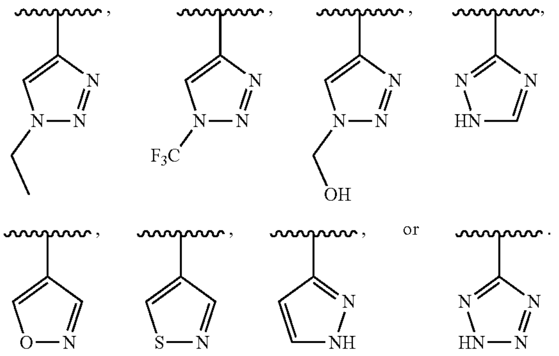
Embodiment 33. The compound of Embodiment 12, having the formula:
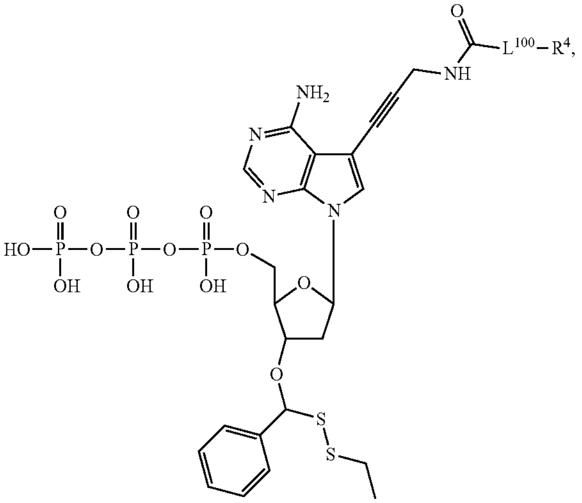
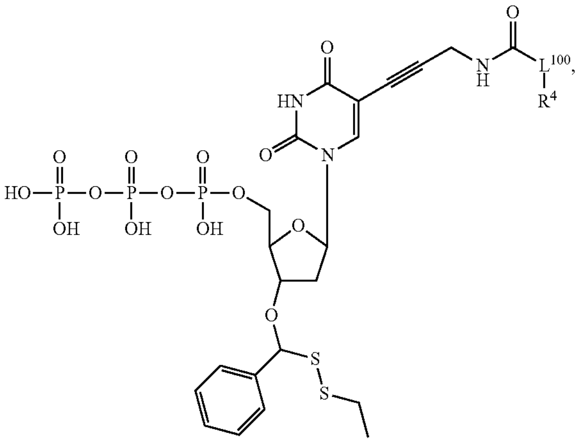
-continued
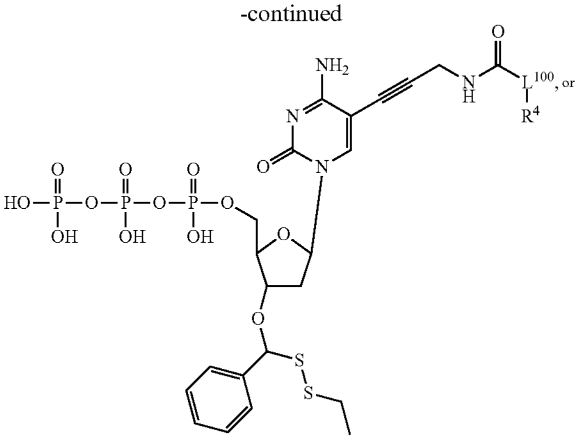
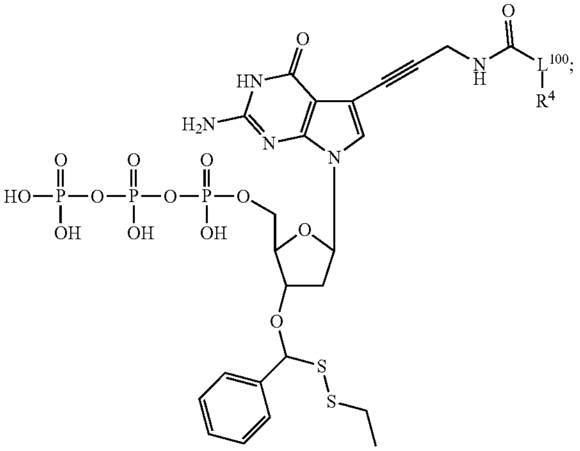
wherein $L^{100}$ is a cleavable linker.
Embodiment 34. The compound of Embodiment 33, wherein $L^{100}$ is
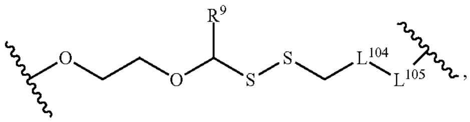
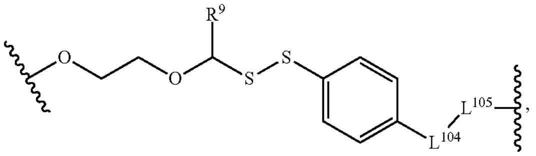
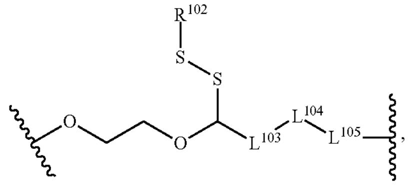
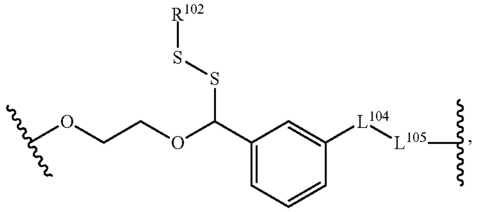
or -continued
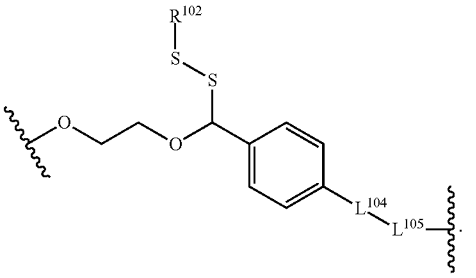
Embodiment 35. The compound of Embodiment 33, wherein $L^{100}$ is
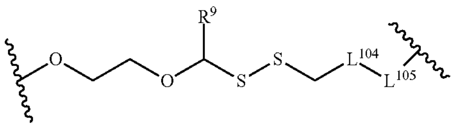
or
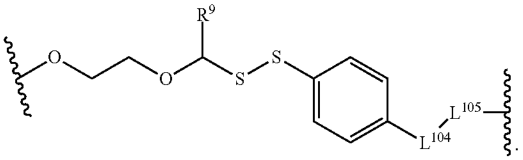
Embodiment 36. The compound of Embodiment 33, wherein $L^{100}$ is
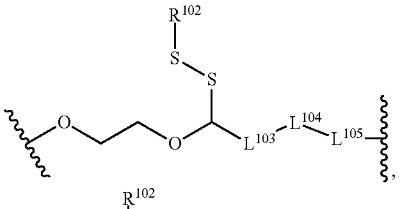
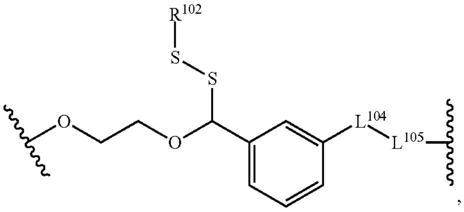
, or
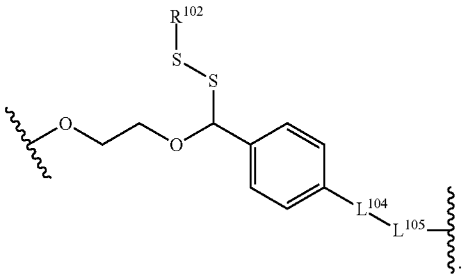
Embodiment 37. The compound of Embodiment 12, having the formula.
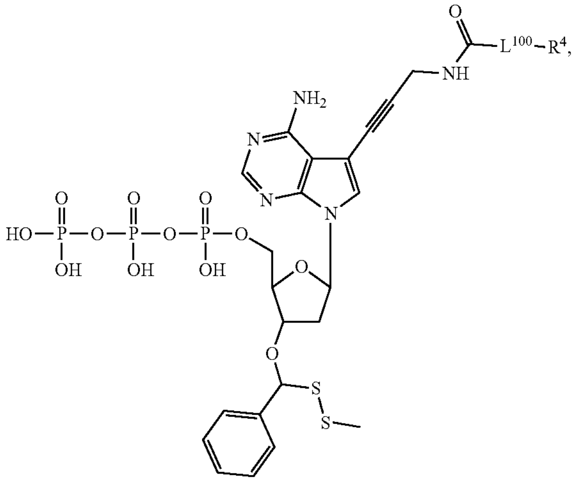
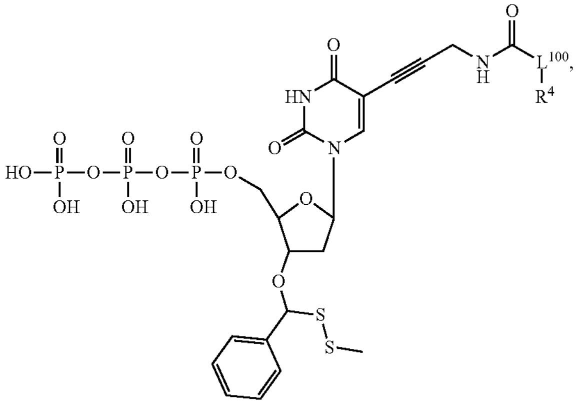
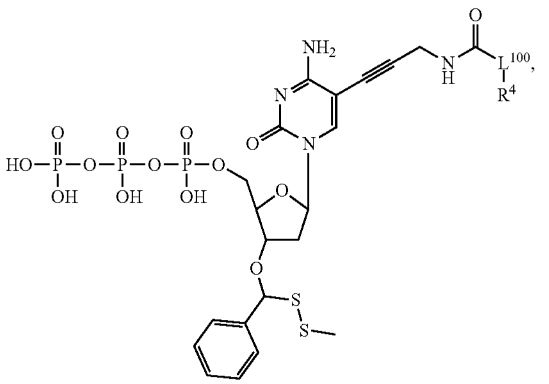
or -continued

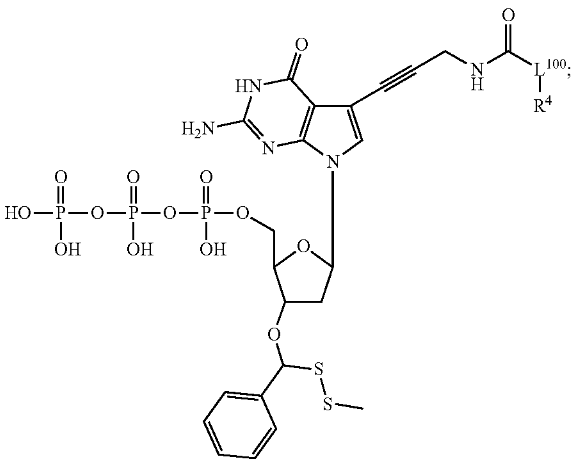

wherein $L^{100}$ is a cleavable linker.

Embodiment 38. The compound of Embodiment 37, wherein $L^{100}$ is

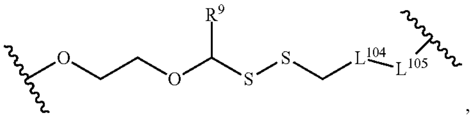

,

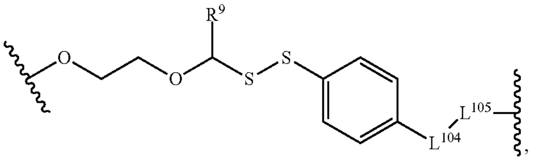

,

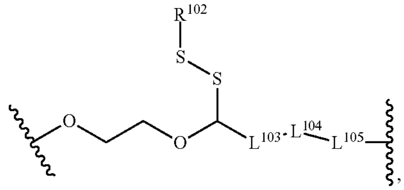

,

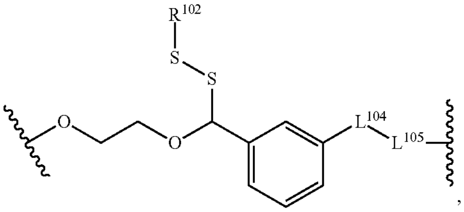

, or

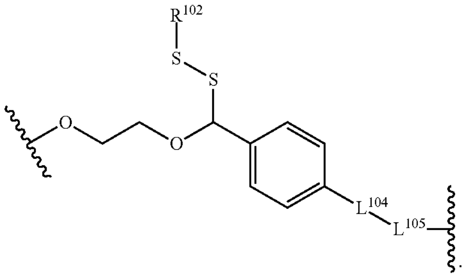

.

Embodiment 39. The compound of Embodiment 37, wherein $L^{100}$ is

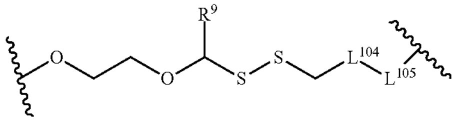

or

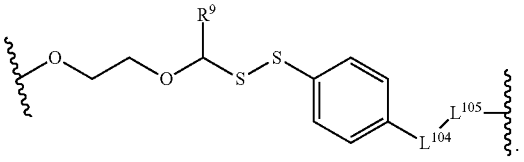

.

Embodiment 40. The compound of Embodiment 37, wherein $L^{100}$ is

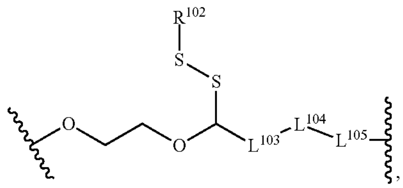

,

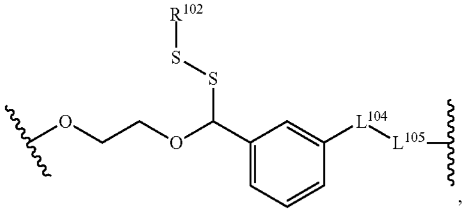

, or

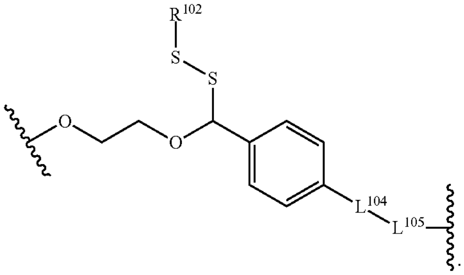

.

Embodiment 41. A method for sequencing a nucleic acid, comprising: i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label; ii) detecting said unique detectable label of each incorporated compound, so as to thereby identify each incorporated compound in said extension strand, thereby sequencing the nucleic acid; wherein each of said four different compounds is independently a compound of any one of Embodiments 1 to 37.

Embodiment 42. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of any one of Embodiments 1 to 37.

Embodiment 43. A nucleic acid polymerase complex comprising a nucleic acid polymerase, wherein said nucleic acid polymerase is bound to a compound of any one of Embodiments 1 to 37.

What is claimed is:

1. A compound having the formula:

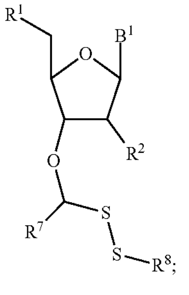

(II)

wherein $B^1$ is a nucleobase;

$R^1$ is a polyphosphate moiety, 5'-O-nucleoside protecting group, monophosphate moiety, nucleic acid moiety, hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $—CCl_3$, $—CBr_3$, $—CF_3$, $—CI_3$, $—CHCl_2$, $—CHBr_2$, $—CHF_2$, $—CHI_2$, $—CH_2Cl$, $—CH_2Br$, $—CH_2F$, $—CH_2I$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, $—N_3$, $—SF_5$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a polymerase-compatible cleavable moiety;

$R^7$ is unsubstituted or substituted cycloalkyl, or substituted or unsubstituted heterocycloalkyl; and $R^8$ is unsubstituted $C_1$-$C_6$ alkyl.

2. The compound of claim 1, wherein $R^2$ is hydrogen.

3. The compound of claim 1, wherein $R^1$ is —OH, a 5'-O-nucleoside protecting group, monophosphate moiety, polyphosphate moiety, or nucleic acid moiety.

4. The compound of claim 1, wherein $R^1$ is a triphosphate moiety.

5. The compound of claim 1, wherein $R^8$ is unsubstituted $C_1$-$C_4$ alkyl.

6. The compound of claim 1, wherein $R^8$ is unsubstituted methyl or unsubstituted ethyl.

7. The compound of claim 1, wherein $B^1$ is a cytosine or a derivative thereof, guanine or a derivative thereof, adenine or a derivative thereof, thymine or a derivative thereof, uracil or a derivative thereof, hypoxanthine or a derivative thereof, xanthine or a derivative thereof, 7-methylguanine or a derivative thereof, 5,6-dihydrouracil or a derivative thereof, 5-methylcytosine or a derivative thereof, or 5-hydroxymethylcytosine or a derivative thereof.

8. The compound of claim 1, wherein $B^1$ is

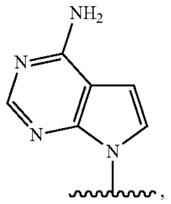

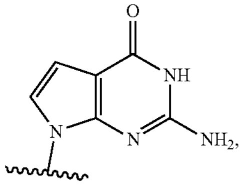

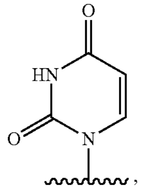

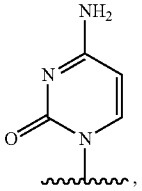

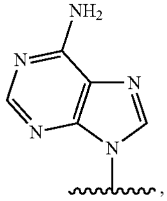

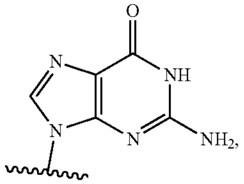

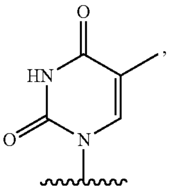

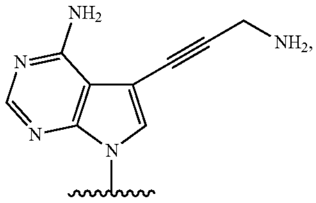

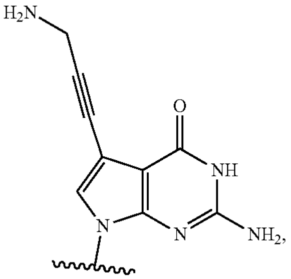

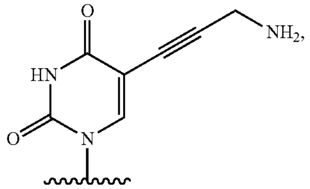

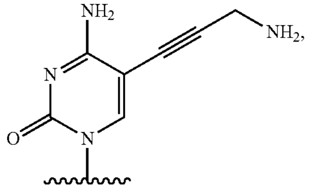

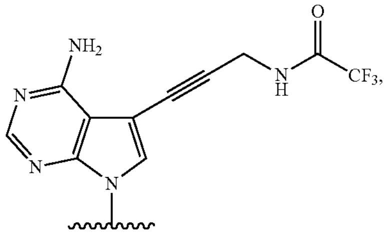

-continued

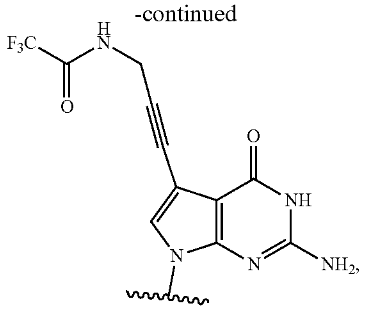

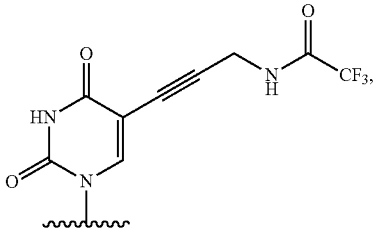

or

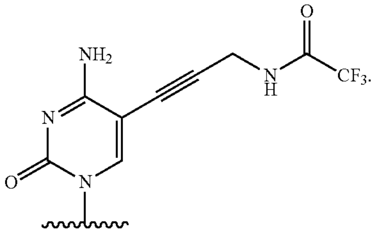

9. The compound of claim 1, wherein $B^1$ is —B-$L^{100}$-$R^4$;

B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof;

$L^{100}$ is a divalent linker; and $R^4$ is a detectable moiety.

10. The compound of claim 9, wherein $L^{100}$ is a divalent linker comprising

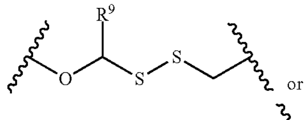

or

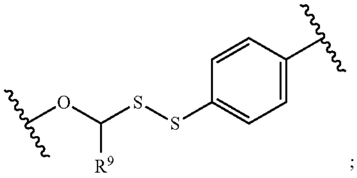

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

11. The compound of claim 9, wherein $L^{100}$ is a divalent linker comprising

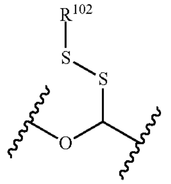

or

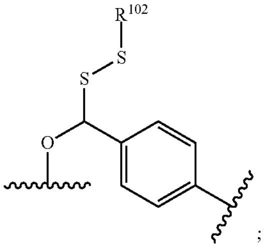

;

wherein $R^{102}$ is unsubstituted $C_1$-$C_4$ alkyl.

12. The compound of claim 9, wherein $L^{100}$ is -$L^{101}$-$L^{102}$-$L^{103}$-$L^{104}$-$L^{105}$-;

$L^{101}$, $L^{102}$, $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

13. The compound of claim 12, wherein $L^{100}$ is

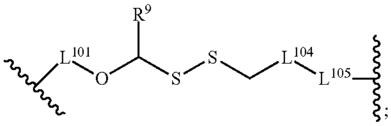

;

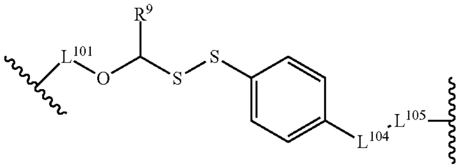

;

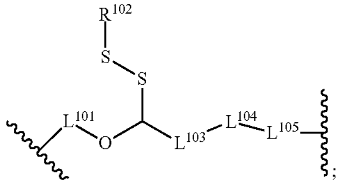

; or

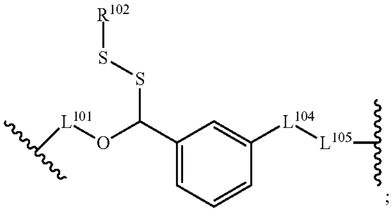

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is unsubstituted $C_1$-$C_4$ alkyl.

14. The compound of claim 12, wherein $L^{100}$ is

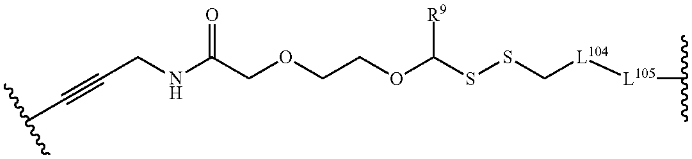

;

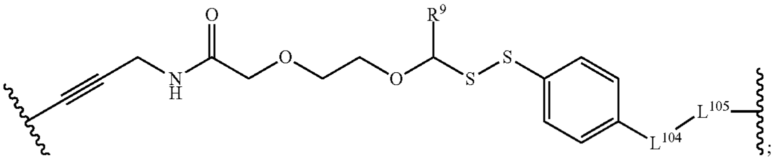

;

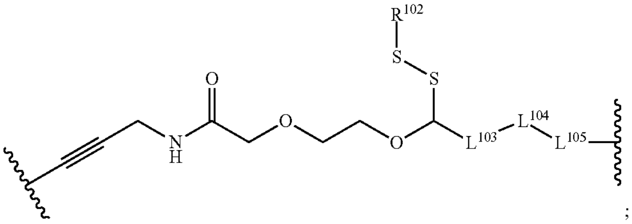

; or

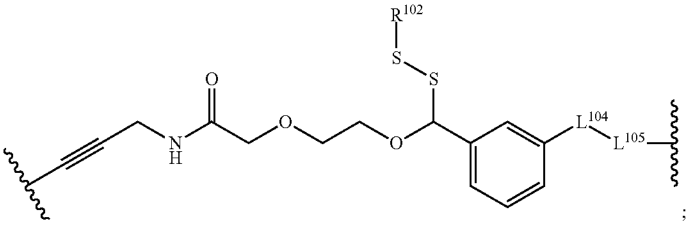

;

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{102}$ is unsubstituted $C_1$-$C_4$ alkyl.

15. The compound of claim 9, wherein $L^{100}$ is

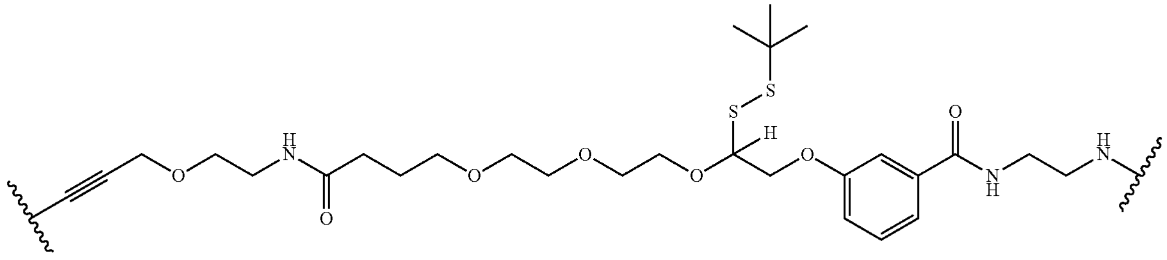

,

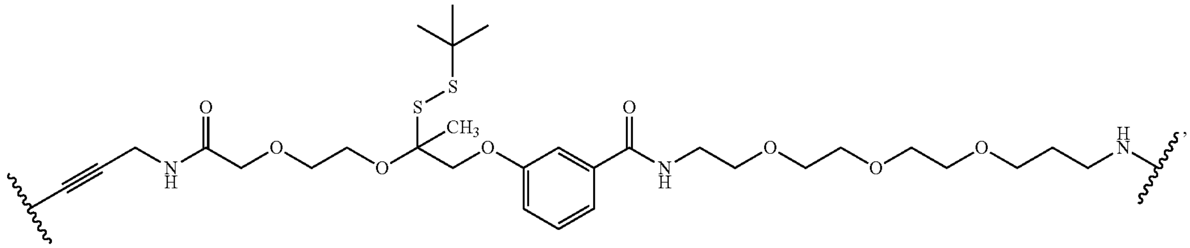

,

-continued
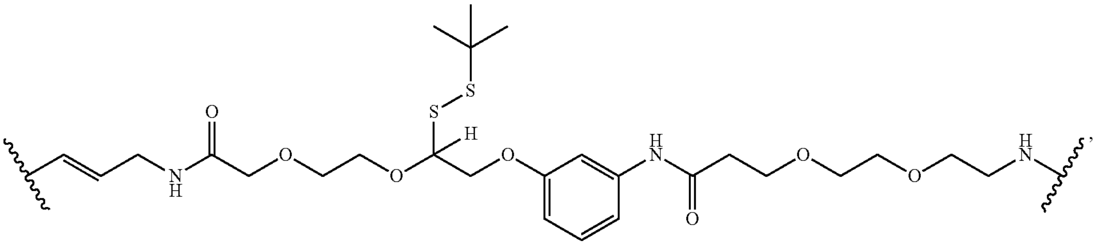
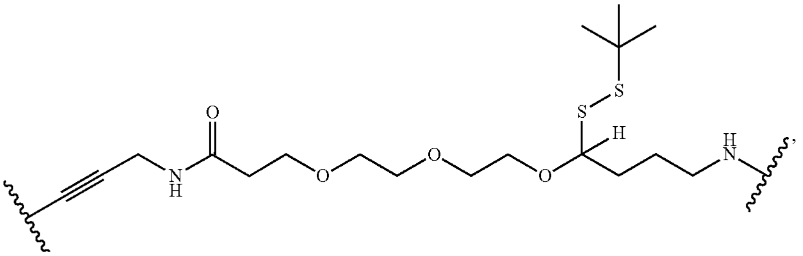
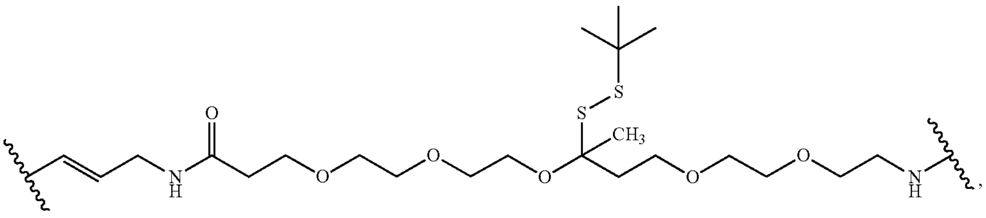
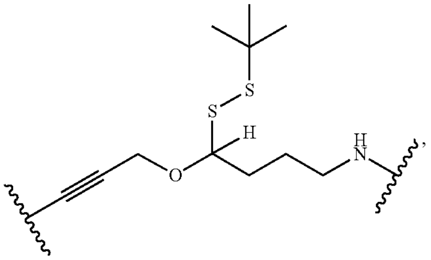
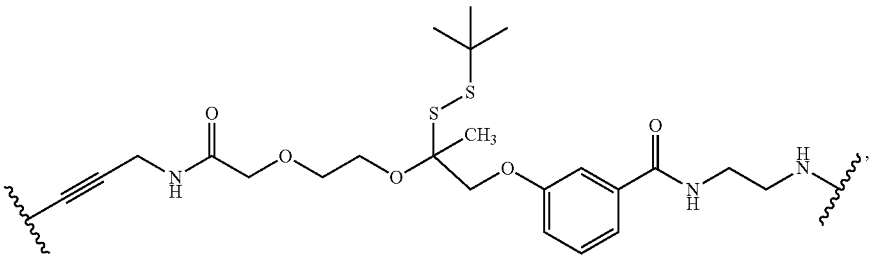
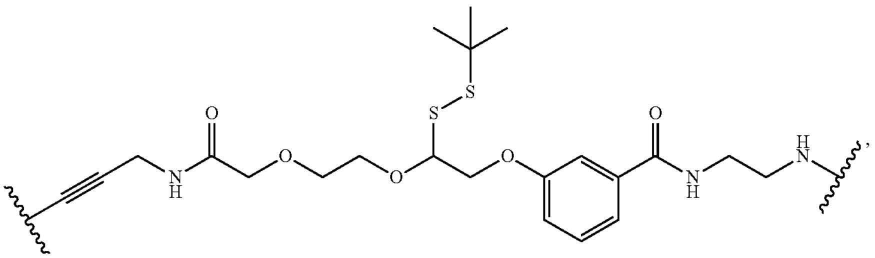
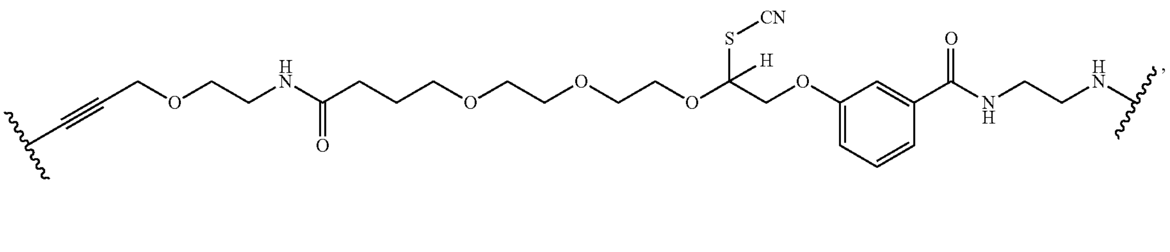

-continued
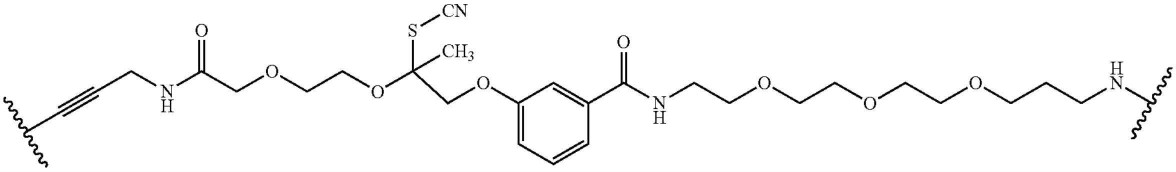
,
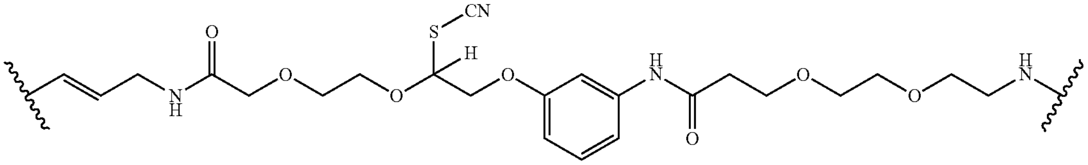
,
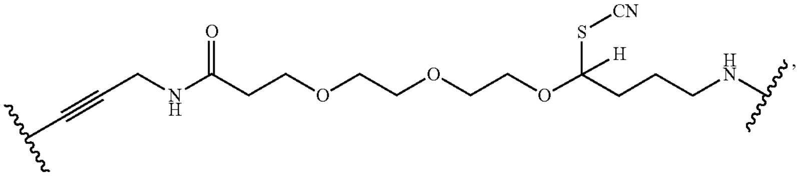
,
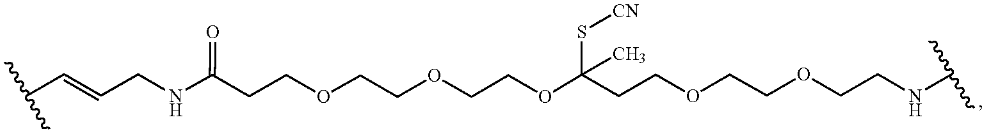
,
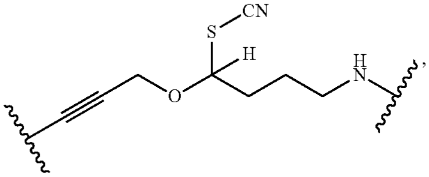
,
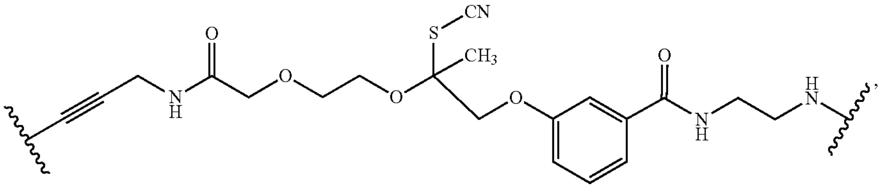
,
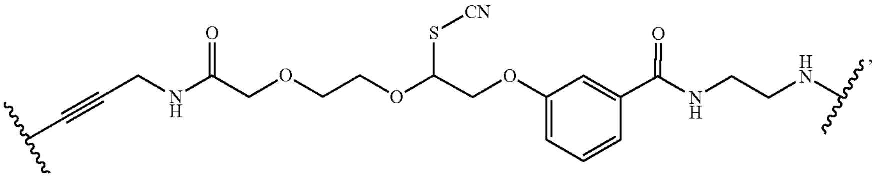
,
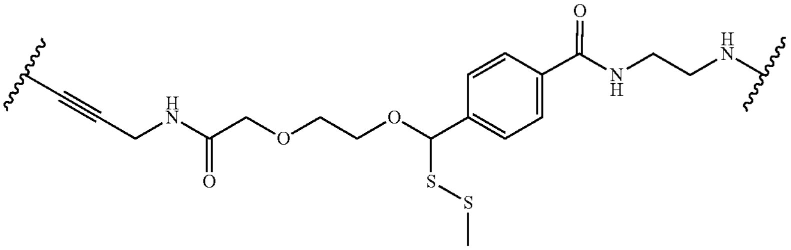
,
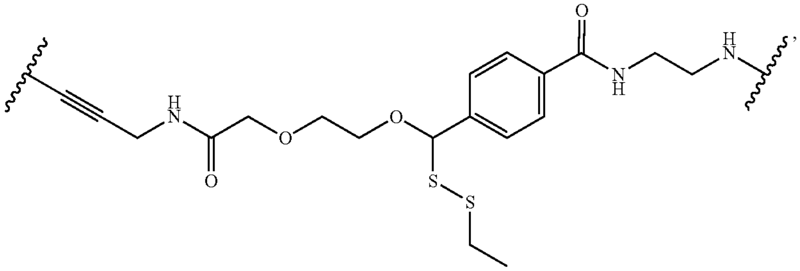
, or -continued
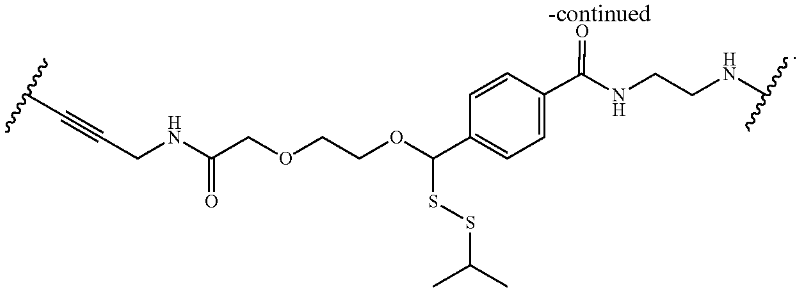
16. The compound of claim 9, wherein $L^{100}$ is
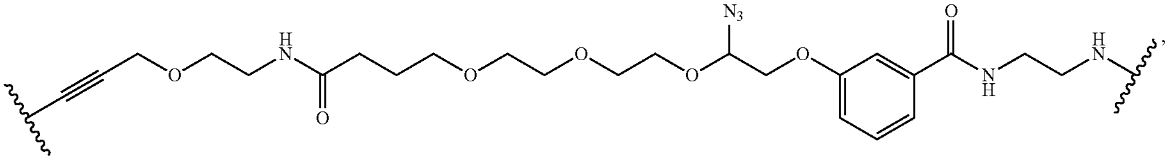
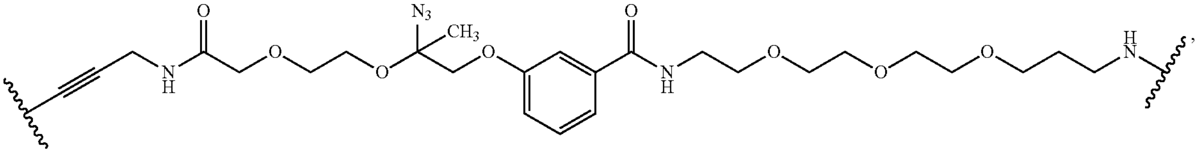
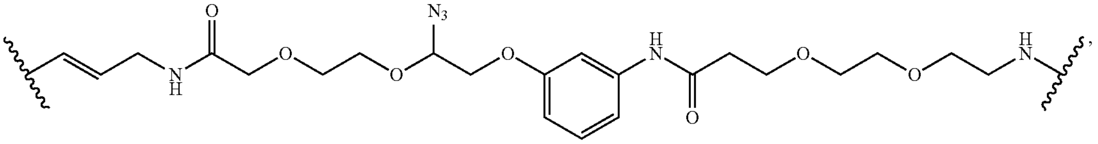
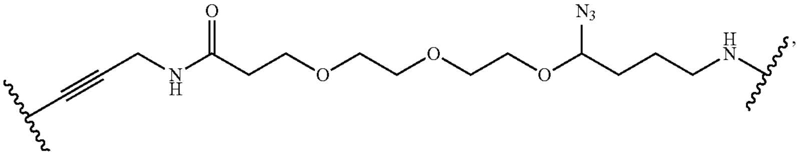
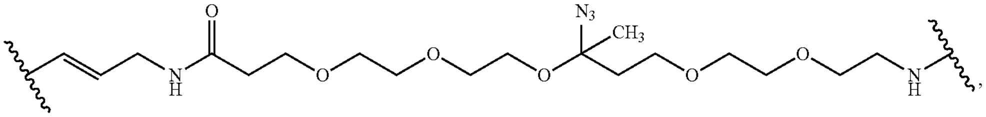
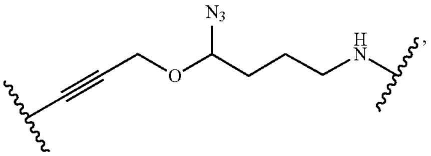
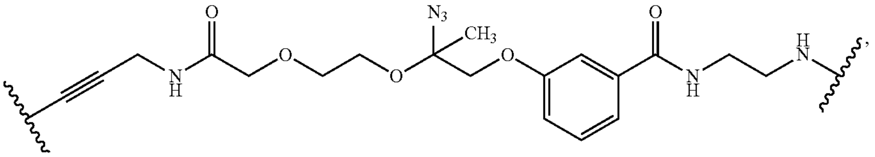
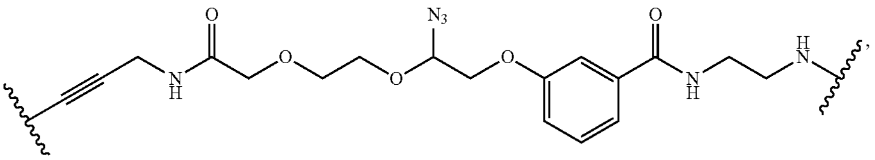

-continued
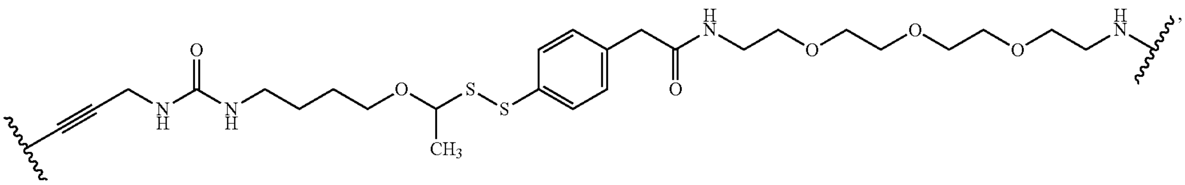
,
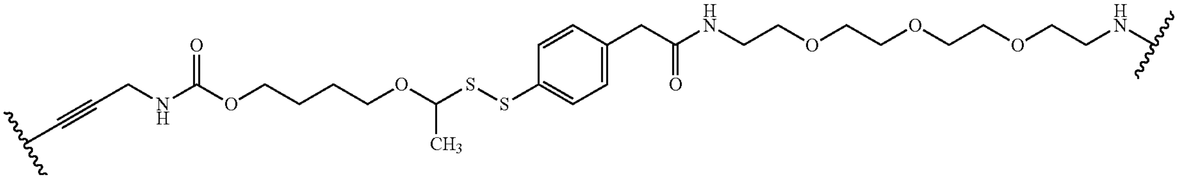
,
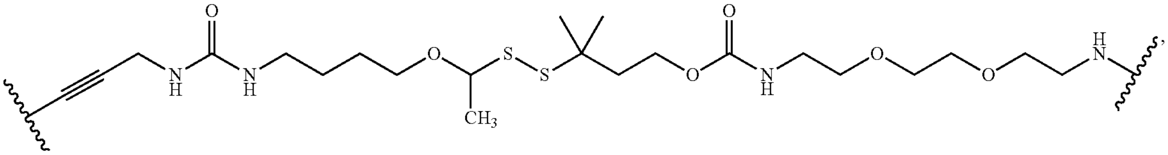
,
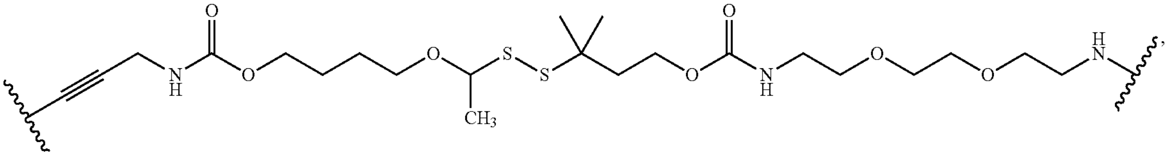
,
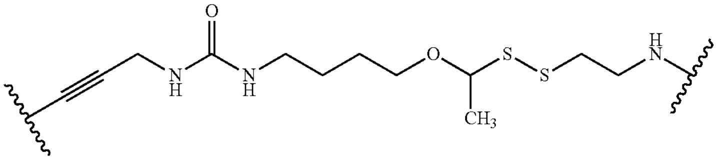
,
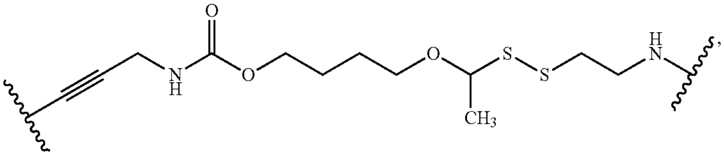
,
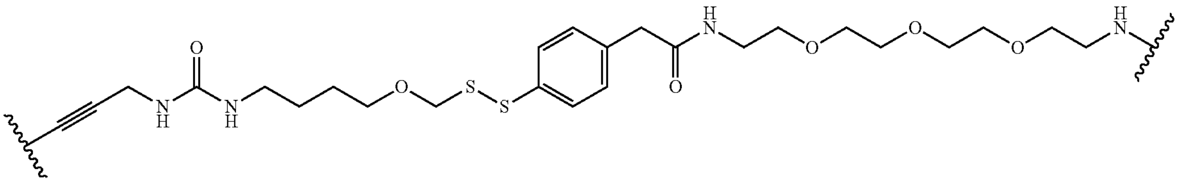
,
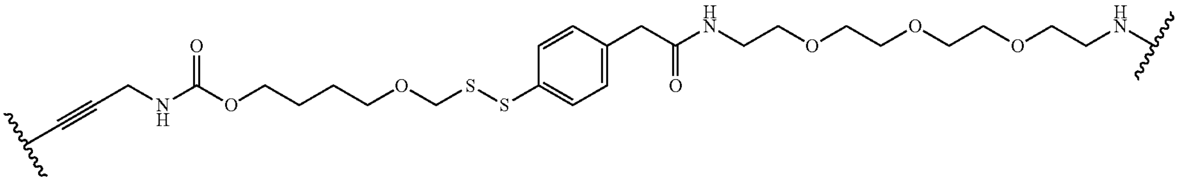
,
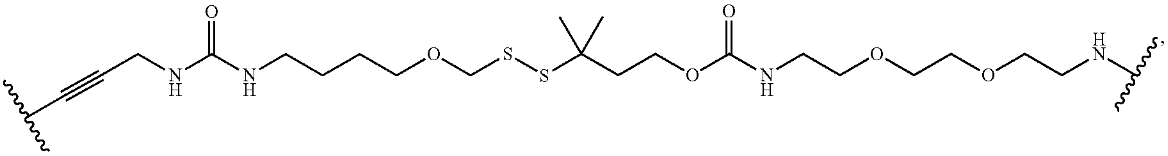
,
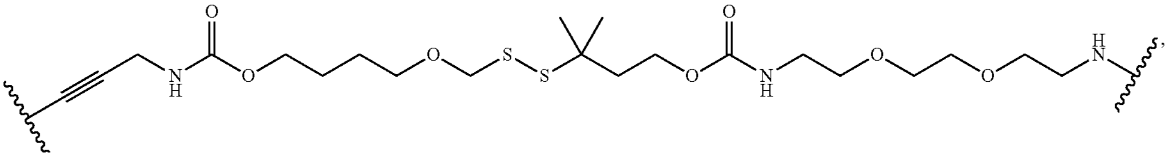
, -continued
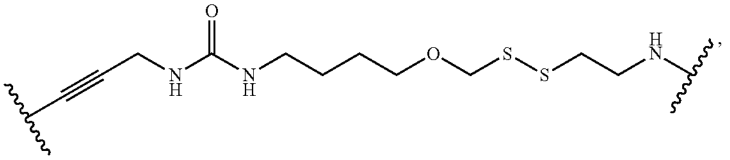
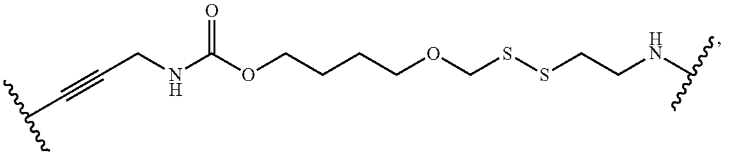
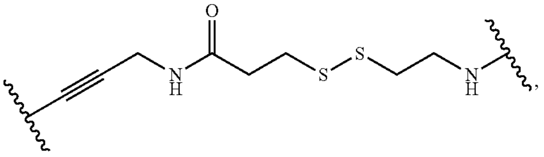
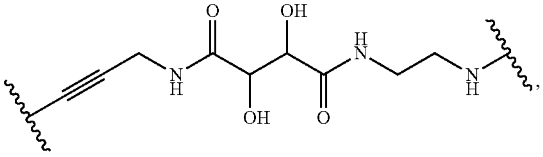
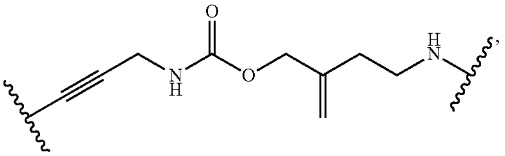
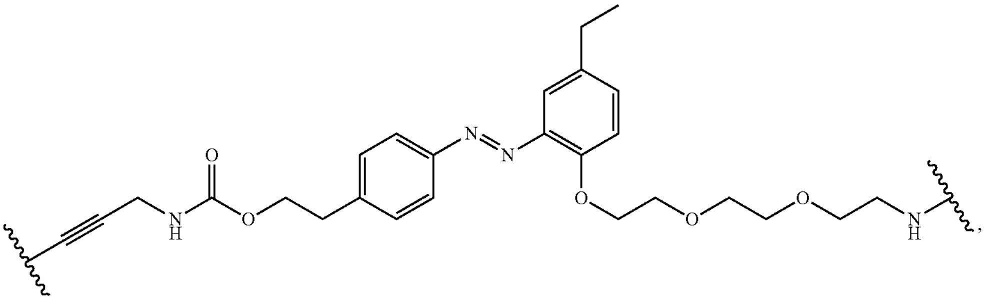
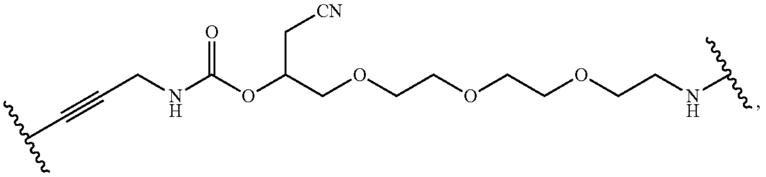
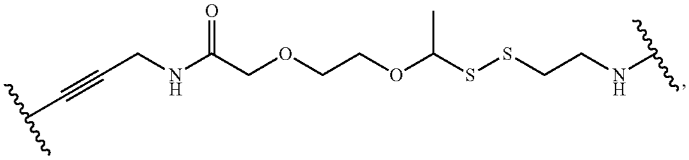
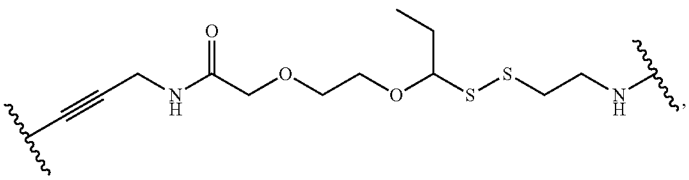
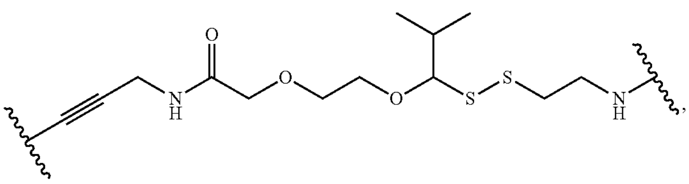

-continued
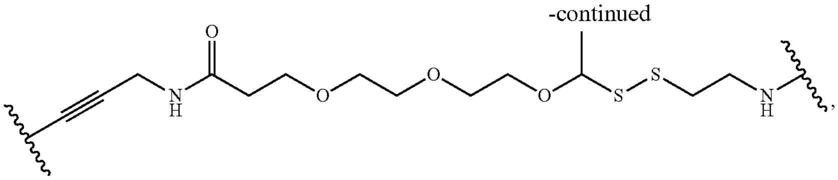
,
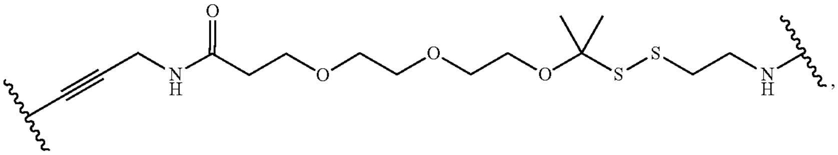
,
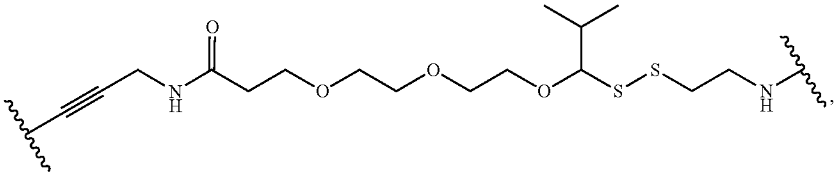
,
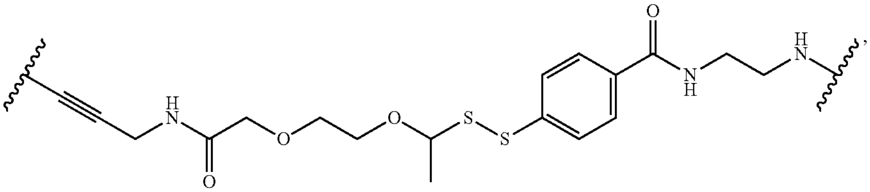
,
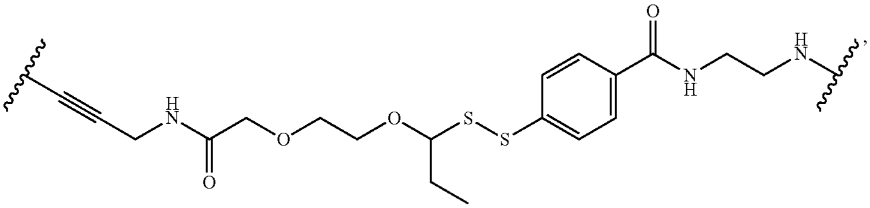
, or
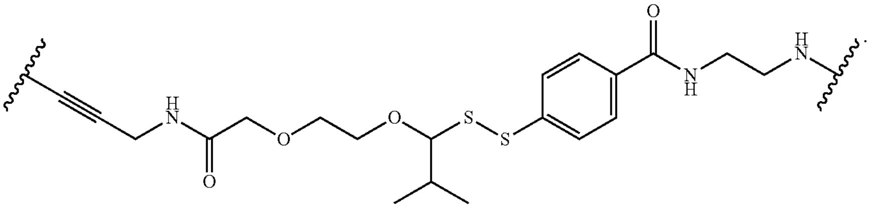
.
17. The compound of claim 9, having the formula:
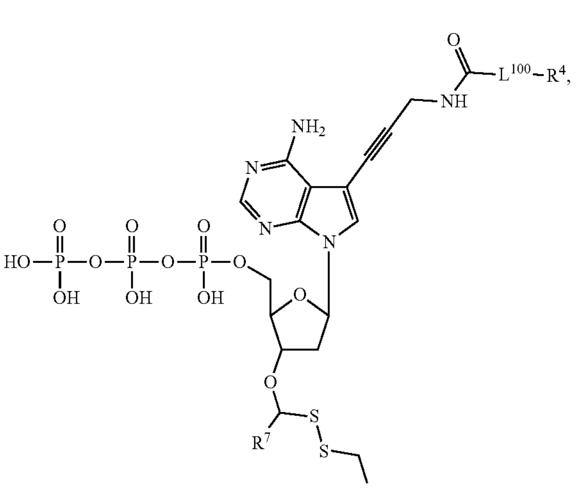
-continued
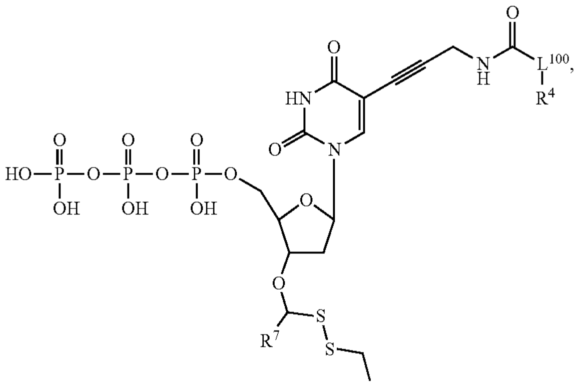

-continued

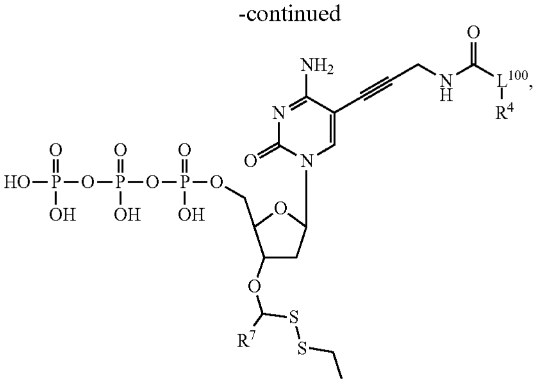

or

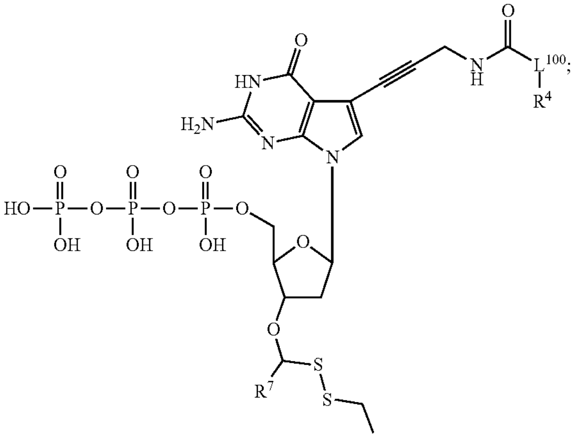

wherein $L^{100}$ is a cleavable linker.

18. The compound of claim 17, wherein $R^7$ is substituted or unsubstituted cycloalkyl.

19. The compound of claim 17, wherein $R^7$ is substituted or unsubstituted heterocycloalkyl.

20. The compound of claim 17, wherein $L^{100}$ is

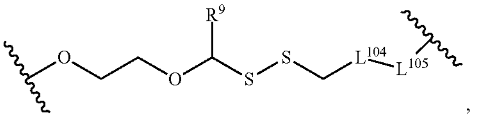

,

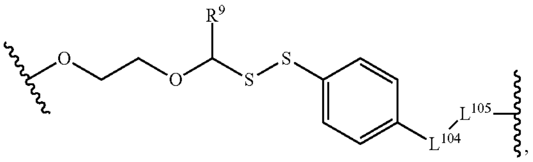

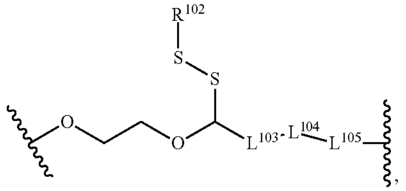

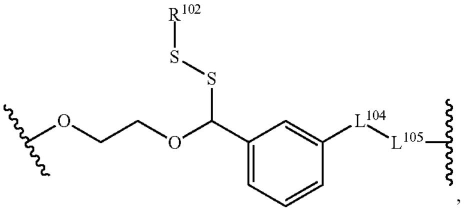

, or

-continued

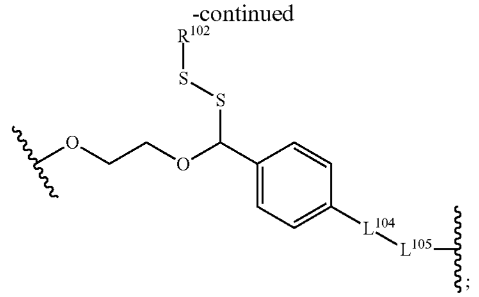

wherein $R^9$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{102}$ is unsubstituted $C_1$-$C_4$ alkyl; and $L^{103}$, $L^{104}$, and $L^{105}$ are independently a bond, —NH—, —O—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

21. The compound of claim 1, wherein $R^7$ is substituted or unsubstituted cycloalkyl.

22. The compound of claim 1, wherein $R^7$ is unsubstituted cycloalkyl.

23. The compound of claim 1, wherein $R^7$ is substituted or unsubstituted heterocycloalkyl.

24. The compound of claim 1, wherein $R^7$ is unsubstituted cycloalkyl or unsubstituted heterocycloalkyl.

25. The compound of claim 1, wherein $R^7$ is

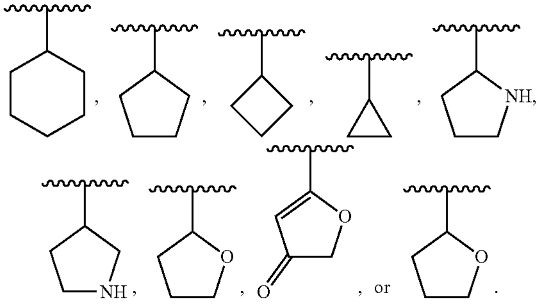

26. A nucleic acid polymerase complex comprising a nucleic acid polymerase, wherein said nucleic acid polymerase is bound to a compound of claim 1.

27. A method for sequencing a nucleic acid, comprising:

(i) incorporating in series with a nucleic acid polymerase, within a reaction vessel, one of four different compounds into a primer to create an extension strand, wherein said primer is hybridized to said nucleic acid and wherein each of the four different compounds comprises a unique detectable label;

(ii) detecting said unique detectable label of each incorporated compound, so as to thereby identify each incorporated compound in said extension strand, thereby sequencing the nucleic acid;

wherein each of said four different compounds is independently a compound of claim 1.

28. A method of incorporating a compound into a primer, the method comprising combining a polymerase, a primer hybridized to nucleic acid template and the compound within a reaction vessel and allowing said polymerase to incorporate said compound into said primer thereby forming an extended primer, wherein said compound is a compound of claim 1.

* * * * *